US012702696B2

(12) United States Patent
Ziegler et al.

(10) Patent No.: US 12,702,696 B2
(45) Date of Patent: Aug. 11, 2026

(54) METHODS AND COMPOSITION FOR MODULATING IMMUNE RESPONSE AND IMMUNE HOMEOSTASIS

(71) Applicants: Massachusetts Institute of Technology, Cambridge, MA (US); President and Fellows of Harvard College, Cambridge, MA (US)

(72) Inventors: Carly G.K. Ziegler, Cambridge, MA (US); Siyi Huang, Cambridge, MA (US); Ulrich H. von Andrian, Cambridge, MA (US); Alexander K. Shalek, Cambridge, MA (US)

(73) Assignees: Massachusetts Institute of Technology, Cambridge, MA (US); President and Fellows of Harvard College, Cambridge, MA (US)

( * ) Notice: Subject to any disclaimer, the term of this patent is extended or adjusted under 35 U.S.C. 154(b) by 565 days.

(21) Appl. No.: 17/072,934

(22) Filed: Oct. 16, 2020

(65) Prior Publication Data

US 2021/0118522 A1 Apr. 22, 2021

Related U.S. Application Data

(60) Provisional application No. 62/916,184, filed on Oct. 16, 2019.

(51) Int. Cl.

| | |
|---|---|
| ***A61K 48/00*** | (2006.01) |
| ***A61K 31/137*** | (2006.01) |
| ***A61K 31/138*** | (2006.01) |
| ***A61K 38/17*** | (2006.01) |
| ***C12N 5/078*** | (2010.01) |
| ***C12N 5/0784*** | (2010.01) |
| ***C12N 5/0787*** | (2010.01) |
| ***C12Q 1/6881*** | (2018.01) |
| ***G01N 33/50*** | (2006.01) |
| ***G16B 5/00*** | (2019.01) |

(52) U.S. Cl.

CPC ........ *A61K 38/1796* (2013.01); *A61K 31/137* (2013.01); *A61K 31/138* (2013.01); *C12N 5/0639* (2013.01); *C12N 5/0642* (2013.01); *C12N 5/0651* (2013.01); *C12Q 1/6881* (2013.01); *G01N 33/5058* (2013.01); *G16B 5/00* (2019.02)

(58) Field of Classification Search

None

See application file for complete search history.

(56) References Cited

U.S. PATENT DOCUMENTS

| | | | |
|---|---|---|---|
| 4,737,323 | A | 4/1988 | Martin et al. |
| 4,837,028 | A | 6/1989 | Allen |
| 5,143,854 | A | 9/1992 | Fodor et al. |
| 5,288,644 | A | 2/1994 | Beavis et al. |
| 5,324,633 | A | 6/1994 | Fodor et al. |
| 5,432,049 | A | 7/1995 | Fischer et al. |
| 5,470,710 | A | 11/1995 | Weiss et al. |
| 5,492,806 | A | 2/1996 | Drmanac et al. |
| 5,503,980 | A | 4/1996 | Cantor |
| 5,510,270 | A | 4/1996 | Fodor et al. |
| 5,525,464 | A | 6/1996 | Drmanac et al. |
| 5,547,839 | A | 8/1996 | Dower et al. |
| 5,580,732 | A | 12/1996 | Grossman et al. |
| 5,580,737 | A | 12/1996 | Polisky et al. |
| 5,660,985 | A | 8/1997 | Pieken et al. |
| 5,661,028 | A | 8/1997 | Foote |
| 5,800,992 | A | 9/1998 | Fodor et al. |
| 5,811,097 | A | 9/1998 | Allison et al. |
| 6,479,626 | B1 | 11/2002 | Kim et al. |
| 6,534,261 | B1 | 3/2003 | Cox et al. |
| 6,607,882 | B1 | 8/2003 | Cox et al. |
| 6,746,838 | B1 | 6/2004 | Choo et al. |
| 6,794,136 | B1 | 9/2004 | Eisenberg et al. |
| 6,824,978 | B1 | 11/2004 | Cox et al. |
| 6,866,997 | B1 | 3/2005 | Choo et al. |
| 6,903,185 | B2 | 6/2005 | Kim et al. |
| 6,933,113 | B2 | 8/2005 | Case et al. |
| 6,979,539 | B2 | 12/2005 | Cox et al. |

(Continued)

FOREIGN PATENT DOCUMENTS

| | | |
|---|---|---|
| EP | 0 785 280 A2 | 7/1997 |
| EP | 0 373 203 B2 | 2/2007 |

(Continued)

OTHER PUBLICATIONS

Baral, et al., "Pain and Immunity: Implications for Host Defence", Nature Reviews Immunology, vol. 19, No. 7, Jul. 2019, 433-447.
Chavan, et al., "Mechanisms and Therapeutic Relevance of Neuro-Immune Communication", Immunity, vol. 46, No. 6, Jun. 20, 2017, 927-942.
Cohen, et al., "Tolerogenic Properties of Lymphatic Endothelial Cells Are Controlled by the Lymph Node Microenvironment", PLoS One, vol. 9, No. 2, Feb. 2014, 13 pages.
Robinson, et al., "Inside Information: The Unique Features of Visceral Sensation", Molecular Interventions, vol. 8, No. 5, Oct. 2008, 242-253.
Thiriot, et al., "Differential DARC/ACKR1 Expression Distinguishes Venular from Non-Venular Endothelial Cells in Murine Tissues", BMC Biology, vol. 15, No. 1, May 19, 2017, 19 pages.
Usoskin, et al., "Unbiased Classification of Sensory Neuron Types by Large-Scale Single-cell RNA Sequencing", Nature Neuroscience, vol. 18, No. 1, Jan. 2015, 145-153.

(Continued)

*Primary Examiner* — Michael D Pak

(74) *Attorney, Agent, or Firm* — F. Brent Nix, Esq.; Johnson, Marcou, Isaacs & Nix, LLC; Ming Zhang

(57) ABSTRACT

The present invention discloses novel methods, uses thereof, and compositions for modulating immune responses and homeostasis in a lymph node (LN). Moreover, structural and molecular characteristics of LN-innervating sensory neurons are provided. The present invention also discloses the target cells for LN-innervating sensory neurons in LN and molecular profiles of these target cells. These molecular characteristics provide therapeutic targets for modulating immune response and immune homeostasis in LN in an animal or a human.

7 Claims, 49 Drawing Sheets
(42 of 49 Drawing Sheet(s) Filed in Color)

Specification includes a Sequence Listing.

(56) References Cited

U.S. PATENT DOCUMENTS

| | | | |
|---|---|---|---|
| 7,013,219 B2 | 3/2006 | Case et al. | |
| 7,030,215 B2 | 4/2006 | Liu et al. | |
| 7,220,719 B2 | 5/2007 | Case et al. | |
| 7,241,573 B2 | 7/2007 | Choo et al. | |
| 7,241,574 B2 | 7/2007 | Choo et al. | |
| 7,585,849 B2 | 9/2009 | Liu et al. | |
| 7,595,376 B2 | 9/2009 | Kim et al. | |
| 8,021,867 B2 | 9/2011 | Smith et al. | |
| 8,119,361 B2 | 2/2012 | Smith et al. | |
| 8,119,381 B2 | 2/2012 | Smith et al. | |
| 8,124,369 B2 | 2/2012 | Smith et al. | |
| 8,129,134 B2 | 3/2012 | Smith et al. | |
| 8,133,697 B2 | 3/2012 | Smith et al. | |
| 8,163,514 B2 | 4/2012 | Smith et al. | |
| 2019/0045582 A1 | 2/2019 | He | |
| 2019/0240293 A1* | 8/2019 | Weinstein | G01N 33/5047 |

FOREIGN PATENT DOCUMENTS

| | | | |
|---|---|---|---|
| WO | 93/11161 | A1 | 6/1993 |
| WO | 95/21265 | A1 | 8/1995 |
| WO | 96/31622 | A1 | 10/1996 |
| WO | 96/40281 | A2 | 12/1996 |
| WO | 97/10365 | A1 | 3/1997 |
| WO | 97/27317 | A1 | 7/1997 |
| WO | 2009/012418 | A2 | 1/2009 |
| WO | 2014/093622 | A2 | 6/2014 |
| WO | 2014/204725 | A1 | 12/2014 |
| WO | 2014/210353 | A2 | 12/2014 |
| WO | 2016/040476 | A1 | 3/2016 |
| WO | 2016/106236 | A1 | 6/2016 |
| WO | 2016/168584 | A1 | 10/2016 |
| WO | 2017/164936 | A1 | 9/2017 |
| WO | 2018/191553 | A1 | 10/2018 |
| WO | 2018/213708 | A1 | 11/2018 |
| WO | 2018/213726 | A1 | 11/2018 |
| WO | 2019/005884 | A1 | 1/2019 |
| WO | 2019/005886 | A1 | 1/2019 |
| WO | 2019/018423 | A1 | 1/2019 |
| WO | 2019/060746 | A1 | 3/2019 |
| WO | 2019/071048 | A1 | 4/2019 |
| WO | 2019/094984 | A1 | 5/2019 |
| WO | 2019/126709 | A1 | 6/2019 |
| WO | 2019/126716 | A1 | 6/2019 |
| WO | 2019/126762 | A2 | 6/2019 |
| WO | 2020/077236 | A1 | 4/2020 |
| WO | 2020/131862 | A1 | 6/2020 |

OTHER PUBLICATIONS

Yamano, et al., "Aire-Expressing ILC3-like Cells in the Lymph Node Display Potent APC Features", Journal of Experimental Medicine, vol. 216, No. 5, 2019, 1027-1037.

Yang, et al., "Genetic Control of the Segregation of Pain-Related Sensory Neurons Innervating the Cutaneous Versus Deep Tissues", Cell Reports, vol. 5, No. 5, Dec. 12, 2013, 1353-1364.

* cited by examiner

FIG. 14A
TdTomato/AAV-FLEX-tdt into Nav1.8Cre
CD31
300 μm

SEQUENCE LISTING

<160> NUMBER OF SEQ ID NOS: 21

<210> SEQ ID NO 1
<211> LENGTH: 37
<212> TYPE: PRT
<213> ORGANISM: Homo sapiens

<400> SEQUENCE: 1

Ala Cys Asp Thr Ala Thr Cys Val Thr His Arg Leu Ala Gly Leu Leu
1 5 10 15

Ser Arg Ser Gly Gly Val Val Lys Asn Asn Phe Val Pro Thr Asn Val
20 25 30

Gly Ser Lys Ala Phe
35

<210> SEQ ID NO 2
<211> LENGTH: 37
<212> TYPE: PRT
<213> ORGANISM: Homo sapiens

<400> SEQUENCE: 2

Ala Cys Asn Thr Ala Thr Cys Val Thr His Arg Leu Ala Gly Leu Leu
1 5 10 15

Ser Arg Ser Gly Gly Met Val Lys Ser Asn Phe Val Pro Thr Asn Val
20 25 30

Gly Ser Lys Ala Phe
35

<210> SEQ ID NO 3
<211> LENGTH: 288
<212> TYPE: PRT
<213> ORGANISM: Artificial Sequence
<220> FEATURE:
<223> OTHER INFORMATION: Synthetic N-terminal capping region

<400> SEQUENCE: 3

Met Asp Pro Ile Arg Ser Arg Thr Pro Ser Pro Ala Arg Glu Leu Leu
1 5 10 15

Ser Gly Pro Gln Pro Asp Gly Val Gln Pro Thr Ala Asp Arg Gly Val
20 25 30

Ser Pro Pro Ala Gly Gly Pro Leu Asp Gly Leu Pro Ala Arg Arg Thr
35 40 45

Met Ser Arg Thr Arg Leu Pro Ser Pro Pro Ala Pro Ser Pro Ala Phe
50 55 60

Ser Ala Asp Ser Phe Ser Asp Leu Leu Arg Gln Phe Asp Pro Ser Leu
65 70 75 80

Phe Asn Thr Ser Leu Phe Asp Ser Leu Pro Pro Phe Gly Ala His His
85 90 95

Thr Glu Ala Ala Thr Gly Glu Trp Asp Glu Val Gln Ser Gly Leu Arg
100 105 110

Ala Ala Asp Ala Pro Pro Pro Thr Met Arg Val Ala Val Thr Ala Ala
115 120 125

Arg Pro Pro Arg Ala Lys Pro Ala Pro Arg Arg Arg Ala Ala Gln Pro
130 135 140

Ser Asp Ala Ser Pro Ala Ala Gln Val Asp Leu Arg Thr Leu Gly Tyr
145 150 155 160

Ser Gln Gln Gln Gln Glu Lys Ile Lys Pro Lys Val Arg Ser Thr Val
165 170 175

```
Ala Gln His His Glu Ala Leu Val Gly His Gly Phe Thr His Ala His
            180                 185                 190

Ile Val Ala Leu Ser Gln His Pro Ala Ala Leu Gly Thr Val Ala Val
        195                 200                 205

Lys Tyr Gln Asp Met Ile Ala Ala Leu Pro Glu Ala Thr His Glu Ala
    210                 215                 220

Ile Val Gly Val Gly Lys Gln Trp Ser Gly Ala Arg Ala Leu Glu Ala
225                 230                 235                 240

Leu Leu Thr Val Ala Gly Glu Leu Arg Gly Pro Pro Leu Gln Leu Asp
                245                 250                 255

Thr Gly Gln Leu Leu Lys Ile Ala Lys Arg Gly Gly Val Thr Ala Val
            260                 265                 270

Glu Ala Val His Ala Trp Arg Asn Ala Leu Thr Gly Ala Pro Leu Asn
        275                 280                 285


<210> SEQ ID NO 4
<211> LENGTH: 183
<212> TYPE: PRT
<213> ORGANISM: Artificial Sequence
<220> FEATURE:
<223> OTHER INFORMATION: Synthetic C-terminal capping region

<400> SEQUENCE: 4

Arg Pro Ala Leu Glu Ser Ile Val Ala Gln Leu Ser Arg Pro Asp Pro
1               5                   10                  15

Ala Leu Ala Ala Leu Thr Asn Asp His Leu Val Ala Leu Ala Cys Leu
            20                  25                  30

Gly Gly Arg Pro Ala Leu Asp Ala Val Lys Lys Gly Leu Pro His Ala
        35                  40                  45

Pro Ala Leu Ile Lys Arg Thr Asn Arg Arg Ile Pro Glu Arg Thr Ser
    50                  55                  60

His Arg Val Ala Asp His Ala Gln Val Val Arg Val Leu Gly Phe Phe
65                  70                  75                  80

Gln Cys His Ser His Pro Ala Gln Ala Phe Asp Asp Ala Met Thr Gln
                85                  90                  95

Phe Gly Met Ser Arg His Gly Leu Leu Gln Leu Phe Arg Arg Val Gly
            100                 105                 110

Val Thr Glu Leu Glu Ala Arg Ser Gly Thr Leu Pro Pro Ala Ser Gln
        115                 120                 125

Arg Trp Asp Arg Ile Leu Gln Ala Ser Gly Met Lys Arg Ala Lys Pro
    130                 135                 140

Ser Pro Thr Ser Thr Gln Thr Pro Asp Gln Ala Ser Leu His Ala Phe
145                 150                 155                 160

Ala Asp Ser Leu Glu Arg Asp Leu Asp Ala Pro Ser Pro Met His Glu
                165                 170                 175

Gly Asp Gln Thr Arg Ala Ser
            180


<210> SEQ ID NO 5
<211> LENGTH: 7
<212> TYPE: PRT
<213> ORGANISM: Simian virus 40

<400> SEQUENCE: 5

Pro Lys Lys Lys Arg Lys Val
1               5
```

<210> SEQ ID NO 6
<211> LENGTH: 10
<212> TYPE: PRT
<213> ORGANISM: Simian virus 40

<400> SEQUENCE: 6

```
Pro Lys Lys Lys Arg Lys Val Glu Ala Ser
1               5                   10
```

<210> SEQ ID NO 7
<211> LENGTH: 16
<212> TYPE: PRT
<213> ORGANISM: Artificial Sequence
<220> FEATURE:
<223> OTHER INFORMATION: Synthetic nucleoplasmin bipartite NLS

<400> SEQUENCE: 7

```
Lys Arg Pro Ala Ala Thr Lys Lys Ala Gly Gln Ala Lys Lys Lys Lys
1               5                   10                  15
```

<210> SEQ ID NO 8
<211> LENGTH: 9
<212> TYPE: PRT
<213> ORGANISM: Homo sapiens

<400> SEQUENCE: 8

```
Pro Ala Ala Lys Arg Val Lys Leu Asp
1               5
```

<210> SEQ ID NO 9
<211> LENGTH: 11
<212> TYPE: PRT
<213> ORGANISM: Homo sapiens

<400> SEQUENCE: 9

```
Arg Gln Arg Arg Asn Glu Leu Lys Arg Ser Pro
1               5                   10
```

<210> SEQ ID NO 10
<211> LENGTH: 38
<212> TYPE: PRT
<213> ORGANISM: Homo sapiens

<400> SEQUENCE: 10

```
Asn Gln Ser Ser Asn Phe Gly Pro Met Lys Gly Gly Asn Phe Gly Gly
1               5                   10                  15

Arg Ser Ser Gly Pro Tyr Gly Gly Gly Gly Gln Tyr Phe Ala Lys Pro
            20                  25                  30

Arg Asn Gln Gly Gly Tyr
        35
```

<210> SEQ ID NO 11
<211> LENGTH: 42
<212> TYPE: PRT
<213> ORGANISM: Homo sapiens

<400> SEQUENCE: 11

```
Arg Met Arg Ile Glx Phe Lys Asn Lys Gly Lys Asp Thr Ala Glu Leu
1               5                   10                  15

Arg Arg Arg Arg Val Glu Val Ser Val Glu Leu Arg Lys Ala Lys Lys
            20                  25                  30

Asp Glu Gln Ile Leu Lys Arg Arg Asn Val
        35                  40
```

<210> SEQ ID NO 12
<211> LENGTH: 8
<212> TYPE: PRT
<213> ORGANISM: Homo sapiens

<400> SEQUENCE: 12

Val Ser Arg Lys Arg Pro Arg Pro
1 5

<210> SEQ ID NO 13
<211> LENGTH: 8
<212> TYPE: PRT
<213> ORGANISM: Homo sapiens

<400> SEQUENCE: 13

Pro Pro Lys Lys Ala Arg Glu Asp
1 5

<210> SEQ ID NO 14
<211> LENGTH: 8
<212> TYPE: PRT
<213> ORGANISM: Homo sapiens

<400> SEQUENCE: 14

Pro Gln Pro Lys Lys Lys Pro Leu
1 5

<210> SEQ ID NO 15
<211> LENGTH: 12
<212> TYPE: PRT
<213> ORGANISM: Mus sp.

<400> SEQUENCE: 15

Ser Ala Leu Ile Lys Lys Lys Lys Lys Met Ala Pro
1 5 10

<210> SEQ ID NO 16
<211> LENGTH: 5
<212> TYPE: PRT
<213> ORGANISM: Influenza virus

<400> SEQUENCE: 16

Asp Arg Leu Arg Arg
1 5

<210> SEQ ID NO 17
<211> LENGTH: 7
<212> TYPE: PRT
<213> ORGANISM: Influenza virus

<400> SEQUENCE: 17

Pro Lys Gln Lys Lys Arg Lys
1 5

<210> SEQ ID NO 18
<211> LENGTH: 10
<212> TYPE: PRT
<213> ORGANISM: Hepatitis D virus

<400> SEQUENCE: 18

Arg Lys Leu Lys Lys Lys Ile Lys Lys Leu
1 5 10

<210> SEQ ID NO 19

-continued

```
<211> LENGTH: 10
<212> TYPE: PRT
<213> ORGANISM: Mus sp.

<400> SEQUENCE: 19

Arg Glu Lys Lys Lys Phe Leu Lys Arg Arg
1               5                   10

<210> SEQ ID NO 20
<211> LENGTH: 20
<212> TYPE: PRT
<213> ORGANISM: Homo sapiens

<400> SEQUENCE: 20

Lys Arg Lys Gly Asp Glu Val Asp Gly Val Asp Glu Val Ala Lys Lys
1               5                   10                  15

Lys Ser Lys Lys
            20

<210> SEQ ID NO 21
<211> LENGTH: 17
<212> TYPE: PRT
<213> ORGANISM: Homo sapiens

<400> SEQUENCE: 21

Arg Lys Cys Leu Gln Ala Gly Met Asn Leu Glu Ala Arg Lys Thr Lys
1               5                   10                  15

Lys
```

METHODS AND COMPOSITION FOR MODULATING IMMUNE RESPONSE AND IMMUNE HOMEOSTASIS

CROSS-REFERENCE TO RELATED APPLICATIONS

This application claims the benefit of U.S. Provisional Application No. 62/916,184, filed Oct. 16, 2019. The entire contents of the above-identified application are hereby fully incorporated herein by reference.

STATEMENT REGARDING FEDERALLY SPONSORED RESEARCH

This invention was made with government support under Grants AR068383, HL066987, GM119419, AI089992, HL095791, CA217377, AI039671, AI118672, HG006193, CA202820, AI138546, HL126554, DA046277, CA233195, and GM007753 awarded by the National Institutes of Health. The U.S. government has certain rights in the invention.

REFERENCE TO AN ELECTRONIC SEQUENCE LISTING

The contents of the electronic sequence listing ("BROD_4830US_ST25.txt"; Size is 8.62 Kilobytes and it was created on Oct. 15, 2020) is herein incorporated by reference in its entirety.

TECHNICAL FIELD

The subject matter disclosed herein is generally directed to compositions and methods for modulating immune response and immune homeostasis in a lymph node (LN) by modulating LN-innervating sensory neurons and their target cells that include lymphatic endothelial cells, blood endothelial cells, and other types of stroma cells in LN. The present invention also discloses isolated cells including LN-innervating peptidergic nociceptor sensory neuron cell and its target cells in LN.

BACKGROUND

The immune system is the primary mechanism of host defense and requires coordinated action among myriad immune and stromal cell types, both within and between the various tissues of the body. One critical immunomodulatory stromal component is the peripheral nervous system (PNS): the neural pathways that directly interface with both the central nervous system (CNS) and all peripheral tissues. The sensory component of the PNS, i.e., sensory neurons in vagal ganglia and dorsal root ganglia (DRGs), provide the CNS with sensory information out in the periphery. The motor commends from the CNS to skeletal muscles and visceral organs are executed by spinal motor neurons and the sympathetic/parasympathetic neurons, respectively. Being pseudounipolar, sensory neurons in vagal ganglia and dorsal root ganglia (DRGs) each send out a bifurcating axon to directly innervate both the peripheral tissues and central targets in the spinal cord and the brainstem. While the sensory nervous system—and, in particular, the nociceptive system—has traditionally been studied as a standalone means of sensing and responding to external and internal noxious stimuli, it has recently been rediscovered to play a key role in shaping immune responses in animal models of asthma, colitis and psoriasis, and infection (Baral et al., 2019; Foster et al., 2017; McMahon et al., 2015; Ordovas-Montanes et al., 2015). In many cases, this nociceptor modulation of immunity involves bioactive neuropeptides, such as calcitonin gene-related peptide (CGRP) and substance p, which are thought to be released from activated peripheral terminals of nociceptors and act on various immune cells and stromal cells with the corresponding neuropeptide receptors (Assas et al., 2014; Baral et al., 2019; Suvas, 2017).

However, while the molecular and cellular components of those biologically-important neuroimmune interactions have begun to be elucidated, deciphering the sequence of events underlying specific interactions remains a major challenge, in part, due to a lack of systematic understanding of the structural, molecular and functional architecture of the neuronal component of the sensory neuron-immune axis. In fact, traditional anatomic and functional characterization, and more recently single-cell RNA-sequencing (scRNA-seq)-based molecular profiling, have revealed remarkable heterogeneity within sensory neurons (Kupari et al., 2019; Usoskin et al., 2015; Wood et al., 2018). Furthermore, peptidergic innervation of putative sensory origin has been observed in most, if not all, peripheral tissues of immunological relevance (e.g., secondary lymphoid organs and barrier tissues), where the density and pattern of innervation, as well as targeted cell types, are highly tissue-specific (Belvisi, 2002; Brierley et al., 2004; Felten et al., 1985; Fink and Weihe, 1988; Oaklander and Siegel, 2005). Such widespread distribution of peptidergic innervation therefore raises the intriguing possibility that sensory neurons targeting different peripheral sites collectively contribute to the overall immune response by engaging in distinct tissue-specific local sensory neuron-immune circuits. If true, the observed immunological consequences of systemic ablation of nociceptors or nociceptor-enriched signaling molecules could in principle originate from the site of immune challenge, i.e. barrier tissues, and/or the draining LNs—the two interdependent compartments involved in diverse local immune responses. Therefore, not only is a systematic interrogation of the entire repertoire of sensory neurons with immunological function needed, it must also be carried out one tissue at a time.

LNs are important for establishing local immunity and peripheral tolerance as demonstrated using mouse models and humans with defective LN organogenesis, as well as surgical models of LN resection (Buettner and Bode, 2012; Karrer et al., 1997; Lakkis et al., 2000; Mooster et al., 2015; Zhou et al., 2003). A host of diverse immune and stromal cell types that are strategically arranged into functionally important compartments, support the various functions of LNs, including collection of antigen-presenting cells, inflammatory mediators, and antigen via afferent lymphatic vessels from distal sites, selective recruitment of vast numbers of naïve and memory lymphocytes from the blood via high endothelial vessels (HEVs), recirculation of naïve, memory and effector lymphocytes through efferent lymphatics. Within the LN, non-endothelial stromal cells organize the avascular space into discrete niches to facilitate antigen encounters, enabling vast numbers of B and T cells to survey antigen and appropriately elicit an immunogenic or tolerogenic response.

As dual innervation of LNs by noradrenergic and peptidergic neurons has been reported in a variety of mammalian species (Felten et al., 1985; Fink and Weihe, 1988), it has been postulated that LN innervation might participate in neuronal control of regional immunity. While there is general consensus on the sympathetic origin of noradrenergic innervation of LNs (Bellinger et al., 1992; Felten et al., 1985), sensory innervation of LNs has been difficult to establish due to the existence of nonpeptidergic sensory neurons for which a definitive marker is lacking as well as the broad expression of neuropeptide and ion channels traditionally used to identify and manipulate sensory neurons, such as CGRP, substance P and the capsaicin receptor (transient receptor potential channel-vanilloid subfamily member 1, TRPV1). (Caterina, 2003; Malin et al., 2011; Shepherd et al., 2005b). These caveats notwithstanding, local application of capsaicin, a neurotoxin historically used to selectively target TRPV1-expressing sensory neurons, to LNs that drain the site of immune challenge or sensitization has been shown to attenuate inflammatory responses by almost completely unknown mechanisms in animal models of arthritis and contact sensitivity, respectively, consistent with a pro-inflammatory role for capsaicin-sensitive sensory innervation of LNs (Felten et al., 1992; Lorton et al., 2000; Shepherd et al., 2005a). More recently, a diphtheria toxin fragment A (DTA)-based genetic model globally deficient in nociceptors revealed a role for sensory neurons—likely those innervating LNs—in regulating antigen flow through peripheral LNs in immunized mice (Hanes et al., 2016). This observation, together with the stimulatory effect of substance P on lymph flow and lymphocyte output through peripheral LNs in sheep, suggests that modulation of lymphatic trafficking is a common mechanism of immune regulation by putative sensory innervation of LNs (Moore et al., 1989). Thus, LNs represent an attractive yet understudied model system to explore organ-specific sensory neuron-immune interactions.

Modulation of immune responses and homeostasis in lymph nodes (LNs) plays key roles in maintaining proper immunity against pathologic challenges. Sensory neurons can be found in LNs. However, whether and how LN-innervating sensory neurons modulate immune responses and homeostasis in LNs remain unknown. Identification of methods and compositions implied in such immunomodulatory activities have profound utility in clinical application for treating diseases and improve health conditions.

Citation or identification of any document in this application is not an admission that such a document is available as prior art to the present invention.

SUMMARY

In one aspect, the present invention provides for a method of modulating an immune response and/or lymph node (LN) homeostasis, comprising administering one or more agents capable of modulating neural stimulation and/or efferent signaling of LN-innervating peptidergic nociceptor sensory neurons. In certain embodiments, the nociceptor sensory neurons innervate an outer cortical region or medulla of LNs. In certain embodiments, the outer cortical region comprises a perivascular space and a capsular/sub-capsular space. In certain embodiments, the LN-innervating nociceptor sensory neurons are characterized by the expression of one or more genes or gene products selected from: one or more gene or gene products of Table 1; Trpc4, Trpm8, Kchnh5, and Ache; Tbxa2r, Il33, Ptgir, and Cd1d; or Ptgir and Prokr2. In certain embodiments, modulating neural stimulation and/or efferent signaling of LN-innervating nociceptor sensory neurons comprises administering an agent that modulates the expression or function of one or more of genes selected from the group consisting of Calca, Clacb, Tac1, Adcyap1, and Gal. In certain embodiments, modulating neural stimulation and/or efferent signaling of LN-innervating nociceptor sensory neurons comprises administering an agent that modulates the expression or function of one or more of genes selected from the group consisting of Ramp1, Calcrl, Tacr1, Adcyap1r1, Galr2, and Galr1. In certain embodiments, modulating neural stimulation and/or efferent signaling of LN-innervating nociceptor sensory neurons comprises modulating the interaction with non-endothelial stroma by administering an agent that modulates the expression or function of one or more of: Col3a1, Col5a2, Col5a1, Col6a1, Col6a2, Col6a3, Col1a2, Col1a2, Lama2, Thbs2, Fn1; Vegfa, Ptn, Mdk, Cxcl12; and Pdgfra, Pdgfrb, Ntrk2. In certain embodiments, modulating neural stimulation and/or efferent signaling of LN-innervating nociceptor sensory neurons comprises modulating the interaction with non-venular blood endothelial cells (BEC 1) by administering an agent that modulates the expression or function of one or more of: Lama5, Itga5, Hspg2; Flt1, Notch4, Fzd5; Sema3f, Sema7a, Nrp1, Plxnd1, Efnb1, Epha4; and Selp, Cxcl1. In certain embodiments, activating neural stimulation and/or efferent signaling of LN-innervating nociceptor sensory neurons comprises modulation of gene expression or function in lymph node stromal cells. In certain embodiments, the LN stromal cells are lymphatic endothelial cells (LECs). In certain embodiments, the LECs are characterized by the expression of one or more genes or gene expression products selected from the group consisting of Fbln2, Aqp1, Fbln5, Inc, and Reln. In certain embodiments, modulating neural stimulation and/or efferent signaling of LN-innervating nociceptor sensory neurons comprises modulating the interaction with LECs by administering an agent that modulates the expression or function of one or more of: Tnc, Fbn1, Nid1; Agrn Nrxn2, Nlgn2; Efnb2, Nrp2, Robo1; Reln, F8, Itgb3, Nrp2; and Gata6, Ets2, Irf7, Nfatc1. In certain embodiments, modulation of gene expression in LECs results in modulation of genes involved in lymphatic development and patterning and/or expression of angiogenic molecules and/or regulation of lymph or antigen flow. In certain embodiments, modulation of genes involved in lymphatic development and patterning and/or angiogenic molecules comprises administering an agent that downregulates the expression or function of one or more of genes selected from the group consisting of Reln, Nrp2, Ephb4, Nfatc1, Lye1, Dlg1, and Glu1. In certain embodiments, modulation of genes involved in lymphatic development and patterning and/or angiogenic molecules and/or regulation of lymph or antigen flow comprises administering an agent that up regulates the expression or function of one or more genes selected from the group consisting of Reln, Nrp2, Ephb4, Nfatc1, Lye1, Dlg1, and Glu1. In certain embodiments, modulation of gene expression in LECs comprises increasing or decreasing lymphocyte homing or egress from lymph nodes. In certain embodiments, decreasing lymphocyte homing or egress from LNs comprises downregulating the expression or function of one or both of genes Acer2 and Asah2. In certain embodiments, increasing lymphocyte homing or egress from LNs comprises upregulating the expression or function of one or both of genes Acer2 and Asah2. In certain embodiments, the one or more agents comprise a small molecule, small molecule degrader, genetic modifying agent, antibody, antibody fragment, antibody-like protein scaffold, aptamer, protein, or any combination thereof. In certain embodiments, the genetic modifying agent comprises a CRISPR system, RNAi system, zinc finger nuclease system, TALE system, or a meganuclease. In certain embodiments, the CRISPR system comprises a CRISPR-Cas base editing system, a prime editor system, or a CAST system. In certain embodiments, modulating an immune response and/or lymph node (LN) homeostasis is used to treat a subject suffering from a disease characterized by aberrant homeostasis or inflammation. In certain embodiments, the disease is selected from the group consisting of an inflammatory disease, autoimmune disease, cancer and an infection.

In another aspect, the present invention provides for an isolated peptidergic nociceptor sensory neuron cell characterized by the expression of one or more genes or gene products selected from: one or more gene or gene products of Table 2; Trpc4, Trpm8, Kchnh5, and Ache; Thxa2r, Il33, Ptgir, and Cd1d; or Ptgir and Prokr2. In certain embodiments, the cell is capable of modulating immune response and homeostasis in a LN in an animal or a human.

In another aspect, the present invention provides for an isolated dendritic cell-like cell (Aire+) characterized by high expression levels of Aire gene or gene product in comparison to the average levels in a LN, and the expression of one or more of genes or gene products selected from the group consisting of Ryr3, Myo5b, Scn3a, and Nrgn; or one or more genes or gene products of Table 2. In certain embodiments, the cell is capable of interacting with a sensory neuron cell and exerting modulatory effect on immune response and homeostasis in a LN in an animal or a human.

In another aspect, the present invention provides for an isolated neutrophil cell (NEUTROPHIL_1) characterized by high expression levels of genes in comparison to the average levels in a LN, wherein the genes code for components of neutrophil granules and effector molecules comprising Elane, Prtn3, Ctsg, Ngp, Ltf, Camp, and Mpo; or one or more genes or gene products of Table 2. In certain embodiments, the cell is capable of interacting with a sensory neuron cell and exerting modulatory effect on immune response and homeostasis in a LN in an animal or a human.

In another aspect, the present invention provides for an isolated neutrophil cell (NEUTROPHIL_2) characterized by: one or more genes or gene products of Table 2; or high expression levels of genes coding for pro-inflammatory molecules comprising Ccl4, Sell, Cxcr2, Cxcl2, Ccl6, Il1b, and Csf3r; and absent or low expression levels of genes coding for effector molecules comprising Elane, Prtn3, Ctsg, Ngp, Ltf, Camp, and Mpo, wherein the high or low expression levels of genes are in comparison to the average levels of these genes in a LN. In certain embodiments, the cell is capable of interacting with a sensory neuron cell and exerting a modulatory effect on immune response and homeostasis in a LN in an animal or a human.

In another aspect, the present invention provides for an isolated non-venular blood endothelial cell (BEC1) characterized by the expression of one or more genes or gene products selected from: one or more genes or gene products of Table 2; Lama5, Itga5, Hspg2; Flt1, Notch4, Fzd5; Sema3f, Sema7a, Nrp1, Plxnd1, Efnb1, Epha4; or Selp, Cxcl1. In certain embodiments, the cell is capable of interacting with a sensory neuron cell and exerting modulatory effect on immune response and homeostasis in a LN in an animal or a human.

In another aspect, the present invention provides for an isolated lymphatic endothelial cell (LEC1) characterized by the expression of gene or gene product of Madcam1; or one or more genes or gene products of Table 2. In certain embodiments, the cell is capable of interacting with a sensory neuron cell and exerting modulatory effect on immune response and homeostasis in a LN in an animal or a human.

In another aspect, the present invention provides for an isolated lymphatic endothelial cell (LEC2) characterized by the expression of one or more genes or gene products selected from: one or more genes or gene products of Table 2; Fbln2, Aqp1, Fbln5, Tnc, and Reln; Tnc, Fbn1, and Nid1; Agrn Nrxn2, and Nlgn2; Efnb2, Nrp2, and Robo1; Reln, F8, Itgb3, and Nrp2; Gata6, Ets2, Irf7, and Nfatc1; or Reln, Nrp2, Ephb4, Nfatc1, Lye1, Dlg1, and Glu1. In certain embodiments, the cell is capable of interacting with a sensory neuron cell and exerting modulatory effect on immune response and homeostasis in a LN in an animal or a human.

In another aspect, the present invention provides for a computational method for integrating distinct datasets to contextualize LN- or skin-innervating neurons with an established scRNA-Seq atlas, comprising: (a) calculating principal components (PC) over all neuronal cells and projecting lymph node-innervating and skin-innervating sensory neurons into the principal components space; (b) creating pseudo-population averages from single-cell transcriptomes of each subtype, and calculating the Spearman correlation between single LN-innervating or skin-innervating sensory neurons and the neuronal subtype pseudo-populations; (c) using hierarchical clustering based upon the similarity of single neuronal cells to the neuronal subtypes defined by the established scRNA-seq atlas to identify transcriptionally distinct neuronal classes within the datasets to be tested; (d) identifying the intersection of expressed genes from the established sensory neuron atlas and LN-innervating and skin-innervating single cells, and eliminating cells identified as non-neuronal from the sensory neuron atlas; (e) performing dimensionality reduction by transforming the data as log 2(1+TPM), calculating the gene variance across all cells, and selecting genes with a variance log 2(1+TPM)>0.5; (f) performing principal component analysis over the log 2-transformed, mean-centered data, and identifying the PCs that reflect major axes of variability between the cell types of the established sensory neuron scRNA-Seq atlas; (g) projecting the data to be tested into the PCs of the sensory neuron atlas to identify the relationship between LN-innervating and skin-innervating cells and major DRG cell types in a reduced dimensional space; (h) visualizing the data by plotting the PC vectors from the established sensory neuron atlas with the PC vectors from the transformed LN-innervating and skin-innervating cells; (i) analyzing the expression similarity between each single cell from the dataset to be tested and the sensory neuron atlas subtypes by assessing the correlation between each single cell to be tested and each subtype of sensory neuron atlas, calculating the average gene expression for each neuron subtype over the log 2(1+TPM) transformed single-cell data, generating pseudo-population averages for each neuron subtype of the established sensory neuron atlas; (j) calculating the Spearman correlation between each single cell to be tested (following log 2(1+TPM) transformation) and the sensory neuron atlas pseudo-population averages; and (k) clustering LN-innervating and skin-innervating single cells by their correlation with each sensory neuron atlas pseudo-population using complete linkage clustering.

In another aspect, the present invention provides for a computational method for inferring cellular interaction partners using receptor-ligand pairings, comprising: (a) selecting genes from single-cell transcriptomic data of a first cell type with non-negligible expression using a cutoff of average log 2(1+TPM)>3; (b) obtaining genes that have intersection within a public database of cell-cell molecular interaction (receptor-ligand interactions), wherein the database comprises a certain number of interactions over a certain number of unique genes; (c) restricting the receptor-ligand pairs and unique potential cognate genes by selecting only interactions with at least one participating gene expressed in the first cell type; (d) assessing the expression of unique potential cognate genes within a second cell type; (e) repeating step (d) for a third, fourth, fifth, or more cell types; (f) developing a summary statistic (interaction potential, IP) to reflect the abundance of the first cell type cognate genes expressed in the second, the third, the fourth, or more cell types, wherein the IP score is calculated by steps comprising: (i) scaling the gene expression data by subtracting the mean and dividing by the standard deviation for each individual gene; (ii) calculating the IP score as the mean of these scaled values for each cell type; and (iii) assigning higher IP scores to cell types that express relatively higher abundances of all cognate genes of the first cell type; (g) ranking the cell types of potential partners by their IP scores; (h) computing statistical significance of the IP scores by comparing the IP scores to a null distribution, wherein the null distribution is formed by shuffling the cell type labels over all single cells to be tested as potential partners and repeated the cell-type averaging, scaling, and IP calculation for 1,000 permutations, wherein the statistical significance is expressed as a P value; (i) selecting the cell types that have a positive IP score or those have IP scores with $P<0.05$; and (j) validating the selected cell types as the cell-cell interaction partners using optogenetic stimulation technique or other techniques.

In another aspect, the present invention provides for a method of screening for agents capable of modulating an immune response and/or lymph node (LN) homeostasis, comprising: applying a candidate agent to a cell population comprising LN-innervating peptidergic nociceptor sensory neurons; and detecting modulation of one or more genes or gene products in any of Tables 1-3 in the cell population by the candidate agent, thereby identifying the agent.

In certain example embodiments, methods are provided for identifying LN-innervating sensory neurons that are characterized by the expression of one or more of Trpc4, Trpm8, Kchnh5, Ache, Tbxa2r, Il33, Ptgir, Prokr2, Cd1d, Calca, Clacb, Tac1, Adcyap1, Gal, Ramp1, Calcrl, Tacr1, Adcyap1r1, Galr2, Galr1, or any one or more genes in Table 1.

In certain example embodiments, methods are provided for modulating the immune response and homeostasis of LN by administering one or more agents to modulate the levels of gene expression or gene products of one or more of Thxa2r, Il33, Ptgir, and Cd1d.

In certain embodiments, methods are provided for modulating the immune response and homeostasis of LN by administering one or more agents to modulate the levels of gene expression products or gene expression for one or more of CGRP (Calca, Calcb), substance P (Tac1), galanin (Gal), and pituitary adenylate cyclase-activating polypeptide (PACAP) (Adcyap1).

In certain embodiments, methods are provided for modulating the immune response and homeostasis of LN by administering one or more agents to modulate the levels of gene expression products or gene expression for one or more of Ramp1, Calcrl, Tacr1, Adcyap1r1, Galr2 and Galr1.

In certain embodiments, methods are provided for identifying the target cells in LNs that are modulated by LN-innervating sensory neurons. One type of such target cells disclosed in the present invention is non-endothelial stroma cell that are characterized by the expression of one or more of Col3a1, Col5a2, Col5a1, Col6a1, Col6a2, Col6a3, Col1a2, Col1a2, Lama2, Thbs2, Fn1, Vegfa, Ptn, Mdk, Cxcl12; Pdgfra, Pdgfrb, and Ntrk2. These genes and their corresponding products serve as therapeutic targets for modulating immune response and homeostasis.

In certain embodiments, methods are provided for identifying the target cells in LNs that are modulated by LN-innervating sensory neurons. One type of such target cells disclosed in the present invention is non-venular blood endothelial cells (BEC1) that are characterized by the expression of one or more of Lama5, Itga5, Hspg2, Flt1, Notch4, Fzd5, Sema3f, Sema7a, Nrp1, Plxnd1, Efnb1, Epha4, Selp, and Cxcl1. These genes and their corresponding products serve as therapeutic targets for modulating immune response and homeostasis.

In certain embodiments, methods are provided for identifying the target cells in LN that are modulated by LN-innervating sensory neurons. One type of such target cells disclosed in the present invention is lymphatic endothelial cells (LECs) that are characterized by the expression of one or more of Fbln2, Aqp1, Fbln5, Tnc, and Reln. These genes and their corresponding products serve as therapeutic targets for modulating immune response and homeostasis. Modulation of these genes or gene expression products will result in modulation of lymphatic development and patterning and/or expression of angiogenic molecules.

In certain embodiments, methods are provided for modulating immune response and homeostasis by administering one or more agents to modulating the expression of any of, or combination thereof, Tnc, Fbn1, Nid1, Agrn Nrxn2, Nlgn2, Efnb2, Nrp2, Robo1, Reln, F8, Itgb3, Nrp2, Gata6, Ets2, Irf7, and Nfatc1.

In certain embodiments, methods are provided for modulating lymphatic development and patterning and/or expression of angiogenic molecules by modulating one or more of genes or gene expression products for Reln, Nrp2, Ephb4, Nfatc1, Lye1, Dlg1, and Glu1.

In certain embodiments, methods are provided for modulating lymphocyte egress from LNs by modulating gene expression or gene expression products for one or both of Acer2 and Asah2.

In certain embodiments, an isolated peptidergic nociceptor sensory neuron cell is provided that is characterized by the expression of genes or gene products comprising genes from Table 1, Trpc4, Trpm8, Kchnh5, Ache, Thxa2r, Il33, Ptgir, Cd1d, Ptgir, and Prokr2.

In certain embodiments, an isolated dendritic cell-like cell is provided that is characterized by high levels of gene expression or gene product of Aire and the expression of genes or gene products comprising Ryr3, Myo5b, Scn3a, and Nrgn.

In certain embodiments, an isolated neutrophil cell is provided that is characterized by high levels of expression of genes coding for components of neutrophil granules and effector molecules comprising Elane, Prtn3, Ctsg, Ngp, Ltf, Camp, and Mpo.

In certain embodiments, an isolated neutrophil cell is provided that is characterized by high levels of expression of genes coding for pro-inflammatory molecules comprising Ccl4, Sell, Cxcr2, Cxcl2, Ccl6, Il1b, and Csf3r and absent of low levels of expression of genes coding for effector molecules comprising Elane, Prtn3, Ctsg, Ngp, Ltf, Camp, and Mpo.

In certain embodiments, an isolated non-venular blood endothelial cell is provided that is characterized by the expression genes or gene products comprising Lama5, Itga5, Hspg2, Flt1, Notch4, Fzd5, Sema3f, Sema7a, Nrp1, Plxnd1, Efnb1, Epha4, Selp, and Cxcl1.

In certain embodiments, an isolated lymphatic endothelial cell is provided that is characterized by the expression of gene or gene product of Madcam1.

In certain embodiments, an isolated lymphatic endothelial cell is provided that is characterized by the expression of genes or gene products comprising Fbln2, Aqp1, Fbln5, Tnc, Reln, Tnc, Fbn1, Nid1, Agrn Nrxn2, Nlgn2, Efnb2, Nrp2, Robo1, Reln, F8, Itgb3, Nrp2, Gata6, Ets2, Irf7, Nfatc1, Reln, Nrp2, Ephb4, Nfatc1, Lye1, Dlg1, and Glu1.

These and other aspects, objects, features, and advantages of the example embodiments will become apparent to those having ordinary skill in the art upon consideration of the following detailed description of example embodiments.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

An understanding of the features and advantages of the present invention will be obtained by reference to the following detailed description that sets forth illustrative embodiments, in which the principles of the invention may be utilized, and the accompanying drawings of which:

FIG. 1A. 3D reconstruction of a representative confocal image of whole-mount popliteal LNs from Nav1.8$^{Cre/+}$; Rosa26$^{LSL\text{-}tdTomato/+}$ animals, stained for tdTomato (red) and β3-Tubulin (green) to mark sensory innervation and total neuronal innervation of LNs, respectively. FIG. 1B. 3D reconstruction of a representative confocal image of whole-mount popliteal LNs from Nav1.8$^{Cre/+}$; Rosa26$^{LSL\text{-}tdTomato/+}$ animals, stained for tdTomato (red), tyrosine hydroxylase (TH) (green) and CD31 (white) to mark sensory fibers, sympathetic fibers and vasculature in and around LNs, respectively. FIGS. 1C and 1D. Representative rendered surfaces for tdTomato$^+$ sensory fibers (red) and TH$^+$ sympathetic fibers (green) within rendered popliteal LNs (grey) of saline-treated (C) and 6-OHDA-treated (D) Nav1.8$^{Cre/+}$; Rosa26$^{LSL\text{-}tdTomato/+}$ animals. FIG. 1E. Quantification of the effect of 6-OHDA treatment on sensory and sympathetic fiber density based on 5 control LNs vs. 5 6-OHDA-treated LNs from 3 pairs of control and sympathectomized mice from 3 litters. For sympathetic fibers, p=0.0232 (*); for sensory fibers, p=0.2050 (ns). FIGS. 1F and 1G. Representative rendered surfaces for tdTomato$^+$ sensory fibers (red) and TH$^+$ sympathetic fibers (green) within rendered popliteal LNs (grey) of age matched Nav1.8$^{Cre/+}$; Rosa26$^{LSL\text{-}tdTomato/+}$ (1F) and Nav1.8-DTA (1G) animals. FIG. 1H. Quantification of the effect of DTA-based developmental ablation of Nav1.8 lineage neurons on sensory and sympathetic fiber density based on 6 control LNs vs. 6 mutant LNs from 3 pairs of mutant and littermate control animals from 3 litters. For sympathetic fibers, p=0.7542 (ns); for sensory fibers, p<0.001 (***).

FIG. 2A. 3D reconstruction of a representative confocal image of tdTomato$^+$ sensory fibers within popliteal LNs of Nav1.8$^{Cre/+}$; Rosa26$^{LSL\text{-}tdTomato/+}$; Prox1-EGFP animals color-coded by penetration depth, i.e., the shortest distance of a point within sensory fibers to the LN surface outlined based on the outermost layer of GFP$^+$ LECs. FIG. 2B. Quantification of the penetration depth of tdTomato$^+$ sensory fibers in popliteal LNs of Nav1.8$^{Cre/+}$; Rosa26$^{LSL\text{-}tdTomato/+}$; Prox1-EGFP animals as percentage of total intranodal sensory fibers found increasing distance away from the LN surface, (a total of 5 LNs from 3 mice). FIG. 2C. A representative confocal section of whole-mount popliteal LNs from Nav1.8$^{Cre/+}$; Rosa26$^{LSL\text{-}tdTomato/+}$; Prox1-EGFP animals, stained for tdTomato (white), LYVE-1 (red) and CD45 (blue) illustrating the spatial relationship between sensory fibers (arrowheads) and the cortex and the medulla of LNs. FIG. 2D. 3D reconstruction of a representative confocal image of whole-mount popliteal LNs from Nav1.8$^{Cre/+}$; Rosa26$^{LSL\text{-}tdTomato/LSL\text{-}tdTomato}$ animals, stained for tdTomato (red) and smooth muscle cell actin (SMA) (blue) highlighting the two main plexuses of sensory nerves within LNs, i.e., perivascular (arrow) and capsular/subcapsular (arrowhead) plexuses. FIG. 2E. 3D reconstruction of a representative confocal image of whole-mount popliteal LNs from Nav1.8$^{Cre}$; Rosa26$^{LSL\text{-}tdTomato/LSL\text{-}tdTomato}$ animals, stained for tdTomato (green), SMA (magenta), CD31 (cyan) demonstrating preferential association between arterioles and sensory fibers inside LNs. FIG. 2F. 3D reconstruction of a representative confocal image of whole-mount popliteal LNs from Nav1.8$^{Cre/+}$; Rosa26$^{LSL\text{-}tdTomato/+}$; Prox1-EGFP animals, stained for tdTomato, GFP, and collagen type 1 (blue) showing the capsular/subcapsular plexus of sensory nerves (white) in relation to the parenchymal sensory fibers (red).

FIG. 3A. Schematic of viral-based, long-term retrograde labeling from the LN, manual single-cell sorting and single-cell RNA-seq pipeline. FIG. 3B. A representative epifluorescence image of tdTomato$^+$ retrogradely-labeled iLN-innervating DRG neurons in a whole-mount spinal cord-DRG preparation without antibody amplification. FIGS. 3C and 3D. Maximum projection view of confocal images of whole-mount ipsilateral T13 (3C) and L1 (3D) DRGs from B stained for tdTomato. FIG. 3E. Single-cell gene expression of neuronal subtype-specific markers in LN-innervating and skin-innervating sensory neurons (Cacna1h, Necab2, Ntrk2, Nefh, Ldhb, Calb1, Cntnap2, Ntrk3, Pvalb, Spp1, Plxnc1, P2rx3, Sst, Tac1, Fam19a1, Calca, Ntrk1, Th, Trpv1, Trpa1, Scn10a). FIG. 3F. Representative confocal sections of whole-mount DRGs containing tdTomato$^+$ retrogradely-labeled iLN-innervating neurons from Rosa26$^{LSL\text{-}tdTomato/LSL\text{-}tdTomato}$ animals following intranodal injection of AAV-Cre, stained for tdTomato (red) and CGRP (green). Percentage of tdTomato$^+$ sensory neurons that express CGRP: 88.39% (mean) ±8.672% (SEM) based on a total of 44 tdTomato$^+$ neurons from 3 mice.

FIG. 4A. Principal Components 2 vs. 4 of Usoskin, Furlan et al. Sensory Neuron Atlas (Usoskin et al., 2015), represented by transparent circles, colored by previously-defined cell types: non-peptidergic nociceptors (NP, light blue); peptidergic nociceptors (PEP, orange); neurofilament containing (NF, red); and tyrosine hydroxylase containing (TH, purple). LN-innervating (yellow squares) and skin-innervating (blue squares) neurons are projected onto the PC space. FIG. 4B. Euclidean distance between each LN-innervating neuron (left) or skin-innervating neuron (right) and neurons in the Usoskin, Furlan et al. Sensory Neuron Atlas, separated by cell type. Dashed lines represent the 99% confidence interval for distance between single cells categorized as the same cell type within the Sensory Neuron Atlas. Box represents 25-75 quantiles, error bars span min-max range. FIG. 4C. Spearman correlation between the scRNA-seq profiles of LN- or skin-innervating neurons and neuronal subsets from the Usoskin et al. Sensory Neuron Atlas. Hierarchical clustering divides LN- and skin-innervating neurons into 4 major subtypes: Neuron Type 1 (PEP1-like, black); Neuron Type 2 (NP-like, tan); Neuron Type 3 (mixed PEP2/NF123, turquoise); and Neuron Type 4 (mixed PEP2/NF12345, dark blue). FIG. 4D. Distribution of Neuron Types 1~4 by innervation target (LN-innervating, n=52; skin-innervating, n=31). FIG. 4E. Differentially expressed genes (SCDE, Holm adjusted p-value <0.01) between each Neuron Type vs. all other Neuron Types. Top color bars denote Neuron Type (top bar) and innervation target (bottom bar, LN-innervating: yellow, skin-innervating: blue).

FIG. 5A. Heatmap of significantly differentially expressed (DE) genes (Holm corrected p-value <0.05, upregulated in LN-innervating: 101 genes; upregulated in skin-innervating: 156 genes). FIG. 5B. Volcano plot comparing fold-change differences and—log 10 (Holm corrected p-values) highlights significantly DE genes (using SCDE). Horizontal dashed line represents significance cutoff of corrected p-value (q-value)<0.05. FIG. 5C. Violin plots for selected genes significantly upregulated in LN-innervating neurons. FIG. 5D. Enriched gene ontologies represented by genes upregulated in LN-innervating neurons (yellow) or skin-innervating neurons (blue). Left y axis: number of DE genes represented by gene ontology term; right y axis: p-value (Fisher's Exact Test) for gene ontology enrichment. FIG. 5E. Identification of sensitive (true positive/(true positive+false negative)) and specific (true negative/(true negative +false positive)) markers for LN-innervating neurons compared to skin-innervating neurons and Usoskin, Furlan et al. Sensory Neuron Atlas. FIG. 5F. Quantification of Ptgir and Prokr2 expression in tdTomato$^+$ retrogradely-labeled LN- or skin-innervating neurons ("TdT+") as percentage of tdTomato$^+$ neurons that are Ptgir$^+$ or Prokr2$^+$ by RNAscope.

FIG. 6A. Schematic for iLN isolation, dissociation, enrichment for rare iLN cell types. FIG. 6B. Visualization of cell types recovered by scRNA-seq of 9,662 cells using t-distributed stochastic neighbor embedding (tSNE).

FIG. 6C. Dot plot representation of genes that distinguish major cell types within LNs (circle diameter reflects the percent of cells expressing a given marker within that cell type, circle color reflects relative expression abundance within that cell type; light grey: low, black: high) All highlighted genes are significantly upregulated in the corresponding cell type, with FDR-corrected p-value <0.001 by likelihood ratio test. FIG. 6D. Schematic of analysis of the expression of receptor-ligand pairs between LN-innervating neurons and potential interacting LN cell types.

FIG. 6E. Heatmap of ligand/receptors among LN-resident cells, for which cognate receptors/ligands are expressed by LN-innervating neurons. Colormap represents average gene expression within each cell type, scaled by each gene. Red: higher relative expression compared to other cell types, blue: lower. FIG. 6F. Barplot of Interaction Potential by cell type. Dashed lines represent 99% confidence interval over randomized permuted data. * p<0.05,  p<0.01, * p<0.001.

FIG. 7A. Schematic for ChR2-mediated activation of LN-innervating neurons and cell isolation protocol for scRNA-seq. FIG. 7B. tSNE visualization of cell types recovered by scRNA-seq of 10,364 cells from both light-stimulated and control LNs in ChR2+ and ChR2− animals. FIG. 7C-7F. Abundance of DE genes with FDR-adjusted p-value <0.05 and Cohen's effect size >0.2, separated by cell type: FIG. 7C. ChR2− (control) mice, upregulated by light stimulation; FIG. 7D. ChR2− (control) mice, downregulated by light stimulation; FIG. 7E. ChR2+ (experimental) mice, upregulated by light stimulation, omitting genes also induced in ChR2− (control) mice; and, FIG. 7F. ChR2+ (experimental) mice, downregulated by light stimulation, omitting genes also repressed in ChR2− (control) mice. FIG. 7G. Relationship between Interaction Potential and abundance of DE genes (Pearson's r: 0.52, p=0.03). FIG. 7H. Heatmap of DE genes between LEC 2 in light-stimulated vs. unstimulated LN in ChR2+ mice. FIG. 7I. Identity of top candidate neuron-interacting molecules in LEC 2 from steady-state LNs (FIG. 6). Blue genes indicate genes that are also DE with neuronal stimulation. J. Enriched gene ontologies among DE genes in LEC 2 following neuronal stimulation. Left y axis: number of DE genes represented by gene ontology term; right y axis: p-value (Fisher's Exact Test) for gene ontology enrichment. FIGS. 7K and 7L, Section view of a representative two-photon micrograph of physical contact between tdTomato$^+$ sensory fibers (red) and GFP$^+$ LECs (green) in the medulla (7K) and on the ceiling of SCS (7L) of whole-mount popliteal LNs from Nav1.8$^{Cre/+}$; Rosa26$^{LSL\text{-}tdTomato/+}$; Prox1-EGFP animals.

FIG. 8A. 3D reconstruction of a representative confocal image of whole-mount popliteal LNs from Bmx-CreERT2 Rosa26eYFP/+ mice. FIG. 8B. Experimental design. FIG. 8C Innervating LN DRG stained for sensory neurons. FIG. 8D. Innervating LN SG stained for sensory neurons. FIG. 8E. Innervating LN DRG stained for TH neurons. FIG. 8F. Innervating LN SG stained for TH neurons. FIG. 8G. Graphs showing percentage of TH+ neurons in DRG and SG.

FIG. 11A. Graphs comparing Prokr2 expression in skin and LN in four neuron types. FIG. 11B. Graphs comparing Ptgir expression in skin and LN in four neuron types. FIG. 11C. Heatmap showing Neuropeptides (Adcyap1, Adipoq, Adipq, Adm, Adm2, Agrp, Agt, Apln, Avp, Calca, Calcb, Cart, Cartpt, Cbln1, Cbln2, Cbln3, Cbln4, Cck, Cgc, Chga, Chgal, Chgb, Cort, Crh, Cst, Dbi, Edn1, Edn2, Edn3, Gal, Galp, Gast, Gcg, Ghrh, Ghrl, Gip, Gnrh1, Gnrh2, Grp, Hcrt, Iapp, Igf1, Igf2, Ins, Ins1, Kiss1, Kng1, Lep, Mln, Nampt, Nmb, Nms, Nmu, Npb, Npff, Nppa, Nppb, Nppc, Nps, Npvf, Npw, Npy, Nts, Nucb2, Nxph1, Nxph2, Nxph3, Nxph4, Oxt, Pbef1, Pdyn, Penk, Pmch, Pnoc, Pomc, Ppy, Prl, Prlh, Pthlh, Pyy, Retla, Retlb, Retlg, Retn, Retnla, Retnlb, Retnlg, Rfrp, Rln1, Rln2, Rln3, Scg2, Scg3, Scg5, Sct, Sgne1, Sst, Tac1, Tac2, Tac3, Trh, Ub15, Ucn, Ucn2, Ucn3, Uts2, Uts2d, Vgf, Vip). FIG. 11D. Heatmap showing Conductive Channels (Scn5a, Scn9a, Scn2a1, Scn4b, Scn8a, Scn1a, Scn1b, Scn10a, Scn11a, Scn2b, Kcnj4, Kcnj12, Tmem38a, Kcnh7, Kcnh8, Hcn4, Kcng4, Kcnq3, Kcns3, Kcnip3, Kcnb1, Kcnc4, Kcnd1, Kcnc1, Hcn2, Abcc8, Kcnd2, Tmem38b, Hcn1, Kcnq2, Kcna1, Kcna2, Kcnh2, Kcnc3, Kcns1, Kcnma1, Kcnip2, Kcnj11, Kcnmb4, Kcnh1, Kcnq5, Kcnv1, Kcnt2, Kcnu1, Kcnb2, Kcnip1, Kcna6, Hcn3, Kcnd3, Kcna4, Kcnip4, Kcnt1, Kcng2, Kcnh6, Kcnc2, Aqp1, Kcnk1, Kcnk13, Kcnk18, Kcnk4, Kcnk3, Kcnk2, Cacna1h, Cacna1d, Cacnb2, Cacna1a, Cacna1b, Cacnb3, Cacnb4, Cacna2d3, Cacng2, Cacna2d1, Cacna2d2, Cacna1c, Nrp1, Nefh, Nefm, Nefl, Ndel1, Ina). FIG. 11E. Heatmap showing Sensory Perception (Trpm7, Trpc4ap, Trpv2, Trpc1, Pkd2, Trpm4, Trpc6, Trpm3, Trpc3, Trpa1, Trpv1, Trpm2, Trpm8, Trpc7, P2ry2, P2rx6, P2rx5, P2ry14, P2ry1, P2rx4, P2rx2, P2rx3, Accn1, Accn2, Accn3, Prokr1, Hcrtr2, Ramp3, Mchr1, Celsr2, Crhr1, Kiss1r, Sstr1, Galr1, Prokr2, Hcrtr1, Npy2r, Celsr3, Crcp, Npy1r, Sstr2, Mrgpre, Mrgprb5, Mrgprd, Mrgprx1, Mrgpra3, Mrgprb4). FIG. 11F-11I. Images comparing Ptgir and Prokr2 expression in skin and LN.

FIG. 12A. tSNE analysis of LN. FIG. 12P. Heatmap showing differentially expressed genes between each cell type.

FIG. 13A. Experimental design for identifying interacting cells. FIG. 13B. Graph showing interaction potential. FIG. 13C. Graph showing interaction score. FIG. 13D. Graph showing interaction score. FIG. 13E. Graph showing interaction potential. FIG. 13F. Heatmap and graph showing the expression of the corresponding neuropeptide receptors among LN cell types. FIG. 13G. Graph showing interaction molecules in NES. FIG. 13H. Graph showing interaction molecules in BEC1.

FIG. 14A. Image from in vivo optogenetic stimulation of iLN-innervating sensory neurons, which were targeted for ChR2 expression along with other Nav1.8 lineage neurons in Nav1.8$^{Cre/+}$; Rosa26$^{ChR2\text{-}eYFP/+}$ (ChR2+) mice. FIG. 14B. Graphs showing genes downregulated and upregulated after light stimulation. FIG. 14C. Experimental design and heatmap showing differentially expressed genes in single cells. FIG. 14D. Heatmap showing correlation between cell types. FIG. 14E. Graph showing changes in LN cellularity upon light exposure. FIG. 14F. Graph showing changes in LN cellularity upon light exposure. FIG. 14G. Graphs showing abundance of differentially expressed genes with substantial effect sizes and interaction potential of cell types.

Figures 1A, 1B, 1C, 1D, 1E, 1F, 1G, 1H:
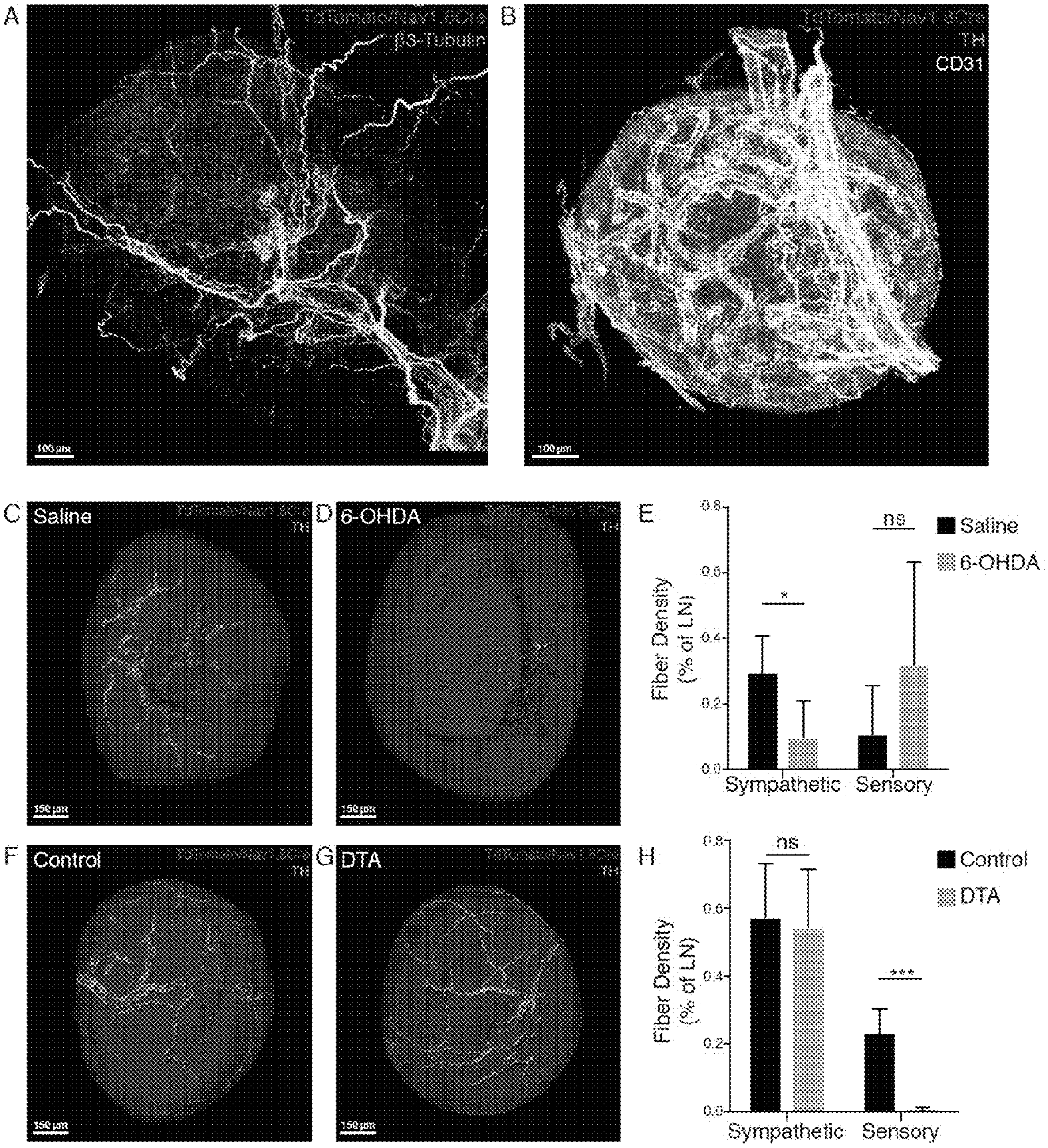
FIG. 1A-1H Dual innervation of peripheral LNs by sensory and sympathetic neurons.

The figures herein are for illustrative purposes only and are not necessarily drawn to scale.

DETAILED DESCRIPTION OF THE EXAMPLE EMBODIMENTS

General Definitions

Unless defined otherwise, technical and scientific terms used herein have the same meaning as commonly understood by one of ordinary skill in the art to which this disclosure pertains. Definitions of common terms and techniques in molecular biology may be found in Molecular Cloning: A Laboratory Manual, 2$^{nd}$ edition (1989) (Sambrook, Fritsch, and Maniatis); Molecular Cloning: A Laboratory Manual, 4$^{th}$ edition (2012) (Green and Sambrook); Current Protocols in Molecular Biology (1987) (F. M. Ausubel et al. eds.); the series Methods in Enzymology (Academic Press, Inc.): PCR 2: A Practical Approach (1995) (M. J. MacPherson, B. D. Hames, and G. R. Taylor eds.): Antibodies, A Laboratory Manual (1988) (Harlow and Lane, eds.): Antibodies A Laboratory Manual, 2$^{nd}$ edition 2013 (E. A. Greenfield ed.); Animal Cell Culture (1987) (R. I. Freshney, ed.); Benjamin Lewin, Genes IX, published by Jones and Bartlet, 2008 (ISBN 0763752223); Kendrew et al. (eds.), The Encyclopedia of Molecular Biology, published by Blackwell Science Ltd., 1994 (ISBN 0632021829); Robert A. Meyers (ed.), Molecular Biology and Biotechnology: a Comprehensive Desk Reference, published by VCH Publishers, Inc., 1995 (ISBN 9780471185710); Singleton et al., Dictionary of Microbiology and Molecular Biology 2nd ed., J. Wiley & Sons (New York, N.Y. 1994), March, Advanced Organic Chemistry Reactions, Mechanisms and Structure 4th ed., John Wiley & Sons (New York, N.Y. 1992); and Marten H. Hofker and Jan van Deursen, Transgenic Mouse Methods and Protocols, 2$^{nd}$ edition (2011).

As used herein, the singular forms "a", "an", and "the" include both singular and plural referents unless the context clearly dictates otherwise.

The term "optional" or "optionally" means that the subsequent described event, circumstance or substituent may or may not occur, and that the description includes instances where the event or circumstance occurs and instances where it does not.

The recitation of numerical ranges by endpoints includes all numbers and fractions subsumed within the respective ranges, as well as the recited endpoints.

The terms "about" or "approximately" as used herein when referring to a measurable value such as a parameter, an amount, a temporal duration, and the like, are meant to encompass variations of and from the specified value, such as variations of +/−10% or less, +/−5% or less, +/−1% or less, and +/−0.1% or less of and from the specified value, insofar such variations are appropriate to perform in the disclosed invention. It is to be understood that the value to which the modifier "about" or "approximately" refers is itself also specifically, and preferably, disclosed.

As used herein, a "biological sample" may contain whole cells and/or live cells and/or cell debris. The biological sample may contain (or be derived from) a "bodily fluid". The present invention encompasses embodiments wherein the bodily fluid is selected from amniotic fluid, aqueous humour, vitreous humour, bile, blood serum, breast milk, cerebrospinal fluid, cerumen (earwax), chyle, chyme, endolymph, perilymph, exudates, feces, female ejaculate, gastric acid, gastric juice, lymph, mucus (including nasal drainage and phlegm), pericardial fluid, peritoneal fluid, pleural fluid, pus, rheum, saliva, sebum (skin oil), semen, sputum, synovial fluid, sweat, tears, urine, vaginal secretion, vomit and mixtures of one or more thereof. Biological samples include cell cultures, bodily fluids, cell cultures from bodily fluids. Bodily fluids may be obtained from a mammal organism, for example by puncture, or other collecting or sampling procedures.

The terms "subject," "individual," and "patient" are used interchangeably herein to refer to a vertebrate, preferably a mammal, more preferably a human. Mammals include, but are not limited to, murines, simians, humans, farm animals, sport animals, and pets. Tissues, cells and their progeny of a biological entity obtained in vivo or cultured in vitro are also encompassed.

Various embodiments are described hereinafter. It should be noted that the specific embodiments are not intended as an exhaustive description or as a limitation to the broader aspects discussed herein. One aspect described in conjunction with a particular embodiment is not necessarily limited to that embodiment and can be practiced with any other embodiment(s). Reference throughout this specification to "one embodiment", "an embodiment," "an example embodiment," means that a particular feature, structure or characteristic described in connection with the embodiment is included in at least one embodiment of the present invention. Thus, appearances of the phrases "in one embodiment," "in an embodiment," or "an example embodiment" in various places throughout this specification are not necessarily all referring to the same embodiment, but may. Furthermore, the particular features, structures or characteristics may be combined in any suitable manner, as would be apparent to a person skilled in the art from this disclosure, in one or more embodiments. Furthermore, while some embodiments described herein include some but not other features included in other embodiments, combinations of features of different embodiments are meant to be within the scope of the invention. For example, in the appended claims, any of the claimed embodiments can be used in any combination.

All publications, published patent documents, and patent applications cited herein are hereby incorporated by reference to the same extent as though each individual publication, published patent document, or patent application was specifically and individually indicated as being incorporated by reference.

Overview

Embodiments disclosed herein provide methods, compositions, and combination for modulating immune response and homeostasis in lymph nodes (LNs) by modulating LN-innervating sensory neurons. Applicants used a combination of high-resolution imaging, retrograde viral tracing, optogenetics, and single-cell transcriptomics (scRNA-seq) surprisingly discovered a sensory neuro-immune circuit that is preferentially located in the outermost cortex of skin-draining LNs. Transcriptomic profiling revealed that most sensory neurons in dermal LNs sensory neurons that innervate dermal LNs are composed of at least four discrete subsets with an overabundance of peptidergic nociceptors, an innervation pattern that is markedly distinct from that in the surrounding skin. Applicants further used single-cell RNA-seq to generate an atlas of all murine LN cells and, based on receptor-ligand expression patterns, nominated and experimentally confirmed using optogenetic approach the target populations among stromal and immune cells. Acute neuronal activation triggered rapid transcriptional changes preferentially in endothelium and other nodal stroma cells, as well as in several innate leukocyte populations. Thus, LNs are monitored by a unique population of sensory neurons that possess profound immunomodulatory potential.

In some embodiments, methods for discovery of LN-innervating sensory neurons are disclosed. These LN-innervating sensory neurons are structurally, anatomically, and molecularly characterized. At the molecular level, the LN-innervating sensory neurons are characterized by the expression of one or more than one of signature genes. By administrating one or more therapeutic agents that target the signature genes, one can modulate the immune response and homeostasis in LNs and/or the whole immune system in a subject. Therefore, the present invention provides a surprising avenue for immunomodulation.

In some embodiments, methods for identification of target cells in LN for LN-innervating sensory neurons are disclosed. These target cells interact with and are modulated by LN-innervating sensory neurons.

In some embodiments, signature genes for these target cells are disclosed. By administrating one or more therapeutic agents that target the signature genes, one can modulate the immune response and homeostasis in LNs and/or the whole immune system in a subject.

In some embodiments, methods of modulating immune response and homeostasis by activating or inhibiting the activities and/or functions of LN-innervating sensory neurons are disclosed. The activation of innervating sensory neurons can be achieved through chemical, physical, and/or other approaches.

In some embodiments, isolated cells are provided. These isolated cells including LN-innervating peptidergic nociceptor sensory neuron cell and LN stroma cells that are identified as the target cells of LN-innervating sensory neurons.

I. Methods and Uses for Modulating Lymph Node-Innervating Sensory Neurons

In some embodiments, provided are methods for using and uses of the compositions containing therapeutic agents, in which therapeutic agents are capable of modulating the levels of genes and/or gene expression products that in turn modulating the immune response and homeostasis of LNs.

As used herein, immune homeostasis is defined as an equilibrium which the immune system reaches. In healthy status, this equilibrium results in the effective discrimination of potentially harmful foreign entities from self. Conversely, dysregulated homeostasis can have severe consequences including the occurrence of infectious disease, autoimmune diseases, and malignant diseases etc.

In some embodiments, the therapeutic agent can be a cell, a protein, an anti-sense RNA, a short-hairpin RNA, a lentiviral-carried nucleic acid molecule, a CRISPR-CAS system, a DNA, a small molecule chemical compound, or any combination thereof. For example, using anti-sense RNA for modulating gene expression activities is a well-established technique [Westbrook and Lucks, Nucleic Acids Research 2017, 45:5614-5624]. Similarly, CRISPR-CAS system that specifically targets the expression of the genes, thus reducing or deleting the expression of the targeted genes, has been well established [Hsu et al., Cell, 2014, 157:1262-1278]. In addition, small chemicals are known be able to modulate gene expression activity [Iskar et al., 2010, PLOS Comput. Biol. 6: e1000925]. A person of ordinary skill in the art can perform such standard molecular technologies to modulate the expression of genes in a cell, in a tissue, or in a subject.

In some embodiments, the therapeutic agent described herein can be used for modulating the signature genes of LN-innervating sensory neurons disclosed in the present invention.

In some embodiments, signature genes or signature gene expression products are disclosed. As used herein, a "signature" may encompass any gene or genes, protein or proteins, or epigenetic element(s) whose expression profile or whose occurrence is associated with a specific cell type, subtype, or cell state of a specific cell type or subtype within a population of cells (e.g., LN-innervating neurons). For ease of discussion, when discussing gene expression, any gene or genes, protein or proteins, or epigenetic element(s) may be substituted. Reference to a gene name throughout the specification encompasses the human gene, mouse gene and all other orthologues as known in the art in other organisms.

As used herein, the terms "signature", "expression profile", or "expression program" may be used interchangeably. It is to be understood that also when referring to proteins (e.g. differentially expressed proteins), such may fall within the definition of "gene" signature.

In some embodiments, levels of expression or activity or prevalence may be compared between different cells in order to characterize or identify for instance signatures specific for cell (sub)populations. Increased or decreased expression or activity of signature genes may be compared between different cells in order to characterize or identify for instance specific cell (sub)populations. Generally, where a decrease of a gene or gene expression product is referred to, this means that the gene or gene expression product is repressed, downregulated, knocked-out, inhibited, antagonized, deactivated or other terms common in the art. Similarly, where an increase of a gene or gene expression product is referred to, this means that the gene or gene expression product is enhanced, upregulated, knocked-in, agonized, activated or other terms common in the art.

In some embodiments, the signature may comprise or consist of one or more genes, proteins and/or epigenetic elements, such as for instance 1, 2, 3, 4, 5, 6, 7, 8, 9, 10 or more. In some embodiments, the signature may comprise or consist of two or more genes, proteins and/or epigenetic elements, such as for instance 2, 3, 4, 5, 6, 7, 8, 9, 10 or more. In some embodiments, the signature may comprise or consist of three or more genes, proteins and/or epigenetic elements, such as for instance 3, 4, 5, 6, 7, 8, 9, 10 or more. In some embodiments, the signature may comprise or consist of four or more genes, proteins and/or epigenetic elements, such as for instance 4, 5, 6, 7, 8, 9, 10 or more. In some embodiments, the signature may comprise or consist of five or more genes, proteins and/or epigenetic elements, such as for instance 5, 6, 7, 8, 9, 10 or more. In some embodiments, the signature may comprise or consist of six or more genes, proteins and/or epigenetic elements, such as for instance 6, 7, 8, 9, 10 or more. In some embodiments, the signature may comprise or consist of seven or more genes, proteins and/or epigenetic elements, such as for instance 7, 8, 9, 10 or more. In some embodiments, the signature may comprise or consist of eight or more genes, proteins and/or epigenetic elements, such as for instance 8, 9, 10 or more. In some embodiments, the signature may comprise or consist of nine or more genes, proteins and/or epigenetic elements, such as for instance 9, 10 or more. In some embodiments, the signature may comprise or consist of ten or more genes, proteins and/or epigenetic elements, such as for instance 10, 11, 12, 13, 14, 15, or more. It is to be understood that a signature according to the invention may for instance also include genes or proteins as well as epigenetic elements combined.

In some embodiments, the detection of a signature in single cells may be used to identify and quantitate for instance specific cell (sub)populations. A signature may include a gene or genes, protein or proteins, or epigenetic element(s) whose expression or occurrence is specific to a cell (sub)population, such that expression or occurrence is exclusive to the cell (sub)population. A gene signature as used herein, may thus refer to any set of up- and down-regulated genes that are representative of a cell type or subtype. A gene signature as used herein, may also refer to any set of up- and down-regulated genes between different cells or cell (sub)populations derived from a gene expression profile. For example, a gene signature may comprise a list of genes differentially expressed in a distinction of interest.

In some embodiments, the modulation of levels of gene expression and/or gene product expression can be either upregulation or downregulation of the levels of gene expression and/or gene product expression.

In some embodiments, the signature genes for LN-innervating sensory neurons are disclosed as one or more of the genes in Table 1.

In some embodiments, the expression of one or more of the genes in Table 1 in LN-innervating sensory neurons is modulated by administering one or more therapeutic agents defined in the present invention. As a result, the activity and/or function of LN-innervating sensory neurons are modulated, thus leading to the modulation of activity and/or function of downstream target cells in LNs.

In some embodiments, the signature genes of LN-innervating sensory neurons comprise Trpc4, Trpm8, Kchnh5, Ache, Tbxa2r, Il33, Ptgir, Cd1d, Ptgir, Prokr2, Calca, Clacb, Tac1, Adcyap1, Gal, Ramp1, Calcrl, Tacr1, Adcyap1r1, Galr2, Galr1, or any combination thereof.

In some embodiments, the expression of one or more of Trpc4, Trpm8, Kchnh5, Ache, Thxa2r, Il33, Ptgir, Cd1d, Ptgir, Prokr2, Calca, Clacb, Tac1, Adcyap1, Gal, Ramp1, Calcrl, Tacr1, Adcyap1r1, Galr2, and Galr1 in LN-innervating sensory neurons is modulated by administering one or more therapeutic agents defined in the present invention. As a result, the activity and/or function of LN-innervating sensory neurons are modulated, thus leading to the modulation of activity and/or function of downstream target cells in LNs.

In some embodiments, the levels of the signature genes or their corresponding gene expression products are reduced by the therapeutic agent or agents.

In some embodiments, the levels of the signature genes or their corresponding gene expression products are increased by the therapeutic agent or agents.

In some embodiments, the LN-innervating sensory neurons have a characteristic of primary anatomic location at the subcapsular region of an LN. In some aspects, the LN-innervating sensory neurons can be located in any location within an LN.

In some embodiments, the LN-innervating sensory neurons can be classified into four types. In some aspects, the type I and/or type III are the primary types of the LN-innervating sensory neurons.

In some embodiments, LN-innervating sensory neurons are variable in soma size. The diversity of cell sizes matches the range of diameters observed in CGRP+ neurons, which are known to include neurons of different sizes.

In some embodiments, the primary type of LN-innervating sensory neurons is peptidergic nociceptor. Peptidergic nociceptor is characterized by the expression of substance P (Tac1) and neurofilament heavy chain (NFH) (Nefh) within Calca+ LN-innervating sensory neurons, which allowing the identification of two LN-innervating peptidergic nociceptor subclasses. In some embodiments, there are 50% of LN-innervating sensory neurons are nociceptors. In some embodiments, there are 60% of LN-innervating sensory neurons are nociceptors. In some embodiments, there are 70% of LN-innervating sensory neurons are nociceptors. In some embodiments, there are 80% or more than 80% of LN-innervating sensory neurons are nociceptors. In some embodiments, there are 90% or more than 90% of LN-innervating sensory neurons are nociceptors.

In some embodiments, the expression of Tac1 and/or Nefh is modulated by administering one or more therapeutic agents defined in the present invention. As a result, the activity and/or function of LN-innervating sensory neurons are modulated, thus leading to the modulation of activity and/or function of downstream target cells in LNs.

In some aspects, the LN-innervating sensory neurons are characterized by the enrichment of Prokr2 and/or Ptgir expression.

In some embodiments, the expression of Prokr2 and/or Ptgir is modulated by administering one or more therapeutic agents defined in the present invention. As a result, the activity and/or function of LN-innervating sensory neurons are modulated, thus leading to the modulation of activity and/or function of downstream target cells in LNs.

In some embodiments, the LN-innervating sensory neurons uniquely expressed genes with inflammatory and/or immune-cell type interacting functions comprising Tbxa2r, Il33, Ptgir, and Cd1d.

In some embodiments, the expression of any one or more than one of Thxa2r, Il33, Ptgir, and Cd1d is modulated by administering one or more therapeutic agents defined in the present invention. As a result, the activity and/or function of LN-innervating sensory neurons are modulated, thus leading to the modulation of activity and/or function of downstream target cells in LNs.

In some embodiments, the modulation of activities and/or functions of LN-innervating sensory neurons as described above leads to modulation of immune response and/or immune homeostasis in LN or a system or a subject.

II. Methods and Uses for Modulating Target Cells of Lymph Node-Innervating Sensory Neurons in Lymph Nodes As used herein, an immune response generally contains innate and adaptive immunity. Innate immunity occurs immediately, when circulating innate cells recognize a problem. Adaptive immunity occurs later, as it relies on the coordination and expansion of specific adaptive immune cells. Immune memory follows the adaptive response, when mature adaptive cells, highly specific to the original pathogen, are retained for later use. Innate immune cells express genetically encoded receptors, called Toll-like receptors (TLRs), which recognize general danger- or pathogen-associated patterns. Collectively, these receptors can broadly recognize viruses, bacteria, fungi, and even non-infectious problems.

In some embodiments, an innate immune response in LNs can be achieved by modulating immune cells comprising neutrophils, eosinophils, basophils, mast cells, monocytes, dendritic cells, and macrophages. Their main feature is the ability to respond quickly and broadly when a problem arises, typically leading to inflammation. Innate immune cells also are important for activating adaptive immunity. Innate cells are critical for host defense, and disorders in innate cell function may cause chronic susceptibility to infection.

In some embodiments, an adaptive immune response in LNs can be achieved by modulating immune cells comprising B lymphocytes (or B cells), T lymphocytes (or T cells), and natural killer cells (NK cells). B cells and T cells bear unique receptors, B-cell receptors (BCRs) and T-cell receptors (TCRs), respectively, that recognize specific signals rather than general patterns. Each receptor recognizes an antigen, which is simply any molecule that may bind to a BCR or TCR. Antigens are derived from a variety of sources including pathogens, host cells, and allergens. Antigens are typically processed by innate immune cells and presented to adaptive cells in LNs. If a B or T cell has a receptor that recognizes an antigen from a pathogen and also receives cues from innate cells that something is wrong, the B or T cell will activate, divide, and disperse to address the problem. B cells make antibodies, which neutralize pathogens, rendering them harmless. T cells carry out multiple functions, including killing infected cells and activating or recruiting other immune cells. The adaptive response has a system of checks and balances to prevent unnecessary activation that could cause damage to the host. If a B or T cell is autoreactive, meaning its receptor recognizes antigens from the body's own cells, the cell will be deleted. Also, if a B or T cell does not receive signals from innate cells, it will not be optimally activated. Immune memory is a feature of the adaptive immune response. After B or T cells are activated, they expand rapidly.

As used herein, an immune response in a LN may include T lymphocyte response, B lymphocyte response, antigen presenting cell (APC) response, and other immune cell response when the system or a subject is challenged with an external or internal pathogens and/or other types of stimuli. In LNs, at the presence of immunologic challenges, the categories of immune cells are activated, and the structural cells including lymphatic endothelial cells (LECs) also change (Lucas & Tamburini, 2019, Front. Immunol. 10:36). Generation of local adaptive immune responses against immunogenic substances and pathogens critically depends on bidirectional flow of information between peripheral tissues—the sites of immune challenge—and the draining LNs, where antigen acquisition/presentation and subsequent lymphocyte differentiation and maturation are orchestrated. To ensure optimal immune responses without detrimental immunopathology, both locations require continuous monitoring and modulation by a multitude of immunoregulatory circuits involving both hematopoietic and stromal cells.

As used herein, immunomodulation is defined as change in immunity locally in LNs and/or the body's immune system, caused by agents that activate or suppress its function.

In some embodiments, a single-cell transcriptomic atlas of mouse LN is disclosed. The single-cell transcriptomic atlas can be used for identifying immune cell types in LN, for monitoring immune response in LN or a subject, and for indicating homeostasis of LNs.

In some embodiments, signature genes for target cells of LN-innervating sensory neurons are disclosed as one or any combination of the genes in Table 2.

In some embodiments, one type of the target cells for LN-innervating sensory neurons is disclosed as dendritic cell-like cells. These cells are characterized by high levels of gene expression or gene product of Aire and the expression of one or more of genes or gene products selected from the group consisting of Ryr3, Myo5b, Scn3a, and Nrgn. As such, this type of cells is termed as $Aire^+$ dendritic cell-like cells in the present invention.

In some embodiments, therapeutic modulation of immune response and homeostasis in a LN comprises agent or agents capable of modulating genes comprising Ryr3, Myo5b, Scn3a, and Nrgn. These agent or agents can be a cell, a protein, an anti-sense RNA, a short-hairpin RNA, a lentiviral-carried nucleic acid molecule, a CRISPR-CAS system, a DNA, a small molecule chemical compound, or any combination thereof. For example, using anti-sense RNA for modulating gene expression activities is a well-established technique [Westbrook and Lucks, Nucleic Acids Research 2017, 45:5614-5624]. Similarly, CRISPR-Cas system that specifically targets the expression of the genes, thus reducing or deleting the expression of the targeted genes, has been well established [Hsu et al., Cell, 2014, 157:1262-1278]. In addition, small chemicals are known be able to modulate gene expression activity [Iskar et al., 2010, PLOS Comput. Biol. 6: e1000925]. Any of these agents or any combination thereof can achieve immunomodulatory effect through modulating the signature genes expressed in Arie$^+$ dendritic cell-like cells in LNs as target cells for LN-innervating sensory neurons.

In some embodiments, one type of target cells for LN-innervating sensory neurons is disclosed as neutrophils that are characterized by high levels of expression of genes coding for components of neutrophil granules and effector molecules comprising Elane, Prtn3, Ctsg, Ngp, Ltf, Camp, and Mpo. As such, this type of cells is termed as Neutrophil-1 cells in the present invention.

In some embodiments, therapeutic modulation of immune response and homeostasis in a LN comprises agent or agents capable of modulating genes comprising Elane, Prtn3, Ctsg, Ngp, Ltf, Camp, and Mpo. These agent or agents can be a cell, a protein, an anti-sense RNA, a short-hairpin RNA, a lentiviral-carried nucleic acid molecule, a CRISPR-CAS system, a DNA, a small molecule chemical compound, or any combination thereof. For example, using anti-sense RNA for modulating gene expression activities is a well-established technique [Westbrook and Lucks, Nucleic Acids Research 2017, 45:5614-5624]. Similarly, CRISPR-Cas system that specifically targets the expression of the genes, thus reducing or deleting the expression of the targeted genes, has been well established [Hsu et al., Cell, 2014, 157:1262-1278]. In addition, small chemicals are known be able to modulate gene expression activity [Iskar et al., 2010, PLOS Comput. Biol. 6: e1000925]. Any of these agents or any combination thereof can achieve immunomodulatory effect through modulating the signature genes expressed in Neutrophil-1 cells in LNs as target cells for LN-innervating sensory neurons.

In some embodiments, one type of target cells for LN-innervating sensory neurons is disclosed as neutrophils that are characterized by high levels of expression of genes coding for pro-inflammatory molecules comprising Ccl4, Sell, Cxcr2, Cxcl2, Ccl6, Il1b, and Csf3r; and absent of low levels of expression of genes coding for effector molecules comprising Elane, Prtn3, Ctsg, Ngp, Ltf, Camp, and Mpo. As such, this type of cells is termed as Neutrophil-2 cells in the present invention.

In some embodiments, therapeutic modulation of immune response and homeostasis in a LN comprises agent or agents capable of modulating genes comprising Ccl4, Sell, Cxcr2, Cxcl2, Ccl6, Il1b, and Csf3r. These agent or agents can be a cell, a protein, an anti-sense RNA, a short-hairpin RNA, a lentiviral-carried nucleic acid molecule, a CRISPR-CAS system, a DNA, a small molecule chemical compound, or any combination thereof. For example, using anti-sense RNA for modulating gene expression activities is a well-established technique [Westbrook and Lucks, Nucleic Acids Research 2017, 45:5614-5624]. Similarly, CRISPR-Cas system that specifically targets the expression of the genes, thus reducing or deleting the expression of the targeted genes, has been well established [Hsu et al., Cell, 2014, 157:1262-1278]. In addition, small chemicals are known be able to modulate gene expression activity [Iskar et al., 2010, PLOS Comput. Biol. 6: e1000925]. Any of these agents or any combination thereof can achieve immunomodulatory effect through modulating the signature genes expressed in Neutrophil-2 cells in LNs as target cells for LN-innervating sensory neurons.

In some embodiments, one type of target cells for LN-innervating sensory neurons is disclosed as non-venular blood endothelial cells that are characterized by the expression of one or more genes or gene products comprising Lama5, Itga5, Hspg2, Flt1, Notch4, Fzd5, Sema3f, Sema7a, Nrp1, Plxnd1, Efnb1, Epha4, Selp, and Cxcl1. As such, this type of cells is termed as BEC1 cells in the present invention.

In some embodiments, therapeutic modulation of immune response and homeostasis in a LN comprises agent or agents capable of modulating genes comprising Lama5, Itga5, Hspg2, Flt1, Notch4, Fzd5, Sema3f, Sema7a, Nrp1, Plxnd1, Efnb1, Epha4, Selp, and Cxcl1. These agent or agents can be a cell, a protein, an anti-sense RNA, a short-hairpin RNA, a lentiviral-carried nucleic acid molecule, a CRISPR-CAS system, a DNA, a small molecule chemical compound, or any combination thereof. For example, using anti-sense RNA for modulating gene expression activities is a well-established technique [Westbrook and Lucks, Nucleic Acids Research 2017, 45:5614-5624]. Similarly, CRISPR-Cas system that specifically targets the expression of the genes, thus reducing or deleting the expression of the targeted genes, has been well established [Hsu et al., Cell, 2014, 157:1262-1278]. In addition, small chemicals are known be able to modulate gene expression activity [Iskar et al., 2010, PLOS Comput. Biol. 6: e1000925]. Any of these agents or any combination thereof can achieve immunomodulatory effect through modulating the signature genes expressed in BEC1 cells in LNs as target cells for LN-innervating sensory neurons.

In some embodiments, one type of target cells for LN-innervating sensory neurons is disclosed as lymphatic endothelial cells that are characterized by the expression of Madcam1. As such, this type of cells is termed as LEC1 cells in the present invention.

In some embodiments, therapeutic modulation of immune response and homeostasis in a LN comprises agent or agents capable of modulating gene expression of Madcam1. These agent or agents can be a cell, a protein, an anti-sense RNA, a short-hairpin RNA, a lentiviral-carried nucleic acid molecule, a CRISPR-CAS system, a DNA, a small molecule chemical compound, or any combination thereof. For example, using anti-sense RNA for modulating gene expression activities is a well-established technique [Westbrook and Lucks, Nucleic Acids Research 2017, 45:5614-5624]. Similarly, CRISPR-Cas system that specifically targets the expression of the genes, thus reducing or deleting the expression of the targeted genes, has been well established [Hsu et al., Cell, 2014, 157:1262-1278]. In addition, small chemicals are known be able to modulate gene expression activity [Iskar et al., 2010, PLOS Comput. Biol. 6: e1000925]. Any of these agents or any combination thereof can achieve immunomodulatory effect through modulating the signature genes expressed in LEC1 cells in LNs as target cells for LN-innervating sensory neurons.

In some embodiment, one type of target cells for LN-innervating sensory neurons is disclosed as lymphatic endothelial cell characterized by the expression of genes or gene products comprising Fbln2, Aqp1, Fbln5, Tnc, Reln, Tnc, Fbn1, Nid1, Agrn Nrxn2, Nlgn2, Efnb2, Nrp2, Robo1, Reln, F8, Itgb3, and Nrp2, Gata6, Ets2, Irf7, Nfatc1, Reln, Nrp2, Ephb4, Nfatc1, Lye1, Dlg1, and Glu1. As such, this type of cells is termed as LEC2 cells in the present invention.

In some embodiments, therapeutic modulation of immune response and homeostasis in a LN comprises agent or agents capable of modulating the expression of genes comprising Fbln2, Aqp1, Fbln5, Tnc, Reln, Tnc, Fbn1, Nid1, Agrn Nrxn2, Nlgn2, Efnb2, Nrp2, Robo1, Reln, F8, Itgb3, and Nrp2, Gata6, Ets2, Irf7, Nfatc1, Reln, Nrp2, Ephb4, Nfatc1, Lye1, Dlg1, and Glu1. These agent or agents can be a cell, a protein, an anti-sense RNA, a short-hairpin RNA, a lentiviral-carried nucleic acid molecule, a CRISPR-CAS system, a DNA, a small molecule chemical compound, or any combination thereof. For example, using anti-sense RNA for modulating gene expression activities is a well-established technique [Westbrook and Lucks, Nucleic Acids Research 2017, 45:5614-5624]. Similarly, CRISPR-Cas system that specifically targets the expression of the genes, thus reducing or deleting the expression of the targeted genes, has been well established [Hsu et al., Cell, 2014, 157:1262-1278]. In addition, small chemicals are known be able to modulate gene expression activity [Iskar et al., 2010, PLOS Comput. Biol. 6: e1000925]. Any of these agents or any combination thereof can achieve immunomodulatory effect through modulating the signature genes expressed in LEC2 cells in LNs as target cells for LN-innervating sensory neurons.

III. Isolated Cells

In some embodiments, an isolated cell or isolated cells are provided herein. The molecular characteristics of these isolated cells are also provided herein. Through modulating the expression of one or more of identified genes of these isolated cells, one can use these isolated cells for diagnosis and treatment of immuno- and/or neuronal diseases or other types of diseases. One can also use these isolated cells for discovery, screening, evaluation, validation of therapeutic targets for treating immuno- and/or neuronal diseases or other types of diseases.

In some embodiments, an isolated peptidergic nociceptor sensory neuron cell is disclosed. This isolated cell is characterized by the expression of one or more genes or gene products selected from one or more gene or gene products of Table lor from group of Trpc4, Trpm8, Kchnh5, and Ache, from group of Thxa2r, Il33, Ptgir, and Cd1d, or from group of Ptgir and Prokr2. In some aspects, this isolated peptidergic nociceptor sensory neuron cell can also be characterized by the expression of other genes or gene products. In some aspects, this isolated cell can be cultured in vitro to be used for drug discovery, screening, evaluation, validation of therapeutic targets for treating immuno- and/or neuronal diseases or other types of diseases. In some aspects, this isolated peptidergic nociceptor sensory neuron cell can be used as a career of genetic and epigenetic modification to express desired gene or genes for diagnosis or treatment use. In some aspects, this isolated peptidergic nociceptor sensory neuron cell can be used directly or indirectly for treatment of immuno- and/or neuronal diseases or other types of diseases.

In some embodiments, an isolated dendritic cell-like cell (Aire+) is disclosed. This isolated cell is characterized by high levels of gene expression or gene product of Aire and the expression of one or more of genes or gene products selected from the group consisting of Ryr3, Myo5b, Scn3a, and Nrgn. In some aspects, this isolated dendritic cell-like cell can also be characterized by the expression of other genes or gene products. In some aspects, this isolated cell can be cultured in vitro to be used for drug discovery, screening, evaluation, validation of therapeutic targets for treating immuno- and/or neuronal diseases or other types of diseases. In some aspects, this isolated dendritic cell-like cell can be used as a career of genetic and epigenetic modification to express desired gene or genes for diagnosis or treatment use. In some aspects, this isolated dendritic cell-like cell can be used directly or indirectly for treatment of immuno- and/or neuronal diseases or other types of diseases.

In some embodiments, an isolated neutrophil cell (NEUTROPHIL-1) is disclosed. This isolated cell is characterized by high levels of expression of genes coding for components of neutrophil granules and effector molecules comprising Elane, Prtn3, Ctsg, Ngp, Ltf, Camp, and Mpo. In some aspects, this isolated neutrophil cell can also be characterized by the expression of other genes or gene products. In some aspects, this isolated cell can be cultured in vitro to be used for drug discovery, screening, evaluation, validation of therapeutic targets for treating immuno- and/or neuronal diseases or other types of diseases. In some aspects, this isolated neutrophil cell can be used as a career of genetic and epigenetic modification to express desired gene or genes for diagnosis or treatment use. In some aspects, this isolated neutrophil cell can be used directly or indirectly for treatment of immuno- and/or neuronal diseases or other types of diseases.

In some embodiments, an isolated neutrophil cell (NEUTROPHIL-2) is disclosed. This isolated cell is characterized by high levels of expression of genes coding for pro-inflammatory molecules comprising Ccl4, Sell, Cxcr2, Cxcl2, Ccl6, Il1b, and Csf3r but absent of low levels of expression of genes coding for effector molecules comprising Elane, Prtn3, Ctsg, Ngp, Ltf, Camp, and Mpo. In some aspects, this isolated neutrophil cell can also be characterized by the expression of other genes or gene products. In some aspects, this isolated cell can be cultured in vitro to be used for drug discovery, screening, evaluation, validation of therapeutic targets for treating immuno- and/or neuronal diseases or other types of diseases. In some aspects, this isolated neutrophil cell can be used as a career of genetic and epigenetic modification to express desired gene or genes for diagnosis or treatment use. In some aspects, this isolated neutrophil cell can be used directly or indirectly for treatment of immuno- and/or neuronal diseases or other types of diseases.

In some embodiments, an isolated non-venular blood endothelial cell (BEC1) is disclosed. This isolated cell is characterized by the expression of one or more genes or gene products selected from group of Lama5, Itga5, Hspg2, or from group of Flt1, Notch4, Fzd5, or from group of Sema3f, Sema7a, Nrp1, Plxnd1, Efnb1, Epha4, or from group of Selp and Cxcl1. In some aspects, this isolated non-venular blood endothelial cell can also be characterized by the expression of other genes or gene products. In some aspects, this isolated cell can be cultured in vitro to be used for drug discovery, screening, evaluation, validation of therapeutic targets for treating immuno- and/or neuronal diseases or other types of diseases. In some aspects, this isolated non-venular blood endothelial cell can be used as a career of genetic and epigenetic modification to express desired gene or genes for diagnosis or treatment use. In some aspects, this isolated non-venular blood endothelial cell can be used directly or indirectly for treatment of immuno- and/or neuronal diseases or other types of diseases.

In some embodiments, an isolated lymphatic endothelial cell (LEC1) is disclosed. This isolated cell is characterized by the expression of gene or gene product of Madcam1. In some aspects, this isolated lymphatic endothelial cell can also be characterized by the expression of other genes or gene products. In some aspects, this isolated cell can be cultured in vitro to be used for drug discovery, screening, evaluation, validation of therapeutic targets for treating immuno- and/or neuronal diseases or other types of diseases. In some aspects, this isolated lymphatic endothelial cell can be used as a career of genetic and epigenetic modification to express desired gene or genes for diagnosis or treatment use. In some aspects, this isolated lymphatic endothelial cell can be used directly or indirectly for treatment of immuno- and/or neuronal diseases or other types of diseases.

In some embodiments, an isolated lymphatic endothelial cell (LEC2) is disclosed. This isolated cell is characterized by the expression of one or more genes or gene products selected from group of Fbln2, Aqp1, Fbln5, Tnc, and Reln, or from group of Tnc, Fbn1, and Nid1, or from group of Agrn Nrxn2, and Nlgn2, or from group of Efnb2, Nrp2, and Robo1, or from group of Reln, F8, Itgb3, and Nrp2, or from group of Gata6, Ets2, Irf7, and Nfatc1, or from group of Reln, Nrp2, Ephb4, Nfatc1, Lye1, Dlg1, and Glu1. In some aspects, this isolated lymphatic endothelial cell can also be characterized by the expression of other genes or gene products. In some aspects, this isolated cell can be cultured in vitro to be used for drug discovery, screening, evaluation, validation of therapeutic targets for treating immuno- and/or neuronal diseases or other types of diseases. In some aspects, this isolated lymphatic endothelial cell can be used as a career of genetic and epigenetic modification to express desired gene or genes for diagnosis or treatment use. In some aspects, this isolated lymphatic endothelial cell can be used directly or indirectly for treatment of immuno- and/or neuronal diseases or other types of diseases.

Therapeutic Agents

In certain embodiments, the present invention provides for one or more therapeutic agents targeting identified cell types and genes expressed thereof. In certain embodiments, the present invention provides for one or more therapeutic agents against combinations of targets identified. Targeting combinations may provide for enhanced or otherwise previously unknown activity in the treatment of disease. In certain embodiments, an agent against is administered in a combination with an agent already known or used clinically. In certain embodiments, targeting the combination may require less of the known agent as compared to the current standard of care and provide for less toxicity and improved treatment. In certain embodiments, the agents are used to modulate cell types. For example, the agents may be used to modulate cells for adoptive cell transfer. In certain embodiments, the one or more agents comprises a small molecule inhibitor, small molecule degrader (e.g., ATTEC, AUTAC, LYTAC, or PROTAC), genetic modifying agent, antibody, antibody fragment, antibody-like protein scaffold, aptamer, protein, or any combination thereof.

The terms "therapeutic agent", "therapeutic capable agent" or "treatment agent" are used interchangeably and refer to a molecule or compound that confers some beneficial effect upon administration to a subject. The beneficial effect includes enablement of diagnostic determinations; amelioration of a disease, symptom, disorder, or pathological condition; reducing or preventing the onset of a disease, symptom, disorder or condition; and generally counteracting a disease, symptom, disorder or pathological condition.

As used herein, "treatment" or "treating," or "palliating" or "ameliorating" are used interchangeably. These terms refer to an approach for obtaining beneficial or desired results including but not limited to a therapeutic benefit and/or a prophylactic benefit. By therapeutic benefit is meant any therapeutically relevant improvement in or effect on one or more diseases, conditions, or symptoms under treatment. For prophylactic benefit, the compositions may be administered to a subject at risk of developing a particular disease, condition, or symptom, or to a subject reporting one or more of the physiological symptoms of a disease, even though the disease, condition, or symptom may not have yet been manifested. As used herein "treating" includes ameliorating, curing, preventing it from becoming worse, slowing the rate of progression, or preventing the disorder from re-occurring (i.e., to prevent a relapse).

The term "effective amount" or "therapeutically effective amount" refers to the amount of an agent that is sufficient to effect beneficial or desired results. The therapeutically effective amount may vary depending upon one or more of: the subject and disease condition being treated, the weight and age of the subject, the severity of the disease condition, the manner of administration and the like, which can readily be determined by one of ordinary skill in the art. The term also applies to a dose that will provide an image for detection by any one of the imaging methods described herein. The specific dose may vary depending on one or more of: the particular agent chosen, the dosing regimen to be followed, whether it is administered in combination with other compounds, timing of administration, the tissue to be imaged, and the physical delivery system in which it is carried.

For example, in methods for treating autoimmunity in a subject, an effective amount of an agent or a combination of agents is any amount that reduces the autoimmune effect, such as reduces or prevents inflammatory responses in immune cells (e.g., sensory neuron regulated immune response).

Neuropeptide Antagonists and Agonists

In certain embodiments, neuropeptide antagonists and agonists are used to modulate an immune response and/or lymph node (LN) homeostasis. In certain embodiments, the agonist is a peptide or peptide fragment. In certain embodiments, the peptide is modified to increase stability or half-life.

Adcyap1 and Adcyap1r1

Adcyap1 (PACAP) functions as a neurotransmitter and neuromodulator and binds to its receptor, Adcyap1r1 (ADCYAP1R1, PAC1, PAC1R, PACAPR, PACAPRI, ADCYAP receptor type I). The Adcyap1 gene encodes a secreted proprotein that is further processed into multiple mature peptides. These peptides stimulate adenylate cyclase and increase cyclic adenosine monophosphate (cAMP) levels, resulting in the transcriptional activation of target genes. The products of this gene are key mediators of neuroendocrine stress responses. Alternative splicing results in multiple transcript variants. Treatments with monoclonal antibodies are being developed targeting PACAP or its receptors for the treatment of primary headache disorders. These include: AMG-301 developed by Amgen Inc., which targets the PAC1 receptor and has completed phase II trials; and ALD1910, developed by Alder BioPharmaceuticals, which targets the peptide and began a phase I study in October 2019 (Bertels, et al., (2019). "Emerging Treatment Targets for Migraine and Other Headaches". Headache: The Journal of Head and Face Pain. 59 (S2): 50-65. Alder BioPharmaceuticals® Announces First-in-Human Dosing in Phase 1 ALD1910 Study for Preventive Treatment of Migraine". GlobeNewswire. 10 Oct. 2019).

Calca and Calcrl/Ramp1

In one aspect, modulating neural stimulation and/or efferent signaling of LN-innervating peptidergic nociceptor sensory neurons may comprise administering a CGRP peptide, or functional domain thereof, to a subject in need thereof. The CGRP protein (also known as: Calcitonin Related Polypeptide Alpha, Calcitonin, Calcitonin Gene-Related Peptide 1, Calcitonin Gene-Related Peptide I, Alpha-Type CGRP, Calcitonin 1, CGRP-I, CALC1, Calcitonin/Calcitonin-Related Polypeptide, Alpha, Katacalcin, CGRP1, CGRP, PCT, CT and KC) (HUGO Gene Nomenclature Committee ID NO. HGNC: 10489) may be any α-CGRP or β-CGRP, their functional variants, functional fragments or any mammalian orthologues thereof. In certain example embodiments, CGRP also includes peptides having under-gone post-translational modifications, such as peptides having covalent attachment of glycosyl groups, acetyl groups, phosphate groups, lipid groups, and the like.

The human peptide α-CGRP (UniProtKB/Swiss-Prot ref.: P06881.3) is encoded by the human gene CALCA (NCBI ref: NG_015960.1, NP_001029125.1) and has the sequence: Ala-Cys-Asp-Thr-Ala-Thr-Cys-Val-Thr-His-Arg-Leu-Ala-Gly-Leu-Leu-Ser-Arg-Ser-Gly-Gly-Val-Val-Lys-Asn-Asn-Phe-Val-Pro-Thr-Asn-Val-Gly-Ser- Lys-Ala-Phe-NH2 (SEQ ID NO: 1). In certain example embodiments, the CGRP to be administered is human α-CGRP. In certain example embodiments, the human α-CGRP to be administered is SEQ ID NO: 1 or a functional variant or fragment thereof.

The human peptide β-CGRP (UniProtKB/Swiss-Protref.: P10092.1) is encoded by the human gene CALCB (NCBI ref: NM_000728.4, NP_000719.1), and has the sequence: Ala-Cys-Asn-Thr-Ala-Thr-Cys-Val-Thr-His-Arg-Leu-Ala-Gly-Leu-Leu-Ser-Arg-Ser-Gly-Gly-Met-Val-Lys-Ser-Asn-Phe-Val-Pro-Thr-Asn-Val-Gly-Ser-Lys- Ala-Phe-NH2 (SEQ ID NO: 2). In certain example embodiments, the CGRP to be administered is human β-CGRP. In certain example embodiments, the human α-CGRP to be administered is SEQ ID NO: 2 or a functional variant or fragment thereof.

In another aspect, methods of modulating neural stimulation and/or efferent signaling of LN-innervating peptidergic nociceptor sensory neurons may comprise administering a CGRP receptor agonist, or functional domain thereof, to a subject in need thereof. CGRP receptors have been described as heterodimeric molecules formed of the calcitonin receptor-like receptor (CRLR), linked to RAMP1 (CALCRL). RAMP1 is a transmembrane domain protein of the RAMP family, which further comprises RAMP2 and RAMP3. Several types of receptors are known that can be activated by CGRP: CGRP receptor (formed of CRLR and of RAMP1), AM2 receptor (formed of CRLR and of RAMP3), and AMY1 and AMY3 receptors (formed of the calcitonin receptor and of RAMP1 and RAMP3, respectively). The CGRP receptors can therefore be distinguished from the AM2, AMY1 and AMY3 receptors by the nature of the transmembrane domain of the RAMP family interacting with CRLR.

As used herein, "CGRP receptor", refers to a protein receptor comprising the CRLR protein Ref NCBI: NP_005786.1), bound to the protein Receptor Activity Modifying Protein 1 (RAMP1) (Ref NCBI: NP_005846.1). Thus, CGRP receptors do not comprise the CRLR protein bound to RAMP2 or RAMP3.

Tac1 and Tacr1

Preprotachykinin-1, (abbreviated PPT-1, PPT-I, or PPT-A), is a precursor protein that in humans is encoded by the TAC1 gene (TAC1, Hs.2563, NK2, TAC2, tachykinin precursor 1, NKNA, NPK). This gene encodes four products of the tachykinin peptide hormone family, substance P and neurokinin A, as well as the related peptides, neuropeptide K and neuropeptide gamma. These hormones are thought to function as neurotransmitters which interact with nerve receptors and smooth muscle cells. They are known to induce behavioral responses and function as vasodilators and secretagogues. Substance P is an antimicrobial peptide with antibacterial and antifungal properties. Multiple transcript variants encoding different isoforms have been found for this gene. In certain embodiments, one or more of these peptides are used to modulate neural stimulation and/or efferent signaling of LN-innervating peptidergic nociceptor sensory neurons.

The tachykinin receptor 1 (TACR1) also known as neurokinin 1 receptor (NK1R) or substance P receptor (SPR) is a G protein coupled receptor found in the central nervous system and peripheral nervous system. The endogenous ligand for this receptor is Substance P, although it has some affinity for other tachykinins. The protein is the product of the TACR1 gene. In certain embodiments, agonists or antagonists are used to modulate signaling. Many selective ligands for NK1 are now available, several of which have gone into clinical use as antiemetics. Non-limiting agonists include GR-73632, a potent and selective agonist (EC50 2 nM), and 5-amino acid polypeptide chain. CAS #133156-06-6. Non-limiting antagonists include Aprepitant, Casopitant, Ezlopitant, Fosaprepitant, Lanepitant, Maropitant, Vestipitant, L-733,060, L-741,671, L-742,694, RP-67580 (potent and selective antagonist, Ki 2.9 nM, (3aR,7aR)-Octahydro-2-[1-imino-2-(2-methoxyphenyl)ethyl]-7,7-diphenyl-4H-isoindol, CAS #135911-02-3), RPR-100,893, CP-96345, CP-99994, GR-205,171, TAK-637, and T-2328.

Gal and Galr1

The neuropeptide galanin (Gal, GAL-GMAP, GALN, GLNN, GMAP, ETL8, galanin and GMAP prepropeptide) elicits a range of biological effects by interaction with specific G-protein-coupled receptors. Galanin is an important neuromodulator present in the brain, gastrointestinal system, and hypothalamusry axis. It is a 30-amino acid non-C-terminally amidated peptide that potently stimulates growth hormone secretion, inhibits cardiac vagal slowing of heart rate, abolishes sinus arrhythmia, and inhibits postprandial gastrointestinal motility. Galanin has been implicated in many biologically diverse functions, including: nociception, waking and sleep regulation, cognition, feeding, regulation of mood, regulation of blood pressure, it also has roles in development as well as acting as a trophic factor. Galanin receptors are seven-trans membrane proteins shown to activate a variety of intracellular second-messenger pathways. Galr1 (GALR1, GALNR, GALNR1, Galanin receptor 1) inhibits adenylyl cyclase via a G protein of the GI/GO family. GALR1 is widely expressed in the brain and spinal cord, as well as in peripheral sites such as the small intestine and heart. Galr2 (GALR2, GAL2-R, GALNR2, GALR-2, Galanin receptor 2) interacts with the N-terminal residues of the galanin peptide. The primary signaling mechanism for GALR2 is through the phospholipase C/protein kinase C pathway (via Gq), in contrast to GALR1, which communicates its intracellular signal by inhibition of adenylyl cyclase through Gi. However, it has been demonstrated that GALR2 couples efficiently to both the Gq and Gi proteins to simultaneously activate 2 independent signal transduction pathways.

In certain embodiments, Gal agonists and antagonists may be used to modulate neural stimulation and/or efferent signaling of LN-innervating peptidergic nociceptor sensory neurons. Non-limiting agonists include the non-selective agonists: Galanin, Galanin 1-15 fragment, Galanin-like peptide, Galmic, Galnon, NAX 5055, and D-Gal (7-Ahp)-B2; GAL1 selective: M617; GAL1/2 selective: M1154; and GAL2 selective: Galanin 2-11 amide (also called AR-M 1896) anticonvulsant in mice CAS #367518-31-8, M1145, M1153, and CYM 2503 (positive allosteric modulator). Non-limiting antagonists include Non-selective: M35 peptide; GAL1 selective: SCH-202,596; and GAL2 selective: M871 peptide.

Small Molecules

In certain embodiments, the one or more agents is a small molecule. The term "small molecule" refers to compounds, preferably organic compounds, with a size comparable to those organic molecules generally used in pharmaceuticals. The term excludes biological macromolecules (e.g., proteins, peptides, nucleic acids, etc.). Preferred small organic molecules range in size up to about 5000 Da, e.g., up to about 4000, preferably up to 3000 Da, more preferably up to 2000 Da, even more preferably up to about 1000 Da, e.g., up to about 900, 800, 700, 600 or up to about 500 Da. In certain embodiments, the small molecule may act as an antagonist or agonist (e.g., blocking a receptor binding site or activating a receptor by binding to a ligand binding site).

One type of small molecule applicable to the present invention is a degrader molecule (see, e.g., Ding, et al., Emerging New Concepts of Degrader Technologies, Trends Pharmacol Sci. 2020 July; 41(7):464-474). The terms "degrader" and "degrader molecule" refer to all compounds capable of specifically targeting a protein for degradation (e.g., ATTEC, AUTAC, LYTAC, or PROTAC, reviewed in Ding, et al. 2020). Proteolysis Targeting Chimera (PROTAC) technology is a rapidly emerging alternative therapeutic strategy with the potential to address many of the challenges currently faced in modern drug development programs. PROTAC technology employs small molecules that recruit target proteins for ubiquitination and removal by the proteasome (see, e.g., Zhou et al., Discovery of a Small-Molecule Degrader of Bromodomain and Extra-Terminal (BET) Proteins with Picomolar Cellular Potencies and Capable of Achieving Tumor Regression. J. Med. Chem. 2018, 61, 462-481; Bondeson and Crews, Targeted Protein Degradation by Small Molecules, Annu Rev Pharmacol Toxicol. 2017 Jan. 6; 57:107-123; and Lai et al., Modular PROTAC Design for the Degradation of Oncogenic BCR-ABL Angew Chem Int Ed Engl. 2016 January 11; 55(2): 807-810). In certain embodiments, LYTACs are particularly advantageous for cell surface proteins as described herein.

Genetic Modifying Agents

In certain embodiments, the one or more modulating agents may be a genetic modifying agent. The genetic modifying agents may manipulate nucleic acids (e.g., genomic DNA or mRNA). The genetic modulating agent can be used to up- or downregulate expression of a gene either by targeting a nuclease or functional domain to a DNA or RNA sequence. The genetic modifying agent may comprise a CRISPR system, a zinc finger nuclease system, a TALEN, a meganuclease or RNAi system.

CRISPR-Cas Modification

In some embodiments, a polynucleotide of the present invention described elsewhere herein can be modified using a CRISPR-Cas and/or Cas-based system (e.g., genomic DNA or mRNA, preferably, for a disease gene). The nucleotide sequence may be or encode one or more components of a CRISPR-Cas system. For example, the nucleotide sequences may be or encode guide RNAs. The nucleotide sequences may also encode CRISPR proteins, variants thereof, or fragments thereof.

In general, a CRISPR-Cas or CRISPR system as used herein and in other documents, such as WO 2014/093622 (PCT/US2013/074667), refers collectively to transcripts and other elements involved in the expression of or directing the activity of CRISPR-associated ("Cas") genes, including sequences encoding a Cas gene, a tracr (trans-activating CRISPR) sequence (e.g., tracrRNA or an active partial tracrRNA), a tracr-mate sequence (encompassing a "direct repeat" and a tracrRNA-processed partial direct repeat in the context of an endogenous CRISPR system), a guide sequence (also referred to as a "spacer" in the context of an endogenous CRISPR system), or "RNA(s)" as that term is herein used (e.g., RNA(s) to guide Cas, such as Cas9, e.g., CRISPR RNA and transactivating (tracr) RNA or a single guide RNA (sgRNA) (chimeric RNA)) or other sequences and transcripts from a CRISPR locus. In general, a CRISPR system is characterized by elements that promote the formation of a CRISPR complex at the site of a target sequence (also referred to as a protospacer in the context of an endogenous CRISPR system). See, e.g., Shmakov et al. (2015) "Discovery and Functional Characterization of Diverse Class 2 CRISPR-Cas Systems", Molecular Cell, DOI: dx.doi.org/10.1016/j.molcel.2015.10.008.

CRISPR-Cas systems can generally fall into two classes based on their architectures of their effector molecules, which are each further subdivided by type and subtype. The two classes are Class 1 and Class 2. Class 1 CRISPR-Cas systems have effector modules composed of multiple Cas proteins, some of which form crRNA-binding complexes, while Class 2 CRISPR-Cas systems include a single, multi-domain crRNA-binding protein.

In some embodiments, the CRISPR-Cas system that can be used to modify a polynucleotide of the present invention described herein can be a Class 1 CRISPR-Cas system. In some embodiments, the CRISPR-Cas system that can be used to modify a polynucleotide of the present invention described herein can be a Class 2 CRISPR-Cas system.

Class 1 CRISPR-Cas Systems

In some embodiments, the CRISPR-Cas system that can be used to modify a polynucleotide of the present invention described herein can be a Class 1 CRISPR-Cas system. Class 1 CRISPR-Cas systems are divided into Types I, II, and IV. Makarova et al. 2020. Nat. Rev. 18:67-83., particularly as described in FIG. 1. Type I CRISPR-Cas systems are divided into 9 subtypes (I-A, I-B, I-C, I-D, I-E, I-F1, I-F2, I-F3, and IG). Makarova et al., 2020. Class 1, Type I CRISPR-Cas systems can contain a Cas3 protein that can have helicase activity. Type III CRISPR-Cas systems are divided into 6 subtypes (III-A, III-B, III-C, III-D, III-E, and III-F). Type III CRISPR-Cas systems can contain a Cas10 that can include an RNA recognition motif called Palm and a cyclase domain that can cleave polynucleotides. Makarova et al., 2020. Type IV CRISPR-Cas systems are divided into 3 subtypes. (IV-A, IV-B, and IV-C). Makarova et al., 2020. Class 1 systems also include CRISPR-Cas variants, including Type I-A, I-B, I-E, I-F and I-U variants, which can include variants carried by transposons and plasmids, including versions of subtype I-F encoded by a large family of Tn7-like transposon and smaller groups of Tn7-like transposons that encode similarly degraded subtype I-B systems. Peters et al., PNAS 114 (35) (2017); DOI: 10.1073/pnas. 1709035114; see also, Makarova et al. 2018. The CRISPR Journal, v. 1, n5, FIG. 5.

The Class 1 systems typically use a multi-protein effector complex, which can, in some embodiments, include ancillary proteins, such as one or more proteins in a complex referred to as a CRISPR-associated complex for antiviral defense (Cascade), one or more adaptation proteins (e.g., Cas1, Cas2, RNA nuclease), and/or one or more accessory proteins (e.g., Cas 4, DNA nuclease), CRISPR associated Rossman fold (CARF) domain containing proteins, and/or RNA transcriptase.

The backbone of the Class 1 CRISPR-Cas system effector complexes can be formed by RNA recognition motif domain-containing protein(s) of the repeat-associated mysterious proteins (RAMPs) family subunits (e.g., Cas 5, Cas6, and/or Cas7). RAMP proteins are characterized by having one or more RNA recognition motif domains. In some embodiments, multiple copies of RAMPs can be present. In some embodiments, the Class I CRISPR-Cas system can include 1, 2, 3, 4, 5, 6, 7, 8, 9, 10, 11, 12 or more Cas5, Cas6, and/or Cas 7 proteins. In some embodiments, the Cas6 protein is an RNAse, which can be responsible for pre-crRNA processing. When present in a Class 1 CRISPR-Cas system, Cas6 can be optionally physically associated with the effector complex.

Class 1 CRISPR-Cas system effector complexes can, in some embodiments, also include a large subunit. The large subunit can be composed of or include a Cas8 and/or Cas10 protein. See, e.g., FIGS. 1 and 2. Koonin E V, Makarova K S. 2019. Phil. Trans. R. Soc. B 374:20180087, DOI: 10.1098/rstb.2018.0087 and Makarova et al. 2020.

Class 1 CRISPR-Cas system effector complexes can, in some embodiments, include a small subunit (for example, Cas11). See, e.g., FIGS. 1 and 2. Koonin E V, Makarova K S. 2019 Origins and Evolution of CRISPR-Cas systems. Phil. Trans. R. Soc. B 374:20180087, DOI: 10.1098/rstb.2018.0087.

In some embodiments, the Class 1 CRISPR-Cas system can be a Type I CRISPR-Cas system. In some embodiments, the Type I CRISPR-Cas system can be a subtype I-A CRISPR-Cas system. In some embodiments, the Type I CRISPR-Cas system can be a subtype I-B CRISPR-Cas system. In some embodiments, the Type I CRISPR-Cas system can be a subtype I-C CRISPR-Cas system. In some embodiments, the Type I CRISPR-Cas system can be a subtype I-D CRISPR-Cas system. In some embodiments, the Type I CRISPR-Cas system can be a subtype I-E CRISPR-Cas system. In some embodiments, the Type I CRISPR-Cas system can be a subtype I-F1 CRISPR-Cas system. In some embodiments, the Type I CRISPR-Cas system can be a subtype I-F2 CRISPR-Cas system. In some embodiments, the Type I CRISPR-Cas system can be a subtype I-F3 CRISPR-Cas system. In some embodiments, the Type I CRISPR-Cas system can be a subtype I-G CRISPR-Cas system. In some embodiments, the Type I CRISPR-Cas system can be a CRISPR-Cas variant, such as a Type I-A, I-B, I-E, I-F and I-U variants, which can include variants carried by transposons and plasmids, including versions of subtype I-F encoded by a large family of Tn7-like transposon and smaller groups of Tn7-like transposons that encode similarly degraded subtype I-B systems as previously described.

In some embodiments, the Class 1 CRISPR-Cas system can be a Type III CRISPR-Cas system. In some embodiments, the Type III CRISPR-Cas system can be a subtype III-A CRISPR-Cas system. In some embodiments, the Type III CRISPR-Cas system can be a subtype III-B CRISPR-Cas system. In some embodiments, the Type III CRISPR-Cas system can be a subtype III-C CRISPR-Cas system. In some embodiments, the Type III CRISPR-Cas system can be a subtype III-D CRISPR-Cas system. In some embodiments, the Type III CRISPR-Cas system can be a subtype III-E CRISPR-Cas system. In some embodiments, the Type III CRISPR-Cas system can be a subtype III-F CRISPR-Cas system.

In some embodiments, the Class 1 CRISPR-Cas system can be a Type IV CRISPR-Cas-system. In some embodiments, the Type IV CRISPR-Cas system can be a subtype IV-A CRISPR-Cas system. In some embodiments, the Type IV CRISPR-Cas system can be a subtype IV-B CRISPR-Cas system. In some embodiments, the Type IV CRISPR-Cas system can be a subtype IV-C CRISPR-Cas system.

The effector complex of a Class 1 CRISPR-Cas system can, in some embodiments, include a Cas3 protein that is optionally fused to a Cas2 protein, a Cas4, a Cas5, a Cas6, a Cas7, a Cas8, a Cas10, a Cas11, or a combination thereof. In some embodiments, the effector complex of a Class 1 CRISPR-Cas system can have multiple copies, such as 1, 2, 3, 4, 5, 6, 7, 8, 9, 10, 11, 12, 13, or 14, of any one or more Cas proteins.

Class 2 CRISPR-Cas Systems

The compositions, systems, and methods described in greater detail elsewhere herein can be designed and adapted for use with Class 2 CRISPR-Cas systems. Thus, in some embodiments, the CRISPR-Cas system is a Class 2 CRISPR-Cas system. Class 2 systems are distinguished from Class 1 systems in that they have a single, large, multi-domain effector protein. In certain example embodiments, the Class 2 system can be a Type II, Type V, or Type VI system, which are described in Makarova et al. "Evolutionary classification of CRISPR-Cas systems: a burst of class 2 and derived variants" Nature Reviews Microbiology, 18:67-81 (February 2020), incorporated herein by reference. Each type of Class 2 system is further divided into subtypes. See Markova et al. 2020, particularly at Figure. 2. Class 2, Type II systems can be divided into 4 subtypes: II-A, II-B, II-C1, and II-C2. Class 2, Type V systems can be divided into 17 subtypes: V-A, V-B1, V-B2, V-C, V-D, V-E, V-F1, V-F1 (V-U3), V-F2, V-F3, V-G, V-H, V-I, V-K (V-U5), V-U1, V-U2, and V-U4. Class 2, Type IV systems can be divided into 5 subtypes: VI-A, VI-B1, VI-B2, VI-C, and VI-D.

The distinguishing feature of these types is that their effector complexes consist of a single, large, multi-domain protein. Type V systems differ from Type II effectors (e.g., Cas9), which contain two nuclear domains that are each responsible for the cleavage of one strand of the target DNA, with the HNH nuclease inserted inside the Ruv-C like nuclease domain sequence. The Type V systems (e.g., Cas12) only contain a RuvC-like nuclease domain that cleaves both strands. Type VI (Cas13) are unrelated to the effectors of Type II and V systems and contain two HEPN domains and target RNA. Cas13 proteins also display collateral activity that is triggered by target recognition. Some Type V systems have also been found to possess this collateral activity with two single-stranded DNA in in vitro contexts.

In some embodiments, the Class 2 system is a Type II system. In some embodiments, the Type II CRISPR-Cas system is a II-A CRISPR-Cas system. In some embodiments, the Type II CRISPR-Cas system is a II-B CRISPR-Cas system. In some embodiments, the Type II CRISPR-Cas system is a II-C1 CRISPR-Cas system. In some embodiments, the Type II CRISPR-Cas system is a II-C2 CRISPR-Cas system. In some embodiments, the Type II system is a Cas9 system. In some embodiments, the Type II system includes a Cas9.

In some embodiments, the Class 2 system is a Type V system. In some embodiments, the Type V CRISPR-Cas system is a V-A CRISPR-Cas system. In some embodiments, the Type V CRISPR-Cas system is a V-B1 CRISPR-Cas system. In some embodiments, the Type V CRISPR-Cas system is a V-B2 CRISPR-Cas system. In some embodiments, the Type V CRISPR-Cas system is a V-C CRISPR-Cas system. In some embodiments, the Type V CRISPR-Cas system is a V-D CRISPR-Cas system. In some embodiments, the Type V CRISPR-Cas system is a V-E CRISPR-Cas system. In some embodiments, the Type V CRISPR-Cas system is a V-F1 CRISPR-Cas system. In some embodiments, the Type V CRISPR-Cas system is a V-F1 (V-U3) CRISPR-Cas system. In some embodiments, the Type V CRISPR-Cas system is a V-F2 CRISPR-Cas system. In some embodiments, the Type V CRISPR-Cas system is a V-F3 CRISPR-Cas system. In some embodiments, the Type V CRISPR-Cas system is a V-G CRISPR-Cas system. In some embodiments, the Type V CRISPR-Cas system is a V-H CRISPR-Cas system. In some embodiments, the Type V CRISPR-Cas system is a V-I CRISPR-Cas system. In some embodiments, the Type V CRISPR-Cas system is a V-K (V-U5) CRISPR-Cas system. In some embodiments, the Type V CRISPR-Cas system is a V-U1 CRISPR-Cas system. In some embodiments, the Type V CRISPR-Cas system is a V-U2 CRISPR-Cas system. In some embodiments, the Type V CRISPR-Cas system is a V-U4 CRISPR-Cas system. In some embodiments, the Type V CRISPR-Cas system includes a Cas12a (Cpf1), Cas12b (C2c1), Cas12c (C2c3), CasX, and/or Cas14.

In some embodiments the Class 2 system is a Type VI system. In some embodiments, the Type VI CRISPR-Cas system is a VI-A CRISPR-Cas system. In some embodiments, the Type VI CRISPR-Cas system is a VI-B1 CRISPR-Cas system. In some embodiments, the Type VI CRISPR-Cas system is a VI-B2 CRISPR-Cas system. In some embodiments, the Type VI CRISPR-Cas system is a VI-C CRISPR-Cas system. In some embodiments, the Type VI CRISPR-Cas system is a VI-D CRISPR-Cas system. In some embodiments, the Type VI CRISPR-Cas system includes a Cas13a (C2c2), Cas13b (Group 29/30), Cas13c, and/or Cas13d.

Specialized Cas-Based Systems

In some embodiments, the system is a Cas-based system that is capable of performing a specialized function or activity. For example, the Cas protein may be fused, operably coupled to, or otherwise associated with one or more functionals domains. In certain example embodiments, the Cas protein may be a catalytically dead Cas protein ("dCas") and/or have nickase activity. A nickase is a Cas protein that cuts only one strand of a double stranded target. In such embodiments, the dCas or nickase provide a sequence specific targeting functionality that delivers the functional domain to or proximate a target sequence. Example functional domains that may be fused to, operably coupled to, or otherwise associated with a Cas protein can be or include, but are not limited to a nuclear localization signal (NLS) domain, a nuclear export signal (NES) domain, a translational activation domain, a transcriptional activation domain (e.g. VP64, p65, MyoD1, HSF1, RTA, and SET7/9), a translation initiation domain, a transcriptional repression domain (e.g., a KRAB domain, NuE domain, NcoR domain, and a SID domain such as a SID4X domain), a nuclease domain (e.g., FokI), a histone modification domain (e.g., a histone acetyltransferase), a light inducible/controllable domain, a chemically inducible/controllable domain, a transposase domain, a homologous recombination machinery domain, a recombinase domain, an integrase domain, and combinations thereof. Methods for generating catalytically dead Cas9 or a nickase Cas9 (WO 2014/204725, Ran et al. Cell. 2013 Sep. 12; 154(6):1380-1389), Cas12 (Liu et al. Nature Communications, 8, 2095 (2017), and Cas13 (WO 2019/005884, WO2019/060746) are known in the art and incorporated herein by reference.

In some embodiments, the functional domains can have one or more of the following activities: methylase activity, demethylase activity, translation activation activity, translation initiation activity, translation repression activity, transcription activation activity, transcription repression activity, transcription release factor activity, histone modification activity, nuclease activity, single-strand RNA cleavage activity, double-strand RNA cleavage activity, single-strand DNA cleavage activity, double-strand DNA cleavage activity, molecular switch activity, chemical inducibility, light inducibility, and nucleic acid binding activity. In some embodiments, the one or more functional domains may comprise epitope tags or reporters. Non-limiting examples of epitope tags include histidine (His) tags, V5 tags, FLAG tags, influenza hemagglutinin (HA) tags, Myc tags, VSV-G tags, and thioredoxin (Trx) tags. Examples of reporters include, but are not limited to, glutathione-S-transferase (GST), horseradish peroxidase (HRP), chloramphenicol acetyltransferase (CAT) beta-galactosidase, beta-glucuronidase, luciferase, green fluorescent protein (GFP), HcRed, DsRed, cyan fluorescent protein (CFP), yellow fluorescent protein (YFP), and auto-fluorescent proteins including blue fluorescent protein (BFP).

The one or more functional domain(s) may be positioned at, near, and/or in proximity to a terminus of the effector protein (e.g., a Cas protein). In embodiments having two or more functional domains, each of the two can be positioned at or near or in proximity to a terminus of the effector protein (e.g., a Cas protein). In some embodiments, such as those where the functional domain is operably coupled to the effector protein, the one or more functional domains can be tethered or linked via a suitable linker (including, but not limited to, GlySer linkers) to the effector protein (e.g., a Cas protein). When there is more than one functional domain, the functional domains can be same or different. In some embodiments, all the functional domains are the same. In some embodiments, all of the functional domains are different from each other. In some embodiments, at least two of the functional domains are different from each other. In some embodiments, at least two of the functional domains are the same as each other.

Other suitable functional domains can be found, for example, in International Patent Publication No. WO 2019/018423.

Split CRISPR-Cas Systems

In some embodiments, the CRISPR-Cas system is a split CRISPR-Cas system. See e.g., Zetche et al., 2015. Nat. Biotechnol. 33(2): 139-142 and WO 2019/018423, the compositions and techniques of which can be used in and/or adapted for use with the present invention. Split CRISPR-Cas proteins are set forth herein and in documents incorporated herein by reference in further detail herein. In certain embodiments, each part of a split CRISPR protein are attached to a member of a specific binding pair, and when bound with each other, the members of the specific binding pair maintain the parts of the CRISPR protein in proximity. In certain embodiments, each part of a split CRISPR protein is associated with an inducible binding pair. An inducible binding pair is one which is capable of being switched "on" or "off" by a protein or small molecule that binds to both members of the inducible binding pair. In some embodiments, CRISPR proteins may preferably split between domains, leaving domains intact. In particular embodiments, said Cas split domains (e.g., RuvC and HNH domains in the case of Cas9) can be simultaneously or sequentially introduced into the cell such that said split Cas domain(s) process the target nucleic acid sequence in the algae cell. The reduced size of the split Cas compared to the wild type Cas allows other methods of delivery of the systems to the cells, such as the use of cell penetrating peptides as described herein.

DNA and RNA Base Editing

In some embodiments, a polynucleotide of the present invention described elsewhere herein can be modified using a base editing system. In some embodiments, a Cas protein is connected or fused to a nucleotide deaminase. Thus, in some embodiments the Cas-based system can be a base editing system. As used herein "base editing" refers generally to the process of polynucleotide modification via a CRISPR-Cas-based or Cas-based system that does not include excising nucleotides to make the modification. Base editing can convert base pairs at precise locations without generating excess undesired editing byproducts that can be made using traditional CRISPR-Cas systems.

In certain example embodiments, the nucleotide deaminase may be a DNA base editor used in combination with a DNA binding Cas protein such as, but not limited to, Class 2 Type II and Type V systems. Two classes of DNA base editors are generally known: cytosine base editors (CBEs) and adenine base editors (ABEs). CBEs convert a C·G base pair into a T·A base pair (Komor et al. 2016. Nature. 533:420-424; Nishida et al. 2016. Science. 353; and Li et al. Nat. Biotech. 36:324-327) and ABEs convert an A·T base pair to a G·C base pair. Collectively, CBEs and ABEs can mediate all four possible transition mutations (C to T, A to G, T to C, and G to A). Rees and Liu. 2018.Nat. Rev. Genet. 19(12): 770-788, particularly at FIGS. 1*b*, 2*a*-2*c*, 3*a*-3*f*, and Table 1. In some embodiments, the base editing system includes a CBE and/or an ABE. In some embodiments, a polynucleotide of the present invention described elsewhere herein can be modified using a base editing system. Rees and Liu. 2018. Nat. Rev. Gent. 19(12):770-788. Base editors also generally do not need a DNA donor template and/or rely on homology-directed repair. Komor et al. 2016. Nature. 533: 420-424; Nishida et al. 2016. Science. 353; and Gaudeli et al. 2017. Nature. 551:464-471. Upon binding to a target locus in the DNA, base pairing between the guide RNA of the system and the target DNA strand leads to displacement of a small segment of ssDNA in an "R-loop". Nishimasu et al. Cell. 156:935-949. DNA bases within the ssDNA bubble are modified by the enzyme component, such as a deaminase. In some systems, the catalytically disabled Cas protein can be a variant or modified Cas can have nickase functionality and can generate a nick in the non-edited DNA strand to induce cells to repair the non-edited strand using the edited strand as a template. Komor et al. 2016. Nature. 533:420-424; Nishida et al. 2016. Science. 353; and Gaudeli et al. 2017. Nature. 551:464-471. Base editors may be further engineered to optimize conversion of nucleotides (e.g. A: T to G: C). Richter et al. 2020. Nature Biotechnology. doi.org/10.1038/s41587-020-0453-z.

Other Example Type V base editing systems are described in WO 2018/213708, WO 2018/213726, PCT/US2018/067207, PCT/US2018/067225, and PCT/US2018/067307 which are incorporated by referenced herein.

In certain example embodiments, the base editing system may be a RNA base editing system. As with DNA base editors, a nucleotide deaminase capable of converting nucleotide bases may be fused to a Cas protein. However, in these embodiments, the Cas protein will need to be capable of binding RNA. Example RNA binding Cas proteins include, but are not limited to, RNA-binding Cas9s such as *Francisella novicida* Cas9 ("FnCas9"), and Class 2 Type VI Cas systems. The nucleotide deaminase may be a cytidine deaminase or an adenosine deaminase, or an adenosine deaminase engineered to have cytidine deaminase activity. In certain example embodiments, the RNA based editor may be used to delete or introduce a post-translation modification site in the expressed mRNA. In contrast to DNA base editors, whose edits are permanent in the modified cell, RNA base editors can provide edits where finer temporal control may be needed, for example in modulating a particular immune response. Example Type VI RNA-base editing systems are described in Cox et al. 2017. Science 358:1019-1027, WO 2019/005884, WO 2019/005886, WO 2019/071048, PCT/US20018/05179, PCT/US2018/067207, which are incorporated herein by reference. An example FnCas9 system that may be adapted for RNA base editing purposes is described in WO 2016/106236, which is incorporated herein by reference.

An example method for delivery of base-editing systems, including use of a split-intein approach to divide CBE and ABE into reconstitutable halves, is described in Levy et al. Nature Biomedical Engineering doi.org/10.1038/s41441-019-0505-5 (2019), which is incorporated herein by reference.

Prime Editors

In some embodiments, a polynucleotide of the present invention described elsewhere herein can be modified using a prime editing system (See e.g. Anzalone et al. 2019. Nature. 576:149-157). Like base editing systems, prime editing systems can be capable of targeted modification of a polynucleotide without generating double stranded breaks and does not require donor templates. Further prime editing systems can be capable of all 12 possible combination swaps. Prime editing can operate via a "search-and-replace" methodology and can mediate targeted insertions, deletions, all 12 possible base-to-base conversion, and combinations thereof. Generally, a prime editing system, as exemplified by PE1, PE2, and PE3 (Id.), can include a reverse transcriptase fused or otherwise coupled or associated with an RNA-programmable nickase, and a prime-editing extended guide RNA (pegRNA) to facility direct copying of genetic information from the extension on the pegRNA into the target polynucleotide. Embodiments that can be used with the present invention include these and variants thereof. Prime editing can have the advantage of lower off-target activity than traditional CRISPR-Cas systems along with few byproducts and greater or similar efficiency as compared to traditional CRISPR-Cas systems.

In some embodiments, the prime editing guide molecule can specify both the target polynucleotide information (e.g. sequence) and contain a new polynucleotide cargo that replaces target polynucleotides. To initiate transfer from the guide molecule to the target polynucleotide, the PE system can nick the target polynucleotide at a target side to expose a 3' hydroxyl group, which can prime reverse transcription of an edit-encoding extension region of the guide molecule (e.g. a prime editing guide molecule or peg guide molecule) directly into the target site in the target polynucleotide. See e.g. Anzalone et al. 2019. Nature. 576:149-157, particularly at FIGS. 1*b*, 1*c*, related discussion, and Supplementary discussion.

In some embodiments, a prime editing system can be composed of a Cas polypeptide having nickase activity, a reverse transcriptase, and a guide molecule. The Cas polypeptide can lack nuclease activity. The guide molecule can include a target binding sequence as well as a primer binding sequence and a template containing the edited polynucleotide sequence. The guide molecule, Cas polypeptide, and/or reverse transcriptase can be coupled together or otherwise associate with each other to form an effector complex and edit a target sequence. In some embodiments, the Cas polypeptide is a Class 2, Type V Cas polypeptide. In some embodiments, the Cas polypeptide is a Cas9 polypeptide (e.g. is a Cas9 nickase). In some embodiments, the Cas polypeptide is fused to the reverse transcriptase. In some embodiments, the Cas polypeptide is linked to the reverse transcriptase.

In some embodiments, the prime editing system can be a PE1 system or variant thereof, a PE2 system or variant thereof, or a PE3 (e.g. PE3, PE3b) system. See e.g., Anzalone et al. 2019. Nature. 576:149-157, particularly at pgs. 2-3, FIGS. 2*a*, 3*a*-3*f*, 4*a*-4*b*, Extended data FIGS. 3*a*-3*b*, 4, The peg guide molecule can be about 10 to about 200 or more nucleotides in length, such as 10 to/or 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199, or 200 or more nucleotides in length. Optimization of the peg guide molecule can be accomplished as described in Anzalone et al. 2019. Nature. 576:149-157, particularly at pg. 3, FIG. 2*a*-2*b*, and Extended Data FIGS. 5*a-c*.

CRISPR Associated Transposase (CAST) Systems

In some embodiments, a polynucleotide of the present invention described elsewhere herein can be modified using a CRISPR Associated Transposase ("CAST") system. CAST system can include a Cas protein that is catalytically inactive, or engineered to be catalytically active, and further comprises a transposase (or subunits thereof) that catalyze RNA-guided DNA transposition. Such systems are able to insert DNA sequences at a target site in a DNA molecule without relying on host cell repair machinery. CAST systems can be Class1 or Class 2 CAST systems. An example Class 1 system is described in Klompe et al. Nature, doi: 10.1038/s41586-019-1323, which is in incorporated herein by reference. An example Class 2 system is described in Strecker et al. Science. 10/1126/science. aax9181 (2019), and PCT/US2019/066835 which are incorporated herein by reference.

Guide Molecules

The CRISPR-Cas or Cas-Based system described herein can, in some embodiments, include one or more guide molecules. The terms guide molecule, guide sequence and guide polynucleotide, refer to polynucleotides capable of guiding Cas to a target genomic locus and are used interchangeably as in foregoing cited documents such as WO 2014/093622 (PCT/US2013/074667). In general, a guide sequence is any polynucleotide sequence having sufficient complementarity with a target polynucleotide sequence to hybridize with the target sequence and direct sequence-specific binding of a CRISPR complex to the target sequence. The guide molecule can be a polynucleotide.

The ability of a guide sequence (within a nucleic acid-targeting guide RNA) to direct sequence-specific binding of a nucleic acid-targeting complex to a target nucleic acid sequence may be assessed by any suitable assay. For example, the components of a nucleic acid-targeting CRISPR system sufficient to form a nucleic acid-targeting complex, including the guide sequence to be tested, may be provided to a host cell having the corresponding target nucleic acid sequence, such as by transfection with vectors encoding the components of the nucleic acid-targeting complex, followed by an assessment of preferential targeting (e.g., cleavage) within the target nucleic acid sequence, such as by Surveyor assay (Qui et al. 2004. BioTechniques. 36(4)702-707). Similarly, cleavage of a target nucleic acid sequence may be evaluated in a test tube by providing the target nucleic acid sequence, components of a nucleic acid-targeting complex, including the guide sequence to be tested and a control guide sequence different from the test guide sequence, and comparing binding or rate of cleavage at the target sequence between the test and control guide sequence reactions. Other assays are possible and will occur to those skilled in the art.

In some embodiments, the guide molecule is an RNA. The guide molecule(s) (also referred to interchangeably herein as guide polynucleotide and guide sequence) that are included in the CRISPR-Cas or Cas based system can be any polynucleotide sequence having sufficient complementarity with a target nucleic acid sequence to hybridize with the target nucleic acid sequence and direct sequence-specific binding of a nucleic acid-targeting complex to the target nucleic acid sequence. In some embodiments, the degree of complementarity, when optimally aligned using a suitable alignment algorithm, can be about or more than about 50%, 60%, 75%, 80%, 85%, 90%, 95%, 97.5%, 99%, or more. Optimal alignment may be determined with the use of any suitable algorithm for aligning sequences, non-limiting examples of which include the Smith-Waterman algorithm, the Needleman-Wunsch algorithm, algorithms based on the Burrows-Wheeler Transform (e.g., the Burrows Wheeler Aligner), ClustalW, Clustal X, BLAT, Novoalign (Novocraft Technologies; available at www.novocraft.com), ELAND (Illumina, San Diego, CA), SOAP (available at soap.genomics.org.cn), and Maq (available at maq.sourceforge.net).

A guide sequence, and hence a nucleic acid-targeting guide, may be selected to target any target nucleic acid sequence. The target sequence may be DNA. The target sequence may be any RNA sequence. In some embodiments, the target sequence may be a sequence within an RNA molecule selected from the group consisting of messenger RNA (mRNA), pre-mRNA, ribosomal RNA (IRNA), transfer RNA (tRNA), micro-RNA (miRNA), small interfering RNA (siRNA), small nuclear RNA (snRNA), small nucleolar RNA (snoRNA), double stranded RNA (dsRNA), non-coding RNA (ncRNA), long non-coding RNA (lncRNA), and small cytoplasmatic RNA (scRNA). In some preferred embodiments, the target sequence may be a sequence within an RNA molecule selected from the group consisting of mRNA, pre-mRNA, and rRNA. In some preferred embodiments, the target sequence may be a sequence within an RNA molecule selected from the group consisting of ncRNA, and lncRNA. In some more preferred embodiments, the target sequence may be a sequence within an mRNA molecule or a pre-mRNA molecule.

In some embodiments, a nucleic acid-targeting guide is selected to reduce the degree secondary structure within the nucleic acid-targeting guide. In some embodiments, about or less than about 75%, 50%, 40%, 30%, 25%, 20%, 15%, 10%, 5%, 1%, or fewer of the nucleotides of the nucleic acid-targeting guide participate in self-complementary base pairing when optimally folded. Optimal folding may be determined by any suitable polynucleotide folding algorithm. Some programs are based on calculating the minimal Gibbs free energy. An example of one such algorithm is mFold, as described by Zuker and Stiegler (Nucleic Acids Res. 9 (1981), 133-148). Another example folding algorithm is the online webserver RNAfold, developed at Institute for Theoretical Chemistry at the University of Vienna, using the centroid structure prediction algorithm (see e.g., A. R. Gruber et al., 2008, Cell 106(1): 23-24; and PA Carr and GM Church, 2009, Nature Biotechnology 27(12): 1151-62).

In certain embodiments, a guide RNA or crRNA may comprise, consist essentially of, or consist of a direct repeat (DR) sequence and a guide sequence or spacer sequence. In certain embodiments, the guide RNA or crRNA may comprise, consist essentially of, or consist of a direct repeat sequence fused or linked to a guide sequence or spacer sequence. In certain embodiments, the direct repeat sequence may be located upstream (i.e., 5') from the guide sequence or spacer sequence. In other embodiments, the direct repeat sequence may be located downstream (i.e., 3') from the guide sequence or spacer sequence.

In certain embodiments, the crRNA comprises a stem loop, preferably a single stem loop. In certain embodiments, the direct repeat sequence forms a stem loop, preferably a single stem loop.

In certain embodiments, the spacer length of the guide RNA is from 15 to 35 nt. In certain embodiments, the spacer length of the guide RNA is at least 15 nucleotides. In certain embodiments, the spacer length is from 15 to 17 nt, e.g., 15, 16, or 17 nt, from 17 to 20 nt, e.g., 17, 18, 19, or 20 nt, from 20 to 24 nt, e.g., 20, 21, 22, 23, or 24 nt, from 23 to 25 nt, e.g., 23, 24, or 25 nt, from 24 to 27 nt, e.g., 24, 25, 26, or 27 nt, from 27 to 30 nt, e.g., 27, 28, 29, or 30 nt, from 30 to 35 nt, e.g., 30, 31, 32, 33, 34, or 35 nt, or 35 nt or longer.

The "tracrRNA" sequence or analogous terms includes any polynucleotide sequence that has sufficient complementarity with a crRNA sequence to hybridize. In some embodiments, the degree of complementarity between the tracrRNA sequence and crRNA sequence along the length of the shorter of the two when optimally aligned is about or more than about 25%, 30%, 40%, 50%, 60%, 70%, 80%, 90%, 95%, 97.5%, 99%, or higher. In some embodiments, the tracr sequence is about or more than about 5, 6, 7, 8, 9, 10, 11, 12, 13, 14, 15, 16, 17, 18, 19, 20, 25, 30, 40, 50, or more nucleotides in length. In some embodiments, the tracr sequence and crRNA sequence are contained within a single transcript, such that hybridization between the two produces a transcript having a secondary structure, such as a hairpin.

In general, degree of complementarity is with reference to the optimal alignment of the sca sequence and tracr sequence, along the length of the shorter of the two sequences. Optimal alignment may be determined by any suitable alignment algorithm and may further account for secondary structures, such as self-complementarity within either the sca sequence or tracr sequence. In some embodiments, the degree of complementarity between the tracr sequence and sca sequence along the length of the shorter of the two when optimally aligned is about or more than about 25%, 30%, 40%, 50%, 60%, 70%, 80%, 90%, 95%, 97.5%, 99%, or higher.

In some embodiments, the degree of complementarity between a guide sequence and its corresponding target sequence can be about or more than about 50%, 60%, 75%, 80%, 85%, 90%, 95%, 97.5%, 99%, or 100%; a guide or RNA or sgRNA can be about or more than about 5, 10, 11, 12, 13, 14, 15, 16, 17, 18, 19, 20, 21, 22, 23, 24, 25, 26, 27, 28, 29, 30, 35, 40, 45, 50, 75, or more nucleotides in length; or guide or RNA or sgRNA can be less than about 75, 50, 45, 40, 35, 30, 25, 20, 15, 12, or fewer nucleotides in length; and tracr RNA can be 30 or 50 nucleotides in length. In some embodiments, the degree of complementarity between a guide sequence and its corresponding target sequence is greater than 94.5% or 95% or 95.5% or 96% or 96.5% or 97% or 97.5% or 98% or 98.5% or 99% or 99.5% or 99.9%, or 100%. Off target is less than 100% or 99.9% or 99.5% or 99% or 99% or 98.5% or 98% or 97.5% or 97% or 96.5% or 96% or 95.5% or 95% or 94.5% or 94% or 93% or 92% or 91% or 90% or 89% or 88% or 87% or 86% or 85% or 84% or 83% or 82% or 81% or 80% complementarity between the sequence and the guide, with it advantageous that off target is 100% or 99.9% or 99.5% or 99% or 99% or 98.5% or 98% or 97.5% or 97% or 96.5% or 96% or 95.5% or 95% or 94.5% complementarity between the sequence and the guide.

In some embodiments according to the invention, the guide RNA (capable of guiding Cas to a target locus) may comprise (1) a guide sequence capable of hybridizing to a genomic target locus in the eukaryotic cell; (2) a tracr sequence; and (3) a tracr mate sequence. All (1) to (3) may reside in a single RNA, i.e., an sgRNA (arranged in a 5' to 3' orientation), or the tracr RNA may be a different RNA than the RNA containing the guide and tracr sequence. The tracr hybridizes to the tracr mate sequence and directs the CRISPR/Cas complex to the target sequence. Where the tracr RNA is on a different RNA than the RNA containing the guide and tracr sequence, the length of each RNA may be optimized to be shortened from their respective native lengths, and each may be independently chemically modified to protect from degradation by cellular RNase or otherwise increase stability.

Many modifications to guide sequences are known in the art and are further contemplated within the context of this invention. Various modifications may be used to increase the specificity of binding to the target sequence and/or increase the activity of the Cas protein and/or reduce off-target effects. Example guide sequence modifications are described in PCT US2019/045582, specifically paragraphs [0178]-[0333]. which is incorporated herein by reference.

Target Sequences, PAMs, and PFSs

Target Sequences

In the context of formation of a CRISPR complex, "target sequence" refers to a sequence to which a guide sequence is designed to have complementarity, where hybridization between a target sequence and a guide sequence promotes the formation of a CRISPR complex. A target sequence may comprise RNA polynucleotides. The term "target RNA" refers to an RNA polynucleotide being or comprising the target sequence. In other words, the target polynucleotide can be a polynucleotide or a part of a polynucleotide to which a part of the guide sequence is designed to have complementarity with and to which the effector function mediated by the complex comprising the CRISPR effector protein and a guide molecule is to be directed. In some embodiments, a target sequence is located in the nucleus or cytoplasm of a cell.

The guide sequence can specifically bind a target sequence in a target polynucleotide. The target polynucleotide may be DNA. The target polynucleotide may be RNA. The target polynucleotide can have one or more (e.g., 1, 2, 3, 4, 5, 6, 7, 8, 9, 10, etc. or more) target sequences. The target polynucleotide can be on a vector. The target polynucleotide can be genomic DNA. The target polynucleotide can be episomal. Other forms of the target polynucleotide are described elsewhere herein.

The target sequence may be DNA. The target sequence may be any RNA sequence. In some embodiments, the target sequence may be a sequence within an RNA molecule selected from the group consisting of messenger RNA (mRNA), pre-mRNA, ribosomal RNA (rRNA), transfer RNA (tRNA), micro-RNA (miRNA), small interfering RNA (siRNA), small nuclear RNA (snRNA), small nucleolar RNA (snoRNA), double stranded RNA (dsRNA), non-coding RNA (ncRNA), long non-coding RNA (lncRNA), and small cytoplasmatic RNA (scRNA). In some preferred embodiments, the target sequence (also referred to herein as a target polynucleotide) may be a sequence within an RNA molecule selected from the group consisting of mRNA, pre-mRNA, and rRNA. In some preferred embodiments, the target sequence may be a sequence within an RNA molecule selected from the group consisting of ncRNA, and lncRNA. In some more preferred embodiments, the target sequence may be a sequence within an mRNA molecule or a pre-mRNA molecule.

PAM and PFS Elements

PAM elements are sequences that can be recognized and bound by Cas proteins. Cas proteins/effector complexes can then unwind the dsDNA at a position adjacent to the PAM element. It will be appreciated that Cas proteins and systems that include them that target RNA do not require PAM sequences (Marraffini et al. 2010. Nature. 463:568-571). Instead, many rely on PFSs, which are discussed elsewhere herein. In certain embodiments, the target sequence should be associated with a PAM (protospacer adjacent motif) or PFS (protospacer flanking sequence or site), that is, a short sequence recognized by the CRISPR complex. Depending on the nature of the CRISPR-Cas protein, the target sequence should be selected, such that its complementary sequence in the DNA duplex (also referred to herein as the non-target sequence) is upstream or downstream of the PAM. In the embodiments, the complementary sequence of the target sequence is downstream or 3' of the PAM or upstream or 5' of the PAM. The precise sequence and length requirements for the PAM differ depending on the Cas protein used, but PAMs are typically 2-5 base pair sequences adjacent the protospacer (that is, the target sequence). Examples of the natural PAM sequences for different Cas proteins are provided herein below and the skilled person will be able to identify further PAM sequences for use with a given Cas protein.

The ability to recognize different PAM sequences depends on the Cas polypeptide(s) included in the system. See e.g., Gleditzsch et al. 2019. RNA Biology. 16(4):504-517. Table A below shows several Cas polypeptides and the PAM sequence they recognize.

TABLE A

Example PAM Sequences

| Cas Protein | PAM Sequence |
|---|---|
| SpCas9 | NGG/NRG |
| SaCas9 | NGRRT or NGRRN |
| NmeCas9 | NNNNGATT |
| CjCas9 | NNNNRYAC |
| StCas9 | NNAGAAW |
| Cas12a (Cpf1) (including LbCpf1 and AsCpf1) | TTTV |
| Cas12b (C2c1) | TTT, TTA, and TTC |
| Cas12c (C2c3) | TA |
| Cas12d (CasY) | TA |
| Cas12e (CasX) | 5'-TTCN-3' |

In a preferred embodiment, the CRISPR effector protein may recognize a 3' PAM. In certain embodiments, the CRISPR effector protein may recognize a 3' PAM which is 5'H, wherein His A, C or U.

Further, engineering of the PAM Interacting (PI) domain on the Cas protein may allow programing of PAM specificity, improve target site recognition fidelity, and increase the versatility of the CRISPR-Cas protein, for example as described for Cas9 in Kleinstiver B P et al. Engineered CRISPR-Cas9 nucleases with altered PAM specificities. Nature. 2015 Jul. 23; 523(7561):481-5. doi: 10.1038/nature14592. As further detailed herein, the skilled person will understand that Cas13 proteins may be modified analogously. Gao et al, "Engineered Cpf1 Enzymes with Altered PAM Specificities," bioRxiv 091611; doi: dx.doi.org/10.1101/091611 (Dec. 4, 2016). Doench et al. created a pool of sgRNAs, tiling across all possible target sites of a panel of six endogenous mouse and three endogenous human genes and quantitatively assessed their ability to produce null alleles of their target gene by antibody staining and flow cytometry. The authors showed that optimization of the PAM improved activity and also provided an on-line tool for designing sgRNAs.

PAM sequences can be identified in a polynucleotide using an appropriate design tool, which are commercially available as well as online. Such freely available tools include, but are not limited to, CRISPRFinder and CRISPRTarget. Mojica et al. 2009. Microbiol. 155 (Pt. 3): 733-740; Atschul et al. 1990. J. Mol. Biol. 215:403-410; Biswass et al. 2013 RNA Biol. 10:817-827; and Grissa et al. 2007. Nucleic Acid Res. 35: W52-57. Experimental approaches to PAM identification can include, but are not limited to, plasmid depletion assays (Jiang et al. 2013. Nat. Biotechnol. 31:233-239; Esvelt et al. 2013. Nat. Methods. 10:1116-1121; Kleinstiver et al. 2015. Nature. 523:481-485), screened by a high-throughput in vivo model called PAM-SCNAR (Pattanayak et al. 2013. Nat. Biotechnol. 31:839-843 and Leenay et al. 2016.Mol. Cell. 16:253), and negative screening (Zetsche et al. 2015. Cell. 163:759-771).

As previously mentioned, CRISPR-Cas systems that target RNA do not typically rely on PAM sequences. Instead such systems typically recognize protospacer flanking sites (PFSs) instead of PAMs Thus, Type VI CRISPR-Cas systems typically recognize protospacer flanking sites (PFSs) instead of PAMs. PFSs represents an analogue to PAMs for RNA targets. Type VI CRISPR-Cas systems employ a Cas13. Some Cas13 proteins analyzed to date, such as Cas13a (C2c2) identified from Leptotrichia shahii (LShCAs13a) have a specific discrimination against G at the 3'end of the target RNA. The presence of a C at the corresponding crRNA repeat site can indicate that nucleotide pairing at this position is rejected. However, some Cas13 proteins (e.g., LwaCAs13a and PspCas13b) do not seem to have a PFS preference. See e.g., Gleditzsch et al. 2019. RNA Biology. 16(4):504-517.

Some Type VI proteins, such as subtype B, have 5'-recognition of D (G, T, A) and a 3'-motif requirement of NAN or NNA. One example is the Cas13b protein identified in Bergeyella zoohelcum (BzCas13b). See e.g., Gleditzsch et al. 2019. RNA Biology. 16(4):504-517.

Overall Type VI CRISPR-Cas systems appear to have less restrictive rules for substrate (e.g., target sequence) recognition than those that target DNA (e.g., Type V and type II).

Zinc Finger Nucleases

In some embodiments, the polynucleotide is modified using a Zinc Finger nuclease or system thereof. One type of programmable DNA-binding domain is provided by artificial zinc-finger (ZF) technology, which involves arrays of ZF modules to target new DNA-binding sites in the genome. Each finger module in a ZF array targets three DNA bases. A customized array of individual zinc finger domains is assembled into a ZF protein (ZFP).

ZFPs can comprise a functional domain. The first synthetic zinc finger nucleases (ZFNs) were developed by fusing a ZF protein to the catalytic domain of the Type IIS restriction enzyme FokI. (Kim, Y. G. et al., 1994, Chimeric restriction endonuclease, Proc. Natl. Acad. Sci. U.S.A. 91, 883-887; Kim, Y. G. et al., 1996, Hybrid restriction enzymes: zinc finger fusions to Fok I cleavage domain. Proc. Natl. Acad. Sci. U.S.A. 93, 1156-1160). Increased cleavage specificity can be attained with decreased off target activity by use of paired ZFN heterodimers, each targeting different nucleotide sequences separated by a short spacer. (Doyon, Y. et al., 2011, Enhancing zinc-finger-nuclease activity with improved obligate heterodimeric architectures. Nat. Methods 8, 74-79). ZFPs can also be designed as transcription activators and repressors and have been used to target many genes in a wide variety of organisms. Exemplary methods of genome editing using ZFNs can be found for example in U.S. Pat. Nos. 6,534,261, 6,607,882, 6,746,838, 6,794,136, 6,824,978, 6,866,997, 6,933,113, 6,979,539, 7,013,219, 7,030,215, 7,220,719, 7,241,573, 7,241,574, 7,585,849, 7,595,376, 6,903,185, and 6,479,626, all of which are specifically incorporated by reference.

TALE Nucleases

In some embodiments, a TALE nuclease or TALE nuclease system can be used to modify a polynucleotide. In some embodiments, the methods provided herein use isolated, non-naturally occurring, recombinant or engineered DNA binding proteins that comprise TALE monomers or TALE monomers or half monomers as a part of their organizational structure that enable the targeting of nucleic acid sequences with improved efficiency and expanded specificity.

Naturally occurring TALEs or "wild type TALEs" are nucleic acid binding proteins secreted by numerous species of proteobacteria. TALE polypeptides contain a nucleic acid binding domain composed of tandem repeats of highly conserved monomer polypeptides that are predominantly 33, 34 or 35 amino acids in length and that differ from each other mainly in amino acid positions 12 and 13. In advantageous embodiments the nucleic acid is DNA. As used herein, the term "polypeptide monomers", "TALE monomers" or "monomers" will be used to refer to the highly conserved repetitive polypeptide sequences within the TALE nucleic acid binding domain and the term "repeat variable di-residues" or "RVD" will be used to refer to the highly variable amino acids at positions 12 and 13 of the polypeptide monomers. As provided throughout the disclosure, the amino acid residues of the RVD are depicted using the IUPAC single letter code for amino acids. A general representation of a TALE monomer which is comprised within the DNA binding domain is $X_{1-11}$-($X_{12}X_{13}$)-$X_{14-33}$ or 34 or 35, where the subscript indicates the amino acid position and X represents any amino acid. $X_{12}X_{13}$ indicate the RVDs. In some polypeptide monomers, the variable amino acid at position 13 is missing or absent and in such monomers, the RVD consists of a single amino acid. In such cases the RVD may be alternatively represented as X*, where X represents $X_{12}$ and (*) indicates that $X_{13}$ is absent. The DNA binding domain comprises several repeats of TALE monomers and this may be represented as ($X_{1-11}$-($X_{12}X_{13}$)-$X_{14-33}$ or 34 or $35)_z$, where in an advantageous embodiment, z is at least 5 to 40. In a further advantageous embodiment, z is at least 10 to 26.

The TALE monomers can have a nucleotide binding affinity that is determined by the identity of the amino acids in its RVD. For example, polypeptide monomers with an RVD of NI can preferentially bind to adenine (A), monomers with an RVD of NG can preferentially bind to thymine (T), monomers with an RVD of HD can preferentially bind to cytosine (C) and monomers with an RVD of NN can preferentially bind to both adenine (A) and guanine (G). In some embodiments, monomers with an RVD of IG can preferentially bind to T. Thus, the number and order of the polypeptide monomer repeats in the nucleic acid binding domain of a TALE determines its nucleic acid target specificity. In some embodiments, monomers with an RVD of NS can recognize all four base pairs and can bind to A, T, G or C. The structure and function of TALEs is further described in, for example, Moscou et al., Science 326:1501 (2009); Boch et al., Science 326:1509-1512 (2009); and Zhang et al., Nature Biotechnology 29:149-153 (2011).

The polypeptides used in methods of the invention can be isolated, non-naturally occurring, recombinant or engineered nucleic acid-binding proteins that have nucleic acid or DNA binding regions containing polypeptide monomer repeats that are designed to target specific nucleic acid sequences.

As described herein, polypeptide monomers having an RVD of HN or NH preferentially bind to guanine and thereby allow the generation of TALE polypeptides with high binding specificity for guanine containing target nucleic acid sequences. In some embodiments, polypeptide monomers having RVDs RN, NN, NK, SN, NH, KN, HN, NQ, HH, RG, KH, RH and SS can preferentially bind to guanine. In some embodiments, polypeptide monomers having RVDs RN, NK, NQ, HH, KH, RH, SS and SN can preferentially bind to guanine and can thus allow the generation of TALE polypeptides with high binding specificity for guanine containing target nucleic acid sequences. In some embodiments, polypeptide monomers having RVDs HH, KH, NH, NK, NQ, RH, RN and SS can preferentially bind to guanine and thereby allow the generation of TALE polypeptides with high binding specificity for guanine containing target nucleic acid sequences. In some embodiments, the RVDs that have high binding specificity for guanine are RN, NH RH and KH. Furthermore, polypeptide monomers having an RVD of NV can preferentially bind to adenine and guanine. In some embodiments, monomers having RVDs of H*, HA, KA, N*, NA, NC, NS, RA, and S* bind to adenine, guanine, cytosine and thymine with comparable affinity.

The predetermined N-terminal to C-terminal order of the one or more polypeptide monomers of the nucleic acid or DNA binding domain determines the corresponding predetermined target nucleic acid sequence to which the polypeptides of the invention will bind. As used herein the monomers and at least one or more half monomers are "specifically ordered to target" the genomic locus or gene of interest. In plant genomes, the natural TALE-binding sites always begin with a thymine (T), which may be specified by a cryptic signal within the non-repetitive N-terminus of the TALE polypeptide; in some cases, this region may be referred to as repeat 0. In animal genomes, TALE binding sites do not necessarily have to begin with a thymine (T) and polypeptides of the invention may target DNA sequences that begin with T, A, G or C. The tandem repeat of TALE monomers always ends with a half-length repeat or a stretch of sequence that may share identity with only the first 20 amino acids of a repetitive full-length TALE monomer and this half repeat may be referred to as a half-monomer. Therefore, it follows that the length of the nucleic acid or DNA being targeted is equal to the number of full monomers plus two.

As described in Zhang et al., Nature Biotechnology 29:149-153 (2011), TALE polypeptide binding efficiency may be increased by including amino acid sequences from the "capping regions" that are directly N-terminal or C-terminal of the DNA binding region of naturally occurring TALEs into the engineered TALEs at positions N-terminal or C-terminal of the engineered TALE DNA binding region. Thus, in certain embodiments, the TALE polypeptides described herein further comprise an N-terminal capping region and/or a C-terminal capping region.

An exemplary amino acid sequence of a N-terminal capping region is:

(SEQ ID NO: 3)
M D P I R S R T P S P A R E L L S G P Q P D G V Q
P T A D R G V S P P A G G P L D G L P A R R T M S
R T R L P S P P A P S P A F S A D S F S D L L R Q
F D P S L F N T S L F D S L P P F G A H H T E A A
T G E W D E V Q S G L R A A D A P P P T M R V A V
T A A R P P R A K P A P R R R A A Q P S D A S P A
A Q V D L R T L G Y S Q Q Q Q E K I K P K V R S T
V A Q H H E A L V G H G F T H A H I V A L S Q H P
A A L G T V A V K Y Q D M I A A L P E A T H E A I
V G V G K Q W S G A R A L E A L L T V A G E L R G
P P L Q L D T G Q L L K I A K R G G V T A V E A V
H A W R N A L T G A P L N

An exemplary amino acid sequence of a C-terminal capping region is:

(SEQ ID NO: 4)
R P A L E S I V A Q L S R P D P A L A A L T N D H
L V A L A C L G G R P A L D A V K K G L P H A P A
L I K R T N R R I P E R T S H R V A D H A Q V V R
V L G F F Q C H S H P A Q A F D D A M T Q F G M S
R H G L L Q L F R R V G V T E L E A R S G T L P P
A S Q R W D R I L Q A S G M K R A K P S P T S T Q
T P D Q A S L H A F A D S L E R D L D A P S P M H
E G D Q T R A S

As used herein the predetermined "N-terminus" to "C terminus" orientation of the N-terminal capping region, the DNA binding domain comprising the repeat TALE monomers and the C-terminal capping region provide structural basis for the organization of different domains in the d-TALEs or polypeptides of the invention.

The entire N-terminal and/or C-terminal capping regions are not necessary to enhance the binding activity of the DNA binding region. Therefore, in certain embodiments, fragments of the N-terminal and/or C-terminal capping regions are included in the TALE polypeptides described herein.

In certain embodiments, the TALE polypeptides described herein contain a N-terminal capping region fragment that included at least 10, 20, 30, 40, 50, 54, 60, 70, 80, 87, 90, 94, 100, 102, 110, 117, 120, 130, 140, 147, 150, 160, 170, 180, 190, 200, 210, 220, 230, 240, 250, 260 or 270 amino acids of an N-terminal capping region. In certain embodiments, the N-terminal capping region fragment amino acids are of the C-terminus (the DNA-binding region proximal end) of an N-terminal capping region. As described in Zhang et al., Nature Biotechnology 29:149-153 (2011), N-terminal capping region fragments that include the C-terminal 240 amino acids enhance binding activity equal to the full length capping region, while fragments that include the C-terminal 147 amino acids retain greater than 80% of the efficacy of the full length capping region, and fragments that include the C-terminal 117 amino acids retain greater than 50% of the activity of the full-length capping region.

In some embodiments, the TALE polypeptides described herein contain a C-terminal capping region fragment that included at least 6, 10, 20, 30, 37, 40, 50, 60, 68, 70, 80, 90, 100, 110, 120, 127, 130, 140, 150, 155, 160, 170, 180 amino acids of a C-terminal capping region. In certain embodiments, the C-terminal capping region fragment amino acids are of the N-terminus (the DNA-binding region proximal end) of a C-terminal capping region. As described in Zhang et al., Nature Biotechnology 29:149-153 (2011), C-terminal capping region fragments that include the C-terminal 68 amino acids enhance binding activity equal to the full-length capping region, while fragments that include the C-terminal 20 amino acids retain greater than 50% of the efficacy of the full-length capping region.

In certain embodiments, the capping regions of the TALE polypeptides described herein do not need to have identical sequences to the capping region sequences provided herein. Thus, in some embodiments, the capping region of the TALE polypeptides described herein have sequences that are at least 50%, 60%, 70%, 80%, 85%, 90%, 91%, 92%, 93%, 94%, 95%, 96%, 97%, 98% or 99% identical or share identity to the capping region amino acid sequences provided herein. Sequence identity is related to sequence homology. Homology comparisons may be conducted by eye, or more usually, with the aid of readily available sequence comparison programs. These commercially available computer programs may calculate percent (%) homology between two or more sequences and may also calculate the sequence identity shared by two or more amino acid or nucleic acid sequences. In some preferred embodiments, the capping region of the TALE polypeptides described herein have sequences that are at least 95% identical or share identity to the capping region amino acid sequences provided herein.

Sequence homologies can be generated by any of a number of computer programs known in the art, which include but are not limited to BLAST or FASTA. Suitable computer programs for carrying out alignments like the GCG Wisconsin Bestfit package may also be used. Once the software has produced an optimal alignment, it is possible to calculate % homology, preferably % sequence identity. The software typically does this as part of the sequence comparison and generates a numerical result.

In some embodiments described herein, the TALE polypeptides of the invention include a nucleic acid binding domain linked to the one or more effector domains. The terms "effector domain" or "regulatory and functional domain" refer to a polypeptide sequence that has an activity other than binding to the nucleic acid sequence recognized by the nucleic acid binding domain. By combining a nucleic acid binding domain with one or more effector domains, the polypeptides of the invention may be used to target the one or more functions or activities mediated by the effector domain to a particular target DNA sequence to which the nucleic acid binding domain specifically binds.

In some embodiments of the TALE polypeptides described herein, the activity mediated by the effector domain is a biological activity. For example, in some embodiments the effector domain is a transcriptional inhibitor (i.e., a repressor domain), such as an mSin interaction domain (SID). SID4X domain or a Krüppel-associated box (KRAB) or fragments of the KRAB domain. In some embodiments the effector domain is an enhancer of transcription (i.e. an activation domain), such as the VP16, VP64 or p65 activation domain. In some embodiments, the nucleic acid binding is linked, for example, with an effector domain that includes but is not limited to a transposase, integrase, recombinase, resolvase, invertase, protease, DNA methyltransferase, DNA demethylase, histone acetylase, histone deacetylase, nuclease, transcriptional repressor, transcriptional activator, transcription factor recruiting, protein nuclear-localization signal or cellular uptake signal.

In some embodiments, the effector domain is a protein domain which exhibits activities which include but are not limited to transposase activity, integrase activity, recombinase activity, resolvase activity, invertase activity, protease activity, DNA methyltransferase activity, DNA demethylase activity, histone acetylase activity, histone deacetylase activity, nuclease activity, nuclear-localization signaling activity, transcriptional repressor activity, transcriptional activator activity, transcription factor recruiting activity, or cellular uptake signaling activity. Other preferred embodiments of the invention may include any combination of the activities described herein.

Meganucleases

In some embodiments, a meganuclease or system thereof can be used to modify a polynucleotide. Meganucleases, which are endodeoxyribonucleases characterized by a large recognition site (double stranded DNA sequences of 12 to 40 base pairs). Exemplary methods for using meganucleases can be found in U.S. Pat. Nos. 8,163,514, 8,133,697, 8,021,867, 8,119,361, 8,119,381, 8,124,369, and 8,129,134, which are specifically incorporated by reference.

Sequences Related to Nucleus Targeting and Transportation

In some embodiments, one or more components (e.g., the Cas protein and/or deaminase, Zn Finger protein, TALE, or meganuclease) in the composition for engineering cells may comprise one or more sequences related to nucleus targeting and transportation. Such sequence may facilitate the one or more components in the composition for targeting a sequence within a cell. In order to improve targeting of the CRISPR-Cas protein and/or the nucleotide deaminase protein or catalytic domain thereof used in the methods of the present disclosure to the nucleus, it may be advantageous to provide one or both of these components with one or more nuclear localization sequences (NLSs).

In some embodiments, the NLSs used in the context of the present disclosure are heterologous to the proteins. Non-limiting examples of NLSs include an NLS sequence derived from: the NLS of the SV40 virus large T-antigen, having the amino acid sequence PKKKRKV (SEQ ID NO: 5) or PKKKRKVEAS (SEQ ID NO: 6); the NLS from nucleoplasmin (e.g., the nucleoplasmin bipartite NLS with the sequence KRPAATKKAGQAKKKK (SEQ ID NO: 7)); the c-myc NLS having the amino acid sequence PAAKRVKLD (SEQ ID NO: 8) or RQRRNELKRSP (SEQ ID NO: 9); hRNPA1 M9 NLS the having the sequence NQSSNFGPMKGGNFGGRSSGPYGGGGQYFAKPRNQGGY (SEQ ID NO: 10); the sequence RMRIZFKNKGKDTAELRRRRVEVSVELRKAKKDEQILKRRNV (SEQ ID NO: 11) of the IBB domain from importin-alpha; the sequences VSRKRPRP (SEQ ID NO: 12) and PPKKARED (SEQ ID NO: 13) of the myoma T protein; the sequence PQPKKKPL (SEQ ID NO: 14) of human p53; the sequence SALIKKKKKMAP (SEQ ID NO: 15) of mouse c-abl IV; the sequences DRLRR (SEQ ID NO: 16) and PKQKKRK (SEQ ID NO: 17) of the influenza virus NS1; the sequence RKLKKKIKKL (SEQ ID NO: 18) of the Hepatitis virus delta antigen; the sequence REKKKFLKRR (SEQ ID NO: 19) of the mouse Mx1 protein; the sequence KRKGDEVDGVDEVAKKKSKK (SEQ ID NO: 20) of the human poly (ADP-ribose) polymerase; and the sequence RKCLQAGMNLEARKTKK (SEQ ID NO: 21) of the steroid hormone receptors (human) glucocorticoid. In general, the one or more NLSs are of sufficient strength to drive accumulation of the DNA-targeting Cas protein in a detectable amount in the nucleus of a eukaryotic cell. In general, strength of nuclear localization activity may derive from the number of NLSs in the CRISPR-Cas protein, the particular NLS(s) used, or a combination of these factors. Detection of accumulation in the nucleus may be performed by any suitable technique. For example, a detectable marker may be fused to the nucleic acid-targeting protein, such that location within a cell may be visualized, such as in combination with a means for detecting the location of the nucleus (e.g., a stain specific for the nucleus such as DAPI). Cell nuclei may also be isolated from cells, the contents of which may then be analyzed by any suitable process for detecting protein, such as immunohistochemistry, Western blot, or enzyme activity assay. Accumulation in the nucleus may also be determined indirectly, such as by an assay for the effect of nucleic acid-targeting complex formation (e.g., assay for deaminase activity) at the target sequence, or assay for altered gene expression activity affected by DNA-targeting complex formation and/or DNA-targeting, as compared to a control not exposed to the CRISPR-Cas protein and deaminase protein, or exposed to a CRISPR-Cas and/or deaminase protein lacking the one or more NLSs.

The CRISPR-Cas and/or nucleotide deaminase proteins may be provided with 1 or more, such as with, 2, 3, 4, 5, 6, 7, 8, 9, 10, or more heterologous NLSs. In some embodiments, the proteins comprises about or more than about 1, 2, 3, 4, 5, 6, 7, 8, 9, 10, or more NLSs at or near the amino-terminus, about or more than about 1, 2, 3, 4, 5, 6, 7, 8, 9, 10, or more NLSs at or near the carboxy-terminus, or a combination of these (e.g., zero or at least one or more NLS at the amino-terminus and zero or at one or more NLS at the carboxy terminus). When more than one NLS is present, each may be selected independently of the others, such that a single NLS may be present in more than one copy and/or in combination with one or more other NLSs present in one or more copies. In some embodiments, an NLS is considered near the N- or C-terminus when the nearest amino acid of the NLS is within about 1, 2, 3, 4, 5, 10, 15, 20, 25, 30, 40, 50, or more amino acids along the polypeptide chain from the N- or C-terminus. In preferred embodiments of the CRISPR-Cas proteins, an NLS attached to the C-terminal of the protein.

In certain embodiments, the CRISPR-Cas protein and the deaminase protein are delivered to the cell or expressed within the cell as separate proteins. In these embodiments, each of the CRISPR-Cas and deaminase protein can be provided with one or more NLSs as described herein. In certain embodiments, the CRISPR-Cas and deaminase proteins are delivered to the cell or expressed with the cell as a fusion protein. In these embodiments one or both of the CRISPR-Cas and deaminase protein is provided with one or more NLSs. Where the nucleotide deaminase is fused to an adaptor protein (such as MS2) as described above, the one or more NLS can be provided on the adaptor protein, provided that this does not interfere with aptamer binding. In particular embodiments, the one or more NLS sequences may also function as linker sequences between the nucleotide deaminase and the CRISPR-Cas protein.

In certain embodiments, guides of the disclosure comprise specific binding sites (e.g. aptamers) for adapter proteins, which may be linked to or fused to an nucleotide deaminase or catalytic domain thereof. When such a guide forms a CRISPR complex (e.g., CRISPR-Cas protein binding to guide and target) the adapter proteins bind and, the nucleotide deaminase or catalytic domain thereof associated with the adapter protein is positioned in a spatial orientation which is advantageous for the attributed function to be effective.

The skilled person will understand that modifications to the guide which allow for binding of the adapter+nucleotide deaminase, but not proper positioning of the adapter+nucleotide deaminase (e.g. due to steric hindrance within the three dimensional structure of the CRISPR complex) are modifications which are not intended. The one or more modified guide may be modified at the tetra loop, the stem loop 1, stem loop 2, or stem loop 3, as described herein, preferably at either the tetra loop or stem loop 2, and in some cases at both the tetra loop and stem loop 2.

In some embodiments, a component (e.g., the dead Cas protein, the nucleotide deaminase protein or catalytic domain thereof, or a combination thereof) in the systems may comprise one or more nuclear export signals (NES), one or more nuclear localization signals (NLS), or any combinations thereof. In some cases, the NES may be an HIV Rev NES. In certain cases, the NES may be MAPK NES. When the component is a protein, the NES or NLS may be at the C terminus of component. Alternatively or additionally, the NES or NLS may be at the N terminus of component. In some examples, the Cas protein and optionally said nucleotide deaminase protein or catalytic domain thereof comprise one or more heterologous nuclear export signal(s) (NES(s)) or nuclear localization signal(s) (NLS(s)), preferably an HIV Rev NES or MAPK NES, preferably C-terminal.

Templates

In some embodiments, the composition for engineering cells comprise a template, e.g., a recombination template. A template may be a component of another vector as described herein, contained in a separate vector, or provided as a separate polynucleotide. In some embodiments, a recombination template is designed to serve as a template in homologous recombination, such as within or near a target sequence nicked or cleaved by a nucleic acid-targeting effector protein as a part of a nucleic acid-targeting complex.

In an embodiment, the template nucleic acid alters the sequence of the target position. In an embodiment, the template nucleic acid results in the incorporation of a modified, or non-naturally occurring base into the target nucleic acid.

The template sequence may undergo a breakage mediated or catalyzed recombination with the target sequence. In an embodiment, the template nucleic acid may include sequence that corresponds to a site on the target sequence that is cleaved by a Cas protein mediated cleavage event. In an embodiment, the template nucleic acid may include sequence that corresponds to both, a first site on the target sequence that is cleaved in a first Cas protein mediated event, and a second site on the target sequence that is cleaved in a second Cas protein mediated event.

In certain embodiments, the template nucleic acid can include sequence which results in an alteration in the coding sequence of a translated sequence, e.g., one which results in the substitution of one amino acid for another in a protein product, e.g., transforming a mutant allele into a wild type allele, transforming a wild type allele into a mutant allele, and/or introducing a stop codon, insertion of an amino acid residue, deletion of an amino acid residue, or a nonsense mutation. In certain embodiments, the template nucleic acid can include sequence which results in an alteration in a non-coding sequence, e.g., an alteration in an exon or in a 5' or 3' non-translated or non-transcribed region. Such alterations include an alteration in a control element, e.g., a promoter, enhancer, and an alteration in a cis-acting or trans-acting control element.

A template nucleic acid having homology with a target position in a target gene may be used to alter the structure of a target sequence. The template sequence may be used to alter an unwanted structure, e.g., an unwanted or mutant nucleotide. The template nucleic acid may include sequence which, when integrated, results in: decreasing the activity of a positive control element; increasing the activity of a positive control element; decreasing the activity of a negative control element; increasing the activity of a negative control element; decreasing the expression of a gene; increasing the expression of a gene; increasing resistance to a disorder or disease; increasing resistance to viral entry; correcting a mutation or altering an unwanted amino acid residue conferring, increasing, abolishing or decreasing a biological property of a gene product, e.g., increasing the enzymatic activity of an enzyme, or increasing the ability of a gene product to interact with another molecule.

The template nucleic acid may include sequence which results in: a change in sequence of 1, 2, 3, 4, 5, 6, 7, 8, 9, 10, 1 1, 12 or more nucleotides of the target sequence.

A template polynucleotide may be of any suitable length, such as about or more than about 10, 15, 20, 25, 50, 75, 100, 150, 200, 500, 1000, or more nucleotides in length. In an embodiment, the template nucleic acid may be 20+/−10, 30+/−10, 40+/−10, 50+/−10, 60+/−10, 70+/−10, 80+/−10, 90+/−10, 100+/−10, 1 10+/−10, 120+/−10, 130+/−10, 140+/−10, 150+/−10, 160+/−10, 170+/−10, 1 80+/−10, 190+/−10, 200+/−10, 210+/−10, of 220+/−10 nucleotides in length. In an embodiment, the template nucleic acid may be 30+/−20, 40+/−20, 50+/−20, 60+/−20, 70+/−20, 80+/−20, 90+/−20, 100+/−20, 1 10+/−20, 120+/−20, 130+/−20, 140+/−20, 150+/−20, 160+/−20, 170+/−20, 180+/−20, 190+/−20, 200+/−20, 210+/−20, of 220+/−20 nucleotides in length. In an embodiment, the template nucleic acid is 10 to 1,000, 20 to 900, 30 to 800, 40 to 700, 50 to 600, 50 to 500, 50 to 400, 50 to 300, 50 to 200, or 50 to 100 nucleotides in length.

In some embodiments, the template polynucleotide is complementary to a portion of a polynucleotide comprising the target sequence. When optimally aligned, a template polynucleotide might overlap with one or more nucleotides of a target sequences (e.g. about or more than about 1, 5, 10, 15, 20, 25, 30, 35, 40, 45, 50, 60, 70, 80, 90, 100 or more nucleotides). In some embodiments, when a template sequence and a polynucleotide comprising a target sequence are optimally aligned, the nearest nucleotide of the template polynucleotide is within about 1, 5, 10, 15, 20, 25, 50, 75, 100, 200, 300, 400, 500, 1000, 5000, 10000, or more nucleotides from the target sequence.

The exogenous polynucleotide template comprises a sequence to be integrated (e.g., a mutated gene). The sequence for integration may be a sequence endogenous or exogenous to the cell. Examples of a sequence to be integrated include polynucleotides encoding a protein or a non-coding RNA (e.g., a microRNA). Thus, the sequence for integration may be operably linked to an appropriate control sequence or sequences. Alternatively, the sequence to be integrated may provide a regulatory function.

An upstream or downstream sequence may comprise from about 20 bp to about 2500 bp, for example, about 50, 100, 200, 300, 400, 500, 600, 700, 800, 900, 1000, 1100, 1200, 1300, 1400, 1500, 1600, 1700, 1800, 1900, 2000, 2100, 2200, 2300, 2400, or 2500 bp. In some methods, the exemplary upstream or downstream sequence have about 200 bp to about 2000 bp, about 600 bp to about 1000 bp, or more particularly about 700 bp to about 1000.

An upstream or downstream sequence may comprise from about 20 bp to about 2500 bp, for example, about 50, 100, 200, 300, 400, 500, 600, 700, 800, 900, 1000, 1100, 1200, 1300, 1400, 1500, 1600, 1700, 1800, 1900, 2000, 2100, 2200, 2300, 2400, or 2500 bp. In some methods, the exemplary upstream or downstream sequence have about 200 bp to about 2000 bp, about 600 bp to about 1000 bp, or more particularly about 700 bp to about 1000

In certain embodiments, one or both homology arms may be shortened to avoid including certain sequence repeat elements. For example, a 5' homology arm may be shortened to avoid a sequence repeat element. In other embodiments, a 3' homology arm may be shortened to avoid a sequence repeat element. In some embodiments, both the 5' and the 3' homology arms may be shortened to avoid including certain sequence repeat elements.

In some methods, the exogenous polynucleotide template may further comprise a marker. Such a marker may make it easy to screen for targeted integrations. Examples of suitable markers include restriction sites, fluorescent proteins, or selectable markers. The exogenous polynucleotide template of the disclosure can be constructed using recombinant techniques (see, for example, Sambrook et al., 2001 and Ausubel et al., 1996).

In certain embodiments, a template nucleic acid for correcting a mutation may be designed for use as a single-stranded oligonucleotide. When using a single-stranded oligonucleotide, 5' and 3' homology arms may range up to about 200 base pairs (bp) in length, e.g., at least 25, 50, 75, 100, 125, 150, 175, or 200 bp in length.

In certain embodiments, a template nucleic acid for correcting a mutation may be designed for use with a homology-independent targeted integration system. Suzuki et al. describe in vivo genome editing via CRISPR/Cas9 mediated homology-independent targeted integration (2016, Nature 540:144-149). Schmid-Burgk, et al. describe use of the CRISPR-Cas9 system to introduce a double-strand break (DSB) at a user-defined genomic location and insertion of a universal donor DNA (Nat Commun. 2016 Jul. 28; 7:12338). Gao, et al. describe "Plug-and-Play Protein Modification Using Homology-Independent Universal Genome Engineering" (Neuron. 2019 Aug. 21; 103(4):583-597).

RNAi

In some embodiments, the genetic modulating agents may be interfering RNAs. In certain embodiments, diseases caused by a dominant mutation in a gene is targeted by silencing the mutated gene using RNAi. In some cases, the nucleotide sequence may comprise coding sequence for one or more interfering RNAs. In certain examples, the nucleotide sequence may be interfering RNA (RNAi). As used herein, the term "RNAi" refers to any type of interfering RNA, including but not limited to, siRNAi, shRNAi, endogenous microRNA and artificial microRNA. For instance, it includes sequences previously identified as siRNA, regardless of the mechanism of down-stream processing of the RNA (i.e. although siRNAs are believed to have a specific method of in vivo processing resulting in the cleavage of mRNA, such sequences can be incorporated into the vectors in the context of the flanking sequences described herein). The term "RNAi" can include both gene silencing RNAi molecules, and also RNAi effector molecules which activate the expression of a gene.

In certain embodiments, a modulating agent may comprise silencing one or more endogenous genes. As used herein, "gene silencing" or "gene silenced" in reference to an activity of an RNAi molecule, for example a siRNA or miRNA refers to a decrease in the mRNA level in a cell for a target gene by at least about 5%, about 10%, about 20%, about 30%, about 40%, about 50%, about 60%, about 70%, about 80%, about 90%, about 95%, about 99%, about 100% of the mRNA level found in the cell without the presence of the miRNA or RNA interference molecule. In one preferred embodiment, the mRNA levels are decreased by at least about 70%, about 80%, about 90%, about 95%, about 99%, about 100%.

As used herein, a "siRNA" refers to a nucleic acid that forms a double stranded RNA, which double stranded RNA has the ability to reduce or inhibit expression of a gene or target gene when the siRNA is present or expressed in the same cell as the target gene. The double stranded RNA siRNA can be formed by the complementary strands. In one embodiment, a siRNA refers to a nucleic acid that can form a double stranded siRNA. The sequence of the siRNA can correspond to the full-length target gene, or a subsequence thereof. Typically, the siRNA is at least about 15-50 nucleotides in length (e.g., each complementary sequence of the double stranded siRNA is about 15-50 nucleotides in length, and the double stranded siRNA is about 15-50 base pairs in length, preferably about 19-30 base nucleotides, preferably about 20-25 nucleotides in length, e.g., 20, 21, 22, 23, 24, 25, 26, 27, 28, 29, or 30 nucleotides in length).

As used herein "shRNA" or "small hairpin RNA" (also called stem loop) is a type of siRNA. In one embodiment, these shRNAs are composed of a short, e.g. about 19 to about 25 nucleotide, antisense strand, followed by a nucleotide loop of about 5 to about 9 nucleotides, and the analogous sense strand. Alternatively, the sense strand can precede the nucleotide loop structure and the antisense strand can follow.

The terms "microRNA" or "miRNA", used interchangeably herein, are endogenous RNAs, some of which are known to regulate the expression of protein-coding genes at the posttranscriptional level. Endogenous microRNAs are small RNAs naturally present in the genome that are capable of modulating the productive utilization of mRNA. The term artificial microRNA includes any type of RNA sequence, other than endogenous microRNA, which is capable of modulating the productive utilization of mRNA. MicroRNA sequences have been described in publications such as Lim, et al., Genes & Development, 17, p. 991-1008 (2003), Lim et al Science 299, 1540 (2003), Lee and Ambros Science, 294, 862 (2001), Lau et al., Science 294, 858-861 (2001), Lagos-Quintana et al, Current Biology, 12, 735-739 (2002), Lagos Quintana et al, Science 294, 853-857 (2001), and Lagos-Quintana et al, RNA, 9, 175-179 (2003), which are incorporated by reference. Multiple microRNAs can also be incorporated into a precursor molecule. Furthermore, miRNA-like stem-loops can be expressed in cells as a vehicle to deliver artificial miRNAs and short interfering RNAs (siRNAs) for the purpose of modulating the expression of endogenous genes through the miRNA and/or RNAi pathways.

As used herein, "double stranded RNA" or "dsRNA" refers to RNA molecules that are comprised of two strands. Double stranded molecules include those comprised of a single RNA molecule that doubles back on itself to form a two-stranded structure. For example, the stem loop structure of the progenitor molecules from which the single-stranded miRNA is derived, called the pre-miRNA (Bartel et al. 2004. Cell 1 16:281-297), comprises a dsRNA molecule.

Antibodies

In certain embodiments, the one or more agents is an antibody. The term "antibody" is used interchangeably with the term "immunoglobulin" herein, and includes intact antibodies, fragments of antibodies, e.g., Fab, F(ab') 2 fragments, and intact antibodies and fragments that have been mutated either in their constant and/or variable region (e.g., mutations to produce chimeric, partially humanized, or fully humanized antibodies, as well as to produce antibodies with a desired trait, e.g., enhanced binding and/or reduced FcR binding). The term "fragment" refers to a part or portion of an antibody or antibody chain comprising fewer amino acid residues than an intact or complete antibody or antibody chain. Fragments can be obtained via chemical or enzymatic treatment of an intact or complete antibody or antibody chain. Fragments can also be obtained by recombinant means. Exemplary fragments include Fab, Fab', F(ab') 2, Fabc, Fd, dAb, $V_{HH}$ and scFv and/or Fv fragments.

As used herein, a preparation of antibody protein having less than about 50% of non-antibody protein (also referred to herein as a "contaminating protein"), or of chemical precursors, is considered to be "substantially free." 40%, 30%, 20%, 10% and more preferably 5% (by dry weight), of non-antibody protein, or of chemical precursors is considered to be substantially free. When the antibody protein or biologically active portion thereof is recombinantly produced, it is also preferably substantially free of culture medium, i.e., culture medium represents less than about 30%, preferably less than about 20%, more preferably less than about 10%, and most preferably less than about 5% of the volume or mass of the protein preparation.

The term "antigen-binding fragment" refers to a polypeptide fragment of an immunoglobulin or antibody that binds antigen or competes with intact antibody (i.e., with the intact antibody from which they were derived) for antigen binding (i.e., specific binding). As such these antibodies or fragments thereof are included in the scope of the invention, provided that the antibody or fragment binds specifically to a target molecule.

It is intended that the term "antibody" encompass any Ig class or any Ig subclass (e.g. the IgG1, IgG2, IgG3, and IgG4 subclasses of IgG) obtained from any source (e.g., humans and non-human primates, and in rodents, lagomorphs, caprines, bovines, equines, ovines, etc.).

The term "Ig class" or "immunoglobulin class", as used herein, refers to the five classes of immunoglobulin that have been identified in humans and higher mammals, IgG, IgM, IgA, IgD, and IgE. The term "Ig subclass" refers to the two subclasses of IgM (H and L), three subclasses of IgA (IgA1, IgA2, and secretory IgA), and four subclasses of IgG (IgG1, IgG2, IgG3, and IgG4) that have been identified in humans and higher mammals. The antibodies can exist in monomeric or polymeric form; for example, IgM antibodies exist in pentameric form, and IgA antibodies exist in monomeric, dimeric or multimeric form.

The term "IgG subclass" refers to the four subclasses of immunoglobulin class IgG-IgG1, IgG2, IgG3, and IgG4 that have been identified in humans and higher mammals by the heavy chains of the immunoglobulins, V1-14, respectively. The term "single-chain immunoglobulin" or "single-chain antibody" (used interchangeably herein) refers to a protein having a two-polypeptide chain structure consisting of a heavy and a light chain, said chains being stabilized, for example, by interchain peptide linkers, which has the ability to specifically bind antigen. The term "domain" refers to a globular region of a heavy or light chain polypeptide comprising peptide loops (e.g., comprising 3 to 4 peptide loops) stabilized, for example, by β pleated sheet and/or intrachain disulfide bond. Domains are further referred to herein as "constant" or "variable", based on the relative lack of sequence variation within the domains of various class members in the case of a "constant" domain, or the significant variation within the domains of various class members in the case of a "variable" domain. Antibody or polypeptide "domains" are often referred to interchangeably in the art as antibody or polypeptide "regions". The "constant" domains of an antibody light chain are referred to interchangeably as "light chain constant regions", "light chain constant domains", "CL" regions or "CL" domains. The "constant" domains of an antibody heavy chain are referred to interchangeably as "heavy chain constant regions", "heavy chain constant domains", "CH" regions or "CH" domains. The "variable" domains of an antibody light chain are referred to interchangeably as "light chain variable regions", "light chain variable domains", "VL" regions or "VL" domains. The "variable" domains of an antibody heavy chain are referred to interchangeably as "heavy chain constant regions", "heavy chain constant domains", "VH" regions or "VH" domains.

The term "region" can also refer to a part or portion of an antibody chain or antibody chain domain (e.g., a part or portion of a heavy or light chain or a part or portion of a constant or variable domain, as defined herein), as well as more discrete parts or portions of said chains or domains. For example, light and heavy chains or light and heavy chain variable domains include "complementarity determining regions" or "CDRs" interspersed among "framework regions" or "FRs", as defined herein.

The term "conformation" refers to the tertiary structure of a protein or polypeptide (e.g., an antibody, antibody chain, domain or region thereof). For example, the phrase "light (or heavy) chain conformation" refers to the tertiary structure of a light (or heavy) chain variable region, and the phrase "antibody conformation" or "antibody fragment conformation" refers to the tertiary structure of an antibody or fragment thereof.

The term "antibody-like protein scaffolds" or "engineered protein scaffolds" broadly encompasses proteinaceous non-immunoglobulin specific-binding agents, typically obtained by combinatorial engineering (such as site-directed random mutagenesis in combination with phage display or other molecular selection techniques). Usually, such scaffolds are derived from robust and small soluble monomeric proteins (such as Kunitz inhibitors or lipocalins) or from a stably folded extra-membrane domain of a cell surface receptor (such as protein A, fibronectin or the ankyrin repeat).

Such scaffolds have been extensively reviewed in Binz et al. (Engineering novel binding proteins from nonimmunoglobulin domains. Nat Biotechnol 2005, 23:1257-1268), Gebauer and Skerra (Engineered protein scaffolds as next-generation antibody therapeutics. Curr Opin Chem Biol. 2009, 13:245-55), Gill and Damle (Biopharmaceutical drug discovery using novel protein scaffolds. Curr Opin Biotechnol 2006, 17:653-658), Skerra (Engineered protein scaffolds for molecular recognition. J Mol Recognit 2000, 13:167-187), and Skerra (Alternative non-antibody scaffolds for molecular recognition. Curr Opin Biotechnol 2007, 18:295-304), and include without limitation affibodies, based on the Z-domain of staphylococcal protein A, a three-helix bundle of 58 residues providing an interface on two of its alphahelices (Nygren, Alternative binding proteins: Affibody binding proteins developed from a small three-helix bundle scaffold. FEBS J 2008, 275:2668-2676); engineered Kunitz domains based on a small (ca. 58 residues) and robust, disulphide-crosslinked serine protease inhibitor, typically of human origin (e.g. LACI-D1), which can be engineered for different protease specificities (Nixon and Wood, Engineered protein inhibitors of proteases. Curr Opin Drug Discov Dev 2006, 9:261-268); monobodies or adnectins based on the 10th extracellular domain of human fibronectin III (10Fn3), which adopts an Ig-like beta-sandwich fold (94 residues) with 2-3 exposed loops, but lacks the central disulphide bridge (Koide and Koide, Monobodies: antibody mimics based on the scaffold of the fibronectin type III domain. Methods Mol Biol 2007, 352:95-109); anticalins derived from the lipocalins, a diverse family of eight-stranded beta-barrel proteins (ca. 180 residues) that naturally form binding sites for small ligands by means of four structurally variable loops at the open end, which are abundant in humans, insects, and many other organisms (Skerra, Alternative binding proteins: Anticalins—harnessing the structural plasticity of the lipocalin ligand pocket to engineer novel binding activities. FEBS J 2008, 275:2677-2683); DARPins, designed ankyrin repeat domains (166 residues), which provide a rigid interface arising from typically three repeated beta-turns (Stumpp et al., DARPins: a new generation of protein therapeutics. Drug Discov Today 2008, 13:695-701); avimers (multimerized LDLR-A module) (Silverman et al., Multivalent avimer proteins evolved by exon shuffling of a family of human receptor domains. Nat Biotechnol 2005, 23:1556-1561); and cysteine-rich knottin peptides (Kolmar, Alternative binding proteins: biological activity and therapeutic potential of cystine-knot miniproteins. FEBS J 2008, 275:2684-2690).

"Specific binding" of an antibody means that the antibody exhibits appreciable affinity for a particular antigen or epitope and, generally, does not exhibit significant cross reactivity. "Appreciable" binding includes binding with an affinity of at least 25 μM. Antibodies with affinities greater than $1\times10^{7}$ $M^{-1}$ (or a dissociation coefficient of 1 μM or less or a dissociation coefficient of 1 nm or less) typically bind with correspondingly greater specificity. Values intermediate of those set forth herein are also intended to be within the scope of the present invention and antibodies of the invention bind with a range of affinities, for example, 100 nM or less, 75 nM or less, 50 nM or less, 25 nM or less, for example 10 nM or less, 5 nM or less, 1 nM or less, or in embodiments 500 μM or less, 100 μM or less, 50 μM or less or 25 μM or less. An antibody that "does not exhibit significant crossreactivity" is one that will not appreciably bind to an entity other than its target (e.g., a different epitope or a different molecule). For example, an antibody that specifically binds to a target molecule will appreciably bind the target molecule but will not significantly react with non-target molecules or peptides. An antibody specific for a particular epitope will, for example, not significantly cross-react with remote epitopes on the same protein or peptide. Specific binding can be determined according to any art-recognized means for determining such binding. Preferably, specific binding is determined according to Scatchard analysis and/or competitive binding assays.

As used herein, the term "affinity" refers to the strength of the binding of a single antigen-combining site with an antigenic determinant. Affinity depends on the closeness of stereochemical fit between antibody combining sites and antigen determinants, on the size of the area of contact between them, on the distribution of charged and hydrophobic groups, etc. Antibody affinity can be measured by equilibrium dialysis or by the kinetic BIACORE™ method. The dissociation constant, Kd, and the association constant, Ka, are quantitative measures of affinity.

As used herein, the term "monoclonal antibody" refers to an antibody derived from a clonal population of antibody-producing cells (e.g., B lymphocytes or B cells) which is homogeneous in structure and antigen specificity. The term "polyclonal antibody" refers to a plurality of antibodies originating from different clonal populations of antibody-producing cells which are heterogeneous in their structure and epitope specificity but which recognize a common antigen. Monoclonal and polyclonal antibodies may exist within bodily fluids, as crude preparations, or may be purified, as described herein.

The term "binding portion" of an antibody (or "antibody portion") includes one or more complete domains, e.g., a pair of complete domains, as well as fragments of an antibody that retain the ability to specifically bind to a target molecule. It has been shown that the binding function of an antibody can be performed by fragments of a full-length antibody. Binding fragments are produced by recombinant DNA techniques, or by enzymatic or chemical cleavage of intact immunoglobulins. Binding fragments include Fab, Fab', F(ab') 2, Fabc, Fd, dAb, Fv, single chains, single-chain antibodies, e.g., scFv, and single domain antibodies.

"Humanized" forms of non-human (e.g., murine) antibodies are chimeric antibodies that contain minimal sequence derived from non-human immunoglobulin. For the most part, humanized antibodies are human immunoglobulins (recipient antibody) in which residues from a hypervariable region of the recipient are replaced by residues from a hypervariable region of a non-human species (donor antibody) such as mouse, rat, rabbit or nonhuman primate having the desired specificity, affinity, and capacity. In some instances, FR residues of the human immunoglobulin are replaced by corresponding non-human residues. Furthermore, humanized antibodies may comprise residues that are not found in the recipient antibody or in the donor antibody. These modifications are made to further refine antibody performance. In general, the humanized antibody will comprise substantially all of at least one, and typically two, variable domains, in which all or substantially all of the hypervariable regions correspond to those of a non-human immunoglobulin and all or substantially all of the FR regions are those of a human immunoglobulin sequence. The humanized antibody optionally also will comprise at least a portion of an immunoglobulin constant region (Fc), typically that of a human immunoglobulin.

Examples of portions of antibodies or epitope-binding proteins encompassed by the present definition include: (i) the Fab fragment, having $V_L$, $C_L$, $V_H$ and CH1 domains; (ii) the Fab' fragment, which is a Fab fragment having one or more cysteine residues at the C-terminus of the CHI domain; (iii) the Fd fragment having $V_H$ and $C_H1$ domains; (iv) the Fd' fragment having $V_H$ and CHI domains and one or more cysteine residues at the C-terminus of the CH1 domain; (v) the Fv fragment having the $V_L$ and $V_H$ domains of a single arm of an antibody; (vi) the dAb fragment (Ward et al., 341 Nature 544 (1989)) which consists of a $V_H$ domain or a $V_L$ domain that binds antigen; (vii) isolated CDR regions or isolated CDR regions presented in a functional framework; (viii) F(ab') 2 fragments which are bivalent fragments including two Fab' fragments linked by a disulphide bridge at the hinge region; (ix) single chain antibody molecules (e.g., single chain Fv; scFv) (Bird et al., 242 Science 423 (1988); and Huston et al., 85 PNAS 5879 (1988)); (x)

"diabodies" with two antigen binding sites, comprising a heavy chain variable domain ($V_H$) connected to a light chain variable domain ($V_L$) in the same polypeptide chain (see, e.g., EP 404,097; WO 93/11161; Hollinger et al., 90 PNAS 6444 (1993)); (xi) "linear antibodies" comprising a pair of tandem Fd segments ($V_H$-$C_h$1-$V_H$-$C_h$1) which, together with complementary light chain polypeptides, form a pair of antigen binding regions (Zapata et al., Protein Eng. 8(10): 1057-62 (1995); and U.S. Pat. No. 5,641,870).

As used herein, a "blocking" antibody or an antibody "antagonist" is one which inhibits or reduces biological activity of the antigen(s) it binds. In certain embodiments, the blocking antibodies or antagonist antibodies or portions thereof described herein completely inhibit the biological activity of the antigen(s).

Antibodies may act as agonists or antagonists of the recognized polypeptides. For example, the present invention includes antibodies which disrupt receptor/ligand interactions either partially or fully. The invention features both receptor-specific antibodies and ligand-specific antibodies. The invention also features receptor-specific antibodies which do not prevent ligand binding but prevent receptor activation. Receptor activation (i.e., signaling) may be determined by techniques described herein or otherwise known in the art. For example, receptor activation can be determined by detecting the phosphorylation (e.g., tyrosine or serine/threonine) of the receptor or of one of its down-stream substrates by immunoprecipitation followed by western blot analysis. In specific embodiments, antibodies are provided that inhibit ligand activity or receptor activity by at least 95%, at least 90%, at least 85%, at least 80%, at least 75%, at least 70%, at least 60%, or at least 50% of the activity in absence of the antibody.

The invention also features receptor-specific antibodies which both prevent ligand binding and receptor activation as well as antibodies that recognize the receptor-ligand complex. Likewise, encompassed by the invention are neutralizing antibodies which bind the ligand and prevent binding of the ligand to the receptor, as well as antibodies which bind the ligand, thereby preventing receptor activation, but do not prevent the ligand from binding the receptor. Further included in the invention are antibodies which activate the receptor. These antibodies may act as receptor agonists, i.e., potentiate or activate either all or a subset of the biological activities of the ligand-mediated receptor activation, for example, by inducing dimerization of the receptor. The antibodies may be specified as agonists, antagonists or inverse agonists for biological activities comprising the specific biological activities of the peptides disclosed herein. The antibody agonists and antagonists can be made using methods known in the art. See, e.g., PCT publication WO 96/40281; U.S. Pat. No. 5,811,097; Deng et al., Blood 92(6):1981-1988 (1998); Chen et al., Cancer Res. 58(16): 3668-3678 (1998); Harrop et al., J. Immunol. 161(4):1786-1794 (1998); Zhu et al., Cancer Res. 58(15):3209-3214 (1998); Yoon et al., J. Immunol. 160(7):3170-3179 (1998); Prat et al., J. Cell. Sci. III (Pt2): 237-247 (1998); Pitard et al., J. Immunol. Methods 205(2):177-190 (1997); Liautard et al., Cytokine 9(4):233-241 (1997); Carlson et al., J. Biol. Chem. 272(17):11295-11301 (1997); Taryman et al., Neuron 14(4): 755-762 (1995); Muller et al., Structure 6(9):1153-1167 (1998); Bartunek et al., Cytokine 8(1):14-20 (1996).

The antibodies as defined for the present invention include derivatives that are modified, i.e., by the covalent attachment of any type of molecule to the antibody, such that covalent attachment does not prevent the antibody from generating an anti-idiotypic response. For example, but not by way of limitation, the antibody derivatives include antibodies that have been modified, e.g., by glycosylation, acetylation, pegylation, phosphorylation, amidation, derivatization by known protecting/blocking groups, proteolytic cleavage, linkage to a cellular ligand or other protein, etc. Any of numerous chemical modifications may be carried out by known techniques, including, but not limited to specific chemical cleavage, acetylation, formylation, metabolic synthesis of tunicamycin, etc. Additionally, the derivative may contain one or more non-classical amino acids.

Simple binding assays can be used to screen for or detect agents that bind to a target protein, or disrupt the interaction between proteins (e.g., a receptor and a ligand). Because certain targets of the present invention are transmembrane proteins, assays that use the soluble forms of these proteins rather than full-length protein can be used, in some embodiments. Soluble forms include, for example, those lacking the transmembrane domain and/or those comprising the IgV domain or fragments thereof which retain their ability to bind their cognate binding partners. Further, agents that inhibit or enhance protein interactions for use in the compositions and methods described herein, can include recombinant peptido-mimetics.

Detection methods useful in screening assays include antibody-based methods, detection of a reporter moiety, detection of cytokines as described herein, and detection of a gene signature as described herein.

Another variation of assays to determine binding of a receptor protein to a ligand protein is through the use of affinity biosensor methods. Such methods may be based on the piezoelectric effect, electrochemistry, or optical methods, such as ellipsometry, optical wave guidance, and surface plasmon resonance (SPR).

Bi-Specific Antibodies

In certain embodiments, the one or more therapeutic agents can be bi-specific antigen-binding constructs, e.g., bi-specific antibodies (bsAb) or BiTEs, that bind two antigens (see, e.g., Suurs et al., A review of bispecific antibodies and antibody constructs in oncology and clinical challenges. Pharmacol Ther. 2019 September; 201:103-119; and Huehls, et al., Bispecific T cell engagers for cancer immunotherapy. Immunol Cell Biol. 2015 March; 93(3): 290-296). The bi-specific antigen-binding construct includes two antigen-binding polypeptide constructs, e.g., antigen binding domains, wherein at least one polypeptide construct specifically binds to a surface protein. In some embodiments, the antigen-binding construct is derived from known antibodies or antigen-binding constructs. In some embodiments, the antigen-binding polypeptide constructs comprise two antigen binding domains that comprise antibody fragments. In some embodiments, the first antigen binding domain and second antigen binding domain each independently comprises an antibody fragment selected from the group of: an scFv, a Fab, and an Fc domain. The antibody fragments may be the same format or different formats from each other. For example, in some embodiments, the antigen-binding polypeptide constructs comprise a first antigen binding domain comprising an scFv and a second antigen binding domain comprising a Fab. In some embodiments, the antigen-binding polypeptide constructs comprise a first antigen binding domain and a second antigen binding domain, wherein both antigen binding domains comprise an scFv. In some embodiments, the first and second antigen binding domains each comprise a Fab. In some embodiments, the first and second antigen binding domains each comprise an Fc domain. Any combination of antibody formats is suitable for the bi-specific antibody constructs disclosed herein.

In certain embodiments, cells are targeted with a bsAb having affinity for both the cell and a payload (e.g., a neuropeptide). In certain embodiments, the bispecific antibody brings endogenous neuropeptides to specific cell types by binding to a cell specific surface marker. In certain embodiments, two targets are disrupted on a cell by the bsAb (e.g., two surface markers). By means of an example, an agent, such as a bi-specific antibody, specifically binds to a gene product expressed on the cell surface of sensory neurons or immune cells.

Aptamers

In certain embodiments, the one or more agents is an aptamer. Nucleic acid aptamers are nucleic acid species that have been engineered through repeated rounds of in vitro selection or equivalently, SELEX (systematic evolution of ligands by exponential enrichment) to bind to various molecular targets such as small molecules, proteins, nucleic acids, cells, tissues and organisms. Nucleic acid aptamers have specific binding affinity to molecules through interactions other than classic Watson-Crick base pairing. Aptamers are useful in biotechnological and therapeutic applications as they offer molecular recognition properties similar to antibodies. In addition to their discriminate recognition, aptamers offer advantages over antibodies as they can be engineered completely in a test tube, are readily produced by chemical synthesis, possess desirable storage properties, and elicit little or no immunogenicity in therapeutic applications. In certain embodiments, RNA aptamers may be expressed from a DNA construct. In other embodiments, a nucleic acid aptamer may be linked to another polynucleotide sequence. The polynucleotide sequence may be a double stranded DNA polynucleotide sequence. The aptamer may be covalently linked to one strand of the polynucleotide sequence. The aptamer may be ligated to the polynucleotide sequence. The polynucleotide sequence may be configured, such that the polynucleotide sequence may be linked to a solid support or ligated to another polynucleotide sequence.

Aptamers, like peptides generated by phage display or monoclonal antibodies ("mAbs"), are capable of specifically binding to selected targets and modulating the target's activity, e.g., through binding, aptamers may block their target's ability to function. A typical aptamer is 10-15 kDa in size (30-45 nucleotides), binds its target with sub-nanomolar affinity, and discriminates against closely related targets (e.g., aptamers will typically not bind other proteins from the same gene family). Structural studies have shown that aptamers are capable of using the same types of binding interactions (e.g., hydrogen bonding, electrostatic complementarity, hydrophobic contacts, steric exclusion) that drives affinity and specificity in antibody-antigen complexes.

Aptamers have a number of desirable characteristics for use in research and as therapeutics and diagnostics including high specificity and affinity, biological efficacy, and excellent pharmacokinetic properties. In addition, they offer specific competitive advantages over antibodies and other protein biologics. Aptamers are chemically synthesized and are readily scaled as needed to meet production demand for research, diagnostic or therapeutic applications. Aptamers are chemically robust. They are intrinsically adapted to regain activity following exposure to factors such as heat and denaturants and can be stored for extended periods (>1 yr) at room temperature as lyophilized powders. Not being bound by a theory, aptamers bound to a solid support or beads may be stored for extended periods.

Oligonucleotides in their phosphodiester form may be quickly degraded by intracellular and extracellular enzymes such as endonucleases and exonucleases. Aptamers can include modified nucleotides conferring improved characteristics on the ligand, such as improved in vivo stability or improved delivery characteristics. Examples of such modifications include chemical substitutions at the ribose and/or phosphate and/or base positions. SELEX identified nucleic acid ligands containing modified nucleotides are described, e.g., in U.S. Pat. No. 5,660,985, which describes oligonucleotides containing nucleotide derivatives chemically modified at the 2' position of ribose, 5 position of pyrimidines, and 8 position of purines, U.S. Pat. No. 5,756,703 which describes oligonucleotides containing various 2'-modified pyrimidines, and U.S. Pat. No. 5,580,737 which describes highly specific nucleic acid ligands containing one or more nucleotides modified with 2'-amino (2'-$NH_2$), 2'-fluoro (2'-F), and/or 2'-0-methyl(2'-OMe) substituents. Modifications of aptamers may also include, modifications at exocyclic amines, substitution of 4-thiouridine, substitution of 5-bromo or 5-iodo-uracil; backbone modifications, phosphorothioate or allyl phosphate modifications, methylations, and unusual base-pairing combinations such as the isobases isocytidine and isoguanosine. Modifications can also include 3' and 5' modifications such as capping. As used herein, the term phosphorothioate encompasses one or more non-bridging oxygen atoms in a phosphodiester bond replaced by one or more sulfur atoms. In further embodiments, the oligonucleotides comprise modified sugar groups, for example, one or more of the hydroxyl groups is replaced with halogen, aliphatic groups, or functionalized as ethers or amines. In one embodiment, the 2'-position of the furanose residue is substituted by any of an O-methyl, O-alkyl, O-allyl, S-alkyl, S-allyl, or halo group. Methods of synthesis of 2'-modified sugars are described, e.g., in Sproat, et al., Nucl. Acid Res. 19:733-738 (1991); Cotten, et al, Nucl. Acid Res. 19:2629-2635 (1991); and Hobbs, et al, Biochemistry 12:5138-5145 (1973). Other modifications are known to one of ordinary skill in the art. In certain embodiments, aptamers include aptamers with improved off-rates as described in International Patent Publication No. WO 2009012418, "Method for generating aptamers with improved off-rates," incorporated herein by reference in its entirety. In certain embodiments aptamers are chosen from a library of aptamers. Such libraries include, but are not limited to those described in Rohloff et al., "Nucleic Acid Ligands With Protein-like Side Chains: Modified Aptamers and Their Use as Diagnostic and Therapeutic Agents," Molecular Therapy Nucleic Acids (2014) 3, e201. Aptamers are also commercially available (see, e.g., SomaLogic, Inc., Boulder, Colorado). In certain embodiments, the present invention may utilize any aptamer containing any modification as described herein.

Administration

In certain embodiments, the therapeutic agents are administered to a subject in need thereof. In certain embodiments, agents are administered in a pharmaceutical composition. A "pharmaceutical composition" refers to a composition that usually contains an excipient, such as a pharmaceutically acceptable carrier that is conventional in the art and that is suitable for administration to cells or to a subject.

The pharmaceutical composition according to the present invention can, in one alternative, include a prodrug. When a pharmaceutical composition according to the present invention includes a prodrug, prodrugs and active metabolites of a compound may be identified using routine techniques known in the art. (See, e.g., Bertolini et al., J. Med. Chem., 40, 2011-2016 (1997); Shan et al., J. Pharm. Sci., 86 (7), 765-767; Bagshawe, Drug Dev. Res., 34, 220-230 (1995); Bodor, Advances in Drug Res., 13, 224-331 (1984); Bundgaard, Design of Prodrugs (Elsevier Press 1985); Larsen, Design and Application of Prodrugs, Drug Design and Development (Krogsgaard-Larsen et al., eds., Harwood Academic Publishers, 1991); Dear et al., J. Chromatogr. B, 748, 281-293 (2000); Spraul et al., J. Pharmaceutical & Biomedical Analysis, 10, 601-605 (1992); and Prox et al., Xenobiol., 3, 103-112 (1992)).

The term "pharmaceutically acceptable" as used throughout this specification is consistent with the art and means compatible with the other ingredients of a pharmaceutical composition and not deleterious to the recipient thereof.

As used herein, "carrier" or "excipient" includes any and all solvents, diluents, buffers (such as, e.g., neutral buffered saline or phosphate buffered saline), solubilizers, colloids, dispersion media, vehicles, fillers, chelating agents (such as, e.g., EDTA or glutathione), amino acids (such as, e.g., glycine), proteins, disintegrants, binders, lubricants, wetting agents, emulsifiers, sweeteners, colorants, flavorings, aromatizers, thickeners, agents for achieving a depot effect, coatings, antifungal agents, preservatives, stabilizers, antioxidants, tonicity controlling agents, absorption delaying agents, and the like. The use of such media and agents for pharmaceutical active components is well known in the art. Such materials should be non-toxic and should not interfere with the activity of the cells or active components.

The precise nature of the carrier or excipient or other material will depend on the route of administration. For example, the composition may be in the form of a parenterally acceptable aqueous solution, which is pyrogen-free and has suitable pH, isotonicity and stability. For general principles in medicinal formulation, the reader is referred to Cell Therapy: Stem Cell Transplantation, Gene Therapy, and Cellular Immunotherapy, by G. Morstyn & W. Sheridan eds., Cambridge University Press, 1996; and Hematopoietic Stem Cell Therapy, E. D. Ball, J. Lister & P. Law, Churchill Livingstone, 2000.

The pharmaceutical composition can be applied parenterally, rectally, orally or topically. Preferably, the pharmaceutical composition may be used for intravenous, intramuscular, subcutaneous, peritoneal, peridural, rectal, nasal, pulmonary, mucosal, or oral application. In a preferred embodiment, the pharmaceutical composition according to the invention is intended to be used as an infusion. The skilled person will understand that compositions which are to be administered orally or topically will usually not comprise cells, although it may be envisioned for oral compositions to also comprise cells, for example when gastro-intestinal tract indications are treated. Each of the cells or active components (e.g., immunomodulants) as discussed herein may be administered by the same route or may be administered by a different route. By means of example, and without limitation, cells may be administered parenterally and other active components may be administered orally.

Liquid pharmaceutical compositions may generally include a liquid carrier such as water or a pharmaceutically acceptable aqueous solution. For example, physiological saline solution, tissue or cell culture media, dextrose or other saccharide solution or glycols such as ethylene glycol, propylene glycol or polyethylene glycol may be included.

The composition may include one or more cell protective molecules, cell regenerative molecules, growth factors, anti-apoptotic factors or factors that regulate gene expression in the cells. Such substances may render the cells independent of their environment.

Such pharmaceutical compositions may contain further components ensuring the viability of the cells therein. For example, the compositions may comprise a suitable buffer system (e.g., phosphate or carbonate buffer system) to achieve desirable pH, more usually near neutral pH, and may comprise sufficient salt to ensure isoosmotic conditions for the cells to prevent osmotic stress. For example, suitable solution for these purposes may be phosphate-buffered saline (PBS), sodium chloride solution, Ringer's Injection or Lactated Ringer's Injection, as known in the art. Further, the composition may comprise a carrier protein, e.g., albumin (e.g., bovine or human albumin), which may increase the viability of the cells.

Further suitably pharmaceutically acceptable carriers or additives are well known to those skilled in the art and for instance may be selected from proteins such as collagen or gelatine, carbohydrates such as starch, polysaccharides, sugars (dextrose, glucose and sucrose), cellulose derivatives like sodium or calcium carboxymethylcellulose, hydroxypropyl cellulose or hydroxypropylmethyl cellulose, pregelatinized starches, pectin agar, carrageenan, clays, hydrophilic gums (acacia gum, guar gum, gum arabic and xanthan gum), alginic acid, alginates, hyaluronic acid, polyglycolic and polylactic acid, dextran, pectins, synthetic polymers such as water-soluble acrylic polymer or polyvinylpyrrolidone, proteoglycans, calcium phosphate and the like.

In certain embodiments, a pharmaceutical cell preparation as taught herein may be administered in a form of liquid composition. In embodiments, the cells or pharmaceutical composition comprising such can be administered systemically, topically, within an organ or at a site of organ dysfunction or lesion.

Preferably, the pharmaceutical compositions may comprise a therapeutically effective amount of the specified immune cells and/or other active components (e.g., immunomodulants). The term "therapeutically effective amount" refers to an amount which can elicit a biological or medicinal response in a tissue, system, animal or human that is being sought by a researcher, veterinarian, medical doctor or other clinician, and in particular can prevent or alleviate one or more of the local or systemic symptoms or features of a disease or condition being treated.

It will be appreciated that administration of therapeutic entities in accordance with the invention will be administered with suitable carriers, excipients, and other agents that are incorporated into formulations to provide improved transfer, delivery, tolerance, and the like. A multitude of appropriate formulations can be found in the formulary known to all pharmaceutical chemists: Remington's Pharmaceutical Sciences (15th ed, Mack Publishing Company, Easton, PA (1975)), particularly Chapter 87 by Blaug, Seymour, therein. These formulations include, for example, powders, pastes, ointments, jellies, waxes, oils, lipids, lipid (cationic or anionic) containing vesicles (such as Lipofectin™), DNA conjugates, anhydrous absorption pastes, oil-in-water and water-in-oil emulsions, emulsions carbowax (polyethylene glycols of various molecular weights), semi-solid gels, and semi-solid mixtures containing carbowax. Any of the foregoing mixtures may be appropriate in treatments and therapies in accordance with the present invention, provided that the active ingredient in the formulation is not inactivated by the formulation and the formulation is physiologically compatible and tolerable with the route of administration. See also Baldrick P. "Pharmaceutical excipient development: the need for preclinical guidance." Regul. Toxicol Pharmacol. 32(2):210-8 (2000), Wang W. "Lyophilization and development of solid protein pharmaceuticals." Int. J. Pharm. 203(1-2):1-60 (2000), Charman W N "Lipids, lipophilic drugs, and oral drug delivery-some emerging concepts." J Pharm Sci. 89(8):967-78 (2000), Powell et al. "Compendium of excipients for parenteral formulations" PDA J Pharm Sci Technol. 52:238-311 (1998) and the citations therein for additional information related to formulations, excipients and carriers well known to pharmaceutical chemists.

The medicaments of the invention are prepared in a manner known to those skilled in the art, for example, by means of conventional dissolving, lyophilizing, mixing, granulating or confectioning processes. Methods well known in the art for making formulations are found, for example, in Remington: The Science and Practice of Pharmacy, 20th ed., ed. A. R. Gennaro, 2000, Lippincott Williams & Wilkins, Philadelphia, and Encyclopedia of Pharmaceutical Technology, eds. J. Swarbrick and J. C. Boylan, 1988-1999, Marcel Dekker, New York.

Administration of medicaments of the invention may be by any suitable means that results in a compound concentration that is effective for treating or inhibiting (e.g., by delaying) the development of a disease. The compound is admixed with a suitable carrier substance, e.g., a pharmaceutically acceptable excipient that preserves the therapeutic properties of the compound with which it is administered. One exemplary pharmaceutically acceptable excipient is physiological saline. The suitable carrier substance is generally present in an amount of 1-95% by weight of the total weight of the medicament. The medicament may be provided in a dosage form that is suitable for administration. Thus, the medicament may be in form of, e.g., tablets, capsules, pills, powders, granulates, suspensions, emulsions, solutions, gels including hydrogels, pastes, ointments, creams, plasters, drenches, delivery devices, injectables, implants, sprays, or aerosols.

Administration can be systemic or local. In addition, it may be advantageous to administer the composition into the central nervous system by any suitable route, including intraventricular and intrathecal injection. Pulmonary administration may also be employed by use of an inhaler or nebulizer, and formulation with an aerosolizing agent. It may also be desirable to administer the agent locally to the area in need of treatment; this may be achieved by, for example, and not by way of limitation, local infusion during surgery, topical application, by injection, by means of a catheter, by means of a suppository, or by means of an implant.

Various delivery systems are known and can be used to administer the pharmacological compositions including, but not limited to, encapsulation in liposomes, microparticles, microcapsules; minicells; polymers; capsules; tablets; and the like. In one embodiment, the agent may be delivered in a vesicle, in particular a liposome. In a liposome, the agent is combined, in addition to other pharmaceutically acceptable carriers, with amphipathic agents such as lipids which exist in aggregated form as micelles, insoluble monolayers, liquid crystals, or lamellar layers in aqueous solution. Suitable lipids for liposomal formulation include, without limitation, monoglycerides, diglycerides, sulfatides, lysolecithin, phospholipids, saponin, bile acids, and the like. Preparation of such liposomal formulations is within the level of skill in the art, as disclosed, for example, in U.S. Pat. Nos. 4,837,028 and 4,737,323. In yet another embodiment, the pharmacological compositions can be delivered in a controlled release system including, but not limited to: a delivery pump (See, for example, Saudek, et al., New Engl. J. Med. 321:574 (1989) and a semi-permeable polymeric material (See, for example, Howard, et al., J. Neurosurg. 71:105 (1989)). Additionally, the controlled release system can be placed in proximity of the therapeutic target (e.g., a tumor), thus requiring only a fraction of the systemic dose. See, for example, Goodson, In: Medical Applications of Controlled Release, 1984. (CRC Press, Boca Raton, Fla.).

The amount of the agents which will be effective in the treatment of a particular disorder or condition will depend on the nature of the disorder or condition and may be determined by standard clinical techniques by those of skill within the art. In addition, in vitro assays may optionally be employed to help identify optimal dosage ranges. The precise dose to be employed in the formulation will also depend on the route of administration, and the overall seriousness of the disease or disorder, and should be decided according to the judgment of the practitioner and each patient's circumstances. Ultimately, the attending physician will decide the amount of the agent with which to treat each individual patient. In certain embodiments, the attending physician will administer low doses of the agent and observe the patient's response. Larger doses of the agent may be administered until the optimal therapeutic effect is obtained for the patient, and at that point the dosage is not increased further. Effective doses may be extrapolated from dose-response curves derived from in vitro or animal model test systems. Ultimately the attending physician will decide on the appropriate duration of therapy using compositions of the present invention. Dosage will also vary according to the age, weight and response of the individual patient.

There are a variety of techniques available for introducing nucleic acids into viable cells. The techniques vary depending upon whether the nucleic acid is transferred into cultured cells in vitro, or in vivo in the cells of the intended host. Techniques suitable for the transfer of nucleic acid into mammalian cells in vitro include the use of liposomes, electroporation, microinjection, cell fusion, DEAE-dextran, the calcium phosphate precipitation method, etc. The currently preferred in vivo gene transfer techniques include transfection with viral (typically retroviral) vectors and viral coat protein-liposome mediated transfection.

Methods for Detection and Isolation of Cells

The invention provides biomarkers for the identification, diagnosis, prognosis and manipulation of disease phenotypes (e.g., immune state), for use in a variety of diagnostic and/or therapeutic indications. The biomarkers may also be used for isolation of cell types described herein. For example, cells are isolated using specific biomarkers or combinations of biomarkers. Combinations of biomarkers include one or more biomarkers expressed on all types of a cell type (e.g., immune cell) and biomarkers that are specific for the subtype for isolation (e.g., LN-innervating peptidergic nociceptor sensory neurons). Biomarkers in the context of the present invention encompasses, without limitation nucleic acids, proteins, reaction products, and metabolites, together with their polymorphisms, mutations, variants, modifications, subunits, fragments, and other analytes or sample-derived measures. In certain embodiments, biomarkers include the signature genes or signature gene products, and/or cells as described herein (e.g., LN-innervating peptidergic nociceptor sensory neurons). Antibodies against the genes described herein for detection and isolation are known in the art.

In certain embodiments, the invention provides uses of the biomarkers for predicting risk for a certain phenotype. In certain embodiments, the invention provides uses of the biomarkers for selecting a treatment. In certain embodiments, a subject having a disease can be classified based on severity of the disease.

The terms "diagnosis" and "monitoring" are commonplace and well-understood in medical practice. By means of further explanation and without limitation the term "diagnosis" generally refers to the process or act of recognizing, deciding on or concluding on a disease or condition in a subject on the basis of symptoms and signs and/or from results of various diagnostic procedures (such as, for example, from knowing the presence, absence and/or quantity of one or more biomarkers characteristic of the diagnosed disease or condition).

The term "monitoring" generally refers to the follow-up of a disease or a condition in a subject for any changes which may occur over time.

The terms "prognosing" or "prognosis" generally refer to an anticipation on the progression of a disease or condition and the prospect (e.g., the probability, duration, and/or extent) of recovery. A good prognosis of the diseases or conditions taught herein may generally encompass anticipation of a satisfactory partial or complete recovery from the diseases or conditions, preferably within an acceptable time period. A good prognosis of such may more commonly encompass anticipation of not further worsening or aggravating of such, preferably within a given time period. A poor prognosis of the diseases or conditions as taught herein may generally encompass anticipation of a substandard recovery and/or unsatisfactorily slow recovery, or to substantially no recovery or even further worsening of such.

The terms also encompass prediction of a disease. The terms "predicting" or "prediction" generally refer to an advance declaration, indication or foretelling of a disease or condition in a subject not (yet) having said disease or condition. For example, a prediction of a disease or condition in a subject may indicate a probability, chance or risk that the subject will develop said disease or condition, for example within a certain time period or by a certain age. Said probability, chance or risk may be indicated inter alia as an absolute value, range or statistics, or may be indicated relative to a suitable control subject or subject population (such as, e.g., relative to a general, normal or healthy subject or subject population). Hence, the probability, chance or risk that a subject will develop a disease or condition may be advantageously indicated as increased or decreased, or as fold-increased or fold-decreased relative to a suitable control subject or subject population. As used herein, the term "prediction" of the conditions or diseases as taught herein in a subject may also particularly mean that the subject has a 'positive' prediction of such, i.e., that the subject is at risk of having such (e.g., the risk is significantly increased vis-à-vis a control subject or subject population). The term "prediction of no" diseases or conditions as taught herein as described herein in a subject may particularly mean that the subject has a 'negative' prediction of such, i.e., that the subject's risk of having such is not significantly increased vis-à-vis a control subject or subject population.

In certain example embodiments, one or more genes in Tables 1~4 may be used as markers to detect the presence of autoimmune disease, such as those disclosed therein. In certain example embodiments, the one or more genes or gene products may be detected by expression in Th17 cell residing in the central nervous system.

Biomarkers

The term "biomarker" is widespread in the art and commonly broadly denotes a biological molecule, more particularly an endogenous biological molecule, and/or a detectable portion thereof, whose qualitative and/or quantitative evaluation in a tested object (e.g., in or on a cell, cell population, tissue, organ, or organism, e.g., in a biological sample of a subject) is predictive or informative with respect to one or more aspects of the tested object's phenotype and/or genotype. The terms "marker" and "biomarker" may be used interchangeably throughout this specification. Biomarkers as intended herein may be nucleic acid-based or peptide-, polypeptide- and/or protein-based. For example, a marker may be comprised of peptide(s), polypeptide(s) and/or protein(s) encoded by a given gene, or of detectable portions thereof. Further, whereas the term "nucleic acid" generally encompasses DNA, RNA and DNA/RNA hybrid molecules, in the context of markers the term may typically refer to heterogeneous nuclear RNA (hnRNA), pre-mRNA, messenger RNA (mRNA), or complementary DNA (cDNA), or detectable portions thereof. Such nucleic acid species are particularly useful as markers, since they contain qualitative and/or quantitative information about the expression of the gene. Particularly preferably, a nucleic acid-based marker may encompass mRNA of a given gene, or cDNA made of the mRNA, or detectable portions thereof. Any such nucleic acid(s), peptide(s), polypeptide(s) and/or protein(s) encoded by or produced from a given gene are encompassed by the term "gene product(s)".

Preferably, markers as intended herein may be extracellular or cell surface markers, as methods to measure extracellular or cell surface marker(s) need not disturb the integrity of the cell membrane and may not require fixation/permeabilization of the cells.

Unless otherwise apparent from the context, reference herein to any marker, such as a peptide, polypeptide, protein, or nucleic acid, may generally also encompass modified forms of said marker, such as bearing post-expression modifications including, for example, phosphorylation, glycosylation, lipidation, methylation, cysteinylation, sulphonation, glutathionylation, acetylation, oxidation of methionine to methionine sulphoxide or methionine sulphone, and the like.

The term "peptide" as used throughout this specification preferably refers to a polypeptide as used herein consisting essentially of 50 amino acids or less, e.g., 45 amino acids or less, preferably 40 amino acids or less, e.g., 35 amino acids or less, more preferably 30 amino acids or less, e.g., 25 or less, 20 or less, 15 or less, 10 or less or 5 or less amino acids.

The term "polypeptide" as used throughout this specification generally encompasses polymeric chains of amino acid residues linked by peptide bonds. Hence, insofar a protein is only composed of a single polypeptide chain, the terms "protein" and "polypeptide" may be used interchangeably herein to denote such a protein. The term is not limited to any minimum length of the polypeptide chain. The term may encompass naturally, recombinantly, semi-synthetically or synthetically produced polypeptides. The term also encompasses polypeptides that carry one or more co- or post-expression-type modifications of the polypeptide chain, such as, without limitation, glycosylation, acetylation, phosphorylation, sulfonation, methylation, ubiquitination, signal peptide removal, N-terminal Met removal, conversion of pro-enzymes or pre-hormones into active forms, etc. The term further also includes polypeptide variants or mutants which carry amino acid sequence variations vis-à-vis a corresponding native polypeptide, such as, e.g., amino acid deletions, additions and/or substitutions. The term contemplates both full-length polypeptides and polypeptide parts or fragments, e.g., naturally-occurring polypeptide parts that ensue from processing of such full-length polypeptides.

The term "protein" as used throughout this specification generally encompasses macromolecules comprising one or more polypeptide chains, i.e., polymeric chains of amino acid residues linked by peptide bonds. The term may encompass naturally, recombinantly, semi-synthetically or synthetically produced proteins. The term also encompasses proteins that carry one or more co- or post-expression-type modifications of the polypeptide chain(s), such as, without limitation, glycosylation, acetylation, phosphorylation, sulfonation, methylation, ubiquitination, signal peptide removal, N-terminal Met removal, conversion of pro-enzymes or pre-hormones into active forms, etc. The term further also includes protein variants or mutants which carry amino acid sequence variations vis-à-vis a corresponding native protein, such as, e.g., amino acid deletions, additions and/or substitutions. The term contemplates both full-length proteins and protein parts or fragments, e.g., naturally-occurring protein parts that ensue from processing of such full-length proteins.

The reference to any marker, including any peptide, polypeptide, protein, or nucleic acid, corresponds to the marker commonly known under the respective designations in the art. The terms encompass such markers of any organism where found, and particularly of animals, preferably warm-blooded animals, more preferably vertebrates, yet more preferably mammals, including humans and non-human mammals, still more preferably of humans.

The terms particularly encompass such markers, including any peptides, polypeptides, proteins, or nucleic acids, with a native sequence, i.e., ones of which the primary sequence is the same as that of the markers found in or derived from nature. A skilled person understands that native sequences may differ between different species due to genetic divergence between such species. Moreover, native sequences may differ between or within different individuals of the same species due to normal genetic diversity (variation) within a given species. Also, native sequences may differ between or even within different individuals of the same species due to somatic mutations, or post-transcriptional or post-translational modifications. Any such variants or isoforms of markers are intended herein. Accordingly, all sequences of markers found in or derived from nature are considered "native". The terms encompass the markers when forming a part of a living organism, organ, tissue or cell, when forming a part of a biological sample, as well as when at least partly isolated from such sources. The terms also encompass markers when produced by recombinant or synthetic means.

In certain embodiments, markers, including any peptides, polypeptides, proteins, or nucleic acids, may be human, i.e., their primary sequence may be the same as a corresponding primary sequence of or present in a naturally occurring human markers. Hence, the qualifier "human" in this connection relates to the primary sequence of the respective markers, rather than to their origin or source. For example, such markers may be present in or isolated from samples of human subjects or may be obtained by other means (e.g., by recombinant expression, cell-free transcription or translation, or non-biological nucleic acid or peptide synthesis).

The reference herein to any marker, including any peptide, polypeptide, protein, or nucleic acid, also encompasses fragments thereof. Hence, the reference herein to measuring (or measuring the quantity of) any one marker may encompass measuring the marker and/or measuring one or more fragments thereof.

For example, any marker and/or one or more fragments thereof may be measured collectively, such that the measured quantity corresponds to the sum amounts of the collectively measured species. In another example, any marker and/or one or more fragments thereof may be measured each individually. The terms encompass fragments arising by any mechanism, in vivo and/or in vitro, such as, without limitation, by alternative transcription or translation, exo- and/or endo-proteolysis, exo- and/or endo-nucleolysis, or degradation of the peptide, polypeptide, protein, or nucleic acid, such as, for example, by physical, chemical and/or enzymatic proteolysis or nucleolysis.

The term "fragment" as used throughout this specification with reference to a peptide, polypeptide, or protein generally denotes a portion of the peptide, polypeptide, or protein, such as typically an N- and/or C-terminally truncated form of the peptide, polypeptide, or protein. Preferably, a fragment may comprise at least about 30%, e.g., at least about 50% or at least about 70%, preferably at least about 80%, e.g., at least about 85%, more preferably at least about 90%, and yet more preferably at least about 95% or even about 99% of the amino acid sequence length of said peptide, polypeptide, or protein. For example, insofar not exceeding the length of the full-length peptide, polypeptide, or protein, a fragment may include a sequence of ≥5 consecutive amino acids, or ≥10 consecutive amino acids, or ≥20 consecutive amino acids, or ≥30 consecutive amino acids, e.g., ≥40 consecutive amino acids, such as for example ≥50 consecutive amino acids, e.g., ≥60, ≥70, ≥80, ≥90, ≥100, ≥200, ≥300, ≥400, ≥500 or ≥600 consecutive amino acids of the corresponding full-length peptide, polypeptide, or protein.

The term "fragment" as used throughout this specification with reference to a nucleic acid (polynucleotide) generally denotes a 5'- and/or 3'-truncated form of a nucleic acid. Preferably, a fragment may comprise at least about 30%, e.g., at least about 50% or at least about 70%, preferably at least about 80%, e.g., at least about 85%, more preferably at least about 90%, and yet more preferably at least about 95% or even about 99% of the nucleic acid sequence length of said nucleic acid. For example, insofar not exceeding the length of the full-length nucleic acid, a fragment may include a sequence of ≥5 consecutive nucleotides, or ≥10 consecutive nucleotides, or ≥20 consecutive nucleotides, or ≥30 consecutive nucleotides, e.g., 240 consecutive nucleotides, such as for example ≥50 consecutive nucleotides, e.g., ≥60, ≥70, ≥80, ≥90, ≥100, ≥200, ≥300, ≥400, ≥500 or ≥600 consecutive nucleotides of the corresponding full-length nucleic acid.

Cells such as immune cells as disclosed herein may in the context of the present specification be said to "comprise the expression" or conversely to "not express" one or more markers, such as one or more genes or gene products; or be described as "positive" or conversely as "negative" for one or more markers, such as one or more genes or gene products; or be said to "comprise" a defined "gene or gene product signature".

Such terms are commonplace and well-understood by the skilled person when characterizing cell phenotypes. By means of additional guidance, when a cell is said to be positive for or to express or comprise expression of a given marker, such as a given gene or gene product, a skilled person would conclude the presence or evidence of a distinct signal for the marker when carrying out a measurement capable of detecting or quantifying the marker in or on the cell. Suitably, the presence or evidence of the distinct signal for the marker would be concluded based on a comparison of the measurement result obtained for the cell to a result of the same measurement carried out for a negative control (for example, a cell known to not express the marker) and/or a positive control (for example, a cell known to express the marker). Where the measurement method allows for a quantitative assessment of the marker, a positive cell may generate a signal for the marker that is at least 1.5-fold higher than a signal generated for the marker by a negative control cell or than an average signal generated for the marker by a population of negative control cells, e.g., at least 2-fold, at least 4-fold, at least 10-fold, at least 20-fold, at least 30-fold, at least 40-fold, at least 50-fold higher or even higher. Further, a positive cell may generate a signal for the marker that is 3.0 or more standard deviations, e.g., 3.5 or more, 4.0 or more, 4.5 or more, or 5.0 or more standard deviations, higher than an average signal generated for the marker by a population of negative control cells.

A marker, for example a gene or gene product, for example a peptide, polypeptide, protein, or nucleic acid, or a group of two or more markers, is "detected" or "measured" in a tested object (e.g., in or on a cell, cell population, tissue, organ, or organism, e.g., in a biological sample of a subject) when the presence or absence and/or quantity of said marker or said group of markers is detected or determined in the tested object, preferably substantially to the exclusion of other molecules and analytes, e.g., other genes or gene products.

The terms "increased" or "increase" or "upregulated" or "upregulate" as used herein generally mean an increase by a statically significant amount. For avoidance of doubt, "increased" means a statistically significant increase of at least 10% as compared to a reference level, including an increase of at least 20%, at least 30%, at least 40%, at least 50%, at least 60%, at least 70%, at least 80%, at least 90%, at least 100% or more, including, for example at least 2-fold, at least 3-fold, at least 4-fold, at least 5-fold, at least 10-fold increase or greater as compared to a reference level, as that term is defined herein.

The term "reduced" or "reduce" or "decrease" or "decreased" or "downregulate" or "downregulated" as used herein generally means a decrease by a statistically significant amount relative to a reference. For avoidance of doubt, "reduced" means statistically significant decrease of at least 10% as compared to a reference level, for example a decrease by at least 20%, at least 30%, at least 40%, at least 50%, or at least 60%, or at least 70%, or at least 80%, at least 90% or more, up to and including a 100% decrease (i.e., absent level as compared to a reference sample), or any decrease between 10-100% as compared to a reference level, as that.

The terms "quantity", "amount" and "level" are synonymous and generally well-understood in the art. The terms as used throughout this specification may particularly refer to an absolute quantification of a marker in a tested object (e.g., in or on a cell, cell population, tissue, organ, or organism, e.g., in a biological sample of a subject), or to a relative quantification of a marker in a tested object, i.e., relative to another value such as relative to a reference value, or to a range of values indicating a base-line of the marker. Such values or ranges may be obtained as conventionally known.

An absolute quantity of a marker may be advantageously expressed as weight or as molar amount, or more commonly as a concentration, e.g., weight per volume or mol per volume. A relative quantity of a marker may be advantageously expressed as an increase or decrease or as a fold-increase or fold-decrease relative to said another value, such as relative to a reference value. Performing a relative comparison between first and second variables (e.g., first and second quantities) may but need not require determining first the absolute values of said first and second variables. For example, a measurement method may produce quantifiable readouts (such as, e.g., signal intensities) for said first and second variables, wherein said readouts are a function of the value of said variables, and wherein said readouts may be directly compared to produce a relative value for the first variable vs. the second variable, without the actual need to first convert the readouts to absolute values of the respective variables.

Reference values may be established according to known procedures previously employed for other cell populations, biomarkers and gene or gene product signatures. For example, a reference value may be established in an individual or a population of individuals characterized by a particular diagnosis, prediction and/or prognosis of said disease or condition (i.e., for whom said diagnosis, prediction and/or prognosis of the disease or condition holds true). Such population may comprise without limitation 2 or more, 10 or more, 100 or more, or even several hundred or more individuals.

A "deviation" of a first value from a second value may generally encompass any direction (e.g., increase: first value>second value; or decrease: first value<second value) and any extent of alteration.

For example, a deviation may encompass a decrease in a first value by, without limitation, at least about 10% (about 0.9-fold or less), or by at least about 20% (about 0.8-fold or less), or by at least about 30% (about 0.7-fold or less), or by at least about 40% (about 0.6-fold or less), or by at least about 50% (about 0.5-fold or less), or by at least about 60% (about 0.4-fold or less), or by at least about 70% (about 0.3-fold or less), or by at least about 80% (about 0.2-fold or less), or by at least about 90% (about 0.1-fold or less), relative to a second value with which a comparison is being made.

For example, a deviation may encompass an increase of a first value by, without limitation, at least about 10% (about 1.1-fold or more), or by at least about 20% (about 1.2-fold or more), or by at least about 30% (about 1.3-fold or more), or by at least about 40% (about 1.4-fold or more), or by at least about 50% (about 1.5-fold or more), or by at least about 60% (about 1.6-fold or more), or by at least about 70% (about 1.7-fold or more), or by at least about 80% (about 1.8-fold or more), or by at least about 90% (about 1.9-fold or more), or by at least about 100% (about 2-fold or more), or by at least about 150% (about 2.5-fold or more), or by at least about 200% (about 3-fold or more), or by at least about 500% (about 6-fold or more), or by at least about 700% (about 8-fold or more), or like, relative to a second value with which a comparison is being made.

Preferably, a deviation may refer to a statistically significant observed alteration. For example, a deviation may refer to an observed alteration which falls outside of error margins of reference values in a given population (as expressed, for example, by standard deviation or standard error, or by a predetermined multiple thereof, e.g., ±1×SD or ±2×SD or ±3×SD, or ±1×SE or ±2×SE or ±3×SE). Deviation may also refer to a value falling outside of a reference range defined by values in a given population (for example, outside of a range which comprises ≥40%, ≥50%, ≥60%, ≥70%, ≥75% or ≥80% or ≥85% or ≥90% or ≥95% or even ≥100% of values in said population).

In a further embodiment, a deviation may be concluded if an observed alteration is beyond a given threshold or cut-off. Such threshold or cut-off may be selected as generally known in the art to provide for a chosen sensitivity and/or specificity of the prediction methods, e.g., sensitivity and/or specificity of at least 50%, or at least 60%, or at least 70%, or at least 80%, or at least 85%, or at least 90%, or at least 95%.

For example, receiver-operating characteristic (ROC) curve analysis can be used to select an optimal cut-off value of the quantity of a given immune cell population, biomarker or gene or gene product signatures, for clinical use of the present diagnostic tests, based on acceptable sensitivity and specificity, or related performance measures which are well-known per se, such as positive predictive value (PPV), negative predictive value (NPV), positive likelihood ratio (LR+), negative likelihood ratio (LR−), Youden index, or similar.

Detection or isolation of a biomarker may be by any means known in the art. Methods of isolating include cell sorting (e.g., with antibody specific for a cell surface marker). Methods of detection include, but are not limited to enzymatic assays, flow cytometry, mass cytometry, fluorescence activated cell sorting (FACS), fluorescence microscopy, affinity separation, magnetic cell separation, microfluidic separation, RNA-seq (e.g., bulk or single cell), quantitative PCR, MERFISH (multiplex (in situ) RNA FISH), immunological assay methods by specific binding between a separable, detectable and/or quantifiable immunological binding agent (antibody) and the marker, mass spectrometry analysis methods, chromatography methods and combinations thereof. Immunological assay methods include without limitation immunohistochemistry, immunocytochemistry, flow cytometry, mass cytometry, fluorescence activated cell sorting (FACS), fluorescence microscopy, fluorescence based cell sorting using microfluidic systems, immunoaffinity adsorption based techniques such as affinity chromatography, magnetic particle separation, magnetic activated cell sorting or bead based cell sorting using microfluidic systems, enzyme-linked immunosorbent assay (ELISA) and ELISPOT based techniques, radioimmunoassay (RIA), Western blot, etc. While particulars of chromatography are well known in the art, for further guidance see, e.g., Meyer M., 1998, ISBN: 047198373X, and "Practical HPLC Methodology and Applications", Bidlingmeyer, B. A., John Wiley & Sons Inc., 1993. Exemplary types of chromatography include, without limitation, high-performance liquid chromatography (HPLC), normal phase HPLC (NP-HPLC), reversed phase HPLC (RP-HPLC), ion exchange chromatography (IEC), such as cation or anion exchange chromatography, hydrophilic interaction liquid chromatography (HILIC), hydrophobic interaction chromatography (HIC), size exclusion chromatography (SEC) including gel filtration chromatography or gel permeation chromatography, chromatofocusing, affinity chromatography such as immunoaffinity, immobilized metal affinity chromatography, and the like.

Detection and Isolation of Biomarkers

In one embodiment, the signature genes, biomarkers, and/or cells expressing biomarkers may be detected or isolated by immunofluorescence, immunohistochemistry (IHC), fluorescence activated cell sorting (FACS), mass spectrometry (MS), mass cytometry (CyTOF), sequencing, WGS (described herein), WES (described herein), RNA-seq, single-cell RNA-seq (described herein), quantitative RT-PCR, single-cell qPCR, FISH, RNA-FISH, MERFISH (multiplex (in situ) RNA FISH) and/or by in situ hybridization. Other methods including absorbance assays and colorimetric assays are known in the art and may be used herein. Detection may comprise primers and/or probes or fluorescently bar-coded oligonucleotide probes for hybridization to RNA (see e.g., Geiss G K, et al., Direct multiplexed measurement of gene expression with color-coded probe pairs. Nat Biotechnol. 2008 March; 26(3):317-25). In certain embodiments, cancer is diagnosed, prognosed, or monitored. For example, a tissue sample may be obtained and analyzed for specific cell markers (IHC) or specific transcripts (e.g., RNA-FISH). In one embodiment, tumor cells are stained for cell subtype specific signature genes. In one embodiment, the cells are fixed. In another embodiment, the cells are formalin fixed and paraffin embedded. Not being bound by a theory, the presence of the tumor subtypes indicate outcome and personalized treatments.

The present invention also may comprise a kit with a detection reagent that binds to one or more biomarkers or can be used to detect one or more biomarkers.

Sequencing

In certain embodiments, sequencing is used to identify expression of genes or transcriptomes in single cells. In certain embodiments, sequencing comprises high-throughput (formerly "next-generation") technologies to generate sequencing reads. Methods for constructing sequencing libraries are known in the art (see, e.g., Head et al., Library construction for next-generation sequencing: Overviews and challenges. Biotechniques. 2014; 56(2): 61-77). A "library" or "fragment library" may be a collection of nucleic acid molecules derived from one or more nucleic acid samples, in which fragments of nucleic acid have been modified, generally by incorporating terminal adapter sequences comprising one or more primer binding sites and identifiable sequence tags. In certain embodiments, the library members (e.g., cDNA) may include sequencing adaptors that are compatible with use in, e.g., Illumina's reversible terminator method, long read nanopore sequencing, Roche's pyrosequencing method (454), Life Technologies' sequencing by ligation (the SOLID platform) or Life Technologies' Ion Torrent platform. Examples of such methods are described in the following references: Margulies et al (Nature 2005 437:376-80); Schneider and Dekker (Nat Biotechnol. 2012 Apr. 10; 30(4):326-8); Ronaghi et al (Analytical Biochemistry 1996 242:84-9); Shendure et al (Science 2005 309: 1728-32); Imelfort et al (Brief Bioinform. 2009 10:609-18); Fox et al (Methods Mol. Biol. 2009; 553:79-108); Appleby et al (Methods Mol. Biol. 2009; 513:19-39); and Morozova et al (Genomics. 2008 92:255-64), which are incorporated by reference for the general descriptions of the methods and the particular steps of the methods, including all starting products, reagents, and final products for each of the steps.

As used herein the term "transcriptome" refers to the set of transcript molecules. In some embodiments, transcript refers to RNA molecules, e.g., messenger RNA (mRNA) molecules, small interfering RNA (siRNA) molecules, transfer RNA (tRNA) molecules, ribosomal RNA (rRNA) molecules, and complimentary sequences, e.g., cDNA molecules. In some embodiments, a transcriptome refers to a set of mRNA molecules. In some embodiments, a transcriptome refers to a set of cDNA molecules. In some embodiments, a transcriptome refers to one or more of mRNA molecules, siRNA molecules, tRNA molecules, rRNA molecules, in a sample, for example, a single cell or a population of cells. In some embodiments, a transcriptome refers to cDNA generated from one or more of mRNA molecules, siRNA molecules, tRNA molecules, rRNA molecules, in a sample, for example, a single cell or a population of cells. In some embodiments, a transcriptome refers to 25%, 50%, 55, 60, 65, 70, 75, 80, 85, 90, 91, 92, 93, 94, 95, 96, 97, 98, 99, 99.9, or 100% of transcripts from a single cell or a population of cells. In some embodiments, transcriptome not only refers to the species of transcripts, such as mRNA species, but also the amount of each species in the sample. In some embodiments, a transcriptome includes each mRNA molecule in the sample, such as all the mRNA molecules in a single cell.

In certain embodiments, the invention involves single-cell RNA sequencing (see, e.g., Kalisky, T., Blainey, P. & Quake, S. R. Genomic Analysis at the Single-Cell Level. Annual review of genetics 45, 431-445, (2011); Kalisky, T. & Quake, S. R. Single-cell genomics. Nature Methods 8, 311-314 (2011); Islam, S. et al. Characterization of the single-cell transcriptional landscape by highly multiplex RNA-seq. Genome Research, (2011); Tang, F. et al. RNA-Seq analysis to capture the transcriptome landscape of a single cell. Nature Protocols 5, 516-535, (2010); Tang, F. et al. mRNA-Seq whole-transcriptome analysis of a single cell. Nature Methods 6, 377-382, (2009); Ramskold, D. et al. Full-length mRNA-Seq from single-cell levels of RNA and individual circulating tumor cells. Nature Biotechnology 30, 777-782, (2012); and Hashimshony, T., Wagner, F., Sher, N. & Yanai, I. CEL-Seq: Single-Cell RNA-Seq by Multiplexed Linear Amplification. Cell Reports, Cell Reports, Volume 2, Issue 3, p666-673, 2012).

In certain embodiments, the present invention involves single-cell RNA sequencing (scRNA-seq). In certain embodiments, the invention involves plate based single-cell RNA sequencing (see, e.g., Picelli, S. et al., 2014, "Full-length RNA-seq from single cells using Smart-seq2" Nature protocols 9, 171-181, doi: 10.1038/nprot.2014.006).

In certain embodiments, the invention involves high-throughput single-cell RNA-seq where the RNAs from different cells are tagged individually, allowing a single library to be created while retaining the cell identity of each read. In this regard reference is made to Macosko et al., 2015, "Highly Parallel Genome-wide Expression Profiling of Individual Cells Using Nanoliter Droplets" Cell 161, 1202-1214; International patent application number PCT/US2015/049178, published as WO2016/040476 on Mar. 17, 2016; Klein et al., 2015, "Droplet Barcoding for Single-Cell Transcriptomics Applied to Embryonic Stem Cells" Cell 161, 1187-1201; International patent application number PCT/US2016/027734, published as WO2016168584A1 on Oct. 20, 2016; Zheng, et al., 2016, "Haplotyping germline and cancer genomes with high-throughput linked-read sequencing" Nature Biotechnology 34, 303-311; Zheng, et al., 2017, "Massively parallel digital transcriptional profiling of single cells" Nat. Commun. 8, 14049 doi: 10.1038/ncomms14049; International patent publication number WO2014210353A2; Zilionis, et al., 2017, "Single-cell barcoding and sequencing using droplet microfluidics" Nat Protoc. Jan; 12(1):44-73; Cao et al., 2017, "Comprehensive single cell transcriptional profiling of a multicellular organism by combinatorial indexing" bioRxiv preprint first posted online Feb. 2, 2017, doi: dx.doi.org/10.1101/104844; Rosenberg et al., 2017, "Scaling single cell transcriptomics through split pool barcoding" bioRxiv preprint first posted online Feb. 2, 2017, doi: dx.doi.org/10.1101/105163; Rosenberg et al., "Single-cell profiling of the developing mouse brain and spinal cord with split-pool barcoding" Science 15 Mar. 2018; Vitak, et al., "Sequencing thousands of single-cell genomes with combinatorial indexing" Nature Methods, 14(3):302-308, 2017; Cao, et al., Comprehensive single-cell transcriptional profiling of a multicellular organism. Science, 357(6352):661-667, 2017; Gierahn et al., "Seq-Well: portable, low-cost RNA sequencing of single cells at high throughput" Nature Methods 14, 395-398 (2017); and Hughes, et al., "Highly Efficient, Massively-Parallel Single-Cell RNA-Seq Reveals Cellular States and Molecular Features of Human Skin Pathology" bioRxiv 689273; doi: doi.org/10.1101/689273, all the contents and disclosure of each of which are herein incorporated by reference in their entirety.

In certain embodiments, the invention involves single nucleus RNA sequencing. In this regard reference is made to Swiech et al., 2014, "In vivo interrogation of gene function in the mammalian brain using CRISPR-Cas9" Nature Biotechnology Vol. 33, pp. 102-106; Habib et al., 2016, "Div-Seq: Single-nucleus RNA-Seq reveals dynamics of rare adult newborn neurons" Science, Vol. 353, Issue 6302, pp. 925-928; Habib et al., 2017, "Massively parallel single-nucleus RNA-seq with DroNc-seq" Nat Methods. 2017 October; 14(10):955-958; International Patent Application No. PCT/US2016/059239, published as WO2017164936 on Sep. 28, 2017; International Patent Application No. PCT/US2018/060860, published as WO/2019/094984 on May 16, 2019; International Patent Application No. PCT/US2019/055894, published as WO/2020/077236 on Apr. 16, 2020; and Drokhlyansky, et al., "The enteric nervous system of the human and mouse colon at single-cell a resolution," bioRxiv 746743; doi: doi.org/10.1101/746743, which are herein incorporated by reference in their entirety.

In certain embodiments, dimension reduction is used to cluster single cells based on differentially expressed genes. In certain embodiments, the dimension reduction technique may be, but is not limited to, Uniform Manifold Approximation and Projection (UMAP) or t-SNE (see, e.g., Becht et al., Evaluation of UMAP as an alternative to t-SNE for single-cell data, bioRxiv 298430; doi.org/10.1101/298430; and Becht et al., 2019, Dimensionality reduction for visualizing single-cell data using UMAP, Nature Biotechnology volume 37, pages 38-44).

MS Methods

Biomarker detection may also be evaluated using mass spectrometry methods. A variety of configurations of mass spectrometers can be used to detect biomarker values. Several types of mass spectrometers are available or can be produced with various configurations. In general, a mass spectrometer has the following major components: a sample inlet, an ion source, a mass analyzer, a detector, a vacuum system, and instrument-control system, and a data system. Difference in the sample inlet, ion source, and mass analyzer generally define the type of instrument and its capabilities. For example, an inlet can be a capillary-column liquid chromatography source or can be a direct probe or stage such as used in matrix-assisted laser desorption. Common ion sources are, for example, electrospray, including nanospray and microspray or matrix-assisted laser desorption. Common mass analyzers include a quadrupole mass filter, ion trap mass analyzer and time-of-flight mass analyzer. Additional mass spectrometry methods are well known in the art (see Burlingame et al., Anal. Chem. 70:647 R-716R (1998); Kinter and Sherman, New York (2000)).

Protein biomarkers and biomarker values can be detected and measured by any of the following: electrospray ionization mass spectrometry (ESI-MS), ESI-MS/MS, ESI-MS/(MS) n, matrix-assisted laser desorption ionization time-of-flight mass spectrometry (MALDI-TOF-MS), surface-enhanced laser desorption/ionization time-of-flight mass spectrometry (SELDI-TOF-MS), desorption/ionization on silicon (DIOS), secondary ion mass spectrometry (SIMS), quadrupole time-of-flight (Q-TOF), tandem time-of-flight (TOF/TOF) technology, called ultraflex III TOF/TOF, atmospheric pressure chemical ionization mass spectrometry (APCI-MS), APCI-MS/MS, APCI-(MS).sup.N, atmospheric pressure photoionization mass spectrometry (APPI-MS), APPI-MS/MS, and APPI-(MS).sup.N, quadrupole mass spectrometry, Fourier transform mass spectrometry (FTMS), quantitative mass spectrometry, and ion trap mass spectrometry.

Sample preparation strategies are used to label and enrich samples before mass spectroscopic characterization of protein biomarkers and determination biomarker values. Labeling methods include but are not limited to isobaric tag for relative and absolute quantitation (iTRAQ) and stable isotope labeling with amino acids in cell culture (SILAC). Capture reagents used to selectively enrich samples for candidate biomarker proteins prior to mass spectroscopic analysis include but are not limited to aptamers, antibodies, nucleic acid probes, chimeras, small molecules, an F(ab') 2 fragment, a single chain antibody fragment, an Fv fragment, a single chain Fv fragment, a nucleic acid, a lectin, a ligand-binding receptor, affibodies, nanobodies, ankyrins, domain antibodies, alternative antibody scaffolds (e.g. diabodies etc.) imprinted polymers, avimers, peptidomimetics, peptoids, peptide nucleic acids, threose nucleic acid, a hormone receptor, a cytokine receptor, and synthetic receptors, and modifications and fragments of these.

Immunoassays

In certain embodiments, immunoassays are used to detect or isolate cell types or cell phenotypes. Immunoassay methods are based on the reaction of an antibody to its corresponding target or analyte and can detect the analyte in a sample depending on the specific assay format. To improve specificity and sensitivity of an assay method based on immunoreactivity, monoclonal antibodies are often used because of their specific epitope recognition. Polyclonal antibodies have also been successfully used in various immunoassays because of their increased affinity for the target as compared to monoclonal antibodies Immunoassays have been designed for use with a wide range of biological sample matrices Immunoassay formats have been designed to provide qualitative, semi-quantitative, and quantitative results.

Quantitative results may be generated through the use of a standard curve created with known concentrations of the specific analyte to be detected. The response or signal from an unknown sample is plotted onto the standard curve, and a quantity or value corresponding to the target in the unknown sample is established.

Numerous immunoassay formats have been designed. ELISA or EIA can be quantitative for the detection of an analyte/biomarker. This method relies on attachment of a label to either the analyte or the antibody and the label component includes, either directly or indirectly, an enzyme. ELISA tests may be formatted for direct, indirect, competitive, or sandwich detection of the analyte. Other methods rely on labels such as, for example, radioisotopes (1125) or fluorescence. Additional techniques include, for example, agglutination, nephelometry, turbidimetry, Western blot, immunoprecipitation, immunocytochemistry, immunohistochemistry, flow cytometry, Luminex assay, and others (see ImmunoAssay: A Practical Guide, edited by Brian Law, published by Taylor & Francis, Ltd., 2005 edition).

Exemplary assay formats include enzyme-linked immunosorbent assay (ELISA), radioimmunoassay, fluorescent, chemiluminescence, and fluorescence resonance energy transfer (FRET) or time resolved-FRET (TR-FRET) immunoassays. Examples of procedures for detecting biomarkers include biomarker immunoprecipitation followed by quantitative methods that allow size and peptide level discrimination, such as gel electrophoresis, capillary electrophoresis, planar electrochromatography, and the like.

Methods of detecting and/or quantifying a detectable label or signal generating material depend on the nature of the label. The products of reactions catalyzed by appropriate enzymes (where the detectable label is an enzyme; see above) can be, without limitation, fluorescent, luminescent, or radioactive or they may absorb visible or ultraviolet light. Examples of detectors suitable for detecting such detectable labels include, without limitation, x-ray film, radioactivity counters, scintillation counters, spectrophotometers, colorimeters, fluorometers, luminometers, and densitometers.

Any of the methods for detection can be performed in any format that allows for any suitable preparation, processing, and analysis of the reactions. This can be, for example, in multi-well assay plates (e.g., 96 wells or 384 wells) or using any suitable array or microarray. Stock solutions for various agents can be made manually or robotically, and all subsequent pipetting, diluting, mixing, distribution, washing, incubating, sample readout, data collection and analysis can be done robotically using commercially available analysis software, robotics, and detection instrumentation capable of detecting a detectable label.

Hybridization Assays

Such applications are hybridization assays in which a nucleic acid that displays "probe" nucleic acids for each of the genes to be assayed/profiled in the profile to be generated is employed. In these assays, a sample of target nucleic acids is first prepared from the initial nucleic acid sample being assayed, where preparation may include labeling of the target nucleic acids with a label, e.g., a member of a signal producing system. Following target nucleic acid sample preparation, the sample is contacted with the array under hybridization conditions, whereby complexes are formed between target nucleic acids that are complementary to probe sequences attached to the array surface. The presence of hybridized complexes is then detected, either qualitatively or quantitatively. Specific hybridization technology which may be practiced to generate the expression profiles employed in the subject methods includes the technology described in U.S. Pat. Nos. 5,143,854; 5,288,644; 5,324,633; 5,432,049; 5,470,710; 5,492,806; 5,503,980; 5,510,270; 5,525,464; 5,547,839; 5,580,732; 5,661,028; 5,800,992, the disclosures of which are herein incorporated by reference, as well as WO 95/21265; WO 96/31622; WO 97/10365; WO 97/27317; EP 373 203; and EP 785 280. In these methods, an array of "probe" nucleic acids that includes a probe for each of the biomarkers whose expression is being assayed is contacted with target nucleic acids as described above. Contact is carried out under hybridization conditions, e.g., stringent hybridization conditions as described above, and unbound nucleic acid is then removed. The resultant pattern of hybridized nucleic acids provides information regarding expression for each of the biomarkers that have been probed, where the expression information is in terms of whether or not the gene is expressed and, typically, at what level, where the expression data, i.e., expression profile, may be both qualitative and quantitative.

Optimal hybridization conditions will depend on the length (e.g., oligomer vs. polynucleotide greater than 200 bases) and type (e.g., RNA, DNA, PNA) of labeled probe and immobilized polynucleotide or oligonucleotide. General parameters for specific (i.e., stringent) hybridization conditions for nucleic acids are described in Sambrook et al., supra, and in Ausubel et al., "Current Protocols in Molecular Biology", Greene Publishing and Wiley-interscience, NY (1987), which is incorporated in its entirety for all purposes. When the cDNA microarrays are used, typical hybridization conditions are hybridization in 5×SSC plus 0.2% SDS at 65

C for 4 hours followed by washes at 25° C. in low stringency wash buffer (1×SSC plus 0.2% SDS) followed by 10 minutes at 25° C. in high stringency wash buffer (0.1SSC plus 0.2% SDS) (see Shena et al., Proc. Natl. Acad. Sci. USA, Vol. 93, p. 10614 (1996)). Useful hybridization conditions are also provided in, e.g., Tijessen, Hybridization With Nucleic Acid Probes", Elsevier Science Publishers B.V. (1993) and Kricka, "Nonisotopic DNA Probe Techniques", Academic Press, San Diego, Calif. (1992).

In certain embodiments, a subject can be categorized based on signature genes or gene programs expressed by a tissue sample obtained from the subject. In certain embodiments, the tissue sample is analyzed by bulk sequencing. In certain embodiments, subtypes can be determined by determining the percentage of specific cell subtypes expressing the identified interacting genetic variants in the sample that contribute to the phenotype. In certain embodiments, gene expression associated with the cells are determined from bulk sequencing reads by deconvolution of the sample. For example, deconvoluting bulk gene expression data obtained from a tumor containing both malignant and non-malignant cells can include defining the relative frequency of a set of cell types in the tumor from the bulk gene expression data using cell type specific gene expression (e.g., cell types may be T cells, fibroblasts, macrophages, mast cells, B/plasma cells, endothelial cells, myocytes and dendritic cells); and defining a linear relationship between the frequency of the non-malignant cell types and the expression of a set of genes, wherein the set of genes comprises genes highly expressed by malignant cells and at most two non-malignant cell types, wherein the set of genes are derived from gene expression analysis of single cells in the tumor or the same tumor type, and wherein the residual of the linear relationship defines the malignant cell-specific (MCS) expression profile (see, e.g., WO 2018/191553; and Puram et al., Cell. 2017 Dec. 14; 171(7):1611-1624.e24).

Exemplary Therapies

The present invention also contemplates the use of the methods of modulating the cells and biomarkers described herein for treating a number of diseases. The present invention also contemplates the use of LN-innervating peptidergic sensory neurons and their target cells in LN disclosed herein for treatment of a variety of immuno- and neuronal diseases and other diseases or pathological conditions.

In some embodiments, the invention disclosed herein relates to a method or methods for therapy of modulating immune response in a patient. In some aspects, this immunomodulatory therapy can be enhancement of immune response in a patient, for example, a patient suffering from malignant diseases, a patient suffering from infectious diseases, and/or a patient suffering from acute or chronic illness that needs an enhanced immune response to help improve the health condition of the patient. In some aspects, this immunomodulatory therapy can be a suppression of immune response in a patient, for example, a patient with autoimmune diseases, a patient with organ or tissue transplantations, a patient with overacting immune system, and/or a patient in need of immune suppression for improvement of his/her health condition.

In some embodiments, the invention disclosed herein relates to compositions and methods for cellular therapy or immunocell therapy or neuronal cell therapy. In some aspects, the isolated cell or cells disclosed herein can be transplanted into patients in need thereof. In some aspects, the isolated cell or cells disclosed herein can be modified genetically, epigenetically, genomically, epigenomically, and/or proteomically to have novel or improved functionality and to be transplanted into patients in need thereof.

In some embodiments, the treatment is for disease/disorder or pathological condition of an organ or a tissue, including, but not limited to, disease of the hematopoietic system, immune system, central nervous system, peripheral nervous system, liver, eye, skeletal muscle, smooth muscle, heart, brain, and kidney, or may comprise treatment for an autoimmune disease, central nervous system disease, cancer and other proliferative diseases, neurodegenerative disorders, inflammatory disease, metabolic disorder, musculoskeletal disorder and the like.

Inflammatory and Autoimmune Diseases

In certain embodiments, modulation of T cell balance may be used to treat inflammatory diseases, disorders or aberrant autoimmune responses. Specific autoimmune responses resulting from an immunotherapy is described further herein. As used throughout the present specification, the terms "autoimmune disease" or "autoimmune disorder" used interchangeably refer to a diseases or disorders caused by an immune response against a self-tissue or tissue component (self-antigen) and include a self-antibody response and/or cell-mediated response. The terms encompass organ-specific autoimmune diseases, in which an autoimmune response is directed against a single tissue, as well as non-organ specific autoimmune diseases, in which an autoimmune response is directed against a component present in two or more, several or many organs throughout the body.

Examples of autoimmune diseases include but are not limited to acute disseminated encephalomyelitis (ADEM); Addison's disease; ankylosing spondylitis; antiphospholipid antibody syndrome (APS); aplastic anemia; autoimmune gastritis; autoimmune hepatitis; autoimmune thrombocytopenia; Behçet's disease; coeliac disease; dermatomyositis; diabetes mellitus type I; Goodpasture's syndrome; Graves' disease; Guillain-Barré syndrome (GBS); Hashimoto's disease; idiopathic thrombocytopenia purpura; inflammatory bowel disease (IBD) including Crohn's disease and ulcerative colitis; mixed connective tissue disease; multiple sclerosis (MS); myasthenia gravis; opsoclonus myoclonus syndrome (OMS); optic neuritis; Ord's thyroiditis; pemphigus; pernicious anaemia; polyarteritis nodosa; polymyositis; primary biliary cirrhosis; primary myxedema; psoriasis; rheumatic fever; rheumatoid arthritis; Reiter's syndrome; scleroderma; Sjögren's syndrome; systemic lupus erythematosus; Takayasu's arteritis; temporal arteritis; vitiligo; warm autoimmune hemolytic anemia; or Wegener's granulomatosis.

Examples of inflammatory diseases or disorders include, but are not limited to, asthma, allergy, allergic rhinitis, allergic airway inflammation, atopic dermatitis (AD), chronic obstructive pulmonary disease (COPD), inflammatory bowel disease (IBD), Irritable bowel syndrome (IBS), multiple sclerosis, arthritis, psoriasis, eosinophilic esophagitis, eosinophilic pneumonia, eosinophilic psoriasis, hypereosinophilic syndrome, graft-versus-host disease, uveitis, cardiovascular disease, pain, multiple sclerosis, lupus, vasculitis, chronic idiopathic urticaria and Eosinophilic Granulomatosis with Polyangiitis (Churg-Strauss Syndrome).

The asthma may be allergic asthma, non-allergic asthma, severe refractory asthma, asthma exacerbations, viral-induced asthma or viral-induced asthma exacerbations, steroid resistant asthma, steroid sensitive asthma, eosinophilic asthma or non-eosinophilic asthma and other related disorders characterized by airway inflammation or airway hyperresponsiveness (AHR).

The COPD may be a disease or disorder associated in part with, or caused by, cigarette smoke, air pollution, occupational chemicals, allergy or airway hyperresponsiveness.

The allergy may be associated with foods, pollen, mold, dust mites, animals, or animal dander.

The IBD may be ulcerative colitis (UC), Crohn's Disease, collagenous colitis, lymphocytic colitis, ischemic colitis, diversion colitis, Behcet's syndrome, infective colitis, indeterminate colitis, and other disorders characterized by inflammation of the mucosal layer of the large intestine or colon.

The arthritis may be selected from the group consisting of osteoarthritis, rheumatoid arthritis and psoriatic arthritis.

Cancer

In one aspect, the invention provides for methods and compositions for treating cancer. The cancer may include, without limitation, liquid tumors such as leukemia (e.g., acute leukemia, acute lymphocytic leukemia, acute myelocytic leukemia, acute myeloblastic leukemia, acute promyelocytic leukemia, acute myelomonocytic leukemia, acute monocytic leukemia, acute erythroleukemia, chronic leukemia, chronic myelocytic leukemia, chronic lymphocytic leukemia), polycythemia vera, lymphoma (e.g., Hodgkin's disease, non-Hodgkin's disease), Waldenstrom macroglobulinemia, heavy chain disease, or multiple myeloma.

The cancer may include, without limitation, solid tumors such as sarcomas and carcinomas. Examples of solid tumors include, but are not limited to fibrosarcoma, myxosarcoma, liposarcoma, chondrosarcoma, osteogenic sarcoma, chordoma, angiosarcoma, endotheliosarcoma, lymphangiosarcoma, lymphangioendotheliosarcoma, synovioma, mesothelioma, Ewing's tumor, leiomyosarcoma, rhabdomyosarcoma, squamous cell carcinoma, basal cell carcinoma, adenocarcinoma, sweat gland carcinoma, sebaceous gland carcinoma, papillary carcinoma, papillary adenocarcinomas, cystadenocarcinoma, medullary carcinoma, epithelial carcinoma, bronchogenic carcinoma, hepatoma, colorectal cancer (e.g., colon cancer, rectal cancer), anal cancer, pancreatic cancer (e.g., pancreatic adenocarcinoma, islet cell carcinoma, neuroendocrine tumors), breast cancer (e.g., ductal carcinoma, lobular carcinoma, inflammatory breast cancer, clear cell carcinoma, mucinous carcinoma), ovarian carcinoma (e.g., ovarian epithelial carcinoma or surface epithelial-stromal tumour including serous tumour, endometrioid tumor and mucinous cystadenocarcinoma, sex-cord-stromal tumor), prostate cancer, liver and bile duct carcinoma (e.g., hepatocellular carcinoma, cholangiocarcinoma, hemangioma), choriocarcinoma, seminoma, embryonal carcinoma, kidney cancer (e.g., renal cell carcinoma, clear cell carcinoma, Wilms tumor, nephroblastoma), cervical cancer, uterine cancer (e.g., endometrial adenocarcinoma, uterine papillary serous carcinoma, uterine clear-cell carcinoma, uterine sarcomas and leiomyosarcomas, mixed mullerian tumors), testicular cancer, germ cell tumor, lung cancer (e.g., lung adenocarcinoma, squamous cell carcinoma, large cell carcinoma, bronchioloalveolar carcinoma, non-small-cell carcinoma, small cell carcinoma, mesothelioma), bladder carcinoma, signet ring cell carcinoma, cancer of the head and neck (e.g., squamous cell carcinomas), esophageal carcinoma (e.g., esophageal adenocarcinoma), tumors of the brain (e.g., glioma, glioblastoma, astrocytoma, medulloblastoma, craniopharyngioma, ependymoma, pinealoma, hemangioblastoma, acoustic neuroma, oligodendroglioma, schwannoma, meningioma), neuroblastoma, retinoblastoma, neuroendocrine tumor, melanoma, cancer of the stomach (e.g., stomach adenocarcinoma, gastrointestinal stromal tumor), or carcinoids. Lymphoproliferative disorders are also considered to be proliferative diseases.

Screening for Modulating Agents

In certain embodiments, the invention provides for screening of agents capable of of modulating neural stimulation and/or efferent signaling of LN-innervating peptidergic nociceptor sensory neurons. In certain embodiments, the method comprises: a) applying a candidate agent to a cell population comprising LN-innervating peptidergic nociceptor sensory neurons; b) detecting modulation of one or more phenotypic aspects of the cell population by the candidate agent, thereby identifying the agent. The phenotypic aspects of the cell population that is modulated may be a gene signature or biomarker specific to a cell type or cell phenotype or phenotype specific to a population of cells (e.g., homeostasis or inflammatory markers). In certain embodiments, steps can include administering candidate modulating agents to cells, detecting identified cell (sub) populations for changes in signatures, or identifying relative changes in cell (sub)populations which may comprise detecting relative abundance of particular gene signatures. The phenotype may be a change in secretion of neuropeptides associated with sensory neurons. In certain embodiments, candidate agents are screened in in vivo models such as described herein. In certain embodiments, candidate agents are screened in in vivo models of a disease as described herein.

The term "agent" broadly encompasses any condition, substance or agent capable of modulating one or more phenotypic aspects of a cell or cell population as disclosed herein. Such conditions, substances or agents may be of physical, chemical, biochemical and/or biological nature. The term "candidate agent" refers to any condition, substance or agent that is being examined for the ability to modulate one or more phenotypic aspects of a cell or cell population as disclosed herein in a method comprising applying the candidate agent to the cell or cell population (e.g., exposing the cell or cell population to the candidate agent or contacting the cell or cell population with the candidate agent) and observing whether the desired modulation takes place.

Agents may include any potential class of biologically active conditions, substances or agents, such as for instance antibodies, proteins, peptides, nucleic acids, oligonucleotides, small molecules, or combinations thereof, as described herein.

The methods of phenotypic analysis can be utilized for evaluating environmental stress and/or state, for screening of chemical libraries, and to screen or identify structural, syntenic, genomic, and/or organism and species variations. For example, a culture of cells, can be exposed to an environmental stress, such as but not limited to heat shock, osmolarity, hypoxia, cold, oxidative stress, radiation, starvation, a chemical (for example a therapeutic agent or potential therapeutic agent) and the like. After the stress is applied, a representative sample can be subjected to analysis, for example at various time points, and compared to a control, such as a sample from an organism or cell, for example a cell from an organism, or a standard value. By exposing cells, or fractions thereof, tissues, or even whole animals, to different members of the chemical libraries, and performing the methods described herein, different members of a chemical library can be screened for their effect on immune phenotypes thereof simultaneously in a relatively short amount of time, for example using a high throughput method.

In some embodiments, screening of test agents involves testing a combinatorial library containing a large number of potential modulator compounds. A combinatorial chemical library may be a collection of diverse chemical compounds generated by either chemical synthesis or biological synthesis, by combining a number of chemical "building blocks" such as reagents. For example, a linear combinatorial chemical library, such as a polypeptide library, is formed by combining a set of chemical building blocks (amino acids) in every possible way for a given compound length (for example the number of amino acids in a polypeptide compound). Millions of chemical compounds can be synthesized through such combinatorial mixing of chemical building blocks.

In certain embodiments, the present invention provides for gene signature screening. The concept of signature screening was introduced by Stegmaier et al. (Gene expression-based high-throughput screening (GE-HTS) and application to leukemia differentiation. Nature Genet. 36, 257-263 (2004)), who realized that if a gene expression signature was the proxy for a phenotype of interest, it could be used to find small molecules that effect that phenotype without knowledge of a validated drug target. The signatures or biological programs of the present invention may be used to screen for drugs that reduce the signature or biological program in cells as described herein. The signature or biological program may be used for GE-HTS. In certain embodiments, pharmacological screens may be used to identify drugs that are selectively toxic to cells having a signature.

The Connectivity Map (cmap) is a collection of genome-wide transcriptional expression data from cultured human cells treated with bioactive small molecules and simple pattern-matching algorithms that together enable the discovery of functional connections between drugs, genes and diseases through the transitory feature of common gene expression changes (see, Lamb et al., The Connectivity Map: Using Gene-Expression Signatures to Connect Small Molecules, Genes, and Disease. Science 29 Sep. 2006: Vol. 313, Issue 5795, pp. 1929-1935, DOI: 10.1126/science.1132939; and Lamb, J., The Connectivity Map: a new tool for biomedical research. Nature Reviews Cancer January 2007: Vol. 7, pp. 54-60). In certain embodiments, Cmap can be used to screen for small molecules capable of modulating a signature or biological program of the present invention in silico.

Further embodiments are illustrated in the following Examples which are given for illustrative purposes only and are not intended to limit the scope of the invention.

EXAMPLES

Example 1. Single-Cell Analysis Identifies Nociceptive Sensory Neurons as Local Modulators of Lymph Node Homeostasis To systemically map sensory neuron-immune circuits within LNs, Applicants conducted an unbiased survey of sensory neurons innervating skin-draining LNs at the anatomic, molecular, and functional levels by developing novel approaches that integrate state-of-the-art imaging, scRNA-seq, and optogenetic technologies. Applicants found that sensory neurons indeed innervate LNs, and they do so with subregional specificity such that the LN periphery—a location prone to inflammation-induced mechanical, chemical and cellular changes—is much more densely innervated than the cell-dense LN cortex. Applicants identified four molecularly-distinct LN-innervating sensory neuronal subtypes with a strong enrichment for peptidergic nociceptors. Then, Applicants generated, to their knowledge, the first draft single-cell "atlas" of mouse steady-state LNs, and used this to nominate putative cellular partners of sensory neurons in LNs. With knowledge of ligands and receptors on both LN-innervating neurons and LN resident cells, Applicants developed an in silico analysis based on trans ligand-receptor interactions and found that stromal cells exhibit the highest potential for interaction with LN sensory fibers. Finally, Applicants experimentally verified predicted LN-resident target cell types using a custom pipeline that combined optogenetic stimulation of LN-innervating sensory neurons with a Seq-Well-based screen for the LN cell types exhibiting the largest transcriptional changes. Together, the results define the anatomic and molecular identity of a previously enigmatic population of sensory neurons that innervate LNs, and uncover a novel sensory neuron-stroma axis within steady state LNs. The experimental and computational frameworks established within this study should be broadly applicable to future analysis of neural circuits in a wide variety of tissues.

Lymph Nodes are Innervated by Both Sensory and Sympathetic Neurons

Figures 8A, 8B:
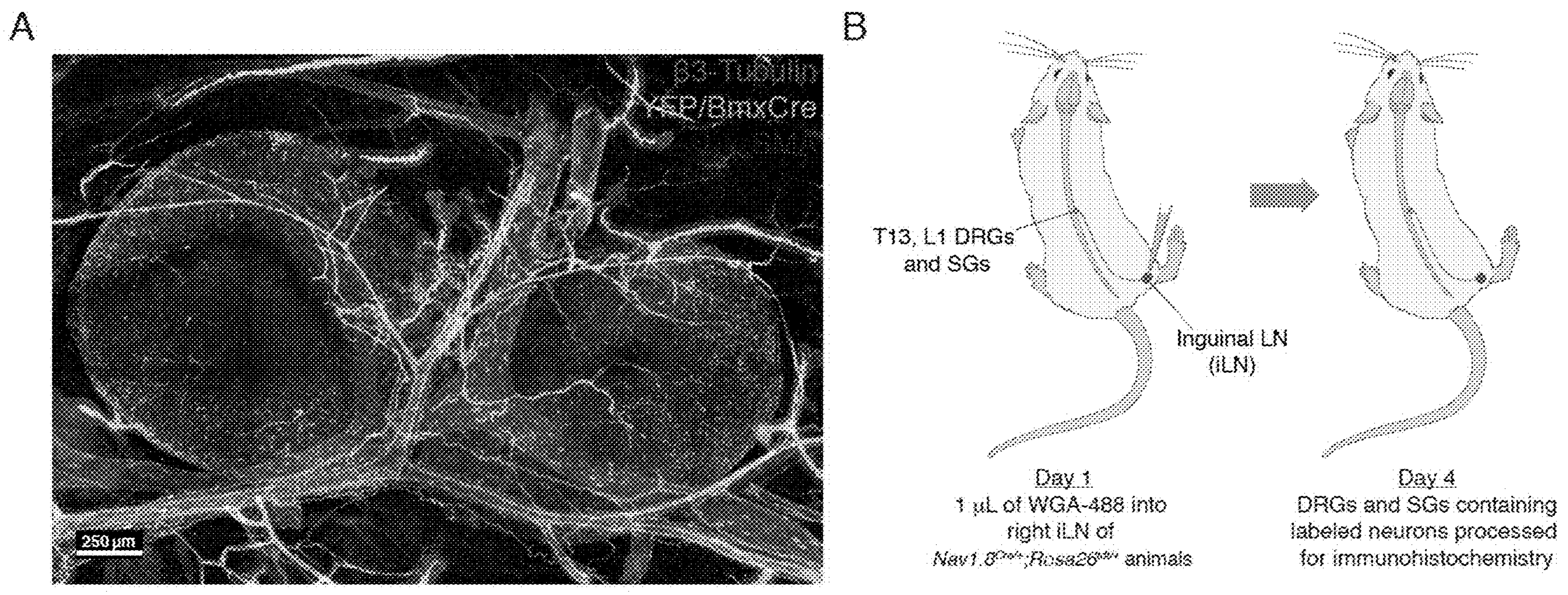
FIG. 8A-8G (Related to FIG. 1) Dual innervation of peripheral LNs by sensory and sympathetic neurons.
Figures 8C, 8D, 8E, 8F, 8G:
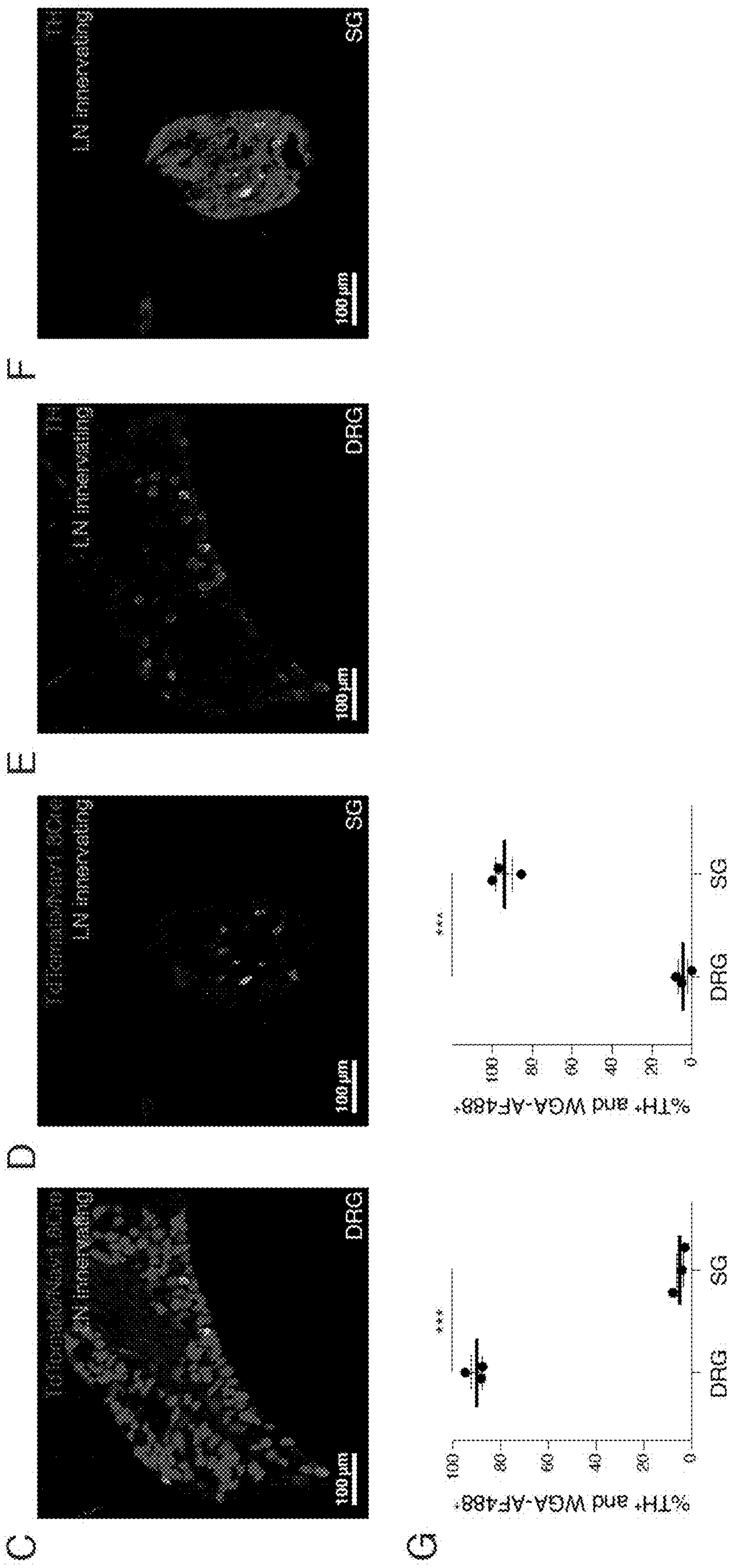
Figures 9A, 9B, 9C:
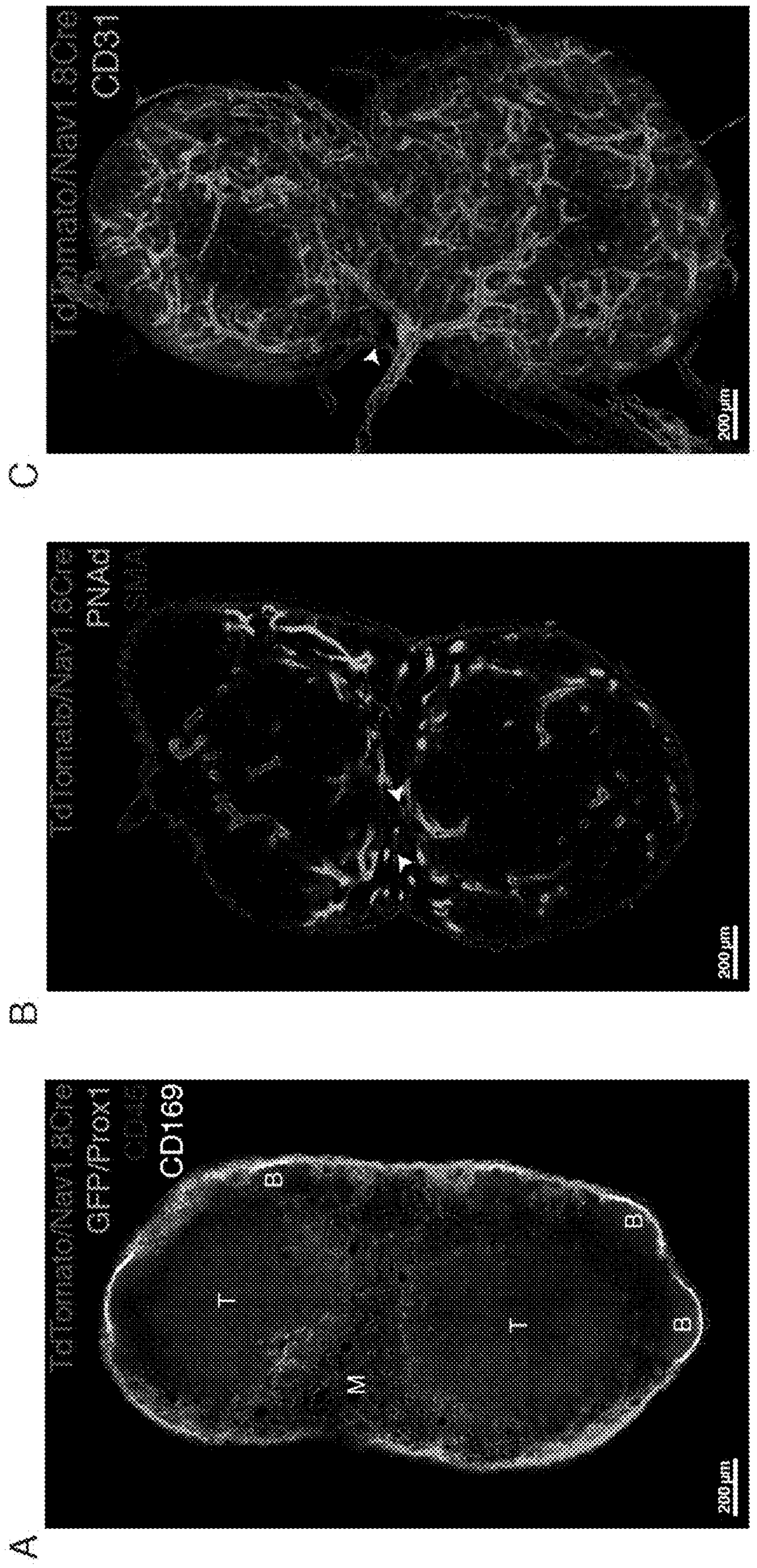
FIG. 9A-9E (Related to FIG. 2) Spatial distribution of sensory innervation of peripheral LNs. Neuronal architecture in and/or around LNs.
Figures 9D, 9E:
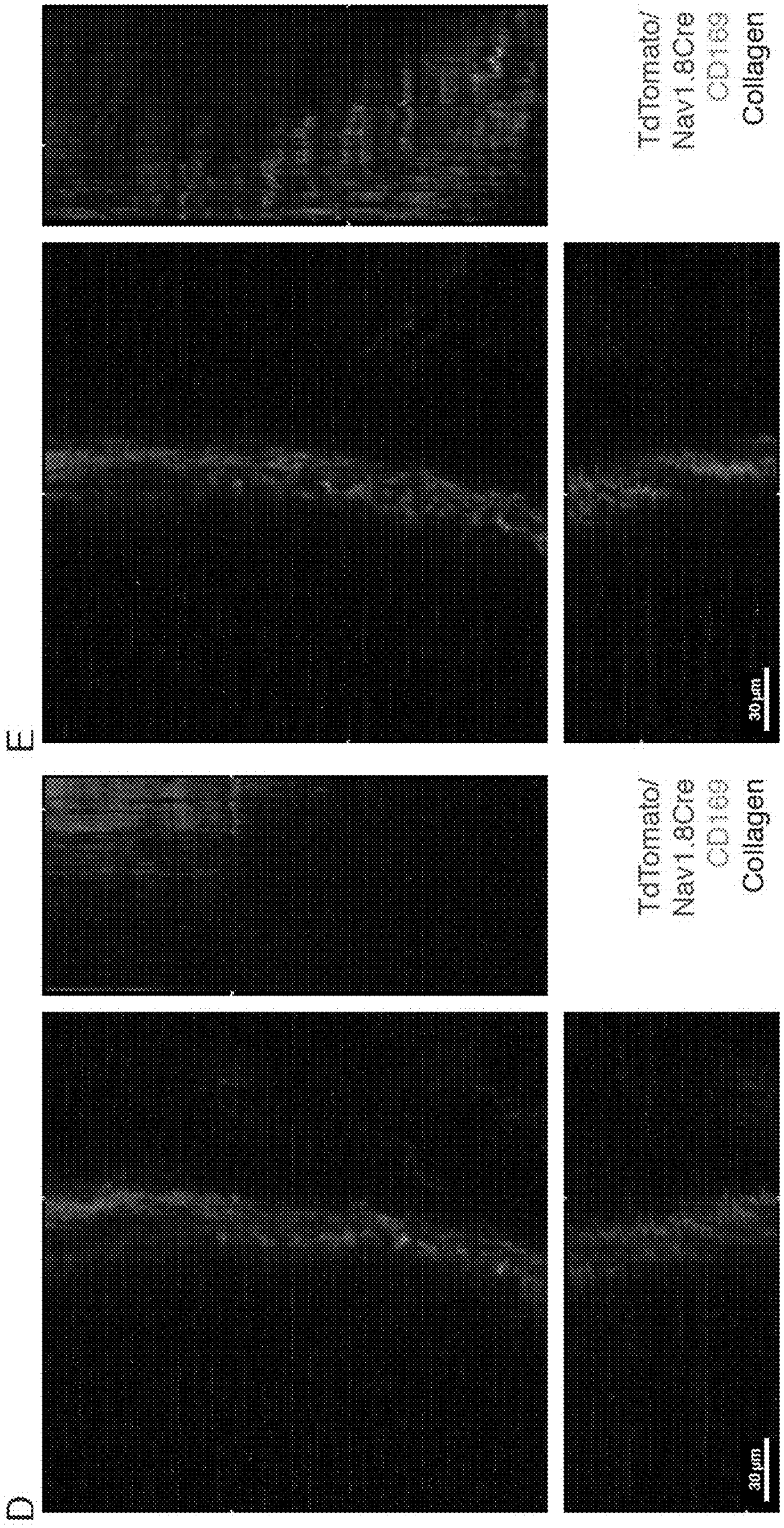

To establish the existence and extent of sensory innervation of lymph nodes (LNs), Applicants genetically labeled peripheral neurons of sensory lineage, including most nociceptors, with tdTomato using Cre expressed under the control of the Nav1.8 locus (encoding a nociceptor-enriched voltage gated sodium channel) (Nassar et al., 2004). To visualize the complete morphology of nerve fibers that are organized in 3D in LNs, the previously described immunolabeling-enabled three-dimensional imaging of solvent-cleared organs (iDISCO) protocol was adapted for LNs (Renier et al., 2014). By co-staining for tdTomato and the pan-neuronal marker β3-tubulin, Applicants observed Cre-mediated tdTomato labeling of nerve fibers, presumably originating from primary sensory neurons, as one major component of total neuronal architecture in and around LNs (FIG. 1A). As a control, Applicants also observed sympathetic innervation of LNs, which expressed tyrosine hydroxylase (TH), a prototypical marker for sympathetic neurons (FIG. 1B). The primary path of entry for nerve fibers into LN were the major blood vessels in the hilum region (FIG. 1B). Incoming nerve fibers preferentially traveled along vessels that were identifiable as small arteries and arterioles based on selective genetic labeling in Bmx-Cre-ERT2 Rosa26eYFP/+ mice in which arterial endothelial cells (ECs) specifically express YFP (FIG. 8A). Within the LN, the arborization pattern of putative sympathetic (tdTomato− TH+) neurons was largely non-overlapping with that of putative sensory (tdTomato+ TH−) neurons. While TH+ neurons densely innervated the vasculature by wrapping around subsets of vessels, tdTomato+ fibers assumed much simpler terminal morphology around vasculature and in addition, branched extensively in the avascular space.

To clarify the anatomic origin of the tdTomato+ and TH+ fibers, Applicants retrogradely labeled LN-innervating sensory and sympathetic neurons in the cell body compartments, i.e., DRGs and SGs, respectively, from the inguinal LN (iLN) by microinjection of a fluorescent neuronal tracer, WGA-AF488, into iLNs of Nav1.8Cre/+; Rosa26tdTomato/+ animals (Robertson, 1990) (FIG. 8B). When tdTomato and TH expression were examined within WGA-labeled populations, Applicants found that >90% of WGA-labeled neurons in DRGs and SGs were tdTomato+ TH− and tdTomato−TH+, respectively, confirming that Nav1.8Cre and TH adequately and specifically label sensory and sympathetic innervation of LNs (FIG. 8C-8G).

To address the interdependence between these two types of innervation, Applicants assessed the sensitivity of each type of fiber to 6-hydroxydopamine (6-OHDA)-mediated chemical sympathectomy or diphtheria toxin A (DTA)-mediated genetic ablation of Nav1.8 lineage neurons. While 6-OHDA treatment led to efficient sympathetic denervation of LNs, the sensory counterpart was not compromised (FIG. 1C-1E). Conversely, developmental ablation of Nav1.8 lineage neurons in Nav1.8Cre/+; Rosa26DTA/tdTomato (Nav1.8-DTA) mice (Abrahamsen et al., 2008) resulted in a selective loss of sensory fibers in LNs (FIG. 1F-1H). Thus, Applicants unexpectedly discovered that LNs receive not only sympathetic but also sensory innervation, two categorically different types of innervation that are anatomically independent of each other.

Sensory Neurons Preferentially Innervate the Periphery of LNs

Figures 2A, 2B, 2C, 2D, 2E, 2F:
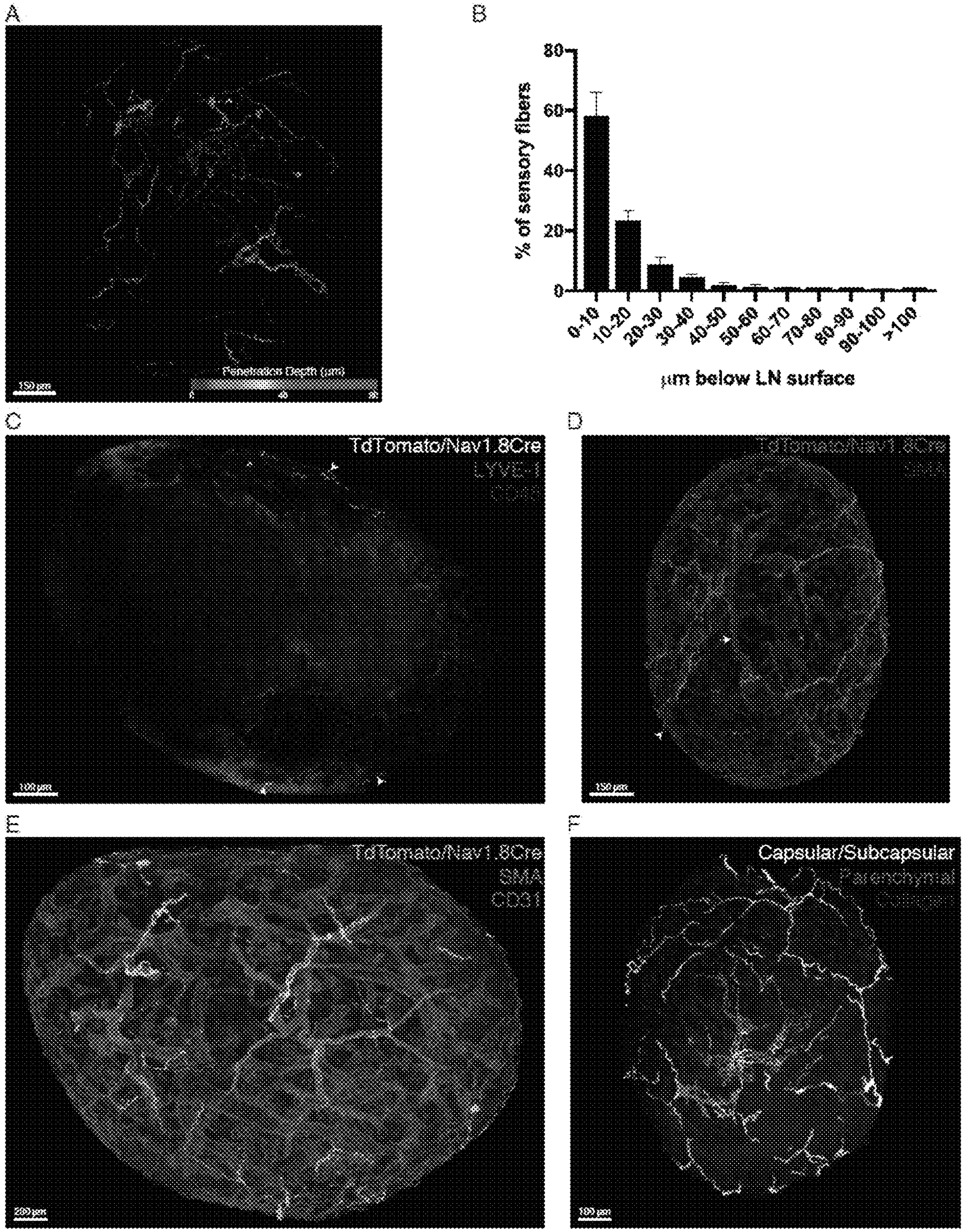
FIG. 2A-2F Spatial distribution of sensory innervation of peripheral LNs.

To map the spatial distribution of sensory fibers within LNs, Applicants visualized sensory innervation within cleared whole-mounts popliteal LNs (popLNs) in relation to various functionally distinct LN compartments. To identify intranodal sensory fibers, i.e., tdTomato+ fibers in LN parenchyma, Applicants genetically labeled together with the sensory fibers the entire lymphatic network in LNs with GFP in Nav1.8Cre/+; Rosa26tdTomato/+; Prox1-GFP animals where GFP expression is under the control of a LEC-specific promoter Prox1. As lymphatic endothelial cells (LECs) line the lymphatic sinuses within LNs including the subcapsular sinus (SCS), the outermost region of the LN proper immediately underneath the LN capsule, sensory fibers below the LN surface—i.e.,—the GFP+ ceiling of the SCS were considered intranodal. Applicants found that sensory fibers that reached LN parenchyma remained close to the surface of LNs with an average maximum penetration depth of ~100 μm (111.6 (mean)±29.16 (SEM)) for popLNs) (FIG. 2A). Notably, ~60% of intranodal sensory fibers were no more than 10 μm away from the surface of popLNs (FIG. 2B). Remarkably, tdTomato+ fibers were almost exclusively located in the medulla, marked by the LEC marker lymphatic vessel endothelial hyaluronan receptor 1 (LYVE-1), with minimal invasion of the CD45-dense LN cortex (FIG. 2C).

Within the more densely-innervated outer cortical region of LNs, sensory innervation organized into two main nerve plexuses, namely perivascular and capsular/subcapsular plexuses, as evidenced by their spatial proximity to cells containing smooth muscle actin at the LN surface and within the walls of feeding arterioles (FIG. 2D). The perivascular fibers coursed through the medulla in tight association with the arterioles, characterized by the characteristic pattern/morphology of smooth muscle cells, until terminating before reaching the capillary network and peripheral node addressin+ (PNAd) high endothelial venules (HEVs) (FIG. 2E). Occasionally, individual axons turned away from the vasculature and meandered in the avascular space (FIG. 2E). The capsular/subcapsular fibers, a branch of the perivascular parental axons, ramified extensively within the collagen-rich capsule and, in some cases, extended into the subcapsular space making contact with CD169+ subcapsular sinus macrophages, an early key player in orchestrating innate and adaptive immune responses to a wide variety of lymph borne antigens/pathogens within LNs (Kuka and Iannacone, 2014) (FIGS. 2F, 9B-9D). Thus, while the LN cortex where the majority of lymphocytes reside is almost devoid of sensory innervation, cells in the LN periphery, particularly those within the perivascular and subcapsular space, are in close proximity to sensory fibers suggesting potential functional interactions. The concentration of sensory fibers in the outermost cortex may allow for more sensitive monitoring of LN reactivity since any rapid change in volume would be most easily detected in the outer cortex. Moreover, the location of sensory fibers in immediate vicinity to the subcapsular sinus gives them easy access to biochemical cues within afferent lymph.

Figures 3A, 3B, 3C, 3D:
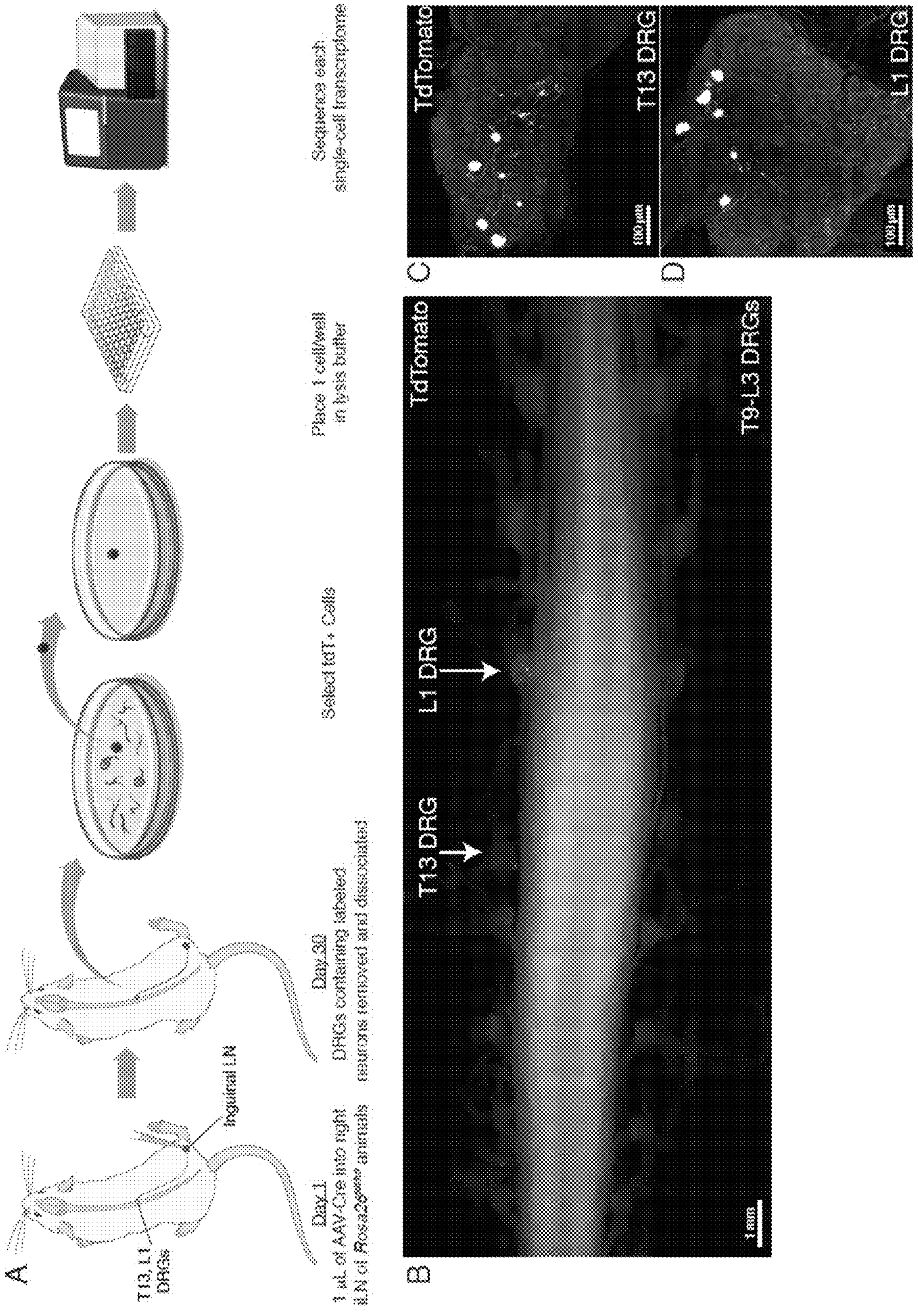
FIG. 3A-3F Retrograde labeling of LN-innervating sensory neurons for single-cell RNA-seq.
Figures 10A, 10B:
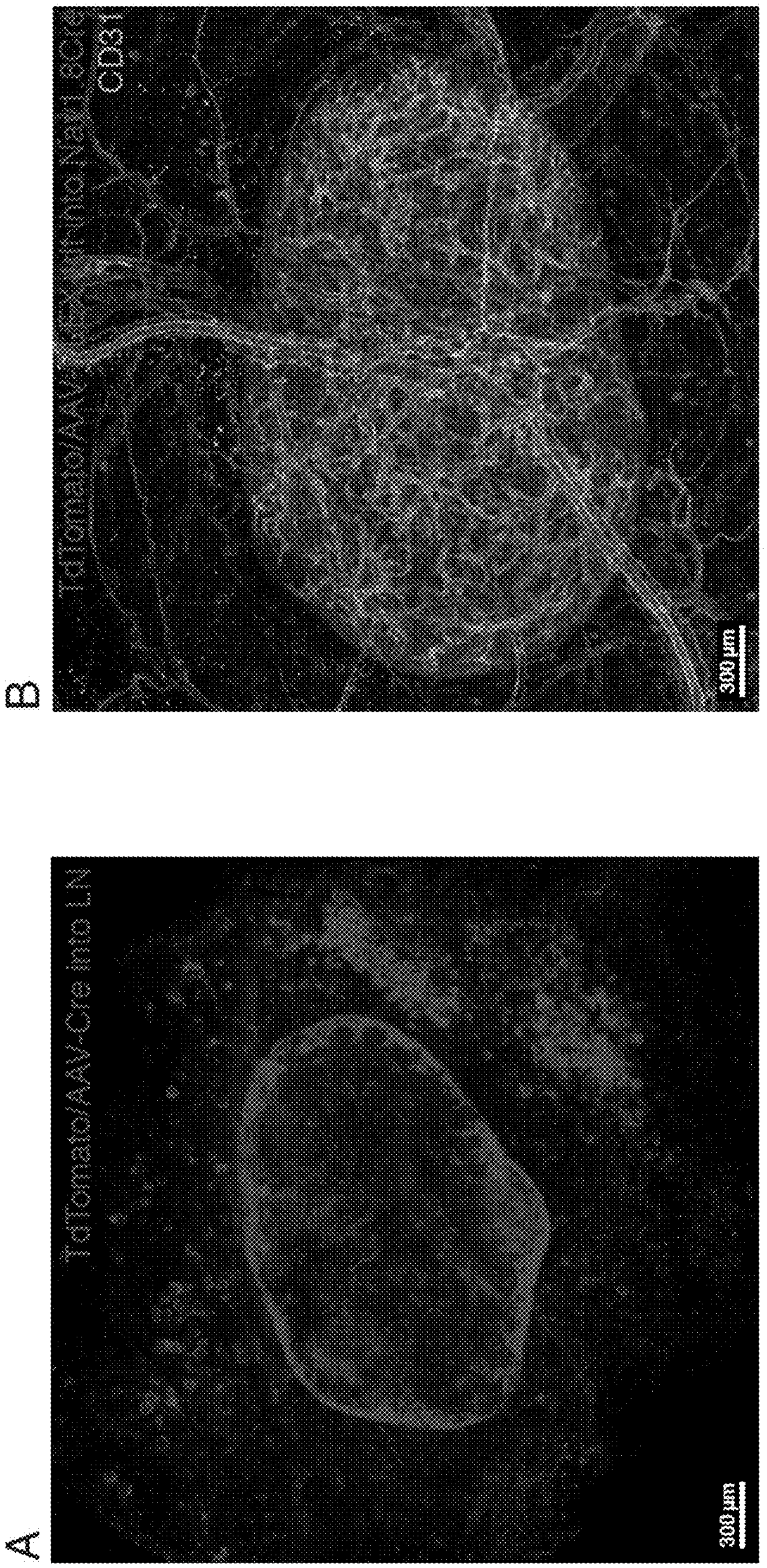
FIG. 10A-10H (Related to FIGS. 2 and 3) Spatial distribution of sensory innervation of peripheral LNs and Retrograde labeling of LN-innervating sensory neurons for single-cell RNA-seq. Neuronal architecture in or/and around LNs.
Figures 10C, 10D, 10E, 10F:
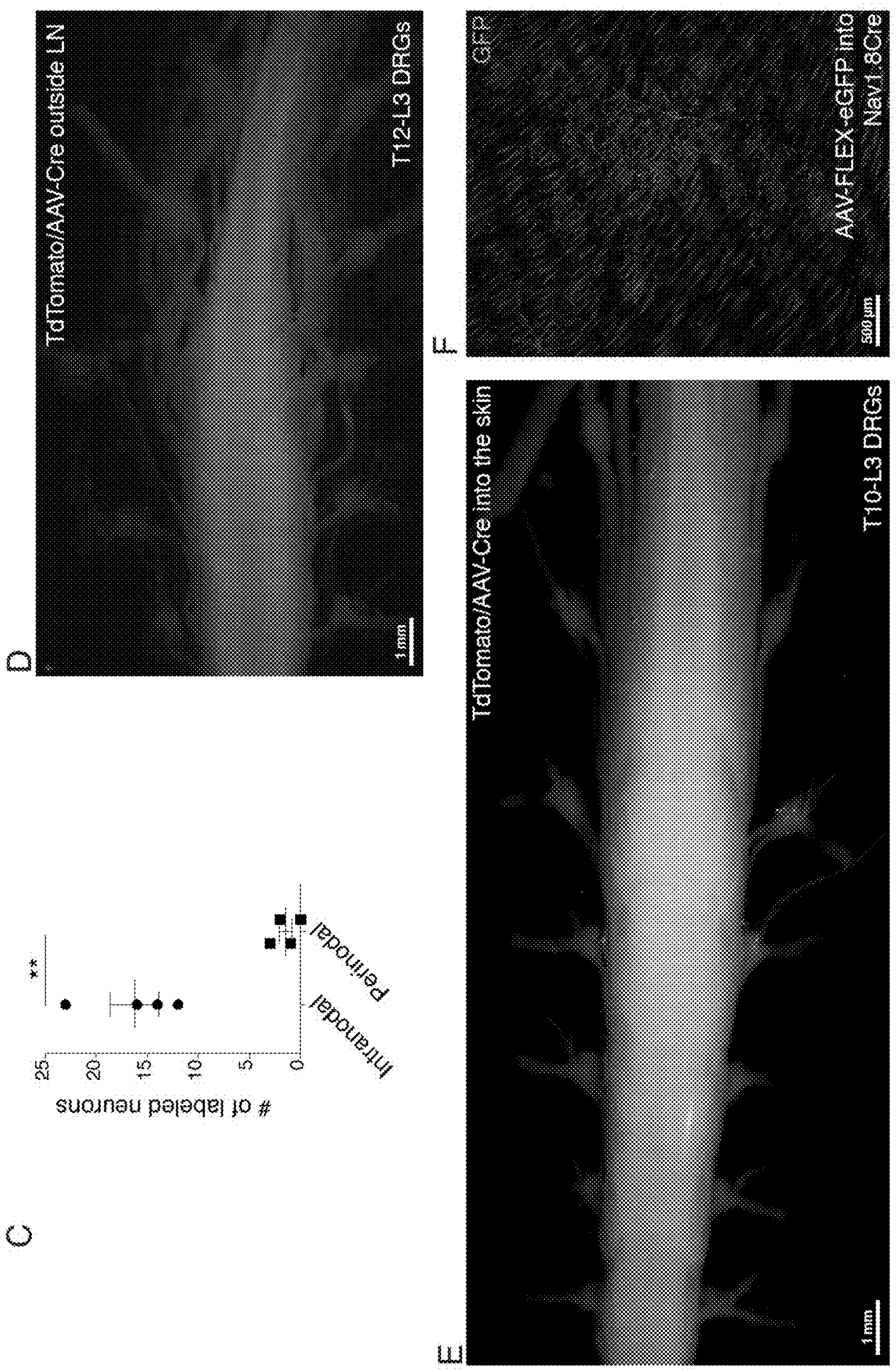

LN-Innervating Sensory Neurons are a Heterogeneous Population Overrepresented by Peptidergic Nociceptors In light of the rich molecular, electrophysiological, and functional heterogeneity within DRG sensory neurons, Applicants sought to reveal the full diversity of LN-innervating sensory neurons with an unbiased single cell RNA-seq-based approach (scRNA-seq). To enable transcriptome-wide molecular profiling of the sensory neurons that project to LNs, Applicants employed a Cre-lox based viral labeling strategy that allowed reliable identification and isolation of LN-innervating sensory neurons in DRGs for scRNA-seq (FIG. 3A). Briefly, Applicants injected Cre-expressing recombinant adeno-associated virus (AAV2/1-Cre), one of the most efficient serotypes with broad tropism towards DRG neurons when delivered into the DRG or the skin (Kuehn et al., 2019; Mason et al., 2010), into the iLN of Rosa26LSL-tdTomato/LSL-tdTomato animals carrying a Cre-dependent tdTomato reporter. Upon entry into sensory fibers, this non-replicating virus travels retrogradely to the cell bodies in DRGs to induce Cre-mediated deletion of a floxed ‘stop’ sequence resulting in selective expression of tdTomato in LN-innervating sensory neurons. Indeed, following unilateral iLN injection, robust tdTomato labeling was consistently observed in ipsilateral T13 and L1 DRGs, i.e., the last thoracic and the first lumbar DRGs, which supply the inguinal region (Takahashi and Nakajima, 1996) (FIG. 3B-3D). TdTomato labeling at the site of injection was largely confined to the injected LN, indicating tight spatial confinement of the injected material (FIG. 10A). To directly assess the specificity of their retrograde labeling strategy, Applicants injected AAV2/1 carrying a Cre-dependent tdTomato cassette (AAV-Flex-tdTomato) into the iLN of Nav1.8Cre animals, in which only sensory neurons express Cre recombinase. The retrogradely-labeled tdTomato+ peripheral terminals exhibited an innervation pattern similar to what was described above for Nav1.8 lineage LN-innervating sensory neurons, thus confirming their identity as LN-innervating sensory neurons (FIGS. 2D and 10B). To rule out the possibility of inadvertent off-target labeling from the vicinity of the injected LNs, Applicants assessed the extent of retrograde labeling of DRG neurons following deliberate perinodal injection of the same amount of virus, mimicking a failed intranodal injection. In comparison with intranodal injections, which consistently resulted in labeling of a small but robust number of DRG neurons (16.25 (mean)±2.394 (SEM), few if any DRG neurons (1.500 (mean)±0.6455 (SEM)) were labeled after deliberate perinodal injections, suggesting that Applicants' intranodal injection strategy targets specifically and selectively the true LN-innervating neurons (FIGS. 10C and 10D).

After manually isolating tdTomato+ single DRG neurons, Applicants performed scRNA-seq using the Smart-Seq2 protocol to yield a final dataset of 52 LN-innervating sensory neurons across 8 mice. To control for potential AAV infection-induced transcriptional changes and to identify peripheral target-specific molecular signatures and neuronal phenotypes, Applicants also generated scRNA-seq libraries from 31 skin-innervating neurons from 4 Rosa26LSL-tdTomato/LSL-tdTomato mice using a similar approach following intradermal injection of Cre-expressing AAV (FIGS. 10E and 10F).

Figure 3E:
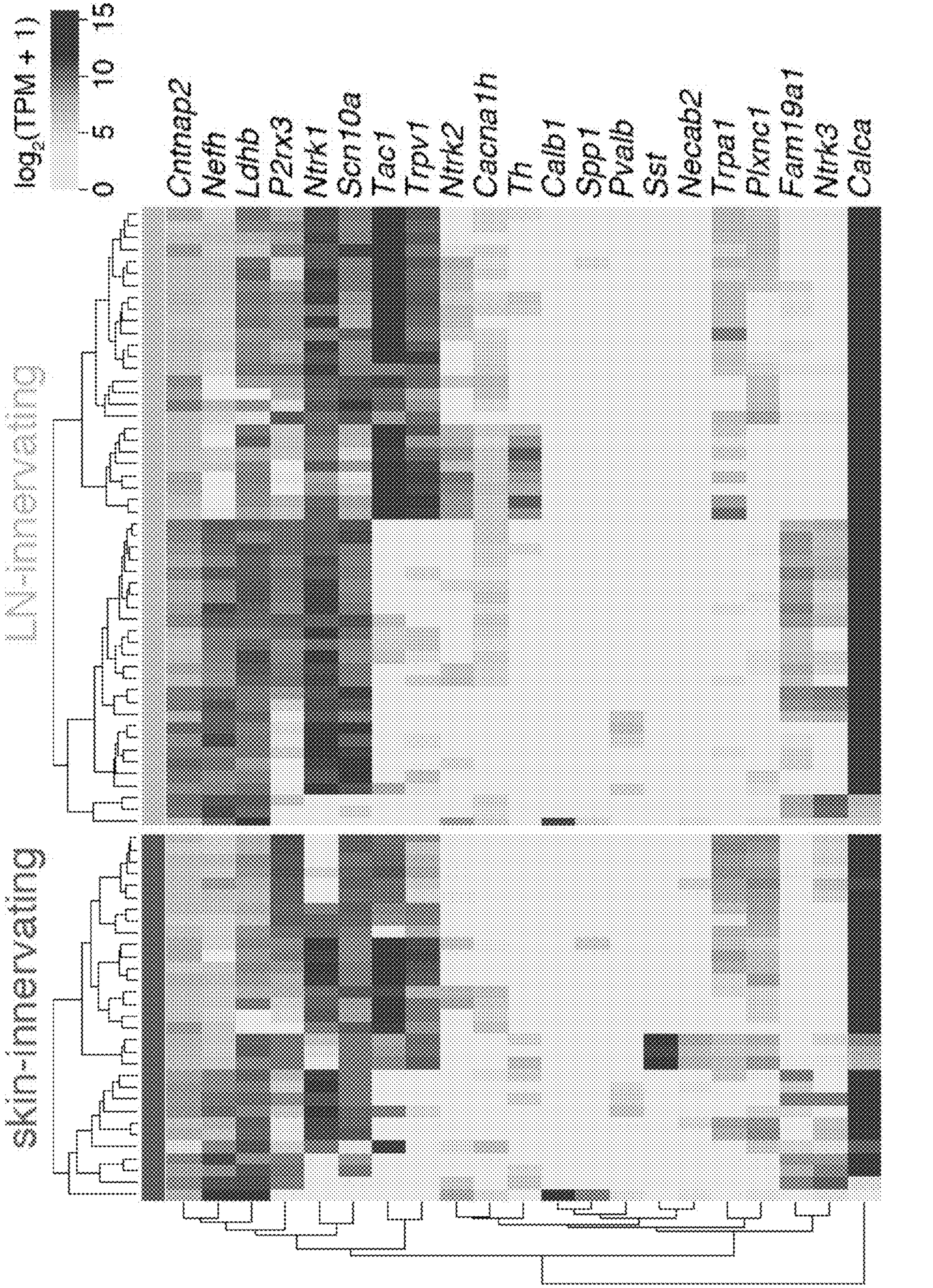
Figure 3F:
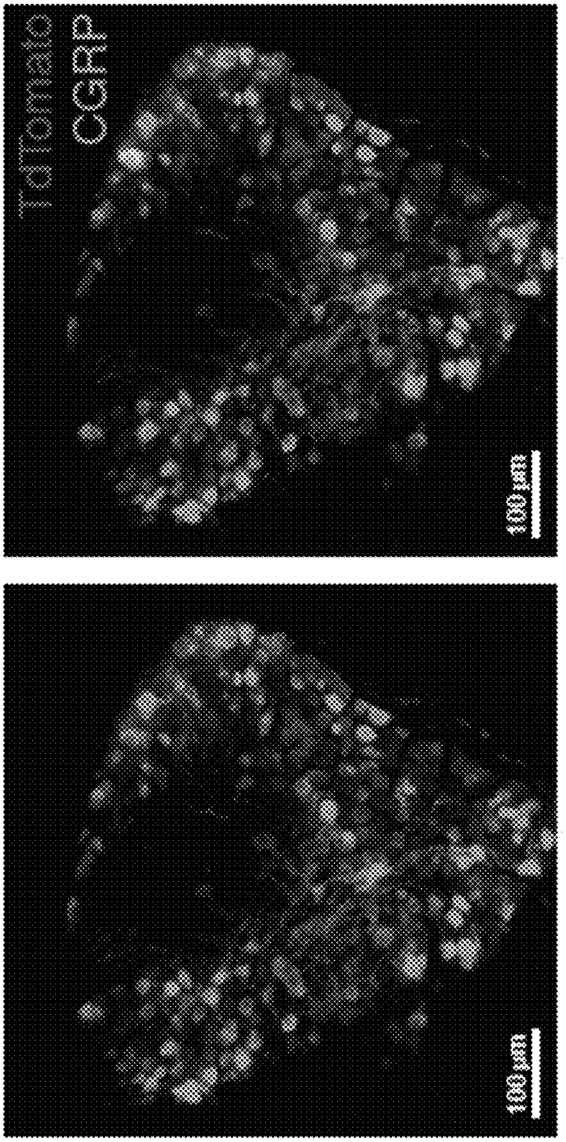
Figures 10G, 10H:
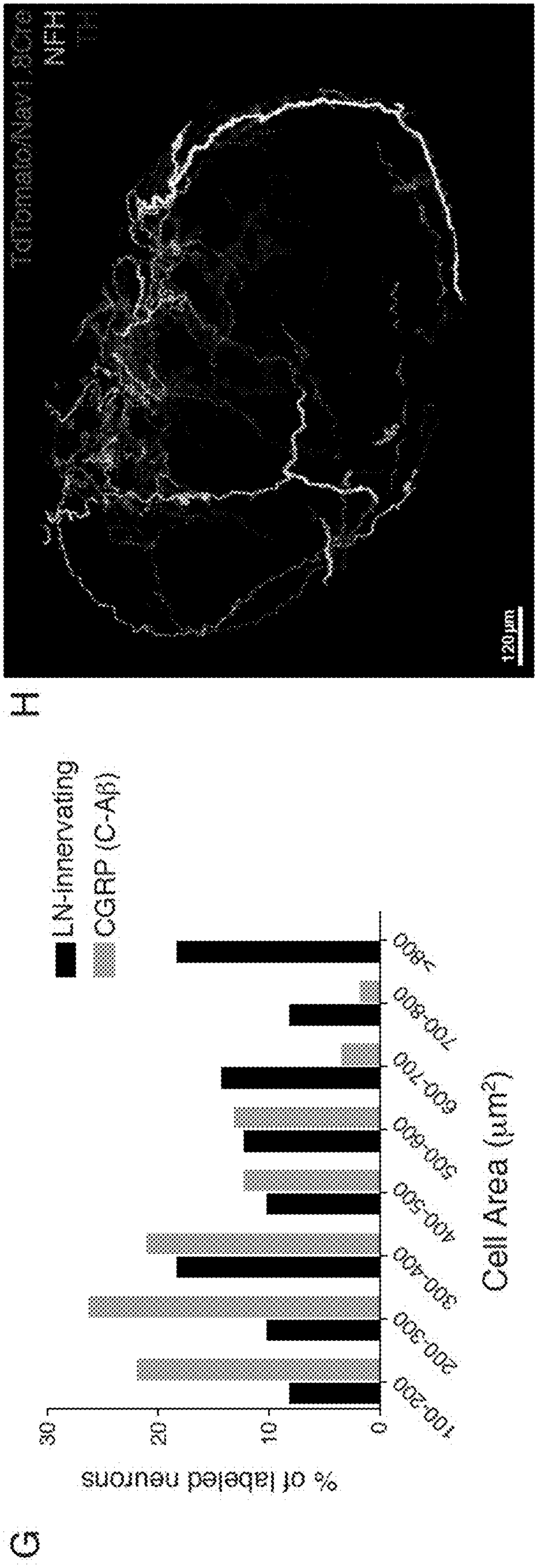

To define the molecular identity of LN-innervating sensory neurons, Applicants first examined the single-cell libraries for their expression of canonical markers for sensory neuron molecular subtypes (FIG. 3E). First, Applicants confirmed that the majority (96% with log 2(1+TPM)>1) of LN-innervating sensory neurons expressed Nav1.8 (Scn10a), and few (23% with log 2(1+TPM)>1) co-expressed TH (Th). Surprisingly, Applicants observed uniform expression of TrkA (Ntrk1) and CGRP (Calca), and little expression of canonical single markers for low-threshold mechanoreceptors, proprioceptors, and nonpeptidergic nociceptors, suggesting that the majority of LN-innervating sensory neurons are peptidergic nociceptors. Indeed, 88% (88.39% (mean)±8.672% (SEM)) of retrogradely-labeled LN-innervating sensory neurons expressed CGRP by immunohistochemistry (FIG. 3F). Notably, mutually exclusive expression of substance P (Tac1) and neurofilament heavy chain (NFH) (Nefh) within Calca+ LN-innervating sensory neurons allowed the identification of two LN-innervating peptidergic nociceptor subclasses akin to the previously defined PEP1 and PEP2 clusters which correspond to thermosensitive unmyelinated nociceptors and lightly myelinated Ad nociceptors, respectively (Usoskin et al., 2015) (FIG. 3E). Consistent with the heterogeneous expression of Nefh, a marker for medium-to-large diameter sensory neurons with myelinated axons (Rice and Albrecht, 2008), whole-mount DRG staining revealed that retrogradely-labeled LN-innervating sensory neurons were variable in soma size. Furthermore, NFH+ myelinated and NFH-unmyelinated sensory fibers were both abundant in the perivascular and capsular/subcapsular space of LNs (FIG. 10H).

Figures 4A, 4B:
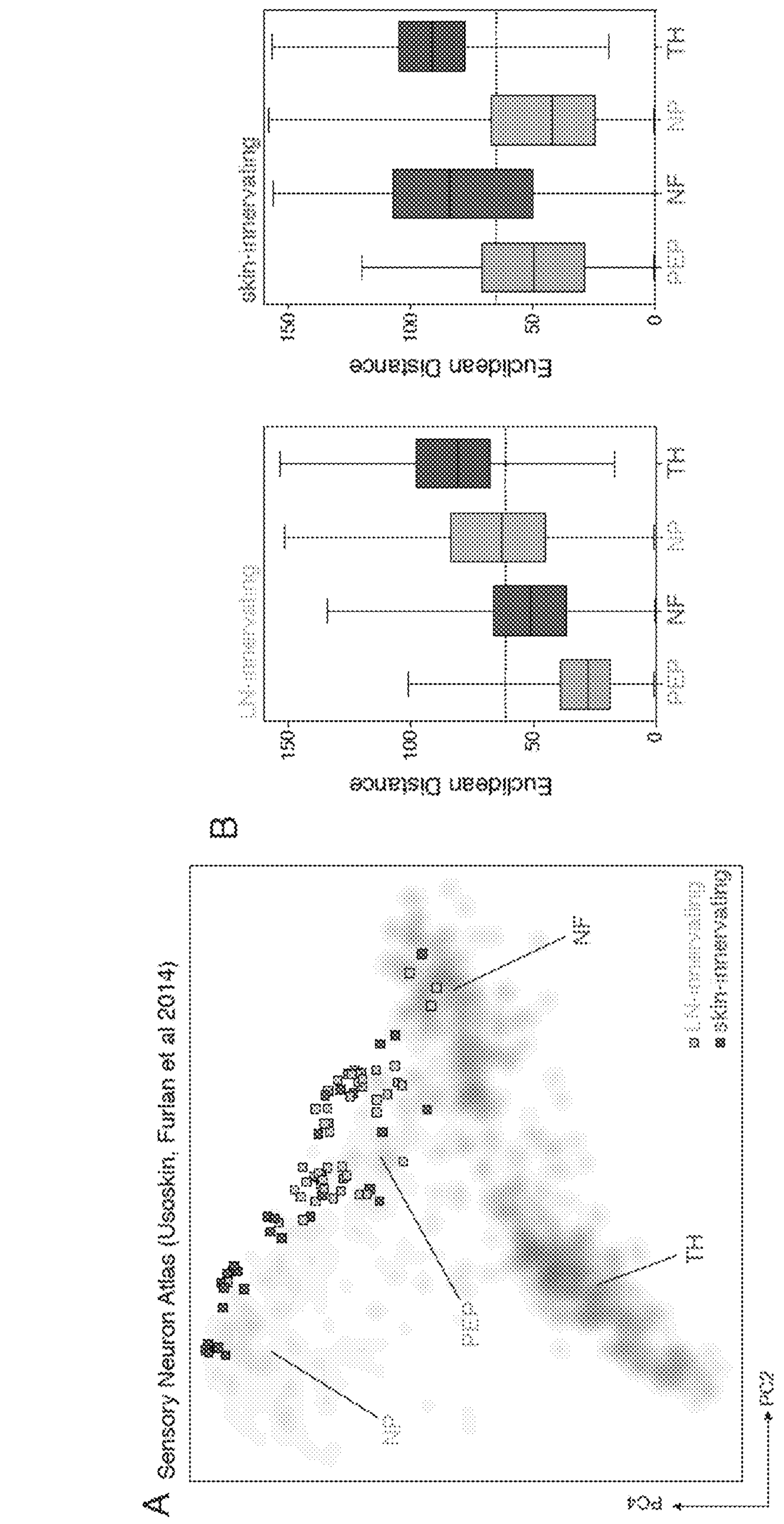
FIG. 4A-4E LN-innervating sensory neurons are primarily peptidergic nociceptors.
Figure 4C:
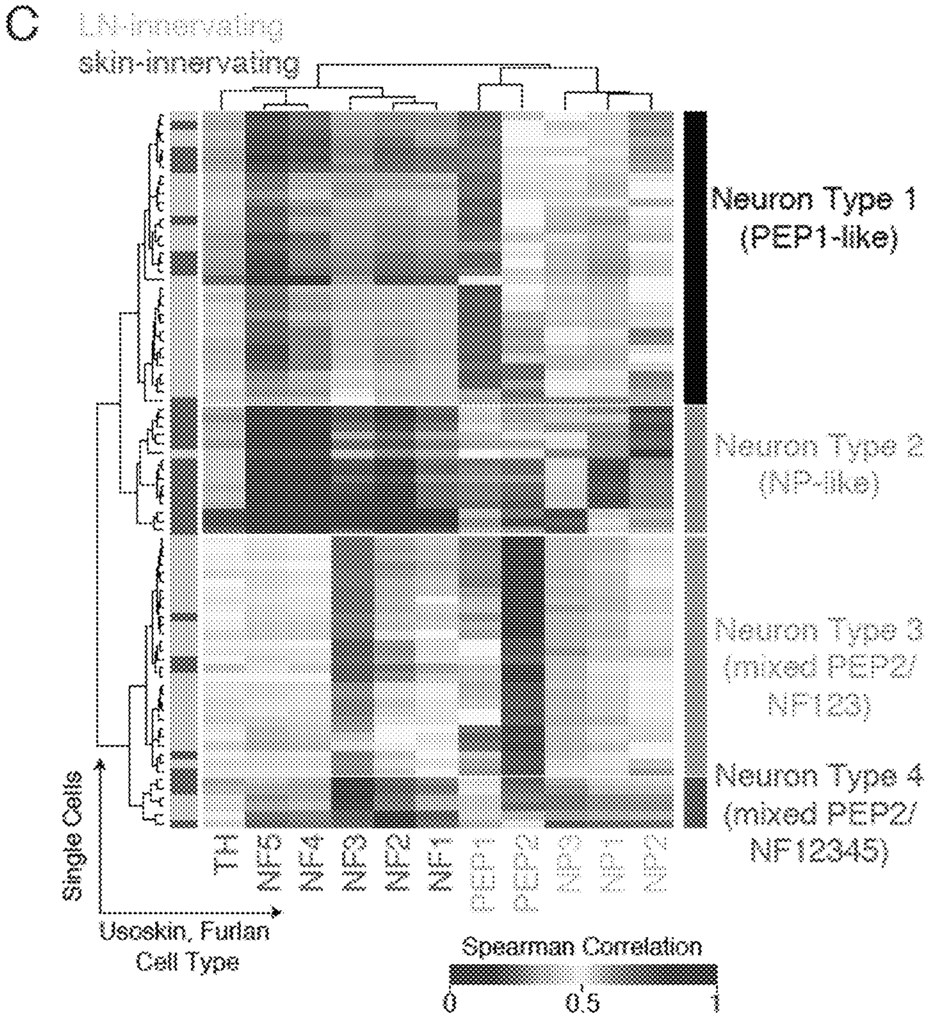
Figure 4D:
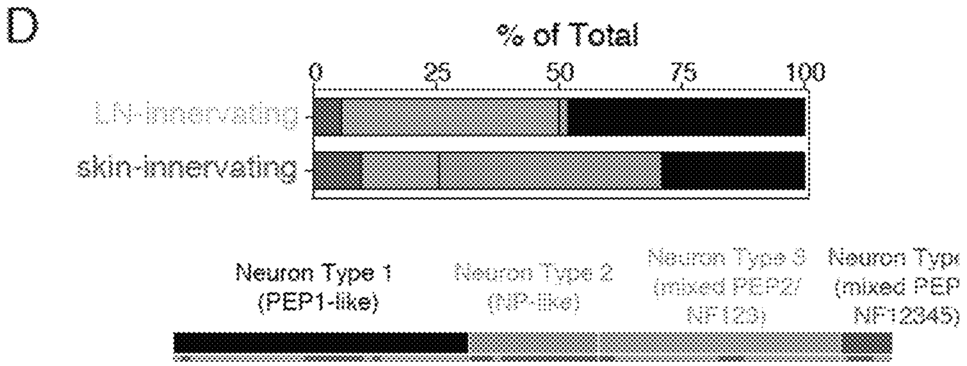

To look beyond the expression of canonical neuronal markers alone, Applicants next sought to contextualize the LN-innervating sensory neurons against a published scRNA-Seq Sensory Neuron Atlas (Usoskin et al., 2015). Using single-cell transcriptomic profiles of 622 DRG neurons, Applicants calculated principal components (PC) over all neuronal cells and projected their LN-innervating and skin-innervating sensory neurons into the principal components space (FIG. 4A). Consistent with the strong peptidergic features (e.g., Calca, Ntrk1 expression) described above, LN-innervating sensory neurons were distributed over an area in PC-space in closest proximity to the peptidergic neurons (PEP) defined by Usoskin et al (FIG. 4B). To directly classify LN-innervating or skin-innervating sensory neurons relative to the 11 published DRG subtypes, Applicants created pseudopopulation averages from single cell transcriptomes of each subtype, and calculated the Spearman correlation between single LN-innervating or skin-innervating sensory neurons and the neuronal subtype pseudopopulations (FIG. 4C). Using hierarchical clustering based upon the similarity of their single neurons to the neuronal subtypes defined by Usoskin et al., Applicants discovered 4 major transcriptionally distinct neuronal classes within their dataset, termed Neuron Types 1 to 4. Each Neuron Type was represented, albeit in very different proportions, in both LN-innervating and skin-innervating sensory neurons, demonstrating both intrinsic heterogeneity within sensory neurons innervating the same target, as well as innervation target-dependent differences in subtype composition (FIG. 4D). Neuron Types 1 and 3 were enriched in the LN-innervating population relative to the skin-innervating population (LN-innervating: 48% Neuron Type 1, 44% Neuron Type 3; skin-innervating: 29% Neuron Type 1, 16% Neuron Type 3). Conversely, Neuron Types 2 and 4, which correspond to nonpeptidergic nociceptors and myelinated non-nociceptors, respectively, were underrepresented in the LN-innervating population compared to the skin-innervating population (LN-innervating: 2% Neuron Type 2, 6% Neuron Type 4; skin-innervating: 45% Neuron Type 2, 10% Neuron Type 4).

Figure 4E:
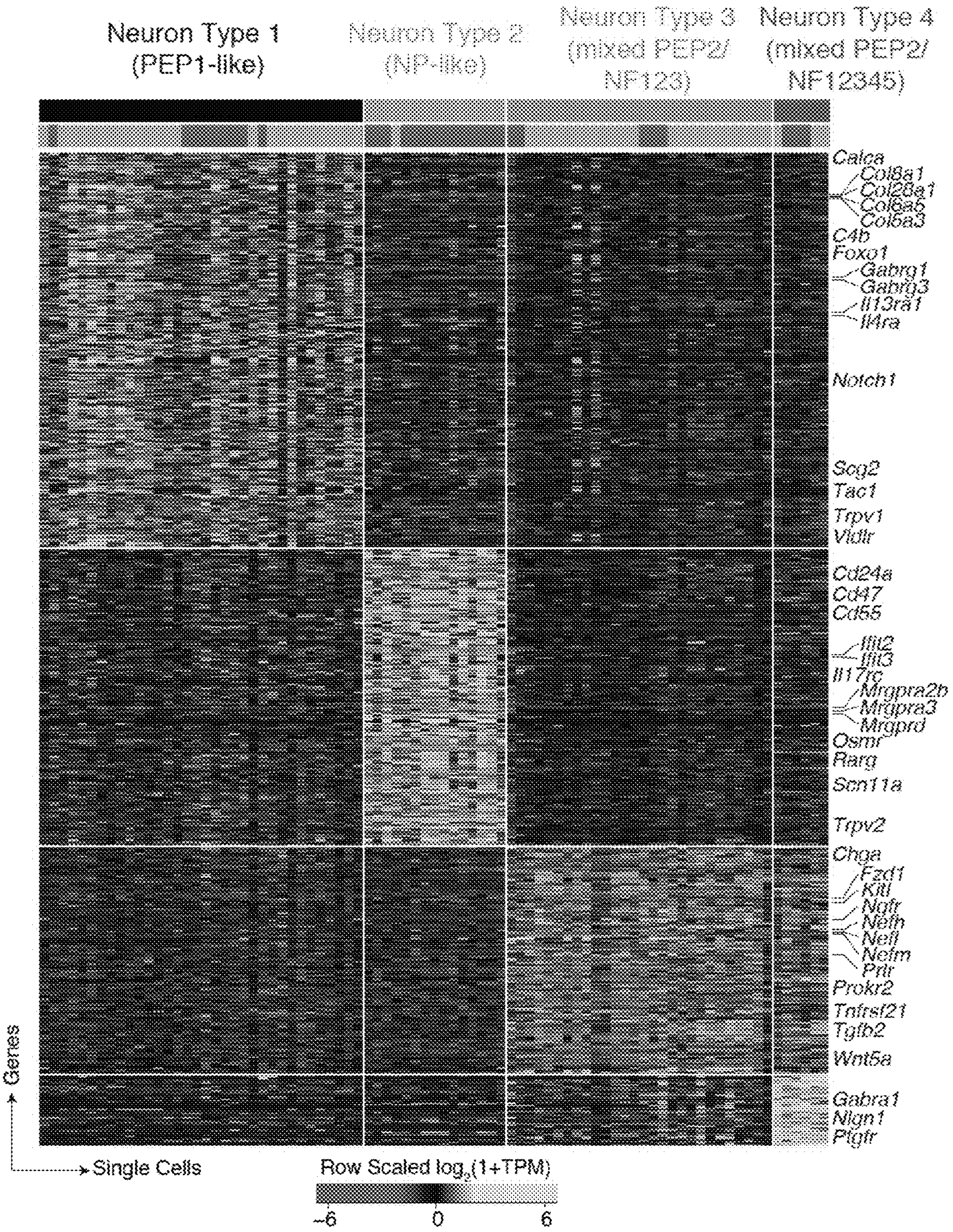

To further understand the distinct molecular phenotypes represented by Neuron Types, Applicants performed differential expression analysis and discovered unique gene modules that cleanly define each Neuron Type (FIG. 4E, Table 1). Together, these data showed that LN-innervating sensory neurons are heterogeneous at the transcriptomic level, yet are strongly enriched for peptidergic phenotypes.

Unique Molecular Characteristics of LN-Innervating Sensory Neurons

Figure 5A:
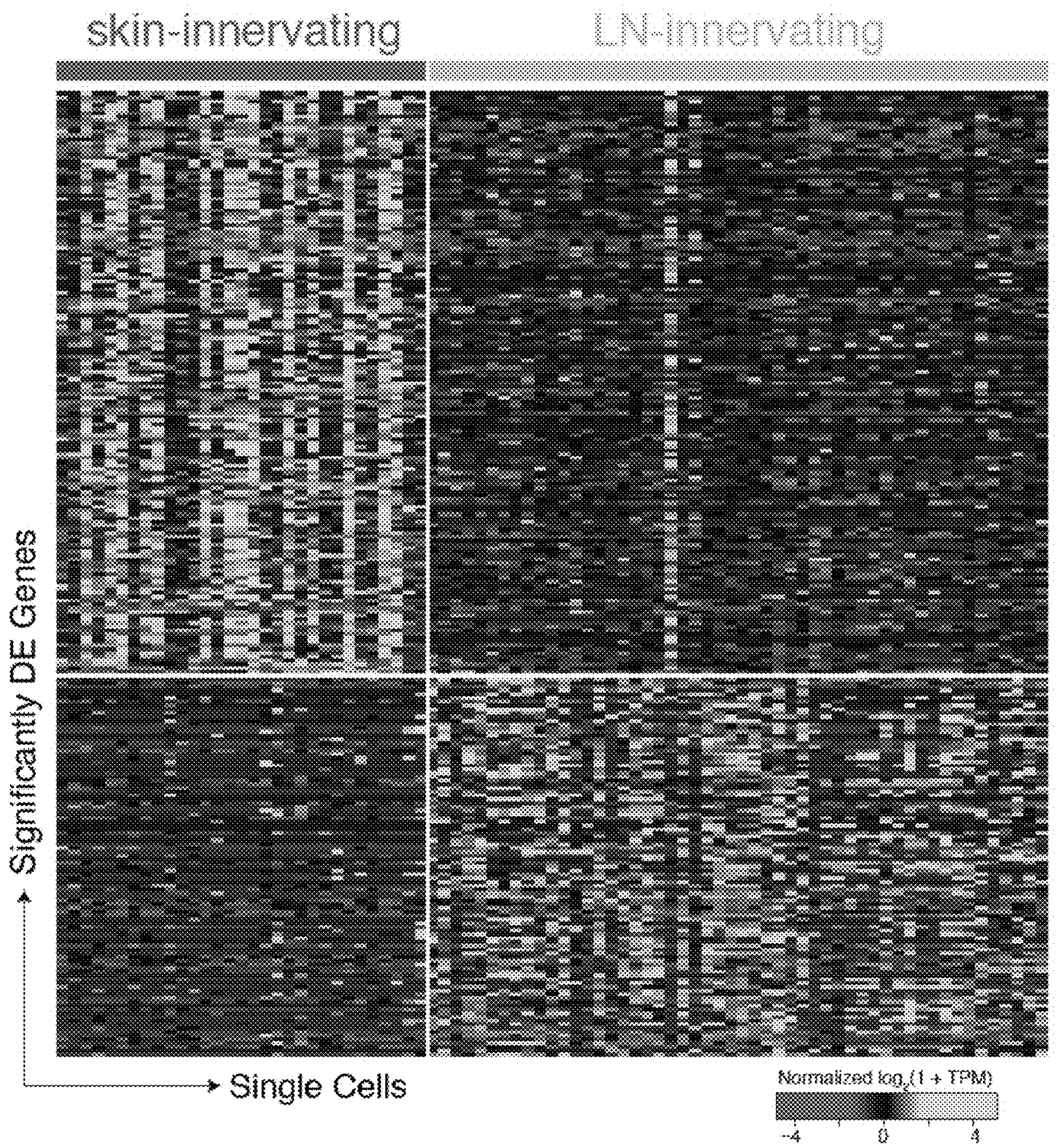
FIG. 5A-5F LN-innervating sensory neurons express unique defining markers and functional pathways.
Figure 5B:
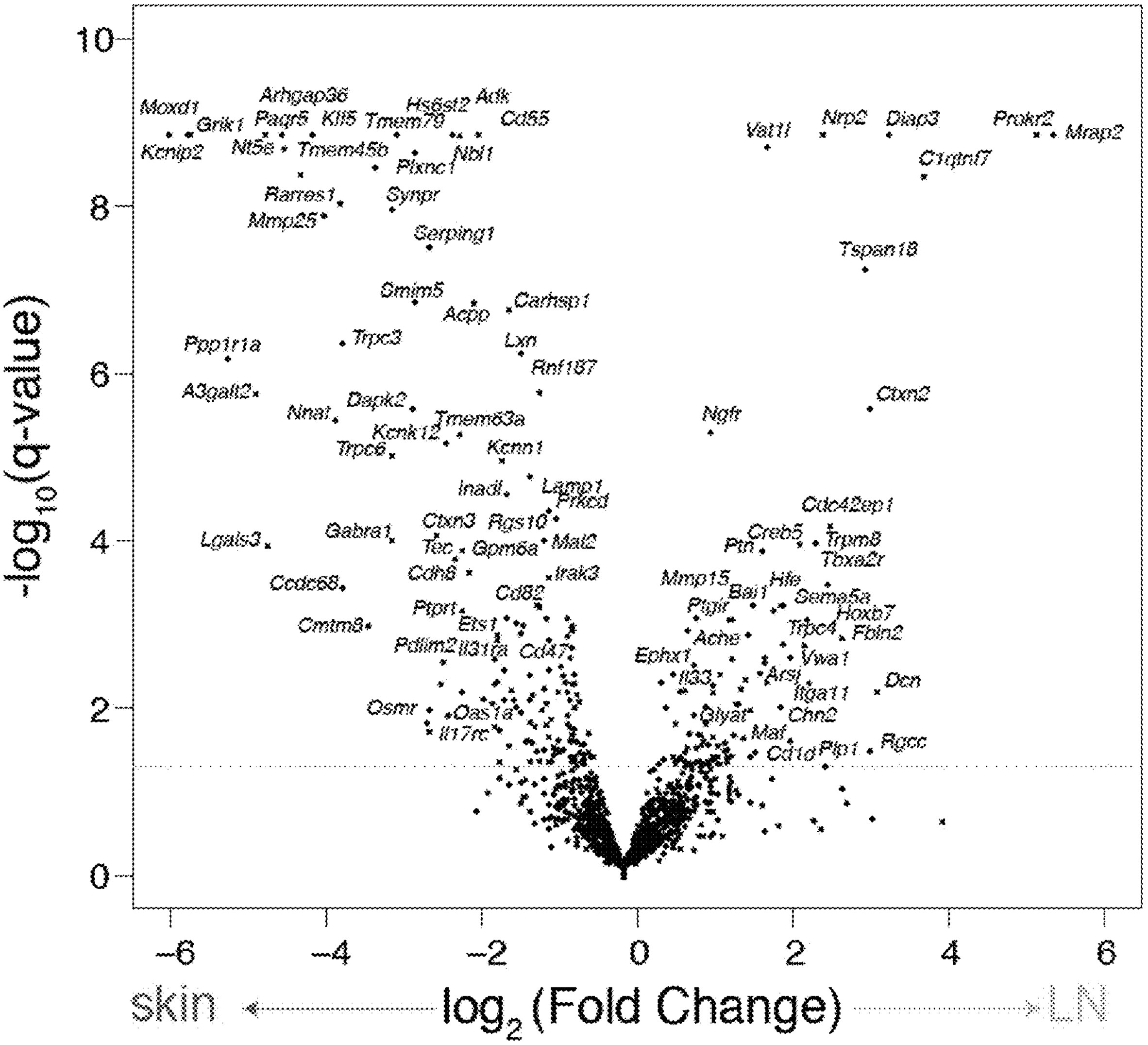
Figures 5C, 5D:
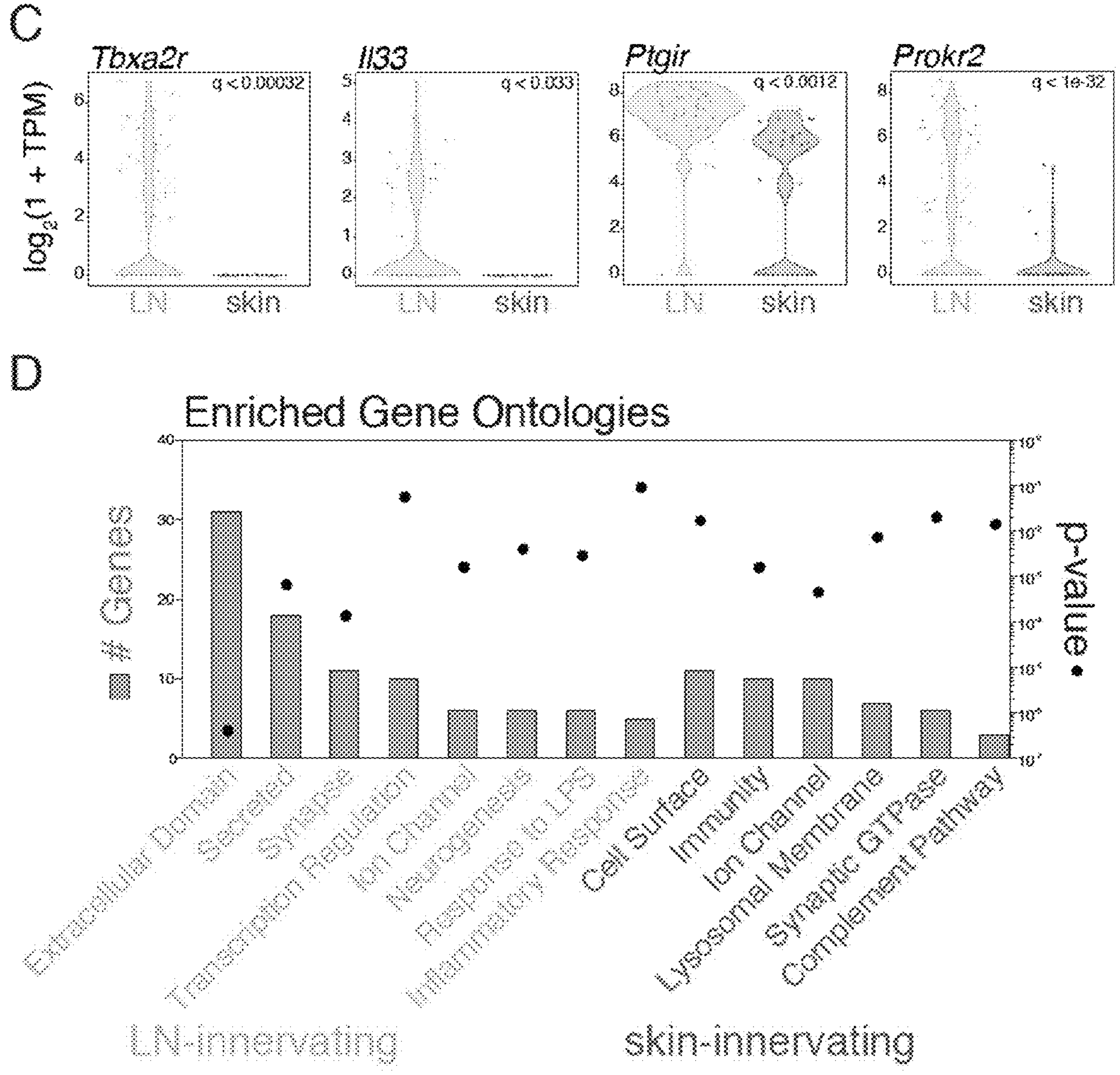

In view of observed innervation target-dependent differences in representation of sensory neuron subtypes, Applicants next directly assessed differences in gene expression between LN-innervating and skin-innervating sensory neurons to define gene programs that support target tissue-specific development and function. Applicants directly compared LN-innervating to skin-innervating sensory neurons, and identified 101 genes significantly upregulated in LN-innervating neurons (Holm adjusted p-value <0.05; FIG. 5A, 5B, Table 1). While some differentially expressed (DE) genes could reflect differential subtype composition, robust gene expression differences between LN- and skin-innervating neurons were observed, even when the two main neuron types, Neuron Types 1 and 3, were analyzed separately, indicating innervation target-dependent molecular distinction between otherwise highly similar neurons (Table 1, FIG. 11A-11B). When DE genes were analyzed for enriched gene ontologies, Applicants observed that LN- and skin-innervating sensory neurons differed with respect to many surface ion-channels and synaptic proteins, in which the LN-specific genes for innervating sensory neuron comprise Trpc4, Trpm8, Kcnh5, Ache. Unique genes were also identified for secreted and cell surface molecules, which may reflect target-specific modes of communication between sensory neurons and their microenvironment (FIGS. 5C, 5D, 11C-11E). Moreover, LN-innervating sensory neurons uniquely expressed genes with inflammatory or immune-cell type interacting functions including Tbxa2r, Il33, Ptgir, and Cd1d, suggesting immunological roles of LN-innervating sensory neurons (FIG. 5C, 5D, Table 1).

Figures 5E, 5F:
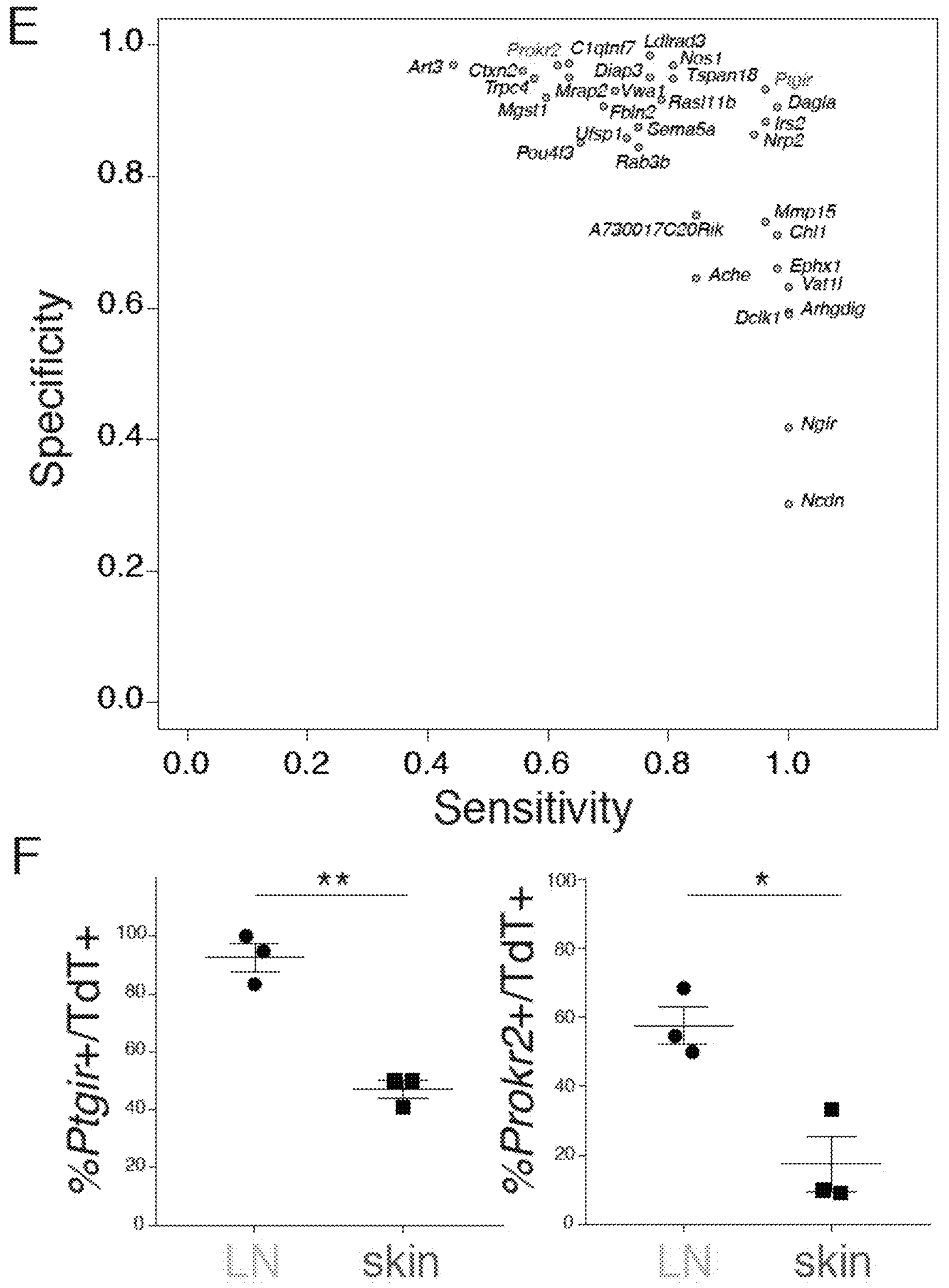
Figures 11A, 11B:
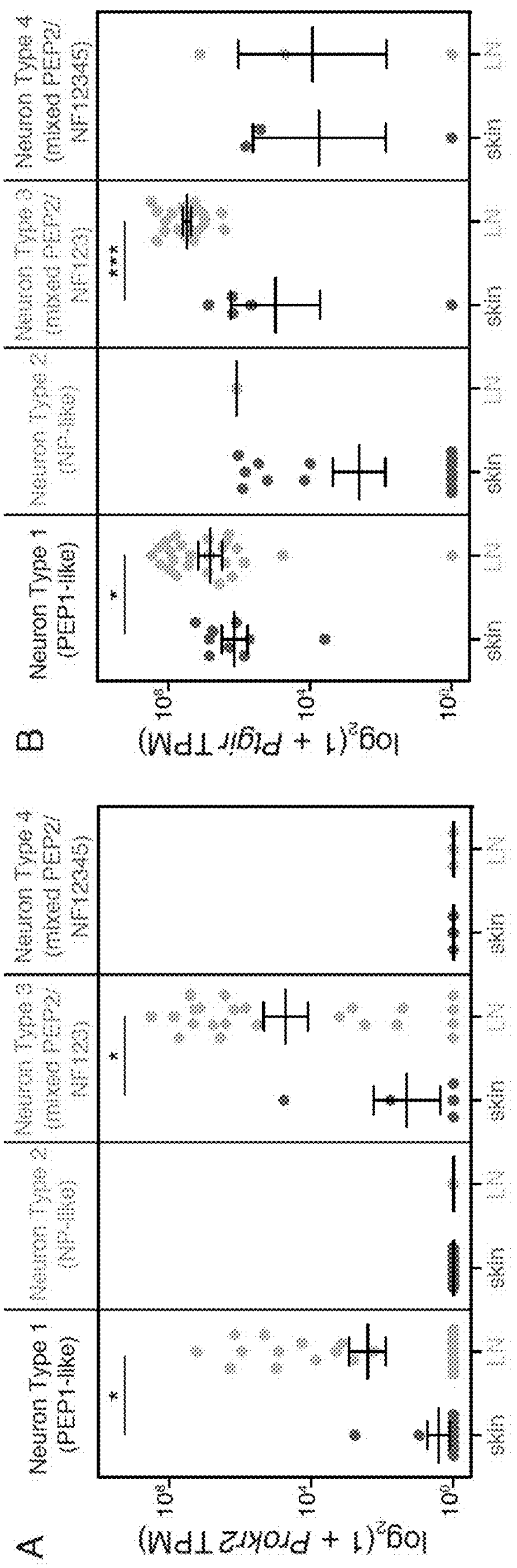
FIG. 11A-11I (Related to FIGS. 4 and 5) LN-innervating sensory neurons are primarily peptidergic nociceptors and LN-innervating sensory neurons express unique defining markers and functional pathways.
Figure 11C:
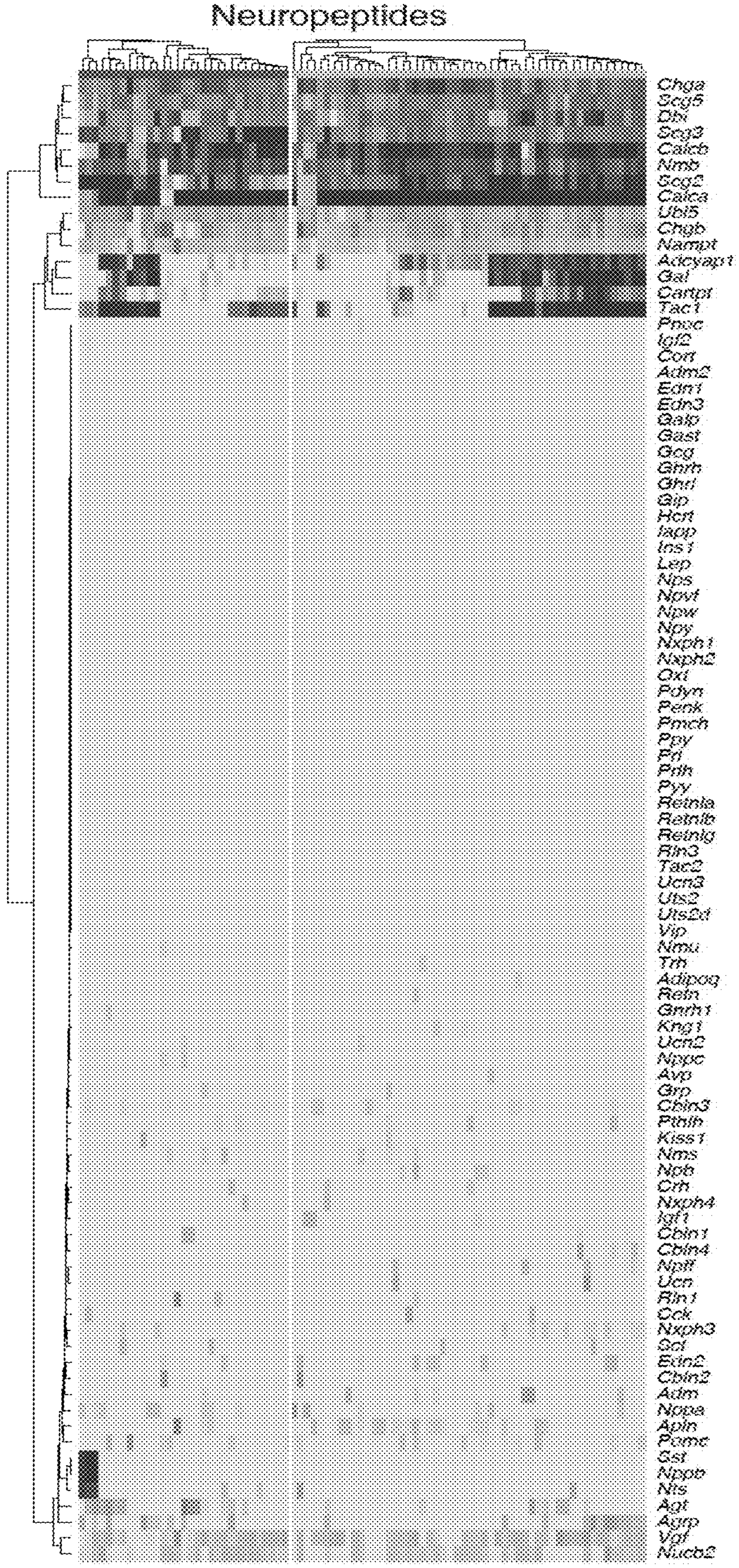
Figure 11D:
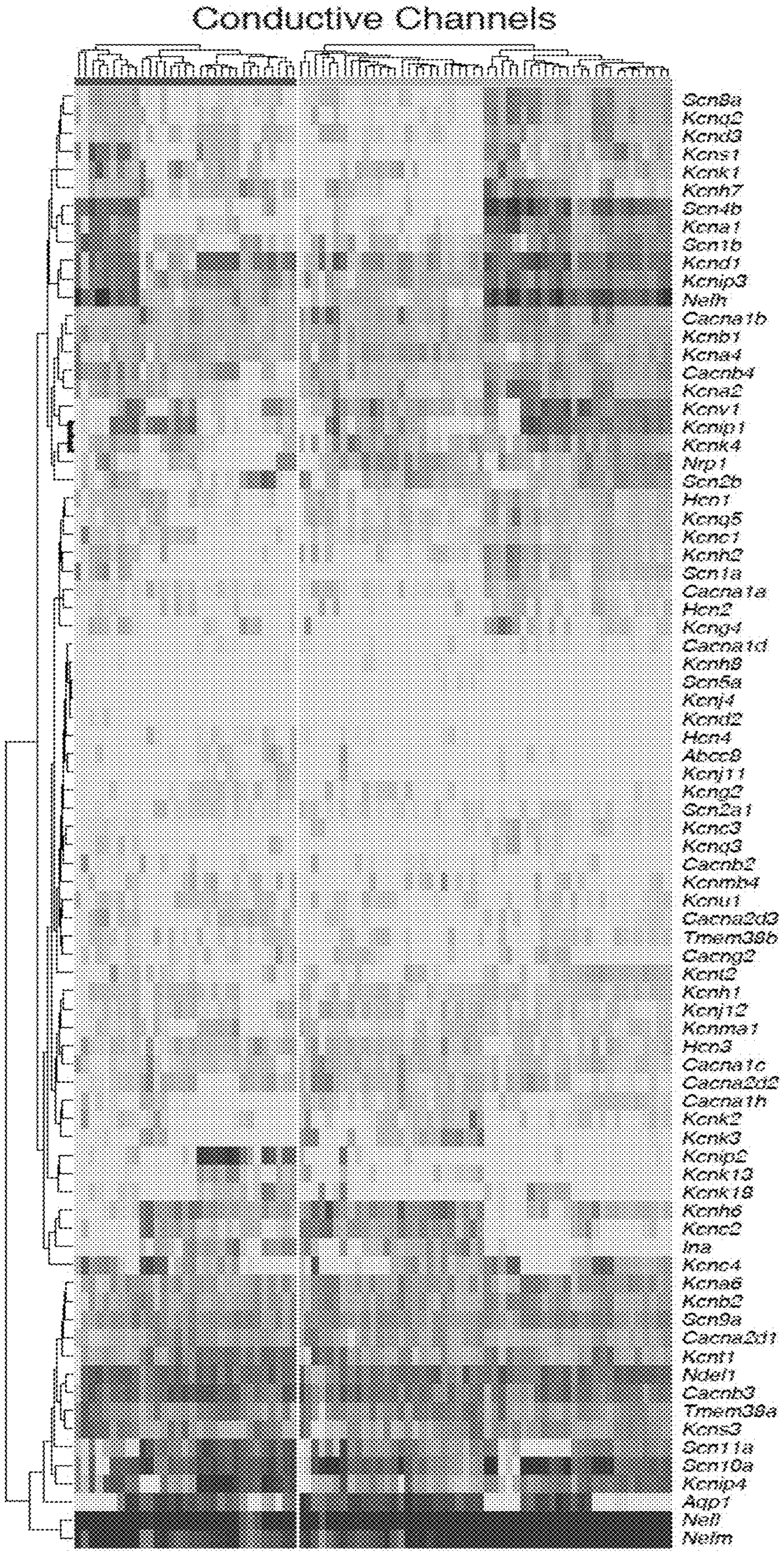
Figure 11E:
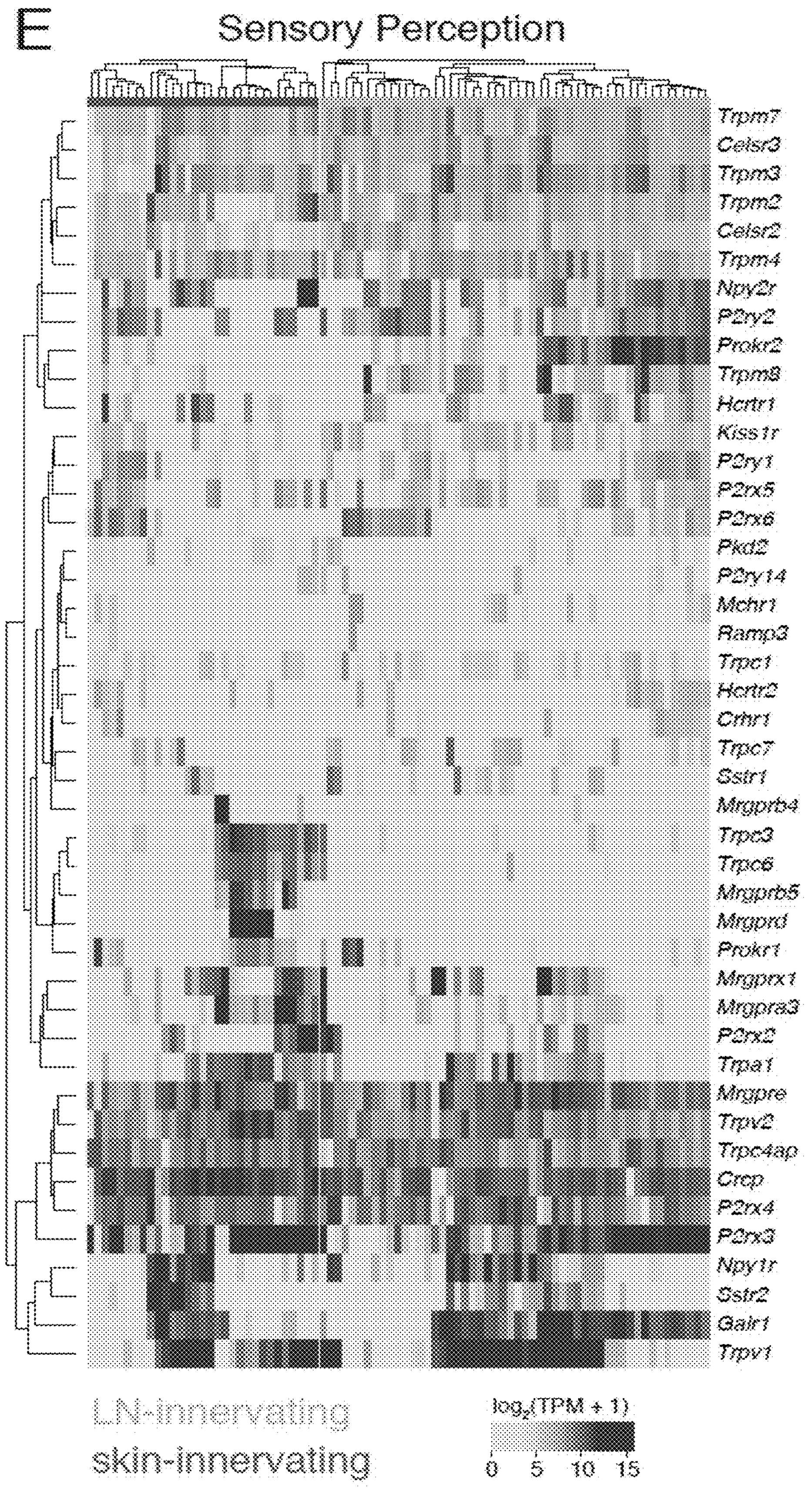
Figures 11F, 11G, 11H, 11I:
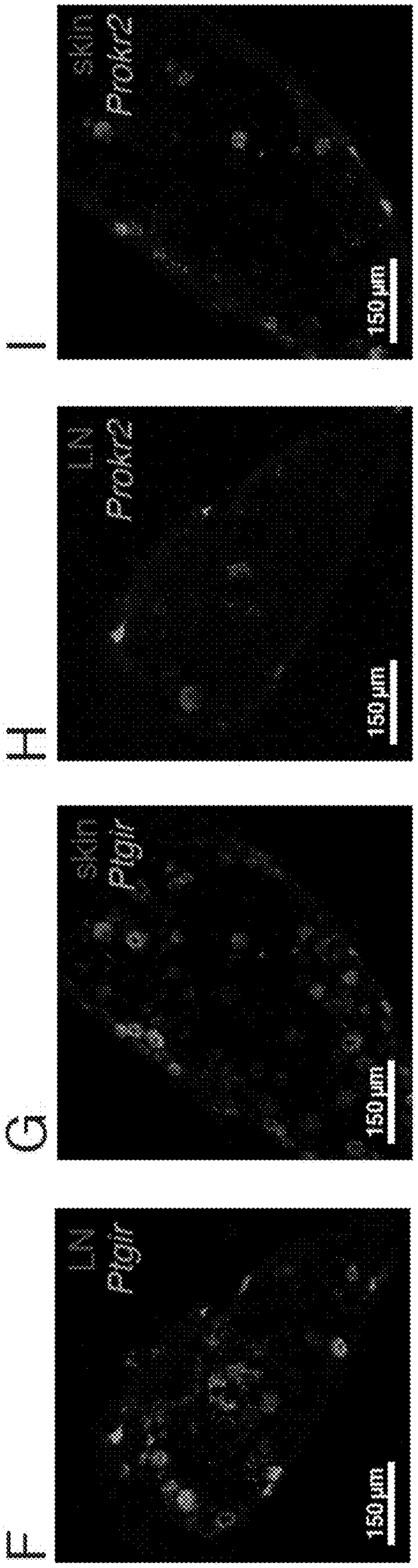

To uncover candidate markers for LN-innervating sensory neurons, Applicants compared LN-innervating neurons to both skin-innervating neurons and the full diversity of sensory neurons captured in the Sensory Neuron Atlas (Usoskin et al., 2015) (Table 1). Applicants determined the true positive rate (sensitivity) and true negative rate (specificity) of LN-innervating neuron gene markers by assessing the fraction of LN-innervating vs. control populations expressing a given gene, and prioritized markers that appeared both specific and selective for LN-innervating neurons (FIG. 5E). For example, Ptgir was identified as a generic marker for LN-innervating sensory neurons with relatively high specificity, while Prokr2 appeared to be more specifically expressed by LN-innervating neurons, with lower sensitivity and enrichment within Neuron Types 1 and 3 (FIGS. 4E, 11A-11B). The expression profiles of Ptgir and Prokr2 in LN- and skin-innervating neurons were further validated by RNAscope-based multiplexed fluorescence in situ hybridization analysis of Ptgir, Prokr2, and tdTomato in DRGs containing tdTomato+ retrogradely labeled LN- or skin-innervating neurons (FIGS. 5F, 11F-11I). Thus, in addition to subtype composition differences, sensory neurons innervating the LN and their skin counterpart are defined by different gene expression programs, with Prokr2 and Ptgir being enriched in LN-innervating sensory neurons.

TABLE 1

Differentially Expressed Genes Specific to Each Type of LN-Innervating Sensory Neurons

| Gene | log2 expression fold change | Z score | Corrected Z Score | p-value | q-value | Upregulated in |
|---|---|---|---|---|---|---|
| Dhdh | 0.494 | 3.414 | 2.582 | 0.000640625 | 0.009824585 | Neuron Type 1 (PEP1-like) |
| Grin3a | 0.577 | 3.415 | 2.583 | 0.000638040 | 0.009797693 | Neuron Type 1 (PEP1-like) |
| Fam198b | 0.988 | 3.418 | 2.587 | 0.000629711 | 0.009695073 | Neuron Type 1 (PEP1-like) |
| Plekhg2 | 0.988 | 3.421 | 2.589 | 0.000624395 | 0.009638425 | Neuron Type 1 (PEP1-like) |
| Rab8b | 0.577 | 3.422 | 2.589 | 0.000622315 | 0.009620623 | Neuron Type 1 (PEP1-like) |
| Cetn3 | 0.371 | 3.422 | 2.589 | 0.000622424 | 0.009620623 | Neuron Type 1 (PEP1-like) |
| Slc30a7 | 0.618 | 3.426 | 2.593 | 0.000613218 | 0.009515790 | Neuron Type 1 (PEP1-like) |
| Ankrd45 | 0.453 | 3.435 | 2.602 | 0.000592687 | 0.009257975 | Neuron Type 1 (PEP1-like) |
| Prmt2 | 0.288 | 3.439 | 2.607 | 0.000583883 | 0.009144915 | Neuron Type 1 (PEP1-like) |
| C530008M17Rik | 0.494 | 3.442 | 2.610 | 0.000576516 | 0.009041557 | Neuron Type 1 (PEP1-like) |
| Epb4.112 | 0.865 | 3.450 | 2.618 | 0.000559906 | 0.008836954 | Neuron Type 1 (PEP1-like) |
| Klh124 | 0.494 | 3.450 | 2.618 | 0.000560405 | 0.008836954 | Neuron Type 1 (PEP1-like) |
| Tead1 | 0.659 | 3.454 | 2.621 | 0.000552839 | 0.008763575 | Neuron Type 1 (PEP1-like) |
| Aplp1 | 0.329 | 3.458 | 2.625 | 0.000544033 | 0.008658952 | Neuron Type 1 (PEP1-like) |
| 2610035D17Rik | 0.535 | 3.459 | 2.625 | 0.000542938 | 0.008653214 | Neuron Type 1 (PEP1-like) |
| Sort1 | 0.947 | 3.463 | 2.631 | 0.000534150 | 0.008524680 | Neuron Type 1 (PEP1-like) |
| Csf2ra | 0.618 | 3.465 | 2.632 | 0.000530391 | 0.008484754 | Neuron Type 1 (PEP1-like) |
| Slc1a5 | 0.865 | 3.469 | 2.636 | 0.000522363 | 0.008382005 | Neuron Type 1 (PEP1-like) |
| Hn1 | 0.247 | 3.477 | 2.644 | 0.000507534 | 0.008199912 | Neuron Type 1 (PEP1-like) |
| Plxdc2 | 0.577 | 3.482 | 2.649 | 0.000497951 | 0.008067221 | Neuron Type 1 (PEP1-like) |
| Ccdc85a | 0.412 | 3.482 | 2.649 | 0.000497042 | 0.008063586 | Neuron Type 1 (PEP1-like) |
| Serpinb8 | 0.577 | 3.483 | 2.650 | 0.000495022 | 0.008041885 | Neuron Type 1 (PEP1-like) |
| Fam174b | 0.412 | 3.493 | 2.660 | 0.000476920 | 0.007812463 | Neuron Type 1 (PEP1-like) |
| Plscr4 | 1.359 | 3.509 | 2.678 | 0.000449607 | 0.007395912 | Neuron Type 1 (PEP1-like) |
| Axl | 1.318 | 3.510 | 2.679 | 0.000448316 | 0.007384982 | Neuron Type 1 (PEP1-like) |
| Rab3b | 0.824 | 3.512 | 2.681 | 0.000445006 | 0.007340731 | Neuron Type 1 (PEP1-like) |
| Caskin2 | 0.988 | 3.521 | 2.692 | 0.000430126 | 0.007105219 | Neuron Type 1 (PEP1-like) |
| Prdx1 | 0.288 | 3.531 | 2.701 | 0.000414718 | 0.006908838 | Neuron Type 1 (PEP1-like) |
| Efemp1 | 1.359 | 3.538 | 2.710 | 0.000403353 | 0.006729030 | Neuron Type 1 (PEP1-like) |
| Gabrb1 | 2.059 | 3.548 | 2.722 | 0.000388184 | 0.006494358 | Neuron Type 1 (PEP1-like) |
| Myt11 | 0.412 | 3.553 | 2.727 | 0.000381065 | 0.006393426 | Neuron Type 1 (PEP1-like) |
| Lamb2 | 1.112 | 3.553 | 2.727 | 0.000380346 | 0.006390462 | Neuron Type 1 (PEP1-like) |
| Ern2 | 0.782 | 3.558 | 2.731 | 0.000374367 | 0.006317040 | Neuron Type 1 (PEP1-like) |
| Col6a5 | 1.071 | 3.570 | 2.744 | 0.000356865 | 0.006065530 | Neuron Type 1 (PEP1-like) |
| Slc39a6 | 0.371 | 3.570 | 2.744 | 0.000357402 | 0.006065530 | Neuron Type 1 (PEP1-like) |
| Fads3 | 0.782 | 3.575 | 2.749 | 0.000350531 | 0.005974761 | Neuron Type 1 (PEP1-like) |
| Nrip3 | 0.453 | 3.577 | 2.751 | 0.000347418 | 0.005938880 | Neuron Type 1 (PEP1-like) |
| Ncoa7 | 0.371 | 3.584 | 2.758 | 0.000338051 | 0.005812497 | Neuron Type 1 (PEP1-like) |
| Tbc1d8 | 0.700 | 3.590 | 2.765 | 0.000330497 | 0.005690921 | Neuron Type 1 (PEP1-like) |
| Plekho2 | 0.700 | 3.598 | 2.773 | 0.000321275 | 0.005556494 | Neuron Type 1 (PEP1-like) |
| Rcn3 | 1.318 | 3.602 | 2.777 | 0.000316049 | 0.005482214 | Neuron Type 1 (PEP1-like) |
| Sostdc1 | 1.606 | 3.603 | 2.778 | 0.000315106 | 0.005473929 | Neuron Type 1 (PEP1-like) |
| Syt4 | 0.412 | 3.605 | 2.780 | 0.000312387 | 0.005434707 | Neuron Type 1 (PEP1-like) |
| Bhlhb9 | 0.453 | 3.607 | 2.782 | 0.000309932 | 0.005399964 | Neuron Type 1 (PEP1-like) |
| Ppp1r14c | 1.277 | 3.608 | 2.783 | 0.000308431 | 0.005381774 | Neuron Type 1 (PEP1-like) |
| Hmgn2 | 0.453 | 3.616 | 2.792 | 0.000298798 | 0.005236967 | Neuron Type 1 (PEP1-like) |
| Mpzl1 | 0.535 | 3.619 | 2.794 | 0.000296195 | 0.005203880 | Neuron Type 1 (PEP1-like) |
| Ifi2711 | 0.329 | 3.625 | 2.801 | 0.000289422 | 0.005095393 | Neuron Type 1 (PEP1-like) |
| Lhfpl5 | 0.494 | 3.626 | 2.802 | 0.000287900 | 0.005076168 | Neuron Type 1 (PEP1-like) |
| Lrrc58 | 0.412 | 3.633 | 2.810 | 0.000280441 | 0.004952519 | Neuron Type 1 (PEP1-like) |
| Flrt1 | 0.659 | 3.638 | 2.815 | 0.000275236 | 0.004882119 | Neuron Type 1 (PEP1-like) |
| Il13ra1 | 1.318 | 3.644 | 2.822 | 0.000268022 | 0.004768523 | Neuron Type 1 (PEP1-like) |
| Mtmr11 | 0.659 | 3.648 | 2.827 | 0.000264105 | 0.004705949 | Neuron Type 1 (PEP1-like) |
| Slc47a2 | 0.988 | 3.650 | 2.829 | 0.000261857 | 0.004672963 | Neuron Type 1 (PEP1-like) |
| Calca | 0.371 | 3.652 | 2.830 | 0.000260175 | 0.004657047 | Neuron Type 1 (PEP1-like) |
| Rspo1 | 1.071 | 3.654 | 2.832 | 0.000257798 | 0.004621533 | Neuron Type 1 (PEP1-like) |
| Rasip1 | 0.988 | 3.663 | 2.842 | 0.000249319 | 0.004483168 | Neuron Type 1 (PEP1-like) |
| Cyp4v3 | 0.906 | 3.664 | 2.843 | 0.000248274 | 0.004471208 | Neuron Type 1 (PEP1-like) |
| As3mt | 1.194 | 3.674 | 2.854 | 0.000239238 | 0.004321700 | Neuron Type 1 (PEP1-like) |
| Rcan3 | 0.453 | 3.675 | 2.855 | 0.000237588 | 0.004298475 | Neuron Type 1 (PEP1-like) |
| Arxes1 | 0.618 | 3.681 | 2.861 | 0.000232522 | 0.004226296 | Neuron Type 1 (PEP1-like) |
| Fam3a | 0.535 | 3.681 | 2.861 | 0.000232010 | 0.004223510 | Neuron Type 1 (PEP1-like) |
| Cnih2 | 0.947 | 3.692 | 2.873 | 0.000222902 | 0.004070295 | Neuron Type 1 (PEP1-like) |
| Neat1 | 1.730 | 3.694 | 2.875 | 0.000220863 | 0.004039322 | Neuron Type 1 (PEP1-like) |
| Ctnnd2 | 0.700 | 3.697 | 2.878 | 0.000218162 | 0.004002348 | Neuron Type 1 (PEP1-like) |
| Jam2 | 1.277 | 3.707 | 2.888 | 0.000209391 | 0.003877687 | Neuron Type 1 (PEP1-like) |
| Afap112 | 1.277 | 3.717 | 2.899 | 0.000201419 | 0.003741813 | Neuron Type 1 (PEP1-like) |
| 9830001H06Rik | 0.659 | 3.724 | 2.906 | 0.000196289 | 0.003658057 | Neuron Type 1 (PEP1-like) |

TABLE 1-continued

Differentially Expressed Genes Specific to Each Type of LN-Innervating Sensory Neurons

| Gene | log2 expression fold change | Z score | Corrected Z Score | p-value | q-value | Upregulated in |
|---|---|---|---|---|---|---|
| Tceal8 | 0.865 | 3.728 | 2.911 | 0.000193005 | 0.003608275 | Neuron Type 1 (PEP1-like) |
| Sorbs2 | 0.988 | 3.729 | 2.911 | 0.000192187 | 0.003598686 | Neuron Type 1 (PEP1-like) |
| Steap3 | 0.577 | 3.729 | 2.911 | 0.000191880 | 0.003598660 | Neuron Type 1 (PEP1-like) |
| Bnip2 | 0.700 | 3.733 | 2.915 | 0.000189062 | 0.003557136 | Neuron Type 1 (PEP1-like) |
| Sdc4 | 1.483 | 3.736 | 2.917 | 0.000187189 | 0.003529367 | Neuron Type 1 (PEP1-like) |
| Pcsk5 | 1.112 | 3.736 | 2.917 | 0.000187286 | 0.003529367 | Neuron Type 1 (PEP1-like) |
| Rarres2 | 1.936 | 3.741 | 2.923 | 0.000183147 | 0.003462458 | Neuron Type 1 (PEP1-like) |
| Wnt9a | 0.824 | 3.754 | 2.939 | 0.000173696 | 0.003294347 | Neuron Type 1 (PEP1-like) |
| Hsd17b11 | 1.071 | 3.766 | 2.951 | 0.000166081 | 0.003165220 | Neuron Type 1 (PEP1-like) |
| P4ha3 | 0.824 | 3.768 | 2.953 | 0.000164752 | 0.003150088 | Neuron Type 1 (PEP1-like) |
| Tmem74 | 0.618 | 3.773 | 2.958 | 0.000161513 | 0.003093162 | Neuron Type 1 (PEP1-like) |
| Itm2a | 1.606 | 3.774 | 2.959 | 0.000160549 | 0.003084740 | Neuron Type 1 (PEP1-like) |
| Terf1 | 0.659 | 3.780 | 2.966 | 0.000156672 | 0.003020094 | Neuron Type 1 (PEP1-like) |
| Plxna3 | 0.824 | 3.784 | 2.970 | 0.000154211 | 0.002982429 | Neuron Type 1 (PEP1-like) |
| Ctsc | 1.359 | 3.790 | 2.976 | 0.000150710 | 0.002919509 | Neuron Type 1 (PEP1-like) |
| Adamts2 | 1.318 | 3.805 | 2.992 | 0.000141861 | 0.002773878 | Neuron Type 1 (PEP1-like) |
| Prkra | 0.535 | 3.805 | 2.992 | 0.000142015 | 0.002773878 | Neuron Type 1 (PEP1-like) |
| Rassf7 | 1.030 | 3.805 | 2.992 | 0.000141519 | 0.002773387 | Neuron Type 1 (PEP1-like) |
| Npcd | 0.577 | 3.806 | 2.992 | 0.000141248 | 0.002772703 | Neuron Type 1 (PEP1-like) |
| Stard13 | 0.700 | 3.809 | 2.995 | 0.000139632 | 0.002745559 | Neuron Type 1 (PEP1-like) |
| Tax1bp3 | 0.535 | 3.812 | 2.998 | 0.000137816 | 0.002718923 | Neuron Type 1 (PEP1-like) |
| Dgkg | 0.618 | 3.816 | 3.002 | 0.000135557 | 0.002678842 | Neuron Type 1 (PEP1-like) |
| Malat1 | 0.494 | 3.826 | 3.013 | 0.000130266 | 0.002587000 | Neuron Type 1 (PEP1-like) |
| Metrn | 1.400 | 3.826 | 3.013 | 0.000130470 | 0.002587000 | Neuron Type 1 (PEP1-like) |
| Slc9a3r1 | 0.947 | 3.833 | 3.021 | 0.000126407 | 0.002523420 | Neuron Type 1 (PEP1-like) |
| Grn | 0.412 | 3.836 | 3.023 | 0.000125142 | 0.002502415 | Neuron Type 1 (PEP1-like) |
| Prss35 | 1.771 | 3.841 | 3.028 | 0.000122504 | 0.002458001 | Neuron Type 1 (PEP1-like) |
| Psd | 1.071 | 3.846 | 3.033 | 0.000120205 | 0.002424273 | Neuron Type 1 (PEP1-like) |
| Ppfia2 | 0.535 | 3.852 | 3.040 | 0.000117127 | 0.002366250 | Neuron Type 1 (PEP1-like) |
| Gm5424 | 0.618 | 3.867 | 3.056 | 0.000109993 | 0.002245065 | Neuron Type 1 (PEP1-like) |
| Cd63 | 1.030 | 3.867 | 3.056 | 0.000110176 | 0.002245065 | Neuron Type 1 (PEP1-like) |
| Adcy7 | 1.483 | 3.869 | 3.057 | 0.000109226 | 0.002233437 | Neuron Type 1 (PEP1-like) |
| Kif13b | 0.782 | 3.872 | 3.060 | 0.000108131 | 0.002214901 | Neuron Type 1 (PEP1-like) |
| Syt16 | 0.865 | 3.873 | 3.060 | 0.000107688 | 0.002213522 | Neuron Type 1 (PEP1-like) |
| Daam2 | 1.441 | 3.875 | 3.063 | 0.000106567 | 0.002194316 | Neuron Type 1 (PEP1-like) |
| Prex2 | 1.400 | 3.880 | 3.068 | 0.000104527 | 0.002156078 | Neuron Type 1 (PEP1-like) |
| Dusp16 | 0.865 | 3.882 | 3.070 | 0.000103475 | 0.002138127 | Neuron Type 1 (PEP1-like) |
| Svil | 0.906 | 3.886 | 3.075 | 0.000101812 | 0.002107448 | Neuron Type 1 (PEP1-like) |
| Gpr35 | 0.782 | 3.897 | 3.087 | 0.000097381 | 0.002022841 | Neuron Type 1 (PEP1-like) |
| Rgs16 | 1.400 | 3.897 | 3.087 | 0.000097198 | 0.002022606 | Neuron Type 1 (PEP1-like) |
| Col1a2 | 1.359 | 3.905 | 3.094 | 0.000094358 | 0.001973611 | Neuron Type 1 (PEP1-like) |
| Lsp1 | 1.359 | 3.909 | 3.099 | 0.000092526 | 0.001942137 | Neuron Type 1 (PEP1-like) |
| Galnt10 | 0.741 | 3.909 | 3.099 | 0.000092671 | 0.001942137 | Neuron Type 1 (PEP1-like) |
| Stac | 0.494 | 3.917 | 3.107 | 0.000089668 | 0.001891257 | Neuron Type 1 (PEP1-like) |
| Chd3 | 0.577 | 3.917 | 3.107 | 0.000089762 | 0.001891257 | Neuron Type 1 (PEP1-like) |
| Nudt11 | 0.618 | 3.918 | 3.107 | 0.000089278 | 0.001887822 | Neuron Type 1 (PEP1-like) |
| 2900008C10Rik | 0.577 | 3.923 | 3.113 | 0.000087329 | 0.001853253 | Neuron Type 1 (PEP1-like) |
| Shisa5 | 0.494 | 3.925 | 3.115 | 0.000086579 | 0.001840670 | Neuron Type 1 (PEP1-like) |
| Pgrmc1 | 0.412 | 3.929 | 3.119 | 0.000085178 | 0.001814145 | Neuron Type 1 (PEP1-like) |
| Pkn1 | 0.824 | 3.932 | 3.121 | 0.000084209 | 0.001800029 | Neuron Type 1 (PEP1-like) |
| Rdh5 | 1.524 | 3.938 | 3.127 | 0.000082159 | 0.001763470 | Neuron Type 1 (PEP1-like) |
| Shd | 0.947 | 3.941 | 3.130 | 0.000081275 | 0.001750017 | Neuron Type 1 (PEP1-like) |
| Fstl1 | 0.412 | 3.964 | 3.156 | 0.000073794 | 0.001600642 | Neuron Type 1 (PEP1-like) |
| Lss | 0.659 | 3.965 | 3.157 | 0.000073297 | 0.001592779 | Neuron Type 1 (PEP1-like) |
| Nrxn1 | 0.535 | 3.966 | 3.158 | 0.000072965 | 0.001588510 | Neuron Type 1 (PEP1-like) |
| Impact | 0.494 | 3.968 | 3.159 | 0.000072477 | 0.001581437 | Neuron Type 1 (PEP1-like) |
| Ap3b1 | 0.659 | 3.969 | 3.160 | 0.000072155 | 0.001579630 | Neuron Type 1 (PEP1-like) |
| Sipx | 1.400 | 3.978 | 3.170 | 0.000069553 | 0.001525501 | Neuron Type 1 (PEP1-like) |
| H2afy | 0.906 | 3.979 | 3.171 | 0.000069175 | 0.001520048 | Neuron Type 1 (PEP1-like) |
| Pmepa1 | 1.236 | 3.983 | 3.174 | 0.000068073 | 0.001501439 | Neuron Type 1 (PEP1-like) |
| Cp | 1.359 | 3.996 | 3.189 | 0.000064436 | 0.001429252 | Neuron Type 1 (PEP1-like) |
| Hey2 | 1.112 | 3.999 | 3.192 | 0.000063543 | 0.001412103 | Neuron Type 1 (PEP1-like) |
| Ptgerl | 0.659 | 4.003 | 3.196 | 0.000062597 | 0.001393710 | Neuron Type 1 (PEP1-like) |
| Nudt10 | 0.741 | 4.013 | 3.207 | 0.000059906 | 0.001341397 | Neuron Type 1 (PEP1-like) |
| Snap47 | 0.329 | 4.018 | 3.211 | 0.000058637 | 0.001320719 | Neuron Type 1 (PEP1-like) |
| Dgka | 1.030 | 4.018 | 3.211 | 0.000058758 | 0.001320719 | Neuron Type 1 (PEP1-like) |
| Tmtc4 | 0.618 | 4.024 | 3.216 | 0.000057296 | 0.001300244 | Neuron Type 1 (PEP1-like) |
| Phip | 0.865 | 4.028 | 3.221 | 0.000056269 | 0.001279417 | Neuron Type 1 (PEP1-like) |
| Vldlr | 1.565 | 4.035 | 3.229 | 0.000054584 | 0.001243508 | Neuron Type 1 (PEP1-like) |
| Sepp1 | 1.071 | 4.040 | 3.235 | 0.000053372 | 0.001218244 | Neuron Type 1 (PEP1-like) |
| Slc4a4 | 0.782 | 4.048 | 3.243 | 0.000051607 | 0.001182545 | Neuron Type 1 (PEP1-like) |
| Lgr5 | 1.647 | 4.051 | 3.246 | 0.000050925 | 0.001171485 | Neuron Type 1 (PEP1-like) |
| Bst2 | 0.865 | 4.066 | 3.261 | 0.000047870 | 0.001109858 | Neuron Type 1 (PEP1-like) |
| Aldoc | 0.782 | 4.066 | 3.261 | 0.000047741 | 0.001109069 | Neuron Type 1 (PEP1-like) |

TABLE 1-continued

Differentially Expressed Genes Specific to Each Type of LN-Innervating Sensory Neurons

| Gene | log2 expression fold change | Z score | Corrected Z Score | p-value | q-value | Upregulated in |
|---|---|---|---|---|---|---|
| Npy5r | 1.359 | 4.070 | 3.265 | 0.000046937 | 0.001095506 | Neuron Type 1 (PEP1-like) |
| Rasl11a | 1.359 | 4.079 | 3.274 | 0.000045170 | 0.001061910 | Neuron Type 1 (PEP1-like) |
| Tmem130 | 0.412 | 4.090 | 3.286 | 0.000043193 | 0.001017454 | Neuron Type 1 (PEP1-like) |
| Zfp3611 | 1.277 | 4.096 | 3.293 | 0.000042055 | 0.000992628 | Neuron Type 1 (PEP1-like) |
| Hap1 | 0.906 | 4.102 | 3.299 | 0.000040911 | 0.000969524 | Neuron Type 1 (PEP1-like) |
| Syf2 | 0.577 | 4.106 | 3.303 | 0.000040256 | 0.000955919 | Neuron Type 1 (PEP1-like) |
| Limd1 | 1.441 | 4.108 | 3.304 | 0.000039913 | 0.000952701 | Neuron Type 1 (PEP1-like) |
| Cd79a | 1.400 | 4.108 | 3.304 | 0.000039959 | 0.000952701 | Neuron Type 1 (PEP1-like) |
| Jun | 0.535 | 4.111 | 3.306 | 0.000039405 | 0.000945098 | Neuron Type 1 (PEP1-like) |
| Zhx2 | 1.236 | 4.111 | 3.306 | 0.000039479 | 0.000945098 | Neuron Type 1 (PEP1-like) |
| Gpr149 | 0.700 | 4.113 | 3.308 | 0.000039025 | 0.000938038 | Neuron Type 1 (PEP1-like) |
| Hspg2 | 1.400 | 4.130 | 3.327 | 0.000036354 | 0.000877417 | Neuron Type 1 (PEP1-like) |
| Agrp | 2.100 | 4.130 | 3.328 | 0.000036216 | 0.000875886 | Neuron Type 1 (PEP1-like) |
| Them4 | 0.535 | 4.138 | 3.334 | 0.000035104 | 0.000855385 | Neuron Type 1 (PEP1-like) |
| Tada1 | 0.577 | 4.136 | 3.334 | 0.000035287 | 0.000855385 | Neuron Type 1 (PEP1-like) |
| Smpdl3a | 0.577 | 4.144 | 3.341 | 0.000034101 | 0.000835003 | Neuron Type 1 (PEP1-like) |
| Gprasp1 | 0.535 | 4.147 | 3.343 | 0.000033657 | 0.000827583 | Neuron Type 1 (PEP1-like) |
| Pnmal1 | 0.947 | 4.151 | 3.347 | 0.000033068 | 0.000816502 | Neuron Type 1 (PEP1-like) |
| Tspan5 | 0.906 | 4.154 | 3.349 | 0.000032690 | 0.000810564 | Neuron Type 1 (PEP1-like) |
| Nfkbia | 0.700 | 4.155 | 3.350 | 0.000032531 | 0.000808345 | Neuron Type 1 (PEP1-like) |
| Nxn | 1.400 | 4.163 | 3.358 | 0.000031387 | 0.000784875 | Neuron Type 1 (PEP1-like) |
| Cdkn1b | 0.700 | 4.165 | 3.359 | 0.000031195 | 0.000781734 | Neuron Type 1 (PEP1-like) |
| Tmbim1 | 0.618 | 4.171 | 3.366 | 0.000030330 | 0.000763299 | Neuron Type 1 (PEP1-like) |
| Cyp2j9 | 0.988 | 4.207 | 3.406 | 0.000025824 | 0.000659776 | Neuron Type 1 (PEP1-like) |
| Pip5k1b | 1.071 | 4.213 | 3.412 | 0.000025227 | 0.000645910 | Neuron Type 1 (PEP1-like) |
| Kirrel3 | 2.512 | 4.221 | 3.420 | 0.000024338 | 0.000625868 | Neuron Type 1 (PEP1-like) |
| Foxo1 | 1.400 | 4.226 | 3.426 | 0.000023738 | 0.000611778 | Neuron Type 1 (PEP1-like) |
| F3 | 1.771 | 4.232 | 3.432 | 0.000023143 | 0.000599076 | Neuron Type 1 (PEP1-like) |
| Arnt2 | 1.030 | 4.233 | 3.432 | 0.000023055 | 0.000598098 | Neuron Type 1 (PEP1-like) |
| Mfsd2a | 2.100 | 4.250 | 3.452 | 0.000021342 | 0.000556713 | Neuron Type 1 (PEP1-like) |
| Entpd2 | 2.389 | 4.250 | 3.452 | 0.000021365 | 0.000556713 | Neuron Type 1 (PEP1-like) |
| Col5a3 | 1.236 | 4.256 | 3.458 | 0.000020779 | 0.000543857 | Neuron Type 1 (PEP1-like) |
| Tiam2 | 1.112 | 4.260 | 3.461 | 0.000020398 | 0.000538251 | Neuron Type 1 (PEP1-like) |
| Cebpd | 1.894 | 4.266 | 3.467 | 0.000019873 | 0.000527168 | Neuron Type 1 (PEP1-like) |
| Pgm2l1 | 0.700 | 4.267 | 3.467 | 0.000019812 | 0.000526748 | Neuron Type 1 (PEP1-like) |
| Cry1 | 0.700 | 4.274 | 3.475 | 0.000019169 | 0.000510801 | Neuron Type 1 (PEP1-like) |
| Kcnj10 | 1.524 | 4.280 | 3.481 | 0.000018680 | 0.000500022 | Neuron Type 1 (PEP1-like) |
| Rnh1 | 0.700 | 4.283 | 3.484 | 0.000018429 | 0.000494434 | Neuron Type 1 (PEP1-like) |
| Tmem229a | 0.782 | 4.284 | 3.485 | 0.000018333 | 0.000492994 | Neuron Type 1 (PEP1-like) |
| Pld5 | 0.700 | 4.286 | 3.485 | 0.000018170 | 0.000492672 | Neuron Type 1 (PEP1-like) |
| Abcc4 | 0.741 | 4.285 | 3.485 | 0.000018259 | 0.000492672 | Neuron Type 1 (PEP1-like) |
| Gprasp2 | 0.700 | 4.285 | 3.485 | 0.000018280 | 0.000492672 | Neuron Type 1 (PEP1-like) |
| Fads2 | 0.741 | 4.289 | 3.486 | 0.000017966 | 0.000489827 | Neuron Type 1 (PEP1-like) |
| Pnp | 0.865 | 4.291 | 3.488 | 0.000017790 | 0.000487225 | Neuron Type 1 (PEP1-like) |
| Ramp2 | 1.894 | 4.296 | 3.493 | 0.000017401 | 0.000477729 | Neuron Type 1 (PEP1-like) |
| Col28a1 | 1.812 | 4.298 | 3.494 | 0.000017263 | 0.000475068 | Neuron Type 1 (PEP1-like) |
| Arxes2 | 0.618 | 4.306 | 3.504 | 0.000016601 | 0.000458984 | Neuron Type 1 (PEP1-like) |
| Fdps | 0.535 | 4.308 | 3.505 | 0.000016456 | 0.000456043 | Neuron Type 1 (PEP1-like) |
| Fam108c | 1.236 | 4.310 | 3.507 | 0.000016334 | 0.000453725 | Neuron Type 1 (PEP1-like) |
| Fkbp1b | 0.577 | 4.322 | 3.520 | 0.000015488 | 0.000431256 | Neuron Type 1 (PEP1-like) |
| Lima1 | 1.236 | 4.329 | 3.529 | 0.000014958 | 0.000417486 | Neuron Type 1 (PEP1-like) |
| Slc7a14 | 0.659 | 4.339 | 3.538 | 0.000014329 | 0.000402797 | Neuron Type 1 (PEP1-like) |
| Trp53i13 | 0.700 | 4.347 | 3.547 | 0.000013810 | 0.000390064 | Neuron Type 1 (PEP1-like) |
| Dcaf12l1 | 0.782 | 4.348 | 3.547 | 0.000013769 | 0.000389824 | Neuron Type 1 (PEP1-like) |
| A4galt | 0.535 | 4.357 | 3.557 | 0.000013181 | 0.000374966 | Neuron Type 1 (PEP1-like) |
| Rab31 | 1.277 | 4.357 | 3.557 | 0.000013212 | 0.000374966 | Neuron Type 1 (PEP1-like) |
| Pla2g16 | 1.771 | 4.358 | 3.557 | 0.000013145 | 0.000374862 | Neuron Type 1 (PEP1-like) |
| Sstr1 | 1.812 | 4.360 | 3.560 | 0.000012985 | 0.000371203 | Neuron Type 1 (PEP1-like) |
| Junb | 0.782 | 4.368 | 3.567 | 0.000012560 | 0.000360813 | Neuron Type 1 (PEP1-like) |
| Irf6 | 2.018 | 4.369 | 3.568 | 0.000012497 | 0.000359881 | Neuron Type 1 (PEP1-like) |
| Sod3 | 2.018 | 4.390 | 3.592 | 0.000011357 | 0.000328659 | Neuron Type 1 (PEP1-like) |
| Pik3r1 | 0.659 | 4.401 | 3.603 | 0.000010777 | 0.000314959 | Neuron Type 1 (PEP1-like) |
| Cyb561 | 0.700 | 4.403 | 3.604 | 0.000010676 | 0.000313567 | Neuron Type 1 (PEP1-like) |
| Vwa1 | 1.441 | 4.406 | 3.607 | 0.000010531 | 0.000310089 | Neuron Type 1 (PEP1-like) |
| Il4ra | 0.824 | 4.406 | 3.607 | 0.000010531 | 0.000310089 | Neuron Type 1 (PEP1-like) |
| Lcor1 | 1.112 | 4.410 | 3.610 | 0.000010333 | 0.000305792 | Neuron Type 1 (PEP1-like) |
| Slc7a2 | 1.441 | 4.415 | 3.615 | 0.000010105 | 0.000300553 | Neuron Type 1 (PEP1-like) |
| C1qtnf7 | 1.071 | 4.416 | 3.616 | 0.000010041 | 0.000299392 | Neuron Type 1 (PEP1-like) |
| Asl | 0.659 | 4.422 | 3.622 | 0.000009787 | 0.000292553 | Neuron Type 1 (PEP1-like) |
| Abca8a | 1.812 | 4.423 | 3.622 | 0.000009749 | 0.000292168 | Neuron Type 1 (PEP1-like) |
| Qk | 1.441 | 4.423 | 3.622 | 0.000009722 | 0.000292105 | Neuron Type 1 (PEP1-like) |
| Slc25a27 | 0.659 | 4.426 | 3.625 | 0.000009604 | 0.000289293 | Neuron Type 1 (PEP1-like) |
| Tle3 | 1.153 | 4.427 | 3.626 | 0.000009539 | 0.000288080 | Neuron Type 1 (PEP1-like) |
| Rab34 | 2.265 | 4.431 | 3.630 | 0.000009364 | 0.000283508 | Neuron Type 1 (PEP1-like) |

TABLE 1-continued

Differentially Expressed Genes Specific to Each Type of LN-Innervating Sensory Neurons

| Gene | log2 expression fold change | Z score | Corrected Z Score | p-value | q-value | Upregulated in |
|---|---|---|---|---|---|---|
| Peli2 | 1.483 | 4.433 | 3.631 | 0.000009288 | 0.000281945 | Neuron Type 1 (PEP1-like) |
| Notch1 | 1.689 | 4.436 | 3.634 | 0.000009178 | 0.000279325 | Neuron Type 1 (PEP1-like) |
| 1700001L19Rik | 1.030 | 4.441 | 3.640 | 0.000008947 | 0.000273001 | Neuron Type 1 (PEP1-like) |
| Fbn1 | 1.483 | 4.443 | 3.641 | 0.000008859 | 0.000271729 | Neuron Type 1 (PEP1-like) |
| Spint2 | 1.936 | 4.446 | 3.644 | 0.000008743 | 0.000268869 | Neuron Type 1 (PEP1-like) |
| Tmem140 | 1.483 | 4.449 | 3.647 | 0.000008613 | 0.000265560 | Neuron Type 1 (PEP1-like) |
| Man2a1 | 1.400 | 4.454 | 3.651 | 0.000008426 | 0.000261212 | Neuron Type 1 (PEP1-like) |
| Fads1 | 0.824 | 4.462 | 3.660 | 0.000008110 | 0.000252694 | Neuron Type 1 (PEP1-like) |
| Gja1 | 1.524 | 4.474 | 3.673 | 0.000007667 | 0.000240162 | Neuron Type 1 (PEP1-like) |
| 5430417L22Rik | 1.318 | 4.485 | 3.683 | 0.000007293 | 0.000230300 | Neuron Type 1 (PEP1-like) |
| Psmb8 | 0.865 | 4.491 | 3.690 | 0.000007083 | 0.000224242 | Neuron Type 1 (PEP1-like) |
| Fgf13 | 0.824 | 4.494 | 3.692 | 0.000006996 | 0.000222101 | Neuron Type 1 (PEP1-like) |
| Fmo1 | 1.936 | 4.503 | 3.701 | 0.000006706 | 0.000214641 | Neuron Type 1 (PEP1-like) |
| Fat1 | 1.441 | 4.507 | 3.705 | 0.000006581 | 0.000211197 | Neuron Type 1 (PEP1-like) |
| Cyp2d22 | 1.812 | 4.515 | 3.714 | 0.000006328 | 0.000203630 | Neuron Type 1 (PEP1-like) |
| Grb10 | 0.947 | 4.528 | 3.729 | 0.000005948 | 0.000191932 | Neuron Type 1 (PEP1-like) |
| C4b | 1.730 | 4.533 | 3.734 | 0.000005818 | 0.000188268 | Neuron Type 1 (PEP1-like) |
| Itih5 | 1.689 | 4.545 | 3.745 | 0.000005495 | 0.000180263 | Neuron Type 1 (PEP1-like) |
| Col8a1 | 1.730 | 4.552 | 3.753 | 0.000005304 | 0.000174500 | Neuron Type 1 (PEP1-like) |
| Fam129b | 0.906 | 4.564 | 3.764 | 0.000005027 | 0.000167072 | Neuron Type 1 (PEP1-like) |
| Eif4ebp1 | 0.906 | 4.563 | 3.764 | 0.000005036 | 0.000167072 | Neuron Type 1 (PEP1-like) |
| Pnck | 0.906 | 4.567 | 3.766 | 0.000004954 | 0.000165667 | Neuron Type 1 (PEP1-like) |
| Ezr | 1.071 | 4.570 | 3.768 | 0.000004888 | 0.000164498 | Neuron Type 1 (PEP1-like) |
| Fabp7 | 1.236 | 4.578 | 3.777 | 0.000004703 | 0.000158831 | Neuron Type 1 (PEP1-like) |
| Camk2b | 0.741 | 4.577 | 3.777 | 0.000004706 | 0.000158831 | Neuron Type 1 (PEP1-like) |
| Ahi1 | 0.865 | 4.585 | 3.784 | 0.000004541 | 0.000154589 | Neuron Type 1 (PEP1-like) |
| Whrn | 1.853 | 4.587 | 3.784 | 0.000004506 | 0.000154269 | Neuron Type 1 (PEP1-like) |
| Samsn1 | 1.194 | 4.590 | 3.787 | 0.000004432 | 0.000152349 | Neuron Type 1 (PEP1-like) |
| Hr | 1.236 | 4.590 | 3.787 | 0.000004437 | 0.000152349 | Neuron Type 1 (PEP1-like) |
| Bgn | 2.018 | 4.600 | 3.797 | 0.000004231 | 0.000146577 | Neuron Type 1 (PEP1-like) |
| Sox10 | 1.771 | 4.608 | 3.805 | 0.000004061 | 0.000141927 | Neuron Type 1 (PEP1-like) |
| Dock6 | 1.647 | 4.617 | 3.812 | 0.000003901 | 0.000137575 | Neuron Type 1 (PEP1-like) |
| Arhgef2 | 2.059 | 4.618 | 3.813 | 0.000003875 | 0.000137069 | Neuron Type 1 (PEP1-like) |
| Lepre14 | 1.359 | 4.622 | 3.817 | 0.000003807 | 0.000135062 | Neuron Type 1 (PEP1-like) |
| D4Wsu53e | 0.577 | 4.624 | 3.818 | 0.000003768 | 0.000134500 | Neuron Type 1 (PEP1-like) |
| Tspan6 | 0.988 | 4.629 | 3.823 | 0.000003678 | 0.000132061 | Neuron Type 1 (PEP1-like) |
| Sema4d | 0.659 | 4.632 | 3.826 | 0.000003620 | 0.000130378 | Neuron Type 1 (PEP1-like) |
| Pik3ip1 | 0.577 | 4.641 | 3.836 | 0.000003466 | 0.000125221 | Neuron Type 1 (PEP1-like) |
| Gria1 | 1.194 | 4.663 | 3.861 | 0.000003116 | 0.000113100 | Neuron Type 1 (PEP1-like) |
| Wls | 1.318 | 4.663 | 3.861 | 0.000003121 | 0.000113100 | Neuron Type 1 (PEP1-like) |
| Rnase4 | 1.236 | 4.681 | 3.880 | 0.000002860 | 0.000104466 | Neuron Type 1 (PEP1-like) |
| Megf10 | 1.812 | 4.680 | 3.880 | 0.000002865 | 0.000104466 | Neuron Type 1 (PEP1-like) |
| Pdpn | 1.894 | 4.690 | 3.890 | 0.000002736 | 0.000100386 | Neuron Type 1 (PEP1-like) |
| Car11 | 0.741 | 4.696 | 3.895 | 0.000002649 | 0.000098128 | Neuron Type 1 (PEP1-like) |
| St3gal1 | 1.277 | 4.702 | 3.901 | 0.000002573 | 0.000095603 | Neuron Type 1 (PEP1-like) |
| Cyr61 | 2.677 | 4.714 | 3.913 | 0.000002432 | 0.000091222 | Neuron Type 1 (PEP1-like) |
| Trip10 | 1.771 | 4.732 | 3.932 | 0.000002228 | 0.000084120 | Neuron Type 1 (PEP1-like) |
| Acaa1a | 0.700 | 4.732 | 3.932 | 0.000002220 | 0.000084070 | Neuron Type 1 (PEP1-like) |
| Arhgap22 | 0.824 | 4.736 | 3.936 | 0.000002178 | 0.000083003 | Neuron Type 1 (PEP1-like) |
| Slc41a3 | 0.741 | 4.749 | 3.948 | 0.000002044 | 0.000078682 | Neuron Type 1 (PEP1-like) |
| Dpyd | 1.071 | 4.753 | 3.952 | 0.000002003 | 0.000077341 | Neuron Type 1 (PEP1-like) |
| Ngb | 1.194 | 4.761 | 3.960 | 0.000001931 | 0.000074802 | Neuron Type 1 (PEP1-like) |
| Vamp4 | 0.700 | 4.773 | 3.974 | 0.000001813 | 0.000070697 | Neuron Type 1 (PEP1-like) |
| Sparc | 5.930 | 4.775 | 3.975 | 0.000001797 | 0.000070315 | Neuron Type 1 (PEP1-like) |
| Smarca1 | 0.906 | 4.787 | 3.989 | 0.000001689 | 0.000066323 | Neuron Type 1 (PEP1-like) |
| Egfl8 | 2.224 | 4.796 | 3.998 | 0.000001622 | 0.000063880 | Neuron Type 1 (PEP1-like) |
| Cartpt | 1.730 | 4.807 | 4.010 | 0.000001529 | 0.000060640 | Neuron Type 1 (PEP1-like) |
| Necab1 | 0.782 | 4.809 | 4.011 | 0.000001514 | 0.000060439 | Neuron Type 1 (PEP1-like) |
| Gstp1 | 0.494 | 4.811 | 4.012 | 0.000001504 | 0.000060247 | Neuron Type 1 (PEP1-like) |
| Ppap2b | 1.524 | 4.819 | 4.018 | 0.000001445 | 0.000058665 | Neuron Type 1 (PEP1-like) |
| Celf3 | 1.112 | 4.818 | 4.018 | 0.000001453 | 0.000058665 | Neuron Type 1 (PEP1-like) |
| Igfbp5 | 1.647 | 4.833 | 4.033 | 0.000001343 | 0.000055116 | Neuron Type 1 (PEP1-like) |
| Tceal5 | 1.647 | 4.840 | 4.039 | 0.000001299 | 0.000053747 | Neuron Type 1 (PEP1-like) |
| Cald1 | 1.771 | 4.840 | 4.039 | 0.000001301 | 0.000053747 | Neuron Type 1 (PEP1-like) |
| Hrh3 | 1.894 | 4.855 | 4.055 | 0.000001205 | 0.000050168 | Neuron Type 1 (PEP1-like) |
| Psme1 | 0.782 | 4.862 | 4.062 | 0.000001165 | 0.000048644 | Neuron Type 1 (PEP1-like) |
| Wnt3 | 2.347 | 4.864 | 4.064 | 0.000001148 | 0.000048228 | Neuron Type 1 (PEP1-like) |
| Lrig1 | 1.853 | 4.864 | 4.064 | 0.000001151 | 0.000048228 | Neuron Type 1 (PEP1-like) |
| Prss23 | 1.771 | 4.899 | 4.102 | 0.000000962 | 0.000040915 | Neuron Type 1 (PEP1-like) |
| Phc1 | 1.565 | 4.905 | 4.109 | 0.000000933 | 0.000039820 | Neuron Type 1 (PEP1-like) |
| Cdh19 | 2.142 | 4.906 | 4.109 | 0.000000927 | 0.000039720 | Neuron Type 1 (PEP1-like) |
| Pdia5 | 1.277 | 4.922 | 4.125 | 0.000000856 | 0.000037058 | Neuron Type 1 (PEP1-like) |
| Slc6a7 | 2.018 | 4.932 | 4.135 | 0.000000816 | 0.000035445 | Neuron Type 1 (PEP1-like) |
| Ralgps2 | 0.906 | 4.959 | 4.165 | 0.000000708 | 0.000031134 | Neuron Type 1 (PEP1-like) |

TABLE 1-continued

Differentially Expressed Genes Specific to Each Type of LN-Innervating Sensory Neurons

| Gene | log2 expression fold change | Z score | Corrected Z Score | p-value | q-value | Upregulated in |
|---|---|---|---|---|---|---|
| Pls3 | 0.700 | 4.980 | 4.187 | 0.000000635 | 0.000028321 | Neuron Type 1 (PEP1-like) |
| Kcnh6 | 1.030 | 5.015 | 4.223 | 0.000000531 | 0.000024059 | Neuron Type 1 (PEP1-like) |
| Litaf | 2.183 | 5.019 | 4.228 | 0.000000519 | 0.000023596 | Neuron Type 1 (PEP1-like) |
| Shf | 1.689 | 5.026 | 4.233 | 0.000000500 | 0.000023088 | Neuron Type 1 (PEP1-like) |
| 2900056M20Rik | 0.988 | 5.025 | 4.233 | 0.000000504 | 0.000023088 | Neuron Type 1 (PEP1-like) |
| Celf2 | 1.071 | 5.029 | 4.235 | 0.000000494 | 0.000022888 | Neuron Type 1 (PEP1-like) |
| Adamts5 | 2.265 | 5.033 | 4.238 | 0.000000484 | 0.000022521 | Neuron Type 1 (PEP1-like) |
| 2810468N07Rik | 1.647 | 5.076 | 4.286 | 0.000000386 | 0.000018181 | Neuron Type 1 (PEP1-like) |
| Adcy5 | 1.236 | 5.088 | 4.299 | 0.000000362 | 0.000017193 | Neuron Type 1 (PEP1-like) |
| Syt5 | 0.782 | 5.105 | 4.316 | 0.000000331 | 0.000015890 | Neuron Type 1 (PEP1-like) |
| Bhlhe40 | 1.318 | 5.121 | 4.334 | 0.000000304 | 0.000014656 | Neuron Type 1 (PEP1-like) |
| Chd5 | 1.277 | 5.145 | 4.361 | 0.000000267 | 0.000012955 | Neuron Type 1 (PEP1-like) |
| Plekha4 | 2.306 | 5.147 | 4.362 | 0.000000265 | 0.000012873 | Neuron Type 1 (PEP1-like) |
| Sema3b | 2.224 | 5.154 | 4.370 | 0.000000255 | 0.000012447 | Neuron Type 1 (PEP1-like) |
| Cnp | 0.906 | 5.165 | 4.382 | 0.000000240 | 0.000011777 | Neuron Type 1 (PEP1-like) |
| Vim | 1.071 | 5.193 | 4.411 | 0.000000207 | 0.000010287 | Neuron Type 1 (PEP1-like) |
| Nid1 | 1.977 | 5.199 | 4.417 | 0.000000201 | 0.000010020 | Neuron Type 1 (PEP1-like) |
| Caly | 1.071 | 5.204 | 4.422 | 0.000000195 | 0.000009791 | Neuron Type 1 (PEP1-like) |
| Nudt17 | 2.142 | 5.276 | 4.503 | 0.000000132 | 0.000006715 | Neuron Type 1 (PEP1-like) |
| Cst3 | 0.659 | 5.281 | 4.505 | 0.000000129 | 0.000006625 | Neuron Type 1 (PEP1-like) |
| Ivns1abp | 0.824 | 5.289 | 4.514 | 0.000000123 | 0.000006368 | Neuron Type 1 (PEP1-like) |
| Slc16a2 | 1.441 | 5.330 | 4.557 | 0.000000098 | 0.000005180 | Neuron Type 1 (PEP1-like) |
| Itgb8 | 2.059 | 5.337 | 4.564 | 0.000000095 | 0.000005025 | Neuron Type 1 (PEP1-like) |
| Ptprz1 | 1.771 | 5.356 | 4.584 | 0.000000085 | 0.000004568 | Neuron Type 1 (PEP1-like) |
| Aspa | 2.595 | 5.367 | 4.595 | 0.000000080 | 0.000004322 | Neuron Type 1 (PEP1-like) |
| Cmtm5 | 3.624 | 5.373 | 4.601 | 0.000000078 | 0.000004212 | Neuron Type 1 (PEP1-like) |
| Fxyd1 | 2.718 | 5.376 | 4.604 | 0.000000076 | 0.000004150 | Neuron Type 1 (PEP1-like) |
| Ssbp2 | 0.906 | 5.424 | 4.657 | 0.000000058 | 0.000003206 | Neuron Type 1 (PEP1-like) |
| Ntrk2 | 3.830 | 5.443 | 4.675 | 0.000000052 | 0.000002933 | Neuron Type 1 (PEP1-like) |
| Cdk18 | 2.471 | 5.453 | 4.686 | 0.000000050 | 0.000002790 | Neuron Type 1 (PEP1-like) |
| Ucp2 | 2.347 | 5.462 | 4.695 | 0.000000047 | 0.000002661 | Neuron Type 1 (PEP1-like) |
| Rgs9 | 1.977 | 5.468 | 4.699 | 0.000000046 | 0.000002614 | Neuron Type 1 (PEP1-like) |
| Cdh13 | 2.347 | 5.467 | 4.699 | 0.000000046 | 0.000002614 | Neuron Type 1 (PEP1-like) |
| Atp1a2 | 2.595 | 5.472 | 4.701 | 0.000000044 | 0.000002595 | Neuron Type 1 (PEP1-like) |
| Tagln2 | 2.142 | 5.472 | 4.701 | 0.000000045 | 0.000002595 | Neuron Type 1 (PEP1-like) |
| St5 | 1.647 | 5.488 | 4.716 | 0.000000041 | 0.000002408 | Neuron Type 1 (PEP1-like) |
| Ntsr2 | 1.524 | 5.500 | 4.729 | 0.000000038 | 0.000002259 | Neuron Type 1 (PEP1-like) |
| Arhgap15 | 1.194 | 5.530 | 4.761 | 0.000000032 | 0.000001928 | Neuron Type 1 (PEP1-like) |
| Tle2 | 1.606 | 5.546 | 4.777 | 0.000000029 | 0.000001776 | Neuron Type 1 (PEP1-like) |
| Nynrin | 2.347 | 5.572 | 4.806 | 0.000000025 | 0.000001538 | Neuron Type 1 (PEP1-like) |
| Dusp1 | 0.988 | 5.588 | 4.821 | 0.000000023 | 0.000001432 | Neuron Type 1 (PEP1-like) |
| Ttyh1 | 2.636 | 5.613 | 4.846 | 0.000000020 | 0.000001258 | Neuron Type 1 (PEP1-like) |
| D430019H16Rik | 1.565 | 5.628 | 4.861 | 0.000000018 | 0.000001165 | Neuron Type 1 (PEP1-like) |
| Pde11a | 1.853 | 5.654 | 4.889 | 0.000000016 | 0.000001012 | Neuron Type 1 (PEP1-like) |
| Gadd45g | 0.906 | 5.672 | 4.905 | 0.000000014 | 0.000000935 | Neuron Type 1 (PEP1-like) |
| Chrna6 | 1.565 | 5.676 | 4.908 | 0.000000014 | 0.000000918 | Neuron Type 1 (PEP1-like) |
| Tcp11l2 | 1.112 | 5.697 | 4.929 | 0.000000012 | 0.000000827 | Neuron Type 1 (PEP1-like) |
| Haus4 | 1.236 | 5.703 | 4.935 | 0.000000012 | 0.000000802 | Neuron Type 1 (PEP1-like) |
| Fam89a | 1.071 | 5.765 | 5.003 | 0.000000008 | 0.000000565 | Neuron Type 1 (PEP1-like) |
| Lyn | 2.389 | 5.835 | 5.079 | 0.000000005 | 0.000000380 | Neuron Type 1 (PEP1-like) |
| Mmd2 | 5.189 | 5.858 | 5.103 | 0.000000005 | 0.000000335 | Neuron Type 1 (PEP1-like) |
| Rit2 | 0.947 | 5.865 | 5.109 | 0.000000005 | 0.000000323 | Neuron Type 1 (PEP1-like) |
| Hpcal4 | 2.471 | 5.939 | 5.191 | 0.000000003 | 0.000000209 | Neuron Type 1 (PEP1-like) |
| Lama4 | 2.306 | 5.948 | 5.200 | 0.000000003 | 0.000000199 | Neuron Type 1 (PEP1-like) |
| 6330403K07Rik | 1.071 | 5.975 | 5.227 | 0.000000002 | 0.000000172 | Neuron Type 1 (PEP1-like) |
| Kcnc2 | 1.977 | 6.019 | 5.275 | 0.000000002 | 0.000000133 | Neuron Type 1 (PEP1-like) |
| Ndn | 0.906 | 6.049 | 5.307 | 0.000000001 | 0.000000111 | Neuron Type 1 (PEP1-like) |
| Emp2 | 2.883 | 6.055 | 5.312 | 0.000000001 | 0.000000108 | Neuron Type 1 (PEP1-like) |
| Paqr6 | 3.377 | 6.067 | 5.321 | 0.000000001 | 0.000000103 | Neuron Type 1 (PEP1-like) |
| Sft2d2 | 2.512 | 6.069 | 5.322 | 0.000000001 | 0.000000103 | Neuron Type 1 (PEP1-like) |
| Atp2b4 | 1.730 | 6.080 | 5.333 | 0.000000001 | 0.000000097 | Neuron Type 1 (PEP1-like) |
| Rnd3 | 1.894 | 6.099 | 5.352 | 0.000000001 | 0.000000087 | Neuron Type 1 (PEP1-like) |
| Sh3kbp1 | 1.359 | 6.133 | 5.386 | 0.000000001 | 0.000000072 | Neuron Type 1 (PEP1-like) |
| C530044C16Rik | 2.553 | 6.208 | 5.467 | 0.000000001 | 0.000000046 | Neuron Type 1 (PEP1-like) |
| Pcbd1 | 1.030 | 6.210 | 5.468 | 0.000000001 | 0.000000045 | Neuron Type 1 (PEP1-like) |
| Ptn | 1.812 | 6.215 | 5.473 | 0.000000001 | 0.000000044 | Neuron Type 1 (PEP1-like) |
| Ncam1 | 1.236 | 6.222 | 5.479 | 0.000000000 | 0.000000043 | Neuron Type 1 (PEP1-like) |
| Mboat2 | 3.377 | 6.239 | 5.497 | 0.000000000 | 0.000000039 | Neuron Type 1 (PEP1-like) |
| Phactr2 | 1.112 | 6.272 | 5.528 | 0.000000000 | 0.000000032 | Neuron Type 1 (PEP1-like) |
| Gpr37l1 | 4.407 | 6.338 | 5.600 | 0.000000000 | 0.000000021 | Neuron Type 1 (PEP1-like) |
| Scg2 | 1.030 | 6.358 | 5.621 | 0.000000000 | 0.000000019 | Neuron Type 1 (PEP1-like) |
| Ndrg2 | 2.142 | 6.385 | 5.649 | 0.000000000 | 0.000000016 | Neuron Type 1 (PEP1-like) |
| Btg2 | 1.359 | 6.477 | 5.750 | 0.000000000 | 0.000000009 | Neuron Type 1 (PEP1-like) |
| Tle6 | 2.677 | 6.482 | 5.754 | 0.000000000 | 0.000000009 | Neuron Type 1 (PEP1-like) |

TABLE 1-continued

Differentially Expressed Genes Specific to Each Type of LN-Innervating Sensory Neurons

| Gene | log2 expression fold change | Z score | Corrected Z Score | p-value | q-value | Upregulated in |
|---|---|---|---|---|---|---|
| Ndrg1 | 5.230 | 6.486 | 5.756 | 0.000000000 | 0.000000009 | Neuron Type 1 (PEP1-like) |
| Slc10a6 | 1.936 | 6.538 | 5.809 | 0.000000000 | 0.000000006 | Neuron Type 1 (PEP1-like) |
| Klf6 | 1.359 | 6.561 | 5.833 | 0.000000000 | 0.000000005 | Neuron Type 1 (PEP1-like) |
| Atp1b2 | 3.830 | 6.560 | 5.833 | 0.000000000 | 0.000000005 | Neuron Type 1 (PEP1-like) |
| Gpr68 | 2.924 | 6.608 | 5.882 | 0.000000000 | 0.000000004 | Neuron Type 1 (PEP1-like) |
| Dcn | 3.253 | 6.618 | 5.891 | 0.000000000 | 0.000000004 | Neuron Type 1 (PEP1-like) |
| Gpm6b | 3.501 | 6.618 | 5.891 | 0.000000000 | 0.000000004 | Neuron Type 1 (PEP1-like) |
| Ctxn1 | 1.030 | 6.670 | 5.943 | 0.000000000 | 0.000000003 | Neuron Type 1 (PEP1-like) |
| Plp1 | 4.901 | 6.712 | 5.987 | 0.000000000 | 0.000000002 | Neuron Type 1 (PEP1-like) |
| Marcksl1 | 3.048 | 6.779 | 6.059 | 0.000000000 | 0.000000001 | Neuron Type 1 (PEP1-like) |
| Zbtb20 | 1.236 | 6.782 | 6.061 | 0.000000000 | 0.000000001 | Neuron Type 1 (PEP1-like) |
| Pttg1ip | 1.441 | 6.791 | 6.069 | 0.000000000 | 0.000000001 | Neuron Type 1 (PEP1-like) |
| Hmgn3 | 1.565 | 6.844 | 6.127 | 0.000000000 | 0.000000001 | Neuron Type 1 (PEP1-like) |
| Bex4 | 3.253 | 6.861 | 6.144 | 0.000000000 | 0.000000001 | Neuron Type 1 (PEP1-like) |
| Hmgcs2 | 3.665 | 6.899 | 6.181 | 0.000000000 | 0.000000001 | Neuron Type 1 (PEP1-like) |
| Phgdh | 4.242 | 6.919 | 6.199 | 0.000000000 | 0.000000001 | Neuron Type 1 (PEP1-like) |
| Mpz | 3.912 | 6.952 | 6.232 | 0.000000000 | 0.000000000 | Neuron Type 1 (PEP1-like) |
| Csrp2 | 1.647 | 7.078 | 6.370 | 0.000000000 | 0.000000000 | Neuron Type 1 (PEP1-like) |
| Fbln5 | 3.459 | 7.117 | 6.412 | 0.000000000 | 0.000000000 | Neuron Type 1 (PEP1-like) |
| Plekhb11 | 3.171 | 7.131 | 6.425 | 0.000000000 | 0.000000000 | Neuron Type 1 (PEP1-like) |
| Usp11 | 1.812 | 7.144 | 6.436 | 0.000000000 | 0.000000000 | Neuron Type 1 (PEP1-like) |
| Kl | 2.965 | 7.147 | 6.438 | 0.000000000 | 0.000000000 | Neuron Type 1 (PEP1-like) |
| Lpar1 | 3.253 | 7.150 | 6.439 | 0.000000000 | 0.000000000 | Neuron Type 1 (PEP1-like) |
| Bex1 | 7.619 | 7.161 | 6.441 | 0.000000000 | 0.000000000 | Neuron Type 1 (PEP1-like) |
| Fxyd6 | 8.401 | 7.161 | 6.441 | 0.000000000 | 0.000000000 | Neuron Type 1 (PEP1-like) |
| Gal | 7.537 | 7.161 | 6.441 | 0.000000000 | 0.000000000 | Neuron Type 1 (PEP1-like) |
| Gfra3 | 8.649 | 7.161 | 6.441 | 0.000000000 | 0.000000000 | Neuron Type 1 (PEP1-like) |
| Gpx3 | 6.301 | 7.161 | 6.441 | 0.000000000 | 0.000000000 | Neuron Type 1 (PEP1-like) |
| Kcnmb2 | 4.571 | 7.161 | 6.441 | 0.000000000 | 0.000000000 | Neuron Type 1 (PEP1-like) |
| Lig1 | 2.924 | 7.161 | 6.441 | 0.000000000 | 0.000000000 | Neuron Type 1 (PEP1-like) |
| Npy1r | 4.777 | 7.161 | 6.441 | 0.000000000 | 0.000000000 | Neuron Type 1 (PEP1-like) |
| S100a11 | 2.183 | 7.161 | 6.441 | 0.000000000 | 0.000000000 | Neuron Type 1 (PEP1-like) |
| Sstr2 | 4.613 | 7.161 | 6.441 | 0.000000000 | 0.000000000 | Neuron Type 1 (PEP1-like) |
| Tac1 | 4.160 | 7.161 | 6.441 | 0.000000000 | 0.000000000 | Neuron Type 1 (PEP1-like) |
| Tmem176a | 2.389 | 7.161 | 6.441 | 0.000000000 | 0.000000000 | Neuron Type 1 (PEP1-like) |
| Zcchc12 | 5.313 | 7.161 | 6.441 | 0.000000000 | 0.000000000 | Neuron Type 1 (PEP1-like) |
| Tipv1 | 2.759 | 7.161 | 6.441 | 0.000000000 | 0.000000000 | Neuron Type 1 (PEP1-like) |
| Nrsn1 | 1.853 | 7.161 | 6.441 | 0.000000000 | 0.000000000 | Neuron Type 1 (PEP1-like) |
| Tmem176b | 1.977 | 7.161 | 6.441 | 0.000000000 | 0.000000000 | Neuron Type 1 (PEP1-like) |
| Ppfibp2 | 3.418 | 7.161 | 6.441 | 0.000000000 | 0.000000000 | Neuron Type 1 (PEP1-like) |
| Adcyap1 | 2.636 | 7.161 | 6.441 | 0.000000000 | 0.000000000 | Neuron Type 1 (PEP1-like) |
| Rxrg | 2.924 | 7.161 | 6.441 | 0.000000000 | 0.000000000 | Neuron Type 1 (PEP1-like) |
| Tcn2 | 2.965 | 7.161 | 6.441 | 0.000000000 | 0.000000000 | Neuron Type 1 (PEP1-like) |
| Ly6e | 4.407 | 7.161 | 6.441 | 0.000000000 | 0.000000000 | Neuron Type 1 (PEP1-like) |
| Chrnb3 | 4.901 | 7.161 | 6.441 | 0.000000000 | 0.000000000 | Neuron Type 1 (PEP1-like) |
| Serpine2 | 4.860 | 7.161 | 6.441 | 0.000000000 | 0.000000000 | Neuron Type 1 (PEP1-like) |
| A730017C20Rik | 1.936 | 7.161 | 6.441 | 0.000000000 | 0.000000000 | Neuron Type 1 (PEP1-like) |
| Stmn1 | 1.071 | 7.161 | 6.441 | 0.000000000 | 0.000000000 | Neuron Type 1 (PEP1-like) |
| Igfbp2 | 2.965 | 7.161 | 6.441 | 0.000000000 | 0.000000000 | Neuron Type 1 (PEP1-like) |
| Acsbg1 | 5.024 | 7.161 | 6.441 | 0.000000000 | 0.000000000 | Neuron Type 1 (PEP1-like) |
| Ednrb | 4.654 | 7.161 | 6.441 | 0.000000000 | 0.000000000 | Neuron Type 1 (PEP1-like) |
| Kcnk3 | 3.871 | 7.161 | 6.441 | 0.000000000 | 0.000000000 | Neuron Type 1 (PEP1-like) |
| Gabrg3 | 3.377 | 7.161 | 6.441 | 0.000000000 | 0.000000000 | Neuron Type 1 (PEP1-like) |
| Rsph9 | 3.048 | 7.160 | 6.441 | 0.000000000 | 0.000000000 | Neuron Type 1 (PEP1-like) |
| Celf4 | 1.277 | 7.159 | 6.441 | 0.000000000 | 0.000000000 | Neuron Type 1 (PEP1-like) |
| Sv2a | 2.389 | 7.154 | 6.441 | 0.000000000 | 0.000000000 | Neuron Type 1 (PEP1-like) |
| Bid | 0.659 | 3.369 | 2.586 | 0.000754545 | 0.009702002 | Neuron Type 2 (NP-like) |
| Entpd3 | 0.535 | 3.388 | 2.606 | 0.000703152 | 0.009151079 | Neuron Type 2 (NP-like) |
| Capn9 | 2.553 | 3.393 | 2.612 | 0.000690883 | 0.009001355 | Neuron Type 2 (NP-like) |
| Gpr137b | 0.577 | 3.401 | 2.620 | 0.000670422 | 0.008783349 | Neuron Type 2 (NP-like) |
| Tnr | 0.988 | 3.402 | 2.621 | 0.000668506 | 0.008767998 | Neuron Type 2 (NP-like) |
| Atg7 | 0.535 | 3.406 | 2.624 | 0.000660321 | 0.008679974 | Neuron Type 2 (NP-like) |
| Acsl5 | 0.453 | 3.414 | 2.634 | 0.000639852 | 0.008429734 | Neuron Type 2 (NP-like) |
| St3gal6 | 0.947 | 3.423 | 2.642 | 0.000620241 | 0.008245149 | Neuron Type 2 (NP-like) |
| 6720468P15Rik | 1.071 | 3.429 | 2.649 | 0.000605359 | 0.008081666 | Neuron Type 2 (NP-like) |
| Seipina3g | 0.659 | 3.429 | 2.649 | 0.000605885 | 0.008081666 | Neuron Type 2 (NP-like) |
| Ctdspl | 0.824 | 3.437 | 2.657 | 0.000588998 | 0.007892170 | Neuron Type 2 (NP-like) |
| Syt51 | 0.494 | 3.441 | 2.662 | 0.000578914 | 0.007765892 | Neuron Type 2 (NP-like) |
| Mbnl2 | 0.371 | 3.443 | 2.664 | 0.000575465 | 0.007728429 | Neuron Type 2 (NP-like) |
| Gm20139 | 1.277 | 3.445 | 2.665 | 0.000571815 | 0.007698681 | Neuron Type 2 (NP-like) |
| Zfp954 | 0.577 | 3.444 | 2.665 | 0.000572597 | 0.007698681 | Neuron Type 2 (NP-like) |
| Hs6st3 | 0.947 | 3.449 | 2.669 | 0.000563665 | 0.007604634 | Neuron Type 2 (NP-like) |
| Selk | 0.329 | 3.450 | 2.671 | 0.000559771 | 0.007560754 | Neuron Type 2 (NP-like) |
| Tpk1 | 0.659 | 3.452 | 2.671 | 0.000557333 | 0.007553817 | Neuron Type 2 (NP-like) |

TABLE 1-continued

Differentially Expressed Genes Specific to Each Type of LN-Innervating Sensory Neurons

| Gene | log2 expression fold change | Z score | Corrected Z Score | p-value | q-value | Upregulated in |
|---|---|---|---|---|---|---|
| Ggta1 | 1.524 | 3.455 | 2.676 | 0.000549685 | 0.007458739 | Neuron Type 2 (NP-like) |
| Hexb | 0.494 | 3.458 | 2.678 | 0.000544391 | 0.007403965 | Neuron Type 2 (NP-like) |
| Lrrn3 | 0.618 | 3.461 | 2.681 | 0.000537670 | 0.007329489 | Neuron Type 2 (NP-like) |
| Plekhg1 | 1.318 | 3.468 | 2.688 | 0.000525035 | 0.007182181 | Neuron Type 2 (NP-like) |
| Rasgef1b | 1.359 | 3.469 | 2.689 | 0.000523335 | 0.007175593 | Neuron Type 2 (NP-like) |
| Ube2e3 | 0.535 | 3.481 | 2.703 | 0.000498774 | 0.006870827 | Neuron Type 2 (NP-like) |
| Cdh8 | 1.565 | 3.490 | 2.711 | 0.000483539 | 0.006715951 | Neuron Type 2 (NP-like) |
| Actr3 | 0.371 | 3.491 | 2.712 | 0.000480550 | 0.006690217 | Neuron Type 2 (NP-like) |
| Pdlim1 | 0.988 | 3.492 | 2.712 | 0.000479344 | 0.006681323 | Neuron Type 2 (NP-like) |
| Nap1l1 | 0.371 | 3.493 | 2.713 | 0.000478157 | 0.006672665 | Neuron Type 2 (NP-like) |
| Lpar5 | 5.066 | 3.499 | 2.720 | 0.000466272 | 0.006522265 | Neuron Type 2 (NP-like) |
| Hmga2-ps1 | 0.865 | 3.508 | 2.729 | 0.000452027 | 0.006345624 | Neuron Type 2 (NP-like) |
| 1830012O16Rik | 1.359 | 3.530 | 2.753 | 0.000415376 | 0.005901440 | Neuron Type 2 (NP-like) |
| Shcl | 0.453 | 3.535 | 2.758 | 0.000408382 | 0.005809083 | Neuron Type 2 (NP-like) |
| Lclatl | 0.577 | 3.537 | 2.759 | 0.000405410 | 0.005794811 | Neuron Type 2 (NP-like) |
| Aff2 | 0.906 | 3.550 | 2.772 | 0.000385251 | 0.005569710 | Neuron Type 2 (NP-like) |
| 1700066M21Rik | 0.577 | 3.556 | 2.778 | 0.000376433 | 0.005466861 | Neuron Type 2 (NP-like) |
| Ttc39c | 0.659 | 3.577 | 2.799 | 0.000347645 | 0.005124605 | Neuron Type 2 (NP-like) |
| Xylt2 | 0.782 | 3.580 | 2.802 | 0.000343172 | 0.005071371 | Neuron Type 2 (NP-like) |
| Sdcl | 2.718 | 3.581 | 2.803 | 0.000341739 | 0.005056536 | Neuron Type 2 (NP-like) |
| Mrgpra2b | 0.618 | 3.587 | 2.808 | 0.000334470 | 0.004980263 | Neuron Type 2 (NP-like) |
| Praf2 | 0.371 | 3.588 | 2.809 | 0.000333209 | 0.004974061 | Neuron Type 2 (NP-like) |
| 2810032G03Rik | 1.236 | 3.591 | 2.811 | 0.000329922 | 0.004937506 | Neuron Type 2 (NP-like) |
| Trpv2 | 0.577 | 3.597 | 2.817 | 0.000322231 | 0.004840867 | Neuron Type 2 (NP-like) |
| Gpr116 | 1.894 | 3.597 | 2.818 | 0.000321293 | 0.004839114 | Neuron Type 2 (NP-like) |
| Adarb1 | 0.824 | 3.603 | 2.823 | 0.000314563 | 0.004755999 | Neuron Type 2 (NP-like) |
| Hexa | 0.535 | 3.608 | 2.828 | 0.000308874 | 0.004682003 | Neuron Type 2 (NP-like) |
| Txndc11 | 0.782 | 3.627 | 2.849 | 0.000286628 | 0.004384292 | Neuron Type 2 (NP-like) |
| Gm2115 | 1.236 | 3.629 | 2.851 | 0.000284975 | 0.004364675 | Neuron Type 2 (NP-like) |
| Fam5b | 0.824 | 3.631 | 2.853 | 0.000281997 | 0.004324693 | Neuron Type 2 (NP-like) |
| 1700003M02Rik | 1.236 | 3.633 | 2.856 | 0.000279651 | 0.004295495 | Neuron Type 2 (NP-like) |
| Egfem1 | 1.030 | 3.633 | 2.856 | 0.000279729 | 0.004295495 | Neuron Type 2 (NP-like) |
| Runx2 | 1.153 | 3.637 | 2.859 | 0.000276084 | 0.004250607 | Neuron Type 2 (NP-like) |
| Mboat1 | 1.483 | 3.638 | 2.860 | 0.000274809 | 0.004236519 | Neuron Type 2 (NP-like) |
| Camk2a | 0.535 | 3.646 | 2.869 | 0.000265894 | 0.004115245 | Neuron Type 2 (NP-like) |
| Ank | 0.782 | 3.650 | 2.873 | 0.000261818 | 0.004062840 | Neuron Type 2 (NP-like) |
| Luzp2 | 0.577 | 3.654 | 2.877 | 0.000257701 | 0.004009514 | Neuron Type 2 (NP-like) |
| Ngfrap1 | 0.494 | 3.657 | 2.880 | 0.000255330 | 0.003977881 | Neuron Type 2 (NP-like) |
| Arhgap1 | 0.535 | 3.662 | 2.886 | 0.000249795 | 0.003896809 | Neuron Type 2 (NP-like) |
| Ptprt | 1.400 | 3.666 | 2.890 | 0.000246047 | 0.003848520 | Neuron Type 2 (NP-like) |
| Stt3b | 0.700 | 3.669 | 2.893 | 0.000243081 | 0.003812254 | Neuron Type 2 (NP-like) |
| Hagh | 0.412 | 3.670 | 2.893 | 0.000242366 | 0.003811194 | Neuron Type 2 (NP-like) |
| Tbrg1 | 0.494 | 3.688 | 2.914 | 0.000225959 | 0.003562719 | Neuron Type 2 (NP-like) |
| Cited1 | 1.441 | 3.695 | 2.922 | 0.000219970 | 0.003472932 | Neuron Type 2 (NP-like) |
| Igsf3 | 0.577 | 3.711 | 2.940 | 0.000206177 | 0.003277131 | Neuron Type 2 (NP-like) |
| Rpl36a | 0.453 | 3.713 | 2.942 | 0.000205105 | 0.003264502 | Neuron Type 2 (NP-like) |
| Mapk4 | 1.194 | 3.731 | 2.963 | 0.000190474 | 0.003043970 | Neuron Type 2 (NP-like) |
| Tm7sf3 | 0.947 | 3.736 | 2.969 | 0.000186622 | 0.002990527 | Neuron Type 2 (NP-like) |
| Cntnap4 | 0.988 | 3.744 | 2.976 | 0.000181144 | 0.002918617 | Neuron Type 2 (NP-like) |
| Anxa11 | 0.865 | 3.754 | 2.986 | 0.000174271 | 0.002823333 | Neuron Type 2 (NP-like) |
| Tspan1 | 1.400 | 3.757 | 2.988 | 0.000172173 | 0.002808657 | Neuron Type 2 (NP-like) |
| Lbh | 0.947 | 3.765 | 2.995 | 0.000166577 | 0.002740143 | Neuron Type 2 (NP-like) |
| Zdhhc13 | 0.659 | 3.774 | 3.005 | 0.000160493 | 0.002654893 | Neuron Type 2 (NP-like) |
| Psd4 | 2.018 | 3.777 | 3.007 | 0.000158952 | 0.002636811 | Neuron Type 2 (NP-like) |
| Tnfaip8l3 | 2.347 | 3.791 | 3.021 | 0.000149992 | 0.002516525 | Neuron Type 2 (NP-like) |
| Ism1 | 1.524 | 3.793 | 3.023 | 0.000148570 | 0.002506200 | Neuron Type 2 (NP-like) |
| Fam189a2 | 1.400 | 3.793 | 3.023 | 0.000148685 | 0.002506200 | Neuron Type 2 (NP-like) |
| Arsb | 0.659 | 3.802 | 3.031 | 0.000143646 | 0.002434336 | Neuron Type 2 (NP-like) |
| Cyp2j12 | 1.277 | 3.810 | 3.041 | 0.000138936 | 0.002360443 | Neuron Type 2 (NP-like) |
| Mrgpra2a | 0.700 | 3.825 | 3.057 | 0.000130738 | 0.002238122 | Neuron Type 2 (NP-like) |
| Ncf2 | 1.771 | 3.826 | 3.057 | 0.000130170 | 0.002234894 | Neuron Type 2 (NP-like) |
| Gpr179 | 1.318 | 3.833 | 3.065 | 0.000126487 | 0.002178019 | Neuron Type 2 (NP-like) |
| Oas1a | 1.730 | 3.842 | 3.074 | 0.000122127 | 0.002112204 | Neuron Type 2 (NP-like) |
| Tmem154 | 1.936 | 3.844 | 3.075 | 0.000121003 | 0.002102026 | Neuron Type 2 (NP-like) |
| Gng12 | 0.782 | 3.846 | 3.078 | 0.000119922 | 0.002086319 | Neuron Type 2 (NP-like) |
| Il17rc | 2.059 | 3.878 | 3.113 | 0.000105244 | 0.001853145 | Neuron Type 2 (NP-like) |
| Rnf125 | 0.618 | 3.884 | 3.118 | 0.000102881 | 0.001819423 | Neuron Type 2 (NP-like) |
| Tubb2b | 0.453 | 3.886 | 3.120 | 0.000101710 | 0.001806854 | Neuron Type 2 (NP-like) |
| Otoa | 3.253 | 3.892 | 3.126 | 0.000099266 | 0.001774140 | Neuron Type 2 (NP-like) |
| Dcx | 1.236 | 3.893 | 3.126 | 0.000098937 | 0.001770947 | Neuron Type 2 (NP-like) |
| Far2 | 0.906 | 3.915 | 3.150 | 0.000090493 | 0.001632196 | Neuron Type 2 (NP-like) |
| Samd12 | 0.782 | 3.928 | 3.164 | 0.000085649 | 0.001554342 | Neuron Type 2 (NP-like) |
| Irak3 | 1.483 | 3.939 | 3.176 | 0.000081987 | 0.001494801 | Neuron Type 2 (NP-like) |
| Tmem164 | 0.700 | 3.945 | 3.182 | 0.000079935 | 0.001464190 | Neuron Type 2 (NP-like) |

TABLE 1-continued

Differentially Expressed Genes Specific to Each Type of LN-Innervating Sensory Neurons

| Gene | log2 expression fold change | Z score | Corrected Z Score | p-value | q-value | Upregulated in |
|---|---|---|---|---|---|---|
| Spns2 | 1.236 | 3.955 | 3.194 | 0.000076470 | 0.001405095 | Neuron Type 2 (NP-like) |
| Dgkz | 0.700 | 3.964 | 3.203 | 0.000073822 | 0.001360683 | Neuron Type 2 (NP-like) |
| Fbxo22 | 0.618 | 3.970 | 3.209 | 0.000071871 | 0.001330967 | Neuron Type 2 (NP-like) |
| Kctd16 | 0.741 | 3.987 | 3.226 | 0.000066961 | 0.001253847 | Neuron Type 2 (NP-like) |
| Lhfpl2 | 1.400 | 4.006 | 3.246 | 0.000061766 | 0.001169586 | Neuron Type 2 (NP-like) |
| Hcn4 | 1.359 | 4.016 | 3.256 | 0.000059254 | 0.001128568 | Neuron Type 2 (NP-like) |
| Acbd4 | 0.659 | 4.016 | 3.256 | 0.000059313 | 0.001128568 | Neuron Type 2 (NP-like) |
| Rasgrp1 | 2.265 | 4.036 | 3.278 | 0.000054377 | 0.001044779 | Neuron Type 2 (NP-like) |
| Ifit2 | 1.194 | 4.080 | 3.325 | 0.000044975 | 0.000884342 | Neuron Type 2 (NP-like) |
| Samd14 | 0.618 | 4.092 | 3.337 | 0.000042783 | 0.000848322 | Neuron Type 2 (NP-like) |
| Bhlhe41 | 1.112 | 4.097 | 3.342 | 0.000041773 | 0.000831086 | Neuron Type 2 (NP-like) |
| Ddah1 | 0.947 | 4.098 | 3.343 | 0.000041643 | 0.000829892 | Neuron Type 2 (NP-like) |
| Myt1 | 1.400 | 4.099 | 3.343 | 0.000041540 | 0.000829253 | Neuron Type 2 (NP-like) |
| Cpe | 0.659 | 4.102 | 3.345 | 0.000041038 | 0.000823419 | Neuron Type 2 (NP-like) |
| Rnf7 | 0.535 | 4.103 | 3.346 | 0.000040729 | 0.000818620 | Neuron Type 2 (NP-like) |
| Ahnak | 0.782 | 4.116 | 3.359 | 0.000038610 | 0.000781352 | Neuron Type 2 (NP-like) |
| Fam19a4 | 2.718 | 4.118 | 3.361 | 0.000038165 | 0.000776263 | Neuron Type 2 (NP-like) |
| Ret | 0.824 | 4.118 | 3.361 | 0.000038227 | 0.000776263 | Neuron Type 2 (NP-like) |
| Bag2 | 1.071 | 4.119 | 3.361 | 0.000038057 | 0.000775502 | Neuron Type 2 (NP-like) |
| Kdelc2 | 1.030 | 4.122 | 3.364 | 0.000037547 | 0.000768823 | Neuron Type 2 (NP-like) |
| Slc35f5 | 0.741 | 4.122 | 3.364 | 0.000037581 | 0.000768823 | Neuron Type 2 (NP-like) |
| Gnaq | 0.906 | 4.122 | 3.364 | 0.000037624 | 0.000768823 | Neuron Type 2 (NP-like) |
| Pvrl1 | 1.894 | 4.121 | 3.364 | 0.000037664 | 0.000768823 | Neuron Type 2 (NP-like) |
| Rasgef1a | 0.865 | 4.127 | 3.369 | 0.000036708 | 0.000754527 | Neuron Type 2 (NP-like) |
| Kcnk18 | 1.977 | 4.128 | 3.369 | 0.000036612 | 0.000753868 | Neuron Type 2 (NP-like) |
| Kcnj11 | 1.771 | 4.153 | 3.397 | 0.000032836 | 0.000682086 | Neuron Type 2 (NP-like) |
| Gnao1 | 0.577 | 4.159 | 3.402 | 0.000032014 | 0.000669729 | Neuron Type 2 (NP-like) |
| Fam43a | 1.977 | 4.165 | 3.408 | 0.000031185 | 0.000653550 | Neuron Type 2 (NP-like) |
| Abcc8 | 1.936 | 4.167 | 3.411 | 0.000030876 | 0.000648227 | Neuron Type 2 (NP-like) |
| Gpd1l | 0.782 | 4.172 | 3.416 | 0.000030184 | 0.000634830 | Neuron Type 2 (NP-like) |
| Cpn1 | 1.318 | 4.204 | 3.446 | 0.000026240 | 0.000568104 | Neuron Type 2 (NP-like) |
| Prokr1 | 2.553 | 4.211 | 3.454 | 0.000025432 | 0.000552648 | Neuron Type 2 (NP-like) |
| Tpm4 | 0.824 | 4.228 | 3.473 | 0.000023565 | 0.000514522 | Neuron Type 2 (NP-like) |
| 9530053A07Rik | 1.565 | 4.233 | 3.477 | 0.000023053 | 0.000506266 | Neuron Type 2 (NP-like) |
| Isl2 | 0.659 | 4.245 | 3.489 | 0.000021893 | 0.000485596 | Neuron Type 2 (NP-like) |
| Lrrc59 | 0.659 | 4.256 | 3.500 | 0.000020828 | 0.000464597 | Neuron Type 2 (NP-like) |
| Mvp | 0.824 | 4.261 | 3.506 | 0.000020323 | 0.000454196 | Neuron Type 2 (NP-like) |
| Actn1 | 1.318 | 4.280 | 3.526 | 0.000018650 | 0.000422413 | Neuron Type 2 (NP-like) |
| Cab39l | 0.659 | 4.313 | 3.561 | 0.000016124 | 0.000368758 | Neuron Type 2 (NP-like) |
| Bcar3 | 1.524 | 4.325 | 3.575 | 0.000015274 | 0.000350683 | Neuron Type 2 (NP-like) |
| Lix1 | 0.824 | 4.336 | 3.586 | 0.000014501 | 0.000336209 | Neuron Type 2 (NP-like) |
| Pitpnc1 | 0.782 | 4.342 | 3.592 | 0.000014110 | 0.000327798 | Neuron Type 2 (NP-like) |
| Wnt2b | 1.853 | 4.356 | 3.606 | 0.000013267 | 0.000311268 | Neuron Type 2 (NP-like) |
| Cmtm7 | 2.471 | 4.371 | 3.622 | 0.000012368 | 0.000291934 | Neuron Type 2 (NP-like) |
| Ttr | 1.689 | 4.379 | 3.630 | 0.000011934 | 0.000283689 | Neuron Type 2 (NP-like) |
| Zfp945 | 1.318 | 4.384 | 3.635 | 0.000011664 | 0.000278089 | Neuron Type 2 (NP-like) |
| Ccdc43 | 0.782 | 4.389 | 3.641 | 0.000011379 | 0.000271850 | Neuron Type 2 (NP-like) |
| Smyd3 | 1.194 | 4.399 | 3.651 | 0.000010865 | 0.000261686 | Neuron Type 2 (NP-like) |
| Snx9 | 1.153 | 4.400 | 3.651 | 0.000010826 | 0.000261284 | Neuron Type 2 (NP-like) |
| Zfp40 | 1.071 | 4.408 | 3.659 | 0.000010443 | 0.000253077 | Neuron Type 2 (NP-like) |
| Gadl1 | 1.606 | 4.418 | 3.669 | 0.000009982 | 0.000243912 | Neuron Type 2 (NP-like) |
| Atp1a3 | 0.741 | 4.430 | 3.682 | 0.000009433 | 0.000231244 | Neuron Type 2 (NP-like) |
| Abca5 | 1.277 | 4.446 | 3.699 | 0.000008758 | 0.000216694 | Neuron Type 2 (NP-like) |
| Adam8 | 1.647 | 4.446 | 3.699 | 0.000008735 | 0.000216594 | Neuron Type 2 (NP-like) |
| Paqr4 | 0.824 | 4.448 | 3.700 | 0.000008649 | 0.000215832 | Neuron Type 2 (NP-like) |
| Ifi27l2a | 2.142 | 4.449 | 3.700 | 0.000008620 | 0.000215556 | Neuron Type 2 (NP-like) |
| Prkar2b | 1.194 | 4.520 | 3.777 | 0.000006194 | 0.000158942 | Neuron Type 2 (NP-like) |
| Slc35f4 | 1.565 | 4.527 | 3.784 | 0.000005994 | 0.000154134 | Neuron Type 2 (NP-like) |
| Grhl3 | 1.894 | 4.531 | 3.788 | 0.000005878 | 0.000151812 | Neuron Type 2 (NP-like) |
| H2-D1 | 0.700 | 4.568 | 3.829 | 0.000004930 | 0.000128472 | Neuron Type 2 (NP-like) |
| Snx7 | 0.700 | 4.594 | 3.858 | 0.000004344 | 0.000114472 | Neuron Type 2 (NP-like) |
| Med10 | 0.824 | 4.603 | 3.866 | 0.000004158 | 0.000110541 | Neuron Type 2 (NP-like) |
| 5830473C10Rik | 2.100 | 4.608 | 3.871 | 0.000004063 | 0.000108265 | Neuron Type 2 (NP-like) |
| Slc7a8 | 1.153 | 4.617 | 3.880 | 0.000003897 | 0.000104562 | Neuron Type 2 (NP-like) |
| Hdac9 | 1.400 | 4.635 | 3.899 | 0.000003564 | 0.000096496 | Neuron Type 2 (NP-like) |
| Mcfd2 | 0.741 | 4.650 | 3.915 | 0.000003324 | 0.000090413 | Neuron Type 2 (NP-like) |
| Sh2d4a | 2.224 | 4.681 | 3.950 | 0.000002852 | 0.000078310 | Neuron Type 2 (NP-like) |
| Cds2 | 0.782 | 4.683 | 3.951 | 0.000002827 | 0.000077986 | Neuron Type 2 (NP-like) |
| Fam83h | 1.277 | 4.691 | 3.958 | 0.000002725 | 0.000075511 | Neuron Type 2 (NP-like) |
| Slc7a7 | 1.030 | 4.699 | 3.965 | 0.000002620 | 0.000073462 | Neuron Type 2 (NP-like) |
| Inadl | 1.194 | 4.729 | 3.997 | 0.000002251 | 0.000064197 | Neuron Type 2 (NP-like) |
| Lipa | 0.988 | 4.756 | 4.024 | 0.000001980 | 0.000057284 | Neuron Type 2 (NP-like) |
| Ugcg | 1.236 | 4.760 | 4.029 | 0.000001935 | 0.000056127 | Neuron Type 2 (NP-like) |
| Ssbp3 | 0.988 | 4.812 | 4.082 | 0.000001496 | 0.000044729 | Neuron Type 2 (NP-like) |

TABLE 1-continued

Differentially Expressed Genes Specific to Each Type of LN-Innervating Sensory Neurons

| Gene | log2 expression fold change | Z score | Corrected Z Score | p-value | q-value | Upregulated in |
|---|---|---|---|---|---|---|
| Tmem200a | 1.194 | 4.811 | 4.082 | 0.000001500 | 0.000044729 | Neuron Type 2 (NP-like) |
| Mrgprd | 7.784 | 4.834 | 4.106 | 0.000001339 | 0.000040221 | Neuron Type 2 (NP-like) |
| Cdk15 | 1.771 | 4.850 | 4.122 | 0.000001235 | 0.000037482 | Neuron Type 2 (NP-like) |
| Agtrap | 1.153 | 4.861 | 4.133 | 0.000001170 | 0.000035783 | Neuron Type 2 (NP-like) |
| Ldb2 | 1.030 | 4.880 | 4.155 | 0.000001060 | 0.000032522 | Neuron Type 2 (NP-like) |
| Pop5 | 0.782 | 4.919 | 4.197 | 0.000000871 | 0.000026998 | Neuron Type 2 (NP-like) |
| Stom | 1.730 | 4.952 | 4.234 | 0.000000734 | 0.000022992 | Neuron Type 2 (NP-like) |
| Elk3 | 1.936 | 4.995 | 4.279 | 0.000000588 | 0.000018754 | Neuron Type 2 (NP-like) |
| Eml1 | 0.824 | 5.017 | 4.303 | 0.000000524 | 0.000016872 | Neuron Type 2 (NP-like) |
| Tpd52 | 0.782 | 5.091 | 4.382 | 0.000000356 | 0.000011781 | Neuron Type 2 (NP-like) |
| Htr4 | 2.059 | 5.119 | 4.412 | 0.000000307 | 0.000010225 | Neuron Type 2 (NP-like) |
| Etv1 | 2.100 | 5.124 | 4.417 | 0.000000299 | 0.000009991 | Neuron Type 2 (NP-like) |
| Slc45a3 | 1.153 | 5.125 | 4.418 | 0.000000298 | 0.000009972 | Neuron Type 2 (NP-like) |
| Dyrk4 | 2.718 | 5.129 | 4.423 | 0.000000291 | 0.000009752 | Neuron Type 2 (NP-like) |
| Rpp25 | 1.936 | 5.140 | 4.434 | 0.000000275 | 0.000009261 | Neuron Type 2 (NP-like) |
| Ap1ar | 1.441 | 5.145 | 4.440 | 0.000000267 | 0.000009010 | Neuron Type 2 (NP-like) |
| Rasa4 | 2.142 | 5.151 | 4.445 | 0.000000259 | 0.000008797 | Neuron Type 2 (NP-like) |
| Kcnk13 | 2.965 | 5.152 | 4.445 | 0.000000258 | 0.000008778 | Neuron Type 2 (NP-like) |
| Txn1 | 0.947 | 5.165 | 4.460 | 0.000000241 | 0.000008213 | Neuron Type 2 (NP-like) |
| Serpina11 | 2.718 | 5.173 | 4.468 | 0.000000230 | 0.000007911 | Neuron Type 2 (NP-like) |
| Aprt | 1.030 | 5.238 | 4.537 | 0.000000163 | 0.000005716 | Neuron Type 2 (NP-like) |
| Dtnbp1 | 1.565 | 5.245 | 4.545 | 0.000000156 | 0.000005496 | Neuron Type 2 (NP-like) |
| Ptrh1 | 1.359 | 5.249 | 4.547 | 0.000000153 | 0.000005439 | Neuron Type 2 (NP-like) |
| N28178 | 0.988 | 5.253 | 4.551 | 0.000000150 | 0.000005334 | Neuron Type 2 (NP-like) |
| Ptma | 0.782 | 5.254 | 4.552 | 0.000000149 | 0.000005326 | Neuron Type 2 (NP-like) |
| Mustn1 | 3.130 | 5.258 | 4.555 | 0.000000146 | 0.000005243 | Neuron Type 2 (NP-like) |
| Rarg | 1.647 | 5.266 | 4.564 | 0.000000139 | 0.000005024 | Neuron Type 2 (NP-like) |
| Ghr | 1.318 | 5.276 | 4.575 | 0.000000132 | 0.000004768 | Neuron Type 2 (NP-like) |
| Dok1 | 1.894 | 5.282 | 4.580 | 0.000000128 | 0.000004641 | Neuron Type 2 (NP-like) |
| Arhgap6 | 1.936 | 5.282 | 4.580 | 0.000000128 | 0.000004639 | Neuron Type 2 (NP-like) |
| Zadh2 | 1.483 | 5.287 | 4.586 | 0.000000124 | 0.000004528 | Neuron Type 2 (NP-like) |
| Mlc1 | 3.089 | 5.292 | 4.590 | 0.000000121 | 0.000004433 | Neuron Type 2 (NP-like) |
| Mal | 1.977 | 5.292 | 4.590 | 0.000000121 | 0.000004433 | Neuron Type 2 (NP-like) |
| Cd47 | 0.865 | 5.307 | 4.605 | 0.000000112 | 0.000004119 | Neuron Type 2 (NP-like) |
| P2rx3 | 1.153 | 5.320 | 4.617 | 0.000000104 | 0.000003899 | Neuron Type 2 (NP-like) |
| Rgs3 | 0.947 | 5.341 | 4.638 | 0.000000093 | 0.000003517 | Neuron Type 2 (NP-like) |
| Osmr | 3.048 | 5.363 | 4.660 | 0.000000082 | 0.000003164 | Neuron Type 2 (NP-like) |
| Krt27 | 2.512 | 5.371 | 4.668 | 0.000000078 | 0.000003038 | Neuron Type 2 (NP-like) |
| Hmox1 | 2.100 | 5.378 | 4.675 | 0.000000076 | 0.000002935 | Neuron Type 2 (NP-like) |
| Mal2 | 1.277 | 5.386 | 4.684 | 0.000000072 | 0.000002816 | Neuron Type 2 (NP-like) |
| Snx10 | 0.947 | 5.423 | 4.723 | 0.000000058 | 0.000002318 | Neuron Type 2 (NP-like) |
| Klk5 | 2.965 | 5.430 | 4.730 | 0.000000056 | 0.000002246 | Neuron Type 2 (NP-like) |
| Gnal | 1.030 | 5.432 | 4.732 | 0.000000056 | 0.000002222 | Neuron Type 2 (NP-like) |
| Ifit3 | 2.306 | 5.449 | 4.750 | 0.000000051 | 0.000002038 | Neuron Type 2 (NP-like) |
| Fam107b | 1.236 | 5.459 | 4.759 | 0.000000048 | 0.000001950 | Neuron Type 2 (NP-like) |
| Gng2 | 1.071 | 5.459 | 4.759 | 0.000000048 | 0.000001948 | Neuron Type 2 (NP-like) |
| Ets1 | 1.977 | 5.463 | 4.761 | 0.000000047 | 0.000001923 | Neuron Type 2 (NP-like) |
| Pkig | 1.359 | 5.482 | 4.779 | 0.000000042 | 0.000001759 | Neuron Type 2 (NP-like) |
| Fam83d | 3.171 | 5.504 | 4.802 | 0.000000037 | 0.000001568 | Neuron Type 2 (NP-like) |
| Lap3 | 1.112 | 5.506 | 4.804 | 0.000000037 | 0.000001556 | Neuron Type 2 (NP-like) |
| 3632451O06Rik | 0.988 | 5.530 | 4.830 | 0.000000032 | 0.000001369 | Neuron Type 2 (NP-like) |
| Myola | 2.800 | 5.569 | 4.872 | 0.000000026 | 0.000001107 | Neuron Type 2 (NP-like) |
| Plcb3 | 1.030 | 5.572 | 4.873 | 0.000000025 | 0.000001097 | Neuron Type 2 (NP-like) |
| Tspan14 | 1.400 | 5.584 | 4.886 | 0.000000023 | 0.000001027 | Neuron Type 2 (NP-like) |
| Slc4a11 | 1.359 | 5.604 | 4.906 | 0.000000021 | 0.000000928 | Neuron Type 2 (NP-like) |
| Zfp385b | 1.606 | 5.608 | 4.909 | 0.000000021 | 0.000000916 | Neuron Type 2 (NP-like) |
| Prkca | 1.277 | 5.654 | 4.958 | 0.000000016 | 0.000000713 | Neuron Type 2 (NP-like) |
| Cadm1 | 0.988 | 5.656 | 4.959 | 0.000000015 | 0.000000709 | Neuron Type 2 (NP-like) |
| Dnajc5b | 2.512 | 5.718 | 5.023 | 0.000000011 | 0.000000508 | Neuron Type 2 (NP-like) |
| Cav2 | 1.771 | 5.739 | 5.042 | 0.000000010 | 0.000000461 | Neuron Type 2 (NP-like) |
| Rab27b | 1.730 | 5.752 | 5.054 | 0.000000009 | 0.000000433 | Neuron Type 2 (NP-like) |
| Rcan2 | 1.153 | 5.806 | 5.110 | 0.000000006 | 0.000000322 | Neuron Type 2 (NP-like) |
| Ston2 | 2.100 | 5.854 | 5.159 | 0.000000005 | 0.000000248 | Neuron Type 2 (NP-like) |
| Dusp26 | 1.153 | 5.885 | 5.192 | 0.000000004 | 0.000000208 | Neuron Type 2 (NP-like) |
| Tmem158 | 2.677 | 5.909 | 5.217 | 0.000000003 | 0.000000181 | Neuron Type 2 (NP-like) |
| Kcng3 | 2.142 | 5.928 | 5.238 | 0.000000003 | 0.000000163 | Neuron Type 2 (NP-like) |
| Kcnt1 | 1.236 | 5.988 | 5.301 | 0.000000002 | 0.000000115 | Neuron Type 2 (NP-like) |
| Skp1a | 1.071 | 6.027 | 5.343 | 0.000000002 | 0.000000091 | Neuron Type 2 (NP-like) |
| Rab15 | 1.441 | 6.061 | 5.380 | 0.000000001 | 0.000000074 | Neuron Type 2 (NP-like) |
| 9430021M05Rik | 3.089 | 6.062 | 5.380 | 0.000000001 | 0.000000074 | Neuron Type 2 (NP-like) |
| Fli1 | 2.636 | 6.085 | 5.405 | 0.000000001 | 0.000000065 | Neuron Type 2 (NP-like) |
| Gna14 | 1.400 | 6.087 | 5.406 | 0.000000001 | 0.000000065 | Neuron Type 2 (NP-like) |
| Scn11a | 1.318 | 6.089 | 5.408 | 0.000000001 | 0.000000064 | Neuron Type 2 (NP-like) |
| Neurog3 | 3.048 | 6.191 | 5.516 | 0.000000001 | 0.000000035 | Neuron Type 2 (NP-like) |

TABLE 1-continued

Differentially Expressed Genes Specific to Each Type of LN-Innervating Sensory Neurons

| Gene | log2 expression fold change | Z score | Corrected Z Score | p-value | q-value | Upregulated in |
|---|---|---|---|---|---|---|
| Golga7b | 1.400 | 6.219 | 5.545 | 0.000000000 | 0.000000029 | Neuron Type 2 (NP-like) |
| Lgals3 | 5.271 | 6.230 | 5.555 | 0.000000000 | 0.000000028 | Neuron Type 2 (NP-like) |
| Dgkh | 1.318 | 6.280 | 5.608 | 0.000000000 | 0.000000020 | Neuron Type 2 (NP-like) |
| Fam178b | 2.924 | 6.300 | 5.628 | 0.000000000 | 0.000000018 | Neuron Type 2 (NP-like) |
| Cysltr2 | 3.377 | 6.302 | 5.630 | 0.000000000 | 0.000000018 | Neuron Type 2 (NP-like) |
| Dpp10 | 2.224 | 6.327 | 5.655 | 0.000000000 | 0.000000016 | Neuron Type 2 (NP-like) |
| Ptgdr | 2.224 | 6.398 | 5.728 | 0.000000000 | 0.000000010 | Neuron Type 2 (NP-like) |
| St6gal2 | 3.295 | 6.412 | 5.743 | 0.000000000 | 0.000000009 | Neuron Type 2 (NP-like) |
| Arpc1b | 1.112 | 6.418 | 5.749 | 0.000000000 | 0.000000009 | Neuron Type 2 (NP-like) |
| Socs2 | 1.565 | 6.455 | 5.785 | 0.000000000 | 0.000000007 | Neuron Type 2 (NP-like) |
| Rgs8 | 2.471 | 6.481 | 5.812 | 0.000000000 | 0.000000006 | Neuron Type 2 (NP-like) |
| Ly86 | 1.565 | 6.497 | 5.829 | 0.000000000 | 0.000000006 | Neuron Type 2 (NP-like) |
| Fez1 | 1.236 | 6.667 | 6.000 | 0.000000000 | 0.000000002 | Neuron Type 2 (NP-like) |
| Cpne3 | 1.894 | 6.721 | 6.056 | 0.000000000 | 0.000000001 | Neuron Type 2 (NP-like) |
| Bcl2l14 | 3.707 | 6.810 | 6.147 | 0.000000000 | 0.000000001 | Neuron Type 2 (NP-like) |
| Ccdc68 | 4.571 | 6.905 | 6.246 | 0.000000000 | 0.000000000 | Neuron Type 2 (NP-like) |
| Slc22a18 | 2.471 | 6.964 | 6.308 | 0.000000000 | 0.000000000 | Neuron Type 2 (NP-like) |
| Arap1 | 2.471 | 6.999 | 6.344 | 0.000000000 | 0.000000000 | Neuron Type 2 (NP-like) |
| Arhgap36 | 2.965 | 7.006 | 6.351 | 0.000000000 | 0.000000000 | Neuron Type 2 (NP-like) |
| Rgs10 | 1.524 | 7.046 | 6.392 | 0.000000000 | 0.000000000 | Neuron Type 2 (NP-like) |
| Dapk2 | 4.160 | 7.060 | 6.405 | 0.000000000 | 0.000000000 | Neuron Type 2 (NP-like) |
| Kcnip4 | 1.565 | 7.070 | 6.414 | 0.000000000 | 0.000000000 | Neuron Type 2 (NP-like) |
| Tec | 3.089 | 7.104 | 6.448 | 0.000000000 | 0.000000000 | Neuron Type 2 (NP-like) |
| Tmem63a | 2.636 | 7.114 | 6.456 | 0.000000000 | 0.000000000 | Neuron Type 2 (NP-like) |
| Mrgpra3 | 3.336 | 7.118 | 6.458 | 0.000000000 | 0.000000000 | Neuron Type 2 (NP-like) |
| Rhov | 1.730 | 7.126 | 6.464 | 0.000000000 | 0.000000000 | Neuron Type 2 (NP-like) |
| Uaca | 2.759 | 7.140 | 6.476 | 0.000000000 | 0.000000000 | Neuron Type 2 (NP-like) |
| Pstpip2 | 2.183 | 7.145 | 6.477 | 0.000000000 | 0.000000000 | Neuron Type 2 (NP-like) |
| Serinc2 | 2.347 | 7.151 | 6.478 | 0.000000000 | 0.000000000 | Neuron Type 2 (NP-like) |
| A3galt2 | 6.466 | 7.161 | 6.479 | 0.000000000 | 0.000000000 | Neuron Type 2 (NP-like) |
| Acpp | 4.983 | 7.161 | 6.479 | 0.000000000 | 0.000000000 | Neuron Type 2 (NP-like) |
| Adk | 2.718 | 7.161 | 6.479 | 0.000000000 | 0.000000000 | Neuron Type 2 (NP-like) |
| Carhsp1 | 2.759 | 7.161 | 6.479 | 0.000000000 | 0.000000000 | Neuron Type 2 (NP-like) |
| Cav1 | 5.972 | 7.161 | 6.479 | 0.000000000 | 0.000000000 | Neuron Type 2 (NP-like) |
| Cd55 | 3.501 | 7.161 | 6.479 | 0.000000000 | 0.000000000 | Neuron Type 2 (NP-like) |
| Cd82 | 3.212 | 7.161 | 6.479 | 0.000000000 | 0.000000000 | Neuron Type 2 (NP-like) |
| Ctxn3 | 6.178 | 7.161 | 6.479 | 0.000000000 | 0.000000000 | Neuron Type 2 (NP-like) |
| Fxyd2 | 2.595 | 7.161 | 6.479 | 0.000000000 | 0.000000000 | Neuron Type 2 (NP-like) |
| Kcnip2 | 6.631 | 7.161 | 6.479 | 0.000000000 | 0.000000000 | Neuron Type 2 (NP-like) |
| Klf5 | 4.160 | 7.161 | 6.479 | 0.000000000 | 0.000000000 | Neuron Type 2 (NP-like) |
| Lxn | 2.759 | 7.161 | 6.479 | 0.000000000 | 0.000000000 | Neuron Type 2 (NP-like) |
| Moxd1 | 7.125 | 7.161 | 6.479 | 0.000000000 | 0.000000000 | Neuron Type 2 (NP-like) |
| Nnat | 4.901 | 7.161 | 6.479 | 0.000000000 | 0.000000000 | Neuron Type 2 (NP-like) |
| Nt5e | 5.271 | 7.161 | 6.479 | 0.000000000 | 0.000000000 | Neuron Type 2 (NP-like) |
| Paqr5 | 5.271 | 7.161 | 6.479 | 0.000000000 | 0.000000000 | Neuron Type 2 (NP-like) |
| Ppp1r1a | 5.930 | 7.161 | 6.479 | 0.000000000 | 0.000000000 | Neuron Type 2 (NP-like) |
| Scg3 | 2.265 | 7.161 | 6.479 | 0.000000000 | 0.000000000 | Neuron Type 2 (NP-like) |
| Synpr | 5.395 | 7.161 | 6.479 | 0.000000000 | 0.000000000 | Neuron Type 2 (NP-like) |
| Tmem45b | 8.731 | 7.161 | 6.479 | 0.000000000 | 0.000000000 | Neuron Type 2 (NP-like) |
| Tmem79 | 3.954 | 7.161 | 6.479 | 0.000000000 | 0.000000000 | Neuron Type 2 (NP-like) |
| Trpc3 | 5.271 | 7.161 | 6.479 | 0.000000000 | 0.000000000 | Neuron Type 2 (NP-like) |
| Trpc6 | 5.148 | 7.161 | 6.479 | 0.000000000 | 0.000000000 | Neuron Type 2 (NP-like) |
| Mmp25 | 5.066 | 7.161 | 6.479 | 0.000000000 | 0.000000000 | Neuron Type 2 (NP-like) |
| Plxnc1 | 3.418 | 7.161 | 6.479 | 0.000000000 | 0.000000000 | Neuron Type 2 (NP-like) |
| Cmtm8 | 5.066 | 7.161 | 6.479 | 0.000000000 | 0.000000000 | Neuron Type 2 (NP-like) |
| Serping1 | 3.871 | 7.161 | 6.479 | 0.000000000 | 0.000000000 | Neuron Type 2 (NP-like) |
| Mrgpra9 | 3.912 | 7.161 | 6.479 | 0.000000000 | 0.000000000 | Neuron Type 2 (NP-like) |
| Gpm6a | 3.459 | 7.161 | 6.479 | 0.000000000 | 0.000000000 | Neuron Type 2 (NP-like) |
| Dgki | 2.471 | 7.161 | 6.479 | 0.000000000 | 0.000000000 | Neuron Type 2 (NP-like) |
| Grik1 | 5.230 | 7.161 | 6.479 | 0.000000000 | 0.000000000 | Neuron Type 2 (NP-like) |
| Fam114a1 | 3.459 | 7.161 | 6.479 | 0.000000000 | 0.000000000 | Neuron Type 2 (NP-like) |
| Plaur | 4.283 | 7.161 | 6.479 | 0.000000000 | 0.000000000 | Neuron Type 2 (NP-like) |
| Rgs4 | 1.771 | 7.161 | 6.479 | 0.000000000 | 0.000000000 | Neuron Type 2 (NP-like) |
| Slc16a12 | 4.489 | 7.161 | 6.479 | 0.000000000 | 0.000000000 | Neuron Type 2 (NP-like) |
| Slc9a3r2 | 1.936 | 7.161 | 6.479 | 0.000000000 | 0.000000000 | Neuron Type 2 (NP-like) |
| Mical1 | 2.471 | 7.161 | 6.479 | 0.000000000 | 0.000000000 | Neuron Type 2 (NP-like) |
| Rarres1 | 4.860 | 7.161 | 6.479 | 0.000000000 | 0.000000000 | Neuron Type 2 (NP-like) |
| Hs6st2 | 2.347 | 7.161 | 6.479 | 0.000000000 | 0.000000000 | Neuron Type 2 (NP-like) |
| Klhl5 | 3.295 | 7.161 | 6.479 | 0.000000000 | 0.000000000 | Neuron Type 2 (NP-like) |
| Nbl1 | 2.224 | 7.161 | 6.479 | 0.000000000 | 0.000000000 | Neuron Type 2 (NP-like) |
| Cyp4f39 | 4.242 | 7.161 | 6.479 | 0.000000000 | 0.000000000 | Neuron Type 2 (NP-like) |
| Kcnn1 | 2.389 | 7.161 | 6.479 | 0.000000000 | 0.000000000 | Neuron Type 2 (NP-like) |
| Ms4a3 | 4.407 | 7.160 | 6.479 | 0.000000000 | 0.000000000 | Neuron Type 2 (NP-like) |
| Cd24a | 1.441 | 7.159 | 6.479 | 0.000000000 | 0.000000000 | Neuron Type 2 (NP-like) |

TABLE 1-continued

| Differentially Expressed Genes Specific to Each Type of LN-Innervating Sensory Neurons | | | | | | |
|---|---|---|---|---|---|---|
| Gene | log2 expression fold change | Z score | Corrected Z Score | p-value | q-value | Upregulated in |
| Prkcd | 1.400 | 7.158 | 6.479 | 0.000000000 | 0.000000000 | Neuron Type 2 (NP-like) |
| Mrgprb5 | 4.613 | 7.157 | 6.479 | 0.000000000 | 0.000000000 | Neuron Type 2 (NP-like) |
| Wipf3 | 2.965 | 7.156 | 6.479 | 0.000000000 | 0.000000000 | Neuron Type 2 (NP-like) |
| Ryr2 | 0.659 | 3.472 | 2.599 | 0.000516475 | 0.009358521 | Neuron Type 3 (mixed PEP2/NF123) |
| Tecr | 0.247 | 3.477 | 2.605 | 0.000506933 | 0.009199777 | Neuron Type 3 (mixed PEP2/NF123) |
| Dym | 0.288 | 3.478 | 2.605 | 0.000505279 | 0.009183913 | Neuron Type 3 (mixed PEP2/NF123) |
| Diras2 | 0.618 | 3.483 | 2.610 | 0.000496488 | 0.009066104 | Neuron Type 3 (mixed PEP2/NF123) |
| Lrrc4c | 0.577 | 3.488 | 2.616 | 0.000486123 | 0.008890616 | Neuron Type 3 (mixed PEP2/NF123) |
| Dclk2 | 0.535 | 3.500 | 2.628 | 0.000465452 | 0.008579167 | Neuron Type 3 (mixed PEP2/NF123) |
| Hrsp12 | 0.412 | 3.508 | 2.638 | 0.000451149 | 0.008341648 | Neuron Type 3 (mixed PEP2/NF123) |
| Egfl7 | 0.371 | 3.516 | 2.647 | 0.000438437 | 0.008132138 | Neuron Type 3 (mixed PEP2/NF123) |
| Dcun1d4 | 0.453 | 3.520 | 2.651 | 0.000431049 | 0.008020366 | Neuron Type 3 (mixed PEP2/NF123) |
| Prrt2 | 0.371 | 3.524 | 2.656 | 0.000424376 | 0.007908711 | Neuron Type 3 (mixed PEP2/NF123) |
| Dbc1 | 0.577 | 3.527 | 2.659 | 0.000419680 | 0.007833583 | Neuron Type 3 (mixed PEP2/NF123) |
| Tsc22d3 | 0.371 | 3.539 | 2.672 | 0.000401818 | 0.007536013 | Neuron Type 3 (mixed PEP2/NF123) |
| Stx11 | 0.947 | 3.541 | 2.674 | 0.000399216 | 0.007499141 | Neuron Type 3 (mixed PEP2/NF123) |
| P2rx6 | 2.018 | 3.545 | 2.679 | 0.000392375 | 0.007394224 | Neuron Type 3 (mixed PEP2/NF123) |
| Greb1 | 0.741 | 3.550 | 2.683 | 0.000385434 | 0.007286371 | Neuron Type 3 (mixed PEP2/NF123) |
| Coro6 | 1.153 | 3.561 | 2.696 | 0.000369055 | 0.007022174 | Neuron Type 3 (mixed PEP2/NF123) |
| Wnt5a | 0.659 | 3.565 | 2.699 | 0.000364279 | 0.006964081 | Neuron Type 3 (mixed PEP2/NF123) |
| Kif5c | 0.329 | 3.564 | 2.699 | 0.000364819 | 0.006964081 | Neuron Type 3 (mixed PEP2/NF123) |
| Pld3 | 0.329 | 3.571 | 2.705 | 0.000355251 | 0.006836834 | Neuron Type 3 (mixed PEP2/NF123) |
| Fam69a | 0.824 | 3.573 | 2.706 | 0.000352837 | 0.006801487 | Neuron Type 3 (mixed PEP2/NF123) |
| Nacc2 | 0.371 | 3.580 | 2.715 | 0.000343734 | 0.006636882 | Neuron Type 3 (mixed PEP2/NF123) |
| Tubb4a | 0.371 | 3.581 | 2.715 | 0.000342584 | 0.006625533 | Neuron Type 3 (mixed PEP2/NF123) |
| Gnwd1 | 0.535 | 3.601 | 2.738 | 0.000317112 | 0.006183676 | Neuron Type 3 (mixed PEP2/NF123) |
| Krt28 | 1.400 | 3.618 | 2.755 | 0.000296549 | 0.005860320 | Neuron Type 3 (mixed PEP2/NF123) |
| Galm | 0.865 | 3.627 | 2.764 | 0.000286721 | 0.005706221 | Neuron Type 3 (mixed PEP2/NF123) |
| Vamp1 | 0.618 | 3.638 | 2.775 | 0.000274554 | 0.005517091 | Neuron Type 3 (mixed PEP2/NF123) |
| Ralyl | 0.412 | 3.638 | 2.775 | 0.000274965 | 0.005517091 | Neuron Type 3 (mixed PEP2/NF123) |
| Pak3 | 0.535 | 3.644 | 2.781 | 0.000268846 | 0.005412774 | Neuron Type 3 (mixed PEP2/NF123) |
| Adcy8 | 1.565 | 3.658 | 2.798 | 0.000254061 | 0.005141457 | Neuron Type 3 (mixed PEP2/NF123) |
| Slitrk3 | 0.906 | 3.662 | 2.801 | 0.000250655 | 0.005090016 | Neuron Type 3 (mixed PEP2/NF123) |
| Luzp1 | 0.494 | 3.667 | 2.807 | 0.000245499 | 0.004993930 | Neuron Type 3 (mixed PEP2/NF123) |
| Ndp | 0.700 | 3.672 | 2.813 | 0.000240641 | 0.004907233 | Neuron Type 3 (mixed PEP2/NF123) |
| Upp2 | 1.153 | 3.672 | 2.813 | 0.000240820 | 0.004907233 | Neuron Type 3 (mixed PEP2/NF123) |
| Klhl25 | 0.782 | 3.676 | 2.817 | 0.000236798 | 0.004842029 | Neuron Type 3 (mixed PEP2/NF123) |
| Rell2 | 0.741 | 3.680 | 2.821 | 0.000232965 | 0.004790855 | Neuron Type 3 (mixed PEP2/NF123) |
| Orai2 | 0.535 | 3.680 | 2.821 | 0.000233278 | 0.004790855 | Neuron Type 3 (mixed PEP2/NF123) |
| Opcml | 0.577 | 3.691 | 2.832 | 0.000223255 | 0.004629388 | Neuron Type 3 (mixed PEP2/NF123) |
| Cntnap2 | 0.535 | 3.694 | 2.835 | 0.000220630 | 0.004584425 | Neuron Type 3 (mixed PEP2/NF123) |
| Lrrc8c | 0.494 | 3.704 | 2.846 | 0.000211917 | 0.004433321 | Neuron Type 3 (mixed PEP2/NF123) |
| Sv2c | 0.618 | 3.732 | 2.875 | 0.000190148 | 0.004035240 | Neuron Type 3 (mixed PEP2/NF123) |
| Foxj1 | 0.988 | 3.752 | 2.896 | 0.000175748 | 0.003778130 | Neuron Type 3 (mixed PEP2/NF123) |
| Camk1d | 0.535 | 3.751 | 2.896 | 0.000175787 | 0.003778130 | Neuron Type 3 (mixed PEP2/NF123) |
| Scn4b | 0.659 | 3.757 | 2.900 | 0.000172146 | 0.003727087 | Neuron Type 3 (mixed PEP2/NF123) |
| Adam23 | 0.700 | 3.760 | 2.903 | 0.000170208 | 0.003691912 | Neuron Type 3 (mixed PEP2/NF123) |
| Dpp6 | 0.371 | 3.760 | 2.904 | 0.000169612 | 0.003685776 | Neuron Type 3 (mixed PEP2/NF123) |
| Ankrd52 | 0.618 | 3.775 | 2.920 | 0.000159720 | 0.003503130 | Neuron Type 3 (mixed PEP2/NF123) |
| Ankrd29 | 0.824 | 3.791 | 2.937 | 0.000150182 | 0.003318664 | Neuron Type 3 (mixed PEP2/NF123) |
| Snap25 | 0.329 | 3.795 | 2.941 | 0.000147584 | 0.003273525 | Neuron Type 3 (mixed PEP2/NF123) |
| Tmem229b | 0.700 | 3.809 | 2.957 | 0.000139287 | 0.003107043 | Neuron Type 3 (mixed PEP2/NF123) |
| Hs3st1 | 1.565 | 3.816 | 2.963 | 0.000135904 | 0.003043107 | Neuron Type 3 (mixed PEP2/NF123) |
| Ncam2 | 0.782 | 3.827 | 2.976 | 0.000129562 | 0.002917750 | Neuron Type 3 (mixed PEP2/NF123) |
| Abhd2 | 0.741 | 3.835 | 2.984 | 0.000125789 | 0.002846953 | Neuron Type 3 (mixed PEP2/NF123) |
| Camk2g | 0.412 | 3.841 | 2.990 | 0.000122645 | 0.002788640 | Neuron Type 3 (mixed PEP2/NF123) |
| Tspyl4 | 0.371 | 3.844 | 2.993 | 0.000121099 | 0.002758805 | Neuron Type 3 (mixed PEP2/NF123) |
| Tm4sf1 | 1.277 | 3.872 | 3.025 | 0.000107798 | 0.002489492 | Neuron Type 3 (mixed PEP2/NF123) |
| Pcolce2 | 0.988 | 3.877 | 3.030 | 0.000105679 | 0.002445351 | Neuron Type 3 (mixed PEP2/NF123) |
| Cntn6 | 1.483 | 3.879 | 3.031 | 0.000105096 | 0.002436664 | Neuron Type 3 (mixed PEP2/NF123) |
| Eda | 1.112 | 3.890 | 3.044 | 0.000100395 | 0.002336855 | Neuron Type 3 (mixed PEP2/NF123) |
| Adam22 | 0.577 | 3.895 | 3.048 | 0.000098079 | 0.002301146 | Neuron Type 3 (mixed PEP2/NF123) |
| Clu | 0.659 | 3.899 | 3.052 | 0.000096564 | 0.002275343 | Neuron Type 3 (mixed PEP2/NF123) |
| Kank4 | 0.988 | 3.913 | 3.066 | 0.000091176 | 0.002169440 | Neuron Type 3 (mixed PEP2/NF123) |
| Nptn | 0.453 | 3.914 | 3.067 | 0.000090735 | 0.002163319 | Neuron Type 3 (mixed PEP2/NF123) |
| Dkk3 | 0.453 | 3.915 | 3.067 | 0.000090376 | 0.002159129 | Neuron Type 3 (mixed PEP2/NF123) |
| Kndc1 | 0.865 | 3.918 | 3.070 | 0.000089303 | 0.002137822 | Neuron Type 3 (mixed PEP2/NF123) |
| Mmp15 | 0.577 | 3.944 | 3.100 | 0.000080057 | 0.001936156 | Neuron Type 3 (mixed PEP2/NF123) |
| Brmsl1 | 0.577 | 3.956 | 3.112 | 0.000076196 | 0.001858046 | Neuron Type 3 (mixed PEP2/NF123) |
| Hs3st3b1 | 1.524 | 3.961 | 3.118 | 0.000074579 | 0.001822393 | Neuron Type 3 (mixed PEP2/NF123) |
| P2ry2 | 0.824 | 3.980 | 3.140 | 0.000068967 | 0.001692275 | Neuron Type 3 (mixed PEP2/NF123) |
| Pid1 | 0.824 | 3.982 | 3.141 | 0.000068443 | 0.001685441 | Neuron Type 3 (mixed PEP2/NF123) |
| C1qtnf1 | 0.700 | 3.981 | 3.141 | 0.000068545 | 0.001685441 | Neuron Type 3 (mixed PEP2/NF123) |
| Irs2 | 0.782 | 3.998 | 3.158 | 0.000063876 | 0.001587201 | Neuron Type 3 (mixed PEP2/NF123) |

TABLE 1-continued

Differentially Expressed Genes Specific to Each Type of LN-Innervating Sensory Neurons

| Gene | log2 expression fold change | Z score | Corrected Z Score | p-value | q-value | Upregulated in |
|---|---|---|---|---|---|---|
| Cyp46a1 | 0.824 | 4.005 | 3.166 | 0.000061917 | 0.001545032 | Neuron Type 3 (mixed PEP2/NF123) |
| Fgfr1 | 0.782 | 4.032 | 3.192 | 0.000055395 | 0.001415269 | Neuron Type 3 (mixed PEP2/NF123) |
| Depdc7 | 1.483 | 4.044 | 3.204 | 0.000052612 | 0.001355934 | Neuron Type 3 (mixed PEP2/NF123) |
| Grm8 | 1.730 | 4.046 | 3.205 | 0.000052137 | 0.001348412 | Neuron Type 3 (mixed PEP2/NF123) |
| Cnih3 | 2.224 | 4.058 | 3.215 | 0.000049469 | 0.001302398 | Neuron Type 3 (mixed PEP2/NF123) |
| Pqlc1 | 0.371 | 4.064 | 3.220 | 0.000048137 | 0.001279802 | Neuron Type 3 (mixed PEP2/NF123) |
| Esr1 | 1.524 | 4.081 | 3.239 | 0.000044796 | 0.001199097 | Neuron Type 3 (mixed PEP2/NF123) |
| Kcna2 | 0.782 | 4.085 | 3.243 | 0.000044025 | 0.001181157 | Neuron Type 3 (mixed PEP2/NF123) |
| Impdh1 | 0.535 | 4.086 | 3.244 | 0.000043804 | 0.001177916 | Neuron Type 3 (mixed PEP2/NF123) |
| Hgf | 0.988 | 4.105 | 3.263 | 0.000040365 | 0.001102058 | Neuron Type 3 (mixed PEP2/NF123) |
| Sema5a | 1.483 | 4.105 | 3.263 | 0.000040422 | 0.001102058 | Neuron Type 3 (mixed PEP2/NF123) |
| Pllp | 2.059 | 4.116 | 3.271 | 0.000038565 | 0.001071280 | Neuron Type 3 (mixed PEP2/NF123) |
| Ppp3ca | 0.494 | 4.130 | 3.287 | 0.000036317 | 0.001011214 | Neuron Type 3 (mixed PEP2/NF123) |
| Itgb6 | 1.441 | 4.149 | 3.307 | 0.000033364 | 0.000942000 | Neuron Type 3 (mixed PEP2/NF123) |
| Vstm2a | 0.782 | 4.148 | 3.307 | 0.000033511 | 0.000942000 | Neuron Type 3 (mixed PEP2/NF123) |
| Sytl2 | 0.741 | 4.163 | 3.322 | 0.000031444 | 0.000894555 | Neuron Type 3 (mixed PEP2/NF123) |
| Mgll | 0.577 | 4.166 | 3.324 | 0.000031028 | 0.000886996 | Neuron Type 3 (mixed PEP2/NF123) |
| Vwc2l | 1.112 | 4.175 | 3.335 | 0.000029771 | 0.000853153 | Neuron Type 3 (mixed PEP2/NF123) |
| Lingo3 | 1.565 | 4.182 | 3.342 | 0.000028933 | 0.000831157 | Neuron Type 3 (mixed PEP2/NF123) |
| Mctp1 | 1.318 | 4.196 | 3.356 | 0.000027155 | 0.000789720 | Neuron Type 3 (mixed PEP2/NF123) |
| Calm3 | 0.535 | 4.199 | 3.359 | 0.000026844 | 0.000782609 | Neuron Type 3 (mixed PEP2/NF123) |
| Lrrn1 | 0.782 | 4.203 | 3.363 | 0.000026338 | 0.000771653 | Neuron Type 3 (mixed PEP2/NF123) |
| Scn1a | 2.306 | 4.210 | 3.371 | 0.000025493 | 0.000748782 | Neuron Type 3 (mixed PEP2/NF123) |
| Clec2l | 1.030 | 4.213 | 3.374 | 0.000025195 | 0.000741868 | Neuron Type 3 (mixed PEP2/NF123) |
| Cadm3 | 0.577 | 4.222 | 3.383 | 0.000024201 | 0.000716190 | Neuron Type 3 (mixed PEP2/NF123) |
| Mgst1 | 1.606 | 4.224 | 3.385 | 0.000023973 | 0.000711234 | Neuron Type 3 (mixed PEP2/NF123) |
| Lhfpl3 | 0.782 | 4.233 | 3.395 | 0.000023051 | 0.000685585 | Neuron Type 3 (mixed PEP2/NF123) |
| Pygb | 0.453 | 4.247 | 3.411 | 0.000021671 | 0.000646318 | Neuron Type 3 (mixed PEP2/NF123) |
| Akr1b8 | 1.236 | 4.266 | 3.432 | 0.000019870 | 0.000598537 | Neuron Type 3 (mixed PEP2/NF123) |
| Chga | 0.535 | 4.274 | 3.441 | 0.000019172 | 0.000580479 | Neuron Type 3 (mixed PEP2/NF123) |
| Lin7b | 0.659 | 4.297 | 3.466 | 0.000017287 | 0.000527490 | Neuron Type 3 (mixed PEP2/NF123) |
| Parva | 0.577 | 4.300 | 3.468 | 0.000017101 | 0.000524530 | Neuron Type 3 (mixed PEP2/NF123) |
| Rasgef1c | 1.524 | 4.305 | 3.473 | 0.000016713 | 0.000513970 | Neuron Type 3 (mixed PEP2/NF123) |
| Begain | 2.059 | 4.307 | 3.475 | 0.000016555 | 0.000510420 | Neuron Type 3 (mixed PEP2/NF123) |
| Fzd1 | 1.441 | 4.308 | 3.476 | 0.000016488 | 0.000509878 | Neuron Type 3 (mixed PEP2/NF123) |
| Bace2 | 1.318 | 4.315 | 3.482 | 0.000015930 | 0.000498501 | Neuron Type 3 (mixed PEP2/NF123) |
| Hapln3 | 1.318 | 4.322 | 3.487 | 0.000015493 | 0.000487899 | Neuron Type 3 (mixed PEP2/NF123) |
| Egflam | 1.524 | 4.343 | 3.510 | 0.000014075 | 0.000448034 | Neuron Type 3 (mixed PEP2/NF123) |
| Chn2 | 1.606 | 4.344 | 3.511 | 0.000013966 | 0.000445762 | Neuron Type 3 (mixed PEP2/NF123) |
| Plcb1 | 0.865 | 4.348 | 3.516 | 0.000013713 | 0.000438899 | Neuron Type 3 (mixed PEP2/NF123) |
| Col11a1 | 1.853 | 4.360 | 3.529 | 0.000012978 | 0.000417631 | Neuron Type 3 (mixed PEP2/NF123) |
| Slc16a6 | 1.318 | 4.367 | 3.535 | 0.000012586 | 0.000407769 | Neuron Type 3 (mixed PEP2/NF123) |
| L3mbtl4 | 1.112 | 4.372 | 3.539 | 0.000012338 | 0.000401413 | Neuron Type 3 (mixed PEP2/NF123) |
| Fat3 | 1.112 | 4.377 | 3.546 | 0.000012009 | 0.000391794 | Neuron Type 3 (mixed PEP2/NF123) |
| Pde2a | 0.577 | 4.381 | 3.548 | 0.000011839 | 0.000388425 | Neuron Type 3 (mixed PEP2/NF123) |
| Cfh | 1.894 | 4.394 | 3.562 | 0.000011137 | 0.000368466 | Neuron Type 3 (mixed PEP2/NF123) |
| Nrp2 | 1.030 | 4.410 | 3.578 | 0.000010360 | 0.000345681 | Neuron Type 3 (mixed PEP2/NF123) |
| Ptger3 | 1.194 | 4.414 | 3.584 | 0.000010128 | 0.000338900 | Neuron Type 3 (mixed PEP2/NF123) |
| Cplx1 | 0.577 | 4.430 | 3.599 | 0.000009444 | 0.000319618 | Neuron Type 3 (mixed PEP2/NF123) |
| Pvrl4 | 0.906 | 4.440 | 3.609 | 0.000009014 | 0.000307722 | Neuron Type 3 (mixed PEP2/NF123) |
| Syt2 | 0.782 | 4.448 | 3.618 | 0.000008656 | 0.000297214 | Neuron Type 3 (mixed PEP2/NF123) |
| Kitl | 1.030 | 4.496 | 3.670 | 0.000006927 | 0.000242810 | Neuron Type 3 (mixed PEP2/NF123) |
| Tgfb2 | 1.071 | 4.496 | 3.670 | 0.000006927 | 0.000242810 | Neuron Type 3 (mixed PEP2/NF123) |
| Tnfrsf21 | 0.535 | 4.510 | 3.681 | 0.000006484 | 0.000232128 | Neuron Type 3 (mixed PEP2/NF123) |
| Pwwp2b | 1.236 | 4.526 | 3.697 | 0.000006010 | 0.000217797 | Neuron Type 3 (mixed PEP2/NF123) |
| Golim4 | 0.906 | 4.532 | 3.704 | 0.000005846 | 0.000212510 | Neuron Type 3 (mixed PEP2/NF123) |
| Kcnab2 | 0.535 | 4.552 | 3.726 | 0.000005310 | 0.000194241 | Neuron Type 3 (mixed PEP2/NF123) |
| Lhfpl4 | 0.618 | 4.565 | 3.740 | 0.000004986 | 0.000184083 | Neuron Type 3 (mixed PEP2/NF123) |
| Prlr | 2.306 | 4.589 | 3.766 | 0.000004456 | 0.000165569 | Neuron Type 3 (mixed PEP2/NF123) |
| Prrt3 | 0.782 | 4.606 | 3.782 | 0.000004103 | 0.000155393 | Neuron Type 3 (mixed PEP2/NF123) |
| Scn1b | 0.947 | 4.620 | 3.796 | 0.000003838 | 0.000147262 | Neuron Type 3 (mixed PEP2/NF123) |
| Gm10754 | 1.647 | 4.661 | 3.839 | 0.000003142 | 0.000123344 | Neuron Type 3 (mixed PEP2/NF123) |
| Kcnip3 | 0.700 | 4.663 | 3.839 | 0.000003122 | 0.000123315 | Neuron Type 3 (mixed PEP2/NF123) |
| Sorcs3 | 1.730 | 4.662 | 3.839 | 0.000003131 | 0.000123315 | Neuron Type 3 (mixed PEP2/NF123) |
| Ngfr | 0.700 | 4.673 | 3.850 | 0.000002968 | 0.000118092 | Neuron Type 3 (mixed PEP2/NF123) |
| Col16a1 | 1.318 | 4.678 | 3.854 | 0.000002898 | 0.000116098 | Neuron Type 3 (mixed PEP2/NF123) |
| Shank1 | 1.400 | 4.750 | 3.935 | 0.000002031 | 0.000083069 | Neuron Type 3 (mixed PEP2/NF123) |
| Scn8a | 1.194 | 4.755 | 3.940 | 0.000001984 | 0.000081405 | Neuron Type 3 (mixed PEP2/NF123) |
| Ywhag | 0.494 | 4.761 | 3.946 | 0.000001930 | 0.000079468 | Neuron Type 3 (mixed PEP2/NF123) |
| Nfasc | 1.153 | 4.763 | 3.947 | 0.000001912 | 0.000079003 | Neuron Type 3 (mixed PEP2/NF123) |
| Hist1h2bc | 0.618 | 4.783 | 3.969 | 0.000001724 | 0.000072278 | Neuron Type 3 (mixed PEP2/NF123) |
| 3110043O21Rik | 0.659 | 4.792 | 3.978 | 0.000001651 | 0.000069442 | Neuron Type 3 (mixed PEP2/NF123) |
| Canikk1 | 0.782 | 4.813 | 4.000 | 0.000001487 | 0.000063215 | Neuron Type 3 (mixed PEP2/NF123) |
| Olfml3 | 1.071 | 4.815 | 4.002 | 0.000001469 | 0.000062696 | Neuron Type 3 (mixed PEP2/NF123) |

TABLE 1-continued

Differentially Expressed Genes Specific to Each Type of LN-Innervating Sensory Neurons

| Gene | log2 expression fold change | Z score | Corrected Z Score | p-value | q-value | Upregulated in |
|---|---|---|---|---|---|---|
| Tuba4a | 0.577 | 4.819 | 4.006 | 0.000001443 | 0.000061782 | Neuron Type 3 (mixed PEP2/NF123) |
| Nfia | 1.030 | 4.822 | 4.008 | 0.000001422 | 0.000061142 | Neuron Type 3 (mixed PEP2/NF123) |
| Igsf21 | 2.224 | 4.828 | 4.015 | 0.000001380 | 0.000059528 | Neuron Type 3 (mixed PEP2/NF123) |
| Nr4a2 | 2.224 | 4.829 | 4.015 | 0.000001371 | 0.000059351 | Neuron Type 3 (mixed PEP2/NF123) |
| Ndrg3 | 0.824 | 4.871 | 4.061 | 0.000001109 | 0.000048918 | Neuron Type 3 (mixed PEP2/NF123) |
| Glrb | 0.782 | 4.873 | 4.062 | 0.000001099 | 0.000048669 | Neuron Type 3 (mixed PEP2/NF123) |
| Pcdhac2 | 0.741 | 4.907 | 4.098 | 0.000000927 | 0.000041660 | Neuron Type 3 (mixed PEP2/NF123) |
| Atp1a1 | 0.659 | 4.928 | 4.120 | 0.000000833 | 0.000037874 | Neuron Type 3 (mixed PEP2/NF123) |
| Stbd1 | 0.700 | 4.938 | 4.131 | 0.000000790 | 0.000036043 | Neuron Type 3 (mixed PEP2/NF123) |
| Kcnt2 | 1.771 | 4.956 | 4.152 | 0.000000720 | 0.000032974 | Neuron Type 3 (mixed PEP2/NF123) |
| Prokr2 | 1.894 | 4.987 | 4.181 | 0.000000614 | 0.000029050 | Neuron Type 3 (mixed PEP2/NF123) |
| Lcp1 | 0.906 | 4.998 | 4.192 | 0.000000578 | 0.000027673 | Neuron Type 3 (mixed PEP2/NF123) |
| Fam81a | 0.988 | 5.004 | 4.197 | 0.000000561 | 0.000027079 | Neuron Type 3 (mixed PEP2/NF123) |
| Rnf157 | 0.906 | 5.003 | 4.197 | 0.000000563 | 0.000027079 | Neuron Type 3 (mixed PEP2/NF123) |
| Tmem56 | 0.865 | 5.007 | 4.200 | 0.000000552 | 0.000026749 | Neuron Type 3 (mixed PEP2/NF123) |
| Paqr9 | 1.359 | 5.036 | 4.229 | 0.000000476 | 0.000023437 | Neuron Type 3 (mixed PEP2/NF123) |
| Nat8l | 0.865 | 5.074 | 4.270 | 0.000000389 | 0.000019561 | Neuron Type 3 (mixed PEP2/NF123) |
| Kcnv1 | 1.071 | 5.095 | 4.293 | 0.000000349 | 0.000017644 | Neuron Type 3 (mixed PEP2/NF123) |
| Kcnq2 | 1.400 | 5.095 | 4.293 | 0.000000349 | 0.000017644 | Neuron Type 3 (mixed PEP2/NF123) |
| Plxna2 | 1.071 | 5.111 | 4.309 | 0.000000321 | 0.000016368 | Neuron Type 3 (mixed PEP2/NF123) |
| Elfn1 | 1.153 | 5.121 | 4.320 | 0.000000304 | 0.000015603 | Neuron Type 3 (mixed PEP2/NF123) |
| Scn7a | 0.988 | 5.139 | 4.337 | 0.000000276 | 0.000014414 | Neuron Type 3 (mixed PEP2/NF123) |
| Sorl1 | 1.071 | 5.183 | 4.381 | 0.000000218 | 0.000011797 | Neuron Type 3 (mixed PEP2/NF123) |
| Airn | 1.524 | 5.197 | 4.396 | 0.000000202 | 0.000011014 | Neuron Type 3 (mixed PEP2/NF123) |
| Syt6 | 0.782 | 5.203 | 4.402 | 0.000000196 | 0.000010740 | Neuron Type 3 (mixed PEP2/NF123) |
| Tm9sf2 | 0.741 | 5.271 | 4.476 | 0.000000135 | 0.000007598 | Neuron Type 3 (mixed PEP2/NF123) |
| Spock3 | 0.865 | 5.290 | 4.495 | 0.000000122 | 0.000006965 | Neuron Type 3 (mixed PEP2/NF123) |
| Grm4 | 1.812 | 5.335 | 4.544 | 0.000000096 | 0.000005528 | Neuron Type 3 (mixed PEP2/NF123) |
| Cyp1b1 | 2.430 | 5.336 | 4.544 | 0.000000095 | 0.000005508 | Neuron Type 3 (mixed PEP2/NF123) |
| Cntn1 | 1.277 | 5.372 | 4.584 | 0.000000078 | 0.000004551 | Neuron Type 3 (mixed PEP2/NF123) |
| Epb4.1l3 | 0.700 | 5.385 | 4.598 | 0.000000072 | 0.000004259 | Neuron Type 3 (mixed PEP2/NF123) |
| Aox1 | 1.153 | 5.408 | 4.620 | 0.000000064 | 0.000003836 | Neuron Type 3 (mixed PEP2/NF123) |
| Kcnd1 | 0.824 | 5.423 | 4.636 | 0.000000059 | 0.000003548 | Neuron Type 3 (mixed PEP2/NF123) |
| Nap1l2 | 0.988 | 5.429 | 4.643 | 0.000000057 | 0.000003436 | Neuron Type 3 (mixed PEP2/NF123) |
| Plch2 | 1.565 | 5.460 | 4.674 | 0.000000048 | 0.000002949 | Neuron Type 3 (mixed PEP2/NF123) |
| P2ry1 | 1.936 | 5.472 | 4.687 | 0.000000045 | 0.000002778 | Neuron Type 3 (mixed PEP2/NF123) |
| Cntnap1 | 1.483 | 5.514 | 4.734 | 0.000000035 | 0.000002201 | Neuron Type 3 (mixed PEP2/NF123) |
| Adam11 | 0.906 | 5.528 | 4.749 | 0.000000032 | 0.000002044 | Neuron Type 3 (mixed PEP2/NF123) |
| 1110008P14Rik | 0.741 | 5.539 | 4.759 | 0.000000030 | 0.000001946 | Neuron Type 3 (mixed PEP2/NF123) |
| Tmem47 | 1.194 | 5.574 | 4.796 | 0.000000025 | 0.000001620 | Neuron Type 3 (mixed PEP2/NF123) |
| Lgmn | 0.741 | 5.611 | 4.836 | 0.000000020 | 0.000001328 | Neuron Type 3 (mixed PEP2/NF123) |
| Nefh | 1.359 | 5.662 | 4.887 | 0.000000015 | 0.000001023 | Neuron Type 3 (mixed PEP2/NF123) |
| Vangl1 | 2.347 | 5.748 | 4.974 | 0.000000009 | 0.000000657 | Neuron Type 3 (mixed PEP2/NF123) |
| Sv2b | 1.359 | 5.784 | 5.014 | 0.000000007 | 0.000000534 | Neuron Type 3 (mixed PEP2/NF123) |
| Pcp4l1 | 0.988 | 5.788 | 5.018 | 0.000000007 | 0.000000523 | Neuron Type 3 (mixed PEP2/NF123) |
| Fam126b | 1.277 | 5.795 | 5.024 | 0.000000007 | 0.000000506 | Neuron Type 3 (mixed PEP2/NF123) |
| Chst2 | 1.483 | 5.820 | 5.051 | 0.000000006 | 0.000000440 | Neuron Type 3 (mixed PEP2/NF123) |
| Ckmt1 | 0.906 | 5.874 | 5.107 | 0.000000004 | 0.000000327 | Neuron Type 3 (mixed PEP2/NF123) |
| Phyhipl | 0.947 | 5.896 | 5.131 | 0.000000004 | 0.000000288 | Neuron Type 3 (mixed PEP2/NF123) |
| Clrn1 | 2.718 | 5.903 | 5.137 | 0.000000004 | 0.000000279 | Neuron Type 3 (mixed PEP2/NF123) |
| Efhd2 | 1.400 | 5.907 | 5.141 | 0.000000003 | 0.000000274 | Neuron Type 3 (mixed PEP2/NF123) |
| Gpr158 | 1.400 | 5.984 | 5.221 | 0.000000002 | 0.000000178 | Neuron Type 3 (mixed PEP2/NF123) |
| Ust | 2.059 | 6.150 | 5.389 | 0.000000001 | 0.000000071 | Neuron Type 3 (mixed PEP2/NF123) |
| Pcdhac1 | 1.730 | 6.211 | 5.451 | 0.000000001 | 0.000000050 | Neuron Type 3 (mixed PEP2/NF123) |
| Cdh4 | 2.018 | 6.249 | 5.491 | 0.000000000 | 0.000000040 | Neuron Type 3 (mixed PEP2/NF123) |
| Lpl | 2.430 | 6.268 | 5.510 | 0.000000000 | 0.000000036 | Neuron Type 3 (mixed PEP2/NF123) |
| Hopx | 1.730 | 6.301 | 5.545 | 0.000000000 | 0.000000029 | Neuron Type 3 (mixed PEP2/NF123) |
| Tagln3 | 0.865 | 6.313 | 5.556 | 0.000000000 | 0.000000028 | Neuron Type 3 (mixed PEP2/NF123) |
| Atp1b1 | 0.906 | 6.362 | 5.604 | 0.000000000 | 0.000000021 | Neuron Type 3 (mixed PEP2/NF123) |
| Pak1ip1 | 0.988 | 6.368 | 5.609 | 0.000000000 | 0.000000020 | Neuron Type 3 (mixed PEP2/NF123) |
| Lynx1 | 0.988 | 6.411 | 5.654 | 0.000000000 | 0.000000016 | Neuron Type 3 (mixed PEP2/NF123) |
| Serpinb1b | 1.524 | 6.463 | 5.710 | 0.000000000 | 0.000000011 | Neuron Type 3 (mixed PEP2/NF123) |
| Spock1 | 1.030 | 6.498 | 5.743 | 0.000000000 | 0.000000009 | Neuron Type 3 (mixed PEP2/NF123) |
| Gng8 | 1.483 | 6.512 | 5.757 | 0.000000000 | 0.000000009 | Neuron Type 3 (mixed PEP2/NF123) |
| Smpd3 | 1.277 | 6.524 | 5.767 | 0.000000000 | 0.000000008 | Neuron Type 3 (mixed PEP2/NF123) |
| Bet3l | 2.347 | 6.598 | 5.843 | 0.000000000 | 0.000000005 | Neuron Type 3 (mixed PEP2/NF123) |
| Prkcb | 1.936 | 6.598 | 5.843 | 0.000000000 | 0.000000005 | Neuron Type 3 (mixed PEP2/NF123) |
| AI593442 | 1.359 | 6.612 | 5.856 | 0.000000000 | 0.000000005 | Neuron Type 3 (mixed PEP2/NF123) |
| Kcnip1 | 1.524 | 6.640 | 5.885 | 0.000000000 | 0.000000004 | Neuron Type 3 (mixed PEP2/NF123) |
| Fam19a1 | 3.583 | 6.786 | 6.040 | 0.000000000 | 0.000000002 | Neuron Type 3 (mixed PEP2/NF123) |
| Sh3gl2 | 1.277 | 6.933 | 6.198 | 0.000000000 | 0.000000001 | Neuron Type 3 (mixed PEP2/NF123) |
| Serpinb1a | 2.018 | 6.997 | 6.260 | 0.000000000 | 0.000000000 | Neuron Type 3 (mixed PEP2/NF123) |
| Tmem25 | 1.153 | 7.000 | 6.261 | 0.000000000 | 0.000000000 | Neuron Type 3 (mixed PEP2/NF123) |
| Nefm | 1.112 | 7.070 | 6.335 | 0.000000000 | 0.000000000 | Neuron Type 3 (mixed PEP2/NF123) |

TABLE 1-continued

Differentially Expressed Genes Specific to Each Type of LN-Innervating Sensory Neurons

| Gene | log2 expression fold change | Z score | Corrected Z Score | p-value | q-value | Upregulated in |
|---|---|---|---|---|---|---|
| Rph3a | 1.441 | 7.072 | 6.336 | 0.000000000 | 0.000000000 | Neuron Type 3 (mixed PEP2/NF123) |
| Thy1 | 1.853 | 7.082 | 6.345 | 0.000000000 | 0.000000000 | Neuron Type 3 (mixed PEP2/NF123) |
| Rasgrf1 | 4.036 | 7.102 | 6.364 | 0.000000000 | 0.000000000 | Neuron Type 3 (mixed PEP2/NF123) |
| Rasl10b | 3.501 | 7.117 | 6.379 | 0.000000000 | 0.000000000 | Neuron Type 3 (mixed PEP2/NF123) |
| Nptx1 | 1.647 | 7.142 | 6.401 | 0.000000000 | 0.000000000 | Neuron Type 3 (mixed PEP2/NF123) |
| Cgnl1 | 1.689 | 7.142 | 6.401 | 0.000000000 | 0.000000000 | Neuron Type 3 (mixed PEP2/NF123) |
| Cplx2 | 2.306 | 7.161 | 6.405 | 0.000000000 | 0.000000000 | Neuron Type 3 (mixed PEP2/NF123) |
| Fgf12 | 2.430 | 7.161 | 6.405 | 0.000000000 | 0.000000000 | Neuron Type 3 (mixed PEP2/NF123) |
| Ly6h | 5.519 | 7.161 | 6.405 | 0.000000000 | 0.000000000 | Neuron Type 3 (mixed PEP2/NF123) |
| S100b | 1.894 | 7.161 | 6.405 | 0.000000000 | 0.000000000 | Neuron Type 3 (mixed PEP2/NF123) |
| Cpne6 | 1.936 | 7.161 | 6.405 | 0.000000000 | 0.000000000 | Neuron Type 3 (mixed PEP2/NF123) |
| Fxyd7 | 1.565 | 7.161 | 6.405 | 0.000000000 | 0.000000000 | Neuron Type 3 (mixed PEP2/NF123) |
| Rimkla | 1.853 | 7.161 | 6.405 | 0.000000000 | 0.000000000 | Neuron Type 3 (mixed PEP2/NF123) |
| Nefl | 1.359 | 7.161 | 6.405 | 0.000000000 | 0.000000000 | Neuron Type 3 (mixed PEP2/NF123) |
| Creg2 | 4.571 | 7.161 | 6.405 | 0.000000000 | 0.000000000 | Neuron Type 3 (mixed PEP2/NF123) |
| Susd2 | 1.441 | 7.161 | 6.405 | 0.000000000 | 0.000000000 | Neuron Type 3 (mixed PEP2/NF123) |
| Htr3b | 2.718 | 7.161 | 6.405 | 0.000000000 | 0.000000000 | Neuron Type 3 (mixed PEP2/NF123) |
| Gm7271 | 5.560 | 7.161 | 6.405 | 0.000000000 | 0.000000000 | Neuron Type 3 (mixed PEP2/NF123) |
| D930028M14Rik | 2.100 | 7.161 | 6.405 | 0.000000000 | 0.000000000 | Neuron Type 3 (mixed PEP2/NF123) |
| Htr3a | 1.400 | 7.160 | 6.405 | 0.000000000 | 0.000000000 | Neuron Type 3 (mixed PEP2/NF123) |
| Abcg2 | 1.894 | 7.160 | 6.405 | 0.000000000 | 0.000000000 | Neuron Type 3 (mixed PEP2/NF123) |
| Fbxo2 | 1.441 | 7.160 | 6.405 | 0.000000000 | 0.000000000 | Neuron Type 3 (mixed PEP2/NF123) |
| S100a16 | 1.853 | 7.154 | 6.405 | 0.000000000 | 0.000000000 | Neuron Type 3 (mixed PEP2/NF123) |
| Lgi2 | 2.142 | 3.724 | 2.599 | 0.000196021 | 0.009347091 | Neuron Type 4 (mixed PEP2/NF12345) |
| Gda | 2.389 | 3.726 | 2.600 | 0.000194848 | 0.009328930 | Neuron Type 4 (mixed PEP2/NF12345) |
| Fam196b | 1.812 | 3.756 | 2.637 | 0.000172421 | 0.008357090 | Neuron Type 4 (mixed PEP2/NF12345) |
| Acsl6 | 0.906 | 3.766 | 2.644 | 0.000166157 | 0.008188269 | Neuron Type 4 (mixed PEP2/NF12345) |
| Necab3 | 1.236 | 3.782 | 2.663 | 0.000155870 | 0.007746133 | Neuron Type 4 (mixed PEP2/NF12345) |
| Adamtsl5 | 2.224 | 3.792 | 2.673 | 0.000149715 | 0.007511021 | Neuron Type 4 (mixed PEP2/NF12345) |
| Lmo1 | 1.030 | 3.795 | 2.675 | 0.000147816 | 0.007471993 | Neuron Type 4 (mixed PEP2/NF12345) |
| Cplx11 | 0.741 | 3.802 | 2.681 | 0.000143249 | 0.007335620 | Neuron Type 4 (mixed PEP2/NF12345) |
| Clu1 | 0.865 | 3.821 | 2.703 | 0.000132911 | 0.006865926 | Neuron Type 4 (mixed PEP2/NF12345) |
| Fgf9 | 1.194 | 3.824 | 2.707 | 0.000131041 | 0.006799145 | Neuron Type 4 (mixed PEP2/NF12345) |
| Esrrg | 1.977 | 3.827 | 2.709 | 0.000129487 | 0.006748229 | Neuron Type 4 (mixed PEP2/NF12345) |
| Hs3st2 | 1.565 | 3.861 | 2.751 | 0.000112916 | 0.005937155 | Neuron Type 4 (mixed PEP2/NF12345) |
| Fam65c | 1.606 | 3.864 | 2.754 | 0.000111534 | 0.005890791 | Neuron Type 4 (mixed PEP2/NF12345) |
| Lgi3 | 0.824 | 3.877 | 2.770 | 0.000105721 | 0.005608952 | Neuron Type 4 (mixed PEP2/NF12345) |
| Fabp3 | 1.030 | 3.973 | 2.878 | 0.000071099 | 0.004008388 | Neuron Type 4 (mixed PEP2/NF12345) |
| B3galt1 | 1.359 | 3.972 | 2.878 | 0.000071129 | 0.004008388 | Neuron Type 4 (mixed PEP2/NF12345) |
| Gabra1 | 3.006 | 3.981 | 2.883 | 0.000068626 | 0.003942811 | Neuron Type 4 (mixed PEP2/NF12345) |
| Epha6 | 1.647 | 3.986 | 2.888 | 0.000067114 | 0.003875237 | Neuron Type 4 (mixed PEP2/NF12345) |
| Kcng4 | 1.730 | 3.986 | 2.888 | 0.000067121 | 0.003875237 | Neuron Type 4 (mixed PEP2/NF12345) |
| Ptk7 | 1.565 | 4.115 | 3.034 | 0.000038683 | 0.002410648 | Neuron Type 4 (mixed PEP2/NF12345) |
| Arhgef3 | 1.565 | 4.121 | 3.040 | 0.000037674 | 0.002369045 | Neuron Type 4 (mixed PEP2/NF12345) |
| Htr7 | 1.565 | 4.120 | 3.040 | 0.000037815 | 0.002369045 | Neuron Type 4 (mixed PEP2/NF12345) |
| Rnf128 | 1.524 | 4.126 | 3.044 | 0.000036916 | 0.002337609 | Neuron Type 4 (mixed PEP2/NF12345) |
| Ppm1j | 1.483 | 4.154 | 3.076 | 0.000032628 | 0.002099953 | Neuron Type 4 (mixed PEP2/NF12345) |
| Prokrl1 | 2.595 | 4.164 | 3.087 | 0.000031215 | 0.002020058 | Neuron Type 4 (mixed PEP2/NF12345) |
| Ntng1 | 4.777 | 4.172 | 3.095 | 0.000030195 | 0.001964873 | Neuron Type 4 (mixed PEP2/NF12345) |
| Sema3d | 1.565 | 4.215 | 3.143 | 0.000024988 | 0.001672220 | Neuron Type 4 (mixed PEP2/NF12345) |
| Nefm1 | 0.906 | 4.222 | 3.149 | 0.000024176 | 0.001636486 | Neuron Type 4 (mixed PEP2/NF12345) |
| Neto1 | 1.647 | 4.290 | 3.228 | 0.000017893 | 0.001247024 | Neuron Type 4 (mixed PEP2/NF12345) |
| A330050F15Rik | 2.471 | 4.355 | 3.306 | 0.000013299 | 0.000944893 | Neuron Type 4 (mixed PEP2/NF12345) |
| Chchd10 | 1.277 | 4.355 | 3.306 | 0.000013317 | 0.000944893 | Neuron Type 4 (mixed PEP2/NF12345) |
| Ehd3 | 1.194 | 4.399 | 3.355 | 0.000010898 | 0.000792293 | Neuron Type 4 (mixed PEP2/NF12345) |
| Cish | 1.565 | 4.416 | 3.371 | 0.000010062 | 0.000750063 | Neuron Type 4 (mixed PEP2/NF12345) |
| Pcdh7 | 1.730 | 4.418 | 3.371 | 0.000009971 | 0.000748030 | Neuron Type 4 (mixed PEP2/NF12345) |
| Nlgn1 | 1.771 | 4.425 | 3.377 | 0.000009648 | 0.000733134 | Neuron Type 4 (mixed PEP2/NF12345) |
| Slc4a2 | 1.236 | 4.449 | 3.406 | 0.000008629 | 0.000659927 | Neuron Type 4 (mixed PEP2/NF12345) |
| Endod1 | 0.988 | 4.507 | 3.467 | 0.000006565 | 0.000526008 | Neuron Type 4 (mixed PEP2/NF12345) |
| Car2 | 1.853 | 4.536 | 3.498 | 0.000005723 | 0.000468107 | Neuron Type 4 (mixed PEP2/NF12345) |
| Ano4 | 1.565 | 4.556 | 3.512 | 0.000005214 | 0.000444870 | Neuron Type 4 (mixed PEP2/NF12345) |
| Kcnk1 | 1.647 | 4.556 | 3.512 | 0.000005225 | 0.000444870 | Neuron Type 4 (mixed PEP2/NF12345) |
| Mest | 1.112 | 4.581 | 3.527 | 0.000004627 | 0.000420595 | Neuron Type 4 (mixed PEP2/NF12345) |
| Fam57b | 1.441 | 4.692 | 3.655 | 0.000002707 | 0.000257121 | Neuron Type 4 (mixed PEP2/NF12345) |
| Syt3 | 1.318 | 4.750 | 3.721 | 0.000002038 | 0.000198329 | Neuron Type 4 (mixed PEP2/NF12345) |
| Cacng5 | 3.459 | 4.773 | 3.743 | 0.000001819 | 0.000181569 | Neuron Type 4 (mixed PEP2/NF12345) |
| Lrrn11 | 1.194 | 4.927 | 3.909 | 0.000000833 | 0.000092602 | Neuron Type 4 (mixed PEP2/NF12345) |
| Fam19a2 | 2.265 | 4.993 | 3.985 | 0.000000595 | 0.000067339 | Neuron Type 4 (mixed PEP2/NF12345) |
| Vamp11 | 1.277 | 5.029 | 4.016 | 0.000000493 | 0.000059256 | Neuron Type 4 (mixed PEP2/NF12345) |
| Kcna1 | 1.277 | 5.071 | 4.060 | 0.000000396 | 0.000049139 | Neuron Type 4 (mixed PEP2/NF12345) |
| Lingo4 | 2.553 | 5.153 | 4.146 | 0.000000256 | 0.000033892 | Neuron Type 4 (mixed PEP2/NF12345) |
| Nell2 | 2.553 | 5.272 | 4.269 | 0.000000135 | 0.000019592 | Neuron Type 4 (mixed PEP2/NF12345) |
| Ankrd34c | 2.924 | 5.293 | 4.290 | 0.000000120 | 0.000017855 | Neuron Type 4 (mixed PEP2/NF12345) |

TABLE 1-continued

Differentially Expressed Genes Specific to Each Type of LN-Innervating Sensory Neurons

| Gene | log2 expression fold change | Z score | Corrected Z Score | p-value | q-value | Upregulated in |
|---|---|---|---|---|---|---|
| Stac2 | 3.253 | 5.308 | 4.305 | 0.000000111 | 0.000016705 | Neuron Type 4 (mixed PEP2/NF12345) |
| Cygb | 1.936 | 5.327 | 4.321 | 0.000000100 | 0.000015499 | Neuron Type 4 (mixed PEP2/NF12345) |
| Slitrk4 | 2.471 | 5.400 | 4.393 | 0.000000066 | 0.000011189 | Neuron Type 4 (mixed PEP2/NF12345) |
| Hhatl | 1.771 | 5.429 | 4.422 | 0.000000057 | 0.000009795 | Neuron Type 4 (mixed PEP2/NF12345) |
| Arhgef4 | 1.359 | 5.436 | 4.426 | 0.000000055 | 0.000009596 | Neuron Type 4 (mixed PEP2/NF12345) |
| Meis2 | 2.471 | 5.531 | 4.531 | 0.000000032 | 0.000005872 | Neuron Type 4 (mixed PEP2/NF12345) |
| Elmo1 | 1.647 | 5.540 | 4.539 | 0.000000030 | 0.000005657 | Neuron Type 4 (mixed PEP2/NF12345) |
| Tesc | 1.894 | 5.549 | 4.542 | 0.000000029 | 0.000005579 | Neuron Type 4 (mixed PEP2/NF12345) |
| P2rx61 | 2.018 | 5.591 | 4.572 | 0.000000023 | 0.000004837 | Neuron Type 4 (mixed PEP2/NF12345) |
| Epn3 | 2.265 | 5.623 | 4.590 | 0.000000019 | 0.000004429 | Neuron Type 4 (mixed PEP2/NF12345) |
| Bcat1 | 2.677 | 5.798 | 4.766 | 0.000000007 | 0.000001883 | Neuron Type 4 (mixed PEP2/NF12345) |
| Atp2b2 | 2.183 | 5.894 | 4.861 | 0.000000004 | 0.000001168 | Neuron Type 4 (mixed PEP2/NF12345) |
| Mab21l2 | 3.212 | 5.944 | 4.910 | 0.000000003 | 0.000000910 | Neuron Type 4 (mixed PEP2/NF12345) |
| Pcp4 | 2.224 | 6.474 | 5.456 | 0.000000000 | 0.000000049 | Neuron Type 4 (mixed PEP2/NF12345) |
| Rcan21 | 1.689 | 6.633 | 5.625 | 0.000000000 | 0.000000018 | Neuron Type 4 (mixed PEP2/NF12345) |
| Gm4980 | 3.459 | 6.649 | 5.636 | 0.000000000 | 0.000000017 | Neuron Type 4 (mixed PEP2/NF12345) |
| Tmem163 | 3.295 | 6.690 | 5.648 | 0.000000000 | 0.000000016 | Neuron Type 4 (mixed PEP2/NF12345) |
| Hapln1 | 4.036 | 6.898 | 5.861 | 0.000000000 | 0.000000005 | Neuron Type 4 (mixed PEP2/NF12345) |
| Ptgfr | 3.459 | 7.050 | 5.989 | 0.000000000 | 0.000000002 | Neuron Type 4 (mixed PEP2/NF12345) |
| Mgst3 | 2.224 | 7.113 | 6.032 | 0.000000000 | 0.000000002 | Neuron Type 4 (mixed PEP2/NF12345) |
| Hapln4 | 4.860 | 7.161 | 6.035 | 0.000000000 | 0.000000002 | Neuron Type 4 (mixed PEP2/NF12345) |
| Baiap2l1 | 5.395 | 7.161 | 6.035 | 0.000000000 | 0.000000002 | Neuron Type 4 (mixed PEP2/NF12345) |
| Htr1d | 4.036 | 7.161 | 6.035 | 0.000000000 | 0.000000002 | Neuron Type 4 (mixed PEP2/NF12345) |
| Tmem108 | 4.242 | 7.160 | 6.035 | 0.000000000 | 0.000000002 | Neuron Type 4 (mixed PEP2/NF12345) |

Example 2. In Silico Analysis Reveals Lymph Note Stromal Cells Exhibiting Highest Potential for Interaction with LN Sensory Fibers scRNA-Seq of Lymph Node Cells Nominates Interacting Partners of Lymph Node-Innervating Sensory Neurons The present disclosure's molecular characterization of LN-innervating sensory neurons revealed expression of many genes and cellular programs poised to support interaction with other LN-resident cells. To systematically map cellular interactions between the sensory nervous system and the various cell types in the LN, it was imperative to have a comprehensive map of LN cell subsets at the molecular level. Applicants therefore generated a single-cell transcriptomic atlas of steady-state murine inguinal LNs (n=7) using the Seq-Well platform.

Figures 6A, 6B:
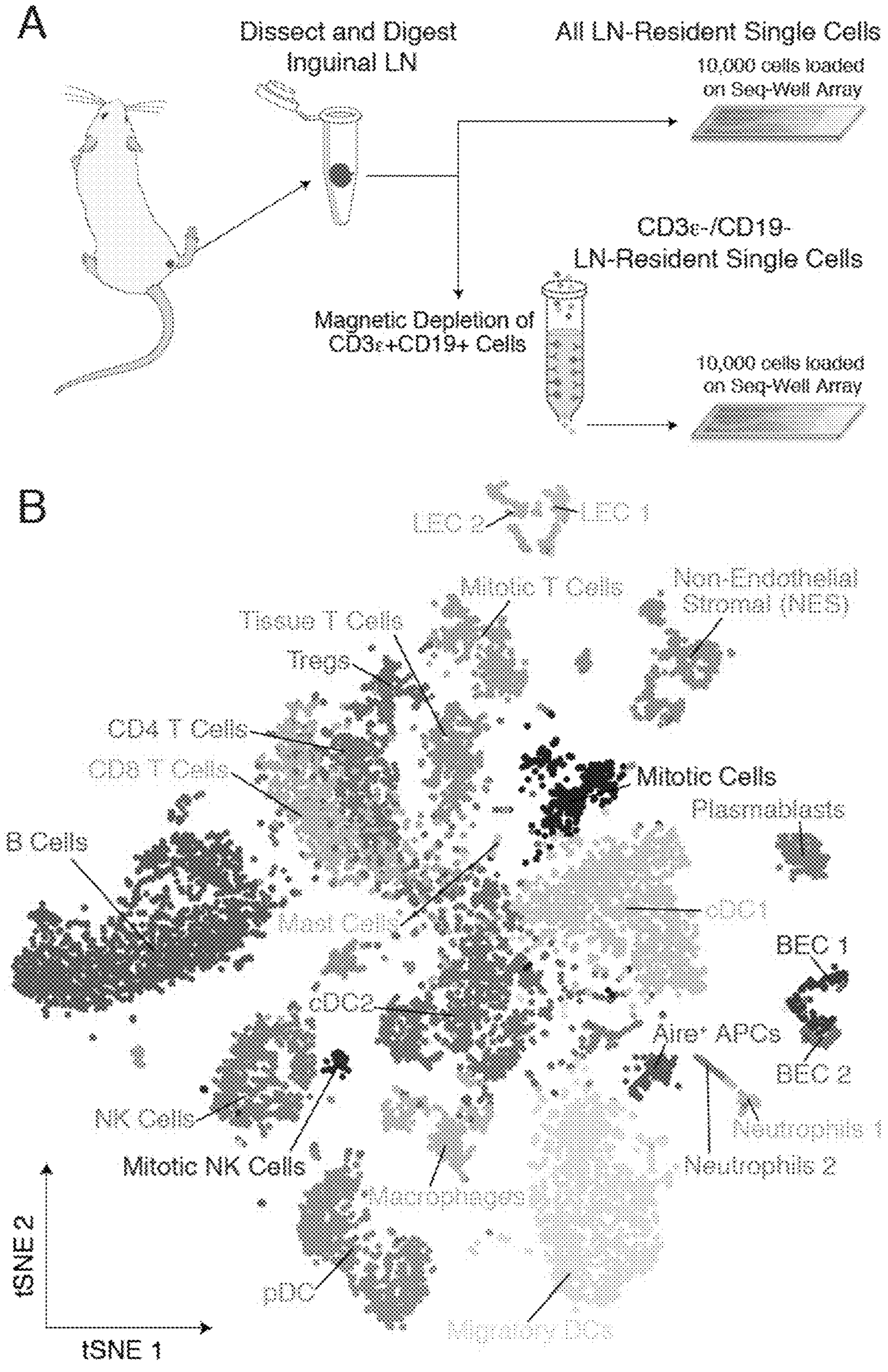
FIG. 6A-6F Single-cell transcriptomic profiling of iLN cells nominates likely interacting partners of iLN-innervating sensory neurons.
Figure 6C:
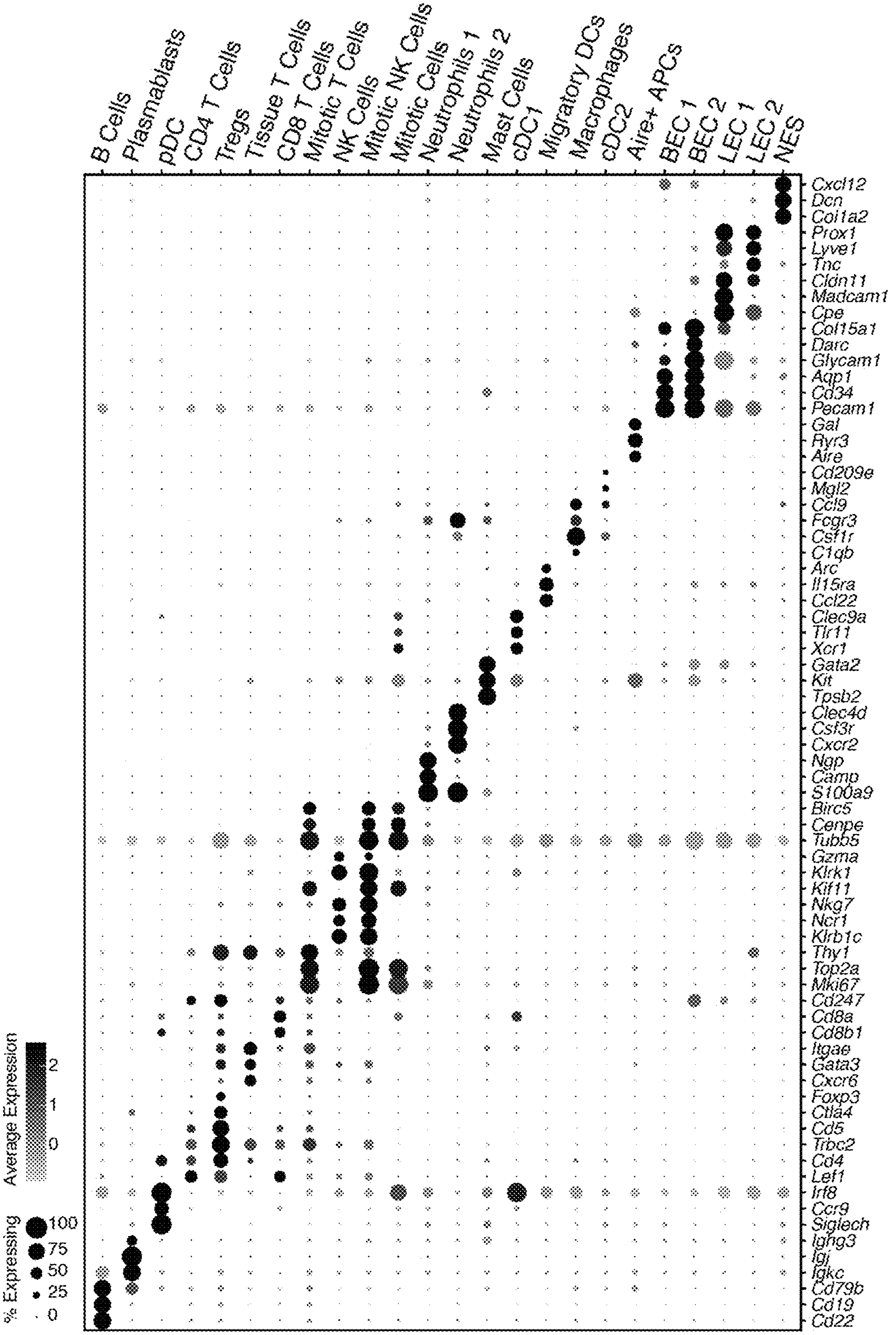
Figures 12A, 12B, 12C, 12D, 12E, 12F, 12G:
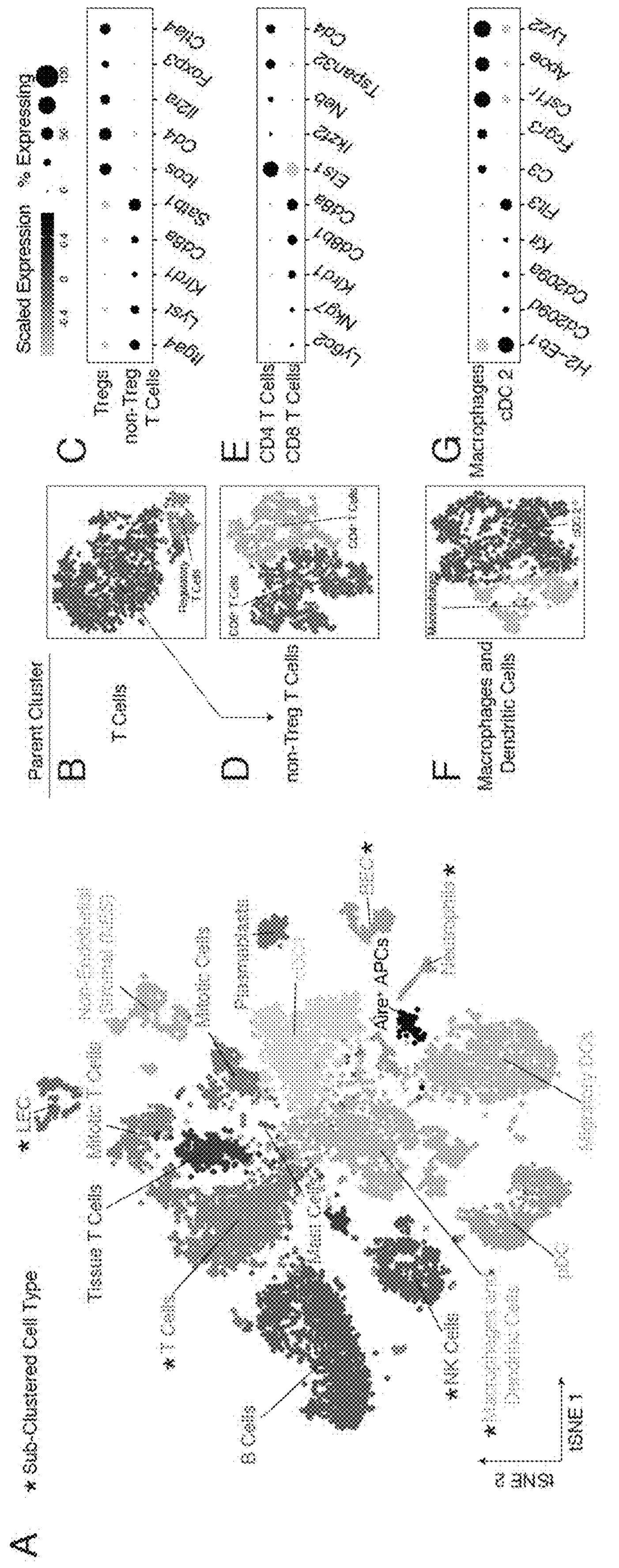
FIG. 12A-12P (Related to FIG. 6) LN-innervating sensory neurons express unique defining markers and functional pathways.
FIG. 12B-12O. Sub-cluster tSNE projections and top differentially expressed genes.
Figures 12H, 12I, 12J, 12K, 12L, 12M, 12N, 12O:
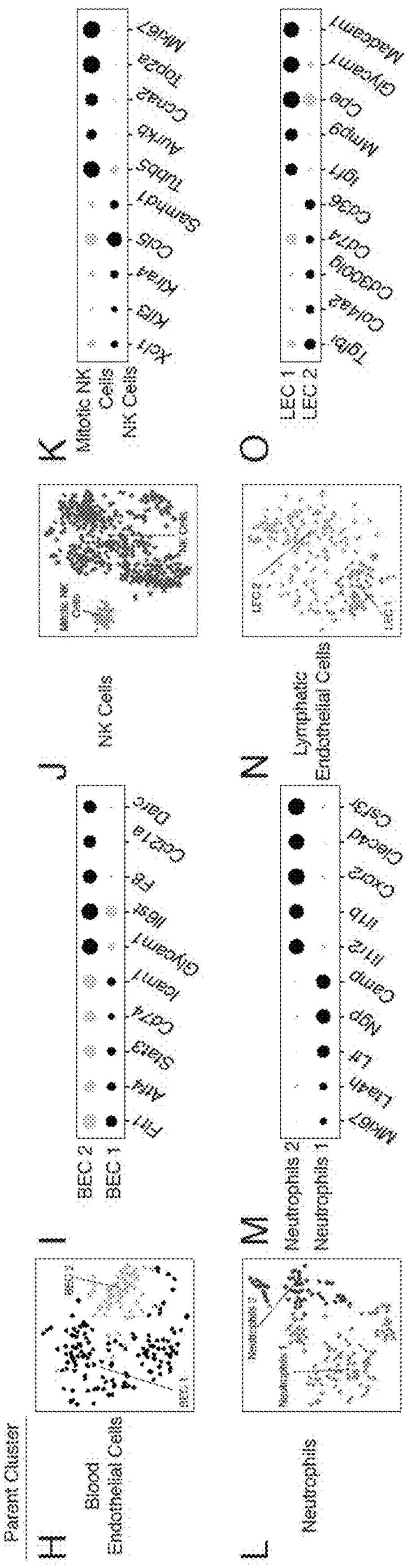
Figure 12P:
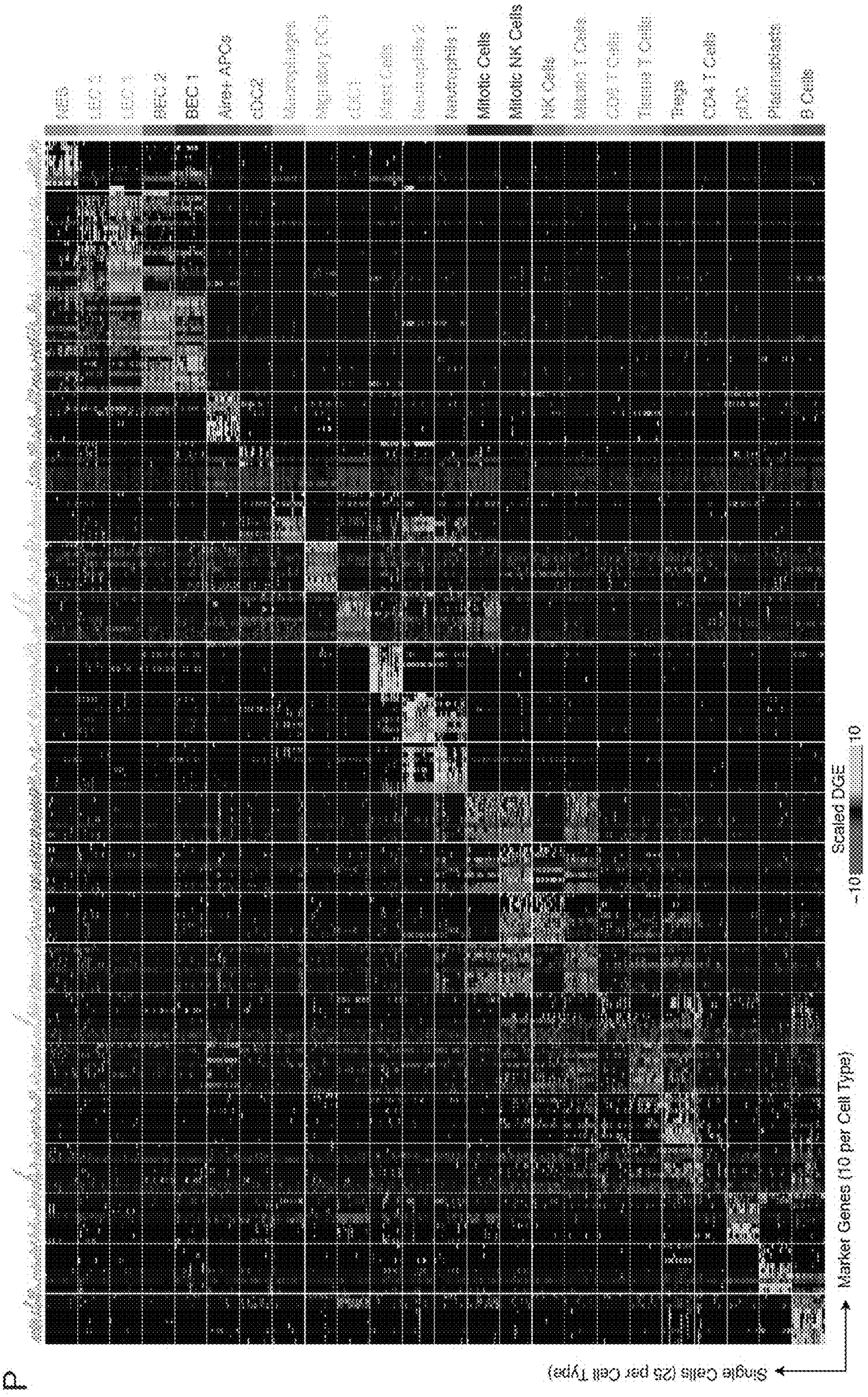

To minimize biases introduced during tissue dissociation, a gentle and permissive dissociation protocol optimized for reliable isolation of both stromal and hemopoietic LN cells was used to efficiently extract cells from both the non-immune and the immune compartments. To increase coverage of the many rare LN cell types—i.e., the non-T, non-B cells—which populate the preferentially-innervated LN periphery (FIG. 2C), Applicants profiled paired LN samples from before and after column-based negative selection of T and B cells (FIG. 6A). Following quality filtering and preprocessing, Applicants recovered libraries from 9,622 single cells and 25,929 unique genes. For unbiased cell type identification, Applicants reduced this high-dimensional data into a lower-dimensional manifold using principal component analysis (PCA) over variable genes, clustered cells using a mutual k nearest-neighbor graph, and visualized these clusters on t-distributed stochastic neighbor embedding (t-SNE) (FIGS. 6B, 12A-12O). Applicants discovered 24 distinct cell types representing all major lymphoid, myeloid and stromal populations. To name cell clusters, Applicants identified gene signatures that defined each cell cluster using a likelihood ratio test, and annotated based on well-defined markers of cell identity (FIGS. 6C, 12P, Table 2). Many cell type clusters were identified by expression of canonical markers (e.g. co-expression of Cd19, Cd22, Cd79a, and Cd79b in B cells).

Following initial clustering of single cells, multiple cell clusters could be further divided into subclusters (FIG. 12A). In these instances, Applicants re-analyzed cell clusters using methods for unbiased cell type identification as described above, and partitioned them into appropriate cell subtypes. For example, Applicants discovered two populations of blood endothelial cells (BECs), which likely correspond to non-venular (BEC 1) and venular endothelial cells (BEC 2, Darc+) (FIG. 12H, 12I) (Thiriot et al., 2017). Additionally, Applicants identified two distinct populations of lymphatic endothelial cells (LECs, Lyve1+), with LEC 1 defined by expression of Madcam1, likely representing subcapsular LECs (Cohen et al., 2014), and LEC 2 defined by unique expression of multiple extracellular matrix or structural proteins, including Fbln2, Aqp1, Fbln5, Tnc and Reln (FIG. 12N, 12O).

Applicants also identified a subtype of dendritic-cell-like cells ($Aire^{+}$ APC) defined by high expression of Aire and multiple tissue-restricted antigens including Ryr3, Myo5b, Scn3a, and Nrgn, which likely correspond to the Aire-expressing ILC3-like cells that have been recently described (Yamano et al., 2019). Similarly, Applicants divided neutrophils into two subtypes: Neutrophils 1 and Neutrophils 2 (FIGS. 12L and 12M). Unlike Neutrophils 1, which expressed high levels of components of neutrophil granules and effector molecules including Elane, Prtn3, Ctsg, Ngp, Ltf, Camp, and Mpo, Neutrophils 2 were defined by elevated expression of pro-inflammatory genes such as Ccl4, Sell, Cxcr2, Cxcl2, Ccl6, Il1b, and Csf3r, and strikingly little to no expression of effector molecules. Other cell types were similarly sub-clustered and are discussed within the computational methods (FIG. 12A-12O).

Figures 6D, 6E, 6F:
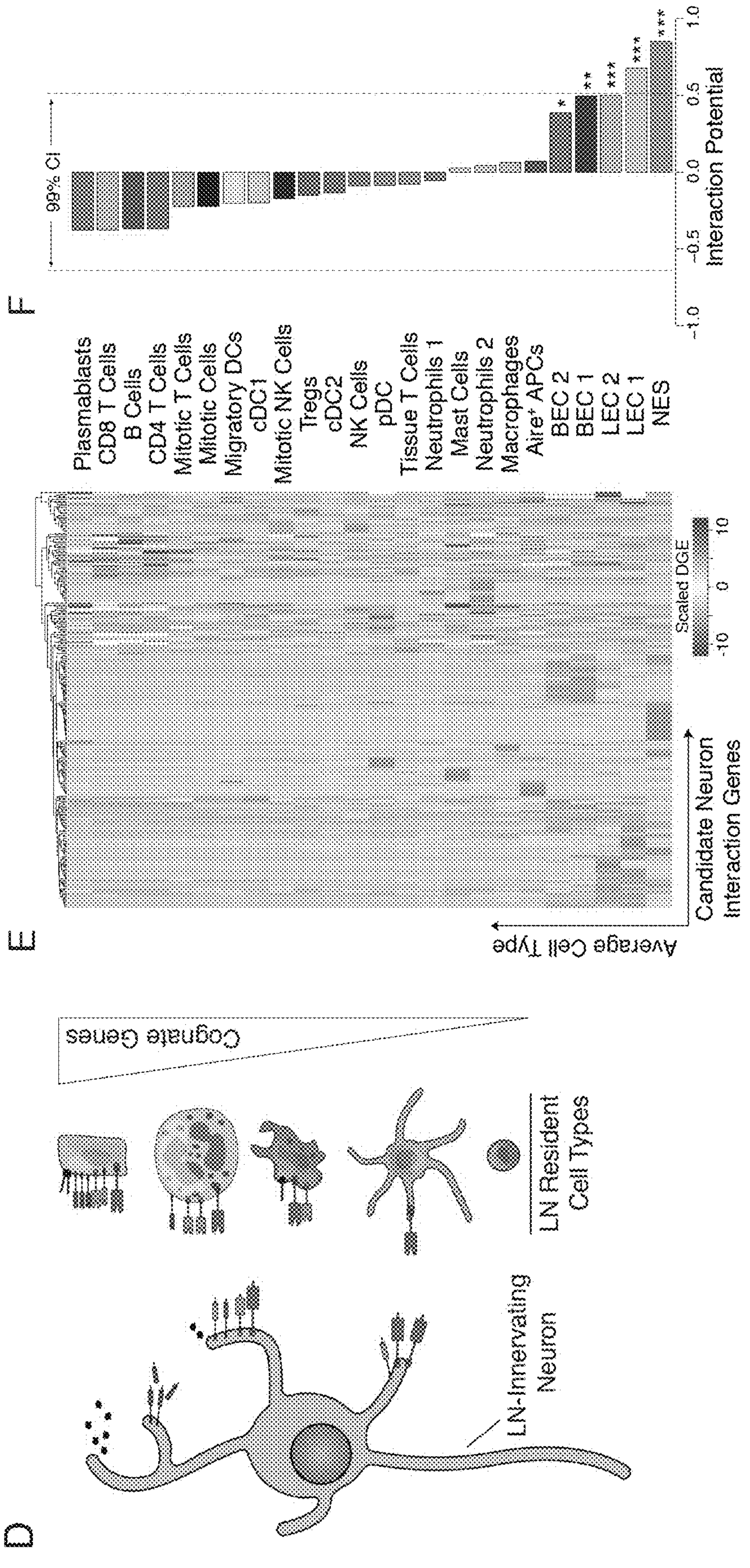
Figure 13A:
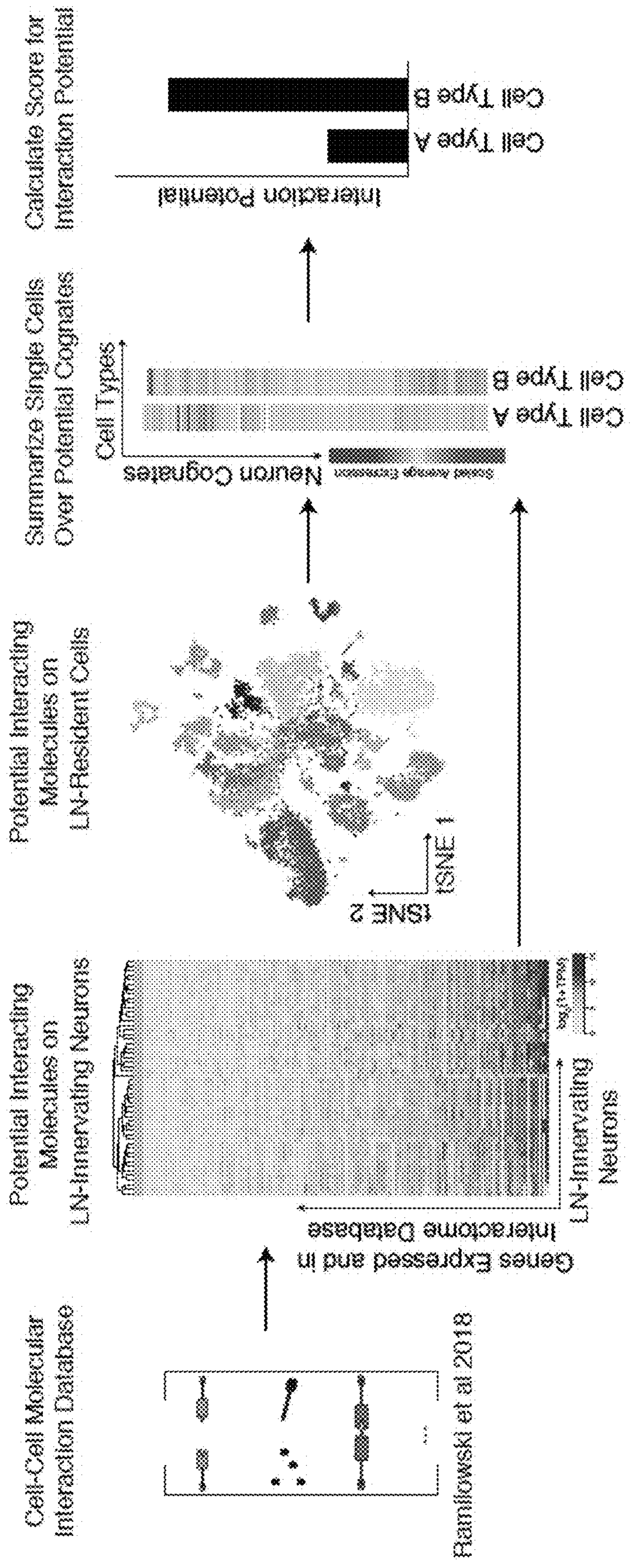
FIG. 13A-13H (Related to FIG. 6) Single-cell transcriptomic profiling of iLN cells nominates likely interacting partners of iLN-innervating sensory neurons.

Next, Applicants sought to determine the relative likelihood of each identified LN cell type interacting with LN-innervating sensory neurons by analyzing expression of ligand-receptor pairs across their two single cell datasets. Applicants reasoned that pairs of interacting cells may rely on inter-cellular ligand-receptor pairs for signaling crosstalk and/or physical association through interaction of membrane-anchored proteins on both cells or via secreted ligands binding to receptors. Therefore, LN cell types with higher expression of cognate receptors or ligands of neuron-expressed molecules should be poised to interact with local sensory innervation. Applicants filtered first for interaction pairs where at least one member was expressed by LN-innervating sensory neurons. Using the respective cognates of each of these molecules, Applicants queried relative expression among all LN cell types (FIGS. 6D, 13A). In this approach, co-expression of many ligand-receptor cognates between a LN-innervating neuron and a LN cell type increased the "Interaction Potential" for that LN cell type (FIGS. 6E, 6F, 13A).

Figure 13B:
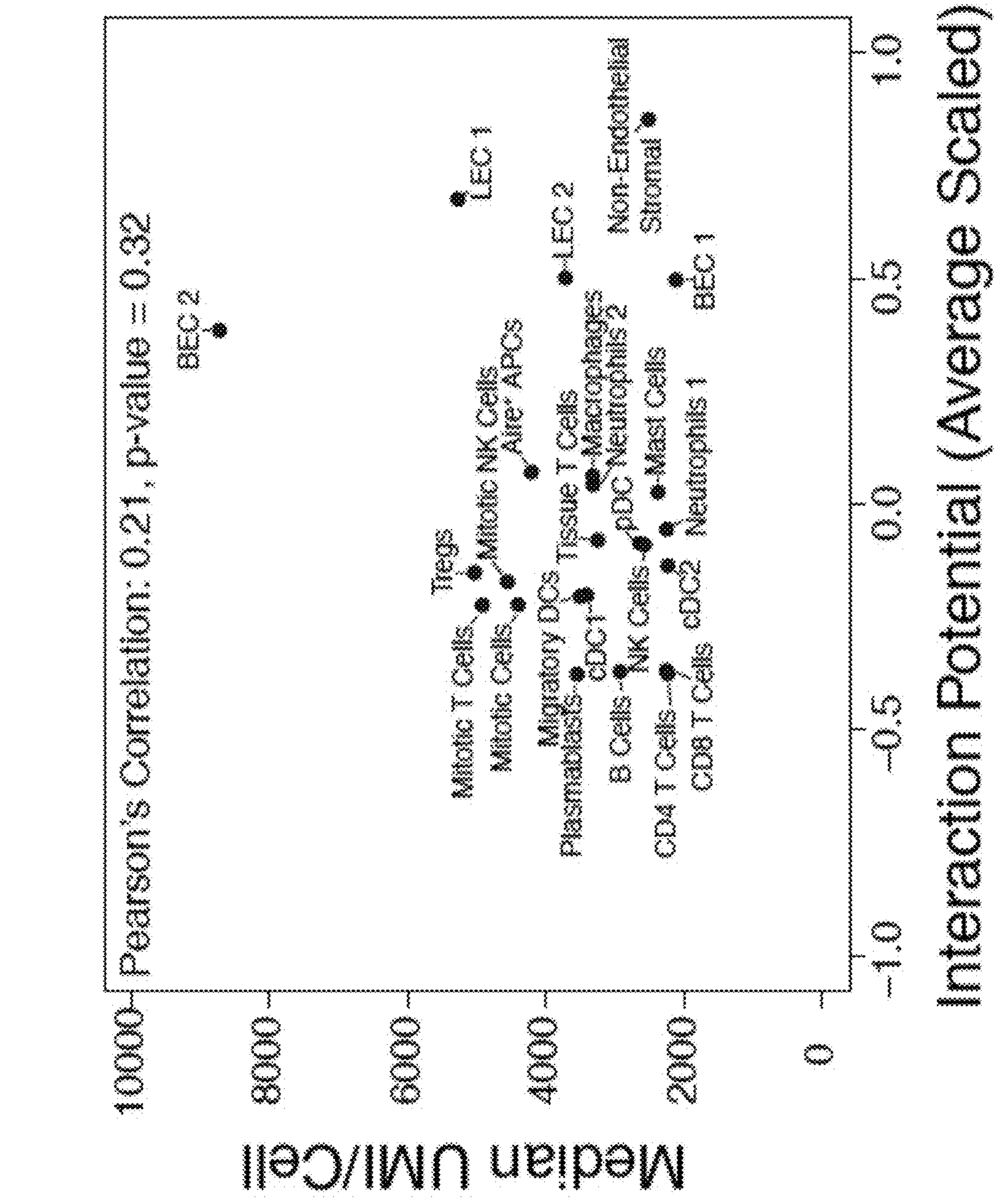
Figure 13C:
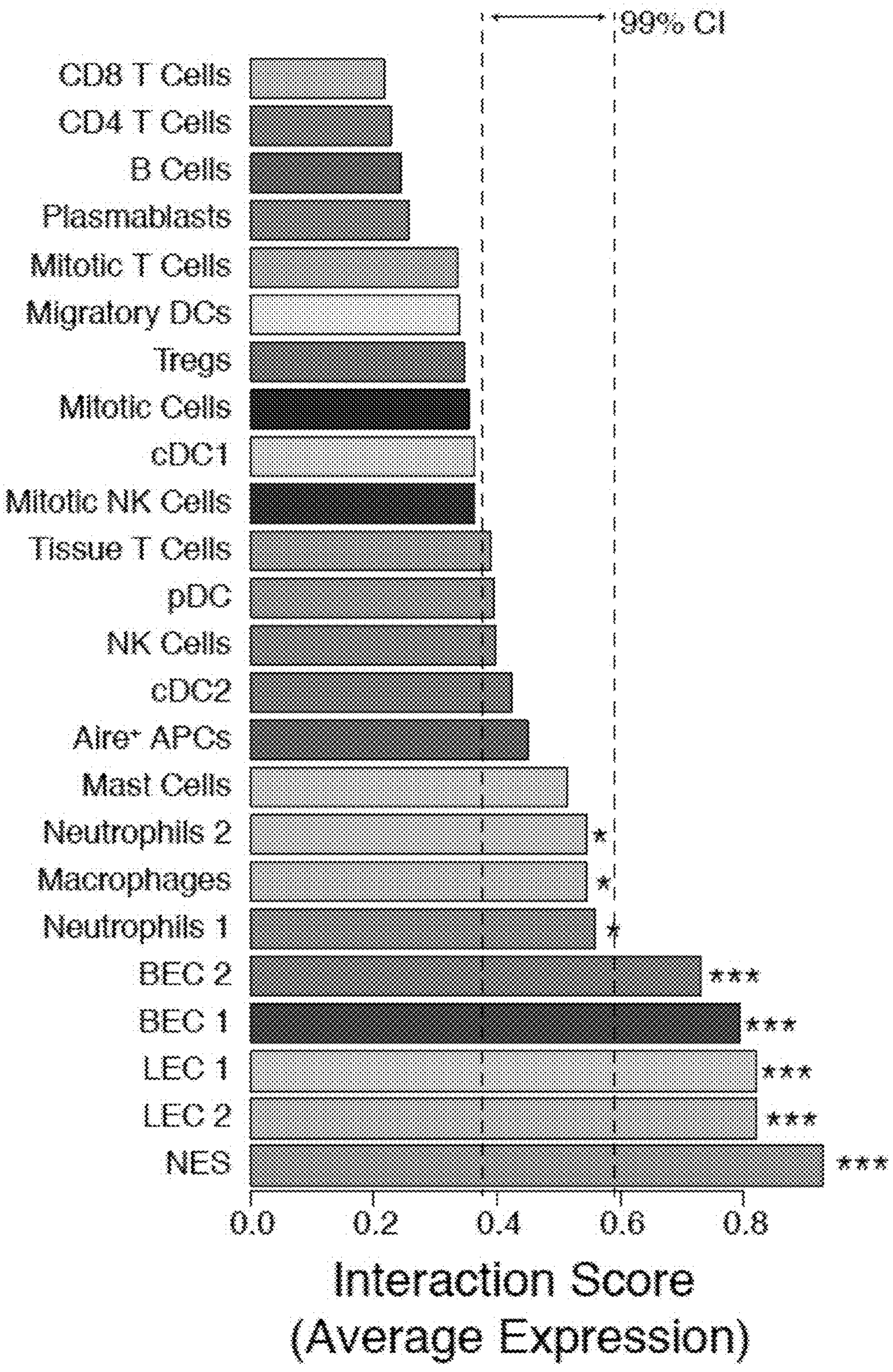
Figure 13D:
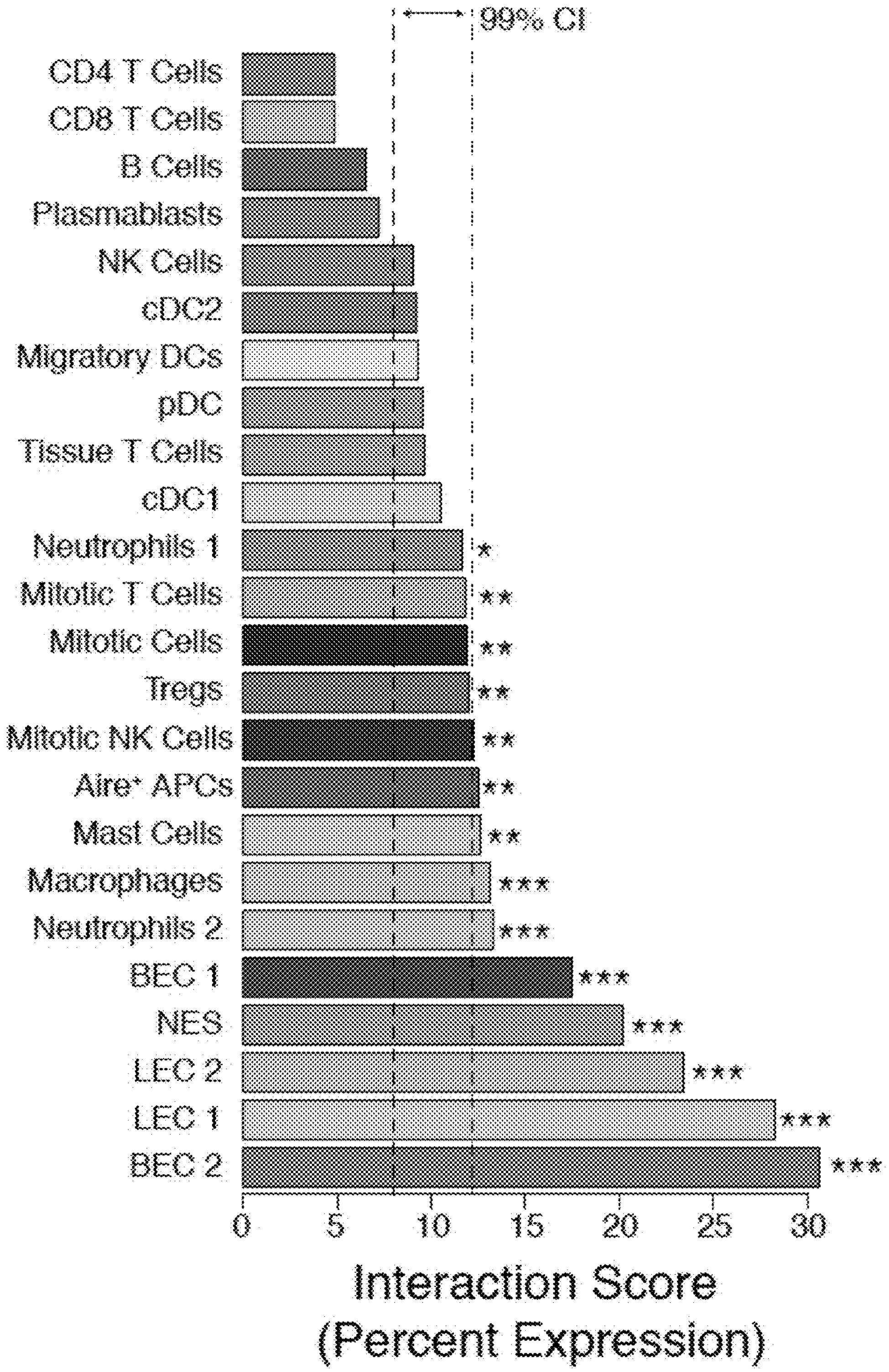
Figure 13E:
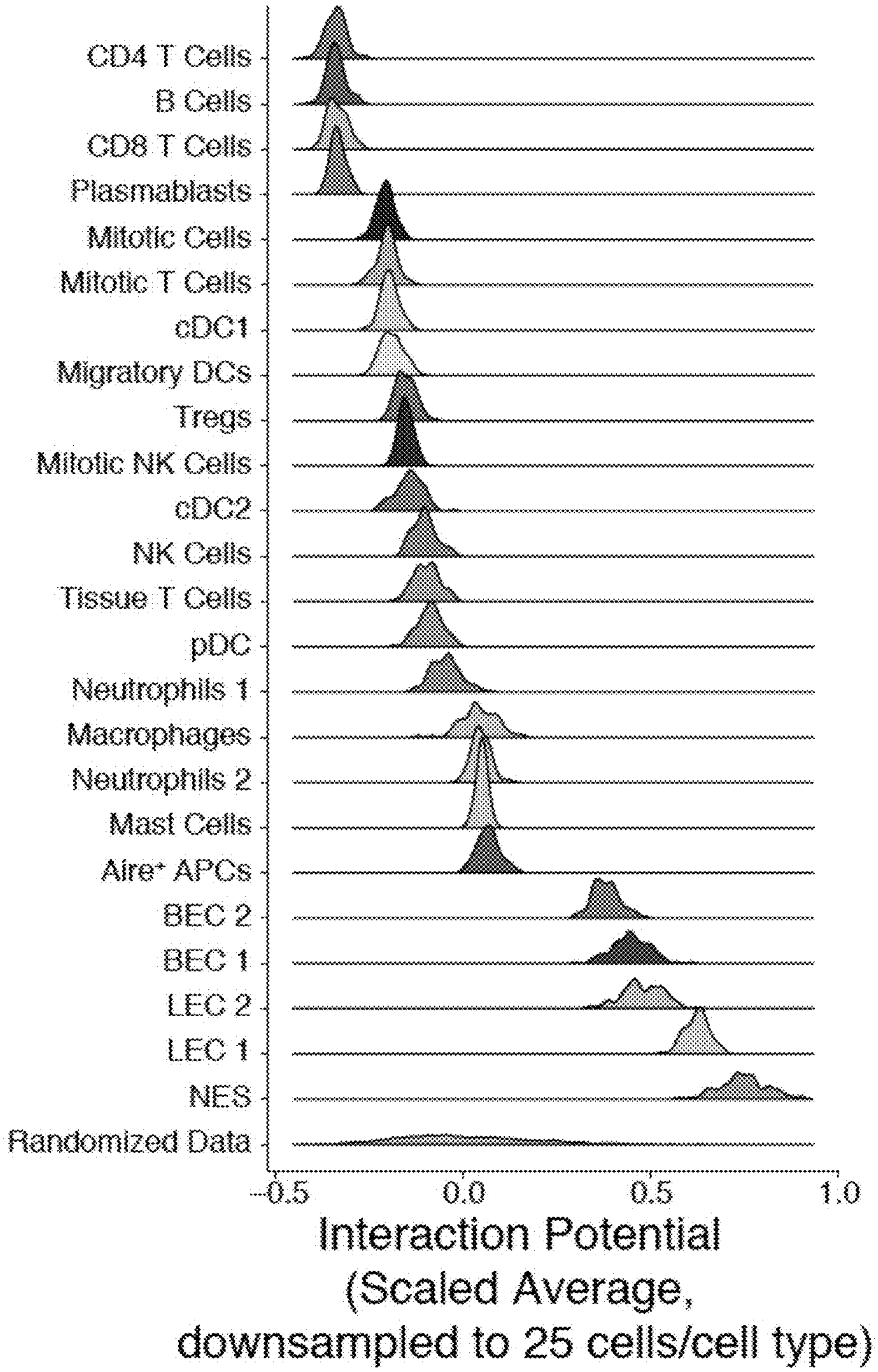
Figure 13F:
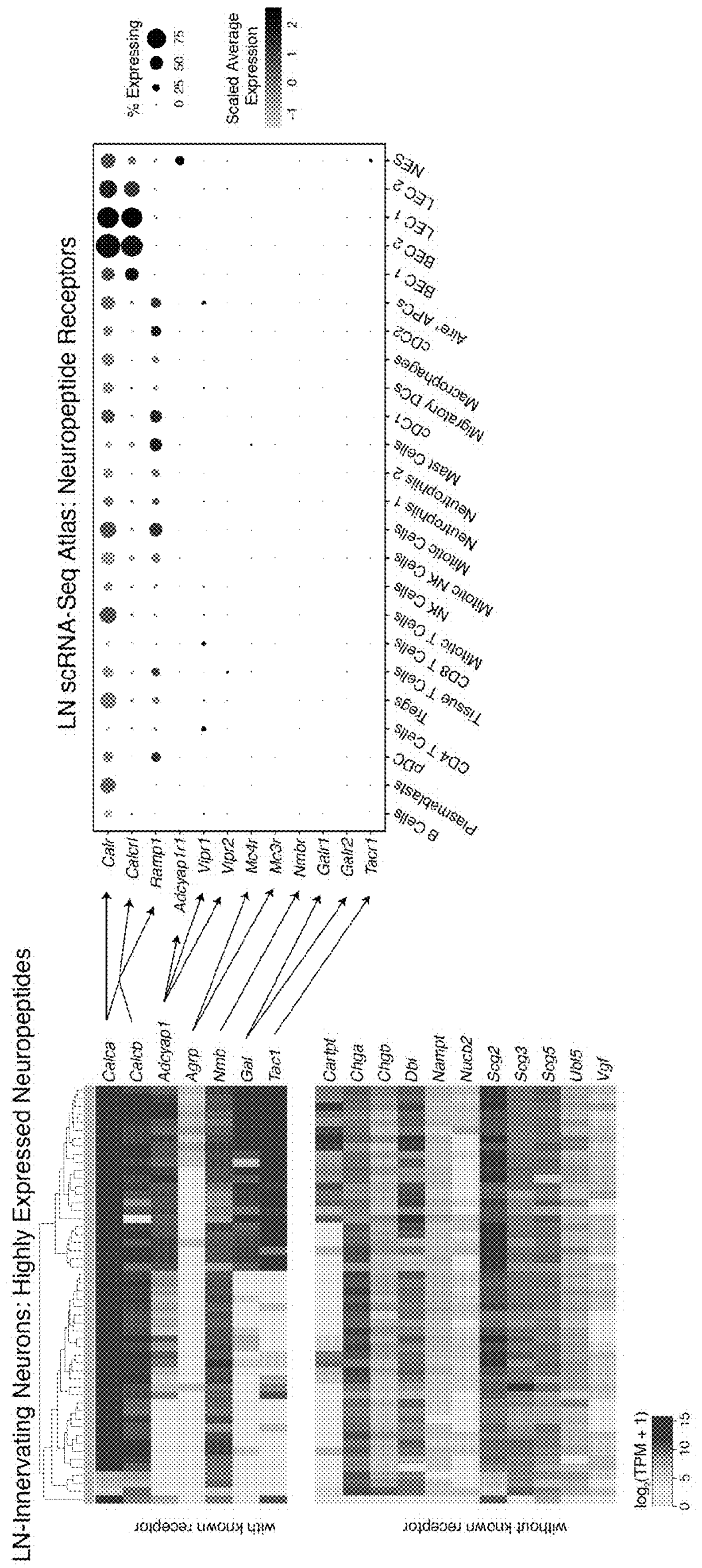

Using this computational strategy, Applicants determined that the non-immune compartment (Non-Endothelial Stroma (NES), BEC 1, BEC 2, LEC 1, LEC 2) exhibited the highest Interaction Potential compared to other LN cell types and randomized data (FIG. 6F). This ranking was stable across multiple different calculation methods, ligand-receptor databases, and summary statistics, and was not influenced by technical confounders such as cell quality and cell type population size (FIG. 13B-13E). Given a strong enrichment for peptidergic signatures among LN-innervating neurons, including high expression of CGRP (Calca, Calcb), substance P (Tac1), galanin (Gal), and pituitary adenylate cyclase-activating polypeptide (PACAP) (Adcyap1), Applicants assessed the expression of the corresponding neuropeptide receptors among LN cell types (FIG. 13F). Ramp1, which together with Calcrl, a ubiquitously expressed gene among LN cell types, forms the CGRP receptor, was more highly expressed in innate immune cell types such as mast cells and dendritic cells (DCs), showing that LN-innervating sensory neurons may signal to select myeloid cell types via CGRP. The receptors for other neuropeptides, Tac1, Adcyap1, and Gal (Tacr1, Adcyap1r1, and Galr2 & Galr1, respectively) were uniquely expressed by non-endothelial stroma, identifying substance P, PACAP, and galanin as potential signaling mediators between LN-innervating neurons and non-endothelial stroma. By contrast, classic neuropeptides were not a primary mode of communication between LN-innervating sensory neurons and LN endothelial cells.

Figures 13G, 13H:
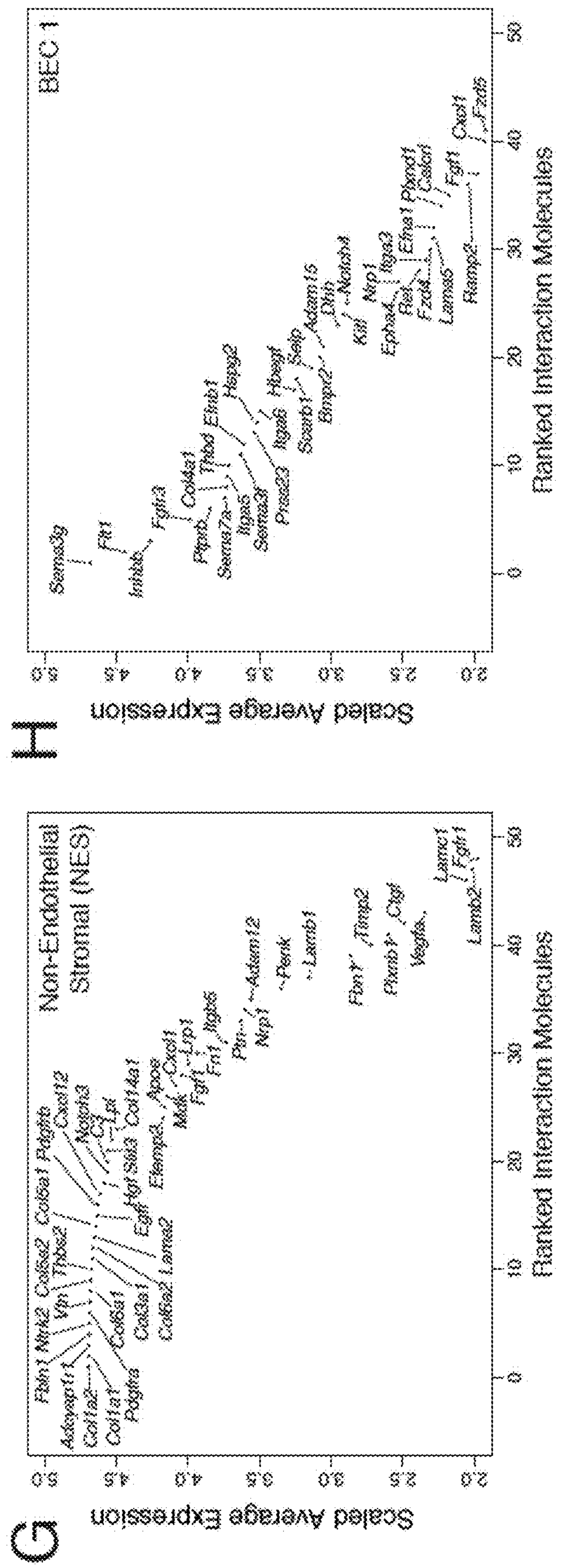

To decipher the nature of the neuron-endothelial and neuron-stromal axis of communication, Applicants analyzed the cognate receptors and ligands responsible for high interaction potentials among the stromal compartments (FIG. 13G, 13H). For example, predicted interaction with non-endothelial stroma was strongly driven by extracellular matrix components (Col3a1, Col5a2, Col5a1, Col6a1, Col6a2, Col6a3, Col1a2, Col1a2, Lama2, Thbs2, Fn1), growth factors/chemokines with diverse roles in neuronal development and function (Vegfa, Ptn, Mdk, Cxcl12), as well as receptors for growth factors known to regulate fibroblast proliferation and differentiation (Pdgfra, Pdgfrb, Ntrk2). Non-venular blood endothelial cells (BEC 1) exhibited high interaction potential based on expression of a distinct set of extracellular matrix and cell adhesion molecules (Lama5, Itga5, Hspg2), receptors of central signaling pathways for vascular development (Flt1, Notch4, Fzd4), classic axon guidance molecules with known roles in leukocyte-endothelial adhesion, angiogenesis, and arterial-venous differentiation (Sema3f, Sema7a, Nrp1, Plxnd1, Efnb1, Epha4), and key trafficking molecules for leukocyte recruitment (Selp, Cxcl1). Thus, the present disclosure's single-cell profiling of murine iLN identified stromal cells as the most likely interacting partners of LN-innervating sensory neurons, and revealed potential communication modalities that mediate cellular interactions.

TABLE 2

Significant Cluster-Defining Genes for Cell Types Identified from the Steady State LN Cell Atlas

| Gene | Cell type | p-value | q-value | Average log fold change | % Expressing in Cluster | % Expressing Rest |
|---|---|---|---|---|---|---|
| Ryr3 | Aire APCs (MacDC4) | 6.92E−109 | 1.79E−104 | 2.411 | 0.693 | 0.013 |
| Gal | Aire APCs (MacDC4) | 2.22E−97 | 5.75E−93 | 1.881 | 0.584 | 0.005 |
| Cdcp1 | Aire APCs (MacDC4) | 4.41E−94 | 1.14E−89 | 1.774 | 0.644 | 0.013 |
| Sh2d4a | Aire APCs (MacDC4) | 1.27E−92 | 3.29E−88 | 1.536 | 0.624 | 0.012 |
| Aire | Aire APCs (MacDC4) | 8.75E−81 | 2.27E−76 | 1.970 | 0.545 | 0.011 |
| Cadm3 | Aire APCs (MacDC4) | 3.33E−80 | 8.65E−76 | 1.521 | 0.703 | 0.033 |
| Myo5b | Aire APCs (MacDC4) | 6.81E−79 | 1.77E−74 | 1.433 | 0.554 | 0.009 |
| Ttn | Aire APCs (MacDC4) | 2.81E−68 | 7.29E−64 | 3.003 | 0.743 | 0.072 |
| Cnr1 | Aire APCs (MacDC4) | 8.93E−67 | 2.31E−62 | 1.271 | 0.416 | 0.003 |
| Nid1 | Aire APCs (MacDC4) | 1.92E−66 | 4.97E−62 | 1.747 | 0.693 | 0.049 |
| Dpp10 | Aire APCs (MacDC4) | 2.09E−66 | 5.41E−62 | 1.180 | 0.475 | 0.008 |
| Adam11 | Aire APCs (MacDC4) | 3.44E−64 | 8.93E−60 | 1.694 | 0.931 | 0.174 |
| Col17a1 | Aire APCs (MacDC4) | 3.32E−59 | 8.62E−55 | 1.715 | 0.386 | 0.004 |
| Scn3a | Aire APCs (MacDC4) | 1.90E−57 | 4.93E−53 | 1.256 | 0.545 | 0.023 |
| Tmem132c | Aire APCs (MacDC4) | 8.03E−57 | 2.08E−52 | 0.917 | 0.416 | 0.008 |
| Clic3 | Aire APCs (MacDC4) | 1.43E−56 | 3.70E−52 | 1.149 | 0.347 | 0.002 |
| Tmprss11d | Aire APCs (MacDC4) | 6.24E−55 | 1.62E−50 | 1.075 | 0.317 | 0.001 |
| Cntn1 | Aire APCs (MacDC4) | 4.44E−54 | 1.15E−49 | 1.516 | 0.505 | 0.021 |
| Atp1b1 | Aire APCs (MacDC4) | 4.60E−53 | 1.19E−48 | 1.841 | 0.713 | 0.161 |
| Kif21a | Aire APCs (MacDC4) | 5.17E−52 | 1.34E−47 | 1.317 | 0.386 | 0.007 |
| Dact3 | Aire APCs (MacDC4) | 2.61E−51 | 6.77E−47 | 0.854 | 0.386 | 0.007 |
| Clmn | Aire APCs (MacDC4) | 2.48E−50 | 6.42E−46 | 1.223 | 0.446 | 0.015 |
| Crispld2 | Aire APCs (MacDC4) | 2.94E−49 | 7.63E−45 | 1.324 | 0.604 | 0.05 |
| Ttyh3 | Aire APCs (MacDC4) | 1.08E−48 | 2.81E−44 | 1.374 | 0.673 | 0.179 |
| Chka | Aire APCs (MacDC4) | 1.41E−48 | 3.65E−44 | 1.504 | 0.743 | 0.167 |
| Adam23 | Aire APCs (MacDC4) | 3.54E−48 | 9.19E−44 | 1.320 | 0.861 | 0.201 |

TABLE 2-continued

Significant Cluster-Defining Genes for Cell Types Identified from the Steady State LN Cell Atlas

| Gene | Cell type | p-value | q-value | Average log fold change | % Expressing in Cluster | % Expressing Rest |
|---|---|---|---|---|---|---|
| Cpe | Aire APCs (MacDC4) | 1.38E−44 | 3.58E−40 | 0.977 | 0.465 | 0.032 |
| Arhgef28 | Aire APCs (MacDC4) | 6.58E−43 | 1.71E−38 | 1.022 | 0.406 | 0.017 |
| Dnmt3a | Aire APCs (MacDC4) | 1.29E−42 | 3.34E−38 | 1.293 | 0.762 | 0.242 |
| Il9r | Aire APCs (MacDC4) | 1.38E−42 | 3.57E−38 | 1.325 | 0.604 | 0.072 |
| Mex3a | Aire APCs (MacDC4) | 1.66E−41 | 4.30E−37 | 0.990 | 0.386 | 0.018 |
| Dscam | Aire APCs (MacDC4) | 3.12E−41 | 8.09E−37 | 1.151 | 0.545 | 0.051 |
| Rab7l1 | Aire APCs (MacDC4) | 1.64E−40 | 4.24E−36 | 1.107 | 0.584 | 0.094 |
| Tbc1d4 | Aire APCs (MacDC4) | 2.74E−40 | 7.10E−36 | 1.362 | 0.901 | 0.295 |
| Nedd4 | Aire APCs (MacDC4) | 5.54E−40 | 1.44E−35 | 1.419 | 0.832 | 0.332 |
| Tmod2 | Aire APCs (MacDC4) | 8.93E−40 | 2.32E−35 | 0.981 | 0.465 | 0.032 |
| Nrxn1 | Aire APCs (MacDC4) | 2.50E−39 | 6.48E−35 | 1.267 | 0.356 | 0.014 |
| Gnb4 | Aire APCs (MacDC4) | 3.84E−38 | 9.95E−34 | 1.319 | 0.683 | 0.138 |
| Slc4a8 | Aire APCs (MacDC4) | 1.50E−37 | 3.88E−33 | 1.333 | 0.723 | 0.14 |
| Stard7 | Aire APCs (MacDC4) | 3.61E−37 | 9.35E−33 | 1.177 | 0.703 | 0.217 |
| Icosl | Aire APCs (MacDC4) | 1.15E−36 | 2.99E−32 | 1.321 | 0.733 | 0.238 |
| Nrgn | Aire APCs (MacDC4) | 1.30E−36 | 3.38E−32 | 0.923 | 0.376 | 0.017 |
| H2-Eb2 | Aire APCs (MacDC4) | 6.22E−36 | 1.61E−31 | 1.176 | 0.574 | 0.086 |
| Rogdi | Aire APCs (MacDC4) | 1.88E−34 | 4.88E−30 | 1.176 | 0.842 | 0.294 |
| Ccr6 | Aire APCs (MacDC4) | 1.15E−33 | 2.99E−29 | 1.085 | 0.545 | 0.077 |
| Fabp5 | Aire APCs (MacDC4) | 1.52E−33 | 3.95E−29 | 1.066 | 0.485 | 0.054 |
| Hook1 | Aire APCs (MacDC4) | 4.23E−33 | 1.10E−28 | 1.086 | 0.525 | 0.071 |
| Kif1b | Aire APCs (MacDC4) | 5.91E−33 | 1.53E−28 | 1.170 | 0.713 | 0.21 |
| Prnp | Aire APCs (MacDC4) | 9.63E−32 | 2.50E−27 | 1.191 | 0.554 | 0.089 |
| Pde1c | Aire APCs (MacDC4) | 3.79E−31 | 9.83E−27 | 0.851 | 0.327 | 0.017 |
| Slc25a37 | Aire APCs (MacDC4) | 5.09E−31 | 1.32E−26 | 1.113 | 0.624 | 0.138 |
| Kit | Aire APCs (MacDC4) | 5.61E−31 | 1.46E−26 | 1.192 | 0.703 | 0.184 |
| Bmp1 | Aire APCs (MacDC4) | 1.00E−30 | 2.61E−26 | 1.023 | 0.396 | 0.038 |
| Plxnc1 | Aire APCs (MacDC4) | 1.65E−30 | 4.29E−26 | 1.030 | 0.832 | 0.33 |
| Colgalt1 | Aire APCs (MacDC4) | 1.78E−30 | 4.61E−26 | 1.051 | 0.832 | 0.361 |
| Micu1 | Aire APCs (MacDC4) | 2.68E−30 | 6.96E−26 | 1.071 | 0.644 | 0.154 |
| Sspo | Aire APCs (MacDC4) | 8.26E−30 | 2.14E−25 | 1.259 | 0.347 | 0.032 |
| Aebp2 | Aire APCs (MacDC4) | 1.17E−29 | 3.04E−25 | 0.998 | 0.782 | 0.377 |
| Cadm1 | Aire APCs (MacDC4) | 1.22E−29 | 3.17E−25 | 1.203 | 0.535 | 0.094 |
| Fgd5 | Aire APCs (MacDC4) | 1.25E−29 | 3.25E−25 | 1.020 | 0.416 | 0.039 |
| Fbrsl1 | Aire APCs (MacDC4) | 2.15E−29 | 5.58E−25 | 1.086 | 0.713 | 0.235 |
| Mlf2 | Aire APCs (MacDC4) | 1.94E−28 | 5.02E−24 | 1.069 | 0.634 | 0.242 |
| S100a4 | Aire APCs (MacDC4) | 2.28E−28 | 5.92E−24 | 1.165 | 0.792 | 0.291 |
| Gria3 | Aire APCs (MacDC4) | 2.62E−28 | 6.80E−24 | 1.039 | 0.505 | 0.074 |
| I830077J02Rik | Aire APCs (MacDC4) | 1.45E−27 | 3.76E−23 | 0.904 | 0.465 | 0.066 |
| Igsf3 | Aire APCs (MacDC4) | 6.10E−27 | 1.58E−22 | 0.896 | 0.386 | 0.038 |
| Chd3 | Aire APCs (MacDC4) | 6.54E−27 | 1.70E−22 | 1.042 | 0.832 | 0.417 |
| 2610528A11Rik | Aire APCs (MacDC4) | 8.77E−27 | 2.27E−22 | 0.947 | 0.267 | 0.011 |
| Zfand6 | Aire APCs (MacDC4) | 3.35E−26 | 8.69E−22 | 0.968 | 0.644 | 0.221 |
| Tmem176b | Aire APCs (MacDC4) | 4.77E−26 | 1.24E−21 | 1.118 | 0.812 | 0.311 |
| Rasal2 | Aire APCs (MacDC4) | 4.97E−26 | 1.29E−21 | 0.959 | 0.465 | 0.07 |
| Gtf2a1 | Aire APCs (MacDC4) | 5.82E−26 | 1.51E−21 | 1.041 | 0.604 | 0.2 |
| Slco5a1 | Aire APCs (MacDC4) | 8.33E−26 | 2.16E−21 | 1.071 | 0.515 | 0.088 |
| Lamp1 | Aire APCs (MacDC4) | 4.55E−25 | 1.18E−20 | 1.011 | 0.832 | 0.402 |
| Ank | Aire APCs (MacDC4) | 5.40E−25 | 1.40E−20 | 1.047 | 0.515 | 0.121 |
| Tmem19 | Aire APCs (MacDC4) | 3.76E−24 | 9.75E−20 | 1.014 | 0.594 | 0.168 |
| Mkrn1 | Aire APCs (MacDC4) | 6.21E−24 | 1.61E−19 | 0.957 | 0.713 | 0.344 |
| Smad4 | Aire APCs (MacDC4) | 1.52E−23 | 3.93E−19 | 0.921 | 0.723 | 0.302 |
| Pde4dip | Aire APCs (MacDC4) | 4.74E−23 | 1.23E−18 | 0.957 | 0.574 | 0.161 |
| Slc38a2 | Aire APCs (MacDC4) | 7.06E−23 | 1.83E−18 | 0.869 | 0.822 | 0.414 |
| Emc8 | Aire APCs (MacDC4) | 1.66E−22 | 4.29E−18 | 0.866 | 0.515 | 0.139 |
| Marcksl1 | Aire APCs (MacDC4) | 8.92E−22 | 2.31E−17 | 0.854 | 0.604 | 0.169 |
| Txnrd1 | Aire APCs (MacDC4) | 1.32E−21 | 3.42E−17 | 0.935 | 0.525 | 0.184 |
| Ift140 | Aire APCs (MacDC4) | 1.52E−21 | 3.93E−17 | 0.910 | 0.634 | 0.214 |
| Hspa4l | Aire APCs (MacDC4) | 3.57E−21 | 9.26E−17 | 1.028 | 0.416 | 0.09 |
| Basp1 | Aire APCs (MacDC4) | 1.37E−20 | 3.54E−16 | 0.924 | 0.574 | 0.151 |
| Il4i1 | Aire APCs (MacDC4) | 1.41E−20 | 3.65E−16 | 0.971 | 0.653 | 0.204 |
| Cfp | Aire APCs (MacDC4) | 3.34E−20 | 8.66E−16 | 1.010 | 0.535 | 0.142 |
| Specc1 | Aire APCs (MacDC4) | 5.65E−20 | 1.47E−15 | 0.859 | 0.436 | 0.089 |
| Sox4 | Aire APCs (MacDC4) | 1.77E−19 | 4.58E−15 | 1.117 | 0.505 | 0.138 |
| Ccnd1 | Aire APCs (MacDC4) | 1.83E−19 | 4.74E−15 | 1.168 | 0.535 | 0.186 |
| Relt | Aire APCs (MacDC4) | 2.43E−19 | 6.30E−15 | 0.875 | 0.564 | 0.167 |
| Ccdc88a | Aire APCs (MacDC4) | 3.74E−19 | 9.69E−15 | 0.952 | 0.782 | 0.365 |
| Il18r1 | Aire APCs (MacDC4) | 4.70E−19 | 1.22E−14 | 0.984 | 0.564 | 0.168 |
| Gpr183 | Aire APCs (MacDC4) | 1.14E−18 | 2.96E−14 | 0.994 | 0.515 | 0.16 |
| Tjp2 | Aire APCs (MacDC4) | 1.39E−18 | 3.61E−14 | 0.874 | 0.426 | 0.091 |
| Slc41a1 | Aire APCs (MacDC4) | 7.03E−18 | 1.82E−13 | 0.958 | 0.455 | 0.126 |
| Cdh2 | Aire APCs (MacDC4) | 3.79E−16 | 9.83E−12 | 0.924 | 0.228 | 0.027 |
| Ogfrl1 | Aire APCs (MacDC4) | 6.30E−16 | 1.63E−11 | 0.960 | 0.594 | 0.248 |

TABLE 2-continued

| Gene | Cell type | p-value | q-value | Average log fold change | % Expressing in Cluster | % Expressing Rest |
|---|---|---|---|---|---|---|
| Significant Cluster-Defining Genes for Cell Types Identified from the Steady State LN Cell Atlas | | | | | | |
| KCTD12 | Aire APCs (MacDC4) | 1.43E−14 | 3.70E−10 | 0.953 | 0.545 | 0.254 |
| Cd22 | B Cells | 0 | 0 | 2.329 | 0.866 | 0.05 |
| Cd19 | B Cells | 0 | 0 | 2.242 | 0.837 | 0.031 |
| Cd79b | B Cells | 0 | 0 | 2.201 | 0.836 | 0.095 |
| Bank1 | B Cells | 0 | 0 | 1.871 | 0.702 | 0.028 |
| Scd1 | B Cells | 0 | 0 | 1.845 | 0.605 | 0.034 |
| Faim3 | B Cells | 0 | 0 | 1.844 | 0.609 | 0.02 |
| Gm19980 | B Cells | 0 | 0 | 1.780 | 0.641 | 0.018 |
| Btla | B Cells | 0 | 0 | 1.761 | 0.841 | 0.257 |
| H2-Ob | B Cells | 0 | 0 | 1.696 | 0.793 | 0.166 |
| Zfp318 | B Cells | 0 | 0 | 1.668 | 0.782 | 0.223 |
| Chst3 | B Cells | 0 | 0 | 1.597 | 0.57 | 0.032 |
| Ebf1 | B Cells | 0 | 0 | 1.594 | 0.659 | 0.056 |
| Pax5 | B Cells | 0 | 0 | 1.567 | 0.61 | 0.017 |
| Ralgps2 | B Cells | 0 | 0 | 1.566 | 0.628 | 0.092 |
| Fcer2a | B Cells | 0 | 0 | 1.543 | 0.563 | 0.021 |
| Ms4a1 | B Cells | 0 | 0 | 1.543 | 0.575 | 0.017 |
| Siglecg | B Cells | 0 | 0 | 1.461 | 0.671 | 0.113 |
| Cr2 | B Cells | 0 | 0 | 1.455 | 0.466 | 0.014 |
| Dok3 | B Cells | 0 | 0 | 1.431 | 0.631 | 0.07 |
| Syk | B Cells | 0 | 0 | 1.393 | 0.821 | 0.333 |
| Mef2c | B Cells | 0 | 0 | 1.376 | 0.646 | 0.164 |
| Sorl1 | B Cells | 0 | 0 | 1.315 | 0.824 | 0.382 |
| Pou2af1 | B Cells | 0 | 0 | 1.314 | 0.529 | 0.038 |
| Blk | B Cells | 0 | 0 | 1.280 | 0.49 | 0.022 |
| Cd37 | B Cells | 0 | 0 | 1.232 | 0.845 | 0.405 |
| Cd72 | B Cells | 0 | 0 | 1.211 | 0.53 | 0.099 |
| Cd79a | B Cells | 0 | 0 | 1.206 | 0.492 | 0.018 |
| B3gnt5 | B Cells | 0 | 0 | 1.202 | 0.5 | 0.064 |
| Cd55 | B Cells | 0 | 0 | 1.157 | 0.58 | 0.082 |
| Fcrl1 | B Cells | 0 | 0 | 1.133 | 0.458 | 0.036 |
| Blnk | B Cells | 0 | 0 | 1.127 | 0.581 | 0.101 |
| Gimap6 | B Cells | 0 | 0 | 1.072 | 0.785 | 0.274 |
| Macf1 | B Cells | 0 | 0 | 1.042 | 0.987 | 0.749 |
| Srpk3 | B Cells | 0.00E+00 | 5.35E−305 | 0.919 | 0.328 | 0.013 |
| Bach2 | B Cells | 4.80E−297 | 1.24E−292 | 1.133 | 0.546 | 0.114 |
| Pgap1 | B Cells | 4.49E−289 | 1.16E−284 | 1.092 | 0.409 | 0.047 |
| Hip1r | B Cells | 2.08E−286 | 5.41E−282 | 1.066 | 0.659 | 0.236 |
| Dmxl1 | B Cells | 1.22E−284 | 3.16E−280 | 1.129 | 0.667 | 0.282 |
| Cxcr5 | B Cells | 2.43E−275 | 6.29E−271 | 0.833 | 0.304 | 0.015 |
| Arhgef18 | B Cells | 2.72E−271 | 7.07E−267 | 1.011 | 0.734 | 0.29 |
| Ikzf3 | B Cells | 3.35E−264 | 8.69E−260 | 0.970 | 0.632 | 0.176 |
| H2-DMb2 | B Cells | 1.00E−261 | 2.59E−257 | 0.990 | 0.533 | 0.131 |
| Hvcn1 | B Cells | 1.76E−261 | 4.55E−257 | 1.091 | 0.623 | 0.218 |
| Gm8369 | B Cells | 2.00E−252 | 5.20E−248 | 0.830 | 0.338 | 0.03 |
| Pxk | B Cells | 1.68E−250 | 4.35E−246 | 0.982 | 0.504 | 0.153 |
| Tnfrsf13c | B Cells | 5.36E−249 | 1.39E−244 | 0.850 | 0.325 | 0.027 |
| Helz2 | B Cells | 4.35E−245 | 1.13E−240 | 1.117 | 0.57 | 0.188 |
| Fchsd2 | B Cells | 1.30E−242 | 3.37E−238 | 1.031 | 0.631 | 0.262 |
| Brwd1 | B Cells | 1.86E−237 | 4.82E−233 | 1.026 | 0.61 | 0.244 |
| Dgkd | B Cells | 3.54E−236 | 9.19E−232 | 0.955 | 0.695 | 0.319 |
| Fcrla | B Cells | 2.53E−230 | 6.57E−226 | 0.950 | 0.438 | 0.082 |
| Sesn1 | B Cells | 1.17E−228 | 3.03E−224 | 0.983 | 0.497 | 0.138 |
| Myole | B Cells | 2.80E−222 | 7.26E−218 | 0.968 | 0.399 | 0.072 |
| Slc12a6 | B Cells | 2.25E−218 | 5.82E−214 | 0.924 | 0.553 | 0.197 |
| Gga2 | B Cells | 4.41E−214 | 1.14E−209 | 0.872 | 0.435 | 0.103 |
| Foxp1 | B Cells | 2.89E−212 | 7.49E−208 | 0.851 | 0.739 | 0.411 |
| Ets1 | B Cells | 4.39E−211 | 1.14E−206 | 0.747 | 0.818 | 0.419 |
| Pou2f2 | B Cells | 2.48E−210 | 6.44E−206 | 0.767 | 0.338 | 0.045 |
| Dennd5b | B Cells | 2.32E−209 | 6.01E−205 | 0.904 | 0.329 | 0.042 |
| Sipa1 | B Cells | 2.33E−205 | 6.05E−201 | 0.860 | 0.621 | 0.292 |
| Lrrk2 | B Cells | 5.53E−205 | 1.43E−200 | 1.004 | 0.569 | 0.204 |
| RP24-312B12.1 | B Cells | 1.08E−204 | 2.80E−200 | 0.782 | 0.324 | 0.04 |
| Bcar3 | B Cells | 5.35E−202 | 1.39E−197 | 0.835 | 0.294 | 0.031 |
| Rasgrp2 | B Cells | 2.65E−200 | 6.87E−196 | 0.923 | 0.574 | 0.191 |
| Carns1 | B Cells | 1.22E−199 | 3.15E−195 | 0.941 | 0.507 | 0.142 |
| Ciita | B Cells | 9.91E−199 | 2.57E−194 | 0.853 | 0.663 | 0.258 |
| mmu-mir-6236 | B Cells | 3.01E−198 | 7.82E−194 | 0.907 | 0.792 | 0.402 |
| Cerk | B Cells | 2.02E−193 | 5.23E−189 | 0.900 | 0.57 | 0.248 |
| Sbk1 | B Cells | 2.38E−193 | 6.17E−189 | 0.773 | 0.35 | 0.06 |
| Fam65b | B Cells | 1.35E−192 | 3.49E−188 | 0.837 | 0.654 | 0.266 |
| Snx2 | B Cells | 2.76E−192 | 7.15E−188 | 0.822 | 0.511 | 0.204 |
| Gimap1 | B Cells | 2.80E−189 | 7.25E−185 | 0.843 | 0.506 | 0.161 |

TABLE 2-continued

Significant Cluster-Defining Genes for Cell Types Identified from the Steady State LN Cell Atlas

| Gene | Cell type | p-value | q-value | Average log fold change | % Expressing in Cluster | % Expressing Rest |
|---|---|---|---|---|---|---|
| Snx29 | B Cells | 5.37E−188 | 1.39E−183 | 0.871 | 0.389 | 0.081 |
| Swap70 | B Cells | 1.75E−187 | 4.53E−183 | 0.910 | 0.584 | 0.244 |
| Lax1 | B Cells | 5.94E−187 | 1.54E−182 | 0.825 | 0.437 | 0.102 |
| Snx5 | B Cells | 2.01E−185 | 5.21E−181 | 0.784 | 0.748 | 0.452 |
| Gimap8 | B Cells | 5.42E−184 | 1.41E−179 | 0.826 | 0.566 | 0.189 |
| Stap1 | B Cells | 1.21E−183 | 3.13E−179 | 0.883 | 0.458 | 0.133 |
| Traf3ip3 | B Cells | 1.61E−181 | 4.19E−177 | 0.791 | 0.657 | 0.285 |
| Sh3bp5 | B Cells | 4.32E−181 | 1.12E−176 | 0.837 | 0.382 | 0.089 |
| Samd9l | B Cells | 8.20E−179 | 2.13E−174 | 0.831 | 0.715 | 0.367 |
| Ms4a4c | B Cells | 1.17E−178 | 3.04E−174 | 0.790 | 0.39 | 0.083 |
| Cmah | B Cells | 7.48E−178 | 1.94E−173 | 0.818 | 0.575 | 0.197 |
| Snx30 | B Cells | 5.72E−168 | 1.48E−163 | 0.870 | 0.459 | 0.155 |
| Mndal | B Cells | 1.04E−164 | 2.70E−160 | 0.764 | 0.659 | 0.329 |
| 1700021K19Rik | B Cells | 2.35E−162 | 6.10E−158 | 0.810 | 0.435 | 0.142 |
| Man1a | B Cells | 7.38E−162 | 1.91E−157 | 0.790 | 0.636 | 0.319 |
| Btk | B Cells | 7.42E−161 | 1.92E−156 | 0.765 | 0.405 | 0.122 |
| Cbx7 | B Cells | 2.72E−160 | 7.05E−156 | 0.769 | 0.6 | 0.265 |
| Lrmp | B Cells | 7.20E−158 | 1.87E−153 | 0.854 | 0.593 | 0.298 |
| Zfp831 | B Cells | 2.78E−156 | 7.21E−152 | 0.820 | 0.411 | 0.108 |
| Itsn2 | B Cells | 1.05E−153 | 2.73E−149 | 0.746 | 0.698 | 0.439 |
| Rasgrp3 | B Cells | 6.57E−153 | 1.70E−148 | 0.864 | 0.366 | 0.098 |
| Filip1l | B Cells | 2.86E−149 | 7.42E−145 | 0.787 | 0.646 | 0.353 |
| Add3 | B Cells | 3.71E−147 | 9.62E−143 | 0.784 | 0.62 | 0.326 |
| Parp1 | B Cells | 2.76E−142 | 7.15E−138 | 0.763 | 0.51 | 0.253 |
| Trim7 | B Cells | 4.05E−141 | 1.05E−136 | 0.825 | 0.484 | 0.183 |
| Haao | B Cells | 1.35E−138 | 3.51E−134 | 0.745 | 0.467 | 0.169 |
| Hivep2 | B Cells | 8.56E−136 | 2.22E−131 | 0.825 | 0.414 | 0.146 |
| 1-Mar | B Cells | 4.23E−133 | 1.10E−128 | 0.756 | 0.505 | 0.198 |
| Pecam1 | BEC 1 | 1.30E−184 | 3.37E−180 | 2.418 | 0.941 | 0.258 |
| Plvap | BEC 1 | 5.98E−170 | 1.55E−165 | 3.152 | 0.897 | 0.054 |
| Cd34 | BEC 1 | 4.38E−167 | 1.14E−162 | 2.532 | 0.838 | 0.028 |
| Aqp1 | BEC 1 | 1.35E−143 | 3.50E−139 | 3.013 | 0.787 | 0.029 |
| Enpp2 | BEC 1 | 1.52E−138 | 3.93E−134 | 2.572 | 0.912 | 0.071 |
| Flt1 | BEC 1 | 1.63E−138 | 4.22E−134 | 2.601 | 0.676 | 0.035 |
| Eng | BEC 1 | 5.33E−137 | 1.38E−132 | 2.169 | 0.809 | 0.059 |
| C130074G19Rik | BEC 1 | 1.85E−136 | 4.80E−132 | 2.051 | 0.706 | 0.016 |
| Cav1 | BEC 1 | 9.50E−136 | 2.46E−131 | 2.234 | 0.713 | 0.019 |
| Cd93 | BEC 1 | 4.99E−132 | 1.29E−127 | 2.365 | 0.779 | 0.067 |
| Ptprb | BEC 1 | 1.34E−130 | 3.47E−126 | 2.516 | 0.699 | 0.022 |
| Cd300lg | BEC 1 | 1.36E−130 | 3.51E−126 | 2.303 | 0.75 | 0.042 |
| Tinagl1 | BEC 1 | 2.25E−127 | 5.84E−123 | 2.155 | 0.654 | 0.015 |
| Ly6c1 | BEC 1 | 1.17E−125 | 3.05E−121 | 2.546 | 0.537 | 0.028 |
| Epas1 | BEC 1 | 1.25E−122 | 3.25E−118 | 2.400 | 0.838 | 0.061 |
| Igfbp7 | BEC 1 | 2.48E−120 | 6.42E−116 | 2.770 | 0.86 | 0.081 |
| Egfl7 | BEC 1 | 8.38E−117 | 2.17E−112 | 1.933 | 0.699 | 0.028 |
| Eltd1 | BEC 1 | 2.17E−113 | 5.62E−109 | 1.919 | 0.632 | 0.02 |
| Col4a1 | BEC 1 | 6.64E−111 | 1.72E−106 | 2.494 | 0.772 | 0.052 |
| Mmrn2 | BEC 1 | 1.07E−110 | 2.77E−106 | 2.098 | 0.691 | 0.026 |
| Gpr116 | BEC 1 | 6.80E−110 | 1.76E−105 | 2.044 | 0.676 | 0.026 |
| Sparc | BEC 1 | 9.85E−110 | 2.55E−105 | 2.352 | 0.824 | 0.064 |
| Sparcl1 | BEC 1 | 3.47E−108 | 9.00E−104 | 2.369 | 0.551 | 0.009 |
| Col15a1 | BEC 1 | 8.85E−107 | 2.30E−102 | 2.083 | 0.603 | 0.021 |
| Cdh5 | BEC 1 | 9.42E−107 | 2.44E−102 | 2.162 | 0.75 | 0.056 |
| Gpr56 | BEC 1 | 4.48E−103 | 1.16E−98 | 1.655 | 0.566 | 0.016 |
| Sptbn1 | BEC 1 | 4.41E−97 | 1.14E−92 | 1.640 | 0.926 | 0.506 |
| Hspg2 | BEC 1 | 7.69E−96 | 1.99E−91 | 2.009 | 0.61 | 0.038 |
| Tie1 | BEC 1 | 3.38E−95 | 8.77E−91 | 1.649 | 0.603 | 0.023 |
| Gpihbp1 | BEC 1 | 7.83E−95 | 2.03E−90 | 1.937 | 0.426 | 0.005 |
| Col4a2 | BEC 1 | 4.51E−92 | 1.17E−87 | 2.227 | 0.64 | 0.042 |
| Prss23 | BEC 1 | 2.34E−91 | 6.06E−87 | 1.899 | 0.566 | 0.019 |
| Pcdh17 | BEC 1 | 1.48E−90 | 3.85E−86 | 1.758 | 0.529 | 0.013 |
| Tm4sf1 | BEC 1 | 4.01E−89 | 1.04E−84 | 1.789 | 0.581 | 0.023 |
| Podxl | BEC 1 | 2.83E−88 | 7.35E−84 | 1.697 | 0.463 | 0.009 |
| Crip2 | BEC 1 | 2.73E−87 | 7.07E−83 | 1.642 | 0.61 | 0.043 |
| Esam | BEC 1 | 6.45E−86 | 1.67E−81 | 1.648 | 0.537 | 0.028 |
| Ushbp1 | BEC 1 | 1.97E−85 | 5.11E−81 | 1.526 | 0.522 | 0.016 |
| Slc9a3r2 | BEC 1 | 6.93E−85 | 1.80E−80 | 1.794 | 0.507 | 0.035 |
| Vwa1 | BEC 1 | 1.06E−83 | 2.74E−79 | 1.500 | 0.485 | 0.015 |
| Abcg2 | BEC 1 | 3.87E−82 | 1.00E−77 | 1.599 | 0.61 | 0.05 |
| Fabp4 | BEC 1 | 1.06E−80 | 2.76E−76 | 2.278 | 0.529 | 0.023 |
| App | BEC 1 | 7.71E−80 | 2.00E−75 | 1.720 | 0.853 | 0.217 |
| Heg1 | BEC 1 | 4.40E−78 | 1.14E−73 | 1.706 | 0.713 | 0.163 |
| Timp3 | BEC 1 | 9.98E−78 | 2.59E−73 | 2.307 | 0.64 | 0.048 |

TABLE 2-continued

| Significant Cluster-Defining Genes for Cell Types Identified from the Steady State LN Cell Atlas | | | | | | |
|---|---|---|---|---|---|---|
| Gene | Cell type | p-value | q-value | Average log fold change | % Expressing in Cluster | % Expressing Rest |
| Cyyr1 | BEC 1 | 1.51E−76 | 3.92E−72 | 1.435 | 0.463 | 0.015 |
| Ehd2 | BEC 1 | 1.88E−75 | 4.88E−71 | 1.577 | 0.5 | 0.027 |
| Glycam1 | BEC 1 | 8.34E−75 | 2.16E−70 | 3.912 | 0.485 | 0.09 |
| Lims2 | BEC 1 | 8.44E−75 | 2.19E−70 | 1.394 | 0.375 | 0.006 |
| Ramp2 | BEC 1 | 1.28E−74 | 3.31E−70 | 1.342 | 0.507 | 0.021 |
| Scarb1 | BEC 1 | 1.96E−74 | 5.09E−70 | 1.758 | 0.529 | 0.124 |
| Kdr | BEC 1 | 5.70E−73 | 1.48E−68 | 1.726 | 0.618 | 0.047 |
| Adamts1 | BEC 1 | 6.00E−73 | 1.56E−68 | 1.795 | 0.463 | 0.016 |
| Rasip1 | BEC 1 | 1.52E−72 | 3.93E−68 | 1.537 | 0.559 | 0.04 |
| Robo4 | BEC 1 | 2.99E−72 | 7.76E−68 | 1.427 | 0.485 | 0.019 |
| Kitl | BEC 1 | 3.14E−71 | 8.15E−67 | 1.644 | 0.537 | 0.036 |
| Ppap2b | BEC 1 | 2.45E−70 | 6.35E−66 | 1.692 | 0.456 | 0.024 |
| Clec14a | BEC 1 | 1.40E−68 | 3.62E−64 | 1.377 | 0.441 | 0.02 |
| Prkcdbp | BEC 1 | 5.31E−68 | 1.38E−63 | 1.388 | 0.441 | 0.022 |
| Ctla2a | BEC 1 | 1.27E−66 | 3.29E−62 | 1.754 | 0.603 | 0.064 |
| Ptrf | BEC 1 | 3.49E−66 | 9.06E−62 | 1.447 | 0.463 | 0.033 |
| Clic5 | BEC 1 | 7.13E−66 | 1.85E−61 | 1.523 | 0.346 | 0.011 |
| Hspb1 | BEC 1 | 3.00E−64 | 7.77E−60 | 1.739 | 0.507 | 0.033 |
| Apold1 | BEC 1 | 4.06E−64 | 1.05E−59 | 1.841 | 0.404 | 0.016 |
| Adam15 | BEC 1 | 4.34E−63 | 1.13E−58 | 1.452 | 0.522 | 0.065 |
| Lama5 | BEC 1 | 5.75E−63 | 1.49E−58 | 1.346 | 0.493 | 0.034 |
| Id1 | BEC 1 | 5.35E−62 | 1.39E−57 | 1.468 | 0.412 | 0.019 |
| Mcam | BEC 1 | 7.49E−62 | 1.94E−57 | 1.344 | 0.412 | 0.016 |
| Ifitm3 | BEC 1 | 1.48E−61 | 3.84E−57 | 1.602 | 0.75 | 0.15 |
| Abcb1a | BEC 1 | 1.98E−60 | 5.13E−56 | 1.379 | 0.449 | 0.028 |
| Lrg1 | BEC 1 | 5.35E−60 | 1.39E−55 | 1.952 | 0.485 | 0.04 |
| Tgm2 | BEC 1 | 1.44E−59 | 3.73E−55 | 1.433 | 0.544 | 0.049 |
| Ace | BEC 1 | 5.25E−59 | 1.36E−54 | 1.451 | 0.478 | 0.028 |
| Adamts9 | BEC 1 | 1.29E−58 | 3.34E−54 | 1.376 | 0.419 | 0.022 |
| Ubd | BEC 1 | 8.40E−58 | 2.18E−53 | 1.794 | 0.419 | 0.02 |
| Fgd5 | BEC 1 | 3.65E−57 | 9.48E−53 | 1.361 | 0.485 | 0.037 |
| Emp1 | BEC 1 | 3.83E−57 | 9.94E−53 | 1.369 | 0.39 | 0.02 |
| Sema7a | BEC 1 | 2.32E−56 | 6.02E−52 | 1.587 | 0.551 | 0.094 |
| Mgll | BEC 1 | 6.03E−55 | 1.56E−50 | 1.485 | 0.441 | 0.035 |
| Nfib | BEC 1 | 8.83E−55 | 2.29E−50 | 1.420 | 0.544 | 0.052 |
| 4931406P16Rik | BEC 1 | 7.49E−53 | 1.94E−48 | 1.355 | 0.544 | 0.131 |
| Entpd1 | BEC 1 | 2.36E−52 | 6.13E−48 | 1.512 | 0.544 | 0.112 |
| Dock9 | BEC 1 | 9.85E−52 | 2.55E−47 | 1.467 | 0.574 | 0.09 |
| Ltbp4 | BEC 1 | 2.18E−50 | 5.65E−46 | 1.543 | 0.456 | 0.037 |
| Slc30a1 | BEC 1 | 7.87E−50 | 2.04E−45 | 1.336 | 0.456 | 0.108 |
| Bace2 | BEC 1 | 2.56E−49 | 6.63E−45 | 1.326 | 0.368 | 0.022 |
| Mcf2l | BEC 1 | 2.82E−49 | 7.31E−45 | 1.488 | 0.309 | 0.014 |
| Ece1 | BEC 1 | 3.30E−49 | 8.56E−45 | 1.358 | 0.64 | 0.202 |
| Calcrl | BEC 1 | 7.41E−48 | 1.92E−43 | 1.487 | 0.507 | 0.107 |
| Itga6 | BEC 1 | 7.69E−47 | 1.99E−42 | 1.340 | 0.485 | 0.104 |
| Abca1 | BEC 1 | 2.09E−45 | 5.42E−41 | 1.343 | 0.669 | 0.182 |
| Clu | BEC 1 | 2.26E−43 | 5.86E−39 | 1.684 | 0.691 | 0.162 |
| Mfge8 | BEC 1 | 3.40E−43 | 8.83E−39 | 1.368 | 0.691 | 0.178 |
| Ndrg1 | BEC 1 | 8.04E−43 | 2.08E−38 | 1.324 | 0.603 | 0.16 |
| Nrp1 | BEC 1 | 8.28E−43 | 2.15E−38 | 1.601 | 0.581 | 0.126 |
| Ly6a | BEC 1 | 1.89E−39 | 4.91E−35 | 1.379 | 0.574 | 0.167 |
| Il6st | BEC 1 | 8.11E−38 | 2.10E−33 | 1.318 | 0.691 | 0.347 |
| Vwf | BEC 1 | 9.17E−38 | 2.38E−33 | 1.626 | 0.294 | 0.039 |
| Igfbp3 | BEC 1 | 2.16E−34 | 5.60E−30 | 1.501 | 0.375 | 0.037 |
| Fbln2 | BEC 1 | 5.04E−30 | 1.31E−25 | 1.350 | 0.228 | 0.014 |
| Pecam1 | BEC 2 | 5.04E−126 | 1.31E−121 | 2.698 | 0.985 | 0.263 |
| Glycam1 | BEC 2 | 1.10E−124 | 2.84E−120 | 4.414 | 0.954 | 0.09 |
| Enpp2 | BEC 2 | 1.11E−110 | 2.88E−106 | 3.049 | 1 | 0.076 |
| Lrg1 | BEC 2 | 1.54E−109 | 3.99E−105 | 2.846 | 1 | 0.04 |
| Pcdh17 | BEC 2 | 9.77E−109 | 2.53E−104 | 2.093 | 0.969 | 0.014 |
| Ushbp1 | BEC 2 | 4.60E−107 | 1.19E−102 | 2.028 | 0.969 | 0.017 |
| Ubd | BEC 2 | 7.34E−106 | 1.90E−101 | 2.652 | 0.954 | 0.019 |
| Cd300lg | BEC 2 | 1.94E−105 | 5.04E−101 | 2.565 | 0.985 | 0.046 |
| Egfl7 | BEC 2 | 1.85E−103 | 4.79E−99 | 2.471 | 0.969 | 0.031 |
| Cyyr1 | BEC 2 | 3.09E−102 | 8.01E−98 | 1.631 | 0.938 | 0.015 |
| Grrp1 | BEC 2 | 6.30E−102 | 1.63E−97 | 1.626 | 0.908 | 0.013 |
| Emcn | BEC 2 | 8.28E−102 | 2.15E−97 | 1.506 | 0.862 | 0.008 |
| Plvap | BEC 2 | 3.88E−101 | 1.01E−96 | 2.922 | 1 | 0.059 |
| Cd34 | BEC 2 | 9.21E−101 | 2.39E−96 | 2.360 | 0.985 | 0.033 |
| C130074G19Rik | BEC 2 | 9.33E−100 | 2.42E−95 | 2.161 | 0.938 | 0.02 |
| Chst4 | BEC 2 | 2.40E−98 | 6.23E−94 | 1.750 | 0.785 | 0.004 |
| Mmrn2 | BEC 2 | 1.74E−97 | 4.52E−93 | 2.240 | 0.985 | 0.029 |
| Col15a1 | BEC 2 | 2.13E−97 | 5.52E−93 | 1.890 | 0.954 | 0.023 |

TABLE 2-continued

Significant Cluster-Defining Genes for Cell Types Identified from the Steady State LN Cell Atlas

| Gene | Cell type | p-value | q-value | Average log fold change | % Expressing in Cluster | % Expressing Rest |
|---|---|---|---|---|---|---|
| Robo4 | BEC 2 | 2.42E−96 | 6.27E−92 | 1.776 | 0.938 | 0.019 |
| Ramp2 | BEC 2 | 1.98E−95 | 5.13E−91 | 1.740 | 0.938 | 0.022 |
| Eng | BEC 2 | 5.57E−95 | 1.44E−90 | 2.275 | 0.985 | 0.064 |
| Clec14a | BEC 2 | 4.40E−94 | 1.14E−89 | 1.630 | 0.923 | 0.019 |
| Eltd1 | BEC 2 | 4.35E−93 | 1.13E−88 | 1.907 | 0.938 | 0.022 |
| Cav1 | BEC 2 | 2.51E−91 | 6.51E−87 | 2.063 | 0.908 | 0.023 |
| Abcg2 | BEC 2 | 8.17E−90 | 2.12E−85 | 2.000 | 0.954 | 0.051 |
| Il6st | BEC 2 | 1.13E−89 | 2.94E−85 | 2.254 | 0.985 | 0.348 |
| Tie1 | BEC 2 | 1.87E−89 | 4.86E−85 | 1.755 | 0.938 | 0.025 |
| Gpr116 | BEC 2 | 3.53E−89 | 9.16E−85 | 2.125 | 0.954 | 0.029 |
| Slco2b1 | BEC 2 | 6.89E−87 | 1.79E−82 | 1.800 | 0.985 | 0.04 |
| Esam | BEC 2 | 4.26E−86 | 1.10E−81 | 1.584 | 0.908 | 0.029 |
| Dsg2 | BEC 2 | 4.37E−86 | 1.13E−81 | 2.128 | 0.923 | 0.029 |
| Ctla2a | BEC 2 | 6.11E−86 | 1.59E−81 | 2.373 | 0.954 | 0.065 |
| Tm4sf1 | BEC 2 | 3.96E−85 | 1.03E−80 | 1.651 | 0.908 | 0.025 |
| Bace2 | BEC 2 | 1.90E−83 | 4.92E−79 | 1.668 | 0.862 | 0.021 |
| Rasip1 | BEC 2 | 1.96E−83 | 5.09E−79 | 1.833 | 0.954 | 0.041 |
| Fut7 | BEC 2 | 1.87E−82 | 4.85E−78 | 1.584 | 0.831 | 0.019 |
| App | BEC 2 | 5.76E−82 | 1.49E−77 | 2.107 | 1 | 0.221 |
| Olfml2a | BEC 2 | 2.28E−80 | 5.90E−76 | 1.586 | 0.8 | 0.013 |
| Aqp1 | BEC 2 | 3.97E−79 | 1.03E−74 | 2.566 | 0.923 | 0.034 |
| Epas1 | BEC 2 | 6.71E−79 | 1.74E−74 | 1.953 | 0.985 | 0.066 |
| Tinagl1 | BEC 2 | 1.09E−78 | 2.82E−74 | 1.633 | 0.831 | 0.019 |
| Fam171a1 | BEC 2 | 1.19E−78 | 3.09E−74 | 1.566 | 0.769 | 0.011 |
| Igfbp7 | BEC 2 | 1.64E−78 | 4.26E−74 | 2.565 | 1 | 0.085 |
| Serpina1e | BEC 2 | 1.05E−77 | 2.73E−73 | 2.222 | 0.677 | 0.005 |
| Kitl | BEC 2 | 1.47E−77 | 3.80E−73 | 1.607 | 0.908 | 0.037 |
| Abcb1a | BEC 2 | 2.72E−77 | 7.06E−73 | 1.589 | 0.862 | 0.028 |
| Kank3 | BEC 2 | 1.11E−76 | 2.87E−72 | 1.624 | 0.938 | 0.046 |
| Nfib | BEC 2 | 1.30E−76 | 3.38E−72 | 1.828 | 0.969 | 0.053 |
| Ptprb | BEC 2 | 2.36E−76 | 6.13E−72 | 1.831 | 0.862 | 0.026 |
| Cdh5 | BEC 2 | 3.90E−76 | 1.01E−71 | 1.996 | 0.954 | 0.059 |
| Dock9 | BEC 2 | 5.48E−76 | 1.42E−71 | 1.865 | 0.985 | 0.091 |
| Itgb4 | BEC 2 | 1.21E−75 | 3.14E−71 | 1.513 | 0.8 | 0.016 |
| Ehd2 | BEC 2 | 3.49E−75 | 9.06E−71 | 1.603 | 0.862 | 0.028 |
| Hspg2 | BEC 2 | 5.45E−75 | 1.41E−70 | 1.687 | 0.908 | 0.04 |
| Darc | BEC 2 | 8.73E−75 | 2.26E−70 | 1.559 | 0.769 | 0.014 |
| Ptrf | BEC 2 | 1.34E−74 | 3.47E−70 | 1.637 | 0.877 | 0.033 |
| Timp3 | BEC 2 | 1.37E−74 | 3.55E−70 | 1.667 | 0.938 | 0.051 |
| F8 | BEC 2 | 1.91E−74 | 4.94E−70 | 1.511 | 0.831 | 0.026 |
| Clu | BEC 2 | 2.17E−73 | 5.64E−69 | 2.825 | 0.985 | 0.164 |
| Ace | BEC 2 | 2.00E−72 | 5.18E−68 | 1.764 | 0.846 | 0.029 |
| Fgd5 | BEC 2 | 3.89E−72 | 1.01E−67 | 1.572 | 0.892 | 0.037 |
| Sparc | BEC 2 | 2.29E−71 | 5.94E−67 | 1.711 | 0.969 | 0.069 |
| Tgm2 | BEC 2 | 1.42E−70 | 3.69E−66 | 1.693 | 0.923 | 0.05 |
| Rfk | BEC 2 | 1.82E−69 | 4.73E−65 | 1.686 | 0.923 | 0.127 |
| Adcy4 | BEC 2 | 7.20E−69 | 1.87E−64 | 1.631 | 0.862 | 0.04 |
| Cd93 | BEC 2 | 9.28E−69 | 2.41E−64 | 2.020 | 0.938 | 0.071 |
| Flt1 | BEC 2 | 4.25E−67 | 1.10E−62 | 1.501 | 0.846 | 0.039 |
| Susd2 | BEC 2 | 5.38E−66 | 1.40E−61 | 1.593 | 0.862 | 0.043 |
| Crim1 | BEC 2 | 7.64E−66 | 1.98E−61 | 1.695 | 0.938 | 0.073 |
| Ltbp2 | BEC 2 | 8.51E−66 | 2.21E−61 | 1.636 | 0.908 | 0.058 |
| Crip2 | BEC 2 | 8.83E−66 | 2.29E−61 | 1.546 | 0.877 | 0.045 |
| Vwf | BEC 2 | 1.21E−65 | 3.14E−61 | 2.112 | 0.8 | 0.038 |
| Mfge8 | BEC 2 | 3.96E−65 | 1.03E−60 | 2.278 | 0.985 | 0.18 |
| Sptbn1 | BEC 2 | 1.47E−64 | 3.82E−60 | 1.581 | 0.985 | 0.508 |
| Fnbp1l | BEC 2 | 7.00E−64 | 1.82E−59 | 1.725 | 0.969 | 0.108 |
| Lifr | BEC 2 | 2.37E−63 | 6.15E−59 | 1.960 | 0.985 | 0.174 |
| Serpina1b | BEC 2 | 3.67E−63 | 9.51E−59 | 1.572 | 0.615 | 0.007 |
| Gda | BEC 2 | 1.41E−60 | 3.66E−56 | 1.630 | 0.846 | 0.047 |
| Col4a1 | BEC 2 | 1.95E−60 | 5.06E−56 | 1.698 | 0.877 | 0.057 |
| Hyal2 | BEC 2 | 2.66E−60 | 6.90E−56 | 1.527 | 0.754 | 0.032 |
| Heg1 | BEC 2 | 6.27E−60 | 1.62E−55 | 1.799 | 0.938 | 0.166 |
| Pkp4 | BEC 2 | 6.33E−60 | 1.64E−55 | 1.526 | 0.892 | 0.076 |
| Ctsl | BEC 2 | 1.77E−59 | 4.59E−55 | 2.023 | 0.954 | 0.13 |
| Apoe | BEC 2 | 1.25E−58 | 3.24E−54 | 1.694 | 1 | 0.308 |
| Col4a2 | BEC 2 | 4.90E−58 | 1.27E−53 | 1.564 | 0.815 | 0.046 |
| Man1a | BEC 2 | 6.14E−58 | 1.59E−53 | 1.708 | 0.954 | 0.36 |
| Sepp1 | BEC 2 | 1.15E−56 | 2.99E−52 | 1.672 | 1 | 0.258 |
| Hip1 | BEC 2 | 1.78E−56 | 4.62E−52 | 1.469 | 0.892 | 0.076 |
| Mkl2 | BEC 2 | 1.45E−52 | 3.77E−48 | 1.535 | 0.908 | 0.117 |
| Abca1 | BEC 2 | 3.90E−52 | 1.01E−47 | 1.615 | 0.985 | 0.183 |
| Adam15 | BEC 2 | 1.16E−51 | 3.02E−47 | 1.485 | 0.815 | 0.067 |

TABLE 2-continued

Significant Cluster-Defining Genes for Cell Types Identified from the Steady State LN Cell Atlas

| Gene | Cell type | p-value | q-value | Average log fold change | % Expressing in Cluster | % Expressing Rest |
|---|---|---|---|---|---|---|
| Ifitm3 | BEC 2 | 4.94E−50 | 1.28E−45 | 1.523 | 0.954 | 0.153 |
| Prss23 | BEC 2 | 7.39E−50 | 1.92E−45 | 1.485 | 0.646 | 0.023 |
| Serpinb9 | BEC 2 | 4.47E−48 | 1.16E−43 | 1.777 | 0.954 | 0.163 |
| Scarb1 | BEC 2 | 3.29E−46 | 8.53E−42 | 1.708 | 0.846 | 0.125 |
| Sult1a1 | BEC 2 | 2.09E−45 | 5.42E−41 | 1.466 | 0.923 | 0.158 |
| Entpd1 | BEC 2 | 5.68E−43 | 1.47E−38 | 1.490 | 0.846 | 0.113 |
| Ehd4 | BEC 2 | 6.70E−42 | 1.74E−37 | 1.499 | 0.892 | 0.209 |
| Pltp | BEC 2 | 1.56E−40 | 4.06E−36 | 1.529 | 0.8 | 0.088 |
| Fabp4 | BEC 2 | 2.12E−15 | 5.51E−11 | 1.628 | 0.323 | 0.028 |
| Dgka | CD4 T Cells | 8.59E−197 | 2.23E−192 | 1.459 | 0.85 | 0.371 |
| 4932438A13Rik | CD4 T Cells | 1.62E−178 | 4.19E−174 | 1.417 | 0.859 | 0.48 |
| Arhgef1 | CD4 T Cells | 1.17E−152 | 3.03E−148 | 1.045 | 0.878 | 0.585 |
| Als2cl | CD4 T Cells | 1.57E−142 | 4.07E−138 | 1.341 | 0.587 | 0.136 |
| Lat | CD4 T Cells | 8.99E−141 | 2.33E−136 | 1.260 | 0.652 | 0.174 |
| Inpp4b | CD4 T Cells | 1.98E−136 | 5.12E−132 | 1.309 | 0.607 | 0.158 |
| Macf1 | CD4 T Cells | 2.27E−132 | 5.89E−128 | 0.932 | 0.97 | 0.774 |
| Lef1 | CD4 T Cells | 1.74E−129 | 4.51E−125 | 1.194 | 0.563 | 0.116 |
| Utrn | CD4 T Cells | 2.37E−128 | 6.15E−124 | 1.164 | 0.826 | 0.472 |
| Satb1 | CD4 T Cells | 9.57E−116 | 2.48E−111 | 1.160 | 0.707 | 0.327 |
| Bcl11b | CD4 T Cells | 1.60E−115 | 4.14E−111 | 1.168 | 0.55 | 0.123 |
| Hmha1 | CD4 T Cells | 6.72E−98 | 1.74E−93 | 0.761 | 0.93 | 0.732 |
| Lck | CD4 T Cells | 2.12E−97 | 5.49E−93 | 1.037 | 0.589 | 0.189 |
| Ikbke | CD4 T Cells | 9.96E−95 | 2.58E−90 | 1.066 | 0.483 | 0.122 |
| Rapgef6 | CD4 T Cells | 7.22E−93 | 1.87E−88 | 0.908 | 0.785 | 0.503 |
| Ms4a4b | CD4 T Cells | 2.41E−92 | 6.25E−88 | 0.976 | 0.62 | 0.199 |
| Arhgap15 | CD4 T Cells | 1.47E−91 | 3.81E−87 | 0.945 | 0.687 | 0.373 |
| Itk | CD4 T Cells | 1.44E−90 | 3.73E−86 | 1.035 | 0.55 | 0.164 |
| Tecpr1 | CD4 T Cells | 1.70E−89 | 4.40E−85 | 1.028 | 0.635 | 0.319 |
| Ms4a6b | CD4 T Cells | 1.66E−83 | 4.30E−79 | 0.985 | 0.613 | 0.261 |
| Il7r | CD4 T Cells | 5.22E−78 | 1.35E−73 | 0.737 | 0.728 | 0.356 |
| Slfn1 | CD4 T Cells | 1.10E−77 | 2.86E−73 | 0.939 | 0.404 | 0.09 |
| Rasal3 | CD4 T Cells | 8.30E−77 | 2.15E−72 | 0.925 | 0.617 | 0.309 |
| Srpk1 | CD4 T Cells | 1.08E−74 | 2.79E−70 | 0.824 | 0.585 | 0.322 |
| A630023P12Rik | CD4 T Cells | 1.64E−74 | 4.26E−70 | 0.832 | 0.261 | 0.031 |
| Traf3ip3 | CD4 T Cells | 2.22E−74 | 5.75E−70 | 0.886 | 0.646 | 0.323 |
| Fyb | CD4 T Cells | 2.40E−74 | 6.22E−70 | 0.779 | 0.789 | 0.488 |
| Pik3ip1 | CD4 T Cells | 9.90E−73 | 2.57E−68 | 0.867 | 0.65 | 0.367 |
| Tspan32 | CD4 T Cells | 6.00E−72 | 1.55E−67 | 0.904 | 0.457 | 0.143 |
| Cd247 | CD4 T Cells | 6.85E−72 | 1.78E−67 | 0.848 | 0.4 | 0.11 |
| Cd5 | CD4 T Cells | 3.93E−71 | 1.02E−66 | 0.949 | 0.361 | 0.076 |
| Gimap4 | CD4 T Cells | 1.46E−70 | 3.80E−66 | 0.919 | 0.589 | 0.226 |
| Ccnd3 | CD4 T Cells | 3.55E−70 | 9.22E−66 | 0.791 | 0.659 | 0.439 |
| Prkcq | CD4 T Cells | 1.88E−68 | 4.87E−64 | 0.873 | 0.452 | 0.136 |
| Galnt6 | CD4 T Cells | 9.01E−67 | 2.34E−62 | 0.948 | 0.446 | 0.165 |
| Kmt2d | CD4 T Cells | 1.27E−65 | 3.29E−61 | 0.796 | 0.689 | 0.465 |
| Cd27 | CD4 T Cells | 1.67E−65 | 4.34E−61 | 0.890 | 0.42 | 0.122 |
| Cd6 | CD4 T Cells | 2.36E−65 | 6.12E−61 | 0.874 | 0.346 | 0.076 |
| Scml4 | CD4 T Cells | 4.67E−65 | 1.21E−60 | 0.879 | 0.428 | 0.123 |
| Neb | CD4 T Cells | 2.76E−64 | 7.15E−60 | 1.410 | 0.226 | 0.038 |
| Plcg1 | CD4 T Cells | 2.96E−64 | 7.67E−60 | 0.822 | 0.485 | 0.231 |
| Slc12a7 | CD4 T Cells | 3.00E−64 | 7.78E−60 | 0.823 | 0.417 | 0.14 |
| Kif21b | CD4 T Cells | 4.66E−64 | 1.21E−59 | 0.768 | 0.702 | 0.448 |
| Cd4 | CD4 T Cells | 1.39E−63 | 3.61E−59 | 0.769 | 0.43 | 0.119 |
| Map4k2 | CD4 T Cells | 1.04E−62 | 2.70E−58 | 0.775 | 0.602 | 0.315 |
| Gramd1a | CD4 T Cells | 3.80E−62 | 9.84E−58 | 0.813 | 0.539 | 0.288 |
| Arhgef18 | CD4 T Cells | 6.25E−62 | 1.62E−57 | 0.806 | 0.652 | 0.339 |
| Pdk1 | CD4 T Cells | 2.97E−61 | 7.71E−57 | 0.763 | 0.393 | 0.157 |
| Dnah8 | CD4 T Cells | 2.86E−60 | 7.43E−56 | 1.058 | 0.376 | 0.102 |
| Ccdc88c | CD4 T Cells | 3.52E−60 | 9.14E−56 | 0.807 | 0.633 | 0.314 |
| Tnrc6b | CD4 T Cells | 1.05E−59 | 2.71E−55 | 0.769 | 0.626 | 0.424 |
| Trbc2 | CD4 T Cells | 2.55E−59 | 6.61E−55 | 0.813 | 0.489 | 0.159 |
| Ankrd55 | CD4 T Cells | 2.09E−57 | 5.42E−53 | 0.916 | 0.563 | 0.274 |
| Ablim1 | CD4 T Cells | 2.15E−57 | 5.59E−53 | 0.771 | 0.73 | 0.392 |
| mmu-mir-6236 | CD4 T Cells | 1.31E−56 | 3.40E−52 | 1.032 | 0.715 | 0.445 |
| Cd28 | CD4 T Cells | 1.95E−56 | 5.07E−52 | 0.837 | 0.352 | 0.094 |
| Tcf7 | CD4 T Cells | 2.11E−55 | 5.47E−51 | 0.833 | 0.567 | 0.243 |
| Znrf1 | CD4 T Cells | 8.04E−54 | 2.09E−49 | 0.786 | 0.515 | 0.283 |
| Kmt2a | CD4 T Cells | 1.27E−53 | 3.29E−49 | 0.727 | 0.757 | 0.577 |
| Faah | CD4 T Cells | 1.36E−52 | 3.52E−48 | 0.779 | 0.413 | 0.136 |
| Ets1 | CD4 T Cells | 4.96E−52 | 1.29E−47 | 0.655 | 0.772 | 0.461 |
| Tnrc6a | CD4 T Cells | 5.11E−52 | 1.32E−47 | 0.680 | 0.639 | 0.459 |
| Gm26551 | CD4 T Cells | 1.90E−50 | 4.93E−46 | 0.718 | 0.237 | 0.046 |
| Chd3 | CD4 T Cells | 9.41E−50 | 2.44E−45 | 0.738 | 0.626 | 0.411 |

TABLE 2-continued

Significant Cluster-Defining Genes for Cell Types Identified from the Steady State LN Cell Atlas

| Gene | Cell type | p-value | q-value | Average log fold change | % Expressing in Cluster | % Expressing Rest |
|---|---|---|---|---|---|---|
| Mdn1 | CD4 T Cells | 1.47E−49 | 3.81E−45 | 0.930 | 0.48 | 0.244 |
| Gm24245 | CD4 T Cells | 7.48E−49 | 1.94E−44 | 0.755 | 0.635 | 0.402 |
| Cd3d | CD4 T Cells | 8.44E−49 | 2.19E−44 | 0.662 | 0.315 | 0.082 |
| Smc4 | CD4 T Cells | 1.61E−48 | 4.16E−44 | 0.767 | 0.62 | 0.43 |
| Arhgap4 | CD4 T Cells | 2.08E−48 | 5.39E−44 | 0.704 | 0.576 | 0.331 |
| Ift80 | CD4 T Cells | 8.08E−48 | 2.09E−43 | 0.800 | 0.254 | 0.075 |
| Nlrc3 | CD4 T Cells | 6.30E−47 | 1.63E−42 | 0.731 | 0.391 | 0.141 |
| Rapgef4 | CD4 T Cells | 2.54E−46 | 6.60E−42 | 0.699 | 0.272 | 0.066 |
| Pydc4 | CD4 T Cells | 6.41E−46 | 1.66E−41 | 0.746 | 0.413 | 0.146 |
| Il27ra | CD4 T Cells | 1.38E−45 | 3.57E−41 | 0.693 | 0.32 | 0.113 |
| Tnik | CD4 T Cells | 1.09E−44 | 2.82E−40 | 0.766 | 0.313 | 0.093 |
| Fam78a | CD4 T Cells | 1.51E−44 | 3.91E−40 | 0.771 | 0.402 | 0.168 |
| Cd3g | CD4 T Cells | 3.81E−44 | 9.87E−40 | 0.689 | 0.335 | 0.095 |
| Gm14085 | CD4 T Cells | 7.96E−44 | 2.06E−39 | 0.734 | 0.204 | 0.033 |
| Dgkz | CD4 T Cells | 3.90E−43 | 1.01E−38 | 0.641 | 0.535 | 0.352 |
| Itpr2 | CD4 T Cells | 5.19E−43 | 1.35E−38 | 0.702 | 0.57 | 0.377 |
| Kbtbd11 | CD4 T Cells | 7.61E−43 | 1.97E−38 | 0.746 | 0.441 | 0.25 |
| Tmc6 | CD4 T Cells | 3.06E−41 | 7.94E−37 | 0.618 | 0.426 | 0.238 |
| Acap1 | CD4 T Cells | 1.31E−40 | 3.40E−36 | 0.696 | 0.58 | 0.343 |
| Gm15564 | CD4 T Cells | 2.99E−40 | 7.75E−36 | 0.711 | 0.898 | 0.671 |
| A430078G23Rik | CD4 T Cells | 6.90E−40 | 1.79E−35 | 0.626 | 0.35 | 0.124 |
| Rasgrp2 | CD4 T Cells | 7.93E−40 | 2.06E−35 | 0.627 | 0.474 | 0.234 |
| Skap1 | CD4 T Cells | 2.34E−37 | 6.07E−33 | 0.627 | 0.4 | 0.163 |
| S1pr1 | CD4 T Cells | 3.35E−37 | 8.70E−33 | 0.650 | 0.396 | 0.167 |
| Carns1 | CD4 T Cells | 6.56E−37 | 1.70E−32 | 0.690 | 0.398 | 0.184 |
| Ipcef1 | CD4 T Cells | 3.55E−36 | 9.21E−32 | 0.693 | 0.385 | 0.17 |
| Phf20l1 | CD4 T Cells | 1.06E−35 | 2.75E−31 | 0.618 | 0.504 | 0.352 |
| Gm26917 | CD4 T Cells | 3.85E−34 | 9.97E−30 | 0.685 | 0.804 | 0.651 |
| Cmah | CD4 T Cells | 5.41E−33 | 1.40E−28 | 0.645 | 0.472 | 0.24 |
| Trbc1 | CD4 T Cells | 8.03E−33 | 2.08E−28 | 0.707 | 0.304 | 0.116 |
| Actn1 | CD4 T Cells | 2.98E−32 | 7.73E−28 | 0.621 | 0.378 | 0.194 |
| Dennd2d | CD4 T Cells | 4.25E−32 | 1.10E−27 | 0.657 | 0.354 | 0.197 |
| Tmem71 | CD4 T Cells | 3.15E−30 | 8.16E−26 | 0.636 | 0.302 | 0.145 |
| Acp5 | CD4 T Cells | 5.47E−30 | 1.42E−25 | 0.623 | 0.352 | 0.165 |
| Camk4 | CD4 T Cells | 1.13E−29 | 2.92E−25 | 0.696 | 0.293 | 0.111 |
| Rasgrp1 | CD4 T Cells | 2.19E−29 | 5.68E−25 | 0.619 | 0.35 | 0.174 |
| Dgka | CD8 T Cells | 7.88E−302 | 2.04E−297 | 1.462 | 0.869 | 0.358 |
| Utrn | CD8 T Cells | 1.02E−261 | 2.65E−257 | 1.338 | 0.876 | 0.459 |
| 4932438A13Rik | CD8 T Cells | 5.62E−232 | 1.46E−227 | 1.310 | 0.848 | 0.472 |
| Macf1 | CD8 T Cells | 2.05E−215 | 5.32E−211 | 0.996 | 0.975 | 0.769 |
| Itk | CD8 T Cells | 7.42E−206 | 1.92E−201 | 1.304 | 0.629 | 0.148 |
| Ms4a4b | CD8 T Cells | 1.96E−188 | 5.07E−184 | 1.223 | 0.681 | 0.185 |
| Lat | CD8 T Cells | 6.52E−174 | 1.69E−169 | 1.161 | 0.625 | 0.164 |
| Arhgef1 | CD8 T Cells | 5.60E−170 | 1.45E−165 | 0.896 | 0.851 | 0.58 |
| Sidt1 | CD8 T Cells | 1.63E−167 | 4.22E−163 | 1.261 | 0.459 | 0.085 |
| Als2cl | CD8 T Cells | 2.09E−167 | 5.41E−163 | 1.207 | 0.544 | 0.129 |
| Gm24245 | CD8 T Cells | 2.69E−163 | 6.96E−159 | 1.146 | 0.752 | 0.387 |
| Lef1 | CD8 T Cells | 6.91E−161 | 1.79E−156 | 1.128 | 0.518 | 0.108 |
| Cd8b1 | CD8 T Cells | 4.07E−160 | 1.06E−155 | 1.192 | 0.49 | 0.083 |
| Lck | CD8 T Cells | 4.53E−153 | 1.17E−148 | 1.083 | 0.606 | 0.178 |
| Rapgef6 | CD8 T Cells | 5.28E−150 | 1.37E−145 | 0.984 | 0.798 | 0.495 |
| Cd8a | CD8 T Cells | 5.91E−148 | 1.53E−143 | 1.200 | 0.561 | 0.156 |
| Prkcq | CD8 T Cells | 1.40E−146 | 3.62E−142 | 1.094 | 0.527 | 0.122 |
| mt-Nd2 | CD8 T Cells | 1.14E−139 | 2.95E−135 | 0.768 | 0.932 | 0.739 |
| Cd27 | CD8 T Cells | 1.62E−132 | 4.21E−128 | 1.019 | 0.479 | 0.111 |
| Satb1 | CD8 T Cells | 6.44E−131 | 1.67E−126 | 0.972 | 0.705 | 0.318 |
| Rasal3 | CD8 T Cells | 2.40E−130 | 6.23E−126 | 0.943 | 0.648 | 0.299 |
| Ikbke | CD8 T Cells | 7.61E−126 | 1.97E−121 | 1.047 | 0.459 | 0.115 |
| Ankrd55 | CD8 T Cells | 2.18E−120 | 5.65E−116 | 1.063 | 0.634 | 0.261 |
| Fam78a | CD8 T Cells | 3.42E−117 | 8.88E−113 | 0.993 | 0.479 | 0.156 |
| Bcl11b | CD8 T Cells | 5.91E−113 | 1.53E−108 | 0.972 | 0.476 | 0.118 |
| Tecpr1 | CD8 T Cells | 1.69E−112 | 4.38E−108 | 0.930 | 0.628 | 0.312 |
| Il7r | CD8 T Cells | 4.66E−110 | 1.21E−105 | 0.789 | 0.74 | 0.346 |
| Slc12a7 | CD8 T Cells | 9.22E−110 | 2.39E−105 | 0.968 | 0.434 | 0.132 |
| Ms4a6b | CD8 T Cells | 2.22E−109 | 5.76E−105 | 0.926 | 0.597 | 0.254 |
| Inpp4b | CD8 T Cells | 1.62E−106 | 4.21E−102 | 0.955 | 0.501 | 0.155 |
| Arhgap15 | CD8 T Cells | 1.63E−106 | 4.22E−102 | 0.883 | 0.66 | 0.368 |
| Dnah8 | CD8 T Cells | 1.62E−105 | 4.20E−101 | 1.179 | 0.391 | 0.094 |
| Hmha1 | CD8 T Cells | 1.21E−104 | 3.14E−100 | 0.640 | 0.908 | 0.729 |
| Gramd1a | CD8 T Cells | 1.18E−103 | 3.06E−99 | 0.876 | 0.573 | 0.28 |
| Scml4 | CD8 T Cells | 1.86E−103 | 4.83E−99 | 0.953 | 0.433 | 0.116 |
| Prrc2c | CD8 T Cells | 4.61E−100 | 1.20E−95 | 0.699 | 0.826 | 0.662 |
| Arhgap9 | CD8 T Cells | 2.44E−99 | 6.32E−95 | 0.787 | 0.597 | 0.332 |

TABLE 2-continued

Significant Cluster-Defining Genes for Cell Types Identified from the Steady State LN Cell Atlas

| Gene | Cell type | p-value | q-value | Average log fold change | % Expressing in Cluster | % Expressing Rest |
|---|---|---|---|---|---|---|
| Traf3ip3 | CD8 T Cells | 1.13E−98 | 2.94E−94 | 0.848 | 0.638 | 0.316 |
| Pik3ip1 | CD8 T Cells | 1.09E−96 | 2.82E−92 | 0.840 | 0.651 | 0.36 |
| Gm25911 | CD8 T Cells | 2.11E−96 | 5.48E−92 | 0.874 | 0.775 | 0.487 |
| Kif21b | CD8 T Cells | 4.66E−96 | 1.21E−91 | 0.791 | 0.722 | 0.441 |
| Nlrc3 | CD8 T Cells | 9.83E−96 | 2.55E−91 | 0.888 | 0.446 | 0.131 |
| Fyb | CD8 T Cells | 1.97E−94 | 5.11E−90 | 0.689 | 0.793 | 0.481 |
| Themis | CD8 T Cells | 1.34E−92 | 3.48E−88 | 0.811 | 0.3 | 0.051 |
| Skap1 | CD8 T Cells | 1.80E−88 | 4.67E−84 | 0.833 | 0.47 | 0.152 |
| Slfn1 | CD8 T Cells | 1.92E−88 | 4.97E−84 | 0.883 | 0.362 | 0.085 |
| Gm14085 | CD8 T Cells | 2.38E−87 | 6.17E−83 | 0.852 | 0.233 | 0.027 |
| Kmt2d | CD8 T Cells | 1.13E−85 | 2.92E−81 | 0.762 | 0.675 | 0.461 |
| Gimap4 | CD8 T Cells | 2.20E−83 | 5.70E−79 | 0.800 | 0.552 | 0.22 |
| Ccnd3 | CD8 T Cells | 7.23E−80 | 1.87E−75 | 0.696 | 0.663 | 0.433 |
| Pydc4 | CD8 T Cells | 7.35E−80 | 1.91E−75 | 0.837 | 0.437 | 0.137 |
| Rnf213 | CD8 T Cells | 3.73E−79 | 9.66E−75 | 0.911 | 0.666 | 0.464 |
| Arhgap4 | CD8 T Cells | 8.99E−78 | 2.33E−73 | 0.729 | 0.592 | 0.324 |
| Ccdc88c | CD8 T Cells | 1.82E−77 | 4.72E−73 | 0.801 | 0.606 | 0.309 |
| Ipcef1 | CD8 T Cells | 1.45E−76 | 3.76E−72 | 0.810 | 0.421 | 0.162 |
| Cmah | CD8 T Cells | 2.16E−75 | 5.59E−71 | 0.787 | 0.544 | 0.229 |
| Kmt2a | CD8 T Cells | 1.23E−73 | 3.20E−69 | 0.676 | 0.777 | 0.571 |
| Galnt6 | CD8 T Cells | 1.34E−72 | 3.48E−68 | 0.800 | 0.431 | 0.16 |
| 2010016I18Rik | CD8 T Cells | 3.24E−72 | 8.40E−68 | 0.645 | 0.25 | 0.045 |
| Gm26917 | CD8 T Cells | 1.40E−71 | 3.62E−67 | 0.798 | 0.845 | 0.644 |
| Arhgef18 | CD8 T Cells | 1.81E−71 | 4.70E−67 | 0.685 | 0.613 | 0.334 |
| Tcf7 | CD8 T Cells | 2.92E−71 | 7.57E−67 | 0.648 | 0.554 | 0.237 |
| Tnik | CD8 T Cells | 9.80E−71 | 2.54E−66 | 0.784 | 0.328 | 0.086 |
| Txk | CD8 T Cells | 2.81E−70 | 7.28E−66 | 0.691 | 0.31 | 0.081 |
| mmu-mir-6236 | CD8 T Cells | 7.11E−69 | 1.84E−64 | 0.996 | 0.722 | 0.438 |
| Map4k2 | CD8 T Cells | 1.65E−68 | 4.27E−64 | 0.677 | 0.541 | 0.313 |
| Cd247 | CD8 T Cells | 4.84E−68 | 1.25E−63 | 0.713 | 0.343 | 0.107 |
| Grap2 | CD8 T Cells | 5.91E−68 | 1.53E−63 | 0.720 | 0.425 | 0.184 |
| Plgrkt | CD8 T Cells | 5.12E−67 | 1.33E−62 | 0.772 | 0.409 | 0.199 |
| Plcg1 | CD8 T Cells | 6.82E−67 | 1.77E−62 | 0.717 | 0.464 | 0.226 |
| Srpk1 | CD8 T Cells | 2.34E−66 | 6.07E−62 | 0.661 | 0.532 | 0.319 |
| Acap1 | CD8 T Cells | 2.91E−66 | 7.55E−62 | 0.692 | 0.603 | 0.336 |
| Mdn1 | CD8 T Cells | 3.91E−66 | 1.01E−61 | 0.903 | 0.455 | 0.241 |
| Zap70 | CD8 T Cells | 5.75E−66 | 1.49E−61 | 0.727 | 0.386 | 0.127 |
| Trbc2 | CD8 T Cells | 1.08E−65 | 2.81E−61 | 0.732 | 0.439 | 0.155 |
| Klrd1 | CD8 T Cells | 1.79E−65 | 4.65E−61 | 0.754 | 0.39 | 0.135 |
| Peli1 | CD8 T Cells | 1.85E−65 | 4.79E−61 | 0.686 | 0.526 | 0.348 |
| Samd9l | CD8 T Cells | 4.54E−65 | 1.18E−60 | 0.736 | 0.635 | 0.4 |
| Il27ra | CD8 T Cells | 4.64E−65 | 1.20E−60 | 0.681 | 0.331 | 0.107 |
| Cd3d | CD8 T Cells | 5.34E−65 | 1.38E−60 | 0.678 | 0.298 | 0.078 |
| Dennd2d | CD8 T Cells | 1.94E−64 | 5.03E−60 | 0.739 | 0.417 | 0.189 |
| Gpr114 | CD8 T Cells | 1.31E−62 | 3.40E−58 | 0.684 | 0.278 | 0.076 |
| Gm15564 | CD8 T Cells | 4.60E−62 | 1.19E−57 | 0.668 | 0.916 | 0.665 |
| Rinl | CD8 T Cells | 2.65E−60 | 6.87E−56 | 0.661 | 0.421 | 0.21 |
| Smc4 | CD8 T Cells | 4.62E−58 | 1.20E−53 | 0.701 | 0.619 | 0.425 |
| Trim12a | CD8 T Cells | 1.24E−57 | 3.22E−53 | 0.667 | 0.473 | 0.272 |
| Cd6 | CD8 T Cells | 8.28E−57 | 2.15E−52 | 0.655 | 0.288 | 0.074 |
| Tbc1d10c | CD8 T Cells | 4.26E−56 | 1.11E−51 | 0.618 | 0.545 | 0.322 |
| Ablim1 | CD8 T Cells | 6.28E−56 | 1.63E−51 | 0.621 | 0.651 | 0.39 |
| Itpr2 | CD8 T Cells | 1.21E−55 | 3.13E−51 | 0.681 | 0.585 | 0.371 |
| Dennd1c | CD8 T Cells | 7.23E−54 | 1.87E−49 | 0.612 | 0.471 | 0.292 |
| Cd5 | CD8 T Cells | 2.58E−52 | 6.69E−48 | 0.625 | 0.278 | 0.076 |
| Gramd3 | CD8 T Cells | 4.28E−52 | 1.11E−47 | 0.641 | 0.44 | 0.275 |
| Pdk1 | CD8 T Cells | 1.47E−49 | 3.82E−45 | 0.624 | 0.332 | 0.156 |
| Fyco1 | CD8 T Cells | 6.96E−46 | 1.80E−41 | 0.659 | 0.43 | 0.269 |
| Faah | CD8 T Cells | 7.33E−44 | 1.90E−39 | 0.684 | 0.341 | 0.135 |
| Acp5 | CD8 T Cells | 9.31E−44 | 2.41E−39 | 0.622 | 0.352 | 0.16 |
| Rasgrp2 | CD8 T Cells | 1.03E−41 | 2.68E−37 | 0.615 | 0.436 | 0.231 |
| Slfn8 | CD8 T Cells | 1.15E−40 | 2.97E−36 | 0.612 | 0.415 | 0.233 |
| Trbc1 | CD8 T Cells | 8.04E−39 | 2.08E−34 | 0.624 | 0.292 | 0.112 |
| Ppt1 | cDC1 (MacDC0) | 0 | 0 | 2.221 | 0.949 | 0.262 |
| Cst3 | cDC1 (MacDC0) | 0 | 0 | 2.024 | 0.989 | 0.562 |
| Naaa | cDC1 (MacDC0) | 0 | 0 | 1.872 | 0.825 | 0.132 |
| Wdfy4 | cDC1 (MacDC0) | 0 | 0 | 1.860 | 0.932 | 0.292 |
| Plbd1 | cDC1 (MacDC0) | 0 | 0 | 1.742 | 0.913 | 0.216 |
| A530099J19Rik | cDC1 (MacDC0) | 0 | 0 | 1.656 | 0.686 | 0.054 |
| 5430435G22Rik | cDC1 (MacDC0) | 0 | 0 | 1.610 | 0.71 | 0.055 |
| Snx22 | cDC1 (MacDC0) | 0 | 0 | 1.499 | 0.616 | 0.05 |
| Rab43 | cDC1 (MacDC0) | 0 | 0 | 1.476 | 0.898 | 0.36 |
| Clec9a | cDC1 (MacDC0) | 0 | 0 | 1.453 | 0.622 | 0.051 |

TABLE 2-continued

| Significant Cluster-Defining Genes for Cell Types Identified from the Steady State LN Cell Atlas | | | | | | |
|---|---|---|---|---|---|---|
| Gene | Cell type | p-value | q-value | Average log fold change | % Expressing in Cluster | % Expressing Rest |
| Mpeg1 | cDC1 (MacDC0) | 0 | 0 | 1.395 | 0.934 | 0.301 |
| H2-Eb1 | cDC1 (MacDC0) | 0 | 0 | 1.388 | 0.993 | 0.598 |
| H2-Ab1 | cDC1 (MacDC0) | 0 | 0 | 1.377 | 0.999 | 0.679 |
| Fgd2 | cDC1 (MacDC0) | 0 | 0 | 1.372 | 0.78 | 0.231 |
| Gcsam | cDC1 (MacDC0) | 0 | 0 | 1.356 | 0.581 | 0.037 |
| Xcr1 | cDC1 (MacDC0) | 0 | 0 | 1.337 | 0.565 | 0.031 |
| Tlr11 | cDC1 (MacDC0) | 0 | 0 | 1.268 | 0.549 | 0.043 |
| Ifi205 | cDC1 (MacDC0) | 0 | 0 | 1.262 | 0.554 | 0.047 |
| Havcr2 | cDC1 (MacDC0) | 0 | 0 | 1.255 | 0.603 | 0.076 |
| Naga | cDC1 (MacDC0) | 0 | 0 | 1.238 | 0.727 | 0.206 |
| Irf8 | cDC1 (MacDC0) | 0 | 0 | 1.208 | 0.951 | 0.446 |
| Psap | cDC1 (MacDC0) | 0 | 0 | 1.198 | 0.961 | 0.622 |
| H2-Aa | cDC1 (MacDC0) | 0 | 0 | 1.178 | 0.984 | 0.606 |
| Cd74 | cDC1 (MacDC0) | 0 | 0 | 1.085 | 0.989 | 0.628 |
| Gm2a | cDC1 (MacDC0) | 0.00E+00 | 4.75E−304 | 1.214 | 0.885 | 0.42 |
| Dock5 | cDC1 (MacDC0) | 5.27E−305 | 1.37E−300 | 1.214 | 0.69 | 0.158 |
| Tlr3 | cDC1 (MacDC0) | 2.39E−303 | 6.20E−299 | 1.056 | 0.473 | 0.041 |
| Mycl | cDC1 (MacDC0) | 3.97E−295 | 1.03E−290 | 1.115 | 0.542 | 0.07 |
| Pak1 | cDC1 (MacDC0) | 1.52E−288 | 3.93E−284 | 1.116 | 0.585 | 0.099 |
| Man2b1 | cDC1 (MacDC0) | 2.01E−287 | 5.22E−283 | 1.062 | 0.837 | 0.421 |
| Pdia5 | cDC1 (MacDC0) | 1.09E−282 | 2.84E−278 | 1.027 | 0.493 | 0.058 |
| Tbc1d9 | cDC1 (MacDC0) | 2.89E−267 | 7.49E−263 | 1.125 | 0.671 | 0.165 |
| Alox5ap | cDC1 (MacDC0) | 4.77E−261 | 1.24E−256 | 1.056 | 0.721 | 0.194 |
| Fnbp1 | cDC1 (MacDC0) | 2.57E−255 | 6.65E−251 | 0.934 | 0.881 | 0.573 |
| Anpep | cDC1 (MacDC0) | 2.82E−252 | 7.31E−248 | 0.965 | 0.487 | 0.064 |
| Mctp1 | cDC1 (MacDC0) | 6.19E−251 | 1.60E−246 | 0.939 | 0.475 | 0.06 |
| Cadm1 | cDC1 (MacDC0) | 3.32E−250 | 8.60E−246 | 1.060 | 0.458 | 0.056 |
| Dnase1l3 | cDC1 (MacDC0) | 6.23E−247 | 1.62E−242 | 1.315 | 0.523 | 0.089 |
| Ckb | cDC1 (MacDC0) | 2.38E−240 | 6.17E−236 | 0.969 | 0.508 | 0.082 |
| Atox1 | cDC1 (MacDC0) | 1.93E−238 | 5.00E−234 | 1.034 | 0.725 | 0.28 |
| Flt3 | cDC1 (MacDC0) | 1.19E−237 | 3.08E−233 | 0.798 | 0.818 | 0.303 |
| Eef1b2 | cDC1 (MacDC0) | 3.30E−237 | 8.55E−233 | 0.928 | 0.856 | 0.578 |
| 4930506M07Rik | cDC1 (MacDC0) | 1.78E−235 | 4.62E−231 | 1.012 | 0.581 | 0.13 |
| Sod1 | cDC1 (MacDC0) | 3.64E−234 | 9.43E−230 | 0.977 | 0.831 | 0.461 |
| 3-Sep | cDC1 (MacDC0) | 8.55E−233 | 2.22E−228 | 0.965 | 0.399 | 0.037 |
| Gusb | cDC1 (MacDC0) | 4.03E−226 | 1.05E−221 | 1.009 | 0.689 | 0.244 |
| Fuca1 | cDC1 (MacDC0) | 4.57E−225 | 1.18E−220 | 1.020 | 0.692 | 0.289 |
| Kit | cDC1 (MacDC0) | 4.71E−224 | 1.22E−219 | 0.925 | 0.599 | 0.141 |
| Aif1 | cDC1 (MacDC0) | 7.92E−222 | 2.05E−217 | 0.846 | 0.488 | 0.081 |
| H2-DMa | cDC1 (MacDC0) | 1.06E−220 | 2.76E−216 | 1.048 | 0.783 | 0.344 |
| Ece1 | cDC1 (MacDC0) | 6.04E−215 | 1.57E−210 | 0.974 | 0.601 | 0.162 |
| Sult1a1 | cDC1 (MacDC0) | 1.77E−214 | 4.58E−210 | 0.920 | 0.55 | 0.117 |
| Cdk14 | cDC1 (MacDC0) | 1.47E−213 | 3.82E−209 | 0.925 | 0.536 | 0.111 |
| Hepacam2 | cDC1 (MacDC0) | 3.96E−213 | 1.03E−208 | 0.772 | 0.314 | 0.018 |
| Ucp2 | cDC1 (MacDC0) | 5.45E−213 | 1.41E−208 | 0.895 | 0.818 | 0.48 |
| Fam149a | cDC1 (MacDC0) | 1.18E−211 | 3.05E−207 | 0.797 | 0.355 | 0.03 |
| Rasgrp4 | cDC1 (MacDC0) | 2.03E−211 | 5.27E−207 | 0.910 | 0.504 | 0.092 |
| Unc93b1 | cDC1 (MacDC0) | 3.19E−208 | 8.26E−204 | 0.855 | 0.792 | 0.357 |
| Gatm | cDC1 (MacDC0) | 1.29E−203 | 3.34E−199 | 0.803 | 0.374 | 0.04 |
| Fgl2 | cDC1 (MacDC0) | 1.08E−202 | 2.79E−198 | 0.942 | 0.607 | 0.166 |
| Cd207 | cDC1 (MacDC0) | 7.00E−197 | 1.81E−192 | 0.846 | 0.324 | 0.026 |
| Txndc15 | cDC1 (MacDC0) | 2.59E−195 | 6.70E−191 | 0.903 | 0.567 | 0.171 |
| Cyp27a1 | cDC1 (MacDC0) | 2.82E−195 | 7.32E−191 | 0.998 | 0.65 | 0.214 |
| H2-DMb1 | cDC1 (MacDC0) | 1.44E−194 | 3.73E−190 | 0.883 | 0.705 | 0.263 |
| Pik3cb | cDC1 (MacDC0) | 4.34E−192 | 1.12E−187 | 0.920 | 0.53 | 0.131 |
| Plekho2 | cDC1 (MacDC0) | 9.34E−184 | 2.42E−179 | 0.937 | 0.615 | 0.212 |
| Gm6377 | cDC1 (MacDC0) | 4.98E−172 | 1.29E−167 | 0.865 | 0.362 | 0.049 |
| Rgs2 | cDC1 (MacDC0) | 9.65E−170 | 2.50E−165 | 0.902 | 0.736 | 0.306 |
| Id2 | cDC1 (MacDC0) | 1.92E−167 | 4.97E−163 | 0.856 | 0.73 | 0.309 |
| Slc8b1 | cDC1 (MacDC0) | 1.12E−165 | 2.91E−161 | 0.752 | 0.396 | 0.069 |
| Ifngr1 | cDC1 (MacDC0) | 2.10E−165 | 5.46E−161 | 0.785 | 0.752 | 0.353 |
| Cd86 | cDC1 (MacDC0) | 5.33E−165 | 1.38E−160 | 0.777 | 0.49 | 0.117 |
| Myo9a | cDC1 (MacDC0) | 3.23E−164 | 8.38E−160 | 0.911 | 0.606 | 0.201 |
| BC028528 | cDC1 (MacDC0) | 2.80E−161 | 7.26E−157 | 0.732 | 0.403 | 0.077 |
| Adam8 | cDC1 (MacDC0) | 7.57E−160 | 1.96E−155 | 0.869 | 0.534 | 0.145 |
| Ciita | cDC1 (MacDC0) | 2.74E−159 | 7.11E−155 | 0.790 | 0.695 | 0.271 |
| Amica1 | cDC1 (MacDC0) | 6.08E−152 | 1.58E−147 | 0.737 | 0.601 | 0.21 |
| Atpif1 | cDC1 (MacDC0) | 5.66E−147 | 1.47E−142 | 0.792 | 0.59 | 0.235 |
| Irf5 | cDC1 (MacDC0) | 3.43E−145 | 8.88E−141 | 0.790 | 0.59 | 0.22 |
| Apobr | cDC1 (MacDC0) | 3.97E−143 | 1.03E−138 | 0.709 | 0.455 | 0.112 |
| Sh3bp1 | cDC1 (MacDC0) | 6.76E−142 | 1.75E−137 | 0.735 | 0.611 | 0.24 |
| Efhd2 | cDC1 (MacDC0) | 2.34E−141 | 6.06E−137 | 0.768 | 0.704 | 0.341 |
| Lrrk2 | cDC1 (MacDC0) | 3.82E−141 | 9.90E−137 | 0.715 | 0.603 | 0.215 |

TABLE 2-continued

Significant Cluster-Defining Genes for Cell Types Identified from the Steady State LN Cell Atlas

| Gene | Cell type | p-value | q-value | Average log fold change | % Expressing in Cluster | % Expressing Rest |
|---|---|---|---|---|---|---|
| Arsb | cDC1 (MacDC0) | 8.47E−140 | 2.20E−135 | 0.799 | 0.517 | 0.166 |
| Nlrp1b | cDC1 (MacDC0) | 3.72E−136 | 9.65E−132 | 0.819 | 0.3 | 0.041 |
| Inpp5d | cDC1 (MacDC0) | 4.79E−135 | 1.24E−130 | 0.724 | 0.747 | 0.429 |
| Rab32 | cDC1 (MacDC0) | 7.48E−133 | 1.94E−128 | 0.709 | 0.408 | 0.099 |
| Taldo1 | cDC1 (MacDC0) | 9.86E−132 | 2.56E−127 | 0.759 | 0.651 | 0.327 |
| Csf2ra | cDC1 (MacDC0) | 1.29E−131 | 3.34E−127 | 0.784 | 0.514 | 0.168 |
| Ppm1m | cDC1 (MacDC0) | 1.51E−131 | 3.93E−127 | 0.738 | 0.583 | 0.231 |
| Plek | cDC1 (MacDC0) | 2.49E−130 | 6.45E−126 | 0.857 | 0.629 | 0.255 |
| Dpy19l1 | cDC1 (MacDC0) | 9.70E−120 | 2.52E−115 | 0.728 | 0.535 | 0.203 |
| Camk1d | cDC1 (MacDC0) | 4.40E−114 | 1.14E−109 | 0.723 | 0.529 | 0.203 |
| Hspa8 | cDC1 (MacDC0) | 1.25E−107 | 3.24E−103 | 0.720 | 0.806 | 0.536 |
| Cxcl9 | cDC1 (MacDC0) | 3.00E−102 | 7.78E−98 | 1.208 | 0.229 | 0.031 |
| Btg2 | cDC1 (MacDC0) | 5.17E−97 | 1.34E−92 | 0.730 | 0.757 | 0.471 |
| Pmaip1 | cDC1 (MacDC0) | 1.12E−87 | 2.90E−83 | 0.768 | 0.472 | 0.187 |
| Nr4a2 | cDC1 (MacDC0) | 4.45E−67 | 1.15E−62 | 0.772 | 0.275 | 0.083 |
| Cd83 | cDC1 (MacDC0) | 5.30E−54 | 1.37E−49 | 0.723 | 0.423 | 0.212 |
| H2-Ab1 | cDC2 (MacDC2) | 1.61E−220 | 4.18E−216 | 1.159 | 0.938 | 0.689 |
| Ifi30 | cDC2 (MacDC2) | 1.89E−220 | 4.89E−216 | 1.263 | 0.701 | 0.365 |
| Gm2a | cDC2 (MacDC2) | 1.22E−194 | 3.18E−190 | 1.130 | 0.754 | 0.438 |
| Cd209a | cDC2 (MacDC2) | 9.51E−194 | 2.47E−189 | 1.049 | 0.329 | 0.027 |
| H2-Eb1 | cDC2 (MacDC2) | 1.23E−192 | 3.20E−188 | 1.154 | 0.885 | 0.613 |
| Cd74 | cDC2 (MacDC2) | 3.90E−179 | 1.01E−174 | 1.058 | 0.89 | 0.642 |
| Mgl2 | cDC2 (MacDC2) | 1.42E−175 | 3.69E−171 | 1.280 | 0.256 | 0.016 |
| H2-Aa | cDC2 (MacDC2) | 1.97E−173 | 5.10E−169 | 1.094 | 0.88 | 0.621 |
| Plbd1 | cDC2 (MacDC2) | 7.72E−169 | 2.00E−164 | 0.928 | 0.68 | 0.248 |
| Ctss | cDC2 (MacDC2) | 1.64E−156 | 4.25E−152 | 0.910 | 0.728 | 0.501 |
| H2-DMa | cDC2 (MacDC2) | 2.41E−156 | 6.26E−152 | 0.999 | 0.659 | 0.362 |
| Csf1r | cDC2 (MacDC2) | 3.34E−154 | 8.66E−150 | 0.929 | 0.376 | 0.063 |
| Ms4a6c | cDC2 (MacDC2) | 8.46E−153 | 2.19E−148 | 1.001 | 0.42 | 0.092 |
| Cd209d | cDC2 (MacDC2) | 9.97E−149 | 2.58E−144 | 1.351 | 0.292 | 0.039 |
| Cd300a | cDC2 (MacDC2) | 4.55E−142 | 1.18E−137 | 0.847 | 0.367 | 0.066 |
| Cd209e | cDC2 (MacDC2) | 4.54E−141 | 1.18E−136 | 1.150 | 0.194 | 0.007 |
| S100a4 | cDC2 (MacDC2) | 7.10E−140 | 1.84E−135 | 0.871 | 0.646 | 0.258 |
| Wfdc17 | cDC2 (MacDC2) | 3.92E−138 | 1.02E−133 | 0.839 | 0.315 | 0.045 |
| Ccl9 | cDC2 (MacDC2) | 3.55E−132 | 9.20E−128 | 1.056 | 0.321 | 0.052 |
| Fcer1g | cDC2 (MacDC2) | 3.13E−126 | 8.13E−122 | 0.922 | 0.595 | 0.243 |
| Abca9 | cDC2 (MacDC2) | 1.33E−125 | 3.46E−121 | 0.913 | 0.274 | 0.037 |
| Gpx1 | cDC2 (MacDC2) | 2.08E−124 | 5.38E−120 | 0.756 | 0.731 | 0.497 |
| Itgax | cDC2 (MacDC2) | 1.08E−118 | 2.80E−114 | 1.003 | 0.473 | 0.176 |
| Lgals3 | cDC2 (MacDC2) | 3.32E−112 | 8.61E−108 | 0.854 | 0.498 | 0.193 |
| Fcgrt | cDC2 (MacDC2) | 4.51E−112 | 1.17E−107 | 0.957 | 0.413 | 0.185 |
| Cfp | cDC2 (MacDC2) | 1.36E−105 | 3.52E−101 | 0.929 | 0.385 | 0.12 |
| Tyrobp | cDC2 (MacDC2) | 2.70E−103 | 7.00E−99 | 0.649 | 0.685 | 0.371 |
| Ubl3 | cDC2 (MacDC2) | 6.79E−97 | 1.76E−92 | 0.705 | 0.492 | 0.331 |
| Ptpro | cDC2 (MacDC2) | 4.43E−96 | 1.15E−91 | 0.664 | 0.291 | 0.062 |
| Flt3 | cDC2 (MacDC2) | 6.80E−95 | 1.76E−90 | 0.768 | 0.628 | 0.329 |
| Gfra2 | cDC2 (MacDC2) | 5.34E−91 | 1.38E−86 | 0.643 | 0.197 | 0.025 |
| Lyz2 | cDC2 (MacDC2) | 2.81E−86 | 7.28E−82 | 0.545 | 0.465 | 0.187 |
| H2-DMb1 | cDC2 (MacDC2) | 2.47E−85 | 6.41E−81 | 0.721 | 0.538 | 0.285 |
| Syngr2 | cDC2 (MacDC2) | 8.50E−85 | 2.20E−80 | 0.695 | 0.568 | 0.375 |
| Ctsh | cDC2 (MacDC2) | 5.54E−84 | 1.44E−79 | 0.650 | 0.63 | 0.403 |
| Sirpa | cDC2 (MacDC2) | 5.91E−83 | 1.53E−78 | 0.752 | 0.427 | 0.152 |
| Pirb | cDC2 (MacDC2) | 6.54E−80 | 1.70E−75 | 0.739 | 0.496 | 0.232 |
| Mefv | cDC2 (MacDC2) | 5.86E−78 | 1.52E−73 | 0.791 | 0.247 | 0.064 |
| Spi1 | cDC2 (MacDC2) | 1.17E−77 | 3.03E−73 | 0.706 | 0.513 | 0.266 |
| Pid1 | cDC2 (MacDC2) | 2.42E−77 | 6.27E−73 | 0.698 | 0.319 | 0.105 |
| Pip4k2a | cDC2 (MacDC2) | 6.73E−77 | 1.74E−72 | 0.613 | 0.586 | 0.411 |
| Cd200r1 | cDC2 (MacDC2) | 1.72E−76 | 4.47E−72 | 0.506 | 0.181 | 0.029 |
| AF251705 | cDC2 (MacDC2) | 1.80E−76 | 4.66E−72 | 0.680 | 0.283 | 0.075 |
| Il6ra | cDC2 (MacDC2) | 2.33E−75 | 6.03E−71 | 0.670 | 0.439 | 0.213 |
| Sulf2 | cDC2 (MacDC2) | 4.37E−75 | 1.13E−70 | 0.738 | 0.334 | 0.124 |
| Anxa5 | cDC2 (MacDC2) | 3.11E−73 | 8.05E−69 | 0.700 | 0.468 | 0.275 |
| Fam46a | cDC2 (MacDC2) | 4.11E−73 | 1.07E−68 | 0.804 | 0.404 | 0.187 |
| Zeb2 | cDC2 (MacDC2) | 8.49E−73 | 2.20E−68 | 0.761 | 0.479 | 0.216 |
| Ccdc88a | cDC2 (MacDC2) | 1.80E−72 | 4.68E−68 | 0.717 | 0.586 | 0.345 |
| Il13ra1 | cDC2 (MacDC2) | 3.17E−72 | 8.22E−68 | 0.632 | 0.312 | 0.106 |
| Napsa | cDC2 (MacDC2) | 5.24E−71 | 1.36E−66 | 0.640 | 0.512 | 0.299 |
| Klf4 | cDC2 (MacDC2) | 1.44E−69 | 3.73E−65 | 0.846 | 0.367 | 0.143 |
| Tifab | cDC2 (MacDC2) | 1.76E−69 | 4.56E−65 | 0.717 | 0.313 | 0.114 |
| Adrbk2 | cDC2 (MacDC2) | 2.98E−69 | 7.72E−65 | 0.719 | 0.462 | 0.209 |
| Ccr2 | cDC2 (MacDC2) | 1.16E−66 | 3.01E−62 | 0.733 | 0.44 | 0.208 |
| Clec10a | cDC2 (MacDC2) | 8.74E−66 | 2.27E−61 | 0.681 | 0.238 | 0.056 |
| Cd244 | cDC2 (MacDC2) | 2.47E−65 | 6.40E−61 | 0.585 | 0.311 | 0.099 |

TABLE 2-continued

Significant Cluster-Defining Genes for Cell Types Identified from the Steady State LN Cell Atlas

| Gene | Cell type | p-value | q-value | Average log fold change | % Expressing in Cluster | % Expressing Rest |
|---|---|---|---|---|---|---|
| Nfam1 | cDC2 (MacDC2) | 2.75E−65 | 7.14E−61 | 0.603 | 0.311 | 0.109 |
| Rgag4 | cDC2 (MacDC2) | 3.06E−65 | 7.94E−61 | 0.535 | 0.246 | 0.065 |
| Trappc5 | cDC2 (MacDC2) | 5.20E−65 | 1.35E−60 | 0.600 | 0.339 | 0.16 |
| Tep1 | cDC2 (MacDC2) | 5.76E−65 | 1.49E−60 | 0.666 | 0.431 | 0.238 |
| Cx3cr1 | cDC2 (MacDC2) | 1.05E−63 | 2.72E−59 | 0.535 | 0.2 | 0.038 |
| Alox5ap | cDC2 (MacDC2) | 5.79E−63 | 1.50E−58 | 0.591 | 0.48 | 0.225 |
| Fgfr1 | cDC2 (MacDC2) | 3.64E−62 | 9.44E−58 | 0.605 | 0.287 | 0.098 |
| Tmem176b | cDC2 (MacDC2) | 3.10E−61 | 8.05E−57 | 0.594 | 0.546 | 0.291 |
| Il1b | cDC2 (MacDC2) | 6.25E−61 | 1.62E−56 | 1.139 | 0.28 | 0.089 |
| Prcp | cDC2 (MacDC2) | 2.04E−59 | 5.30E−55 | 0.564 | 0.414 | 0.228 |
| Igsf6 | cDC2 (MacDC2) | 2.26E−59 | 5.85E−55 | 0.570 | 0.257 | 0.072 |
| Rnd3 | cDC2 (MacDC2) | 4.72E−57 | 1.22E−52 | 0.591 | 0.344 | 0.133 |
| Rab43 | cDC2 (MacDC2) | 1.79E−56 | 4.64E−52 | 0.470 | 0.599 | 0.398 |
| Fcgr2b | cDC2 (MacDC2) | 2.26E−55 | 5.86E−51 | 0.690 | 0.352 | 0.165 |
| Cybb | cDC2 (MacDC2) | 4.18E−55 | 1.08E−50 | 0.484 | 0.468 | 0.23 |
| Ramp1 | cDC2 (MacDC2) | 6.26E−55 | 1.62E−50 | 0.580 | 0.405 | 0.2 |
| Rassf4 | cDC2 (MacDC2) | 4.46E−54 | 1.16E−49 | 0.624 | 0.52 | 0.287 |
| Fos | cDC2 (MacDC2) | 1.55E−53 | 4.03E−49 | 0.676 | 0.565 | 0.331 |
| Ly86 | cDC2 (MacDC2) | 3.25E−53 | 8.43E−49 | 0.579 | 0.389 | 0.198 |
| Lyn | cDC2 (MacDC2) | 1.21E−52 | 3.14E−48 | 0.552 | 0.528 | 0.325 |
| Gpr141 | cDC2 (MacDC2) | 1.92E−52 | 4.98E−48 | 0.507 | 0.202 | 0.051 |
| Cyp4f16 | cDC2 (MacDC2) | 1.98E−52 | 5.14E−48 | 0.571 | 0.262 | 0.092 |
| Cbfa2t3 | cDC2 (MacDC2) | 6.21E−52 | 1.61E−47 | 0.627 | 0.446 | 0.236 |
| Fam105a | cDC2 (MacDC2) | 6.50E−52 | 1.68E−47 | 0.540 | 0.436 | 0.263 |
| 1810033B17Rik | cDC2 (MacDC2) | 1.10E−51 | 2.85E−47 | 0.478 | 0.213 | 0.057 |
| Rgl1 | cDC2 (MacDC2) | 6.98E−50 | 1.81E−45 | 0.498 | 0.238 | 0.074 |
| 5031439G07Rik | cDC2 (MacDC2) | 3.35E−49 | 8.69E−45 | 0.566 | 0.396 | 0.214 |
| Fgd2 | cDC2 (MacDC2) | 1.62E−48 | 4.19E−44 | 0.525 | 0.501 | 0.267 |
| Ybx3 | cDC2 (MacDC2) | 3.08E−48 | 8.00E−44 | 0.591 | 0.404 | 0.254 |
| Rgs2 | cDC2 (MacDC2) | 2.71E−46 | 7.02E−42 | 0.597 | 0.543 | 0.331 |
| Atf3 | cDC2 (MacDC2) | 1.29E−45 | 3.36E−41 | 0.823 | 0.303 | 0.129 |
| Fgr | cDC2 (MacDC2) | 5.07E−45 | 1.32E−40 | 0.455 | 0.324 | 0.133 |
| S100a6 | cDC2 (MacDC2) | 2.35E−44 | 6.09E−40 | 0.477 | 0.404 | 0.213 |
| Alcam | cDC2 (MacDC2) | 3.48E−43 | 9.03E−39 | 0.485 | 0.331 | 0.168 |
| Ctnna1 | cDC2 (MacDC2) | 4.27E−41 | 1.11E−36 | 0.521 | 0.463 | 0.313 |
| Rnf150 | cDC2 (MacDC2) | 4.53E−41 | 1.17E−36 | 0.514 | 0.248 | 0.096 |
| Pmaip1 | cDC2 (MacDC2) | 1.19E−39 | 3.09E−35 | 0.634 | 0.365 | 0.201 |
| Evi2a | cDC2 (MacDC2) | 1.46E−39 | 3.79E−35 | 0.489 | 0.366 | 0.203 |
| Tbc1d9 | cDC2 (MacDC2) | 5.30E−38 | 1.37E−33 | 0.520 | 0.387 | 0.2 |
| Themis2 | cDC2 (MacDC2) | 6.53E−35 | 1.69E−30 | 0.468 | 0.349 | 0.181 |
| Bcl11a | cDC2 (MacDC2) | 4.09E−33 | 1.06E−28 | 0.489 | 0.4 | 0.222 |
| Rasa4 | cDC2 (MacDC2) | 8.36E−31 | 2.17E−26 | 0.479 | 0.387 | 0.23 |
| Plek | cDC2 (MacDC2) | 2.48E−25 | 6.44E−21 | 0.474 | 0.434 | 0.28 |
| Cyp1b1 | LEC 1 | 5.20E−142 | 1.35E−137 | 3.243 | 0.986 | 0.038 |
| Cpe | LEC 1 | 8.16E−141 | 2.11E−136 | 3.400 | 0.986 | 0.03 |
| Cd55 | LEC 1 | 1.21E−123 | 3.13E−119 | 2.544 | 1 | 0.147 |
| Clu | LEC 1 | 9.93E−123 | 2.57E−118 | 3.233 | 1 | 0.164 |
| Madcam1 | LEC 1 | 1.71E−120 | 4.43E−116 | 2.225 | 0.903 | 0.009 |
| Jam3 | LEC 1 | 2.36E−112 | 6.13E−108 | 2.352 | 0.917 | 0.028 |
| Astn1 | LEC 1 | 2.98E−112 | 7.74E−108 | 1.981 | 0.819 | 0.007 |
| Sema3a | LEC 1 | 8.53E−112 | 2.21E−107 | 2.225 | 0.875 | 0.009 |
| Dsg2 | LEC 1 | 4.77E−109 | 1.24E−104 | 2.677 | 0.944 | 0.028 |
| Postn | LEC 1 | 3.56E−107 | 9.23E−103 | 3.169 | 0.889 | 0.02 |
| Creg2 | LEC 1 | 1.28E−105 | 3.31E−101 | 2.263 | 0.847 | 0.011 |
| Sema3d | LEC 1 | 2.10E−105 | 5.44E−101 | 2.197 | 0.903 | 0.014 |
| Csf1 | LEC 1 | 4.18E−103 | 1.08E−98 | 2.483 | 0.972 | 0.072 |
| Prox1 | LEC 1 | 6.15E−101 | 1.60E−96 | 2.136 | 0.861 | 0.014 |
| Tspan7 | LEC 1 | 4.07E−100 | 1.05E−95 | 2.181 | 0.861 | 0.032 |
| C1ql3 | LEC 1 | 1.21E−99 | 3.15E−95 | 1.712 | 0.764 | 0.006 |
| Ltbp2 | LEC 1 | 1.65E−99 | 4.28E−95 | 2.453 | 0.917 | 0.057 |
| Serpina3n | LEC 1 | 2.26E−98 | 5.85E−94 | 2.720 | 0.931 | 0.033 |
| Cldn11 | LEC 1 | 1.44E−92 | 3.74E−88 | 1.607 | 0.806 | 0.013 |
| Timp3 | LEC 1 | 2.90E−91 | 7.52E−87 | 2.541 | 0.944 | 0.05 |
| Arhgap29 | LEC 1 | 8.20E−91 | 2.13E−86 | 2.241 | 0.917 | 0.057 |
| Fxyd6 | LEC 1 | 2.54E−89 | 6.59E−85 | 1.549 | 0.792 | 0.012 |
| Kdr | LEC 1 | 1.13E−88 | 2.92E−84 | 2.354 | 0.931 | 0.048 |
| Slc38a4 | LEC 1 | 3.43E−87 | 8.90E−83 | 1.414 | 0.722 | 0.007 |
| Ptprm | LEC 1 | 1.49E−86 | 3.86E−82 | 1.858 | 0.833 | 0.025 |
| Itga2b | LEC 1 | 2.13E−85 | 5.53E−81 | 2.071 | 0.792 | 0.023 |
| App | LEC 1 | 3.64E−85 | 9.44E−81 | 2.138 | 0.944 | 0.221 |
| Plvap | LEC 1 | 9.83E−85 | 2.55E−80 | 2.090 | 0.944 | 0.059 |
| Stab1 | LEC 1 | 8.22E−83 | 2.13E−78 | 1.707 | 0.819 | 0.023 |
| Bmp2 | LEC 1 | 9.31E−83 | 2.41E−78 | 1.634 | 0.764 | 0.014 |

TABLE 2-continued

Significant Cluster-Defining Genes for Cell Types Identified from the Steady State LN Cell Atlas

| Gene | Cell type | p-value | q-value | Average log fold change | % Expressing in Cluster | % Expressing Rest |
|---|---|---|---|---|---|---|
| Ces2g | LEC 1 | 2.66E−82 | 6.89E−78 | 1.674 | 0.792 | 0.021 |
| Ces2e | LEC 1 | 1.69E−80 | 4.38E−76 | 1.389 | 0.667 | 0.007 |
| Tgm2 | LEC 1 | 4.14E−79 | 1.07E−74 | 2.037 | 0.889 | 0.049 |
| Clec1a | LEC 1 | 3.00E−78 | 7.78E−74 | 1.845 | 0.792 | 0.026 |
| Mmp9 | LEC 1 | 3.15E−76 | 8.18E−72 | 1.689 | 0.722 | 0.015 |
| Phldb2 | LEC 1 | 3.30E−76 | 8.55E−72 | 1.860 | 0.792 | 0.027 |
| Lyve1 | LEC 1 | 1.07E−75 | 2.77E−71 | 2.533 | 0.778 | 0.022 |
| Timp4 | LEC 1 | 3.54E−75 | 9.18E−71 | 1.604 | 0.667 | 0.008 |
| Mmrn2 | LEC 1 | 1.01E−74 | 2.63E−70 | 1.718 | 0.819 | 0.029 |
| Rasip1 | LEC 1 | 9.49E−73 | 2.46E−68 | 1.692 | 0.833 | 0.041 |
| Glycam1 | LEC 1 | 1.38E−72 | 3.57E−68 | 1.641 | 0.944 | 0.089 |
| Igfbp4 | LEC 1 | 9.14E−72 | 2.37E−67 | 1.945 | 0.903 | 0.068 |
| Smad1 | LEC 1 | 1.04E−70 | 2.69E−66 | 1.857 | 0.917 | 0.146 |
| Ptprk | LEC 1 | 1.48E−70 | 3.84E−66 | 1.461 | 0.736 | 0.022 |
| Coch | LEC 1 | 2.79E−70 | 7.24E−66 | 2.738 | 0.542 | 0.003 |
| Pvrl2 | LEC 1 | 1.53E−69 | 3.98E−65 | 1.593 | 0.764 | 0.028 |
| Gna12 | LEC 1 | 6.90E−69 | 1.79E−64 | 1.619 | 0.889 | 0.124 |
| Itga9 | LEC 1 | 1.34E−68 | 3.48E−64 | 1.766 | 0.764 | 0.028 |
| Col12a1 | LEC 1 | 2.05E−68 | 5.31E−64 | 1.772 | 0.681 | 0.015 |
| Clca1 | LEC 1 | 3.10E−68 | 8.04E−64 | 1.569 | 0.694 | 0.017 |
| Sparc | LEC 1 | 3.26E−68 | 8.45E−64 | 1.400 | 0.875 | 0.069 |
| Ptpn14 | LEC 1 | 5.08E−67 | 1.32E−62 | 1.736 | 0.736 | 0.034 |
| Gng12 | LEC 1 | 6.80E−67 | 1.76E−62 | 1.848 | 0.847 | 0.137 |
| Cdh5 | LEC 1 | 3.94E−66 | 1.02E−61 | 1.834 | 0.875 | 0.059 |
| Lifr | LEC 1 | 5.81E−66 | 1.51E−61 | 1.970 | 0.944 | 0.174 |
| Lrg1 | LEC 1 | 6.63E−65 | 1.72E−60 | 1.446 | 0.792 | 0.041 |
| C3 | LEC 1 | 3.70E−64 | 9.61E−60 | 1.546 | 0.806 | 0.1 |
| Tjp1 | LEC 1 | 9.95E−63 | 2.58E−58 | 1.609 | 0.778 | 0.038 |
| Cp | LEC 1 | 1.00E−61 | 2.59E−57 | 1.604 | 0.819 | 0.052 |
| Igf1 | LEC 1 | 1.15E−61 | 2.99E−57 | 1.580 | 0.694 | 0.023 |
| Nfib | LEC 1 | 2.99E−61 | 7.76E−57 | 1.422 | 0.819 | 0.053 |
| Tgfbr3 | LEC 1 | 7.69E−61 | 1.99E−56 | 1.930 | 0.847 | 0.089 |
| Gria3 | LEC 1 | 1.13E−60 | 2.94E−56 | 1.681 | 0.847 | 0.072 |
| Vcam1 | LEC 1 | 1.04E−59 | 2.70E−55 | 1.899 | 0.861 | 0.075 |
| Amotl1 | LEC 1 | 1.56E−59 | 4.05E−55 | 1.602 | 0.764 | 0.041 |
| Tmem2 | LEC 1 | 1.69E−59 | 4.38E−55 | 1.599 | 0.806 | 0.06 |
| Il33 | LEC 1 | 6.49E−59 | 1.68E−54 | 1.459 | 0.681 | 0.022 |
| Maf | LEC 1 | 9.40E−59 | 2.44E−54 | 1.808 | 0.833 | 0.095 |
| Nudt4 | LEC 1 | 9.13E−58 | 2.37E−53 | 1.771 | 0.889 | 0.151 |
| Calcrl | LEC 1 | 1.49E−56 | 3.87E−52 | 1.713 | 0.806 | 0.108 |
| Sema5a | LEC 1 | 4.88E−56 | 1.27E−51 | 1.647 | 0.597 | 0.02 |
| F8 | LEC 1 | 6.03E−56 | 1.56E−51 | 2.004 | 0.667 | 0.027 |
| Timp2 | LEC 1 | 6.58E−56 | 1.71E−51 | 1.593 | 0.931 | 0.13 |
| Lama4 | LEC 1 | 1.27E−55 | 3.29E−51 | 1.480 | 0.722 | 0.035 |
| Tspan3 | LEC 1 | 2.75E−55 | 7.12E−51 | 1.674 | 0.944 | 0.231 |
| Lamb3 | LEC 1 | 3.38E−55 | 8.77E−51 | 1.590 | 0.583 | 0.016 |
| Mme | LEC 1 | 2.92E−54 | 7.57E−50 | 1.395 | 0.583 | 0.014 |
| Msr1 | LEC 1 | 6.72E−54 | 1.74E−49 | 1.748 | 0.556 | 0.018 |
| Nceh1 | LEC 1 | 3.62E−53 | 9.39E−49 | 1.582 | 0.792 | 0.114 |
| Efnb2 | LEC 1 | 1.44E−52 | 3.72E−48 | 1.538 | 0.694 | 0.038 |
| Flrt3 | LEC 1 | 1.98E−52 | 5.13E−48 | 1.440 | 0.611 | 0.021 |
| Nid1 | LEC 1 | 2.20E−52 | 5.70E−48 | 1.601 | 0.722 | 0.051 |
| Cpd | LEC 1 | 1.74E−51 | 4.51E−47 | 1.620 | 0.861 | 0.146 |
| Arrdc4 | LEC 1 | 2.27E−51 | 5.89E−47 | 1.557 | 0.806 | 0.093 |
| Cfh | LEC 1 | 2.24E−50 | 5.82E−46 | 1.422 | 0.681 | 0.038 |
| Uxs1 | LEC 1 | 8.41E−50 | 2.18E−45 | 1.509 | 0.722 | 0.082 |
| Birc2 | LEC 1 | 1.63E−49 | 4.22E−45 | 1.549 | 0.903 | 0.297 |
| Arhgef12 | LEC 1 | 5.58E−48 | 1.45E−43 | 1.523 | 0.833 | 0.121 |
| Nedd4 | LEC 1 | 1.07E−47 | 2.77E−43 | 1.463 | 0.931 | 0.333 |
| Ppfibp1 | LEC 1 | 1.33E−47 | 3.46E−43 | 1.483 | 0.778 | 0.116 |
| Ifitm3 | LEC 1 | 4.33E−47 | 1.12E−42 | 1.585 | 0.917 | 0.153 |
| Slc43a3 | LEC 1 | 7.46E−46 | 1.93E−41 | 1.388 | 0.792 | 0.096 |
| Serpina3g | LEC 1 | 2.73E−45 | 7.08E−41 | 1.586 | 0.833 | 0.161 |
| Sepp1 | LEC 1 | 1.14E−44 | 2.95E−40 | 1.782 | 0.931 | 0.258 |
| Prnp | LEC 1 | 5.39E−44 | 1.40E−39 | 1.639 | 0.722 | 0.089 |
| Il6st | LEC 1 | 1.07E−42 | 2.77E−38 | 1.442 | 0.931 | 0.348 |
| Man1a | LEC 1 | 1.10E−41 | 2.84E−37 | 1.426 | 0.931 | 0.36 |
| Ano6 | LEC 1 | 2.15E−41 | 5.59E−37 | 1.453 | 0.889 | 0.241 |
| Fn1 | LEC 1 | 1.47E−36 | 3.82E−32 | 1.555 | 0.597 | 0.047 |
| H1f0 | LEC 1 | 1.07E−32 | 2.77E−28 | 1.387 | 0.75 | 0.167 |
| Mmrn1 | LEC 2 | 3.95E−181 | 1.02E−176 | 2.980 | 0.757 | 0.009 |
| Stab2 | LEC 2 | 1.19E−176 | 3.08E−172 | 2.837 | 0.743 | 0.011 |
| Clca1 | LEC 2 | 2.37E−171 | 6.15E−167 | 2.391 | 0.765 | 0.011 |

TABLE 2-continued

Significant Cluster-Defining Genes for Cell Types Identified from the Steady State LN Cell Atlas

| Gene | Cell type | p-value | q-value | Average log fold change | % Expressing in Cluster | % Expressing Rest |
|---|---|---|---|---|---|---|
| Sepp1 | LEC 2 | 4.17E−164 | 1.08E−159 | 3.024 | 0.897 | 0.254 |
| Tnc | LEC 2 | 9.08E−154 | 2.35E−149 | 2.719 | 0.684 | 0.017 |
| Lyve1 | LEC 2 | 1.12E−152 | 2.91E−148 | 3.674 | 0.721 | 0.018 |
| Timp3 | LEC 2 | 4.77E−151 | 1.24E−146 | 2.694 | 0.86 | 0.045 |
| Prox1 | LEC 2 | 3.81E−143 | 9.89E−139 | 2.087 | 0.721 | 0.011 |
| Cpe | LEC 2 | 5.47E−139 | 1.42E−134 | 2.134 | 0.779 | 0.026 |
| Sema3d | LEC 2 | 1.20E−136 | 3.11E−132 | 2.228 | 0.684 | 0.011 |
| Stab1 | LEC 2 | 1.68E−136 | 4.36E−132 | 2.276 | 0.691 | 0.02 |
| Kdr | LEC 2 | 2.63E−136 | 6.81E−132 | 2.417 | 0.801 | 0.044 |
| Fxyd6 | LEC 2 | 3.05E−133 | 7.90E−129 | 1.774 | 0.654 | 0.009 |
| Phldb2 | LEC 2 | 1.70E−131 | 4.40E−127 | 1.940 | 0.721 | 0.023 |
| Jam3 | LEC 2 | 8.17E−129 | 2.12E−124 | 1.755 | 0.728 | 0.025 |
| Sdpr | LEC 2 | 1.70E−125 | 4.40E−121 | 2.171 | 0.647 | 0.023 |
| Flt4 | LEC 2 | 1.32E−120 | 3.42E−116 | 1.983 | 0.596 | 0.011 |
| Cldn5 | LEC 2 | 1.31E−118 | 3.41E−114 | 1.356 | 0.581 | 0.007 |
| F8 | LEC 2 | 2.06E−117 | 5.35E−113 | 2.440 | 0.654 | 0.023 |
| Cp | LEC 2 | 4.78E−111 | 1.24E−106 | 2.089 | 0.787 | 0.047 |
| Tbx1 | LEC 2 | 2.72E−109 | 7.05E−105 | 1.380 | 0.566 | 0.009 |
| Tgfa | LEC 2 | 5.38E−106 | 1.40E−101 | 1.427 | 0.544 | 0.008 |
| Tgm2 | LEC 2 | 5.10E−105 | 1.32E−100 | 1.867 | 0.721 | 0.046 |
| Tjp1 | LEC 2 | 1.42E−102 | 3.69E−98 | 1.694 | 0.684 | 0.034 |
| Aplp2 | LEC 2 | 4.06E−102 | 1.05E−97 | 1.900 | 0.801 | 0.259 |
| Creg2 | LEC 2 | 1.79E−101 | 4.65E−97 | 1.635 | 0.559 | 0.01 |
| Igfbp7 | LEC 2 | 2.18E−101 | 5.64E−97 | 2.156 | 0.831 | 0.081 |
| Il6st | LEC 2 | 3.59E−101 | 9.30E−97 | 1.949 | 0.794 | 0.346 |
| Cyp4b1 | LEC 2 | 5.48E−101 | 1.42E−96 | 1.527 | 0.5 | 0.005 |
| Plvap | LEC 2 | 1.31E−100 | 3.39E−96 | 1.653 | 0.765 | 0.056 |
| Fabp4 | LEC 2 | 3.09E−98 | 8.01E−94 | 2.110 | 0.625 | 0.022 |
| Nid1 | LEC 2 | 6.58E−97 | 1.71E−92 | 1.716 | 0.721 | 0.047 |
| Lama4 | LEC 2 | 1.55E−96 | 4.02E−92 | 1.749 | 0.662 | 0.031 |
| Cdh5 | LEC 2 | 2.39E−96 | 6.18E−92 | 1.835 | 0.735 | 0.056 |
| Tie1 | LEC 2 | 3.95E−96 | 1.02E−91 | 1.320 | 0.625 | 0.022 |
| Ptprb | LEC 2 | 2.27E−95 | 5.90E−91 | 1.651 | 0.625 | 0.023 |
| Pvrl2 | LEC 2 | 2.72E−95 | 7.05E−91 | 1.445 | 0.61 | 0.026 |
| Ptprm | LEC 2 | 2.14E−94 | 5.56E−90 | 1.363 | 0.618 | 0.022 |
| Erg | LEC 2 | 2.03E−93 | 5.27E−89 | 1.269 | 0.588 | 0.018 |
| Dock9 | LEC 2 | 3.39E−93 | 8.79E−89 | 1.831 | 0.691 | 0.089 |
| Itga9 | LEC 2 | 7.83E−93 | 2.03E−88 | 1.817 | 0.581 | 0.026 |
| Sema3a | LEC 2 | 1.16E−92 | 3.01E−88 | 1.449 | 0.507 | 0.009 |
| Cd55 | LEC 2 | 2.92E−92 | 7.56E−88 | 1.893 | 0.794 | 0.144 |
| Cyp1b1 | LEC 2 | 1.61E−91 | 4.17E−87 | 1.875 | 0.676 | 0.036 |
| Stt3b | LEC 2 | 7.52E−91 | 1.95E−86 | 1.616 | 0.691 | 0.271 |
| Arhgap29 | LEC 2 | 2.01E−90 | 5.22E−86 | 1.738 | 0.691 | 0.054 |
| Gpr116 | LEC 2 | 2.71E−90 | 7.04E−86 | 1.962 | 0.618 | 0.026 |
| Cd36 | LEC 2 | 1.96E−87 | 5.08E−83 | 2.192 | 0.581 | 0.068 |
| S100a16 | LEC 2 | 9.71E−87 | 2.52E−82 | 1.278 | 0.559 | 0.02 |
| Angpt2 | LEC 2 | 1.06E−86 | 2.76E−82 | 1.812 | 0.471 | 0.016 |
| Nfib | LEC 2 | 1.55E−86 | 4.03E−82 | 1.518 | 0.706 | 0.049 |
| Clec1a | LEC 2 | 2.09E−86 | 5.42E−82 | 1.479 | 0.574 | 0.024 |
| App | LEC 2 | 8.69E−86 | 2.25E−81 | 1.784 | 0.809 | 0.218 |
| Fmo1 | LEC 2 | 1.30E−85 | 3.37E−81 | 1.323 | 0.515 | 0.015 |
| Fibin | LEC 2 | 2.10E−85 | 5.44E−81 | 1.393 | 0.397 | 0.003 |
| Nudt4 | LEC 2 | 5.33E−83 | 1.38E−78 | 1.846 | 0.743 | 0.148 |
| Kank3 | LEC 2 | 6.41E−82 | 1.66E−77 | 1.437 | 0.64 | 0.044 |
| Egfl7 | LEC 2 | 3.10E−80 | 8.04E−76 | 1.264 | 0.574 | 0.029 |
| Ltbp4 | LEC 2 | 4.08E−80 | 1.06E−75 | 1.910 | 0.596 | 0.035 |
| Nr2f2 | LEC 2 | 1.08E−78 | 2.80E−74 | 1.375 | 0.618 | 0.038 |
| Ptpn14 | LEC 2 | 6.21E−78 | 1.61E−73 | 1.319 | 0.574 | 0.032 |
| Col12a1 | LEC 2 | 7.09E−78 | 1.84E−73 | 1.556 | 0.485 | 0.013 |
| Maf | LEC 2 | 1.07E−77 | 2.77E−73 | 1.523 | 0.721 | 0.092 |
| Igfbp4 | LEC 2 | 1.48E−76 | 3.83E−72 | 1.853 | 0.647 | 0.066 |
| Rasip1 | LEC 2 | 3.99E−76 | 1.03E−71 | 1.301 | 0.596 | 0.039 |
| Mmrn2 | LEC 2 | 2.96E−75 | 7.67E−71 | 1.463 | 0.559 | 0.028 |
| Tmem2 | LEC 2 | 8.54E−75 | 2.21E−70 | 1.533 | 0.625 | 0.057 |
| Mgll | LEC 2 | 1.35E−71 | 3.49E−67 | 1.586 | 0.515 | 0.033 |
| Ppfibp1 | LEC 2 | 2.04E−71 | 5.28E−67 | 1.481 | 0.669 | 0.113 |
| Itga2b | LEC 2 | 1.24E−70 | 3.21E−66 | 1.379 | 0.507 | 0.022 |
| Reln | LEC 2 | 4.06E−70 | 1.05E−65 | 1.615 | 0.39 | 0.009 |
| Tgfbr3 | LEC 2 | 1.73E−69 | 4.49E−65 | 1.561 | 0.669 | 0.086 |
| Slc43a3 | LEC 2 | 1.02E−68 | 2.65E−64 | 1.555 | 0.669 | 0.093 |
| Timp2 | LEC 2 | 2.30E−68 | 5.97E−64 | 1.551 | 0.735 | 0.128 |
| Smad1 | LEC 2 | 4.33E−67 | 1.12E−62 | 1.427 | 0.669 | 0.144 |
| Csf1 | LEC 2 | 1.93E−66 | 5.01E−62 | 1.509 | 0.654 | 0.071 |

TABLE 2-continued

Significant Cluster-Defining Genes for Cell Types Identified from the Steady State LN Cell Atlas

| Gene | Cell type | p-value | q-value | Average log fold change | % Expressing in Cluster | % Expressing Rest |
|---|---|---|---|---|---|---|
| Cts1 | LEC 2 | 7.60E−65 | 1.97E−60 | 1.742 | 0.721 | 0.127 |
| F2r | LEC 2 | 1.00E−64 | 2.60E−60 | 1.459 | 0.64 | 0.072 |
| Fstl1 | LEC 2 | 6.78E−64 | 1.76E−59 | 1.488 | 0.551 | 0.04 |
| Ifitm3 | LEC 2 | 8.04E−63 | 2.09E−58 | 1.475 | 0.787 | 0.15 |
| Timp4 | LEC 2 | 8.78E−59 | 2.28E−54 | 1.293 | 0.36 | 0.008 |
| Ltbp2 | LEC 2 | 4.61E−58 | 1.20E−53 | 1.515 | 0.566 | 0.056 |
| Gng12 | LEC 2 | 2.26E−57 | 5.87E−53 | 1.349 | 0.618 | 0.136 |
| Nedd4 | LEC 2 | 1.61E−55 | 4.17E−51 | 1.347 | 0.794 | 0.331 |
| Lepr | LEC 2 | 1.07E−54 | 2.77E−50 | 1.374 | 0.493 | 0.037 |
| Tm4sf1 | LEC 2 | 1.32E−54 | 3.42E−50 | 1.396 | 0.441 | 0.025 |
| Btbd3 | LEC 2 | 1.98E−54 | 5.12E−50 | 1.279 | 0.493 | 0.049 |
| Crim1 | LEC 2 | 7.36E−54 | 1.91E−49 | 1.302 | 0.566 | 0.072 |
| Snrk | LEC 2 | 2.55E−52 | 6.62E−48 | 1.317 | 0.632 | 0.17 |
| Arhgef7 | LEC 2 | 1.87E−50 | 4.86E−46 | 1.282 | 0.662 | 0.175 |
| Tns1 | LEC 2 | 1.97E−50 | 5.11E−46 | 1.446 | 0.625 | 0.136 |
| Plcb4 | LEC 2 | 1.56E−49 | 4.06E−45 | 1.271 | 0.581 | 0.108 |
| Ctsd | LEC 2 | 6.36E−48 | 1.65E−43 | 1.276 | 0.735 | 0.268 |
| Sned1 | LEC 2 | 5.88E−47 | 1.52E−42 | 1.368 | 0.566 | 0.082 |
| Ndrg1 | LEC 2 | 7.15E−46 | 1.85E−41 | 1.293 | 0.647 | 0.159 |
| Mrc1 | LEC 2 | 2.20E−45 | 5.71E−41 | 1.532 | 0.426 | 0.036 |
| Apold1 | LEC 2 | 3.06E−40 | 7.92E−36 | 1.320 | 0.331 | 0.017 |
| KCTD12 | LEC 2 | 6.90E−39 | 1.79E−34 | 1.266 | 0.669 | 0.251 |
| Cyr61 | LEC 2 | 9.77E−39 | 2.53E−34 | 1.634 | 0.346 | 0.026 |
| Prss23 | LEC 2 | 5.13E−26 | 1.33E−21 | 1.321 | 0.265 | 0.023 |
| Lyz2 | Macrophages (MacDC3) | 0 | 0 | 3.243 | 0.941 | 0.189 |
| Pla2g7 | Macrophages (MacDC3) | 8.23E−259 | 2.13E−254 | 2.115 | 0.769 | 0.041 |
| Clec4a3 | Macrophages (MacDC3) | 3.11E−184 | 8.07E−180 | 1.521 | 0.566 | 0.024 |
| Igsf6 | Macrophages (MacDC3) | 7.61E−180 | 1.97E−175 | 1.615 | 0.691 | 0.07 |
| Ctss | Macrophages (MacDC3) | 1.69E−167 | 4.37E−163 | 1.484 | 0.931 | 0.51 |
| Sirpa | Macrophages (MacDC3) | 3.20E−164 | 8.29E−160 | 1.570 | 0.797 | 0.158 |
| Cybb | Macrophages (MacDC3) | 2.25E−137 | 5.83E−133 | 1.594 | 0.828 | 0.235 |
| Tgfbi | Macrophages (MacDC3) | 2.47E−137 | 6.40E−133 | 1.561 | 0.781 | 0.178 |
| Fcgr3 | Macrophages (MacDC3) | 3.80E−133 | 9.84E−129 | 1.219 | 0.509 | 0.034 |
| Fcer1g | Macrophages (MacDC3) | 1.41E−132 | 3.66E−128 | 1.480 | 0.822 | 0.259 |
| Ccl6 | Macrophages (MacDC3) | 9.68E−130 | 2.51E−125 | 1.728 | 0.569 | 0.065 |
| Emr4 | Macrophages (MacDC3) | 2.83E−123 | 7.35E−119 | 1.347 | 0.425 | 0.023 |
| Lilrb4 | Macrophages (MacDC3) | 2.97E−122 | 7.70E−118 | 1.088 | 0.525 | 0.046 |
| Ms4a6c | Macrophages (MacDC3) | 4.22E−122 | 1.10E−117 | 1.387 | 0.634 | 0.107 |
| Zeb2 | Macrophages (MacDC3) | 5.08E−122 | 1.32E−117 | 1.305 | 0.803 | 0.223 |
| Cd300a | Macrophages (MacDC3) | 3.59E−121 | 9.31E−117 | 1.182 | 0.603 | 0.078 |
| Gda | Macrophages (MacDC3) | 8.04E−118 | 2.08E−113 | 1.213 | 0.484 | 0.038 |
| Lrp1 | Macrophages (MacDC3) | 2.32E−117 | 6.02E−113 | 1.260 | 0.569 | 0.066 |
| F13a1 | Macrophages (MacDC3) | 6.21E−117 | 1.61E−112 | 1.557 | 0.334 | 0.007 |
| Tyrobp | Macrophages (MacDC3) | 8.72E−117 | 2.26E−112 | 1.142 | 0.922 | 0.384 |
| Lgals3 | Macrophages (MacDC3) | 1.13E−114 | 2.94E−110 | 1.480 | 0.722 | 0.206 |
| Klra2 | Macrophages (MacDC3) | 6.03E−113 | 1.56E−108 | 1.082 | 0.319 | 0.007 |
| Gpx1 | Macrophages (MacDC3) | 9.20E−112 | 2.39E−107 | 1.251 | 0.897 | 0.508 |
| Psap | Macrophages (MacDC3) | 7.24E−111 | 1.88E−106 | 1.197 | 0.95 | 0.649 |
| Apobec1 | Macrophages (MacDC3) | 1.77E−110 | 4.58E−106 | 1.206 | 0.647 | 0.133 |
| Mafb | Macrophages (MacDC3) | 3.66E−110 | 9.48E−106 | 1.300 | 0.325 | 0.011 |
| Hp | Macrophages (MacDC3) | 5.71E−110 | 1.48E−105 | 1.332 | 0.384 | 0.021 |
| Ifitm3 | Macrophages (MacDC3) | 3.83E−108 | 9.93E−104 | 1.603 | 0.634 | 0.143 |
| C1qb | Macrophages (MacDC3) | 7.85E−108 | 2.04E−103 | 2.058 | 0.284 | 0.007 |
| Ccl9 | Macrophages (MacDC3) | 1.00E−107 | 2.60E−103 | 1.259 | 0.538 | 0.063 |
| Ctsb | Macrophages (MacDC3) | 6.59E−107 | 1.71E−102 | 1.434 | 0.791 | 0.41 |
| Lamp1 | Macrophages (MacDC3) | 1.44E−106 | 3.74E−102 | 1.267 | 0.828 | 0.392 |
| AF251705 | Macrophages (MacDC3) | 5.95E−106 | 1.54E−101 | 1.199 | 0.547 | 0.08 |
| Ifi204 | Macrophages (MacDC3) | 3.54E−105 | 9.18E−101 | 1.248 | 0.428 | 0.042 |
| Gngt2 | Macrophages (MacDC3) | 5.54E−103 | 1.44E−98 | 1.288 | 0.541 | 0.101 |
| C1qc | Macrophages (MacDC3) | 1.19E−100 | 3.08E−96 | 1.786 | 0.266 | 0.006 |
| Plac8 | Macrophages (MacDC3) | 8.87E−98 | 2.30E−93 | 1.682 | 0.625 | 0.262 |
| Clec4a1 | Macrophages (MacDC3) | 1.76E−97 | 4.57E−93 | 0.877 | 0.391 | 0.025 |
| Apoc2 | Macrophages (MacDC3) | 3.48E−94 | 9.01E−90 | 0.882 | 0.247 | 0.003 |
| Itgam | Macrophages (MacDC3) | 4.10E−94 | 1.06E−89 | 1.158 | 0.484 | 0.059 |
| Gsr | Macrophages (MacDC3) | 6.51E−92 | 1.69E−87 | 1.153 | 0.544 | 0.102 |
| Msrb1 | Macrophages (MacDC3) | 1.69E−90 | 4.39E−86 | 1.094 | 0.522 | 0.104 |
| Lst1 | Macrophages (MacDC3) | 9.83E−88 | 2.55E−83 | 0.938 | 0.416 | 0.045 |
| Clqa | Macrophages (MacDC3) | 1.05E−87 | 2.73E−83 | 1.877 | 0.241 | 0.008 |
| Apoe | Macrophages (MacDC3) | 5.21E−87 | 1.35E−82 | 1.577 | 0.753 | 0.297 |
| AI607873 | Macrophages (MacDC3) | 1.25E−83 | 3.23E−79 | 1.143 | 0.534 | 0.105 |
| Fth1 | Macrophages (MacDC3) | 7.98E−82 | 2.07E−77 | 1.161 | 0.941 | 0.712 |
| Axl | Macrophages (MacDC3) | 1.07E−81 | 2.78E−77 | 1.204 | 0.341 | 0.035 |
| Xdh | Macrophages (MacDC3) | 5.64E−79 | 1.46E−74 | 1.143 | 0.534 | 0.112 |

TABLE 2-continued

Significant Cluster-Defining Genes for Cell Types Identified from the Steady State LN Cell Atlas

| Gene | Cell type | p-value | q-value | Average log fold change | % Expressing in Cluster | % Expressing Rest |
|---|---|---|---|---|---|---|
| Ace | Macrophages (MacDC3) | 1.16E−78 | 3.01E−74 | 1.375 | 0.322 | 0.025 |
| Ctsa | Macrophages (MacDC3) | 2.48E−78 | 6.43E−74 | 0.990 | 0.728 | 0.32 |
| Emilin2 | Macrophages (MacDC3) | 1.66E−77 | 4.30E−73 | 0.895 | 0.356 | 0.032 |
| Pirb | Macrophages (MacDC3) | 2.16E−74 | 5.61E−70 | 1.042 | 0.706 | 0.243 |
| Ctsc | Macrophages (MacDC3) | 1.36E−73 | 3.54E−69 | 1.088 | 0.644 | 0.247 |
| Cd68 | Macrophages (MacDC3) | 4.19E−72 | 1.09E−67 | 1.051 | 0.491 | 0.111 |
| Slc11a1 | Macrophages (MacDC3) | 7.72E−71 | 2.00E−66 | 0.917 | 0.381 | 0.049 |
| Ctsz | Macrophages (MacDC3) | 8.08E−71 | 2.10E−66 | 1.069 | 0.7 | 0.37 |
| Cebpb | Macrophages (MacDC3) | 1.81E−69 | 4.70E−65 | 0.973 | 0.397 | 0.062 |
| Fcgr2b | Macrophages (MacDC3) | 7.78E−69 | 2.02E−64 | 1.114 | 0.569 | 0.171 |
| Gpr141 | Macrophages (MacDC3) | 5.35E−67 | 1.39E−62 | 1.006 | 0.381 | 0.055 |
| Lyz1 | Macrophages (MacDC3) | 1.56E−66 | 4.06E−62 | 2.312 | 0.25 | 0.03 |
| Siglec1 | Macrophages (MacDC3) | 3.46E−66 | 8.96E−62 | 0.854 | 0.166 | 0.001 |
| Ccr2 | Macrophages (MacDC3) | 7.04E−66 | 1.83E−61 | 1.274 | 0.597 | 0.218 |
| Spi1 | Macrophages (MacDC3) | 1.03E−64 | 2.67E−60 | 0.898 | 0.709 | 0.276 |
| Cyba | Macrophages (MacDC3) | 4.80E−64 | 1.24E−59 | 0.858 | 0.806 | 0.482 |
| Cx3cr1 | Macrophages (MacDC3) | 5.06E−64 | 1.31E−59 | 1.033 | 0.338 | 0.044 |
| Lyn | Macrophages (MacDC3) | 2.34E−61 | 6.06E−57 | 0.894 | 0.734 | 0.332 |
| Sdc3 | Macrophages (MacDC3) | 7.23E−61 | 1.87E−56 | 1.013 | 0.441 | 0.124 |
| Tpd52 | Macrophages (MacDC3) | 1.42E−60 | 3.68E−56 | 0.928 | 0.569 | 0.187 |
| Lgmn | Macrophages (MacDC3) | 3.47E−60 | 9.00E−56 | 1.002 | 0.469 | 0.142 |
| Ncf2 | Macrophages (MacDC3) | 2.04E−59 | 5.29E−55 | 0.922 | 0.478 | 0.119 |
| Smpdl3a | Macrophages (MacDC3) | 2.12E−59 | 5.50E−55 | 0.994 | 0.488 | 0.155 |
| Tnfrsf1b | Macrophages (MacDC3) | 3.53E−59 | 9.15E−55 | 0.925 | 0.622 | 0.217 |
| Chi3l3 | Macrophages (MacDC3) | 2.62E−57 | 6.79E−53 | 0.947 | 0.212 | 0.013 |
| Ap1s2 | Macrophages (MacDC3) | 3.79E−57 | 9.82E−53 | 0.949 | 0.366 | 0.09 |
| Itm2b | Macrophages (MacDC3) | 1.70E−56 | 4.40E−52 | 0.909 | 0.841 | 0.642 |
| Nadk | Macrophages (MacDC3) | 4.79E−56 | 1.24E−51 | 0.920 | 0.616 | 0.27 |
| Prdx5 | Macrophages (MacDC3) | 4.92E−56 | 1.27E−51 | 0.985 | 0.522 | 0.19 |
| Myo1f | Macrophages (MacDC3) | 8.22E−53 | 2.13E−48 | 0.912 | 0.603 | 0.216 |
| Bach1 | Macrophages (MacDC3) | 7.14E−52 | 1.85E−47 | 0.919 | 0.534 | 0.192 |
| Lgals3bp | Macrophages (MacDC3) | 1.36E−51 | 3.52E−47 | 0.988 | 0.531 | 0.221 |
| Sat1 | Macrophages (MacDC3) | 2.61E−50 | 6.76E−46 | 0.898 | 0.625 | 0.292 |
| Ifi30 | Macrophages (MacDC3) | 3.66E−49 | 9.48E−45 | 0.947 | 0.744 | 0.387 |
| Ninj1 | Macrophages (MacDC3) | 1.23E−48 | 3.19E−44 | 0.874 | 0.366 | 0.094 |
| Vcam1 | Macrophages (MacDC3) | 1.96E−47 | 5.07E−43 | 1.563 | 0.272 | 0.074 |
| Cfp | Macrophages (MacDC3) | 1.73E−45 | 4.47E−41 | 1.076 | 0.416 | 0.137 |
| Slc43a2 | Macrophages (MacDC3) | 2.85E−44 | 7.39E−40 | 0.869 | 0.584 | 0.24 |
| Ifi27l2a | Macrophages (MacDC3) | 2.25E−43 | 5.85E−39 | 0.966 | 0.466 | 0.158 |
| Acp2 | Macrophages (MacDC3) | 2.86E−43 | 7.42E−39 | 0.875 | 0.353 | 0.104 |
| Ctsd | Macrophages (MacDC3) | 6.36E−43 | 1.65E−38 | 1.021 | 0.538 | 0.266 |
| Rgs2 | Macrophages (MacDC3) | 7.23E−40 | 1.87E−35 | 0.873 | 0.709 | 0.34 |
| Sepp1 | Macrophages (MacDC3) | 4.28E−38 | 1.11E−33 | 1.316 | 0.575 | 0.252 |
| Pltp | Macrophages (MacDC3) | 5.94E−37 | 1.54E−32 | 0.981 | 0.341 | 0.084 |
| Irf7 | Macrophages (MacDC3) | 3.24E−34 | 8.39E−30 | 0.893 | 0.488 | 0.221 |
| Fos | Macrophages (MacDC3) | 8.24E−33 | 2.14E−28 | 0.859 | 0.675 | 0.343 |
| Dusp1 | Macrophages (MacDC3) | 2.17E−29 | 5.63E−25 | 0.863 | 0.509 | 0.264 |
| Atf3 | Macrophages (MacDC3) | 3.32E−27 | 8.62E−23 | 1.044 | 0.375 | 0.139 |
| Fn1 | Macrophages (MacDC3) | 1.64E−22 | 4.26E−18 | 1.176 | 0.206 | 0.046 |
| Ly6c2 | Macrophages (MacDC3) | 5.13E−20 | 1.33E−15 | 0.935 | 0.359 | 0.156 |
| Mcpt4 | Mast Cells | 8.62E−62 | 2.23E−57 | 4.696 | 0.92 | 0.002 |
| Tpsb2 | Mast Cells | 1.42E−59 | 3.67E−55 | 4.270 | 0.88 | 0.002 |
| Cpa3 | Mast Cells | 4.44E−58 | 1.15E−53 | 4.685 | 0.88 | 0.004 |
| Cma1 | Mast Cells | 4.53E−55 | 1.17E−50 | 4.519 | 0.8 | 0.005 |
| Gata2 | Mast Cells | 1.26E−54 | 3.28E−50 | 3.320 | 0.8 | 0.015 |
| Hdc | Mast Cells | 1.83E−42 | 4.73E−38 | 3.386 | 0.8 | 0.016 |
| Mrgprb1 | Mast Cells | 1.18E−40 | 3.06E−36 | 3.036 | 0.6 | 0 |
| Serpinb1a | Mast Cells | 7.12E−38 | 1.85E−33 | 2.827 | 0.8 | 0.113 |
| Slc6a4 | Mast Cells | 1.27E−37 | 3.29E−33 | 2.447 | 0.56 | 0.004 |
| Tpsab1 | Mast Cells | 1.24E−36 | 3.22E−32 | 2.594 | 0.64 | 0.001 |
| Kit | Mast Cells | 8.95E−33 | 2.32E−28 | 2.568 | 0.8 | 0.188 |
| Ccl7 | Mast Cells | 3.68E−32 | 9.55E−28 | 2.553 | 0.68 | 0.007 |
| Fcer1a | Mast Cells | 6.74E−32 | 1.75E−27 | 2.487 | 0.52 | 0.001 |
| Slc18a2 | Mast Cells | 1.20E−31 | 3.12E−27 | 1.873 | 0.56 | 0.001 |
| Mrgprb2 | Mast Cells | 2.03E−29 | 5.26E−25 | 1.333 | 0.44 | 0 |
| Cyp11a1 | Mast Cells | 1.08E−28 | 2.79E−24 | 2.003 | 0.48 | 0.001 |
| Tph1 | Mast Cells | 3.63E−27 | 9.40E−23 | 1.395 | 0.44 | 0 |
| Slc45a3 | Mast Cells | 8.29E−27 | 2.15E−22 | 1.796 | 0.6 | 0.012 |
| Rab27b | Mast Cells | 1.97E−26 | 5.10E−22 | 1.827 | 0.56 | 0.006 |
| Il1rl1 | Mast Cells | 5.54E−26 | 1.44E−21 | 2.421 | 0.6 | 0.01 |
| Ccl2 | Mast Cells | 7.35E−25 | 1.91E−20 | 2.152 | 0.64 | 0.014 |
| Ndrg1 | Mast Cells | 8.84E−25 | 2.29E−20 | 2.285 | 0.76 | 0.165 |
| Mrgprx2 | Mast Cells | 2.87E−24 | 7.45E−20 | 1.304 | 0.4 | 0 |

TABLE 2-continued

Significant Cluster-Defining Genes for Cell Types Identified from the Steady State LN Cell Atlas

| Gene | Cell type | p-value | q-value | Average log fold change | % Expressing in Cluster | % Expressing Rest |
|---|---|---|---|---|---|---|
| Slc7a8 | Mast Cells | 6.66E−23 | 1.73E−18 | 1.783 | 0.44 | 0.008 |
| Hs6st2 | Mast Cells | 6.19E−22 | 1.60E−17 | 1.275 | 0.44 | 0.003 |
| Kcne3 | Mast Cells | 2.42E−20 | 6.27E−16 | 1.284 | 0.44 | 0.006 |
| Atp8b5 | Mast Cells | 4.26E−20 | 1.11E−15 | 1.442 | 0.4 | 0.002 |
| Padi2 | Mast Cells | 7.22E−20 | 1.87E−15 | 1.953 | 0.64 | 0.143 |
| Gnai1 | Mast Cells | 9.53E−20 | 2.47E−15 | 1.615 | 0.48 | 0.009 |
| Osbpl8 | Mast Cells | 7.25E−19 | 1.88E−14 | 1.705 | 0.64 | 0.301 |
| Smarca1 | Mast Cells | 9.48E−18 | 2.46E−13 | 1.198 | 0.4 | 0.003 |
| Creb3l1 | Mast Cells | 3.02E−17 | 7.84E−13 | 1.210 | 0.44 | 0.008 |
| Rab44 | Mast Cells | 8.22E−17 | 2.13E−12 | 1.249 | 0.48 | 0.009 |
| Stard13 | Mast Cells | 1.48E−16 | 3.84E−12 | 1.355 | 0.4 | 0.008 |
| Tmem64 | Mast Cells | 1.29E−15 | 3.33E−11 | 1.645 | 0.64 | 0.152 |
| Vwa5a | Mast Cells | 3.24E−14 | 8.39E−10 | 1.686 | 0.64 | 0.181 |
| Jun | Mast Cells | 5.38E−14 | 1.39E−09 | 1.812 | 0.96 | 0.322 |
| Chst1 | Mast Cells | 9.62E−14 | 2.49E−09 | 1.446 | 0.48 | 0.023 |
| Maob | Mast Cells | 1.06E−13 | 2.76E−09 | 1.110 | 0.4 | 0.009 |
| Adora3 | Mast Cells | 1.71E−13 | 4.44E−09 | 1.137 | 0.44 | 0.015 |
| Plek | Mast Cells | 3.29E−13 | 8.54E−09 | 1.869 | 0.72 | 0.294 |
| Cgnl1 | Mast Cells | 3.57E−13 | 9.26E−09 | 1.466 | 0.44 | 0.026 |
| Cobl | Mast Cells | 4.18E−13 | 1.08E−08 | 1.270 | 0.36 | 0.008 |
| Junb | Mast Cells | 4.72E−13 | 1.23E−08 | 1.275 | 1 | 0.49 |
| Pmp22 | Mast Cells | 6.49E−13 | 1.68E−08 | 1.353 | 0.44 | 0.019 |
| Asph | Mast Cells | 9.27E−13 | 2.40E−08 | 1.449 | 0.48 | 0.07 |
| Egr1 | Mast Cells | 1.30E−12 | 3.38E−08 | 1.740 | 0.8 | 0.199 |
| Tmem158 | Mast Cells | 1.34E−12 | 3.47E−08 | 1.166 | 0.4 | 0.015 |
| Srgn | Mast Cells | 1.99E−12 | 5.17E−08 | 1.264 | 0.92 | 0.534 |
| Mitf | Mast Cells | 2.30E−12 | 5.96E−08 | 1.423 | 0.4 | 0.031 |
| Pdxk | Mast Cells | 3.66E−12 | 9.49E−08 | 1.419 | 0.52 | 0.139 |
| Gp49a | Mast Cells | 4.72E−12 | 1.22E−07 | 1.473 | 0.52 | 0.034 |
| Papss2 | Mast Cells | 7.40E−12 | 1.92E−07 | 1.503 | 0.52 | 0.072 |
| Fam129b | Mast Cells | 1.16E−11 | 3.00E−07 | 1.326 | 0.52 | 0.078 |
| Emilin2 | Mast Cells | 1.25E−11 | 3.24E−07 | 1.572 | 0.48 | 0.042 |
| Ldha | Mast Cells | 2.55E−11 | 6.61E−07 | 1.286 | 0.64 | 0.383 |
| Plau | Mast Cells | 4.10E−11 | 1.06E−06 | 1.205 | 0.36 | 0.016 |
| Tns1 | Mast Cells | 6.94E−11 | 1.80E−06 | 1.675 | 0.6 | 0.141 |
| Nr4a1 | Mast Cells | 1.51E−10 | 3.92E−06 | 1.383 | 0.88 | 0.276 |
| Slc7a5 | Mast Cells | 2.36E−10 | 6.13E−06 | 1.244 | 0.4 | 0.056 |
| Fosb | Mast Cells | 2.66E−10 | 6.90E−06 | 1.847 | 0.76 | 0.207 |
| Ago2 | Mast Cells | 4.31E−10 | 1.12E−05 | 1.288 | 0.76 | 0.32 |
| Cd63 | Mast Cells | 4.48E−10 | 1.16E−05 | 1.577 | 0.56 | 0.135 |
| Tmem9 | Mast Cells | 5.89E−10 | 1.53E−05 | 1.183 | 0.44 | 0.057 |
| Nfkbiz | Mast Cells | 6.99E−10 | 1.81E−05 | 1.592 | 0.76 | 0.299 |
| Slc29a1 | Mast Cells | 7.33E−10 | 1.90E−05 | 1.200 | 0.56 | 0.097 |
| Nr4a3 | Mast Cells | 8.73E−10 | 2.26E−05 | 1.864 | 0.6 | 0.126 |
| Rgs2 | Mast Cells | 1.50E−09 | 3.89E−05 | 1.195 | 0.92 | 0.351 |
| Hpgds | Mast Cells | 1.68E−09 | 4.35E−05 | 1.110 | 0.36 | 0.019 |
| Rgs1 | Mast Cells | 1.90E−09 | 4.92E−05 | 1.496 | 0.76 | 0.188 |
| Lilrb4 | Mast Cells | 2.07E−09 | 5.38E−05 | 1.378 | 0.48 | 0.06 |
| Hes1 | Mast Cells | 2.64E−09 | 6.83E−05 | 1.352 | 0.4 | 0.032 |
| Sqstm1 | Mast Cells | 3.35E−09 | 8.68E−05 | 1.216 | 0.8 | 0.427 |
| Fcer1g | Mast Cells | 7.05E−09 | 0.000182772 | 1.339 | 0.84 | 0.277 |
| Ext1 | Mast Cells | 7.08E−09 | 0.000183616 | 1.162 | 0.56 | 0.111 |
| Ly6a | Mast Cells | 1.23E−08 | 0.00031804 | 1.269 | 0.6 | 0.171 |
| Suco | Mast Cells | 2.71E−08 | 0.00070318 | 1.252 | 0.6 | 0.289 |
| Itga9 | Mast Cells | 7.73E−08 | 0.002004172 | 1.116 | 0.4 | 0.033 |
| Lat2 | Mast Cells | 8.38E−08 | 0.002173099 | 1.123 | 0.44 | 0.122 |
| Rabgef1 | Mast Cells | 9.71E−08 | 0.002517376 | 1.224 | 0.44 | 0.128 |
| Tgfbr1 | Mast Cells | 1.40E−07 | 0.003624539 | 1.223 | 0.52 | 0.174 |
| Itm2c | Mast Cells | 1.41E−07 | 0.003662846 | 1.200 | 0.68 | 0.447 |
| Zeb2 | Mast Cells | 1.69E−07 | 0.004374148 | 1.139 | 0.72 | 0.241 |
| Gcsam | Mast Cells | 4.02E−07 | 0.010420863 | 1.218 | 0.48 | 0.095 |
| Lgals9 | Mast Cells | 4.93E−07 | 0.012781668 | 1.160 | 0.56 | 0.193 |
| Fnip1 | Mast Cells | 7.99E−07 | 0.020715184 | 1.106 | 0.6 | 0.193 |
| Fosl2 | Mast Cells | 9.93E−07 | 0.025740067 | 1.172 | 0.56 | 0.125 |
| Ctsd | Mast Cells | 1.72E−06 | 0.044555662 | 1.178 | 0.64 | 0.274 |
| Il1b | Mast Cells | 2.21E−06 | 0.057413548 | 1.535 | 0.52 | 0.107 |
| Fscn1 | Migratory DCs (MacDC1) | 0 | 0 | 3.117 | 0.869 | 0.085 |
| Cacnb3 | Migratory DCs (MacDC1) | 0 | 0 | 2.821 | 0.93 | 0.065 |
| Ccl22 | Migratory DCs (MacDC1) | 0 | 0 | 2.781 | 0.627 | 0.032 |
| Ccl5 | Migratory DCs (MacDC1) | 0 | 0 | 2.509 | 0.862 | 0.216 |
| Ccr7 | Migratory DCs (MacDC1) | 0 | 0 | 2.486 | 0.916 | 0.188 |
| Pfkfb3 | Migratory DCs (MacDC1) | 0 | 0 | 2.450 | 0.903 | 0.212 |
| Epsti1 | Migratory DCs (MacDC1) | 0 | 0 | 2.416 | 0.874 | 0.325 |

TABLE 2-continued

Significant Cluster-Defining Genes for Cell Types Identified from the Steady State LN Cell Atlas

| Gene | Cell type | p-value | q-value | Average log fold change | % Expressing in Cluster | % Expressing Rest |
|---|---|---|---|---|---|---|
| Tmem123 | Migratory DCs (MacDC1) | 0 | 0 | 2.408 | 0.92 | 0.43 |
| Adcy6 | Migratory DCs (MacDC1) | 0 | 0 | 2.212 | 0.84 | 0.079 |
| Synpo2 | Migratory DCs (MacDC1) | 0 | 0 | 2.088 | 0.739 | 0.046 |
| Slc4a8 | Migratory DCs (MacDC1) | 0 | 0 | 2.064 | 0.747 | 0.068 |
| Cxcl16 | Migratory DCs (MacDC1) | 0 | 0 | 2.038 | 0.874 | 0.159 |
| Zmynd15 | Migratory DCs (MacDC1) | 0 | 0 | 2.031 | 0.707 | 0.044 |
| Il4i1 | Migratory DCs (MacDC1) | 0 | 0 | 2.025 | 0.801 | 0.133 |
| Apol7c | Migratory DCs (MacDC1) | 0 | 0 | 1.972 | 0.503 | 0.017 |
| H2-M2 | Migratory DCs (MacDC1) | 0 | 0 | 1.956 | 0.645 | 0.03 |
| Plxnc1 | Migratory DCs (MacDC1) | 0 | 0 | 1.885 | 0.892 | 0.263 |
| Tbc1d4 | Migratory DCs (MacDC1) | 0 | 0 | 1.877 | 0.877 | 0.227 |
| Samsn1 | Migratory DCs (MacDC1) | 0 | 0 | 1.848 | 0.856 | 0.223 |
| Etv3 | Migratory DCs (MacDC1) | 0 | 0 | 1.788 | 0.85 | 0.278 |
| Anxa3 | Migratory DCs (MacDC1) | 0 | 0 | 1.787 | 0.736 | 0.045 |
| Strip2 | Migratory DCs (MacDC1) | 0 | 0 | 1.781 | 0.797 | 0.129 |
| Serpinb6b | Migratory DCs (MacDC1) | 0 | 0 | 1.762 | 0.576 | 0.123 |
| Il15ra | Migratory DCs (MacDC1) | 0 | 0 | 1.748 | 0.68 | 0.072 |
| Relb | Migratory DCs (MacDC1) | 0 | 0 | 1.734 | 0.858 | 0.22 |
| Net1 | Migratory DCs (MacDC1) | 0 | 0 | 1.715 | 0.772 | 0.188 |
| Mxd1 | Migratory DCs (MacDC1) | 0 | 0 | 1.608 | 0.738 | 0.143 |
| Nudt17 | Migratory DCs (MacDC1) | 0 | 0 | 1.598 | 0.622 | 0.021 |
| Slco5a1 | Migratory DCs (MacDC1) | 0 | 0 | 1.597 | 0.613 | 0.026 |
| Marcks | Migratory DCs (MacDC1) | 0 | 0 | 1.583 | 0.852 | 0.283 |
| Gadd45b | Migratory DCs (MacDC1) | 0 | 0 | 1.573 | 0.841 | 0.249 |
| Basp1 | Migratory DCs (MacDC1) | 0 | 0 | 1.556 | 0.643 | 0.093 |
| Lrrk1 | Migratory DCs (MacDC1) | 0 | 0 | 1.547 | 0.84 | 0.283 |
| Rogdi | Migratory DCs (MacDC1) | 0 | 0 | 1.544 | 0.829 | 0.232 |
| Neat1 | Migratory DCs (MacDC1) | 0 | 0 | 1.543 | 0.848 | 0.449 |
| Zfc3h1 | Migratory DCs (MacDC1) | 0 | 0 | 1.535 | 0.834 | 0.388 |
| Traf1 | Migratory DCs (MacDC1) | 0 | 0 | 1.512 | 0.846 | 0.315 |
| Marcksl1 | Migratory DCs (MacDC1) | 0 | 0 | 1.476 | 0.594 | 0.12 |
| Socs2 | Migratory DCs (MacDC1) | 0 | 0 | 1.476 | 0.612 | 0.045 |
| Adam23 | Migratory DCs (MacDC1) | 0 | 0 | 1.469 | 0.741 | 0.139 |
| Arhgef40 | Migratory DCs (MacDC1) | 0 | 0 | 1.462 | 0.605 | 0.079 |
| Arhgap31 | Migratory DCs (MacDC1) | 0 | 0 | 1.460 | 0.68 | 0.161 |
| Bmp2k | Migratory DCs (MacDC1) | 0 | 0 | 1.448 | 0.851 | 0.366 |
| Ankrd33b | Migratory DCs (MacDC1) | 0 | 0 | 1.433 | 0.587 | 0.027 |
| Mreg | Migratory DCs (MacDC1) | 0 | 0 | 1.405 | 0.564 | 0.022 |
| Lad1 | Migratory DCs (MacDC1) | 0 | 0 | 1.370 | 0.483 | 0.017 |
| Rap2b | Migratory DCs (MacDC1) | 0 | 0 | 1.366 | 0.646 | 0.165 |
| Fam49a | Migratory DCs (MacDC1) | 0 | 0 | 1.365 | 0.651 | 0.139 |
| Birc2 | Migratory DCs (MacDC1) | 0 | 0 | 1.359 | 0.769 | 0.241 |
| Slc27a3 | Migratory DCs (MacDC1) | 0 | 0 | 1.346 | 0.382 | 0.014 |
| Eno2 | Migratory DCs (MacDC1) | 0 | 0 | 1.295 | 0.496 | 0.019 |
| Tmcc3 | Migratory DCs (MacDC1) | 0 | 0 | 1.280 | 0.604 | 0.081 |
| Tmem150c | Migratory DCs (MacDC1) | 0 | 0 | 1.245 | 0.521 | 0.02 |
| Arc | Migratory DCs (MacDC1) | 0 | 0 | 1.042 | 0.412 | 0.015 |
| Slc22a23 | Migratory DCs (MacDC1) | 0 | 0 | 1.025 | 0.435 | 0.027 |
| Tspan3 | Migratory DCs (MacDC1) | 1.80849429321758e−310 | 4.69E−306 | 1.394 | 0.667 | 0.18 |
| Tbc1d8 | Migratory DCs (MacDC1) | 3.49E−303 | 9.05E−299 | 1.161 | 0.788 | 0.262 |
| Lsp1 | Migratory DCs (MacDC1) | 1.67E−301 | 4.33E−297 | 1.143 | 0.913 | 0.597 |
| Wnk1 | Migratory DCs (MacDC1) | 3.72E−298 | 9.64E−294 | 1.087 | 0.829 | 0.582 |
| Spsb1 | Migratory DCs (MacDC1) | 6.23E−298 | 1.61E−293 | 1.020 | 0.451 | 0.042 |
| Poglut1 | Migratory DCs (MacDC1) | 1.14E−297 | 2.95E−293 | 1.132 | 0.61 | 0.127 |
| Ly75 | Migratory DCs (MacDC1) | 5.40E−293 | 1.40E−288 | 1.275 | 0.613 | 0.143 |
| Mical3 | Migratory DCs (MacDC1) | 1.47E−290 | 3.80E−286 | 1.136 | 0.565 | 0.094 |
| Htra2 | Migratory DCs (MacDC1) | 7.02E−288 | 1.82E−283 | 1.120 | 0.625 | 0.158 |
| N4bp2l1 | Migratory DCs (MacDC1) | 9.57E−281 | 2.48E−276 | 1.127 | 0.607 | 0.158 |
| Batf3 | Migratory DCs (MacDC1) | 1.87E−275 | 4.85E−271 | 1.174 | 0.61 | 0.133 |
| Npr1 | Migratory DCs (MacDC1) | 4.14E−273 | 1.07E−268 | 1.235 | 0.387 | 0.029 |
| Fnbpl1 | Migratory DCs (MacDC1) | 3.75E−271 | 9.73E−267 | 1.053 | 0.494 | 0.065 |
| Rnf19b | Migratory DCs (MacDC1) | 2.14E−270 | 5.56E−266 | 1.141 | 0.77 | 0.327 |
| Arhgap22 | Migratory DCs (MacDC1) | 9.05E−265 | 2.35E−260 | 1.089 | 0.466 | 0.062 |
| Myo1g | Migratory DCs (MacDC1) | 9.32E−263 | 2.42E−258 | 1.053 | 0.821 | 0.442 |
| Cd63 | Migratory DCs (MacDC1) | 5.17E−257 | 1.34E−252 | 1.007 | 0.53 | 0.085 |
| Psme2 | Migratory DCs (MacDC1) | 9.20E−257 | 2.39E−252 | 1.077 | 0.617 | 0.261 |
| Spred1 | Migratory DCs (MacDC1) | 1.47E−255 | 3.82E−251 | 1.113 | 0.509 | 0.092 |
| Dok1 | Migratory DCs (MacDC1) | 1.27E−254 | 3.28E−250 | 1.053 | 0.544 | 0.131 |
| Irf1 | Migratory DCs (MacDC1) | 1.39E−250 | 3.60E−246 | 1.190 | 0.73 | 0.36 |
| Ogfrl1 | Migratory DCs (MacDC1) | 1.83E−248 | 4.74E−244 | 1.193 | 0.634 | 0.202 |
| Txndc17 | Migratory DCs (MacDC1) | 9.38E−244 | 2.43E−239 | 1.241 | 0.526 | 0.179 |
| Gnb4 | Migratory DCs (MacDC1) | 2.76E−240 | 7.15E−236 | 1.162 | 0.489 | 0.099 |
| Icam1 | Migratory DCs (MacDC1) | 1.12E−237 | 2.92E−233 | 1.083 | 0.682 | 0.25 |

TABLE 2-continued

| Significant Cluster-Defining Genes for Cell Types Identified from the Steady State LN Cell Atlas | | | | | | |
|---|---|---|---|---|---|---|
| Gene | Cell type | p-value | q-value | Average log fold change | % Expressing in Cluster | % Expressing Rest |
| Fam53b | Migratory DCs (MacDC1) | 9.67E−236 | 2.51E−231 | 1.062 | 0.618 | 0.196 |
| Tnfrsf1b | Migratory DCs (MacDC1) | 7.81E−235 | 2.03E−230 | 1.053 | 0.629 | 0.179 |
| Cblb | Migratory DCs (MacDC1) | 4.00E−233 | 1.04E−228 | 1.023 | 0.652 | 0.213 |
| Serpinb9 | Migratory DCs (MacDC1) | 5.75E−229 | 1.49E−224 | 1.298 | 0.536 | 0.121 |
| Tmem19 | Migratory DCs (MacDC1) | 5.07E−226 | 1.31E−221 | 1.004 | 0.534 | 0.126 |
| Gtpbp1 | Migratory DCs (MacDC1) | 2.20E−218 | 5.70E−214 | 1.069 | 0.612 | 0.254 |
| Rnf115 | Migratory DCs (MacDC1) | 9.88E−207 | 2.56E−202 | 1.028 | 0.529 | 0.18 |
| Il12b | Migratory DCs (MacDC1) | 4.68E−203 | 1.21E−198 | 1.188 | 0.247 | 0.007 |
| AW112010 | Migratory DCs (MacDC1) | 5.84E−199 | 1.52E−194 | 1.110 | 0.57 | 0.174 |
| Vwa5a | Migratory DCs (MacDC1) | 2.58E−198 | 6.69E−194 | 1.112 | 0.473 | 0.145 |
| Cdkn1a | Migratory DCs (MacDC1) | 4.69E−198 | 1.22E−193 | 1.007 | 0.495 | 0.1 |
| Nav1 | Migratory DCs (MacDC1) | 5.04E−198 | 1.31E−193 | 0.974 | 0.649 | 0.208 |
| Crip1 | Migratory DCs (MacDC1) | 1.38E−192 | 3.59E−188 | 1.042 | 0.731 | 0.377 |
| Itm2c | Migratory DCs (MacDC1) | 1.37E−186 | 3.55E−182 | 1.007 | 0.726 | 0.412 |
| Pla2g16 | Migratory DCs (MacDC1) | 4.23E−186 | 1.10E−181 | 1.016 | 0.506 | 0.173 |
| Lima1 | Migratory DCs (MacDC1) | 4.15E−172 | 1.07E−167 | 1.017 | 0.461 | 0.106 |
| Cd40 | Migratory DCs (MacDC1) | 3.67E−161 | 9.53E−157 | 1.080 | 0.364 | 0.075 |
| Clic4 | Migratory DCs (MacDC1) | 4.15E−159 | 1.07E−154 | 1.005 | 0.584 | 0.254 |
| Sned1 | Migratory DCs (MacDC1) | 1.84E−139 | 4.77E−135 | 1.256 | 0.322 | 0.059 |
| Top2a | Mitotic Cells | 8.58E−279 | 2.22E−274 | 1.989 | 0.935 | 0.11 |
| Mki67 | Mitotic Cells | 1.54E−275 | 3.99E−271 | 2.012 | 0.968 | 0.152 |
| Kif11 | Mitotic Cells | 2.95E−215 | 7.66E−211 | 1.465 | 0.771 | 0.054 |
| Tubb5 | Mitotic Cells | 1.90E−193 | 4.92E−189 | 1.530 | 0.965 | 0.505 |
| Kif23 | Mitotic Cells | 5.06E−191 | 1.31E−186 | 1.503 | 0.758 | 0.077 |
| Cenpf | Mitotic Cells | 9.72E−189 | 2.52E−184 | 1.711 | 0.674 | 0.042 |
| Cenpe | Mitotic Cells | 6.87E−184 | 1.78E−179 | 1.525 | 0.706 | 0.056 |
| Cdca8 | Mitotic Cells | 4.57E−172 | 1.19E−167 | 1.254 | 0.687 | 0.058 |
| Kif15 | Mitotic Cells | 5.32E−167 | 1.38E−162 | 1.384 | 0.681 | 0.059 |
| Nusap1 | Mitotic Cells | 6.50E−161 | 1.69E−156 | 1.163 | 0.635 | 0.05 |
| Ckap2l | Mitotic Cells | 2.59E−156 | 6.72E−152 | 1.283 | 0.6 | 0.041 |
| Kif4 | Mitotic Cells | 1.45E−155 | 3.75E−151 | 1.080 | 0.587 | 0.038 |
| Spag5 | Mitotic Cells | 5.99E−150 | 1.55E−145 | 1.004 | 0.565 | 0.035 |
| Aspm | Mitotic Cells | 1.20E−147 | 3.11E−143 | 1.243 | 0.581 | 0.04 |
| Cdca3 | Mitotic Cells | 1.68E−145 | 4.35E−141 | 1.038 | 0.587 | 0.044 |
| Ncapd2 | Mitotic Cells | 5.01E−144 | 1.30E−139 | 1.177 | 0.723 | 0.102 |
| Iqgap3 | Mitotic Cells | 1.66E−143 | 4.29E−139 | 1.028 | 0.468 | 0.019 |
| Casc5 | Mitotic Cells | 2.43E−143 | 6.31E−139 | 1.264 | 0.668 | 0.075 |
| Ccna2 | Mitotic Cells | 1.77E−140 | 4.58E−136 | 1.041 | 0.574 | 0.045 |
| H2-Ab1 | Mitotic Cells | 1.48E−137 | 3.84E−133 | 1.219 | 0.99 | 0.705 |
| Birc5 | Mitotic Cells | 5.88E−137 | 1.53E−132 | 1.027 | 0.571 | 0.046 |
| Cdk1 | Mitotic Cells | 7.14E−135 | 1.85E−130 | 1.043 | 0.571 | 0.048 |
| Prc1 | Mitotic Cells | 1.04E−134 | 2.70E−130 | 1.115 | 0.577 | 0.049 |
| Ncapg | Mitotic Cells | 3.88E−133 | 1.01E−128 | 1.069 | 0.565 | 0.045 |
| Plbd1 | Mitotic Cells | 8.98E−132 | 2.33E−127 | 1.150 | 0.923 | 0.27 |
| Tacc3 | Mitotic Cells | 9.13E−130 | 2.37E−125 | 1.203 | 0.658 | 0.098 |
| Tmpo | Mitotic Cells | 1.05E−129 | 2.73E−125 | 1.191 | 0.881 | 0.364 |
| Bub1 | Mitotic Cells | 2.18E−129 | 5.65E−125 | 0.860 | 0.494 | 0.029 |
| Aurkb | Mitotic Cells | 5.52E−129 | 1.43E−124 | 1.108 | 0.532 | 0.043 |
| Tpx2 | Mitotic Cells | 1.32E−128 | 3.42E−124 | 1.138 | 0.594 | 0.06 |
| Mis18bp1 | Mitotic Cells | 7.51E−125 | 1.95E−120 | 1.041 | 0.503 | 0.035 |
| Foxm1 | Mitotic Cells | 3.52E−123 | 9.13E−119 | 0.977 | 0.51 | 0.038 |
| C330027C09Rik | Mitotic Cells | 2.41E−122 | 6.25E−118 | 0.932 | 0.532 | 0.048 |
| Knstrn | Mitotic Cells | 2.85E−121 | 7.40E−117 | 1.081 | 0.574 | 0.064 |
| Ube2c | Mitotic Cells | 3.39E−121 | 8.79E−117 | 1.218 | 0.51 | 0.04 |
| Incenp | Mitotic Cells | 1.62E−120 | 4.21E−116 | 1.145 | 0.687 | 0.119 |
| Kif14 | Mitotic Cells | 1.83E−119 | 4.76E−115 | 0.921 | 0.468 | 0.029 |
| Cdca2 | Mitotic Cells | 2.74E−119 | 7.11E−115 | 0.981 | 0.513 | 0.042 |
| Bub1b | Mitotic Cells | 2.17E−117 | 5.63E−113 | 1.029 | 0.571 | 0.063 |
| Plk1 | Mitotic Cells | 2.28E−116 | 5.92E−112 | 0.926 | 0.494 | 0.038 |
| Racgap1 | Mitotic Cells | 5.91E−115 | 1.53E−110 | 1.099 | 0.684 | 0.124 |
| Cep55 | Mitotic Cells | 6.37E−115 | 1.65E−110 | 0.891 | 0.458 | 0.03 |
| Ncaph | Mitotic Cells | 1.50E−113 | 3.89E−109 | 0.938 | 0.513 | 0.046 |
| H2-Eb1 | Mitotic Cells | 1.06E−111 | 2.75E−107 | 0.936 | 0.977 | 0.629 |
| Cd74 | Mitotic Cells | 4.01E−109 | 1.04E−104 | 0.844 | 0.987 | 0.656 |
| Kif20a | Mitotic Cells | 9.80E−109 | 2.54E−104 | 0.895 | 0.461 | 0.034 |
| Kif20b | Mitotic Cells | 3.74E−106 | 9.70E−102 | 1.067 | 0.594 | 0.083 |
| Ccnb2 | Mitotic Cells | 5.01E−106 | 1.30E−101 | 1.096 | 0.494 | 0.046 |
| Spc24 | Mitotic Cells | 2.49E−105 | 6.46E−101 | 0.843 | 0.465 | 0.038 |
| Wdfy4 | Mitotic Cells | 2.22E−104 | 5.76E−100 | 1.163 | 0.894 | 0.343 |
| Cenpa | Mitotic Cells | 2.13E−102 | 5.53E−98 | 1.115 | 0.606 | 0.101 |
| Anln | Mitotic Cells | 5.33E−101 | 1.38E−96 | 0.944 | 0.461 | 0.041 |
| H2afx | Mitotic Cells | 1.37E−100 | 3.56E−96 | 0.893 | 0.506 | 0.059 |
| Cit | Mitotic Cells | 5.91E−99 | 1.53E−94 | 0.894 | 0.49 | 0.051 |

TABLE 2-continued

Significant Cluster-Defining Genes for Cell Types Identified from the Steady State LN Cell Atlas

| Gene | Cell type | p-value | q-value | Average log fold change | % Expressing in Cluster | % Expressing Rest |
|---|---|---|---|---|---|---|
| Tuba1b | Mitotic Cells | 7.59E−99 | 1.97E−94 | 1.042 | 0.6 | 0.122 |
| Hmmr | Mitotic Cells | 1.05E−98 | 2.72E−94 | 0.900 | 0.429 | 0.033 |
| Ccnf | Mitotic Cells | 9.70E−97 | 2.51E−92 | 0.779 | 0.403 | 0.027 |
| H2-Aa | Mitotic Cells | 1.33E−96 | 3.44E−92 | 0.908 | 0.977 | 0.636 |
| Naaa | Mitotic Cells | 2.47E−96 | 6.42E−92 | 1.124 | 0.726 | 0.19 |
| Smc2 | Mitotic Cells | 3.26E−96 | 8.45E−92 | 0.982 | 0.61 | 0.108 |
| Ckap2 | Mitotic Cells | 8.64E−95 | 2.24E−90 | 0.771 | 0.4 | 0.029 |
| Cst3 | Mitotic Cells | 4.02E−94 | 1.04E−89 | 1.099 | 0.961 | 0.596 |
| Hjurp | Mitotic Cells | 5.00E−92 | 1.30E−87 | 1.098 | 0.771 | 0.26 |
| Dlgap5 | Mitotic Cells | 2.73E−90 | 7.09E−86 | 0.787 | 0.461 | 0.051 |
| 5430435G22Rik | Mitotic Cells | 2.55E−89 | 6.62E−85 | 0.951 | 0.597 | 0.11 |
| Sgol2 | Mitotic Cells | 2.45E−88 | 6.34E−84 | 0.766 | 0.403 | 0.034 |
| Gas2l3 | Mitotic Cells | 9.48E−88 | 2.46E−83 | 0.783 | 0.394 | 0.032 |
| Espl1 | Mitotic Cells | 1.13E−87 | 2.93E−83 | 0.838 | 0.448 | 0.048 |
| Gpx1 | Mitotic Cells | 9.95E−85 | 2.58E−80 | 0.882 | 0.923 | 0.507 |
| Alox5ap | Mitotic Cells | 1.02E−84 | 2.65E−80 | 0.810 | 0.761 | 0.233 |
| Pak1 | Mitotic Cells | 9.15E−84 | 2.37E−79 | 0.897 | 0.629 | 0.136 |
| Gm2a | Mitotic Cells | 2.10E−80 | 5.44E−76 | 0.848 | 0.913 | 0.455 |
| Sod1 | Mitotic Cells | 3.35E−79 | 8.68E−75 | 0.940 | 0.877 | 0.488 |
| Anp32e | Mitotic Cells | 7.38E−78 | 1.91E−73 | 0.925 | 0.729 | 0.288 |
| Diap3 | Mitotic Cells | 1.46E−72 | 3.78E−68 | 0.777 | 0.4 | 0.047 |
| Hirip3 | Mitotic Cells | 2.27E−72 | 5.90E−68 | 0.775 | 0.458 | 0.069 |
| Dbf4 | Mitotic Cells | 3.04E−72 | 7.88E−68 | 0.773 | 0.484 | 0.081 |
| Ifi205 | Mitotic Cells | 4.12E−72 | 1.07E−67 | 0.846 | 0.497 | 0.088 |
| Rab43 | Mitotic Cells | 2.22E−71 | 5.75E−67 | 0.837 | 0.852 | 0.403 |
| Naga | Mitotic Cells | 5.89E−71 | 1.53E−66 | 0.841 | 0.726 | 0.247 |
| A530099J19Rik | Mitotic Cells | 8.63E−70 | 2.24E−65 | 0.874 | 0.529 | 0.108 |
| Hist1h1b | Mitotic Cells | 2.50E−69 | 6.48E−65 | 0.776 | 0.365 | 0.04 |
| Arhgap11a | Mitotic Cells | 1.78E−66 | 4.63E−62 | 0.793 | 0.532 | 0.122 |
| H2-DMb1 | Mitotic Cells | 9.49E−66 | 2.46E−61 | 0.786 | 0.765 | 0.295 |
| Ptma | Mitotic Cells | 1.39E−65 | 3.60E−61 | 0.855 | 0.745 | 0.323 |
| Nucks1 | Mitotic Cells | 1.97E−65 | 5.10E−61 | 0.871 | 0.781 | 0.354 |
| Rrm1 | Mitotic Cells | 3.46E−65 | 8.96E−61 | 0.837 | 0.539 | 0.121 |
| Ppt1 | Mitotic Cells | 5.81E−65 | 1.51E−60 | 0.885 | 0.761 | 0.322 |
| Hist1h1e | Mitotic Cells | 5.49E−64 | 1.42E−59 | 0.819 | 0.542 | 0.126 |
| Lmnb1 | Mitotic Cells | 2.70E−63 | 7.00E−59 | 0.773 | 0.581 | 0.152 |
| Whsc1 | Mitotic Cells | 4.22E−63 | 1.09E−58 | 0.899 | 0.652 | 0.212 |
| Dock5 | Mitotic Cells | 5.61E−62 | 1.46E−57 | 0.771 | 0.652 | 0.201 |
| Dek | Mitotic Cells | 6.86E−60 | 1.78E−55 | 0.844 | 0.8 | 0.419 |
| Ckap5 | Mitotic Cells | 1.26E−59 | 3.28E−55 | 0.810 | 0.629 | 0.197 |
| Hmgb2 | Mitotic Cells | 2.30E−59 | 5.97E−55 | 0.771 | 0.513 | 0.124 |
| Atad2 | Mitotic Cells | 6.45E−58 | 1.67E−53 | 0.911 | 0.555 | 0.155 |
| Ezh2 | Mitotic Cells | 2.12E−57 | 5.49E−53 | 0.827 | 0.629 | 0.209 |
| Anp32b | Mitotic Cells | 1.10E−55 | 2.85E−51 | 0.769 | 0.755 | 0.357 |
| Arl6ip1 | Mitotic Cells | 5.36E−53 | 1.39E−48 | 0.836 | 0.755 | 0.385 |
| Hspa1a | Mitotic Cells | 1.65E−18 | 4.29E−14 | 0.805 | 0.584 | 0.344 |
| Top2a | Mitotic T Cells | 4.83E−279 | 1.25E−274 | 2.117 | 0.898 | 0.107 |
| Ccna2 | Mitotic T Cells | 2.01E−223 | 5.20E−219 | 1.473 | 0.672 | 0.038 |
| Kif11 | Mitotic T Cells | 2.97E−218 | 7.69E−214 | 1.475 | 0.713 | 0.052 |
| 2810417H13Rik | Mitotic T Cells | 8.20E−207 | 2.13E−202 | 1.186 | 0.634 | 0.036 |
| Tubb5 | Mitotic T Cells | 6.91E−198 | 1.79E−193 | 1.492 | 0.928 | 0.504 |
| Kif15 | Mitotic T Cells | 8.09E−183 | 2.10E−178 | 1.263 | 0.658 | 0.056 |
| Thy1 | Mitotic T Cells | 1.50E−182 | 3.89E−178 | 1.583 | 0.832 | 0.169 |
| Birc5 | Mitotic T Cells | 6.39E−179 | 1.66E−174 | 1.202 | 0.603 | 0.042 |
| Rrm1 | Mitotic T Cells | 1.05E−177 | 2.72E−173 | 1.435 | 0.7 | 0.112 |
| Uhrf1 | Mitotic T Cells | 8.20E−174 | 2.13E−169 | 1.258 | 0.647 | 0.061 |
| Cdca8 | Mitotic T Cells | 7.61E−172 | 1.97E−167 | 1.229 | 0.634 | 0.056 |
| Ccnb2 | Mitotic T Cells | 3.07E−169 | 7.96E−165 | 1.161 | 0.579 | 0.04 |
| Lmnb1 | Mitotic T Cells | 3.25E−168 | 8.44E−164 | 1.358 | 0.733 | 0.144 |
| Ncapd2 | Mitotic T Cells | 5.43E−167 | 1.41E−162 | 1.307 | 0.708 | 0.099 |
| Ncapg | Mitotic T Cells | 5.00E−166 | 1.30E−161 | 1.125 | 0.579 | 0.042 |
| Cenpf | Mitotic T Cells | 1.51E−165 | 3.90E−161 | 1.418 | 0.579 | 0.042 |
| Nusap1 | Mitotic T Cells | 8.00E−163 | 2.07E−158 | 1.289 | 0.59 | 0.048 |
| Cdca3 | Mitotic T Cells | 8.26E−161 | 2.14E−156 | 1.008 | 0.567 | 0.042 |
| Rrm2 | Mitotic T Cells | 1.41E−160 | 3.65E−156 | 0.980 | 0.518 | 0.029 |
| Lig1 | Mitotic T Cells | 1.52E−160 | 3.93E−156 | 1.226 | 0.656 | 0.081 |
| Tpx2 | Mitotic T Cells | 6.91E−158 | 1.79E−153 | 1.279 | 0.598 | 0.057 |
| Casc5 | Mitotic T Cells | 3.84E−155 | 9.95E−151 | 1.169 | 0.642 | 0.072 |
| Ncaph | Mitotic T Cells | 2.87E−152 | 7.45E−148 | 1.037 | 0.551 | 0.042 |
| Cenpe | Mitotic T Cells | 6.55E−151 | 1.70E−146 | 1.268 | 0.592 | 0.057 |
| Mcm5 | Mitotic T Cells | 8.01E−151 | 2.08E−146 | 1.286 | 0.645 | 0.09 |
| Hmgb2 | Mitotic T Cells | 2.99E−150 | 7.76E−146 | 1.182 | 0.68 | 0.115 |
| Hmmr | Mitotic T Cells | 2.05E−148 | 5.32E−144 | 0.996 | 0.488 | 0.028 |

TABLE 2-continued

Significant Cluster-Defining Genes for Cell Types Identified from the Steady State LN Cell Atlas

| Gene | Cell type | p-value | q-value | Average log fold change | % Expressing in Cluster | % Expressing Rest |
|---|---|---|---|---|---|---|
| Prc1 | Mitotic T Cells | 2.43E−147 | 6.30E−143 | 1.079 | 0.556 | 0.047 |
| Tacc3 | Mitotic T Cells | 1.10E−145 | 2.86E−141 | 1.211 | 0.667 | 0.095 |
| Ckap2l | Mitotic T Cells | 9.89E−144 | 2.56E−139 | 1.036 | 0.526 | 0.041 |
| Kif4 | Mitotic T Cells | 4.53E−143 | 1.18E−138 | 1.077 | 0.515 | 0.038 |
| Asf1b | Mitotic T Cells | 2.60E−142 | 6.74E−138 | 0.862 | 0.51 | 0.037 |
| Dut | Mitotic T Cells | 3.09E−142 | 8.00E−138 | 1.205 | 0.634 | 0.106 |
| Plk1 | Mitotic T Cells | 7.66E−141 | 1.99E−136 | 0.999 | 0.501 | 0.035 |
| Aspm | Mitotic T Cells | 4.27E−140 | 1.11E−135 | 1.143 | 0.515 | 0.04 |
| Lgals1 | Mitotic T Cells | 1.97E−139 | 5.10E−135 | 1.582 | 0.804 | 0.291 |
| Hist1h1b | Mitotic T Cells | 7.56E−139 | 1.96E−134 | 1.231 | 0.488 | 0.033 |
| Kif22 | Mitotic T Cells | 1.01E−137 | 2.62E−133 | 0.845 | 0.482 | 0.032 |
| Clspn | Mitotic T Cells | 1.68E−136 | 4.36E−132 | 0.925 | 0.49 | 0.035 |
| Smc2 | Mitotic T Cells | 2.77E−136 | 7.19E−132 | 1.171 | 0.656 | 0.103 |
| Kif20a | Mitotic T Cells | 8.62E−135 | 2.24E−130 | 0.846 | 0.471 | 0.031 |
| Dnmt1 | Mitotic T Cells | 7.74E−134 | 2.01E−129 | 1.293 | 0.747 | 0.234 |
| Hist1h1e | Mitotic T Cells | 7.80E−133 | 2.02E−128 | 1.414 | 0.636 | 0.12 |
| Cdk1 | Mitotic T Cells | 2.20E−132 | 5.70E−128 | 0.910 | 0.521 | 0.047 |
| Spag5 | Mitotic T Cells | 4.56E−129 | 1.18E−124 | 0.867 | 0.474 | 0.035 |
| Incenp | Mitotic T Cells | 1.76E−125 | 4.56E−121 | 1.142 | 0.653 | 0.117 |
| Tuba1b | Mitotic T Cells | 9.00E−125 | 2.33E−120 | 1.031 | 0.634 | 0.118 |
| Ube2c | Mitotic T Cells | 2.57E−124 | 6.67E−120 | 0.986 | 0.477 | 0.039 |
| Dlgap5 | Mitotic T Cells | 1.80E−123 | 4.66E−119 | 0.918 | 0.501 | 0.047 |
| Gmnn | Mitotic T Cells | 1.28E−122 | 3.33E−118 | 0.849 | 0.523 | 0.056 |
| Ncl | Mitotic T Cells | 1.35E−121 | 3.51E−117 | 1.069 | 0.887 | 0.629 |
| Mcm3 | Mitotic T Cells | 2.67E−119 | 6.91E−115 | 1.188 | 0.639 | 0.14 |
| Psat1 | Mitotic T Cells | 1.26E−118 | 3.27E−114 | 0.895 | 0.518 | 0.06 |
| Racgap1 | Mitotic T Cells | 2.40E−118 | 6.23E−114 | 1.039 | 0.656 | 0.121 |
| Ldha | Mitotic T Cells | 1.12E−117 | 2.89E−113 | 1.214 | 0.755 | 0.369 |
| Ncapg2 | Mitotic T Cells | 1.08E−115 | 2.81E−111 | 0.996 | 0.548 | 0.073 |
| Kif23 | Mitotic T Cells | 4.66E−114 | 1.21E−109 | 0.954 | 0.567 | 0.081 |
| Cit | Mitotic T Cells | 1.17E−112 | 3.03E−108 | 0.846 | 0.479 | 0.049 |
| Rad21 | Mitotic T Cells | 1.56E−110 | 4.05E−106 | 1.116 | 0.807 | 0.334 |
| Bub1b | Mitotic T Cells | 1.50E−107 | 3.90E−103 | 0.851 | 0.507 | 0.063 |
| Anp32e | Mitotic T Cells | 4.54E−107 | 1.18E−102 | 1.057 | 0.769 | 0.284 |
| Mcm4 | Mitotic T Cells | 3.15E−105 | 8.18E−101 | 1.064 | 0.614 | 0.127 |
| Mcm2 | Mitotic T Cells | 3.39E−105 | 8.79E−101 | 1.010 | 0.554 | 0.094 |
| Mcm6 | Mitotic T Cells | 5.62E−105 | 1.46E−100 | 1.076 | 0.606 | 0.134 |
| Ptprcap | Mitotic T Cells | 3.21E−104 | 8.33E−100 | 1.029 | 0.813 | 0.296 |
| E2f2 | Mitotic T Cells | 6.98E−103 | 1.81E−98 | 0.926 | 0.523 | 0.076 |
| Mcm7 | Mitotic T Cells | 1.02E−102 | 2.65E−98 | 0.981 | 0.59 | 0.113 |
| Cbx5 | Mitotic T Cells | 8.73E−102 | 2.26E−97 | 1.051 | 0.672 | 0.181 |
| Tmpo | Mitotic T Cells | 3.39E−100 | 8.80E−96 | 1.015 | 0.799 | 0.365 |
| Cenpa | Mitotic T Cells | 1.81E−99 | 4.69E−95 | 1.079 | 0.556 | 0.1 |
| Ybx1 | Mitotic T Cells | 2.19E−95 | 5.67E−91 | 0.964 | 0.829 | 0.51 |
| Pcna | Mitotic T Cells | 4.60E−95 | 1.19E−90 | 0.989 | 0.601 | 0.145 |
| S100a10 | Mitotic T Cells | 8.89E−95 | 2.31E−90 | 1.162 | 0.744 | 0.254 |
| Hnrnpab | Mitotic T Cells | 9.41E−95 | 2.44E−90 | 1.016 | 0.824 | 0.482 |
| Icos | Mitotic T Cells | 3.86E−94 | 1.00E−89 | 0.930 | 0.543 | 0.094 |
| Anp32b | Mitotic T Cells | 7.30E−94 | 1.89E−89 | 0.901 | 0.78 | 0.354 |
| Pfn1 | Mitotic T Cells | 9.37E−94 | 2.43E−89 | 0.873 | 0.882 | 0.59 |
| Atp5b | Mitotic T Cells | 2.95E−87 | 7.64E−83 | 0.897 | 0.813 | 0.549 |
| Hsp90ab1 | Mitotic T Cells | 8.56E−87 | 2.22E−82 | 0.958 | 0.926 | 0.73 |
| Nucks1 | Mitotic T Cells | 9.77E−87 | 2.53E−82 | 0.965 | 0.744 | 0.353 |
| Spn | Mitotic T Cells | 1.35E−85 | 3.51E−81 | 0.982 | 0.711 | 0.224 |
| Trbc2 | Mitotic T Cells | 1.52E−85 | 3.94E−81 | 1.144 | 0.623 | 0.157 |
| Whsc1 | Mitotic T Cells | 2.94E−85 | 7.63E−81 | 0.973 | 0.672 | 0.208 |
| Hdgf | Mitotic T Cells | 7.19E−84 | 1.86E−79 | 0.918 | 0.678 | 0.229 |
| Nme1 | Mitotic T Cells | 1.78E−83 | 4.61E−79 | 0.953 | 0.573 | 0.153 |
| Smc4 | Mitotic T Cells | 9.78E−83 | 2.54E−78 | 0.957 | 0.813 | 0.424 |
| Pkm | Mitotic T Cells | 2.27E−82 | 5.90E−78 | 0.953 | 0.738 | 0.334 |
| Cdc25b | Mitotic T Cells | 7.47E−80 | 1.94E−75 | 0.847 | 0.452 | 0.074 |
| Eif5a | Mitotic T Cells | 2.14E−79 | 5.55E−75 | 0.969 | 0.691 | 0.351 |
| Vim | Mitotic T Cells | 1.33E−76 | 3.45E−72 | 0.945 | 0.909 | 0.578 |
| Npm1 | Mitotic T Cells | 6.26E−76 | 1.62E−71 | 0.933 | 0.702 | 0.362 |
| Capg | Mitotic T Cells | 6.95E−73 | 1.80E−68 | 0.856 | 0.617 | 0.179 |
| Arl6ip1 | Mitotic T Cells | 2.17E−68 | 5.63E−64 | 0.944 | 0.727 | 0.384 |
| Hjurp | Mitotic T Cells | 3.45E−67 | 8.95E−63 | 0.878 | 0.691 | 0.26 |
| Rps2 | Mitotic T Cells | 1.12E−64 | 2.92E−60 | 0.844 | 0.774 | 0.485 |
| Pa2g4 | Mitotic T Cells | 6.22E−62 | 1.61E−57 | 0.876 | 0.617 | 0.252 |
| Ranbp1 | Mitotic T Cells | 5.64E−61 | 1.46E−56 | 0.861 | 0.584 | 0.212 |
| Anxa6 | Mitotic T Cells | 1.28E−59 | 3.32E−55 | 0.842 | 0.702 | 0.335 |
| Ybx3 | Mitotic T Cells | 1.53E−59 | 3.96E−55 | 0.872 | 0.647 | 0.254 |
| Cxcr2 | Neutrophils 1 | 1.52E−112 | 3.94E−108 | 3.125 | 0.929 | 0.008 |

TABLE 2-continued

Significant Cluster-Defining Genes for Cell Types Identified from the Steady State LN Cell Atlas

| Gene | Cell type | p-value | q-value | Average log fold change | % Expressing in Cluster | % Expressing Rest |
|---|---|---|---|---|---|---|
| Csf3r | Neutrophils 1 | 7.49E−107 | 1.94E−102 | 3.095 | 0.946 | 0.016 |
| Msrb1 | Neutrophils 1 | 1.22E−101 | 3.17E−97 | 2.686 | 0.946 | 0.113 |
| Clec4d | Neutrophils 1 | 5.52E−97 | 1.43E−92 | 2.532 | 0.875 | 0.008 |
| Ccr1 | Neutrophils 1 | 8.63E−97 | 2.24E−92 | 2.520 | 0.911 | 0.02 |
| Grina | Neutrophils 1 | 5.81E−93 | 1.51E−88 | 2.429 | 0.911 | 0.189 |
| S100a9 | Neutrophils 1 | 1.79E−87 | 4.64E−83 | 3.739 | 0.982 | 0.053 |
| Hp | Neutrophils 1 | 2.02E−84 | 5.24E−80 | 3.036 | 0.946 | 0.027 |
| S100a8 | Neutrophils 1 | 7.09E−84 | 1.84E−79 | 3.767 | 0.946 | 0.048 |
| Gda | Neutrophils 1 | 1.79E−83 | 4.64E−79 | 2.794 | 0.893 | 0.048 |
| Gsr | Neutrophils 1 | 2.45E−78 | 6.36E−74 | 2.418 | 0.929 | 0.112 |
| Mmp8 | Neutrophils 1 | 2.06E−76 | 5.33E−72 | 3.133 | 0.768 | 0.009 |
| Nlrp12 | Neutrophils 1 | 1.30E−75 | 3.37E−71 | 1.644 | 0.661 | 0.002 |
| Il1r2 | Neutrophils 1 | 2.47E−74 | 6.41E−70 | 2.520 | 0.857 | 0.042 |
| Slc40a1 | Neutrophils 1 | 1.50E−73 | 3.88E−69 | 2.245 | 0.732 | 0.007 |
| Ifitm1 | Neutrophils 1 | 1.62E−73 | 4.21E−69 | 2.793 | 0.75 | 0.03 |
| Wfdc17 | Neutrophils 1 | 2.21E−70 | 5.72E−66 | 2.940 | 0.786 | 0.068 |
| Hdc | Neutrophils 1 | 3.18E−69 | 8.25E−65 | 2.321 | 0.786 | 0.014 |
| Adipor1 | Neutrophils 1 | 4.19E−68 | 1.09E−63 | 1.902 | 0.875 | 0.276 |
| Mmp9 | Neutrophils 1 | 1.33E−66 | 3.44E−62 | 2.474 | 0.786 | 0.016 |
| Srgn | Neutrophils 1 | 1.17E−64 | 3.04E−60 | 1.993 | 0.982 | 0.532 |
| Mxd1 | Neutrophils 1 | 1.26E−64 | 3.28E−60 | 2.455 | 0.946 | 0.207 |
| C5ar1 | Neutrophils 1 | 1.52E−64 | 3.95E−60 | 1.717 | 0.661 | 0.006 |
| Pla2g7 | Neutrophils 1 | 2.03E−64 | 5.28E−60 | 2.379 | 0.929 | 0.06 |
| Pygl | Neutrophils 1 | 3.52E−63 | 9.13E−59 | 2.222 | 0.875 | 0.069 |
| Cd300lf | Neutrophils 1 | 7.31E−62 | 1.90E−57 | 2.122 | 0.839 | 0.053 |
| Cd33 | Neutrophils 1 | 1.12E−59 | 2.91E−55 | 2.003 | 0.821 | 0.045 |
| Retnlg | Neutrophils 1 | 1.57E−59 | 4.07E−55 | 3.530 | 0.661 | 0.012 |
| Chi3l1 | Neutrophils 1 | 2.36E−59 | 6.12E−55 | 2.152 | 0.643 | 0.007 |
| Gp49a | Neutrophils 1 | 9.78E−59 | 2.53E−54 | 2.054 | 0.786 | 0.031 |
| Itgam | Neutrophils 1 | 9.36E−58 | 2.43E−53 | 2.323 | 0.857 | 0.068 |
| Fbxl5 | Neutrophils 1 | 5.99E−57 | 1.55E−52 | 1.897 | 0.875 | 0.239 |
| Cd300ld | Neutrophils 1 | 2.57E−56 | 6.67E−52 | 1.875 | 0.714 | 0.02 |
| Il1b | Neutrophils 1 | 1.14E−55 | 2.95E−51 | 3.374 | 0.821 | 0.103 |
| Ccl6 | Neutrophils 1 | 7.61E−55 | 1.97E−50 | 2.577 | 0.839 | 0.077 |
| Arg2 | Neutrophils 1 | 3.79E−54 | 9.82E−50 | 1.669 | 0.643 | 0.012 |
| Slfn4 | Neutrophils 1 | 1.50E−51 | 3.90E−47 | 2.575 | 0.589 | 0.012 |
| Socs3 | Neutrophils 1 | 8.20E−51 | 2.13E−46 | 2.223 | 0.804 | 0.103 |
| Sorl1 | Neutrophils 1 | 1.28E−50 | 3.33E−46 | 1.795 | 0.982 | 0.442 |
| Lcp1 | Neutrophils 1 | 3.01E−50 | 7.80E−46 | 1.623 | 0.946 | 0.631 |
| Alox5ap | Neutrophils 1 | 8.98E−50 | 2.33E−45 | 2.031 | 0.929 | 0.246 |
| 1810033B17Rik | Neutrophils 1 | 1.34E−49 | 3.47E−45 | 1.941 | 0.75 | 0.069 |
| Gcnt2 | Neutrophils 1 | 1.23E−48 | 3.20E−44 | 2.007 | 0.768 | 0.06 |
| S100a11 | Neutrophils 1 | 1.24E−48 | 3.20E−44 | 1.724 | 0.821 | 0.203 |
| Trem1 | Neutrophils 1 | 1.30E−48 | 3.38E−44 | 1.911 | 0.554 | 0.007 |
| Tpd52 | Neutrophils 1 | 2.21E−48 | 5.73E−44 | 1.821 | 0.875 | 0.196 |
| Taldo1 | Neutrophils 1 | 2.47E−48 | 6.41E−44 | 1.730 | 0.893 | 0.358 |
| Dmxl2 | Neutrophils 1 | 3.44E−47 | 8.91E−43 | 1.600 | 0.679 | 0.031 |
| Lcn2 | Neutrophils 1 | 3.62E−47 | 9.39E−43 | 2.538 | 0.643 | 0.018 |
| Dusp1 | Neutrophils 1 | 1.27E−46 | 3.30E−42 | 1.985 | 0.929 | 0.268 |
| Bst1 | Neutrophils 1 | 1.29E−46 | 3.36E−42 | 1.808 | 0.768 | 0.066 |
| Tyrobp | Neutrophils 1 | 1.94E−46 | 5.04E−42 | 1.837 | 0.982 | 0.399 |
| Niacr1 | Neutrophils 1 | 3.72E−45 | 9.63E−41 | 2.231 | 0.5 | 0.009 |
| Lilrb4 | Neutrophils 1 | 3.98E−45 | 1.03E−40 | 1.807 | 0.768 | 0.057 |
| H2-Q10 | Neutrophils 1 | 4.25E−45 | 1.10E−40 | 1.777 | 0.536 | 0.024 |
| Ets2 | Neutrophils 1 | 8.86E−45 | 2.30E−40 | 1.947 | 0.75 | 0.101 |
| Slpi | Neutrophils 1 | 1.60E−44 | 4.14E−40 | 1.984 | 0.643 | 0.025 |
| Fcgr3 | Neutrophils 1 | 2.52E−44 | 6.52E−40 | 1.735 | 0.75 | 0.046 |
| Slc16a3 | Neutrophils 1 | 2.52E−43 | 6.54E−39 | 1.880 | 0.589 | 0.033 |
| Clec4e | Neutrophils 1 | 4.10E−43 | 1.06E−38 | 1.731 | 0.554 | 0.014 |
| 1100001G20Rik | Neutrophils 1 | 7.17E−43 | 1.86E−38 | 1.918 | 0.554 | 0.01 |
| Zyx | Neutrophils 1 | 2.57E−42 | 6.65E−38 | 1.747 | 0.893 | 0.371 |
| Tlr13 | Neutrophils 1 | 1.02E−40 | 2.64E−36 | 1.628 | 0.679 | 0.06 |
| Fxyd5 | Neutrophils 1 | 5.29E−40 | 1.37E−35 | 1.652 | 0.911 | 0.425 |
| Nudt4 | Neutrophils 1 | 5.02E−38 | 1.30E−33 | 1.784 | 0.821 | 0.153 |
| Themis2 | Neutrophils 1 | 9.68E−38 | 2.51E−33 | 1.708 | 0.786 | 0.195 |
| Fgl2 | Neutrophils 1 | 1.13E−37 | 2.94E−33 | 1.877 | 0.732 | 0.21 |
| Ctsd | Neutrophils 1 | 1.43E−37 | 3.70E−33 | 1.725 | 0.893 | 0.271 |
| Tnfaip2 | Neutrophils 1 | 9.14E−37 | 2.37E−32 | 1.878 | 0.732 | 0.088 |
| Emilin2 | Neutrophils 1 | 1.78E−36 | 4.61E−32 | 1.573 | 0.625 | 0.039 |
| Slfn2 | Neutrophils 1 | 3.32E−36 | 8.61E−32 | 1.637 | 0.839 | 0.383 |
| Cpd | Neutrophils 1 | 4.82E−36 | 1.25E−31 | 1.720 | 0.75 | 0.148 |
| Gadd45a | Neutrophils 1 | 9.42E−36 | 2.44E−31 | 1.568 | 0.571 | 0.06 |
| Cebpb | Neutrophils 1 | 1.55E−34 | 4.01E−30 | 1.607 | 0.643 | 0.07 |

TABLE 2-continued

Significant Cluster-Defining Genes for Cell Types Identified from the Steady State LN Cell Atlas

| Gene | Cell type | p-value | q-value | Average log fold change | % Expressing in Cluster | % Expressing Rest |
|---|---|---|---|---|---|---|
| Jhdm1d | Neutrophils 1 | 1.86E−34 | 4.83E−30 | 1.557 | 0.875 | 0.37 |
| Slfn1 | Neutrophils 1 | 5.66E−34 | 1.47E−29 | 1.737 | 0.696 | 0.101 |
| Pfkfb4 | Neutrophils 1 | 9.24E−34 | 2.40E−29 | 1.571 | 0.643 | 0.067 |
| Rdh12 | Neutrophils 1 | 1.42E−33 | 3.67E−29 | 1.530 | 0.536 | 0.039 |
| Asprv1 | Neutrophils 1 | 8.28E−33 | 2.15E−28 | 1.903 | 0.446 | 0.02 |
| Slc2a3 | Neutrophils 1 | 1.77E−32 | 4.58E−28 | 1.692 | 0.643 | 0.106 |
| Irg1 | Neutrophils 1 | 2.49E−32 | 6.47E−28 | 1.854 | 0.339 | 0.004 |
| Junb | Neutrophils 1 | 8.43E−32 | 2.19E−27 | 1.621 | 0.964 | 0.488 |
| Prdx5 | Neutrophils 1 | 2.73E−31 | 7.07E−27 | 1.633 | 0.75 | 0.198 |
| Il18rap | Neutrophils 1 | 3.59E−31 | 9.32E−27 | 1.556 | 0.839 | 0.142 |
| Pag1 | Neutrophils 1 | 2.19E−30 | 5.67E−26 | 1.559 | 0.768 | 0.199 |
| Lrg1 | Neutrophils 1 | 2.21E−30 | 5.73E−26 | 1.909 | 0.589 | 0.043 |
| Cd14 | Neutrophils 1 | 4.79E−30 | 1.24E−25 | 1.854 | 0.5 | 0.035 |
| Adam8 | Neutrophils 1 | 5.38E−30 | 1.39E−25 | 1.570 | 0.804 | 0.184 |
| Entpd1 | Neutrophils 1 | 7.34E−28 | 1.90E−23 | 1.552 | 0.696 | 0.115 |
| Cxcl2 | Neutrophils 1 | 1.15E−27 | 2.98E−23 | 2.814 | 0.375 | 0.018 |
| Crispld2 | Neutrophils 1 | 1.63E−25 | 4.23E−21 | 1.529 | 0.554 | 0.053 |
| Osm | Neutrophils 1 | 1.69E−25 | 4.39E−21 | 1.562 | 0.446 | 0.028 |
| Anxa1 | Neutrophils 1 | 4.10E−25 | 1.06E−20 | 1.738 | 0.625 | 0.146 |
| Nlrp3 | Neutrophils 1 | 7.86E−24 | 2.04E−19 | 1.634 | 0.393 | 0.038 |
| Ifitm6 | Neutrophils 1 | 1.22E−23 | 3.16E−19 | 2.127 | 0.411 | 0.024 |
| Cd177 | Neutrophils 1 | 1.61E−14 | 4.18E−10 | 1.529 | 0.268 | 0.012 |
| Ccl4 | Neutrophils 1 | 1.96E−09 | 5.08E−05 | 1.615 | 0.321 | 0.066 |
| Ptgs2 | Neutrophils 1 | 1.09E−08 | 0.000283854 | 1.638 | 0.214 | 0.03 |
| Thbs1 | Neutrophils 1 | 1.17E−08 | 0.000302668 | 1.683 | 0.196 | 0.033 |
| Ngp | Neutrophils 1 | 2.90E−08 | 0.00075138 | 1.790 | 0.214 | 0.02 |
| S100a9 | Neutrophils 2 | 6.59E−201 | 1.71E−196 | 4.730 | 0.957 | 0.047 |
| S100a8 | Neutrophils 2 | 8.22E−201 | 2.13E−196 | 4.489 | 0.974 | 0.042 |
| Ngp | Neutrophils 2 | 2.35E−185 | 6.10E−181 | 4.799 | 0.829 | 0.011 |
| Camp | Neutrophils 2 | 3.18E−181 | 8.24E−177 | 4.697 | 0.803 | 0.012 |
| Lcn2 | Neutrophils 2 | 1.25E−155 | 3.24E−151 | 3.901 | 0.778 | 0.012 |
| Ltf | Neutrophils 2 | 3.36E−153 | 8.70E−149 | 4.467 | 0.709 | 0.008 |
| Anxa1 | Neutrophils 2 | 1.28E−130 | 3.33E−126 | 2.454 | 0.624 | 0.143 |
| Chi313 | Neutrophils 2 | 1.32E−122 | 3.43E−118 | 3.553 | 0.641 | 0.012 |
| 1100001G20Rik | Neutrophils 2 | 2.76E−120 | 7.15E−116 | 2.396 | 0.624 | 0.006 |
| Cd177 | Neutrophils 2 | 8.17E−99 | 2.12E−94 | 2.388 | 0.538 | 0.007 |
| Hp | Neutrophils 2 | 1.50E−87 | 3.89E−83 | 2.507 | 0.632 | 0.025 |
| Prdx5 | Neutrophils 2 | 2.25E−78 | 5.84E−74 | 1.819 | 0.581 | 0.196 |
| Ifitm6 | Neutrophils 2 | 2.55E−77 | 6.62E−73 | 2.361 | 0.47 | 0.021 |
| Itgb2l | Neutrophils 2 | 2.59E−74 | 6.72E−70 | 1.467 | 0.376 | 0.004 |
| Chi3l1 | Neutrophils 2 | 9.34E−68 | 2.42E−63 | 1.639 | 0.419 | 0.006 |
| Lyz2 | Neutrophils 2 | 7.48E−67 | 1.94E−62 | 2.071 | 0.863 | 0.206 |
| Trem3 | Neutrophils 2 | 2.81E−63 | 7.29E−59 | 1.360 | 0.385 | 0.006 |
| Tkt | Neutrophils 2 | 9.96E−58 | 2.58E−53 | 1.329 | 0.607 | 0.305 |
| Fcnb | Neutrophils 2 | 6.85E−57 | 1.78E−52 | 1.626 | 0.274 | 0.001 |
| Ckap4 | Neutrophils 2 | 1.08E−56 | 2.80E−52 | 1.491 | 0.479 | 0.071 |
| Retnlg | Neutrophils 2 | 1.70E−56 | 4.42E−52 | 2.215 | 0.41 | 0.011 |
| Itgam | Neutrophils 2 | 2.87E−54 | 7.44E−50 | 1.789 | 0.556 | 0.067 |
| Aldh2 | Neutrophils 2 | 3.09E−50 | 8.01E−46 | 1.389 | 0.581 | 0.215 |
| Arhgdib | Neutrophils 2 | 5.79E−49 | 1.50E−44 | 1.230 | 0.692 | 0.474 |
| Pygl | Neutrophils 2 | 4.60E−47 | 1.19E−42 | 1.594 | 0.479 | 0.069 |
| Dstn | Neutrophils 2 | 1.18E−46 | 3.06E−42 | 1.392 | 0.479 | 0.145 |
| Clec5a | Neutrophils 2 | 1.25E−44 | 3.24E−40 | 0.814 | 0.325 | 0.009 |
| Abca13 | Neutrophils 2 | 1.76E−43 | 4.57E−39 | 0.904 | 0.291 | 0.005 |
| Fpr2 | Neutrophils 2 | 4.49E−42 | 1.16E−37 | 1.197 | 0.308 | 0.008 |
| Nfe2 | Neutrophils 2 | 5.11E−42 | 1.33E−37 | 0.802 | 0.333 | 0.011 |
| Sgms2 | Neutrophils 2 | 2.59E−41 | 6.70E−37 | 0.828 | 0.282 | 0.006 |
| Serpinb1a | Neutrophils 2 | 1.95E−39 | 5.05E−35 | 1.500 | 0.513 | 0.11 |
| Prtn3 | Neutrophils 2 | 3.00E−39 | 7.78E−35 | 1.699 | 0.214 | 0.003 |
| Lta4h | Neutrophils 2 | 5.23E−39 | 1.36E−34 | 1.223 | 0.444 | 0.182 |
| Ms4a3 | Neutrophils 2 | 1.20E−38 | 3.11E−34 | 0.879 | 0.197 | 0.001 |
| Mmp9 | Neutrophils 2 | 2.21E−38 | 5.72E−34 | 1.806 | 0.325 | 0.017 |
| Cybb | Neutrophils 2 | 4.69E−38 | 1.22E−33 | 1.598 | 0.641 | 0.249 |
| Mmp8 | Neutrophils 2 | 4.08E−37 | 1.06E−32 | 2.087 | 0.291 | 0.01 |
| Slpi | Neutrophils 2 | 5.84E−37 | 1.51E−32 | 0.856 | 0.368 | 0.025 |
| Pglyrp1 | Neutrophils 2 | 9.54E−37 | 2.47E−32 | 1.084 | 0.368 | 0.047 |
| Gda | Neutrophils 2 | 8.24E−35 | 2.14E−30 | 1.300 | 0.444 | 0.048 |
| Cxcr2 | Neutrophils 2 | 1.62E−34 | 4.20E−30 | 0.885 | 0.265 | 0.01 |
| Slfn4 | Neutrophils 2 | 2.63E−34 | 6.81E−30 | 1.179 | 0.299 | 0.012 |
| Ncf1 | Neutrophils 2 | 3.50E−34 | 9.07E−30 | 1.182 | 0.53 | 0.304 |
| Hdc | Neutrophils 2 | 2.42E−33 | 6.27E−29 | 0.758 | 0.282 | 0.015 |
| Mpo | Neutrophils 2 | 1.61E−32 | 4.17E−28 | 2.736 | 0.179 | 0.004 |
| Msrb1 | Neutrophils 2 | 3.76E−32 | 9.74E−28 | 1.201 | 0.487 | 0.113 |

TABLE 2-continued

Significant Cluster-Defining Genes for Cell Types Identified from the Steady State LN Cell Atlas

| Gene | Cell type | p-value | q-value | Average log fold change | % Expressing in Cluster | % Expressing Rest |
|---|---|---|---|---|---|---|
| Lrg1 | Neutrophils 2 | 4.00E−32 | 1.04E−27 | 1.258 | 0.41 | 0.042 |
| Gsr | Neutrophils 2 | 8.01E−32 | 2.08E−27 | 1.128 | 0.47 | 0.112 |
| Gpi1 | Neutrophils 2 | 2.05E−31 | 5.31E−27 | 0.966 | 0.615 | 0.393 |
| Ltb4r1 | Neutrophils 2 | 1.93E−30 | 5.00E−26 | 0.746 | 0.308 | 0.02 |
| G6pdx | Neutrophils 2 | 7.31E−30 | 1.89E−25 | 1.103 | 0.385 | 0.11 |
| Pgd | Neutrophils 2 | 2.18E−29 | 5.66E−25 | 1.097 | 0.487 | 0.186 |
| Ccr1 | Neutrophils 2 | 1.23E−28 | 3.19E−24 | 0.775 | 0.308 | 0.022 |
| Fcgr3 | Neutrophils 2 | 2.96E−28 | 7.68E−24 | 0.863 | 0.393 | 0.046 |
| Dgat2 | Neutrophils 2 | 4.90E−28 | 1.27E−23 | 0.783 | 0.291 | 0.02 |
| Adpgk | Neutrophils 2 | 2.08E−27 | 5.40E−23 | 1.109 | 0.496 | 0.169 |
| Hk3 | Neutrophils 2 | 2.65E−27 | 6.87E−23 | 0.959 | 0.35 | 0.047 |
| Clec4a2 | Neutrophils 2 | 9.00E−27 | 2.33E−22 | 0.889 | 0.35 | 0.038 |
| Mgst1 | Neutrophils 2 | 5.11E−26 | 1.32E−21 | 0.747 | 0.359 | 0.04 |
| 1810033B17Rik | Neutrophils 2 | 3.13E−25 | 8.13E−21 | 0.967 | 0.41 | 0.068 |
| Igsf6 | Neutrophils 2 | 1.33E−24 | 3.44E−20 | 1.139 | 0.427 | 0.087 |
| Pkm | Neutrophils 2 | 9.52E−24 | 2.47E−19 | 0.842 | 0.581 | 0.347 |
| Megf9 | Neutrophils 2 | 1.57E−23 | 4.07E−19 | 0.808 | 0.316 | 0.041 |
| Ly6c2 | Neutrophils 2 | 3.63E−23 | 9.41E−19 | 0.840 | 0.547 | 0.158 |
| Syne1 | Neutrophils 2 | 6.47E−23 | 1.68E−18 | 1.105 | 0.504 | 0.245 |
| Fam101b | Neutrophils 2 | 1.97E−22 | 5.12E−18 | 1.014 | 0.419 | 0.094 |
| Agpat2 | Neutrophils 2 | 1.24E−21 | 3.21E−17 | 0.747 | 0.316 | 0.043 |
| Rab3d | Neutrophils 2 | 1.79E−21 | 4.64E−17 | 0.937 | 0.359 | 0.085 |
| 4632428N05Rik | Neutrophils 2 | 2.54E−21 | 6.59E−17 | 0.926 | 0.479 | 0.235 |
| Crispld2 | Neutrophils 2 | 2.94E−21 | 7.63E−17 | 0.844 | 0.35 | 0.052 |
| Abhd5 | Neutrophils 2 | 2.17E−20 | 5.64E−16 | 0.741 | 0.325 | 0.055 |
| Lipg | Neutrophils 2 | 3.76E−20 | 9.75E−16 | 0.767 | 0.162 | 0.005 |
| Alox5ap | Neutrophils 2 | 4.06E−20 | 1.05E−15 | 1.028 | 0.624 | 0.246 |
| Cd24a | Neutrophils 2 | 8.33E−20 | 2.16E−15 | 0.941 | 0.504 | 0.177 |
| Mettl9 | Neutrophils 2 | 3.25E−19 | 8.42E−15 | 0.849 | 0.333 | 0.114 |
| 6430548M08Rik | Neutrophils 2 | 4.92E−19 | 1.27E−14 | 0.827 | 0.274 | 0.039 |
| Ceacam1 | Neutrophils 2 | 5.00E−19 | 1.30E−14 | 0.782 | 0.308 | 0.05 |
| Itgb2 | Neutrophils 2 | 7.85E−18 | 2.04E−13 | 0.821 | 0.607 | 0.401 |
| Ncf2 | Neutrophils 2 | 1.20E−17 | 3.12E−13 | 0.804 | 0.427 | 0.128 |
| Clec12a | Neutrophils 2 | 1.69E−17 | 4.39E−13 | 0.929 | 0.419 | 0.144 |
| Gadd45a | Neutrophils 2 | 2.59E−17 | 6.72E−13 | 0.747 | 0.308 | 0.06 |
| Alas1 | Neutrophils 2 | 3.39E−17 | 8.78E−13 | 0.811 | 0.316 | 0.097 |
| Txn1 | Neutrophils 2 | 7.95E−17 | 2.06E−12 | 0.763 | 0.641 | 0.319 |
| Ncf4 | Neutrophils 2 | 9.83E−17 | 2.55E−12 | 0.861 | 0.444 | 0.205 |
| Cd63 | Neutrophils 2 | 1.14E−16 | 2.95E−12 | 0.754 | 0.47 | 0.132 |
| Slc2a3 | Neutrophils 2 | 6.94E−16 | 1.80E−11 | 0.895 | 0.35 | 0.106 |
| Taldo1 | Neutrophils 2 | 2.04E−15 | 5.28E−11 | 0.751 | 0.607 | 0.358 |
| Ifitm3 | Neutrophils 2 | 3.73E−15 | 9.68E−11 | 0.765 | 0.487 | 0.155 |
| Gpx1 | Neutrophils 2 | 1.02E−14 | 2.64E−10 | 0.761 | 0.769 | 0.518 |
| Mxd1 | Neutrophils 2 | 1.16E−14 | 3.01E−10 | 0.870 | 0.538 | 0.207 |
| Dgat1 | Neutrophils 2 | 4.01E−14 | 1.04E−09 | 0.725 | 0.291 | 0.07 |
| Vasp | Neutrophils 2 | 1.47E−13 | 3.80E−09 | 0.705 | 0.53 | 0.353 |
| Flot1 | Neutrophils 2 | 1.02E−12 | 2.63E−08 | 0.707 | 0.393 | 0.141 |
| Cpne3 | Neutrophils 2 | 3.43E−12 | 8.89E−08 | 0.759 | 0.453 | 0.265 |
| Golim4 | Neutrophils 2 | 5.69E−12 | 1.48E−07 | 0.743 | 0.35 | 0.135 |
| Nhsl2 | Neutrophils 2 | 7.00E−12 | 1.82E−07 | 0.707 | 0.256 | 0.055 |
| Fcer1g | Neutrophils 2 | 1.17E−10 | 3.03E−06 | 0.710 | 0.556 | 0.275 |
| S100a6 | Neutrophils 2 | 8.75E−09 | 0.000226934 | 0.735 | 0.41 | 0.23 |
| Mki67 | Neutrophils 2 | 5.07E−08 | 0.001313719 | 0.783 | 0.402 | 0.175 |
| Klrb1c | NK Cells | 0 | 0 | 2.223 | 0.736 | 0.021 |
| Il18rap | NK Cells | 0 | 0 | 2.101 | 0.81 | 0.105 |
| Klrk1 | NK Cells | 0 | 0 | 1.863 | 0.77 | 0.118 |
| Ncr1 | NK Cells | 0 | 0 | 1.618 | 0.56 | 0.013 |
| Nkg7 | NK Cells | 8.88347617017985e−310 | 2.30E−305 | 1.791 | 0.662 | 0.06 |
| Ctsw | NK Cells | 1.95E−294 | 5.05E−290 | 1.695 | 0.743 | 0.109 |
| Il2rb | NK Cells | 5.41E−294 | 1.40E−289 | 1.659 | 0.682 | 0.081 |
| Samd3 | NK Cells | 1.02E−259 | 2.64E−255 | 1.401 | 0.504 | 0.019 |
| Klre1 | NK Cells | 2.87E−255 | 7.43E−251 | 1.504 | 0.436 | 0.012 |
| Gzma | NK Cells | 4.91E−254 | 1.27E−249 | 2.609 | 0.452 | 0.022 |
| Jak1 | NK Cells | 2.04E−246 | 5.30E−242 | 1.308 | 0.917 | 0.629 |
| Eomes | NK Cells | 1.87E−231 | 4.84E−227 | 1.636 | 0.447 | 0.02 |
| Klra4 | NK Cells | 5.72E−231 | 1.48E−226 | 1.821 | 0.411 | 0.015 |
| Klrd1 | NK Cells | 4.34E−212 | 1.13E−207 | 1.465 | 0.645 | 0.123 |
| Klrb1f | NK Cells | 5.45E−211 | 1.41E−206 | 1.278 | 0.467 | 0.029 |
| Ccl5 | NK Cells | 1.12E−203 | 2.90E−199 | 1.318 | 0.84 | 0.256 |
| Xcl1 | NK Cells | 4.83E−188 | 1.25E−183 | 1.504 | 0.373 | 0.014 |
| Il18r1 | NK Cells | 1.91E−184 | 4.94E−180 | 1.414 | 0.682 | 0.141 |
| Ms4a4b | NK Cells | 7.44E−182 | 1.93E−177 | 1.342 | 0.732 | 0.188 |
| Ptprc | NK Cells | 2.48E−178 | 6.42E−174 | 0.904 | 0.969 | 0.798 |

TABLE 2-continued

Significant Cluster-Defining Genes for Cell Types Identified from the Steady State LN Cell Atlas

| Gene | Cell type | p-value | q-value | Average log fold change | % Expressing in Cluster | % Expressing Rest |
|---|---|---|---|---|---|---|
| Klrb1b | NK Cells | 5.83E−173 | 1.51E−168 | 1.718 | 0.472 | 0.052 |
| Klra7 | NK Cells | 1.74E−169 | 4.51E−165 | 1.314 | 0.305 | 0.008 |
| Adamts14 | NK Cells | 6.16E−164 | 1.60E−159 | 1.133 | 0.332 | 0.012 |
| Ugcg | NK Cells | 1.33E−163 | 3.46E−159 | 1.244 | 0.664 | 0.237 |
| Gimap4 | NK Cells | 1.32E−159 | 3.42E−155 | 1.327 | 0.679 | 0.216 |
| Car2 | NK Cells | 4.50E−156 | 1.17E−151 | 1.242 | 0.368 | 0.026 |
| Prf1 | NK Cells | 6.01E−153 | 1.56E−148 | 1.121 | 0.341 | 0.019 |
| Spry2 | NK Cells | 2.07E−152 | 5.38E−148 | 1.119 | 0.368 | 0.028 |
| Klrc2 | NK Cells | 2.86E−144 | 7.40E−140 | 0.817 | 0.262 | 0.006 |
| Klri2 | NK Cells | 2.63E−136 | 6.83E−132 | 1.273 | 0.271 | 0.014 |
| Klra8 | NK Cells | 4.70E−135 | 1.22E−130 | 1.539 | 0.251 | 0.008 |
| Ctla2a | NK Cells | 4.76E−132 | 1.24E−127 | 1.088 | 0.408 | 0.051 |
| Txk | NK Cells | 2.79E−129 | 7.22E−125 | 1.045 | 0.467 | 0.074 |
| Vps37b | NK Cells | 4.22E−125 | 1.09E−120 | 1.462 | 0.587 | 0.245 |
| Tbx21 | NK Cells | 4.19E−122 | 1.09E−117 | 0.882 | 0.302 | 0.022 |
| AW112010 | NK Cells | 6.95E−121 | 1.80E−116 | 1.175 | 0.594 | 0.196 |
| Ifng | NK Cells | 5.78E−119 | 1.50E−114 | 1.121 | 0.233 | 0.008 |
| Ccr5 | NK Cells | 3.97E−118 | 1.03E−113 | 1.062 | 0.429 | 0.079 |
| Ctla2b | NK Cells | 7.40E−116 | 1.92E−111 | 0.876 | 0.323 | 0.033 |
| Klra1 | NK Cells | 4.36E−113 | 1.13E−108 | 0.766 | 0.242 | 0.01 |
| Pde2a | NK Cells | 3.30E−110 | 8.57E−106 | 1.046 | 0.558 | 0.147 |
| Arl4d | NK Cells | 1.30E−108 | 3.38E−104 | 0.827 | 0.262 | 0.019 |
| Ahnak | NK Cells | 7.93E−104 | 2.06E−99 | 0.869 | 0.876 | 0.576 |
| Sytl3 | NK Cells | 1.97E−99 | 5.12E−95 | 0.860 | 0.352 | 0.051 |
| Ifngr1 | NK Cells | 2.00E−99 | 5.18E−95 | 1.022 | 0.7 | 0.377 |
| Itga2 | NK Cells | 7.35E−99 | 1.90E−94 | 0.885 | 0.284 | 0.032 |
| Cd7 | NK Cells | 4.98E−98 | 1.29E−93 | 1.006 | 0.488 | 0.127 |
| Stat4 | NK Cells | 7.68E−92 | 1.99E−87 | 0.944 | 0.472 | 0.13 |
| Cd2 | NK Cells | 1.25E−89 | 3.23E−85 | 0.962 | 0.481 | 0.133 |
| Emb | NK Cells | 1.10E−88 | 2.85E−84 | 1.089 | 0.555 | 0.223 |
| Sh2d2a | NK Cells | 2.02E−88 | 5.23E−84 | 0.956 | 0.4 | 0.1 |
| Fcer1g | NK Cells | 2.40E−88 | 6.23E−84 | 0.876 | 0.652 | 0.255 |
| Gzmb | NK Cells | 4.54E−87 | 1.18E−82 | 1.190 | 0.189 | 0.008 |
| Gimap6 | NK Cells | 1.58E−86 | 4.09E−82 | 0.930 | 0.697 | 0.325 |
| Ets1 | NK Cells | 1.31E−85 | 3.40E−81 | 0.796 | 0.797 | 0.456 |
| Cpne7 | NK Cells | 5.61E−85 | 1.45E−80 | 0.848 | 0.246 | 0.023 |
| Atp11b | NK Cells | 1.63E−84 | 4.23E−80 | 0.879 | 0.603 | 0.31 |
| Chsy1 | NK Cells | 4.93E−81 | 1.28E−76 | 0.874 | 0.433 | 0.143 |
| Dok2 | NK Cells | 5.79E−78 | 1.50E−73 | 0.737 | 0.329 | 0.063 |
| QrfP | NK Cells | 9.98E−78 | 2.59E−73 | 0.712 | 0.215 | 0.017 |
| Trbc1 | NK Cells | 3.52E−77 | 9.13E−73 | 0.787 | 0.429 | 0.106 |
| Ccr2 | NK Cells | 2.22E−76 | 5.77E−72 | 0.991 | 0.56 | 0.211 |
| Ctsd | NK Cells | 1.86E−75 | 4.82E−71 | 0.851 | 0.569 | 0.257 |
| Bin2 | NK Cells | 3.34E−75 | 8.67E−71 | 0.833 | 0.6 | 0.292 |
| Tyrobp | NK Cells | 3.25E−72 | 8.43E−68 | 0.766 | 0.732 | 0.382 |
| Gimap8 | NK Cells | 1.55E−68 | 4.03E−64 | 0.802 | 0.562 | 0.223 |
| Neurl3 | NK Cells | 5.95E−66 | 1.54E−61 | 0.857 | 0.576 | 0.27 |
| Tcf7 | NK Cells | 8.11E−66 | 2.10E−61 | 0.833 | 0.573 | 0.24 |
| Hs3st3b1 | NK Cells | 1.29E−65 | 3.34E−61 | 0.786 | 0.298 | 0.066 |
| Evl | NK Cells | 1.61E−65 | 4.17E−61 | 0.746 | 0.639 | 0.359 |
| 1-Sep | NK Cells | 4.21E−64 | 1.09E−59 | 0.744 | 0.627 | 0.319 |
| Tecpr1 | NK Cells | 1.16E−63 | 3.00E−59 | 0.798 | 0.625 | 0.316 |
| Ptpn22 | NK Cells | 3.43E−63 | 8.89E−59 | 0.769 | 0.628 | 0.343 |
| Itgb1 | NK Cells | 1.10E−62 | 2.84E−58 | 0.791 | 0.662 | 0.397 |
| Gimap5 | NK Cells | 4.93E−62 | 1.28E−57 | 0.776 | 0.391 | 0.125 |
| Atp8b4 | NK Cells | 3.07E−61 | 7.96E−57 | 0.813 | 0.488 | 0.19 |
| Sytl2 | NK Cells | 1.51E−59 | 3.92E−55 | 0.666 | 0.219 | 0.031 |
| S100a10 | NK Cells | 6.90E−59 | 1.79E−54 | 0.744 | 0.544 | 0.255 |
| Fxyd5 | NK Cells | 1.45E−56 | 3.75E−52 | 0.702 | 0.661 | 0.414 |
| Itgal | NK Cells | 5.50E−56 | 1.43E−51 | 0.723 | 0.564 | 0.29 |
| Padi2 | NK Cells | 7.85E−56 | 2.03E−51 | 0.682 | 0.393 | 0.129 |
| Pnrc1 | NK Cells | 1.66E−55 | 4.31E−51 | 0.708 | 0.592 | 0.415 |
| Skap1 | NK Cells | 1.97E−55 | 5.10E−51 | 0.711 | 0.454 | 0.157 |
| Serpinb9 | NK Cells | 2.18E−55 | 5.65E−51 | 0.722 | 0.431 | 0.152 |
| Ccnd2 | NK Cells | 2.02E−54 | 5.25E−50 | 0.866 | 0.469 | 0.189 |
| Spata13 | NK Cells | 1.39E−53 | 3.60E−49 | 0.709 | 0.399 | 0.153 |
| Pde3b | NK Cells | 1.57E−53 | 4.07E−49 | 0.808 | 0.37 | 0.126 |
| Spn | NK Cells | 1.81E−53 | 4.69E−49 | 0.688 | 0.519 | 0.226 |
| Cd97 | NK Cells | 6.33E−53 | 1.64E−48 | 0.732 | 0.61 | 0.364 |
| Hcst | NK Cells | 2.65E−51 | 6.86E−47 | 0.699 | 0.346 | 0.114 |
| Usp48 | NK Cells | 3.05E−51 | 7.91E−47 | 0.718 | 0.557 | 0.351 |
| Rbl2 | NK Cells | 2.44E−49 | 6.32E−45 | 0.681 | 0.542 | 0.32 |
| Prkacb | NK Cells | 1.30E−46 | 3.38E−42 | 0.671 | 0.499 | 0.286 |

TABLE 2-continued

Significant Cluster-Defining Genes for Cell Types Identified from the Steady State LN Cell Atlas

| Gene | Cell type | p-value | q-value | Average log fold change | % Expressing in Cluster | % Expressing Rest |
|---|---|---|---|---|---|---|
| Bcl2l11 | NK Cells | 5.72E−46 | 1.48E−41 | 0.700 | 0.377 | 0.151 |
| Gem | NK Cells | 1.49E−45 | 3.85E−41 | 0.672 | 0.275 | 0.076 |
| Nbeal2 | NK Cells | 2.30E−41 | 5.96E−37 | 0.667 | 0.372 | 0.166 |
| Dusp5 | NK Cells | 6.57E−38 | 1.70E−33 | 0.744 | 0.364 | 0.167 |
| 5830416P10Rik | NK Cells | 3.67E−36 | 9.52E−32 | 0.733 | 0.298 | 0.113 |
| Bcl2 | NK Cells | 5.69E−36 | 1.48E−31 | 0.692 | 0.436 | 0.215 |
| Bhlhe40 | NK Cells | 6.53E−35 | 1.69E−30 | 0.737 | 0.32 | 0.138 |
| Siglech | pDC | 0 | 0 | 3.367 | 0.988 | 0.072 |
| Ccr9 | pDC | 0 | 0 | 1.978 | 0.692 | 0.062 |
| Cd300c | pDC | 0 | 0 | 1.869 | 0.715 | 0.033 |
| Lair1 | pDC | 0 | 0 | 1.826 | 0.663 | 0.05 |
| Pld4 | pDC | 0 | 0 | 1.825 | 0.911 | 0.256 |
| Irf8 | pDC | 0 | 0 | 1.802 | 0.988 | 0.465 |
| Bst2 | pDC | 0 | 0 | 1.727 | 0.737 | 0.175 |
| Tex2 | pDC | 0 | 0 | 1.722 | 0.736 | 0.116 |
| Smim5 | pDC | 0 | 0 | 1.627 | 0.579 | 0.02 |
| Tcf4 | pDC | 0 | 0 | 1.594 | 0.84 | 0.265 |
| Fyn | pDC | 0 | 0 | 1.575 | 0.895 | 0.38 |
| Cyth4 | pDC | 0 | 0 | 1.488 | 0.867 | 0.358 |
| Klk1 | pDC | 5.70E−308 | 1.48E−303 | 1.694 | 0.444 | 0.007 |
| Obscn | pDC | 1.72E−294 | 4.47E−290 | 1.905 | 0.473 | 0.016 |
| Tfrc | pDC | 8.44E−285 | 2.19E−280 | 1.665 | 0.698 | 0.166 |
| Rpgrip1 | pDC | 9.59E−285 | 2.49E−280 | 1.769 | 0.663 | 0.126 |
| Runx2 | pDC | 6.02E−281 | 1.56E−276 | 1.473 | 0.681 | 0.124 |
| Mctp2 | pDC | 3.87E−279 | 1.00E−274 | 1.428 | 0.605 | 0.065 |
| Ly6c2 | pDC | 4.32E−279 | 1.12E−274 | 1.765 | 0.718 | 0.122 |
| Ptprs | pDC | 3.52E−278 | 9.11E−274 | 1.513 | 0.673 | 0.154 |
| Adam11 | pDC | 1.00E−269 | 2.60E−265 | 1.714 | 0.736 | 0.142 |
| Tubgcp5 | pDC | 1.97E−269 | 5.12E−265 | 1.459 | 0.641 | 0.121 |
| Ly6d | pDC | 2.38E−256 | 6.18E−252 | 1.773 | 0.594 | 0.095 |
| Atp1b1 | pDC | 1.09E−248 | 2.83E−244 | 1.516 | 0.66 | 0.13 |
| 2810442I21Rik | pDC | 1.13E−248 | 2.93E−244 | 1.312 | 0.444 | 0.024 |
| Nucb2 | pDC | 7.93E−247 | 2.06E−242 | 1.444 | 0.569 | 0.112 |
| Cox6a2 | pDC | 4.02E−239 | 1.04E−234 | 1.217 | 0.36 | 0.006 |
| Dirc2 | pDC | 3.80E−231 | 9.85E−227 | 1.289 | 0.568 | 0.101 |
| Tyrobp | pDC | 1.32E−230 | 3.43E−226 | 1.460 | 0.85 | 0.369 |
| Cybb | pDC | 5.33E−230 | 1.38E−225 | 1.402 | 0.789 | 0.215 |
| Chdh | pDC | 4.61E−224 | 1.19E−219 | 1.184 | 0.437 | 0.03 |
| Pdzd4 | pDC | 3.94E−221 | 1.02E−216 | 1.124 | 0.455 | 0.033 |
| Lifr | pDC | 1.72E−219 | 4.47E−215 | 1.349 | 0.701 | 0.142 |
| Slco4a1 | pDC | 2.05E−218 | 5.32E−214 | 1.072 | 0.371 | 0.014 |
| Slc44a2 | pDC | 2.90E−217 | 7.52E−213 | 1.275 | 0.71 | 0.262 |
| Tcirg1 | pDC | 1.12E−215 | 2.91E−211 | 1.335 | 0.675 | 0.241 |
| Spns3 | pDC | 3.54E−212 | 9.17E−208 | 1.172 | 0.456 | 0.043 |
| Lrrc16a | pDC | 6.47E−212 | 1.68E−207 | 1.343 | 0.557 | 0.087 |
| Fyb | pDC | 2.10E−211 | 5.46E−207 | 1.162 | 0.867 | 0.476 |
| Mpeg1 | pDC | 4.53E−208 | 1.17E−203 | 1.464 | 0.866 | 0.332 |
| Fgr | pDC | 2.76E−202 | 7.16E−198 | 1.278 | 0.608 | 0.119 |
| Ctsl | pDC | 1.03E−199 | 2.67E−195 | 1.400 | 0.602 | 0.102 |
| Ctsb | pDC | 8.57E−197 | 2.22E−192 | 1.341 | 0.737 | 0.4 |
| Tmem229b | pDC | 1.23E−190 | 3.18E−186 | 1.200 | 0.518 | 0.119 |
| Sema4b | pDC | 1.74E−185 | 4.52E−181 | 1.195 | 0.542 | 0.102 |
| Cacna1e | pDC | 2.91E−183 | 7.55E−179 | 1.313 | 0.478 | 0.065 |
| Klra17 | pDC | 1.32E−182 | 3.41E−178 | 1.101 | 0.452 | 0.047 |
| Sh3bgr | pDC | 1.23E−180 | 3.20E−176 | 0.928 | 0.285 | 0.006 |
| Clec10a | pDC | 2.63E−180 | 6.82E−176 | 1.097 | 0.455 | 0.047 |
| Plac8 | pDC | 4.72E−179 | 1.22E−174 | 1.397 | 0.698 | 0.243 |
| Stat2 | pDC | 1.65E−176 | 4.27E−172 | 1.299 | 0.689 | 0.307 |
| Dntt | pDC | 4.03E−175 | 1.04E−170 | 0.921 | 0.292 | 0.008 |
| Psap | pDC | 4.84E−175 | 1.25E−170 | 0.988 | 0.953 | 0.637 |
| Bcr | pDC | 1.21E−172 | 3.14E−168 | 1.106 | 0.502 | 0.093 |
| Slamf9 | pDC | 4.63E−172 | 1.20E−167 | 1.125 | 0.356 | 0.028 |
| Pltp | pDC | 3.72E−168 | 9.63E−164 | 1.237 | 0.479 | 0.065 |
| Rnase6 | pDC | 1.57E−165 | 4.07E−161 | 1.177 | 0.568 | 0.177 |
| Atp3a2 | pDC | 4.13E−164 | 1.07E−159 | 1.119 | 0.627 | 0.211 |
| Rell1 | pDC | 2.92E−162 | 7.58E−158 | 1.145 | 0.487 | 0.132 |
| Ptprf | pDC | 4.29E−160 | 1.11E−155 | 1.034 | 0.4 | 0.044 |
| Rabgap11 | pDC | 2.31E−157 | 6.00E−153 | 1.035 | 0.769 | 0.394 |
| Eepd1 | pDC | 4.36E−156 | 1.13E−151 | 1.006 | 0.391 | 0.048 |
| Slc41a2 | pDC | 3.58E−151 | 9.27E−147 | 0.984 | 0.405 | 0.054 |
| Pacsin1 | pDC | 8.93E−151 | 2.31E−146 | 0.978 | 0.415 | 0.057 |
| Spib | pDC | 1.31E−149 | 3.39E−145 | 1.133 | 0.542 | 0.129 |
| Irf2bp2 | pDC | 8.44E−143 | 2.19E−138 | 0.988 | 0.661 | 0.295 |

TABLE 2-continued

Significant Cluster-Defining Genes for Cell Types Identified from the Steady State LN Cell Atlas

| Gene | Cell type | p-value | q-value | Average log fold change | % Expressing in Cluster | % Expressing Rest |
|---|---|---|---|---|---|---|
| Prkcd | pDC | 5.68E−141 | 1.47E−136 | 1.031 | 0.701 | 0.357 |
| Ctsh | pDC | 6.77E−141 | 1.75E−136 | 0.981 | 0.776 | 0.4 |
| Card11 | pDC | 1.13E−140 | 2.94E−136 | 1.071 | 0.6 | 0.198 |
| Snx5 | pDC | 1.58E−138 | 4.10E−134 | 0.933 | 0.766 | 0.475 |
| Ppfia4 | pDC | 4.19E−137 | 1.09E−132 | 1.047 | 0.533 | 0.149 |
| Gm12503 | pDC | 6.23E−137 | 1.62E−132 | 0.917 | 0.246 | 0.009 |
| Zc3h12c | pDC | 2.90E−135 | 7.52E−131 | 1.178 | 0.551 | 0.157 |
| Cd4 | pDC | 2.92E−131 | 7.57E−127 | 1.150 | 0.507 | 0.106 |
| Mvb12a | pDC | 1.44E−130 | 3.75E−126 | 0.974 | 0.499 | 0.194 |
| Bcl11a | pDC | 1.14E−127 | 2.96E−123 | 1.080 | 0.617 | 0.213 |
| Rps6ka1 | pDC | 1.63E−127 | 4.22E−123 | 0.947 | 0.627 | 0.275 |
| Pgls | pDC | 3.23E−125 | 8.38E−121 | 0.911 | 0.583 | 0.307 |
| Snx18 | pDC | 1.35E−123 | 3.50E−119 | 1.012 | 0.505 | 0.169 |
| Tbc1d8 | pDC | 3.25E−123 | 8.43E−119 | 0.945 | 0.731 | 0.293 |
| Ifnar1 | pDC | 9.63E−120 | 2.50E−115 | 0.958 | 0.673 | 0.357 |
| Xbp1 | pDC | 2.45E−119 | 6.34E−115 | 0.973 | 0.569 | 0.23 |
| Prkca | pDC | 8.58E−119 | 2.23E−114 | 0.993 | 0.427 | 0.087 |
| Slc39a14 | pDC | 1.41E−116 | 3.65E−112 | 0.917 | 0.38 | 0.071 |
| Sell | pDC | 1.73E−115 | 4.47E−111 | 0.946 | 0.705 | 0.298 |
| Plekhm3 | pDC | 2.79E−112 | 7.24E−108 | 0.978 | 0.537 | 0.191 |
| Tspan13 | pDC | 1.26E−110 | 3.27E−106 | 0.950 | 0.516 | 0.267 |
| Rhobtb2 | pDC | 3.80E−105 | 9.84E−101 | 0.933 | 0.45 | 0.141 |
| Serp1 | pDC | 4.78E−105 | 1.24E−100 | 0.911 | 0.653 | 0.428 |
| Npc1 | pDC | 2.33E−102 | 6.03E−98 | 0.923 | 0.479 | 0.17 |
| Gns | pDC | 9.22E−101 | 2.39E−96 | 0.902 | 0.563 | 0.251 |
| Serinc5 | pDC | 9.08E−97 | 2.35E−92 | 0.907 | 0.427 | 0.13 |
| Plaur | pDC | 8.63E−88 | 2.24E−83 | 0.925 | 0.325 | 0.067 |
| Ly6a | pDC | 1.12E−79 | 2.91E−75 | 0.905 | 0.443 | 0.153 |
| Trib1 | pDC | 7.24E−79 | 1.88E−74 | 0.932 | 0.417 | 0.144 |
| Cd8b1 | pDC | 2.91E−56 | 7.53E−52 | 1.015 | 0.324 | 0.096 |
| Ccl4 | pDC | 6.16E−45 | 1.60E−40 | 1.125 | 0.22 | 0.056 |
| Igkc | Plasmablasts | 0 | 0 | 5.510 | 0.865 | 0.201 |
| Igj | Plasmablasts | 0 | 0 | 5.361 | 1 | 0.028 |
| Ighm | Plasmablasts | 0 | 0 | 5.056 | 0.794 | 0.497 |
| Txndc5 | Plasmablasts | 1.22E−232 | 3.15E−228 | 2.350 | 0.858 | 0.21 |
| Trp53inp1 | Plasmablasts | 1.87E−189 | 4.84E−185 | 2.282 | 0.839 | 0.312 |
| Iglc2 | Plasmablasts | 1.38E−179 | 3.57E−175 | 4.064 | 0.942 | 0.175 |
| Xbp1 | Plasmablasts | 7.27E−164 | 1.89E−159 | 2.059 | 0.865 | 0.243 |
| Ighg3 | Plasmablasts | 8.64E−162 | 2.24E−157 | 5.557 | 0.465 | 0.082 |
| Prg2 | Plasmablasts | 4.59E−156 | 1.19E−151 | 1.831 | 0.587 | 0.002 |
| Herpud1 | Plasmablasts | 1.05E−155 | 2.72E−151 | 1.939 | 0.903 | 0.342 |
| Iglv1 | Plasmablasts | 1.01E−152 | 2.62E−148 | 4.185 | 0.639 | 0.01 |
| Mzb1 | Plasmablasts | 2.64E−136 | 6.83E−132 | 1.949 | 0.703 | 0.05 |
| Derl3 | Plasmablasts | 9.74E−134 | 2.53E−129 | 1.493 | 0.574 | 0.008 |
| Slc3a2 | Plasmablasts | 3.76E−133 | 9.74E−129 | 1.797 | 0.845 | 0.256 |
| Igha | Plasmablasts | 1.93E−128 | 5.00E−124 | 5.100 | 0.271 | 0.05 |
| Ighg2b | Plasmablasts | 1.97E−120 | 5.12E−116 | 5.527 | 0.284 | 0.035 |
| Eaf2 | Plasmablasts | 3.15E−118 | 8.17E−114 | 1.245 | 0.535 | 0.007 |
| Pdia4 | Plasmablasts | 5.72E−109 | 1.48E−104 | 1.591 | 0.755 | 0.211 |
| Fam46c | Plasmablasts | 1.72E−107 | 4.47E−103 | 1.820 | 0.774 | 0.159 |
| Chst1 | Plasmablasts | 6.79E−104 | 1.76E−99 | 1.495 | 0.535 | 0.016 |
| Creld2 | Plasmablasts | 2.22E−102 | 5.76E−98 | 1.567 | 0.652 | 0.107 |
| Hsp90b1 | Plasmablasts | 8.39E−96 | 2.17E−91 | 1.524 | 0.89 | 0.532 |
| Pou2af1 | Plasmablasts | 2.04E−89 | 5.30E−85 | 1.711 | 0.735 | 0.098 |
| Serp1 | Plasmablasts | 2.36E−87 | 6.13E−83 | 1.383 | 0.897 | 0.435 |
| Prlr | Plasmablasts | 3.54E−86 | 9.19E−82 | 1.032 | 0.374 | 0.003 |
| Slpi | Plasmablasts | 5.93E−84 | 1.54E−79 | 2.304 | 0.471 | 0.021 |
| Edem1 | Plasmablasts | 1.10E−82 | 2.85E−78 | 1.401 | 0.735 | 0.281 |
| Tnfrsf17 | Plasmablasts | 4.31E−80 | 1.12E−75 | 0.670 | 0.29 | 0 |
| Pls1 | Plasmablasts | 2.59E−78 | 6.72E−74 | 0.881 | 0.342 | 0.003 |
| Cacna1h | Plasmablasts | 1.68E−77 | 4.35E−73 | 0.938 | 0.381 | 0.006 |
| Sdc1 | Plasmablasts | 6.12E−75 | 1.59E−70 | 0.986 | 0.477 | 0.021 |
| Ssr4 | Plasmablasts | 1.30E−67 | 3.37E−63 | 1.256 | 0.703 | 0.274 |
| Txndc11 | Plasmablasts | 1.40E−66 | 3.64E−62 | 1.305 | 0.677 | 0.183 |
| Pon3 | Plasmablasts | 4.70E−66 | 1.22E−61 | 0.941 | 0.439 | 0.022 |
| Igkj1 | Plasmablasts | 2.26E−63 | 5.86E−59 | 1.204 | 0.31 | 0.008 |
| Ube2j1 | Plasmablasts | 9.91E−59 | 2.57E−54 | 1.220 | 0.658 | 0.221 |
| Ckap4 | Plasmablasts | 3.55E−55 | 9.19E−51 | 0.995 | 0.548 | 0.069 |
| Clptm1l | Plasmablasts | 1.41E−52 | 3.66E−48 | 1.065 | 0.716 | 0.24 |
| Rexo2 | Plasmablasts | 5.88E−52 | 1.53E−47 | 1.179 | 0.645 | 0.184 |
| Ly6a | Plasmablasts | 3.86E−50 | 1.00E−45 | 1.243 | 0.671 | 0.164 |
| Ell2 | Plasmablasts | 6.56E−50 | 1.70E−45 | 1.072 | 0.6 | 0.123 |
| Wipi1 | Plasmablasts | 1.86E−49 | 4.82E−45 | 0.948 | 0.458 | 0.048 |

TABLE 2-continued

Significant Cluster-Defining Genes for Cell Types Identified from the Steady State LN Cell Atlas

| Gene | Cell type | p-value | q-value | Average log fold change | % Expressing in Cluster | % Expressing Rest |
|---|---|---|---|---|---|---|
| Rgcc | Plasmablasts | 3.03E−48 | 7.85E−44 | 1.069 | 0.535 | 0.079 |
| Sec11c | Plasmablasts | 1.91E−47 | 4.96E−43 | 1.005 | 0.735 | 0.375 |
| Creb3l2 | Plasmablasts | 1.92E−47 | 4.97E−43 | 0.977 | 0.523 | 0.085 |
| Fkbp2 | Plasmablasts | 2.07E−46 | 5.37E−42 | 1.086 | 0.574 | 0.142 |
| Ly6c2 | Plasmablasts | 2.10E−46 | 5.45E−42 | 1.409 | 0.671 | 0.154 |
| Hdlbp | Plasmablasts | 5.42E−46 | 1.41E−41 | 1.059 | 0.761 | 0.37 |
| Sel1l | Plasmablasts | 3.98E−45 | 1.03E−40 | 1.112 | 0.69 | 0.267 |
| Iglv2 | Plasmablasts | 7.75E−45 | 2.01E−40 | 2.882 | 0.2 | 0.004 |
| Ighg2c | Plasmablasts | 1.92E−44 | 4.97E−40 | 4.181 | 0.258 | 0.013 |
| Lax1 | Plasmablasts | 5.76E−44 | 1.49E−39 | 1.106 | 0.619 | 0.143 |
| Prdx4 | Plasmablasts | 6.47E−44 | 1.68E−39 | 0.968 | 0.51 | 0.104 |
| Tnfrsf13b | Plasmablasts | 2.25E−43 | 5.83E−39 | 0.998 | 0.594 | 0.133 |
| Dennd5b | Plasmablasts | 4.27E−43 | 1.11E−38 | 1.056 | 0.503 | 0.076 |
| Fam214a | Plasmablasts | 8.91E−43 | 2.31E−38 | 0.967 | 0.626 | 0.149 |
| Edem2 | Plasmablasts | 5.63E−42 | 1.46E−37 | 1.000 | 0.574 | 0.169 |
| Pck2 | Plasmablasts | 2.70E−41 | 7.01E−37 | 1.007 | 0.51 | 0.11 |
| Manea | Plasmablasts | 1.85E−39 | 4.81E−35 | 0.921 | 0.497 | 0.095 |
| Kcnn4 | Plasmablasts | 3.53E−39 | 9.15E−35 | 0.963 | 0.548 | 0.127 |
| Prdm1 | Plasmablasts | 8.62E−39 | 2.24E−34 | 0.896 | 0.4 | 0.046 |
| Enpp1 | Plasmablasts | 6.17E−38 | 1.60E−33 | 0.677 | 0.361 | 0.035 |
| Ighj3 | Plasmablasts | 2.78E−37 | 7.21E−33 | 1.257 | 0.168 | 0.013 |
| Fut8 | Plasmablasts | 6.79E−37 | 1.76E−32 | 0.848 | 0.548 | 0.127 |
| Reln | Plasmablasts | 9.91E−37 | 2.57E−32 | 0.662 | 0.232 | 0.01 |
| Jund | Plasmablasts | 3.24E−36 | 8.40E−32 | 1.072 | 0.71 | 0.358 |
| Etl4 | Plasmablasts | 4.48E−36 | 1.16E−31 | 0.729 | 0.316 | 0.025 |
| H13 | Plasmablasts | 2.91E−35 | 7.55E−31 | 0.880 | 0.748 | 0.419 |
| Irf4 | Plasmablasts | 2.03E−33 | 5.28E−29 | 1.084 | 0.503 | 0.125 |
| Tmem154 | Plasmablasts | 8.61E−33 | 2.23E−28 | 0.777 | 0.49 | 0.102 |
| Hspa5 | Plasmablasts | 2.10E−32 | 5.44E−28 | 0.886 | 0.916 | 0.567 |
| Nucb1 | Plasmablasts | 2.48E−32 | 6.44E−28 | 0.900 | 0.626 | 0.274 |
| Spcs2 | Plasmablasts | 1.13E−31 | 2.93E−27 | 0.859 | 0.574 | 0.25 |
| Tram2 | Plasmablasts | 1.60E−31 | 4.14E−27 | 0.711 | 0.4 | 0.062 |
| St8sia6 | Plasmablasts | 2.20E−30 | 5.70E−26 | 0.683 | 0.439 | 0.082 |
| Ly6d | Plasmablasts | 4.76E−29 | 1.23E−24 | 0.769 | 0.503 | 0.123 |
| Blnk | Plasmablasts | 7.82E−29 | 2.03E−24 | 0.709 | 0.574 | 0.163 |
| Fos | Plasmablasts | 2.90E−28 | 7.53E−24 | 1.053 | 0.729 | 0.348 |
| Fosb | Plasmablasts | 1.92E−27 | 4.99E−23 | 0.991 | 0.613 | 0.202 |
| Pim1 | Plasmablasts | 2.52E−27 | 6.53E−23 | 0.741 | 0.665 | 0.256 |
| Arfgap3 | Plasmablasts | 7.50E−27 | 1.94E−22 | 0.683 | 0.426 | 0.093 |
| Spcs1 | Plasmablasts | 6.37E−26 | 1.65E−21 | 0.801 | 0.465 | 0.171 |
| Rhob | Plasmablasts | 1.35E−24 | 3.50E−20 | 0.897 | 0.484 | 0.133 |
| Cd93 | Plasmablasts | 1.76E−24 | 4.57E−20 | 0.782 | 0.374 | 0.072 |
| Cd28 | Plasmablasts | 6.28E−24 | 1.63E−19 | 0.644 | 0.426 | 0.101 |
| Jun | Plasmablasts | 1.07E−22 | 2.78E−18 | 0.821 | 0.697 | 0.318 |
| Sec61a1 | Plasmablasts | 3.11E−22 | 8.06E−18 | 0.770 | 0.645 | 0.358 |
| Fndc3a | Plasmablasts | 3.83E−22 | 9.92E−18 | 0.774 | 0.606 | 0.275 |
| Pik3cg | Plasmablasts | 6.33E−22 | 1.64E−17 | 0.748 | 0.613 | 0.261 |
| Hyou1 | Plasmablasts | 1.01E−20 | 2.62E−16 | 0.783 | 0.497 | 0.182 |
| Ctss | Plasmablasts | 1.78E−20 | 4.61E−16 | 0.646 | 0.845 | 0.518 |
| Pnpla2 | Plasmablasts | 3.41E−20 | 8.84E−16 | 0.739 | 0.568 | 0.243 |
| Lman1 | Plasmablasts | 3.57E−18 | 9.26E−14 | 0.704 | 0.471 | 0.171 |
| Sesn1 | Plasmablasts | 6.75E−18 | 1.75E−13 | 0.703 | 0.497 | 0.184 |
| Nek7 | Plasmablasts | 2.35E−17 | 6.08E−13 | 0.652 | 0.529 | 0.242 |
| Manf | Plasmablasts | 4.00E−17 | 1.04E−12 | 0.699 | 0.439 | 0.184 |
| Mtdh | Plasmablasts | 8.94E−17 | 2.32E−12 | 0.648 | 0.716 | 0.485 |
| Dnajc3 | Plasmablasts | 2.45E−14 | 6.36E−10 | 0.693 | 0.594 | 0.341 |
| Egr1 | Plasmablasts | 1.31E−12 | 3.39E−08 | 0.650 | 0.471 | 0.196 |
| D17H6S56E-5 | Plasmablasts | 4.75E−11 | 1.23E−06 | 0.694 | 0.652 | 0.457 |
| C3 | Stromal | 0 | 0 | 4.243 | 0.642 | 0.082 |
| Dcn | Stromal | 0 | 0 | 3.988 | 0.82 | 0.024 |
| Apoe | Stromal | 0 | 0 | 3.456 | 0.935 | 0.286 |
| Cxcl12 | Stromal | 0 | 0 | 3.401 | 0.802 | 0.031 |
| Serping1 | Stromal | 0 | 0 | 3.392 | 0.807 | 0.025 |
| Col1a2 | Stromal | 0 | 0 | 3.373 | 0.789 | 0.011 |
| C4b | Stromal | 0 | 0 | 3.319 | 0.774 | 0.018 |
| Col3a1 | Stromal | 0 | 0 | 2.848 | 0.609 | 0.006 |
| Igfbp3 | Stromal | 0 | 0 | 2.811 | 0.672 | 0.014 |
| C1s | Stromal | 0 | 0 | 2.667 | 0.747 | 0.021 |
| Bgn | Stromal | 0 | 0 | 2.602 | 0.729 | 0.014 |
| Pdgfra | Stromal | 0 | 0 | 2.174 | 0.624 | 0.004 |
| Hmgcs2 | Stromal | 1.55399355363125e−313 | 0.00E+00 | 2.187 | 0.634 | 0.017 |
| Aebp1 | Stromal | 2.37E−308 | 6.15E−304 | 2.268 | 0.624 | 0.016 |
| Igfbp7 | Stromal | 1.10E−307 | 2.85E−303 | 2.308 | 0.777 | 0.062 |

TABLE 2-continued

Significant Cluster-Defining Genes for Cell Types Identified from the Steady State LN Cell Atlas

| Gene | Cell type | p-value | q-value | Average log fold change | % Expressing in Cluster | % Expressing Rest |
|---|---|---|---|---|---|---|
| Col1a1 | Stromal | 1.59E−304 | 4.13E−300 | 2.352 | 0.566 | 0.005 |
| Col6a1 | Stromal | 9.96E−300 | 2.58E−295 | 1.902 | 0.541 | 0.003 |
| Abcc9 | Stromal | 7.17E−297 | 1.86E−292 | 1.969 | 0.551 | 0.004 |
| Htra1 | Stromal | 5.40E−296 | 1.40E−291 | 1.831 | 0.579 | 0.008 |
| Cygb | Stromal | 6.49E−292 | 1.68E−287 | 1.937 | 0.571 | 0.01 |
| Rarres2 | Stromal | 1.90E−281 | 4.92E−277 | 1.621 | 0.534 | 0.004 |
| Cp | Stromal | 3.90E−277 | 1.01E−272 | 2.135 | 0.674 | 0.031 |
| Col6a2 | Stromal | 4.97E−271 | 1.29E−266 | 1.797 | 0.516 | 0.004 |
| Cpxm1 | Stromal | 5.69E−269 | 1.48E−264 | 2.015 | 0.556 | 0.012 |
| Clu | Stromal | 1.95E−268 | 5.05E−264 | 2.628 | 0.825 | 0.142 |
| Itih5 | Stromal | 1.41E−267 | 3.65E−263 | 2.214 | 0.627 | 0.036 |
| Epas1 | Stromal | 3.35E−266 | 8.68E−262 | 2.196 | 0.692 | 0.045 |
| Sparc | Stromal | 1.11E−264 | 2.87E−260 | 2.479 | 0.704 | 0.048 |
| Lepr | Stromal | 1.60E−264 | 4.16E−260 | 2.348 | 0.591 | 0.02 |
| Bicc1 | Stromal | 1.31E−259 | 3.39E−255 | 1.474 | 0.524 | 0.007 |
| Des | Stromal | 2.67E−255 | 6.92E−251 | 1.473 | 0.489 | 0.004 |
| Mfge8 | Stromal | 6.97E−255 | 1.81E−250 | 2.566 | 0.744 | 0.161 |
| Enpp2 | Stromal | 5.03E−254 | 1.30E−249 | 2.291 | 0.732 | 0.055 |
| Rgs5 | Stromal | 8.21E−254 | 2.13E−249 | 2.414 | 0.529 | 0.011 |
| Nrp1 | Stromal | 1.04E−247 | 2.70E−243 | 2.058 | 0.657 | 0.109 |
| Chrdl1 | Stromal | 1.11E−242 | 2.87E−238 | 1.498 | 0.466 | 0.003 |
| Cald1 | Stromal | 1.23E−242 | 3.19E−238 | 1.816 | 0.551 | 0.018 |
| Abca8a | Stromal | 3.95E−238 | 1.02E−233 | 1.427 | 0.436 | 0.002 |
| Dact1 | Stromal | 2.19E−237 | 5.69E−233 | 1.645 | 0.496 | 0.01 |
| Ddr2 | Stromal | 6.65E−237 | 1.72E−232 | 1.421 | 0.494 | 0.008 |
| Col4a1 | Stromal | 8.52E−237 | 2.21E−232 | 1.951 | 0.637 | 0.037 |
| Pcolce | Stromal | 4.59E−236 | 1.19E−231 | 1.532 | 0.516 | 0.013 |
| Dclk1 | Stromal | 7.74E−236 | 2.01E−231 | 1.654 | 0.536 | 0.017 |
| Col6a3 | Stromal | 9.26E−235 | 2.40E−230 | 1.580 | 0.446 | 0.002 |
| Dsc3 | Stromal | 3.91E−227 | 1.01E−222 | 1.794 | 0.419 | 0.002 |
| Prelp | Stromal | 7.86E−227 | 2.04E−222 | 1.396 | 0.461 | 0.006 |
| Slco2b1 | Stromal | 5.61E−226 | 1.45E−221 | 1.681 | 0.566 | 0.024 |
| Igfbp5 | Stromal | 2.19E−224 | 5.68E−220 | 1.987 | 0.434 | 0.003 |
| Colec12 | Stromal | 7.34E−224 | 1.90E−219 | 1.587 | 0.509 | 0.014 |
| Gstm1 | Stromal | 7.71E−224 | 2.00E−219 | 1.618 | 0.534 | 0.026 |
| Fmod | Stromal | 2.00E−222 | 5.19E−218 | 1.521 | 0.409 | 0.002 |
| Thbs2 | Stromal | 1.50E−214 | 3.88E−210 | 1.688 | 0.416 | 0.003 |
| Timp2 | Stromal | 3.86E−214 | 1.00E−209 | 1.853 | 0.672 | 0.113 |
| Mylk | Stromal | 4.21E−210 | 1.09E−205 | 1.769 | 0.559 | 0.036 |
| Col4a2 | Stromal | 4.20E−208 | 1.09E−203 | 1.649 | 0.571 | 0.028 |
| Abi3bp | Stromal | 4.99E−208 | 1.29E−203 | 1.511 | 0.491 | 0.013 |
| Spon1 | Stromal | 8.41E−208 | 2.18E−203 | 1.743 | 0.471 | 0.013 |
| Cyp1b1 | Stromal | 2.56E−205 | 6.65E−201 | 1.473 | 0.534 | 0.024 |
| Fn1 | Stromal | 6.51E−201 | 1.69E−196 | 2.377 | 0.544 | 0.03 |
| Lp1 | Stromal | 3.85E−197 | 9.99E−193 | 1.694 | 0.491 | 0.017 |
| Scara5 | Stromal | 1.49E−194 | 3.87E−190 | 1.732 | 0.378 | 0.003 |
| Rnase4 | Stromal | 7.47E−193 | 1.94E−188 | 1.576 | 0.514 | 0.031 |
| Thsd7a | Stromal | 1.01E−192 | 2.62E−188 | 1.574 | 0.501 | 0.024 |
| Fstl1 | Stromal | 1.99E−192 | 5.15E−188 | 1.538 | 0.524 | 0.027 |
| Egfr | Stromal | 2.76E−188 | 7.17E−184 | 1.465 | 0.469 | 0.016 |
| Dpt | Stromal | 4.29E−188 | 1.11E−183 | 2.050 | 0.363 | 0.004 |
| Adh1 | Stromal | 6.56E−188 | 1.70E−183 | 1.434 | 0.401 | 0.006 |
| Nedd4 | Stromal | 9.82E−188 | 2.55E−183 | 1.535 | 0.727 | 0.321 |
| Inmt | Stromal | 1.17E−186 | 3.03E−182 | 2.689 | 0.391 | 0.011 |
| Rcn3 | Stromal | 8.34E−180 | 2.16E−175 | 1.457 | 0.551 | 0.06 |
| Lrp1 | Stromal | 9.57E−178 | 2.48E−173 | 1.782 | 0.581 | 0.061 |
| Myh11 | Stromal | 2.33E−176 | 6.04E−172 | 1.523 | 0.381 | 0.006 |
| Slc43a3 | Stromal | 4.73E−175 | 1.23E−170 | 1.711 | 0.584 | 0.081 |
| Nfib | Stromal | 1.50E−173 | 3.89E−169 | 1.508 | 0.546 | 0.038 |
| Pcdhga9 | Stromal | 1.23E−170 | 3.20E−166 | 1.377 | 0.536 | 0.059 |
| Serpina3n | Stromal | 3.33E−170 | 8.63E−166 | 1.862 | 0.466 | 0.021 |
| Tagln | Stromal | 2.13E−169 | 5.53E−165 | 1.486 | 0.393 | 0.011 |
| App | Stromal | 5.38E−168 | 1.40E−163 | 1.547 | 0.717 | 0.205 |
| Pam | Stromal | 8.02E−162 | 2.08E−157 | 1.411 | 0.544 | 0.066 |
| Vcam1 | Stromal | 3.59E−158 | 9.32E−154 | 1.493 | 0.561 | 0.06 |
| Ltbp4 | Stromal | 1.43E−156 | 3.71E−152 | 1.434 | 0.461 | 0.025 |
| Grem1 | Stromal | 6.46E−152 | 1.68E−147 | 1.385 | 0.298 | 0.002 |
| Tmem176b | Stromal | 1.54E−151 | 4.00E−147 | 1.482 | 0.777 | 0.296 |
| Acta2 | Stromal | 1.68E−151 | 4.35E−147 | 1.400 | 0.351 | 0.014 |
| Cxcl13 | Stromal | 3.26E−146 | 8.45E−142 | 2.240 | 0.331 | 0.009 |
| Klf9 | Stromal | 4.42E−141 | 1.15E−136 | 1.378 | 0.521 | 0.081 |
| Igfbp4 | Stromal | 5.94E−139 | 1.54E−134 | 1.510 | 0.514 | 0.055 |
| Cyr61 | Stromal | 3.28E−135 | 8.50E−131 | 1.701 | 0.376 | 0.016 |

TABLE 2-continued

Significant Cluster-Defining Genes for Cell Types Identified from the Steady State LN Cell Atlas

| Gene | Cell type | p-value | q-value | Average log fold change | % Expressing in Cluster | % Expressing Rest |
|---|---|---|---|---|---|---|
| Sepp1 | Stromal | 3.33E−134 | 8.64E−130 | 1.400 | 0.739 | 0.242 |
| Fmo2 | Stromal | 7.35E−122 | 1.91E−117 | 1.466 | 0.303 | 0.009 |
| Col14a1 | Stromal | 1.32E−109 | 3.42E−105 | 1.398 | 0.246 | 0.005 |
| Gm10800 | Stromal | 4.04E−100 | 1.05E−95 | 2.374 | 0.246 | 0.087 |
| Postn | Stromal | 9.03E−97 | 2.34E−92 | 1.696 | 0.293 | 0.015 |
| Egr1 | Stromal | 3.70E−94 | 9.58E−90 | 1.798 | 0.506 | 0.187 |
| Cxcl1 | Stromal | 6.73E−70 | 1.75E−65 | 1.538 | 0.213 | 0.015 |
| Il7r | T Cell Subtype 1 | 7.10E−274 | 1.84E−269 | 1.797 | 0.943 | 0.349 |
| Il18r1 | T Cell Subtype 1 | 1.42E−235 | 3.67E−231 | 1.770 | 0.833 | 0.143 |
| Cxcr6 | T Cell Subtype 1 | 2.69E−192 | 6.97E−188 | 1.346 | 0.534 | 0.037 |
| Rora | T Cell Subtype 1 | 6.64E−180 | 1.72E−175 | 1.634 | 0.606 | 0.086 |
| Itgae | T Cell Subtype 1 | 2.39E−172 | 6.19E−168 | 1.733 | 0.631 | 0.11 |
| Emb | T Cell Subtype 1 | 1.93E−168 | 5.01E−164 | 1.421 | 0.778 | 0.219 |
| Hlf | T Cell Subtype 1 | 1.52E−144 | 3.94E−140 | 1.147 | 0.453 | 0.033 |
| Ccr6 | T Cell Subtype 1 | 1.54E−137 | 3.99E−133 | 1.408 | 0.498 | 0.064 |
| Gata3 | T Cell Subtype 1 | 4.48E−131 | 1.16E−126 | 1.208 | 0.5 | 0.061 |
| Thy1 | T Cell Subtype 1 | 1.00E−126 | 2.61E−122 | 1.408 | 0.692 | 0.172 |
| Il17rb | T Cell Subtype 1 | 4.37E−122 | 1.13E−117 | 1.284 | 0.397 | 0.033 |
| S100a10 | T Cell Subtype 1 | 1.01E−113 | 2.61E−109 | 1.200 | 0.719 | 0.252 |
| Ccnd2 | T Cell Subtype 1 | 3.69E−113 | 9.56E−109 | 1.201 | 0.675 | 0.185 |
| Tcf7 | T Cell Subtype 1 | 7.33E−111 | 1.90E−106 | 1.166 | 0.744 | 0.237 |
| Lmo4 | T Cell Subtype 1 | 8.12E−111 | 2.10E−106 | 1.367 | 0.586 | 0.261 |
| Il2ra | T Cell Subtype 1 | 2.02E−109 | 5.23E−105 | 1.144 | 0.421 | 0.044 |
| Atp2b4 | T Cell Subtype 1 | 4.84E−109 | 1.26E−104 | 1.237 | 0.571 | 0.131 |
| Rarg | T Cell Subtype 1 | 9.24E−101 | 2.40E−96 | 1.060 | 0.507 | 0.104 |
| S100a4 | T Cell Subtype 1 | 3.86E−99 | 1.00E−94 | 1.074 | 0.781 | 0.275 |
| Ahnak | T Cell Subtype 1 | 1.31E−93 | 3.38E−89 | 0.993 | 0.892 | 0.58 |
| Ccr10 | T Cell Subtype 1 | 1.66E−93 | 4.31E−89 | 1.112 | 0.313 | 0.027 |
| Maf | T Cell Subtype 1 | 1.93E−92 | 5.01E−88 | 0.911 | 0.48 | 0.084 |
| Cd7 | T Cell Subtype 1 | 4.21E−92 | 1.09E−87 | 1.184 | 0.554 | 0.13 |
| Pxdc1 | T Cell Subtype 1 | 6.46E−91 | 1.67E−86 | 1.030 | 0.409 | 0.063 |
| Ptprcap | T Cell Subtype 1 | 2.17E−90 | 5.63E−86 | 1.047 | 0.741 | 0.296 |
| Tnfrsf25 | T Cell Subtype 1 | 8.61E−90 | 2.23E−85 | 0.777 | 0.357 | 0.038 |
| Faah | T Cell Subtype 1 | 6.80E−88 | 1.76E−83 | 0.980 | 0.557 | 0.131 |
| Rbl2 | T Cell Subtype 1 | 3.68E−86 | 9.54E−82 | 1.007 | 0.685 | 0.317 |
| Ikzf3 | T Cell Subtype 1 | 5.10E−86 | 1.32E−81 | 1.080 | 0.635 | 0.224 |
| Nebl | T Cell Subtype 1 | 2.66E−81 | 6.90E−77 | 0.813 | 0.308 | 0.029 |
| Icos | T Cell Subtype 1 | 5.53E−81 | 1.43E−76 | 1.070 | 0.461 | 0.096 |
| Acsbg1 | T Cell Subtype 1 | 2.04E−78 | 5.30E−74 | 0.880 | 0.3 | 0.036 |
| Ets1 | T Cell Subtype 1 | 6.35E−77 | 1.65E−72 | 0.862 | 0.86 | 0.459 |
| Cish | T Cell Subtype 1 | 3.11E−76 | 8.06E−72 | 0.841 | 0.318 | 0.039 |
| 8-Sep | T Cell Subtype 1 | 8.90E−76 | 2.31E−71 | 0.880 | 0.36 | 0.057 |
| Znrf1 | T Cell Subtype 1 | 5.92E−75 | 1.54E−70 | 0.939 | 0.66 | 0.278 |
| Il18rap | T Cell Subtype 1 | 6.27E−74 | 1.63E−69 | 0.810 | 0.512 | 0.13 |
| Camk4 | T Cell Subtype 1 | 9.43E−73 | 2.44E−68 | 1.021 | 0.463 | 0.105 |
| Tnfsf14 | T Cell Subtype 1 | 1.61E−72 | 4.16E−68 | 0.701 | 0.305 | 0.036 |
| F2r | T Cell Subtype 1 | 5.58E−72 | 1.45E−67 | 1.084 | 0.369 | 0.068 |
| Cd82 | T Cell Subtype 1 | 3.02E−71 | 7.84E−67 | 0.955 | 0.569 | 0.234 |
| Trbc2 | T Cell Subtype 1 | 8.56E−71 | 2.22E−66 | 0.944 | 0.552 | 0.158 |
| Fam184b | T Cell Subtype 1 | 1.71E−70 | 4.43E−66 | 0.876 | 0.16 | 0.003 |
| Esyt2 | T Cell Subtype 1 | 1.09E−69 | 2.83E−65 | 0.900 | 0.638 | 0.287 |
| Rab27a | T Cell Subtype 1 | 4.05E−68 | 1.05E−63 | 0.887 | 0.53 | 0.171 |
| Capg | T Cell Subtype 1 | 1.27E−67 | 3.30E−63 | 0.898 | 0.527 | 0.181 |
| Itgb7 | T Cell Subtype 1 | 1.68E−66 | 4.36E−62 | 0.870 | 0.702 | 0.343 |
| Id2 | T Cell Subtype 1 | 1.72E−66 | 4.46E−62 | 0.846 | 0.717 | 0.338 |
| Axin2 | T Cell Subtype 1 | 2.60E−65 | 6.73E−61 | 0.839 | 0.318 | 0.053 |
| Podnl1 | T Cell Subtype 1 | 8.00E−65 | 2.07E−60 | 0.660 | 0.261 | 0.031 |
| Ttn | T Cell Subtype 1 | 1.58E−64 | 4.09E−60 | 1.503 | 0.357 | 0.067 |
| Ar | T Cell Subtype 1 | 3.20E−64 | 8.29E−60 | 0.807 | 0.296 | 0.038 |
| Klrb1b | T Cell Subtype 1 | 3.77E−61 | 9.78E−57 | 1.324 | 0.335 | 0.065 |
| Limd2 | T Cell Subtype 1 | 1.95E−59 | 5.05E−55 | 0.733 | 0.764 | 0.446 |
| Spock2 | T Cell Subtype 1 | 3.66E−59 | 9.49E−55 | 0.762 | 0.234 | 0.025 |
| Cd96 | T Cell Subtype 1 | 5.71E−59 | 1.48E−54 | 0.737 | 0.399 | 0.09 |
| Shisa5 | T Cell Subtype 1 | 3.91E−58 | 1.01E−53 | 0.731 | 0.818 | 0.529 |
| Cntnap1 | T Cell Subtype 1 | 4.85E−58 | 1.26E−53 | 0.754 | 0.232 | 0.027 |
| Cntn1 | T Cell Subtype 1 | 6.18E−58 | 1.60E−53 | 0.943 | 0.204 | 0.018 |
| Fam102a | T Cell Subtype 1 | 1.77E−57 | 4.59E−53 | 0.770 | 0.473 | 0.153 |
| Esyt1 | T Cell Subtype 1 | 4.61E−57 | 1.20E−52 | 0.784 | 0.648 | 0.335 |
| S100a6 | T Cell Subtype 1 | 5.47E−57 | 1.42E−52 | 0.895 | 0.547 | 0.218 |
| Ahcyl2 | T Cell Subtype 1 | 8.96E−57 | 2.32E−52 | 0.932 | 0.478 | 0.199 |
| Tnk2 | T Cell Subtype 1 | 1.11E−56 | 2.87E−52 | 0.752 | 0.446 | 0.13 |
| Tmem64 | T Cell Subtype 1 | 2.17E−56 | 5.63E−52 | 0.885 | 0.406 | 0.142 |
| Itgb3 | T Cell Subtype 1 | 5.05E−56 | 1.31E−51 | 0.817 | 0.382 | 0.091 |

TABLE 2-continued

Significant Cluster-Defining Genes for Cell Types Identified from the Steady State LN Cell Atlas

| Gene | Cell type | p-value | q-value | Average log fold change | % Expressing in Cluster | % Expressing Rest |
|---|---|---|---|---|---|---|
| 5830411N06Rik | T Cell Subtype 1 | 5.55E−55 | 1.44E−50 | 0.797 | 0.17 | 0.01 |
| Diap1 | T Cell Subtype 1 | 7.84E−55 | 2.03E−50 | 0.737 | 0.677 | 0.387 |
| Skap1 | T Cell Subtype 1 | 8.40E−55 | 2.18E−50 | 0.705 | 0.505 | 0.16 |
| Ly6e | T Cell Subtype 1 | 8.63E−55 | 2.24E−50 | 0.660 | 0.869 | 0.663 |
| Slc25a24 | T Cell Subtype 1 | 2.29E−53 | 5.94E−49 | 0.841 | 0.379 | 0.116 |
| Spn | T Cell Subtype 1 | 8.08E−52 | 2.09E−47 | 0.857 | 0.554 | 0.229 |
| Gng2 | T Cell Subtype 1 | 5.42E−51 | 1.41E−46 | 0.796 | 0.527 | 0.235 |
| Stk10 | T Cell Subtype 1 | 3.42E−48 | 8.87E−44 | 0.746 | 0.655 | 0.34 |
| Acpp | T Cell Subtype 1 | 6.38E−48 | 1.65E−43 | 0.644 | 0.246 | 0.036 |
| Tmem66 | T Cell Subtype 1 | 6.91E−48 | 1.79E−43 | 0.705 | 0.606 | 0.312 |
| Atp1b3 | T Cell Subtype 1 | 8.00E−48 | 2.07E−43 | 0.753 | 0.626 | 0.352 |
| 1-Sep | T Cell Subtype 1 | 1.05E−47 | 2.73E−43 | 0.738 | 0.655 | 0.323 |
| Rgcc | T Cell Subtype 1 | 1.60E−45 | 4.15E−41 | 0.739 | 0.328 | 0.075 |
| Sptssa | T Cell Subtype 1 | 8.74E−45 | 2.27E−40 | 0.686 | 0.458 | 0.198 |
| Txnip | T Cell Subtype 1 | 3.30E−44 | 8.56E−40 | 0.727 | 0.746 | 0.498 |
| Itk | T Cell Subtype 1 | 7.70E−44 | 2.00E−39 | 0.654 | 0.483 | 0.169 |
| Amica1 | T Cell Subtype 1 | 5.45E−43 | 1.41E−38 | 0.762 | 0.552 | 0.239 |
| Rasgrp1 | T Cell Subtype 1 | 1.49E−42 | 3.85E−38 | 0.772 | 0.456 | 0.17 |
| Tab2 | T Cell Subtype 1 | 2.98E−42 | 7.71E−38 | 0.678 | 0.66 | 0.427 |
| St3gal6 | T Cell Subtype 1 | 6.01E−42 | 1.56E−37 | 0.664 | 0.369 | 0.108 |
| Nav2 | T Cell Subtype 1 | 8.03E−42 | 2.08E−37 | 0.668 | 0.266 | 0.053 |
| Clint1 | T Cell Subtype 1 | 1.09E−41 | 2.84E−37 | 0.675 | 0.613 | 0.387 |
| Lcp2 | T Cell Subtype 1 | 7.93E−41 | 2.06E−36 | 0.658 | 0.552 | 0.24 |
| Anxa6 | T Cell Subtype 1 | 1.52E−39 | 3.93E−35 | 0.663 | 0.631 | 0.337 |
| Furin | T Cell Subtype 1 | 6.47E−39 | 1.68E−34 | 0.665 | 0.451 | 0.197 |
| Plec | T Cell Subtype 1 | 9.10E−39 | 2.36E−34 | 0.690 | 0.643 | 0.357 |
| Prr13 | T Cell Subtype 1 | 9.50E−39 | 2.46E−34 | 0.643 | 0.515 | 0.247 |
| Lgals1 | T Cell Subtype 1 | 8.47E−38 | 2.20E−33 | 0.825 | 0.589 | 0.298 |
| Arid5a | T Cell Subtype 1 | 7.04E−37 | 1.82E−32 | 0.701 | 0.517 | 0.243 |
| Nfatc3 | T Cell Subtype 1 | 2.21E−34 | 5.74E−30 | 0.643 | 0.53 | 0.292 |
| AI504432 | T Cell Subtype 1 | 6.16E−34 | 1.60E−29 | 0.706 | 0.411 | 0.165 |
| Tgfbr2 | T Cell Subtype 1 | 2.67E−31 | 6.92E−27 | 0.658 | 0.549 | 0.283 |
| Syne2 | T Cell Subtype 1 | 4.08E−29 | 1.06E−24 | 0.782 | 0.411 | 0.209 |
| Padi2 | T Cell Subtype 1 | 9.95E−29 | 2.58E−24 | 0.640 | 0.335 | 0.136 |
| Cd5 | Tregs | 2.96E−110 | 7.66E−106 | 1.502 | 0.81 | 0.078 |
| Cd3g | Tregs | 9.63E−110 | 2.50E−105 | 1.422 | 0.84 | 0.094 |
| Ctla4 | Tregs | 6.59E−107 | 1.71E−102 | 1.438 | 0.607 | 0.025 |
| Trbc2 | Tregs | 7.32E−100 | 1.90E−95 | 1.736 | 0.877 | 0.163 |
| Folr4 | Tregs | 7.18E−98 | 1.86E−93 | 1.308 | 0.54 | 0.018 |
| Ikzf2 | Tregs | 9.87E−93 | 2.56E−88 | 1.919 | 0.577 | 0.056 |
| Cd3e | Tregs | 8.20E−85 | 2.13E−80 | 1.177 | 0.663 | 0.061 |
| Cd3d | Tregs | 2.27E−84 | 5.89E−80 | 1.328 | 0.712 | 0.083 |
| Cd28 | Tregs | 1.42E−82 | 3.67E−78 | 1.301 | 0.736 | 0.095 |
| Foxp3 | Tregs | 1.72E−76 | 4.45E−72 | 1.329 | 0.399 | 0.01 |
| Cd6 | Tregs | 7.37E−76 | 1.91E−71 | 1.305 | 0.669 | 0.079 |
| Bcl11b | Tregs | 2.11E−75 | 5.47E−71 | 1.144 | 0.785 | 0.132 |
| Icos | Tregs | 5.91E−75 | 1.53E−70 | 1.554 | 0.681 | 0.101 |
| Cd2 | Tregs | 2.44E−74 | 6.34E−70 | 1.282 | 0.779 | 0.143 |
| Lat | Tregs | 1.24E−71 | 3.21E−67 | 1.136 | 0.84 | 0.185 |
| Il2ra | Tregs | 6.82E−69 | 1.77E−64 | 1.615 | 0.54 | 0.052 |
| Ccnd2 | Tregs | 1.50E−67 | 3.88E−63 | 1.337 | 0.822 | 0.195 |
| Lck | Tregs | 1.67E−67 | 4.32E−63 | 1.019 | 0.834 | 0.197 |
| Cd4 | Tregs | 5.33E−64 | 1.38E−59 | 1.227 | 0.712 | 0.124 |
| Skap1 | Tregs | 1.03E−63 | 2.68E−59 | 0.916 | 0.773 | 0.164 |
| Tnfrsf18 | Tregs | 1.56E−61 | 4.04E−57 | 1.082 | 0.632 | 0.096 |
| Il2rb | Tregs | 2.72E−61 | 7.05E−57 | 1.042 | 0.663 | 0.106 |
| Tnfrsf4 | Tregs | 1.48E−60 | 3.83E−56 | 1.393 | 0.497 | 0.055 |
| Lrig1 | Tregs | 1.65E−59 | 4.29E−55 | 0.905 | 0.497 | 0.045 |
| Ets1 | Tregs | 2.61E−59 | 6.76E−55 | 1.052 | 0.982 | 0.467 |
| Nt5e | Tregs | 3.43E−59 | 8.90E−55 | 1.072 | 0.491 | 0.043 |
| Thy1 | Tregs | 2.88E−58 | 7.47E−54 | 1.220 | 0.779 | 0.183 |
| Inpp4b | Tregs | 1.17E−57 | 3.04E−53 | 1.005 | 0.755 | 0.169 |
| Nsg2 | Tregs | 1.19E−54 | 3.08E−50 | 0.841 | 0.503 | 0.054 |
| Trac | Tregs | 4.51E−54 | 1.17E−49 | 0.711 | 0.429 | 0.033 |
| Ptprcap | Tregs | 8.27E−52 | 2.14E−47 | 1.000 | 0.865 | 0.306 |
| Tox | Tregs | 2.96E−51 | 7.68E−47 | 0.873 | 0.528 | 0.07 |
| Shisa5 | Tregs | 1.17E−49 | 3.04E−45 | 0.913 | 0.951 | 0.534 |
| Rac2 | Tregs | 2.88E−48 | 7.47E−44 | 0.919 | 0.908 | 0.427 |
| Lcp2 | Tregs | 1.26E−47 | 3.26E−43 | 0.896 | 0.785 | 0.244 |
| Limd2 | Tregs | 4.47E−47 | 1.16E−42 | 0.873 | 0.926 | 0.452 |
| Sh2d2a | Tregs | 5.69E−47 | 1.48E−42 | 0.689 | 0.577 | 0.109 |
| Cd247 | Tregs | 3.07E−46 | 7.96E−42 | 0.885 | 0.601 | 0.115 |
| Trbc1 | Tregs | 2.76E−45 | 7.15E−41 | 1.064 | 0.595 | 0.117 |

TABLE 2-continued

Significant Cluster-Defining Genes for Cell Types Identified from the Steady State LN Cell Atlas

| Gene | Cell type | p-value | q-value | Average log fold change | % Expressing in Cluster | % Expressing Rest |
|---|---|---|---|---|---|---|
| Zap70 | Tregs | 3.67E−45 | 9.52E−41 | 0.963 | 0.632 | 0.137 |
| Rasgrp1 | Tregs | 3.97E−42 | 1.03E−37 | 0.877 | 0.675 | 0.174 |
| Cd27 | Tregs | 7.62E−42 | 1.98E−37 | 0.677 | 0.583 | 0.129 |
| Spn | Tregs | 7.42E−41 | 1.92E−36 | 0.817 | 0.748 | 0.234 |
| Trat1 | Tregs | 9.06E−41 | 2.35E−36 | 0.656 | 0.38 | 0.04 |
| Tcf7 | Tregs | 1.15E−40 | 2.99E−36 | 1.045 | 0.748 | 0.25 |
| Prkcq | Tregs | 1.67E−40 | 4.33E−36 | 0.685 | 0.601 | 0.143 |
| Ifi27l2a | Tregs | 1.71E−40 | 4.43E−36 | 1.075 | 0.632 | 0.16 |
| Kbtbd11 | Tregs | 1.74E−40 | 4.51E−36 | 0.898 | 0.761 | 0.251 |
| Lrrc32 | Tregs | 3.93E−40 | 1.02E−35 | 1.099 | 0.313 | 0.024 |
| Ms4a4b | Tregs | 4.05E−40 | 1.05E−35 | 0.762 | 0.706 | 0.211 |
| Itk | Tregs | 2.15E−39 | 5.56E−35 | 0.691 | 0.644 | 0.174 |
| Myh9 | Tregs | 2.51E−39 | 6.52E−35 | 0.706 | 0.988 | 0.769 |
| Ms4a6b | Tregs | 6.35E−39 | 1.65E−34 | 0.884 | 0.773 | 0.269 |
| Prkch | Tregs | 5.05E−38 | 1.31E−33 | 0.740 | 0.626 | 0.159 |
| Atp1b3 | Tregs | 1.67E−37 | 4.32E−33 | 0.823 | 0.84 | 0.356 |
| Gata3 | Tregs | 5.00E−37 | 1.30E−32 | 0.827 | 0.454 | 0.073 |
| Ipcef1 | Tregs | 5.71E−37 | 1.48E−32 | 0.799 | 0.638 | 0.172 |
| Ikzf4 | Tregs | 2.12E−36 | 5.51E−32 | 0.806 | 0.344 | 0.035 |
| Cd96 | Tregs | 2.73E−36 | 7.09E−32 | 0.756 | 0.497 | 0.096 |
| Cish | Tregs | 6.79E−36 | 1.76E−31 | 0.850 | 0.368 | 0.045 |
| Tspan32 | Tregs | 6.95E−35 | 1.80E−30 | 0.669 | 0.583 | 0.15 |
| Ptpn7 | Tregs | 7.92E−35 | 2.05E−30 | 0.728 | 0.534 | 0.118 |
| Camk4 | Tregs | 1.29E−34 | 3.36E−30 | 0.781 | 0.521 | 0.113 |
| S100a10 | Tregs | 7.20E−34 | 1.87E−29 | 0.793 | 0.736 | 0.264 |
| Smc4 | Tregs | 8.68E−34 | 2.25E−29 | 0.863 | 0.859 | 0.432 |
| Tiam1 | Tregs | 1.23E−33 | 3.19E−29 | 0.905 | 0.595 | 0.168 |
| Lbh | Tregs | 1.20E−32 | 3.11E−28 | 0.779 | 0.693 | 0.256 |
| Ablim1 | Tregs | 1.69E−31 | 4.38E−27 | 0.787 | 0.847 | 0.4 |
| Maf | Tregs | 9.79E−31 | 2.54E−26 | 0.861 | 0.46 | 0.095 |
| Pdcd4 | Tregs | 1.40E−30 | 3.63E−26 | 0.788 | 0.877 | 0.508 |
| Ift80 | Tregs | 1.60E−30 | 4.14E−26 | 0.784 | 0.423 | 0.078 |
| Capg | Tregs | 5.69E−30 | 1.48E−25 | 0.781 | 0.607 | 0.188 |
| Galnt6 | Tregs | 3.25E−29 | 8.43E−25 | 0.672 | 0.577 | 0.172 |
| Chd3 | Tregs | 3.94E−29 | 1.02E−24 | 0.767 | 0.834 | 0.414 |
| Syt11 | Tregs | 6.38E−28 | 1.65E−23 | 0.744 | 0.387 | 0.072 |
| Spata13 | Tregs | 7.53E−27 | 1.95E−22 | 0.651 | 0.546 | 0.161 |
| Themis | Tregs | 1.35E−26 | 3.51E−22 | 0.685 | 0.362 | 0.064 |
| Trp53inp1 | Tregs | 8.11E−26 | 2.10E−21 | 0.727 | 0.724 | 0.314 |
| Nrp1 | Tregs | 2.55E−25 | 6.61E−21 | 0.678 | 0.46 | 0.126 |
| Prkca | Tregs | 6.89E−24 | 1.79E−19 | 0.752 | 0.429 | 0.105 |
| Ski | Tregs | 3.26E−23 | 8.45E−19 | 0.651 | 0.564 | 0.193 |
| Dusp4 | Tregs | 3.54E−23 | 9.17E−19 | 0.704 | 0.258 | 0.034 |
| Nrn1 | Tregs | 8.38E−23 | 2.17E−18 | 0.729 | 0.178 | 0.011 |
| Itgal | Tregs | 2.13E−22 | 5.51E−18 | 0.658 | 0.681 | 0.299 |
| Ptger4 | Tregs | 3.46E−22 | 8.97E−18 | 0.661 | 0.521 | 0.17 |
| Cd69 | Tregs | 8.17E−22 | 2.12E−17 | 0.691 | 0.448 | 0.127 |
| Tnfrsf9 | Tregs | 8.23E−21 | 2.14E−16 | 0.728 | 0.276 | 0.047 |
| Itgae | Tregs | 3.95E−20 | 1.02E−15 | 1.033 | 0.423 | 0.127 |
| Slfn2 | Tregs | 1.29E−19 | 3.34E−15 | 0.648 | 0.73 | 0.38 |
| Dusp2 | Tregs | 2.19E−19 | 5.68E−15 | 0.734 | 0.577 | 0.237 |
| Hif1a | Tregs | 1.09E−18 | 2.82E−14 | 0.719 | 0.528 | 0.241 |
| Bzw2 | Tregs | 1.43E−18 | 3.70E−14 | 0.659 | 0.448 | 0.149 |
| Lclat1 | Tregs | 2.73E−18 | 7.08E−14 | 0.674 | 0.313 | 0.081 |
| Gbp7 | Tregs | 4.73E−18 | 1.23E−13 | 0.695 | 0.466 | 0.159 |
| Itgb1 | Tregs | 1.09E−17 | 2.83E−13 | 0.678 | 0.718 | 0.407 |
| Tnfsf8 | Tregs | 1.10E−17 | 2.85E−13 | 0.720 | 0.276 | 0.057 |
| Hivep2 | Tregs | 1.80E−17 | 4.66E−13 | 0.673 | 0.491 | 0.179 |
| Zfp281 | Tregs | 4.05E−16 | 1.05E−11 | 0.664 | 0.466 | 0.176 |
| Hivep3 | Tregs | 2.20E−12 | 5.69E−08 | 0.669 | 0.264 | 0.077 |
| Cd8b1 | Tregs | 1.14E−10 | 2.96E−06 | 0.820 | 0.301 | 0.108 |

Example 3. Activation of Lymph Node-Innervating Sensory Neurons Modulates Immune Responses and Immune Homeostasis in Lymph Node To directly explore functional interactions between LN-innervating sensory neurons and LN cells, Applicants systematically interrogated the effects of acute activation of LN-innervating sensory neurons on gene expression in all identifiable LN cell types by integrating optogenetic stimulation with Seq-Well scRNA-seq profiling. This enabled Applicants to assess the potential neuron-to-immune signaling axis within LNs without a priori knowledge of the responding cells downstream. Optogenetics, the combined use of optics and genetics for temporally and spatially precise control of neuronal activity with light, commonly involves genetic targeting of the light gated cation channel channelrhodopsin, e.g. channelrhodopsin-2 (ChR2), to specific neurons of interest, thereby rendering targeted neurons activatable by blue light. To specifically drive activation within their neurons of interest, Applicants developed an in vivo optogenetic stimulation paradigm whereby iLN-innervating sensory neurons, which were targeted for ChR2 expression along with other Nav1.8 lineage neurons in Nav1.$8^{Cre/+}$; Rosa$26^{ChR2\text{-}eYFP/+}$ (ChR2+) mice were specifically activated with blue light (473 nm) directed through an optical fiber (200 μm) towards a region of the subiliac artery adjacent to the hilus of iLNs, the predominant site of entry of LN-bound sensory fibers (FIGS. 1A, 1B, 7A and 14A).

Figures 7A, 7B:
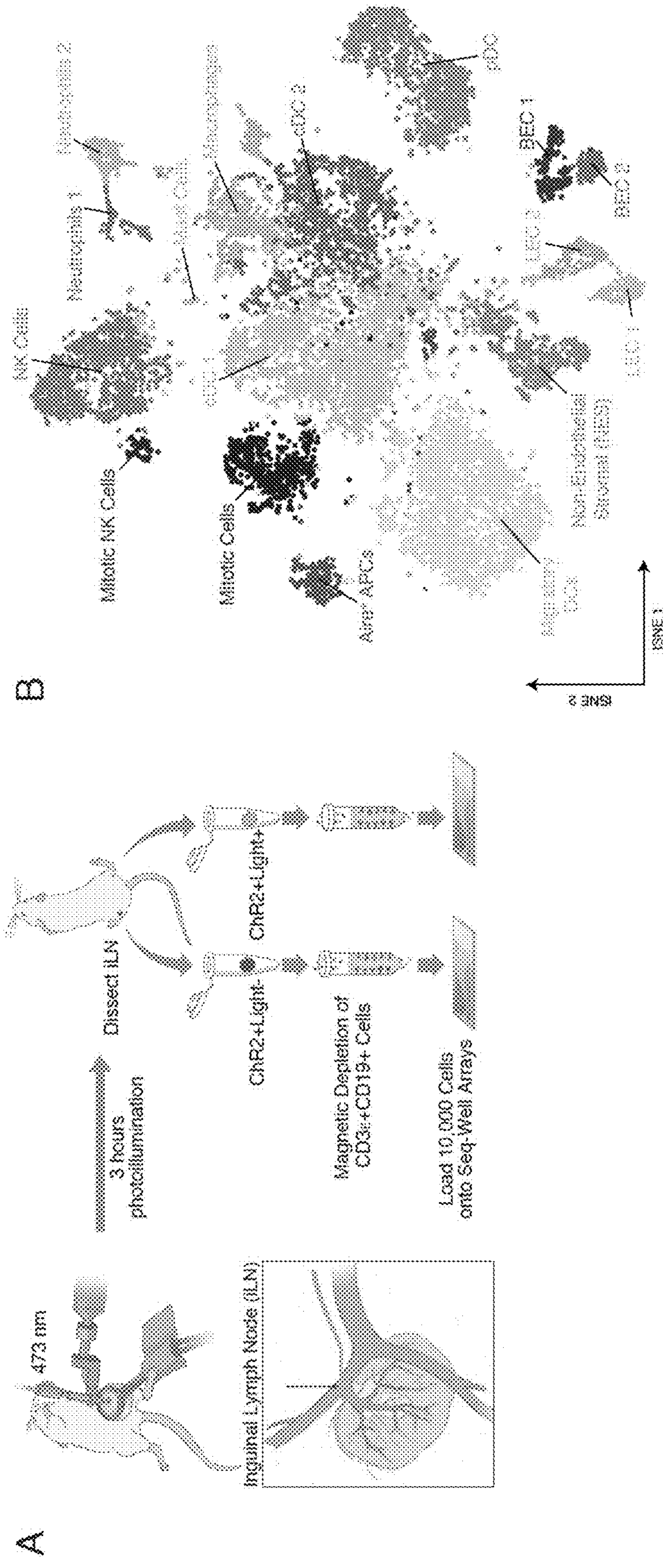
FIG. 7A-7L Optogenetics-assisted identification of potential postsynaptic cellular targets of LN-innervating sensory neurons in peripheral LNs.
Figures 7C, 7D, 7E, 7F:
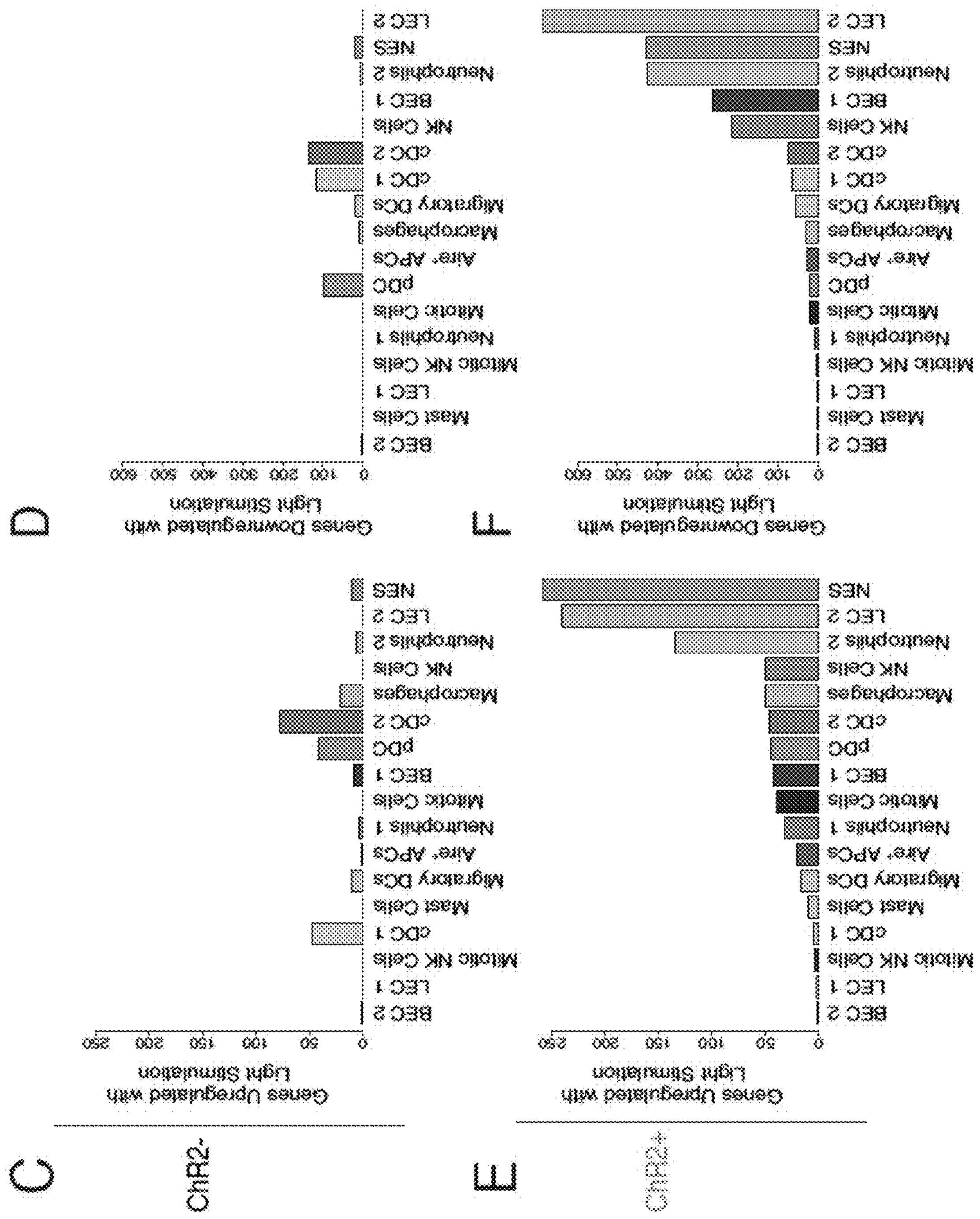
Figure 14A:
FIG. 14A-14G (Related to FIG. 7) Optogenetics-assisted identification of potential postsynaptic cellular targets of LN-innervating sensory neurons in peripheral LNs.
Figure 14B:
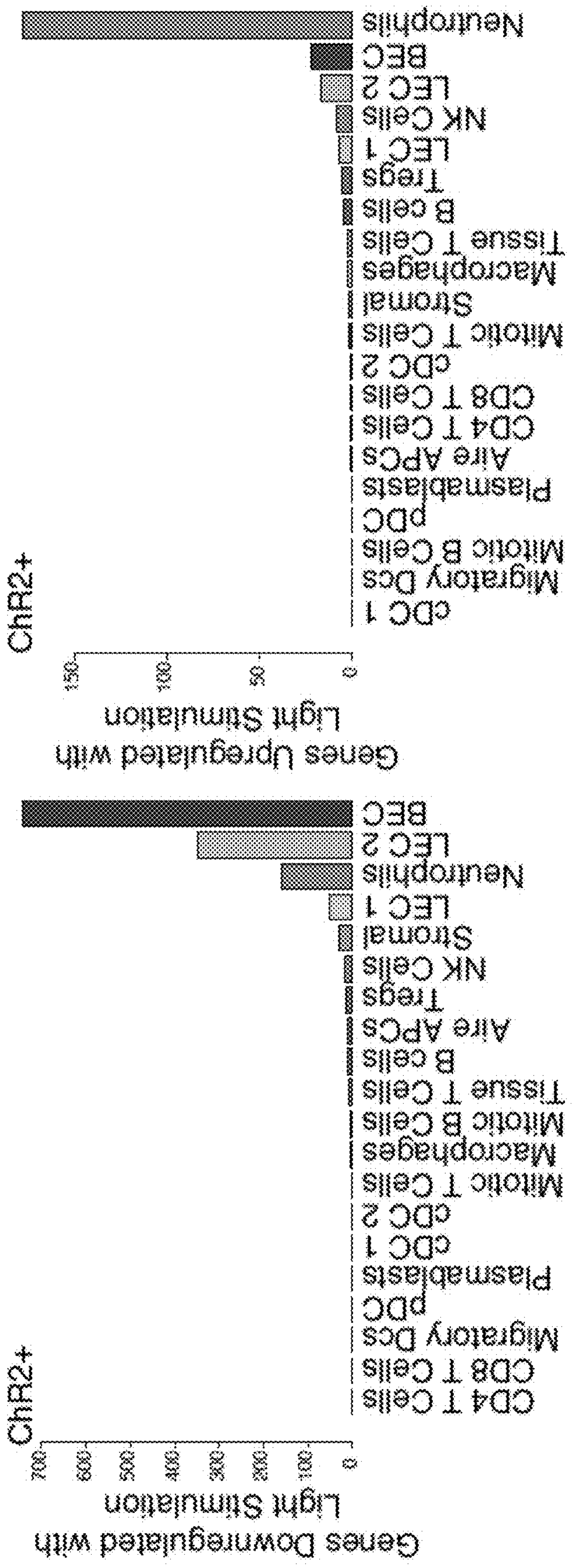
Figure 14C:
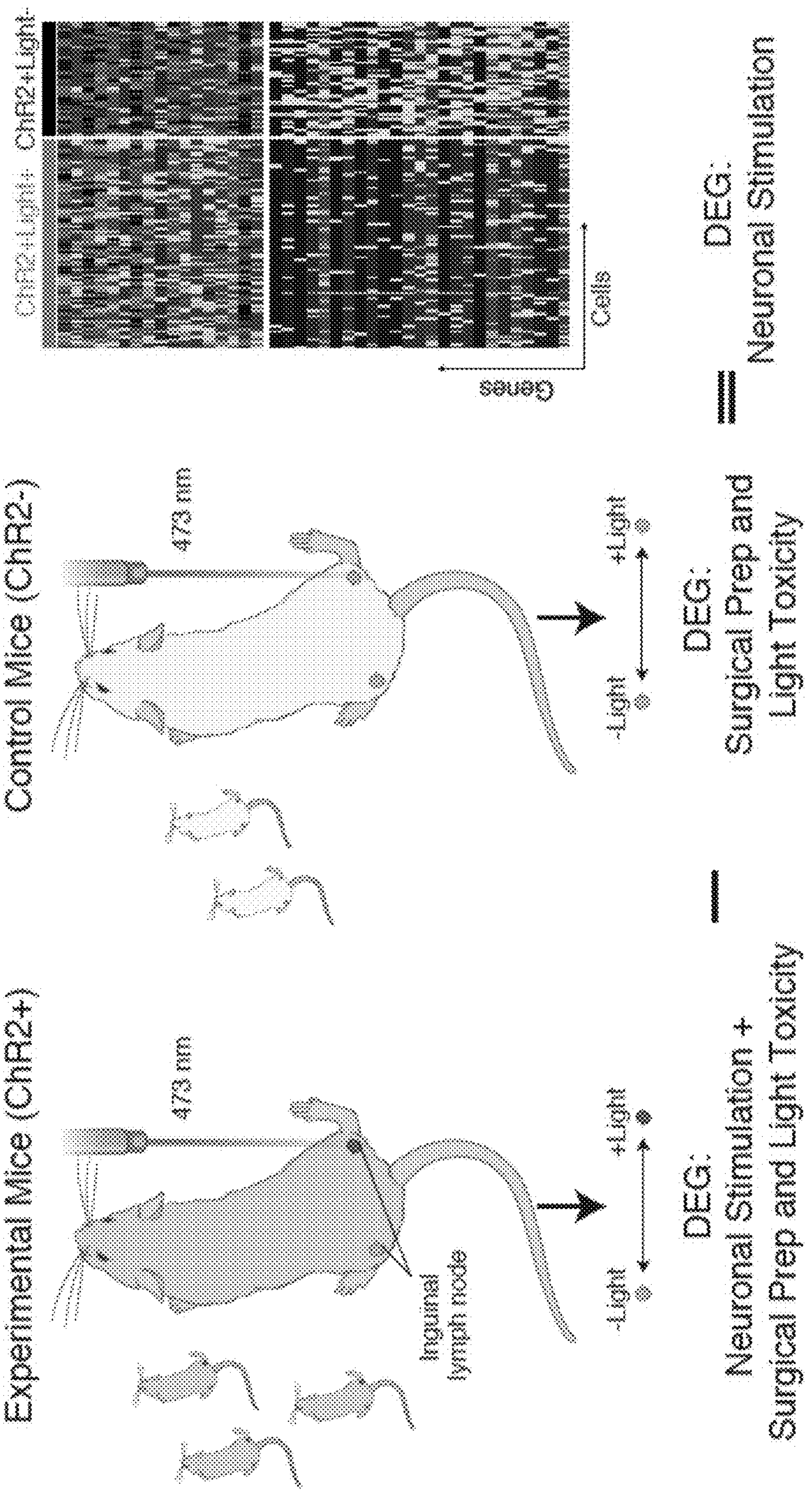

Following 3 hours of pulsed light exposure, iLNs from both the stimulated and unstimulated sides were processed in parallel and analyzed using Seq-Well as described above so that transcriptional changes can be tracked simultaneously in all identified cell types as a universal readout of their responses to neuronal stimulation (FIG. 7A). Within a preliminary cohort, Applicants observed negligible transcriptional change among T cells and B cells,, consistent with the low interaction potential between T, B cells and LN-innervating sensory neurons based on the present disclosure's previous anatomical and molecular characterization (FIG. 14B). Applicants therefore enriched non-T and non-B cells as described above for the steady state iLN atlas and focused the analysis on LN cells within the non-T, non-B cell compartment. To serve as a control and to isolate the ChR2-dependent effect of optogenetic activation, a separate cohort of Nav1.$8^{Cre/+}$; Rosa$26^{eYFP/+}$ (ChR2−) animals, which expressed eYFP instead of ChR2 in Nav1.8 lineage neurons, was subjected to identical photo-stimulation, dissociation, cellular enrichment, and Seq-Well analysis. The changes in cellular composition and gene expression in ChR2+ animals, but not in ChR2− animals were true effects of local stimulation of LN afferents (FIG. 14C). The final dataset included 4 ChR2+ mice and 3 ChR2− mice, two iLN per mouse (one light-exposed, one control), and contained 26,887 unique genes over 10,364 cells after filtering for quality and removing residual T and B cells.

Figure 14D:
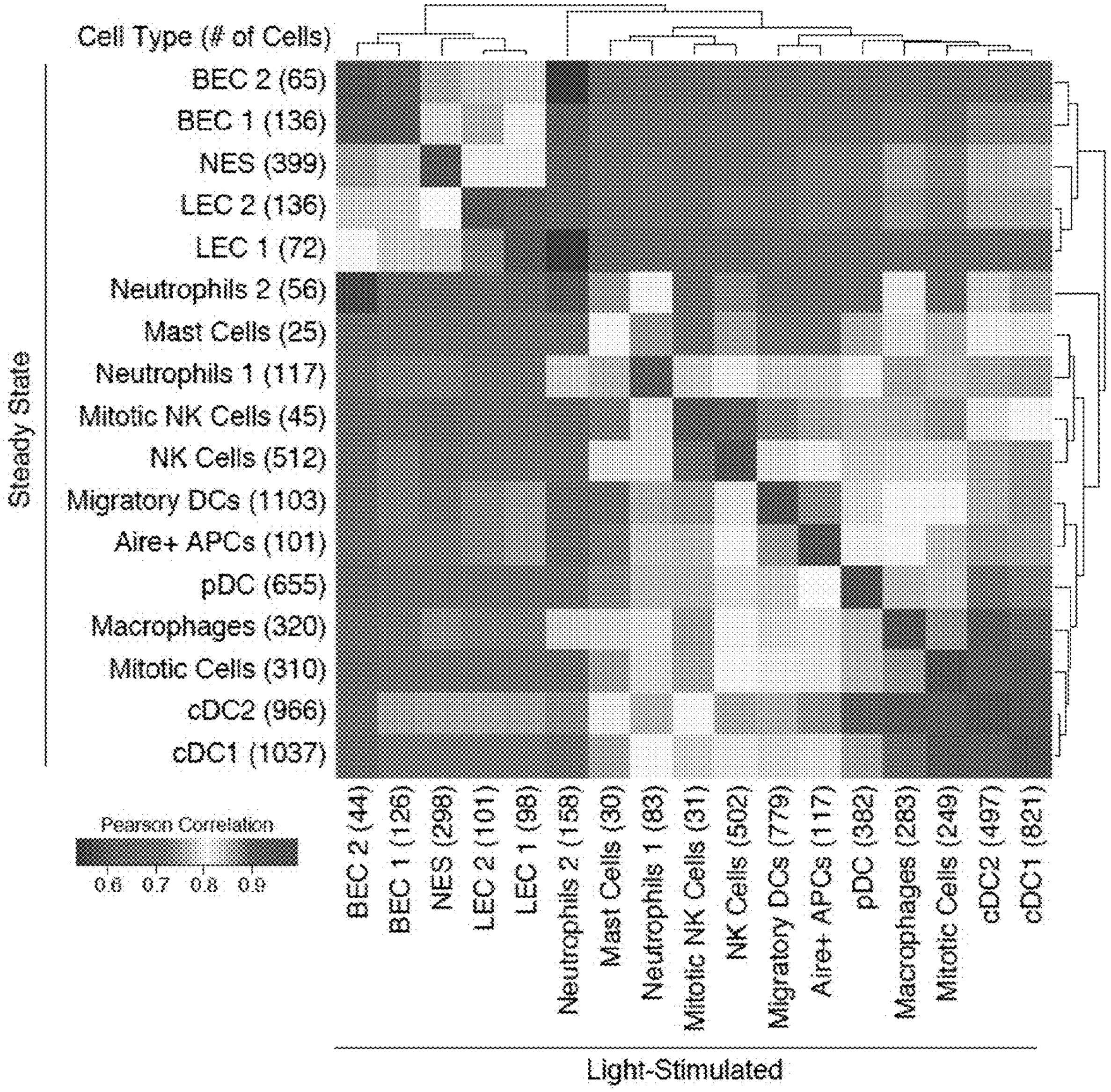
Figures 14E, 14F:
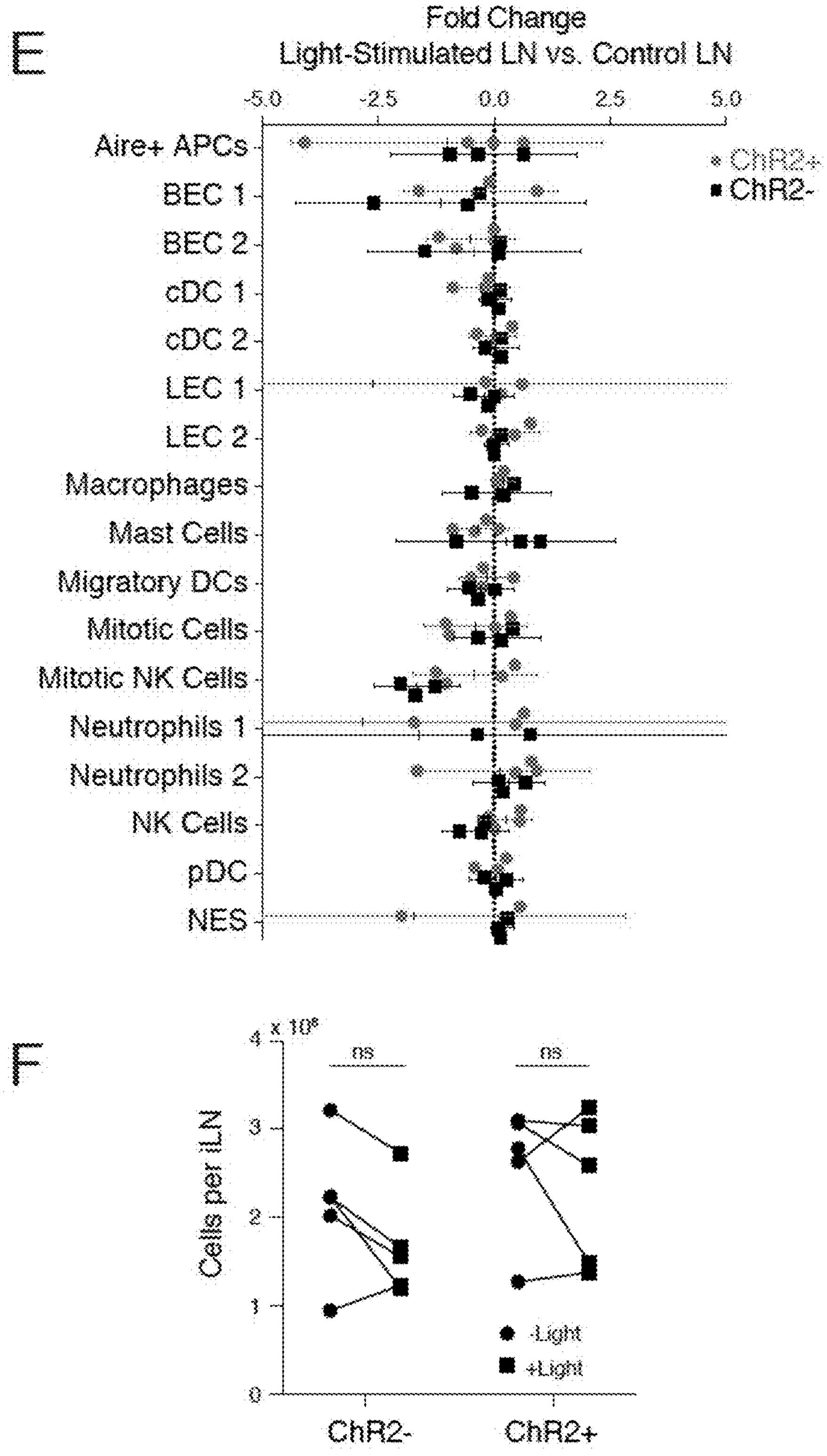

Using methods described above for the steady-state LN cell atlas, Applicants identified a total of 17 cell types based on gene expression patterns, which were in good agreement with the diversity of LN cells described above (FIGS. 6B, 7B, 14D). Surprisingly, Applicants did not observe significant and consistent light-induced changes in the abundance of any cell type in either ChR2+ or ChR2− animals, nor did Applicants observe changes in LN cellularity upon light exposure (FIGS. 14E and 14F). These data not only confirm that the surgical/photo stimulation procedures did not dramatically alter the ecosystem of the exposed LNs compared to the contralateral side, but also suggest that on the short timescale of this analysis (3h), activation of LN-innervating sensory neurons did not significantly affect processes that could alter the cellular composition of LNs.

Figure 7G:
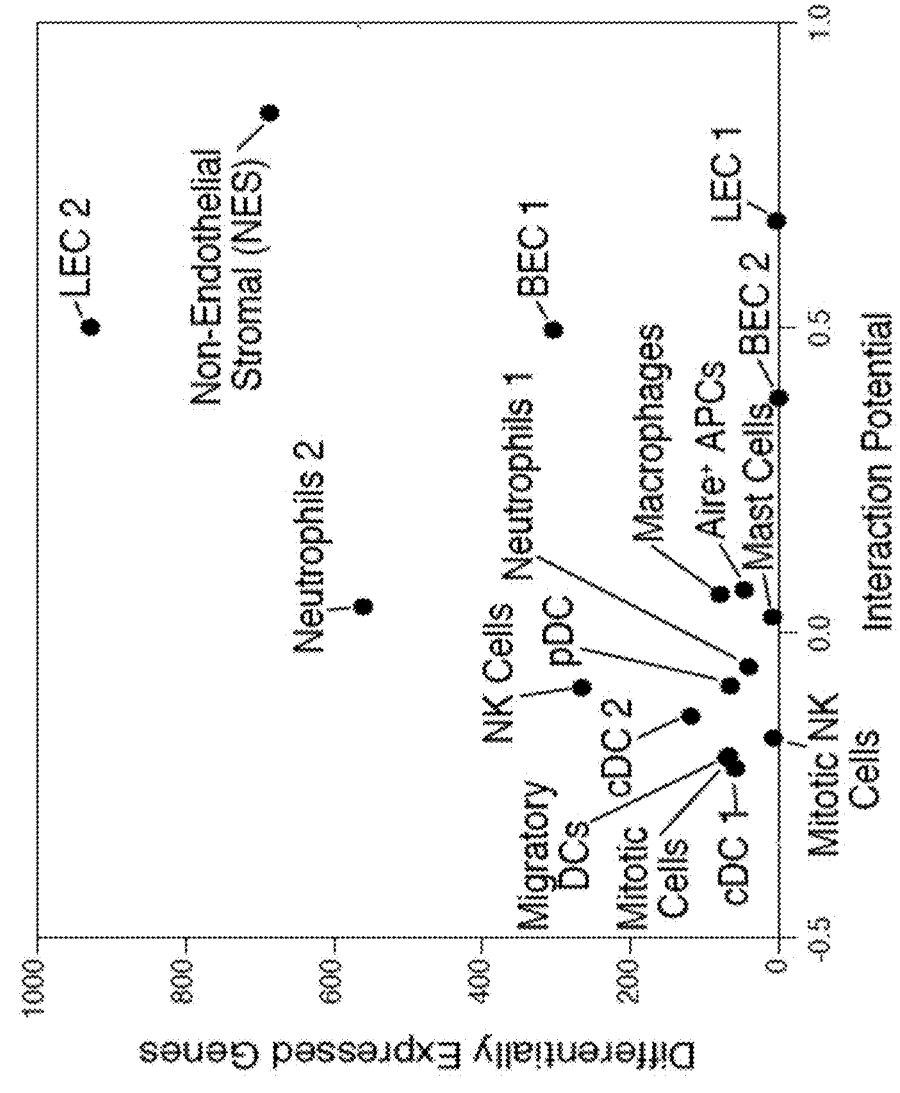
Figure 14G:
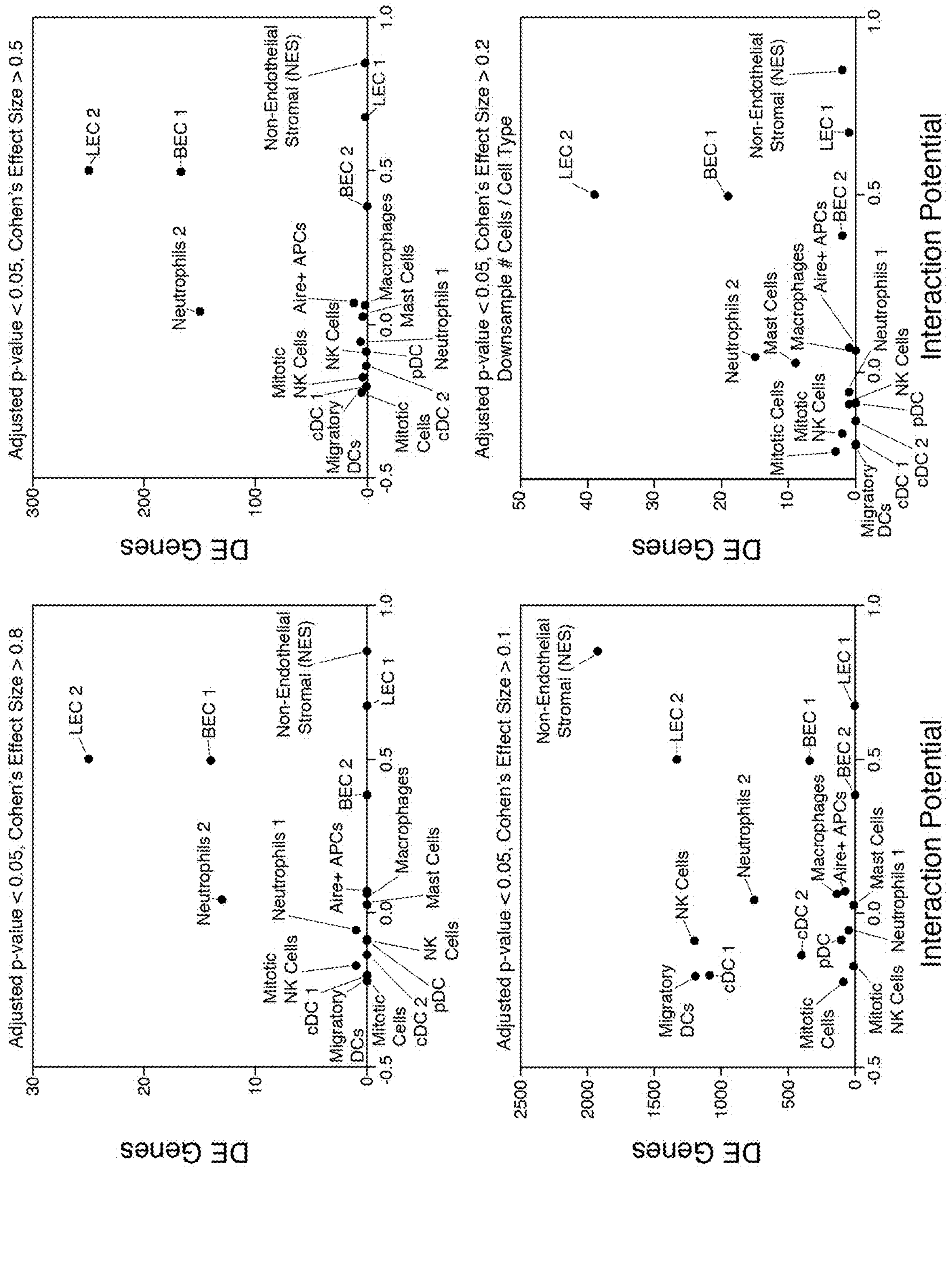

To identify changes induced by ChR2-mediated neuronal excitation within each cell type, Applicants compared gene expression between the same cell type in ChR2+ light-exposed LNs and ChR2+ control LNs. Among significantly DE genes (FDR-corrected p-value <0.05, Cohen's d>0.2), Applicants filtered identified hits to remove genes with similar changes in ChR2− animals, and genes with a negligible effect size, calculated using Cohen's d. Remarkably, Applicants detected robust ChR2-dependent transcriptional changes in a subset of cell types: LEC 2, BEC 1, non-endothelial stroma, Neutrophils 2, and NK cells, indicating potent and selective modulatory capabilities of LN-innervating sensory neurons (FIG. 7C-7F). Applicants confirmed that this ranking was independent of the effect size cutoff and was robust to downsampling of single cells to match the abundance of cells in each cell type group (FIG. 14G). Strikingly, Applicants found that the magnitude of change in gene expression (as measured by number of DE genes) was significantly correlated with the Interaction Potential derived from the steady state iLN atlas, i.e., the cell types predicted in silico to be most likely to interact with LN-innervating sensory neurons also experienced the largest magnitude transcriptional change upon experimental neuronal stimulation (Pearson's r=0.52, p<0.03, FIGS. 7G, 14G).

Figure 7H:
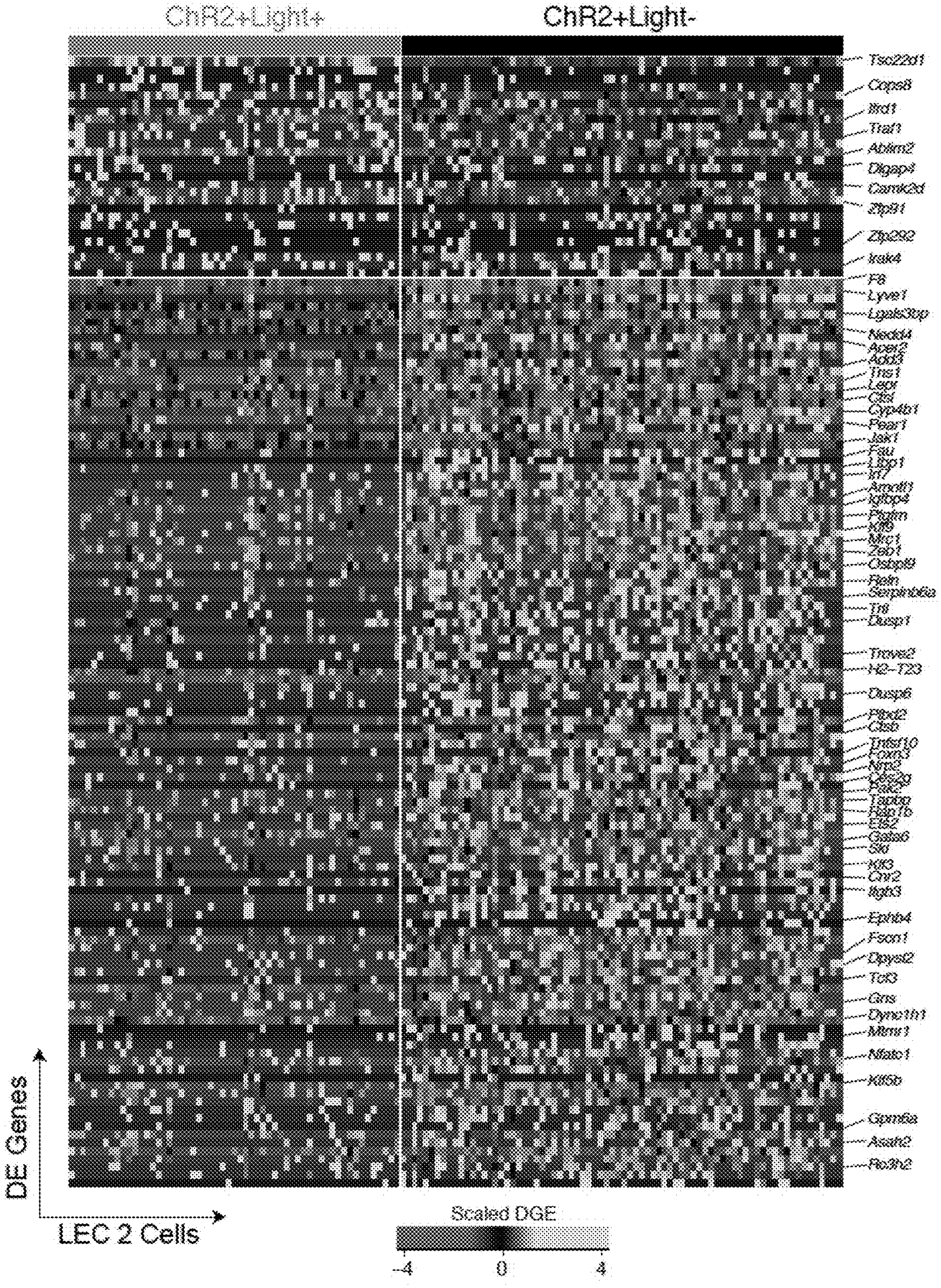
Figures 7I, 7J:
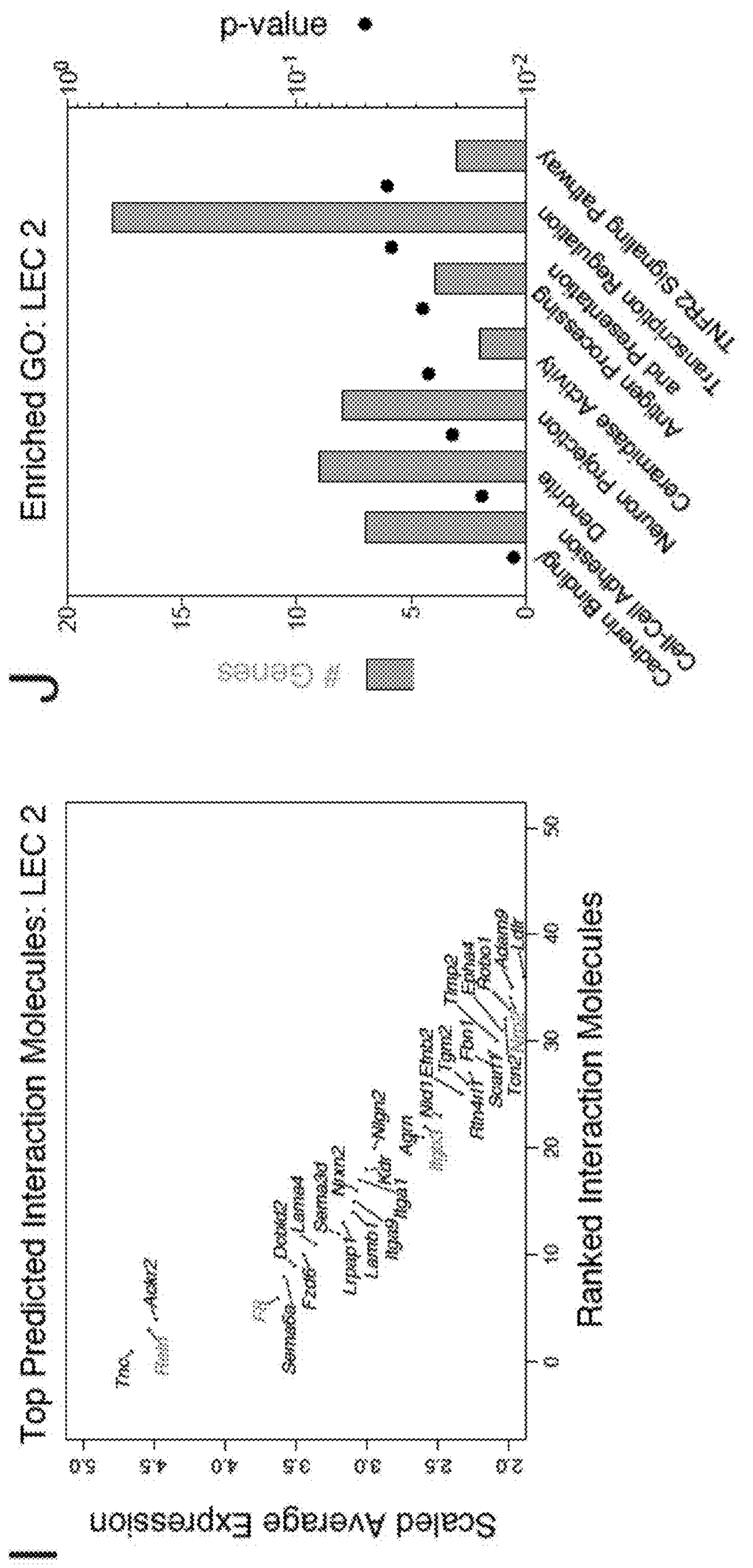
Figures 7K, 7L:
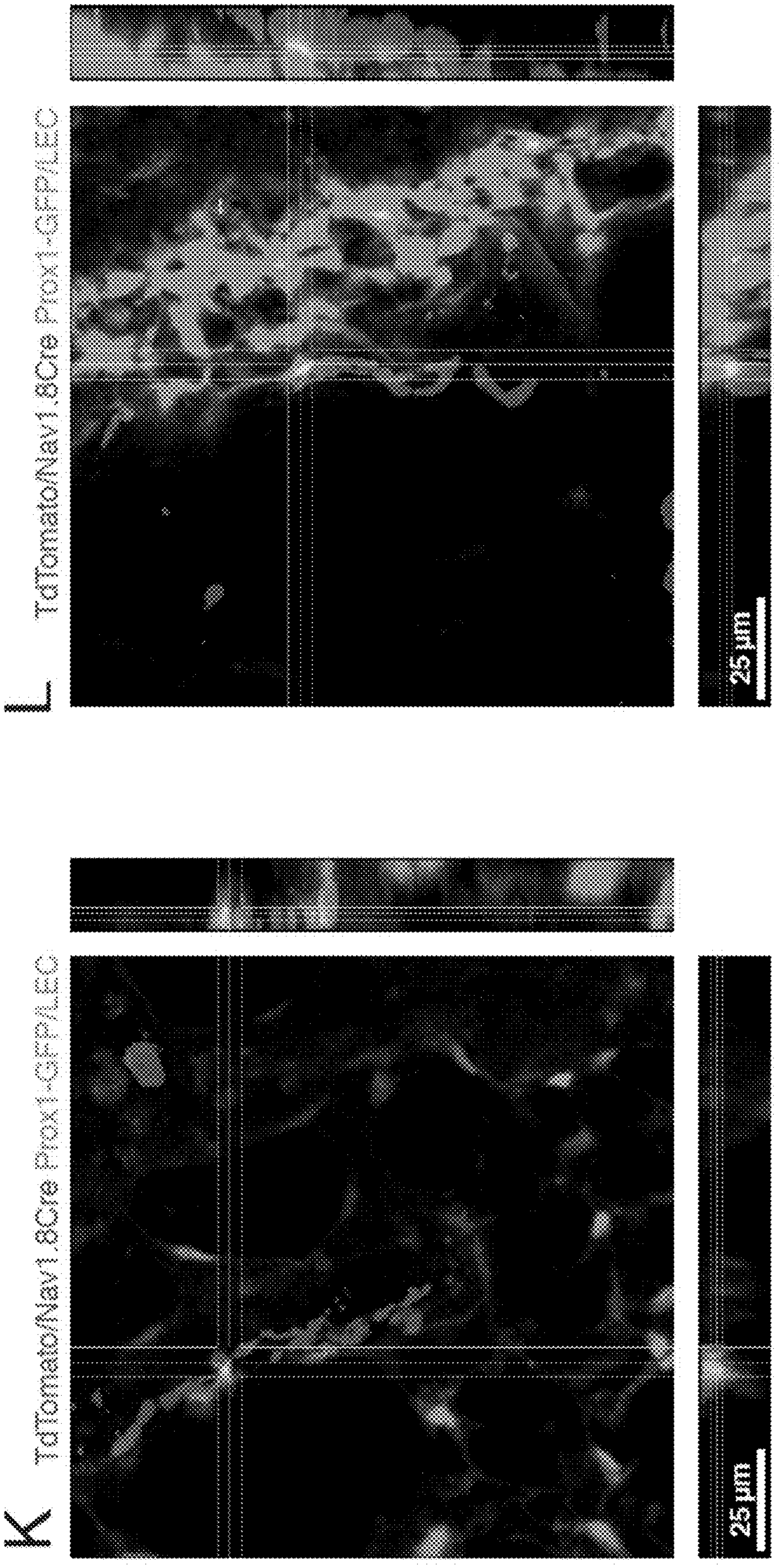

The top-impacted LN cell type was observed to be LEC 2, based on the abundance of differentially expressed genes with substantial effect sizes (FIG. 14G). LEC 2 cells were among the cell types with the highest Interaction Potential (FIGS. 6F, 7G), and were characterized by high expression of potential molecular mediators of interaction with LN-innervating neurons, including extracellular matrix molecules (Tnc, Fbn1, Nid1), synaptic proteins (Agrn, Nrxn2, Nlgn2) (Sudhof, 2018; Wu et al., 2010), and axon guidance molecules known to regulate lymphangiogenesis (Efnb2, Nrp2, Robo1) (Vaahtomeri et al., 2017; Yang et al., 2010) (FIG. 7I). Interestingly, Applicants observed that some interaction-capable molecules, such as Reln, F8, Itgb3, and Nrp2, were downregulated following neuronal stimulation, suggesting a potential negative feedback loop that may act to maintain/restore homeostasis by limiting the effect of neuronal stimulation on LEC 2 once initiated (FIG. 7I). Among neuronal stimulation-induced gene expression changes in LEC 2, which were dominated by downregulation, there was overrepresentation of genes in multiple pathways involved in neuronal synapses and dendrite projection, ceramidase activity, cathepsin expression, pathways involved in antigen processing and presentation, and multiple transcriptional regulators including Gata6, Ets2, Irf7 and Nfatc1 (FIG. 7J). Interestingly, Applicants observed a general trend toward downregulation of LEC-enriched genes including key regulators of lymphatic development and patterning, e.g., Reln, Nrp2, Ephb4, Nfatc1, Lyve1, as well as angiogenic molecules, e.g., Dlg1, Glu1, suggesting anti-angiogenic/lymphangiogenic action of LN-innervating sensory neurons (Cho et al., 2019; Eelen et al., 2018; Kulkarni et al., 2009; Lutter et al., 2012; Vaahtomeri et al., 2017; Wu et al., 2014; Zhang et al., 2015). Moreover, downregulation of ceramidases, i.e., Acer2 and Asah2, implicated in production of sphingosine-1-phosphate (S1P) in LECs, a major source of SIP in lymph, may impact lymphocyte egress from LNs, a process previously shown to be under the control of adrenergic nerves (Mao and Obeid, 2008; Nakai et al., 2014; Pappu et al., 2007; Pham et al., 2010). Consistent with the observation that LEC 2 exhibited the largest neuronal activation-evoked transcriptional changes, direct contact between sensory nerves and LECs was frequently observed in the medulla and on the ceiling of the SCS, providing further support for direct communication between LECs and sensory innervation of LNs (FIG. 7K, 7L). Thus, these data not only corroborate Applicants' analysis of Interaction Potential among candidate post-synaptic cell types, but also suggest that sensory neurons innervating LNs, when activated, may rapidly remodel the non-immune compartment to influence LN homeostasis.

Example 4. Discussion

Despite their critical roles in regulating immune processes at barrier tissues and lymphoid organs, neuroimmune interactions have yet to be systematically studied in LNs. Here, Applicants directly addressed this unmet need by analyzing the morphological, molecular, and functional attributes of the sensory neurons that innervate LNs. Applicants found that fibers of definitive sensory origin are preferentially located in the LN periphery, including the perivascular and capsular/subcapsular spaces. The data show that LN-innervating sensory neurons are a heterogeneous population with strong peptidergic nociceptor signatures, and are molecularly-distinct from their skin-innervating counterparts. Applicants conclude that sensory neurons are most likely to interact with LN stromal cells, including BECs, LECs, and NES, based on ligand-receptor pair expression in trans and the magnitude of transcriptional change following optogenetic stimulation of LN-innervating neurons. The study therefore identifies the sensory neuron-stroma axis within skin-draining LNs as a previously unappreciated mode of neuroimmune communication in the periphery.

The observations of the spatial distribution of sensory innervation in skin-draining LNs are largely in line with previous descriptions of putative sensory fibers within LNs. These include: the existence of the two nerve plexuses, concentration of fibers in the medulla, preferential association with arterioles, and spatial proximity between sensory fibers and LN resident cells, such as smooth muscle cells and lymphatic endothelial cells (Felten et al., 1985; Fink and Weihe, 1988). Unlike previous sectioning-based approaches, the whole-mount immunolabeling protocol allowed reliable identification and 3D visualization of the entire network of neuronal fibers, a prerequisite for quantitative description of neuronal architecture in LNs. The ability to identify LN sensory innervation through genetic labeling and retrograde tracing instead of canonical markers or ultrastructural features allowed us to perform unbiased and complete morphological characterization of a heterogeneous neuronal population. Applicants observed that sensory fibers are enriched in the LN periphery, a location prone to inflammation-induced mechanical, chemical, and cellular changes, which suggests a possible role for those neurons as local sentinels of lymph node activation. This idea is particularly attractive in light of clinical reports of painful LNs as a result of infection and cancer, an observation suggesting functional activation of sensory nervous system by the immune system at LNs. However, the exact type(s) of stimulus that those sensory neurons are tuned to and the nature of the neuronal response have yet to be defined.

Although molecular differences between sensory neurons innervating different targets have been noted previously (Robinson and Gebhart, 2008; Yang et al., 2013), this work represents, to Applicants knowledge, the first attempt to address innervation target-dependent phenotypic differences within sensory neurons at whole genome level. Consistent with previously-described differential preferences of peptidergic and nonpeptidergic nociceptors for the skin vs. visceral organs (Robinson and Gebhart, 2008), peptidergic nociceptors are overrepresented in LN-innervating sensory neurons, whereas nonpeptidergic nociceptors are enriched in the skin-innervating population from the same axial levels. Beyond shifts in subtype composition, Applicants observed substantial and reproducible gene expression differences between sensory neurons innervating different tissues, likely reflecting tissue-specific functional or developmental requirements—an interesting hypothesis that merits further investigation. Recent work has demonstrated that the influence of nociceptors on inflammation is highly context-dependent (Foster et al., 2017). Notably, even when the site of inflammation is the same, nociceptors can play pro-inflammatory roles in psoriasis-like inflammation and candidal infection (Kashem et al., 2015; Riol-Blanco et al., 2014), or immunosuppressive roles in *Streptococcus pyogenes* and *Streptococcus aureus* infections (Chiu et al., 2013; Pinho-Ribeiro et al., 2018). Among many other possibilities, this may reflect differential contributions of organ-specific nociceptor-immune interactions in draining LNs and in the skin to different models of inflammation. Innervation target-dependent subtype composition and gene expression differences that Applicants uncovered are consistent with the notion that sensory neuron-immune interactions are organized in an organ-specific manner, thereby contributing to the context-dependent nature of sensory neuronal regulation of immunity.

The identification of LN-innervating sensory neurons of varying cell sizes, myelination statuses, and molecular classes further suggests that, within LNs, different subsets of sensory neurons will presumably have different activation thresholds for the same or different stimuli. This could result in differential activation, and subsequent recruitment by local neuroimmune circuits in different immunological context. This represents yet another mechanism by which the apparent context-dependent role for nociceptors might arise. The gene modules that distinguish different subtypes of LN-innervating sensory neurons, as well as LN- and skin-innervating sensory neurons as a whole in this study could thus provide a valuable molecular toolkit to further study the specific immunomodulatory role of individual neuronal populations.

Analysis of ligand-receptor gene expression patterns in single-cell datasets has been instrumental in deconstructing the complex cellular communication network in the context of tissue development, function and cancer biology (Camp et al., 2017; Cohen et al., 2018; Kumar et al., 2018; Vento-Tormo et al., 2018). The possibility of applying this powerful approach to study neuron-non-neuronal cell interactions has, to Applicants knowledge, not been explored until the current study. It is important to emphasize that the predictions from in silico cellular interaction analysis were systematically tested and upheld by the optogenetic experiments, demonstrating the utility of this analysis in uncovering novel neuroimmune crosstalk. While this dataset, which did not take interactions amongst LN cells into consideration, does not allow us to assign biologically important source(s) of ligand/receptors pairs, it does reveal interesting candidate molecular mediators of sensory neuron-non-neuronal interactions at LNs, which can be experimentally tested by more targeted approaches. For example, expression patterns of classic synaptogenic complexes, i.e., agrin-alpha3Na+/K+-ATPase and neurexin-neuroligin (Hilgenberg et al., 2006; Sudhof, 2018), in LN-innervating sensory neurons and LEC 2 might suggest a novel function for those classical signaling molecules in establishing synapse-like sensory neuron-LEC contacts within LNs. Additionally, Applicants note that the intercellular interaction network was generated based on expression data from cells at steady state, and thus is most relevant to steady state LNs. The sensory neuron-immune interactions in inflamed LNs are potentially distinct and remain to be addressed with similar approaches.

Optogenetic-mediated circuit mapping has revolutionized the field of neuroscience by linking neurons to network activity and behavior. The downstream output is typically measured by electrophysiology, calcium imaging and behavioral assays. Only recently has it been applied to interrogate neuronal circuits underlying neuromodulation of peripheral tissues (Chang et al., 2015; Mickle et al., 2019; Rajendran et al., 2019; Williams et al., 2016; Zeng et al., 2015). In those few cases, optogenetics-induced effects were generally assessed based on specific hypotheses, such as select physiological or cellular functions. While this targeted approach has undoubtedly helped to reveal complex interplay between the nervous system and peripheral tissues, it is not particularly useful for addressing the cellular mechanism and extent of neuromodulation in a tissue, especially one with complex and varied functional outputs, such as LNs. This is a challenge that Applicants have begun to address with the use of scRNA-seq as an unbiased and high-throughput readout of neuronal influence on various LN cell types, assuming that potential modulatory effects of optogenetic stimulation can be measured at the transcriptional levels for all the possible postsynaptic target cells. Crucially, the most impacted postsynaptic target cells, i.e., stromal cells, also appear to be the most likely interacting partners of LN-innervating sensory neurons based on morphological and molecular criteria. As inflammation is likely an endogenous stimulus of LN-innervating sensory neurons, this finding suggests that inflammation-induced remodeling of LN stroma might be, in part, mediated by local sensory innervation. While the current optogenetic stimulation paradigm was specifically designed to capture immediate effects of local activation of LN sensory afferents, thus identifying potential direct non-neuronal responders, alternative modes of activation that are more amenable to temporal profiling of neuronal effects should be explored to map non-neuronal responses over a longer period of time.

The identification of LEC 2 as the top postsynaptic target of LN-innervating sensory neurons is particularly intriguing, as local sensory afferents have been implicated in the processes of antigen, lymph, and lymphocyte flow through LNs, all of which heavily depend on LECs (Hanes et al., 2016; Moore et al., 1989). The extent to which this novel sensory neuron-LEC 2 circuit contributes to those processes and the underlying molecular mechanism represent interesting future directions. Applicants found that two ceramidases, Acer2 and Asah2, implicated in S1P production, were downregulated by optogenetic stimulation in LEC 2, suggesting sensory neurons may impact lymphocyte trafficking by negatively-regulating SIP-mediated lymphocyte egress from LNs (Mao and Obeid, 2008; Pappu et al., 2007; Pham et al., 2010). In light of the inhibitory effect of sympathetic neurons on lymphocyte egress from LNs in physiological and pathological conditions (Nakai et al., 2014), sensory and sympathetic innervation of LNs may act together or independently of each other to limit lymphocyte exit from LNs, thus altering adaptive immune responses.

One unique feature of sensory neurons is their remarkable ability to act in a motor neuron-like, or efferent, fashion in a process known as the "axon reflex" (Chiu et al., 2012; Richardson and Vasko, 2002). That is, the ability of action potentials generated locally at peripheral terminals to back-propagate to neighboring axonal collaterals once they reach axonal branch points. Local release of effector molecules from activated peripheral terminals could thus directly impact peripheral function without engaging the CNS. The more conventional sensory or afferent function of sensory neurons requires activation of monosynaptic or polysynaptic reflex-like neural circuit in the CNS, which, for visceral organs, culminates in motor output from the autonomic nervous system mediated by sympathetic and parasympathetic neurons. While both efferent and afferent functions have been discussed in the context of immunomodulation (Baral et al., 2019; Chavan et al., 2017), their relative contributions to a given immunological process are almost completely unknown. Since LNs are dually innervated by sympathetic and sensory neurons, which could potentially support the classic reflex-like circuit, the robust modulatory effects of optogenetic stimulation of LN-innervating sensory neurons could result from either their efferent or afferent action or both. Therefore, the circuit-level mechanisms underlying optogenetics-induced gene expression changes remain an important open question. Studying the dependence of this process on sympathetic output to LNs should help close this knowledge gap.

In conclusion, Applicants established LNs as a point of convergence between the sensory nervous system and the immune system by identifying a molecularly distinct and heterogeneous population of sensory neurons with remarkable capacity to impact LN function and homeostasis. This study represents the first comprehensive morphological, molecular and functional analysis of the landscape of sensory innervation of any organ with immunological function, and could serve as a guide for future study of neuroimmune interactions elsewhere in the body.

Example 5. Methods

Experimental Model and Subject Details

Mouse lines used in this study were all previously described and include Nav1.8Cre (RRID:IMSR_EM:04582) (Nassar et al., 2004), Rosa26$^{LSL-tdTomato}$ (RRID:IMSR_JAX:007914), Bmx-CreER$^{T2}$ (MGI: 5513853) (Ehling et al., 2013), Rosa26$^{LSL-DTA}$ (RRID:IMSR_JAX:009669), Prox1-EGFP (MGI: 4847348) (Choi et al., 2011), Rosa26$^{LSL-ChR2-eYFP}$ (RRID:IMSR_JAX:024109), and Rosa26$^{LSL-eYFP}$ (RRID:IMSR_JAX:007903). All of the animals were handled according to approved institutional animal care and use committee (IACUC) protocols of Harvard Medical School. Unless indicated otherwise, adult mice of both sexes between 6-12 weeks of age were used for various experiments.

Whole Mount Immunohistochemistry

Whole mount immunohistochemistry of LNs was performed using an iDISCO protocol with methanol pretreatment optimized for LNs (Renier et al., 2014). Briefly, adult animals (6-12 weeks) were perfused with 25 mL of PBS (Hyclone) and 25 mL of 4% paraformaldehyde (PFA, Sigma) sequentially at room temperature (RT). Peripheral lymph nodes (PLNs), including popliteal and inguinal lymph nodes (popLNs and iLNs), were postfixed with 4% PFA for 1 hr at 4° C. For methanol pretreatment, fixed LNs were washed sequentially in 50% methanol (Fisher Scientific) (in PBS) for 1 hr, 100% methanol for 1 hr, 50% methanol for 1 hr, PBS for 1 hr twice, and PBS/0.2% Triton X-100 (VWR) for 1 hr twice at RT. LNs were then left in PBS/0.2% Triton X-100/20% DMSO (Sigma)/0.3 M glycine (BioRad) overnight at RT and blocked in PBS/0.2% Triton X-100/10% DMSO/6% donkey serum (Jackson Immunoresearch) or goat serum (Gibco)/anti-CD16/CD32 (Fc block) (Bio X cell) overnight at RT. LNs were subsequently washed in PBS/0.2% Tween-20 (Fisher Scientific)/10 μg/mL heparin (Sigma) (PTwH), for 1 hr twice at RT, before incubation with antibody mix in PTwH/5% DMSO/3% donkey or goat serum/Fc block 1:100 for 3 days at RT. LNs were extensively washed in PTwH for at least 6 times over the course of a day at RT. For unconjugated antibodies, LNs were further incubated with a secondary antibody mix including a panel of species-specific anti-IgG (H+L) Alexa Fluro 488, 546, 647 and 594-conjugated antibodies (Invitrogen or Jackson Immunoresearch) in PTwH/5% DMSO/3% donkey or goat serum/Fc block 1:100 for 3 more days at RT. LNs were washed in the same way as after primary antibody incubation for 1 day. Immunolabeled LNs following one round of antibody incubation for conjugated antibodies (or two for unconjugated antibodies) were then processed for clearing, which includes sequential incubation with 50% methanol for 1 hr, 100% methanol for 1 hr for three times and a mixture of 1-part benzyl alcohol (Sigma): 2-parts benzyl benzoate (Sigma) (BABB) overnight at RT. For tdTomato immunolabeling, goat anti-mCherry antibody (ACRIS) was preabsorbed against PLNs from $tdTomato^-$ animals overnight at RT prior to use.

Whole mount immunohistochemistry of DRGs and the skin was performed as described previously (Li et al., 2011). Briefly, DRGs inside vertebral column and the depilated hairy skin from PFA-perfused animals (6-12 weeks) were postfixed with 4% PFA for 1 hr or Zamboni fixative (Fisher Scientific) overnight, respectively at 4° C. Samples were washed every 30 min with PBS/0.3% Triton-100 (0.3% PBST) for 4-6 hr, then incubated with primary antibodies in antibody diluent (0.3% PBST/20% DMSO/5% donkey or goat serum) for 2-3 days at RT. Samples were then washed with 0.3% PBST every 30 min for 5-8 hr before incubation with secondary antibodies in antibody diluent for 2-3 days at RT. After extensive washes as described above, samples were dehydrated and cleared in 50% methanol for 1 hr, 100% methanol for 1 hr for three times and BABB overnight at RT.

Cleared whole mount tissues were imaged in BABB between two coverglasses using Olympus FV3000 confocal imaging system, except for those shown in FIGS. 7K and 7L, which were acquired on BioRad 2100MP system.

The antibodies used were: rabbit anti-CGRP (Immunostar, 24112, 1:500), chicken anti-GFP (Aves Labs, GFP-1020, 1:500), chicken anti-NF200 (Aves Labs, NFH, 1:500), rabbit anti-Tyrosine Hydroxylase (Millipore, AB152, 1:500), goat anti mCherry antibody (1:500, ACRIS AB0040-200), rabbit anti-βIII-Tubulin (Biolegend, 802001, 1:500), Alexa Fluor 647-conjugated rat anti-CD31 (Biolegend, 102416, 1:50), FITC-conjugated mouse anti-smooth muscle actin (aSMA) (Sigma, F3777-. 2ML, 1:500), eFluor 660-conjugated mouse anti-smooth muscle actin (aSMA) (Thermo Fisher, 50-9760-82, 1:100), eFluor 660-conjugated rat anti-CD169 (Thermo Fisher, 50-5755-80, 1:50), Pacific Blue-conjugated rat anti-CD45 (Biolegend, 103126, 1:50), Alexa Fluor 488-conjugated rat anti-PNAd (Thermo Fisher, 53-6036-82, 1:50)

Retrograde Labeling of LN-Innervating Neurons

To retrogradely label LN-innervating neurons, adult animals (6-12 weeks) were anesthetized by intraperitoneal injection of ketamine (Patterson Vet) (50 mg kg-1) and xylazine (Patterson Vet) (10 mg kg-1). The skin overlying the targeted iLN was shaved and depilated so that the LN underneath was visible percutaneously. A 5 mm incision was made directly on top of the iLN. The iLN was microdissected without perturbing afferent lymphatic vessels and surrounding blood vessels. 1 μl of Adeno-Associated Virus (AAV) (AAV2/1.CMV.HI.eGFP-Cre.WPRE.SV40, titer >=8E+12 vg/mL, Addgene) mixed with 0.5 μl of fast green (Sigma) was injected into the iLN of $Rosa26^{LSL\text{-}tdTomato/LSL\text{-}tdTomato}$ animals using a pulled and trimmed glass pipette (FHC) which was connected to a 5 mL syringe through the aspiration assembly system (Sigma). The injection site was immediately rinsed with 2 mL of saline (Patterson Vet) to wash away any off-target virus before the incision was closed with sutures. Animals were sacrificed between 1 month and 6 months after injection for histology or scRNA-seq. To directly visualize the axonal projections of sensory neurons retrogradely labeled from the iLN, AAV carrying Cre-dependent tdTomato cassette (AAV2/1.CAG.Flex.tdTomato.WPRE.bGH, titer $\geq 10^{13}$ vg/mL, Addgene) was injected into the iLN $Nav1.8^{Cre/+}$ animals as described above. For WGA-based retrograde labeling, 1 μl of WGA-AF488 (2 mg/mL in PBS, Invitrogen) was injected into the iLN of $Nav1.8^{Cre/+}$; $Rosa26^{LSL\text{-}tdTomato/+}$ animals as described before and the animals were processed for histology 4 days post injection. Retrograde labeling of skin-innervating neurons was described previously (Kuehn et al., 2019). Briefly, following ketamine-xylazine mediated anesthesia, a single injection of 0.2 μl of various AAV2/1 viruses as described above and 0.1 μl of fast green was delivered using the injection device described above intradermally into the patch of depilated skin overlying the iLN of adult mice (6-12 weeks). Animals were sacrificed between 1 month and 6 months after injection for immunohistochemistry, RNAscope, or scRNA-seq.

Immunohistochemistry of Tissue Sections

Adult animals (6-12 weeks) were perfused with 25 mL of PBS and 25 mL of 4% PFA sequentially at RT. The intact vertebral column was postfixed overnight with 4% PFA at 4° C. DRGs were subsequently dissected and processed for cryosectioning. 14 μm serial cryosections were collected and processed for immunohistochemistry as described previously (Li et al., 2011). In brief, sections were postfixed with 4% PFA for 10 min at RT. Following three washes with PBS, they were incubated with blocking buffer (PBS with 5% normal goat serum and 0.3% Triton-100) for 1 hr at RT. The sections were then incubated with Rabbit anti-TH (Millipore) in the same blocking buffer overnight at 4° C. The following day, sections were washed three times with wash buffer (PBS with 0.3% Triton-100) before incubation with goat Alexa Fluor 647-conjugated anti-rabbit (Invitrogen) for 1 hr at RT. Sections were then washed for three times with wash buffer before mounting in Fluoromount Aqueous Mounting Medium (Sigma). WGA-488 and tdTomato were visualized directly based on endogenous fluorescence. All the sections with $tdTomato^+$ cells were imaged at 20× using Olympus FV3000 confocal imaging system.

Intravital Two-Photon Microscopy

Adult $Nav1.8^{Cre/+}$; $Rosa26^{LSL\text{-}tdTomato/+}$ animals (6-12 weeks) were given 1 μg of FITC-conjugated rat anti-CD169 antibody (BioRad) diluted in a total volume of 20 μl of PBS into the right footpad to label $CD169^+$ subscapular macrophages inside the draining LN. Immediately after, the animals were prepared microsurgically for intravital two-photon microscopy as described before (Mempel et al., 2004). Briefly, anesthesia during surgical preparation and imaging was achieved through the ketamine-xylazine method as described above. The right popLN was exposed and positioned with the cortex facing outwards with minimal perturbation to afferent lymphatic vessels and surrounding blood vessels, while the animal was immobilized onto a custom-built stage by its hip bone and the vertebral column. The imaging chamber was created around the exposed LN with high vacuum grease (VWR) on the side and a coverslip on top. A thermocouple (Omega) was placed next to the LN to monitor the local temperature, which was maintained between 36.5 and 37° C. by a custom-built water bath heating system. Two-photon imaging was performed on a Bio-Rad Radiance 2100MP Confocal/Multiphoton microscopy system with two MaiTai Ti:sapphire lasers (Spectra-Physics) tuned to 800 nm and 900 nm for two photon excitation and second harmonic generation. Z-stacks of sensory innervation of the capsular/subcapsular space on the cortical side were acquired in 1 μm steps with a 20×, 0.95 numerical aperture objective (Olympus).

Manual Cell Sorting for scRNA-seq

Adult mice with retrogradely-labeled LN- or skin-innervating neurons were sacrificed by $CO_2$ asphyxiation. T13 and L1 DRGs ipsilateral to the side of injection were quickly removed without nerves attached and checked for tdTomato labeling in cold HBSS (1×, no $Ca^{2+}$ or $Mg^{2+}$) (VWR) under Leica MZ10 F stereomicroscope with fluorescence. DRGs were immediately digested with 1 mL of papain solution (HBSS/10 mM HEPES (VWR)/500 μM EDTA (Westnet)/0.4 mg/mL L-Cysteine (Sigma)/1.5 mM $CaCl_2$) (Sigma)/20 unit/mL Papain (Worthington)) in a 37° C. water bath for 10 min, with agitation every 2 min. DRGs were further digested with 1 mL of collagenase type II/dispase solution (HBSS/10 mM HEPES/4 mg/mL collagenase type II (Worthington)/5 mg/mL dispase (Thermo Fisher)) in a 37° C. water bath for 30 min, with agitation every 10 min. Following centrifugation at 400 g for 4 min, digested DRGs were mechanically disrupted in 0.2 mL of complete L15 medium (L15 (Invitrogen)/10 mM HEPES/10% FBS (Germini)) by passing them first through a 1000 μL pipette tip up to 10 times, and then through a 200 μL pipette tip up to 5 times until the tissues were fully dissociated. To remove myelin/axonal debris, the cell suspension diluted in 1 mL of complete L15 medium was carefully layered on top of 5 mL of Percoll gradient (L15/10 mM HEPES/20% Percoll (GE Healthcare) and centrifuged at 400 g for 9 min. After removing the supernatant, cells were washed in 2 mL of L15/10 mM HEPES and centrifuged at 750 g for 3 min. Finally, cells were resuspended in 1 mL of cold sorting buffer (L15/10 mM HEPES/1 mg/mL BSA (VWR)/25 μg/mL DNase I (Roche)), and subjected to fluorescence-assisted single-cell picking as described previously (Hempel et al., 2007). Briefly, the cell suspension diluted in 3 mL of sorting buffer was immediately transferred to a 35 mm petri dish (Scanning dish) with lane markings 6 mm apart and let sit on ice until most cells had settled to the bottom which normally takes 15-20 min. Rare fluorescent cells were readily identified under Leica MZ10 F stereomicroscope with fluorescence (transillumination off) by scanning the bottom of the dish lane by lane to maximize recovery and avoid rescanning. Zoom was set such that the field of view corresponded to the width of a single lane. To pick out fluorescent cells with minimal contamination from nonfluorescent cells, a pulled and trimmed micropipette (World Precision Instruments) was carefully lowered under transillumination into the sorting buffer until it was in the vicinity of the target cell. Simultaneous positive pressure was applied by mouth through the aspiration assembly system, as described above for retrograde labeling. Once the micropipette was in position, the target cell was gently aspirated into the micropipette through capillary action by transient release of positive pressure. The micropipette was quickly removed to prevent aspiration of unwanted cells or debris. The content of the micropipette, including the target cell, was expelled gently into a droplet of cold fresh sorting buffer on a different 35 mm petri dish (wash dish 1) under transillumination. Wash dish 1 was kept on ice while subsequent scans for fluorescent cells occurred. Once 16 or all the fluorescent cells, whichever comes first, were collected in wash dish 1, cells were washed two additional times by moving them one by one into a new droplet of sorting buffer on clean 35 mm petri dishes. Micropipettes were not reused for different cells to avoid cross contamination. After the final wash, each fluorescent cell was pipetted up and down the micropipette three times to remove unwanted contamination before being ejected into 10 μl of cold RLT (Qiagen) supplemented with 1% β-mercaptoethanol (Sigma) in a 96-well plate, and snap-frozen on dry ice and stored at −80° C. The entire manual sorting procedure was routinely completed in 1.5 hr.

scRNA-seq of Neurons Using Smart-Seq2

Single-cell libraries were generated according to the Smart-Seq2 protocol. Briefly, RNA from single-cell lysates was purified using AMPure RNA Clean Spri beads (Beckman Coulter) at a 2.2× volume ratio, and mixed with oligo-dT primer (SmartSeq2 3' Oligo-dT Primer), dNTPs (NEB), and RNase inhibitor (Fisher Scientific) at 72° C. for 3 minutes on a thermal cycler to anneal the 3' primer to polyadenylated mRNA. Reverse transcription was carried out in a master mix of Maxima RNaseH-minus RT enzyme and buffer (Fisher Scientific), MgCl2 (Sigma), Betaine (Sigma), RNase inhibitor, and a 5' template switch oligonucleotide (SmartSeq2 5' TSO) using the following protocol: 42° C. for 90 minutes, followed by 10 cycles of 50° C. for 2 minutes, 42° C. for 2 minutes, and followed by inactivation at 70° C. for 15 minutes. Whole transcriptome amplification was achieved by addition of KAPA HiFi HotStart ReadyMix (Kapa Biosystems) and IS PCR primer (ISPCR) to the reverse transcription product and amplification on a thermal cycler using the following protocol: 98° C. for 3 minutes, followed by 21 cycles of 98° C. for 15 seconds, 67° C. for 20 seconds, 72° C. for 6 minutes, followed by a final 5-minute extension at 72° C. Libraries were purified using AMPure XP SPRI beads at a volume ratio of 0.8× followed by 0.9×. Library size was assessed using a High-Sensitivity DNA chip (Agilent Bioanalyzer), confirming the expected size distribution of ~1000-2000 bp. Tagmentation reactions were carried out with the Nextera XT DNA Sample Preparation Kit (Illumina) using 250 μg of cDNA per single cell as input, with modified manufacturer's instructions as described. Libraries were purified twice with AMPure XP SPRI beads at a volume ratio of 0.9×, size distribution assessed using a High Sensitivity DNA chip (Agilent Bioanalyzer) and Qubit High-Sensitivity DNA kit (Invitrogen). Libraries were pooled and sequenced using NextSeq500/550 High Output v2 kits (75 cycles, Illumina) using 30-30 paired end sequencing with 8-mer dual indexing.

RNAscope

The RNAscope Fluorescent Multiplex Assay (ACD Biosystems) was performed according to RNAscope Multiplex Fluorescent Reagent Kit v2 user manual for fresh-frozen tissue samples. Briefly, 14 μm fresh frozen sections from T13 and L1 DRGs with each side containing retrogradely-labeled $tdTomato^+$ LN- or skin-innervating neurons from the same animal were hybridized with RNAscope probes for Ptgir (487851), tdTomato (317041-C2), and Prokr2 (498431-C3) simultaneously. The probes were amplified and detected with TSA plus fluorescein, cyanine 3 and cyanine 5 (Perkin Elmer). The ACD 3-plex negative control probe was run in parallel on separate sections in each experiment to assess the background level and set the acquisition parameter. All sections with $tdTomato^+$ cells were imaged at 20× using an Olympus FV3000 confocal imaging system. The frequency of $Ptgir^+$ or $Prokr2^+$ DRG neurons among the $tdTomato^+$ LN- or skin-innervating population was determined by considering all the $tdTomato^+$ cells that were recovered and uniquely-defined from a single animal.

Tamoxifen Treatment

Tamoxifen (Sigma) was dissolved in corn oil (Sigma) at a concentration of 20 mg/mL by shaking overnight at 37° C., and stored at 4° C. for the duration of the injections. For labeling arterial vessels with Bmx-$CreER^{T2}$, 0.5 mg of tamoxifen was delivered intraperitoneally into Bmx-Cre- $ER^{T2}$; $Rosa26^{eYFP/+}$ animals between 4-6 weeks of age daily for three consecutive days. Animals were analyzed between 1-3 weeks later.

6-OHDA Treatment

For sympathetic denervation, the stock solution of 6-hydroxydopamine (6-OHDA) (Sigma) was prepared in water at 42 mg/mL and stored at −20° C. $Nav1.8^{Cre/+}$; $Rosa26^{LSL\text{-}tdTomato/+}$ animals from the same litter between the ages of 6-12 weeks were injected intraperitoneally with 6-OHDA (100 mg kg-1) or an equal volume of saline daily for 5 consecutive days. Animals were analyzed the following day.

Optogenetic Stimulation of iLN-Innervating Sensory Neurons

Age-matched adult $Nav1.8^{Cre/+}$; $Rosa26^{LSL\text{-}ChR2\text{-}eYFP/+}$ (ChR2+) or $Nav1.8^{Cre/+}$; $Rosa26^{LSL\text{-}eYFP/+}$ (ChR2−) animals (6-12 weeks) were deeply anesthetized (isoflurane, 1.5%-2%, Patterson Vet) maintained at normal body temperature with a water bath heating system (Baxter) during surgical preparation and photostimulation. The animals were surgically prepared for intravital optogenetic stimulation using a method that was adapted from a previously-described protocol for intravital microcopy of iLNs (von Andrian, 1996). Briefly, the skin with the left iLN was flipped inside out following a small incision immediately left to the midline and glued onto a metal block to keep the medulla side of LN exposed. Care was taken not to overstretch the skin flap and damage lymphatic and blood vessels. The site of illumination was the branch point of the antero-posterior-running segment of the y-shaped superficial epigastric artery from where LN feeding arterioles emerged was located and exposed with microdissection without compromising the blood vessel integrity while the tissue was kept moist with normal saline. The stimulation chamber was then built around the iLN with vacuum grease on the side to keep solution from leaking, as well as a metal hairpin shaped tubing with hot water flowing inside on top of vacuum grease to maintain the tissue between 36.5 and 37° C. A thermocouple was placed next to the branch point to monitor the temperature at the tissue. An optic fiber (200 μm core, Thorlabs) coupled to a DPSS laser light source (473 nm, Shanghai Laser & Optics Century) was positioned for focal illumination directly on top of the branch point. The stimulation chamber was subsequently filled to the metal tubing with GenTeal Tears Lubricant Eye Gel (Alcon) to keep the tissue from drying out during stimulation. Pulsed light stimulation (5 m pulses, 125 $mW/mm^2$ intensity, 20 Hz) was delivered to the targeted region for 3 hr under the control of a shutter system (Uniblitz). iLNs from both sides were immediately removed after light stimulation and kept in ice cold LN media (HBSS (Corning)/2% FBS/10 mM HEPES/2 mM $CaCl_2$)) until subsequent processing.

Lymph Node Dissociation and Single Cell Isolation

LNs were kept on ice until processing, <60 minutes between animal sacrifice and tissue digestion. LN media was aspirated, and each LN was placed in 1 mL of pre-warmed digestion media (0.8 mg/mL dispase, 0.2 mg/mL collagenase P (Roche), 50 μg/mL of DNase I in LN media). Using a pair of needle-nose forceps, the capsule of each LN was gently pierced, and the LN in digestion media were placed in a 37° C. water bath for 20 minutes with no agitation. Next, LNs were gently agitated without touching the tissue, pelleted by gravity, and the 1 mL of digestion media supernatant was removed and placed in a collection tube on ice containing 10 mL of quenching buffer (PBS/5 mM EDTA/5% FBS). A fresh 1 mL of digestion buffer was added to each LN, and the LNs were placed back in the 37° C. water bath for an additional 5 minutes. The LN was gently agitated and triturated using a 1000 μL pipette tip, solid capsular and stromal matter was allowed to settle to the bottom of the tube without centrifuging, and the supernatant digestion media was added to the same collection tube containing quenching buffer. 5-minute incubation periods in fresh digestion buffer and trituration with a 1000 μL pipette tip continued until LNs were completely digested, typically requiring 3-4 additional digestion steps. The cellular suspension in quenching buffer was filtered through a 100 μm filter, and washed with an additional 15 mL of quenching buffer. Single-cell suspensions were centrifuged at 300 g for 3 minutes at 4° C., and counted using a hemocytometer and light microscope. Applicants recovered an average of 4.00+/−0.53 million cells per LN, and observed no differences in cellularity by treatment group or animal genotype. Applicants saved an aliquot of 60,000 cells from each sample in quenching media on ice as the unenriched sample, and centrifuged the remaining cells at 300 g for 3 minutes at 4° C. Next, using the Miltenyi CD3& microbead kit and CD19 mouse microbead kit, all remaining LN cells were stained according to manufacturer instructions with the following modifications. First, single cells were stained with CD3& biotin for 10 minutes on ice, washed once with MACS buffer (PBS/0.5% BSA (Sigma)/2 mM EDTA) and stained simultaneously with CD19 microbeads and biotin microbeads. Cells were isolated using LD columns (Miltenyi) according to manufacturer specifications and the flow-through was collected as the non-T and non-B enriched sample. Single cells from both enriched and unenriched samples were pelleted by centrifugation at 300 g for 3 minutes at 4° C., and counted using a hemocytometer with trypan blue staining to estimate cell viability. Across 14 LNs, Applicants recovered an average of 270,000+/−31,000 (mean±/−SEM) cells per lymph node following CD3s and CD19 depletion with >90% viability.

For LN cellularity analysis, single-cell suspensions of the two iLNs from the same ChR2+ or ChR2− mouse (6-12 weeks) were prepared as above. The cells were then filtered through steel mesh and resuspended at the appropriate cell density in FACS buffer before being acquired on a BD Accuri™ C6 Plus flow cytometer (BD Biosciences).

LN scRNA-seq Using Seq-Well

Single cells from each lymph node prior to and post CD3& and CD19 depletion were kept separate and diluted to 15,000 cells in 200 μL complete media (RPMI 1640/10% FBS). Seq-Well was performed as described with changes noted below. Briefly, a pre-functionalized PDMS array containing ~86,000 nanowells was loaded with mRNA capture beads (ChemGenes) and suspended in complete media for at least 20 minutes. 15,000 cells were deposited onto the top of each PDMS array and let settle by gravity into distinct wells. The array was gently washed with PBS and sealed using a functionalized polycarbonate membrane with a pore size of 0.01 μm, which allows exchange of buffers without permitting mixing of cell materials between different wells. Seq-Well arrays were sealed in a dry 37° C. oven for 40 minutes and submerged in a lysis buffer containing 5 M guanidium thiocyanate (Sigma), 1 mM EDTA, 1% beta-mercaptoethanol and 0.05% sarkosyl (Sigma) for 20 minutes at room temperature. Arrays were transferred to hybridization buffer containing 2 M NaCl (Fisher Scientific) with 8% (v/v) polyethylene glycol (PEG, Sigma) and agitated for 40 minutes at room temperature, mRNA capture beads with mRNA hybridized were collected from each Seq-Well array, and beads were resuspended in a master mix for reverse transcription containing Maxima H Minus Reverse Transcriptase and buffer, dNTPs, RNase inhibitor, a 5' template switch oligonucleotide (Seq-Well 5' TSO), and PEG for 30 minutes at room temperature, and overnight at 52° C. with end-over-end rotation. Exonuclease digestion was carried out as described previously: beads were washed with TE with 0.01% tween-20 (Fisher Scientific) and TE with 0.5% SDS (Sigma), denatured while rotating for 5 minutes in 0.2 mM NaOH, and resuspended in ExoI (NEB) for 1 hour at 37° C. with end-over-end rotation. Next, beads were washed with TE+0.01% tween-20, and second strand synthesis was carried out by resuspending beads in a master mix containing Klenow Fragment (NEB), dNTPs, PEG, and the dN-SMRT oligonucleotide (Seq-Well Second Strand Primer) to enable random priming off of the beads. PCR was carried out as described using 2×KAPA HiFi Hotstart Readymix and ISPCR primer (SeqWell ISPCR), and placed on a thermal cycler using the following protocol: 95° C. for 3 minutes, followed by 4 cycles of 98° C. for 20 seconds, 65° C. for 45 seconds, 72° C. for 3 minutes, followed by 12 cycles of 98° C. for 20 seconds, 67° C. for 20 seconds, 72° C. for 3 minutes, followed by a final 5-minute extension at 72° C. Post-whole transcriptome amplification proceeded as described above for SmartSeq2 libraries, with the following exceptions: AMPure XP SPRI bead cleanup occurred first at a 0.6× volume ratio, followed by 0.8×. Library size was analyzed using an Agilent Tapestation hsD5000 kit, confirming the expected peak at ~1000 bp, and absence of smaller peaks corresponding to primer. Libraries were quantified using Qubit High-Sensitivity DNA kit and prepared for Illumina sequencing using Nextera XT DNA Sample Preparation kit using 900 μg of cDNA library as input to tagmentation reactions. Amplified final libraries were purified twice with AMPure XP SPRI beads as before, with a volume ratio of 0.6× followed by 0.8×. Libraries from 3 Seq-Well arrays were pooled and sequenced together using a NextSeq 500/550 High Output v2 kit (75 cycles) using a paired end read structure with custom read 1 primer (SeqWell CRIP): read 1:20 bases, read 2:50 bases, read 1 index: 8 bases.

Image Analysis

All image analyses were performed in Imaris 9.2.1 or 7.4.2 as detailed below. To better visualize neuronal architecture in and/or around LNs, for all LN images except for FIGS. 7K, 7L, S1A, S2C, S2D, S3A, S3B and S7A, an isosurface for the LN was generated by manually drawing LN contours on 2D slices every fifth slice and was used to mask the original images so that only what was inside the LN mask was shown. Depending on the purpose of the experiment, LN isosurfaces were defined with varying degrees of stringency: based on the outermost layer of LECs in FIGS. 2A and 2C, on collagen type I staining in FIG. 2F, on SMA staining in FIGS. 2D, 2E and 9A, or tdTomato background staining everywhere else. In FIGS. 2A, 2C, 2D, 2E, 2F, 9A and 10H, additional masking of the channel(s) where nerves were stained was performed with isosurfaces generated for neuronal signal within LNs based on morphology, i.e. fiber-like structures that can be traced through multiple slices, to highlight neuronal structures. To better visualize fibers in the capsular/subcapsular space of LNs as shown in FIG. 2F, intranodal sensory fibers and total sensory fibers within and below the capsule were isolated by masking the original channel with LN isosurfaces defined based on GFP (LECs) and collagen type I staining, respectively. The resulting channel after subtracting the former channel from the latter one corresponds to the capsular/subcapsular plexus. Original, processed images and rendered isosurfaces were viewed as 3D reconstructions in surpass view with orthogonal camera setting unless indicated otherwise.

For quantification of innervation density of LNs as in FIGS. 1C-1F, relevant channels were first masked with the LN isosurface as described above. Isosurfaces for sensory and sympathetic fibers within the masked channels, i.e., inside the LN, were then generated by automatic creation based on features that distinguish neuronal signal from everything else, e.g., intensity, sphericity, followed by manual editing. Sensory or sympathetic fiber density for a given LN was defined as the ratio of the volume of isosurfaces for sensory or sympathetic fibers within the LN to that for the LN.

For quantification of penetration depth of intranodal sensory fibers, the outermost layer of LECs, which demarcates the LN boundary, was used to precisely segment LNs into isosurfaces. Isosurfaces for intranodal sensory fibers, sensory fibers within the relevant channel after applying the LN isosurface as a mask, were generated as described above. Using the distance transformation function, the closest distance from any given voxel within the LN isosurface to the surface of the LN in μm was computed and converted into an intensity value for that given voxel in a separate channel. To determine penetration depth of intranodal sensory fibers, the distance transformation channel was masked against isosurfaces for intranodal sensory fibers to generate a new channel where the penetration depth at any given voxel within the intranodal sensory fibers was encoded as the intensity value for that specific voxel with the maximum intensity value representing the maximum penetration depth for a given LN. Such a channel, when displayed in surpass view as in FIG. 2A, allowed direct visualization of the spatial relationship between intranodal sensory fibers and the nearest LN surface. Additionally, the penetration depth of intranodal sensory fibers was described in FIG. 2B in the form of the percentage of total intranodal fibers found within LN spaces with increasing distance away from the LN surface. For that analysis, the original distance transformation channel, as described above, was used to create a series of isosurfaces of decreasing sizes which represent increasingly-deep LN spaces with its closest distance to the LN surface increasing from 0 to 100 μm with 10 μm intervals. For example, 10 was set as the intensity threshold cutoff during automatic creation so that all voxels with intensity value larger than and equal to 10 were selected in one single surface which corresponds to the LN space 10 μm and more below the LN surface. To calculate the percentage of total intranodal sensory fibers in any of those LN spaces, the isosurface for total sensory fibers and that for a said LN space, e.g., 10 μm and more below the surface, as described above, were each used to generate their corresponding binary channels, where all voxels outside of a surface were set as 0, while those inside were set at 100. Colocalization analysis was then performed on those two binary channels, and the percentage of non 0 voxels in the binary nerve channel that were colocalized was plotted in FIG. 2B.

Neuron scRNA-seq Data Preprocessing

Single cells were sequenced to a depth of 1.6+/−0.1 million (mean±/−SEM) reads per cell. Pooled libraries were demultiplexed using bcl2fastq (v2.17.1.14) with default settings, and aligned using STAR to the mouse UCSC genome reference (version mm 10), and a gene expression matrix was generated using RSEM (v1.2.3) in paired-end mode. Single-cell libraries with fewer than 3,000 unique genes and fewer than 17% of reads mapping to transcriptomic regions were excluded from subsequent analysis, resulting in a final dataset of 52 LN-innervating neurons collected from 8 mice, and 31 skin-innervating neurons collected from 4 mice. Among cells retained for analysis, the number of unique genes captured was 9,843+/−229 (mean±/−SEM) among LN-innervating neurons and 9,653+/−302 among skin-innervating neurons. Libraries from LN-innervating neurons contained 50.45+/−2.3% transcriptome-aligning fragments, libraries from skin-innervating neurons contained 58.33+/−2.9%. Among all alignment and library quality metrics assessed, Applicants found no significant differences between LN-innervating and skin-innervating neurons (see FIG. 11A-11C). All analysis of gene expression was completed using the normalized RSEM output as transcripts per million (TPM).

Neuron scRNA-seq Differential Gene Expression

All analysis of scRNA-seq data was carried out using the R language for Statistical Computing. Single-cell libraries were first assessed for expression of canonical neuronal markers and known lineage-defining genes from accompanying imaging data, such as Nav1.8 (Scn10a) and tyrosine hydroxylase (Th). The full list of markers is supplied in Table 1. To directly assess differences in gene expression between LN-innervating and skin-innervating neurons, Applicants used the R package Single Cell Differential Expression (SCDE, version 1.99.1) with default input parameters. A cutoff of Holm corrected Z score >1.96 or <−1.96 (corresponding to a corrected p-value <0.05) was used to identify significantly DE genes for subsequent analysis. Heatmaps were created using the R package gplots (version 3.0.1). DAVID was used for analysis of over-represented gene ontologies over significantly DE genes.

Analysis of Neuron scRNA-Seq with Usoskin, Furlan et al. Sensory Neuron Atlas

As their target-specific single cells do not represent the full diversity of neurons contained in the DRG, Applicants utilized the scRNA-seq atlas published by Usoskin, Furlan et al. Nature Neuroscience 2015 (subsequently referred to as the "Sensory Neuron Atlas"). Using the raw data and accompanying metadata hosted at http://linnarssonlab.org/drg/, Applicants first identified the intersection of expressed genes from the Sensory Neuron Atlas and LN-innervating and skin-innervating single cells, and eliminated cells identified as non-neuronal ("NON" and "NON outlier") from the Sensory Neuron Atlas, resulting in a dataset of 148 neurofilamentous (NF), 81 peptidergic (PEP), 251 tyrosine hydroxylase (TH), 169 non-peptidergic (NP), and 39 "Central, unsolved" cells. To mimic the dimensionality reduction methods the previous authors used to identify major neuronal cell types, Applicants transformed the data as log 2(1+TPM), and calculated the gene variance across all cells. Applicants cut to genes with a variance log 2(1+TPM)>0.5, resulting in 11,778 genes. Next, Applicants performed principal component analysis over the log 2-transformed, mean-centered data, and found that PC2 and PC4 reflected major axes of variability between TH, PEP, NF, and NP cell types-identified by the authors of the previous study as "Level.1" cell type subsets (FIG. 4A). To identify how LN-innervating and skin-innervating cells related to major DRG cell types in a reduced dimensional space, Applicants projected their target-specific data into PC2 and PC4 of the Sensory Neuron Atlas. This was completed by first calculating the principal components of the Sensory Neuron Atlas:

$$X-c_m=USV^T \qquad \text{(Equation 1)}$$

where X is the log 2(1+TPM) data matrix of M genes by N cells from the Sensory Neuron Atlas. Equation 1 calculates the singular value decomposition of this matrix after subtracting the average of each row (gene) of X, denoted $c_m$, from X. U represents a matrix of M orthonormal vectors corresponding to M genes and V represents a matrix of N orthonormal vectors corresponding to N cells. To apply this same dimensionality reduction transformation to their new dataset of LN-innervating and skin-innervating single cells, Y, Applicants use Equation 2:

$$PC_i = \sum_{m=1}^{M}(Y-c_m)u_i \qquad \text{(Equation 2)}$$

Y represents the log 2(1+TPM) transformed matrix of Applicants' innervation-target-specific data, and $c_m$ refers to the same vector of row (gene) averages calculated from X. The centered Y matrix is multiplied as a dot product with the $i^{th}$ principal component gene eigenvector, or the $i^{th}$ column vector of U, denoted $u_i$. By taking the sum over all transformed rows for each column (cell), Applicants project the LN-innervating and skin-innervating data (Y) into the principal component space calculated for the Sensory Neuron Atlas (X), denoted $PC_i$. This data is visualized by plotting the $PC_2$ and $PC_4$ vectors from the Sensory Neuron Atlas (transparent circles, FIG. 4A), with the $PC_2$ and $PC_4$ vectors from the transformed LN-innervating and skin-innervating cells (filled squares). The Euclidean distance between each innervation-target-specific single cell and all cells within the Sensory Neuron Atlas was calculated over PC2 and PC4 (FIG. 4B). The range of cell-to-cell Euclidean distances between like-cells (e.g. PEP-to-PEP) within the Sensory Neuron Atlas is represented by a dashed line corresponding to the 99% ile.

To analyze the expression similarity between each single cell from their target-specific dataset and the Sensory Neuron Atlas subtypes in a more directed, supervised manner, Applicants assessed how each single cell correlated with each subtype of Sensory Neuron Atlas. Applicants elected to use the more detailed neuronal subtypes defined by Usoskin, Furlan, et al., termed "Level.3", which breaks some of the major neuron subtypes, NP, PEP, and NF, into subtypes based on intra-population diversity. Applicants calculated the average gene expression for each neuron subtype (e.g. NP1) over the log 2(1+TPM) transformed single-cell data, generating pseudo-population averages for each Usoskin, Furlan-defined "Level.3" neuron subtype. Next, Applicants only considered genes in their pseudo-population averages that were designated as "subtype-defining" by the Usoskin, Furlan et al. analysis, corresponding to the top 50 genes upregulated within each cell type when compared to all other cell types in their Sensory Neuron Atlas, yielding 379 unique genes. Applicants similarly restricted their LN-innervating and skin-innervating single-cell libraries to only these 379 unique genes and calculated the Spearman correlation between each target-specific single cell (following log 2(1+TPM) transformation) and the Sensory Neuron Atlas pseudo-population averages (FIG. 4C). Applicants clustered LN-innervating and skin-innervating single cells by their correlation with each Sensory Neuron Atlas pseudo-population using complete linkage clustering, and using a cut height of 0.8 retained 4 distinct Neuron Types: Neuron type 1 "PEP1-like" (LN-innervating cells: 25, skin-innervating cells: 9), Neuron type 2 "NP-like" (LN-innervating cells: 1, skin-innervating cells: 14), Neuron type 3 "mixed PEP/NF123" (LN-innervating cells: 23, skin-innervating cells: 5), and Neuron type 4 "mixed PEP2/NF12345" (LN-innervating cells: 3, skin-innervating cells: 3) (FIG. 4C).

To assess the gene expression phenotype of each Neuron Type, Applicants used SCDE to identify DE genes between cells of each Neuron Type compared to all cells of the 3 remaining Neuron Types. SCDE was run as described above with default input parameters, genes with a Holm-corrected p-value <0.01 were considered significant and presented in FIG. 4E and Table 1.

LN Seq-Well Data Preprocessing

Reads were aligned and processed according to the Drop-Seq Computational Protocol v2.0 (github.com/broadinstitute/Drop-seq). Briefly, reads were first demultiplexed according to index read 1 using bcl2fastq (v2.17.1.14) with default settings. Read 1 was split into the first 12 base pairs corresponding to the cell barcode (CB), and the 13-20$^{th}$ base pairs, which encode the unique molecular identifier (UMI). CBs, UMIs, and read 2 sequences with low base quality were discarded, as were any that contained non-random sequences (e.g. primer sequences, poly-A tails). Following CB and UMI tagging, read 2 was aligned to the mouse genome (version mm10) using STAR v2.5.2b with default parameters including "--limitOutSJcollapsed 1000000--twopassMode Basic". STAR alignments were merged to recover cell and molecular barcodes, and any sequences within hamming edit distance 1 were merged, as these likely originated from the same original sequence. Additional methods to correct for bead synthesis errors in the CB or UMI are detailed in the Drop-Seq Computational Protocol v2.0 ("DetectBeadSynthesisErrors" function). Digital gene expression matrices for each array were retained following quality filtering and UMI-correction, and further processed using the R language for Statistical Computing. Cells with fewer than 300 unique genes were removed from analysis.

Dimensionality Reduction, Clustering, Visualization, and Cell Type Identification of LN Seq-Well Data Applicants restricted their primary analysis of LN-resident cell types to only arrays corresponding to steady state inguinal LN without surgical manipulation or optogenetic stimulation. A total of 9,662 cells were retained with 25,929 unique genes expressed across 7 mice with 1 LN per mouse. For 2 mice, Applicants sequenced arrays corresponding to all LN cells prior to CD3s/CD19 depletion as well as CD3s/CD19 depleted cells on a separate array. The average cell recovery per array was 1,074+/−141 (mean±/−SEM) cells, with an average gene count of 1,581+/−11 genes and average UMI per cell of 4,251+/−48 UMI (mean±/−SEM). Data was normalized and scaled using the Seurat R package (github.com/satija.lab/seurat): transforming the data to log. (UMI+1) and applying a scale factor of 10,000. Applicants confirmed equivalent depth and cell quality across each of their arrays and the absence of major batch effects introduced by sequencing work-up day or other technical factors, and thus did not regress any batch-related covariates out of their data, including individual cell quality or mitochondrial percent. To identify major axes of variation within their data, Applicants first subsetted their data to only highly-variable genes across all cells-all genes with dispersion (calculated as the variance to mean ratio)>1.1 were kept, resulting in 2,348 variable genes. Principal component analysis was applied to the cells cut to variable genes for the top 100 principal components. Using the JackStraw function within Seurat, Applicants identified the top significant PCs, and compared these significant PCs to the variance explained by each dimension, ultimately choosing 41 PCs for subsequent clustering and further dimensionality reduction. Critically, Applicants completed all of the following analysis over a range of variable gene cutoffs and principal components to ensure that their cell identification results were robust to parameter choice.

For 2D visualization, Applicants used the Barnes-Hut implementation of t-distributed stochastic neighbor embedding (t-SNE) with "perplexity" set to 40. This tSNE projection of the steady state LN atlas is represented in FIGS. 6B, 12A. To identify clusters of transcriptionally-similar cells, Applicants employed unsupervised clustering with the Louvain algorithm with the Jaccard correction. Briefly, this method involves constructing a k-nearest neighbor graph over the Euclidean distance between cells in the 41-PC reduced space, followed by a shared nearest neighbor (SNN)-based clustering and modularity optimization. Applicants implemented this using the FindClusters tool within the Seurat R package with default parameters and k.param set to 20 and resolution set to 0.4. Here, Applicants intentionally underclustered their data to avoid erroneously splitting cells with shared cell type functions, as the variable genes calculated for this dimensionally-reduced space likely did not fully reflect more nuanced cell type differences (e.g. variable behavior between Neutrophil subtypes). The "Parent Cluster" results from first-pass cell type clustering are represented in the tSNE plot and clusters identified in FIG. 12A. Applicants used the Seurat function FindAllMarkers to identity differentially-expressed genes upregulated within each cluster compared to all other cells in the dataset and tested differential expression using the likelihood-ratio test for single-cell gene expression (by setting test.use to "bimod"). The top 100 differentially-expressed genes for each cluster were analyzed, as ranked by the average fold change and restricted to only those with FDR-corrected p-values <0.05. Next, to assess if any cell subtypes existed within each cluster, Applicants restricted their data to only cells within a single "Parent Cluster" and recalculated the variable genes over these cells. The above analysis, from calculation of variable genes to tSNE visualization and cluster identification, was repeated for each cluster listed in FIG. 12A. Cell types for which Applicants could identify sub-clusters with significant differentially-expressed genes are marked with asterisks next to their names in FIG. 12A, and the sub-cluster tSNE projections and top differentially expressed genes are represented in FIG. 12B-12O. For the T cell parent cluster, Applicants required two iterative sub-clustering steps to fully enumerate all constituent cell types: the first clustering step differentiated regulatory T cells (Tregs) from the remaining T cells (FIG. 12B, 12C), and subsequent clustering on the non-Treg T cells uncovered CD4 T cells vs. CD8 T cells. All differentially-expressed genes within each sub-cluster can be found in Table 2.

After exhaustive assessment for cell subclusters within each cell type, Applicants identified 24 unique cell types within their steady state dataset (FIG. 6B). Applicants calculated the differentially expressed genes between each cell type and all other cells using a likelihood ratio test (using the FindAllMarkers function with test.use set to "bimod"), the results of this analysis are presented in FIGS. 6C, 12P, and Table 2. By identifying canonical marker genes within these DE gene lists from the literature and using resources such as ImmGen, Applicants attributed cell identities to each cell type within their dataset, as named in FIGS. 6B, 6C, and 12P.

Analysis of Cellular Receptor-Ligand Pairs

Applicants reasoned that cells or cell types within the LN that interact with innervating neurons would likely express proteins that enable such contact or communication. As Applicants generated unbiased single-cell transcriptomic data from LN-innervating neurons and the potential targeted cell types, Applicants incorporated databases of ligand and receptor pairs to understand if any of the LN-resident cell types expressed a high abundance of cognate molecules and would thus be poised to interact with innervating neurons. A general schematic of this method is provided in FIG. 13A.

Applicants used the database of receptor-ligand interactions curated by Ramilowski et al, which consists of 2,422 total interactions over 708 unique genes (originally provided as human genes, and converted to mouse orthologs using the HUGO database). First, data from LN-innervating neurons was limited to only genes with non-negligible expression, using a cutoff of average log 2(1+TPM)>3, yielding 6,666 total genes for subsequent analysis. The intersection of genes within the Ramilowski interaction database and those expressed at non-negligible levels among LN-innervating neurons yielded 184 total genes. After limiting to only interactions with at least one participating gene expressed in the LN-innervating neurons, the interaction database was restricted to 750 total receptor-ligand pairs, and 471 unique potential cognates. Applicants next assessed the expression of these 471 cognate genes within the LN-resident cell atlas. First, Applicants summarized the expression of individual cells within the LN-resident atlas by taking the pseudo-population average of each cell type (over non-log single-cell data). Applicants limited the LN-resident atlas data to only genes with non-negligible expression across all cell type pseudo-populations, cutting to genes with an average UMI expression >1, yielding 256 total potential cognates (from the previous 471). Next, Applicants developed a summary statistic to reflect the abundance of neuron cognates expressed within LN-resident cell types. First, Applicants scaled their data by subtracting the mean and dividing by the standard deviation for each individual gene; this enabled Applicants to assess the contribution of all genes equally such that signal was not dominated by genes with high total expression (FIG. 6E). Finally, Applicants calculated the "Interaction Potential" (IP) as the mean of these scaled values for each cell type: cell types that expressed relatively higher abundances of all candidate neuron-cognates received a higher IP score. Applicants' null model states that the interaction potentials they calculated are no more extreme than the IP they would have recovered by chance. To test their experimentally-derived IP, Applicants generated a null distribution by shuffling the cell type labels over all single cells within the LN-resident cell atlas, and repeated the "cell type" averaging, scaling, and IP calculation for 1,000 permutations. By comparing their true IP scores to the null distribution, Applicants were able to identify certain cell types with significantly higher IP than observed by chance and could attribute a P-value to each cell type (FIG. 6F, 99% confidence interval denoted by dashed vertical lines). The results of this approach are presented in FIGS. 6D-6F, 13A, 13B.

Crucially, Applicants were concerned that the method of calculation of the IP, the summary statistics applied, the choice of raw vs. scaled data, or confounding factors that differentiate cell types, including average genes/cell and number of cells per cell type, would influence their ranked list of top interacting cell types and bias their results. For example, Applicants wondered whether differences in quality metrics or other technical factors between cell types might result in higher or lower IP rankings. For instance, a cell type with significantly higher RNA recovery per cell than another cell type would appear to have a higher interaction potential. Applicants found no correlation between the IP (as reported in FIG. 6F) and the median UMI per cell for each cell type (FIG. 13B, p=0.32). To address bias introduced by their choice in summary statistic or data normalization, Applicants repeated the above pipeline without gene-wise scaling across cell types (FIG. 13C), or by calculating the percent of cells with non-zero expression of a given gene, in the place of calculating of average expression per cell type (FIG. 13D). In both of these cases, Applicants observed that non-endothelial stroma, LEC 1, LEC 2, BEC 1, and BEC 2 remained the top-scoring cell types for Interaction Potential (significance calculated by permutation test as described above). Finally, Applicants reasoned that variations in the number of cells per cell type might limit their ability to compare between different cell types. Applicants iteratively down-sampled their single-cell data to analyze interaction potentials (using the method in FIG. 6D-6F) for only 25 total cells per cell type—the histograms of these calculations after 1,000 iterations are plotted in FIG. 13E. Critically, non-endothelial stroma, LEC 1, LEC 2, BEC 1, and BEC 2 cell types remained top-ranking in Interaction Potential after controlling for cell abundance per cell type.

Finally, Applicants derived an alternative statistical testing strategy to assess the overrepresentation of neuron-interaction cognates among expressed genes between different cell types. Here, Applicants binarized their data to classify genes as "expressed" or "not expressed" within a cell type, using an average gene expression cutoff of 1. Applicants considered the list of 256 potential neuronal cognate genes and used a Fisher's Exact Test to assess whether the cognate gene list was overrepresented among expressed genes for a given cell type (mimicking the field-standard for gene ontology enrichment analysis), and a Holm correction to adjust for multiple tests. In close agreement with the results from their interaction potential statistic above, Applicants found significant overrepresentation of potential neuronal cognate genes in the following cell types (listed in decreasing statistical significance): non-endothelial stroma ($p=1.6\times10^{-28}$), BEC 1 ($p=2.5\times10^{-22}$), LEC 1 ($p=4.5\times10^{-22}$), BEC 2 ($p=8.3\times10^{-21}$), LEC 2 ($p=9.6\times10^{-20}$), Macrophages ($p=8.7\times10^{-9}$), Mast Cells ($p=6.5\times10^{-8}$), Neutrophils 2 ($p=5.2\times10^{-6}$), Neutrophils 1 ($p=1.8\times10^{-4}$), pDC ($p=1.7\times10^{-3}$), Aire$^+$ APCs ($p=3.4\times10^{-3}$), and cDC2 ($8.9\times10^{-3}$). All other cell types were non-significant by a Holm-adjusted p-value cutoff of 0.01. Critically, this ranking was not sensitive to the choice of binarization cutoff, tested over a range of 0.5-10 UMI, (data not shown).

Differential Gene Expression Following Optogenetic Stimulation

Cells were partitioned into the cell types annotated in FIG. 7B. Using the Seurat function DiffExpTest, which employs a likelihood ratio test to identify differentially expressed genes, Applicants analyzed cells for each cell type from ChR2+Light+ LN vs. ChR2+Light− LN. Similarly, Applicants identified differentially expressed genes by cell type between ChR2−Light+ LN vs. Chr2−Light− LN. Applicants reasoned that the DE genes in ChR2+ mice represented both the effects of neuronal stimulation, as well as changes induced by surgery and/or phototoxicity, while the DE genes in the ChR2− mice only correspond to changes due to surgery and/or phototoxicity. For each cell type, Applicants identified genes DE in ChR2+ animals by a Holm-adjusted p-value cutoff of 0.05, and eliminated genes from these lists that were also DE (using the same cutoff) in ChR2− LN. Applicants calculated the effect size using Cohen's d, and restricted their gene lists to only those genes with a non-negligible effect size, using a cutoff of 0.2 (analysis the effect of various effect-size cutoffs in FIG. 15F). The results of these analyses for each cell type can be found in Table 3. In FIG. 7H, Applicants further restricted their DE gene lists for heatmap visualization, and in FIG. 7J for gene ontology analysis (using DAVID, as described above) by only including genes that were also DE between LNs harvested from the same mouse in at least 2 of 4 ChR2+ mice.

Statistical Testing

Applicants used unpaired two-tailed Student's t-tests within Prism software for comparison of fiber density within denervation studies and retrograde labeling (FIGS. 1E, 1H, 8G) and RNAScope quantification (FIG. 5F). All other statistical tests corresponding to differential gene expression or assessment of interaction potential are described above and completed using R language for Statistical Computing. Tests of correlation and correlation significance are annotated by the correlation model used (Pearson vs. Spearman) were completed using R language for Statistical Computing. Parameters such as sample size, number of replicates, number of independent experiments, measures of center, dispersion, and precision (mean±SEM) and statistical significances are reported in Figures and Figure Legends. A P-value less than 0.05 was considered significant unless otherwise reported; a more stringent cutoff of 0.01 was used in some instances, and annotated as such. Where appropriate, a Holm correction was used to account for multiple tests, as noted in the Figure Legends.

TABLE 3

Differential gene expression following optogenetic stimulation

| Genes | P-value | FDR Adjusted p-value | Average Expression + Light | SD Expression + Light | Average Expression − Light | SD Expression − Light | Fraction Expressing + Light | Fraction Expressing − Light | Cohen's Effect Size | Direction (1: upregulated with + Light; −1: down-regulated with + Light) |
|---|---|---|---|---|---|---|---|---|---|---|
| Galnt1 | 0.00003 | 0.02202 | 0.79912 | 1.80149 | 2.60676 | 3.21695 | 0.20000 | 0.52475 | −0.69335 | −1 |
| Hsp90ab1 | 0.00006 | 0.03179 | 7.69289 | 8.89564 | 15.50512 | 14.09140 | 0.64706 | 0.85149 | −0.66298 | −1 |
| Fau | 0.00005 | 0.02964 | 0.14372 | 0.58173 | 1.07901 | 2.08455 | 0.07059 | 0.31683 | −0.61117 | −1 |
| Usp25 | 0.00014 | 0.04345 | 0.23045 | 0.97011 | 1.22366 | 2.09180 | 0.07059 | 0.32673 | −0.60916 | −1 |
| Adipor2 | 0.00009 | 0.03973 | 0.21381 | 0.65861 | 1.11428 | 2.04017 | 0.11765 | 0.32673 | −0.59400 | −1 |
| Rps15 | 0.00012 | 0.04329 | 1.28879 | 2.34542 | 3.15784 | 3.91076 | 0.31765 | 0.63366 | −0.57964 | −1 |
| Akrle1 | 0.00003 | 0.02329 | 0.00000 | 0.00000 | 0.38188 | 0.95676 | 0.00000 | 0.17822 | −0.56447 | −1 |
| Prdx6 | 0.00011 | 0.04329 | 0.41372 | 1.17656 | 1.41952 | 2.29241 | 0.12941 | 0.40594 | −0.55203 | −1 |
| Ttp53 | 0.00019 | 0.04981 | 0.44216 | 1.35291 | 1.34004 | 1.95684 | 0.14118 | 0.42574 | −0.53376 | −1 |
| 1110008 L16Rik | 0.00001 | 0.01323 | 0.03269 | 0.21191 | 0.65593 | 1.98049 | 0.02353 | 0.14851 | −0.44251 | −1 |
| Psmc2 | 0.00008 | 0.03557 | 0.48830 | 1.53829 | 1.28533 | 2.19990 | 0.11765 | 0.39604 | −0.41990 | −1 |
| Larp7 | 0.00000 | 0.00974 | 0.05683 | 0.36827 | 0.35795 | 0.96239 | 0.02353 | 0.15842 | −0.41327 | −1 |
| Il17ra | 0.00004 | 0.02598 | 0.05650 | 0.36613 | 0.36294 | 1.03816 | 0.02353 | 0.14851 | −0.39368 | −1 |
| Kdsr | 0.00004 | 0.02598 | 0.07352 | 0.47641 | 0.43494 | 1.22488 | 0.02353 | 0.12871 | −0.38891 | −1 |
| B630005 N14Rik | 0.00019 | 0.04928 | 0.51835 | 1.55526 | 1.17688 | 1.98724 | 0.14118 | 0.41584 | −0.36906 | −1 |
| Clec4a4 | 0.00014 | 0.04329 | 0.21856 | 1.05660 | 0.66802 | 1.36605 | 0.04706 | 0.24752 | −0.36806 | −1 |
| 1810058I 24Rik | 0.00004 | 0.02598 | 0.07044 | 0.31906 | 0.29670 | 0.82334 | 0.04706 | 0.14851 | −0.36239 | −1 |
| Ddb2 | 0.00018 | 0.04860 | 0.08974 | 0.58179 | 0.41856 | 1.17353 | 0.02353 | 0.14851 | −0.35502 | −1 |
| Srgap2 | 0.00002 | 0.01454 | 0.07599 | 0.49244 | 0.51476 | 1.84494 | 0.02353 | 0.12871 | −0.32496 | −1 |
| Gm26735 | 0.00006 | 0.03001 | 0.06593 | 0.42725 | 0.25310 | 0.75442 | 0.02353 | 0.11881 | −0.30531 | −1 |
| Eif3h | 0.00012 | 0.04329 | 1.66649 | 3.34889 | 2.56425 | 2.68247 | 0.32941 | 0.60396 | −0.29589 | −1 |
| Mbd2 | 0.00012 | 0.04329 | 0.66810 | 1.84295 | 1.21119 | 1.97076 | 0.15294 | 0.41584 | −0.28465 | −1 |
| Vps45 | 0.00003 | 0.02202 | 0.03325 | 0.21549 | 0.25756 | 1.28730 | 0.02353 | 0.05941 | −0.24304 | −1 |
| Ift80 | 0.00000 | 0.00974 | 0.10035 | 0.65032 | 0.31411 | 1.07359 | 0.02353 | 0.11881 | −0.24083 | −1 |
| Praf2 | 0.00001 | 0.01331 | 0.06413 | 0.41558 | 0.19786 | 0.70406 | 0.02353 | 0.07921 | −0.23133 | −1 |
| Tmub2 | 0.00000 | 0.00827 | 0.29932 | 1.95371 | 0.67151 | 1.28875 | 0.04706 | 0.26733 | −0.22489 | −1 |
| Zfp36 | 0.00012 | 0.04329 | 1.25779 | 4.22103 | 2.10383 | 3.29169 | 0.15294 | 0.41584 | −0.22352 | −1 |
| Pum2 | 0.00008 | 0.03739 | 1.78982 | 3.71887 | 2.51050 | 2.81867 | 0.32941 | 0.61386 | −0.21841 | −1 |
| RP24-390G17.1 | 0.00000 | 0.00974 | 0.09233 | 0.59830 | 0.00678 | 0.06815 | 0.02353 | 0.00990 | 0.20090 | 1 |
| 2410127 L17Rik | 0.00013 | 0.04329 | 0.16283 | 0.99573 | 0.01854 | 0.13113 | 0.03529 | 0.01980 | 0.20317 | 1 |
| Lap3 | 0.00014 | 0.04371 | 0.36344 | 1.51314 | 0.10957 | 0.38117 | 0.07059 | 0.08911 | 0.23008 | 1 |
| Cyb5r1 | 0.00018 | 0.04868 | 0.25457 | 1.35256 | 0.02481 | 0.17621 | 0.03529 | 0.01980 | 0.23822 | 1 |
| Asap1 | 0.00016 | 0.04650 | 1.98760 | 4.46869 | 1.11845 | 1.89579 | 0.28235 | 0.34653 | 0.25322 | 1 |
| Tbx3 | 0.00012 | 0.04329 | 1.07375 | 2.75744 | 0.52155 | 1.20985 | 0.16471 | 0.19802 | 0.25934 | 1 |
| Wars2 | 0.00007 | 0.03434 | 0.29216 | 1.23576 | 0.04464 | 0.22340 | 0.05882 | 0.03960 | 0.27875 | 1 |
| Arftp1 | 0.00005 | 0.02964 | 0.75873 | 1.95068 | 0.33945 | 0.80984 | 0.16471 | 0.16832 | 0.28074 | 1 |
| Htra2 | 0.00012 | 0.04329 | 2.38608 | 4.62400 | 1.36333 | 2.04549 | 0.34118 | 0.41584 | 0.28606 | 1 |
| Ahr | 0.00001 | 0.01331 | 0.75961 | 2.48779 | 0.21879 | 0.65453 | 0.11765 | 0.10891 | 0.29732 | 1 |
| Kazn | 0.00003 | 0.02329 | 0.28685 | 1.26859 | 0.01676 | 0.11848 | 0.05882 | 0.01980 | 0.29979 | 1 |
| Smarcd2 | 0.00001 | 0.01323 | 1.54635 | 3.34458 | 0.75207 | 1.24696 | 0.31765 | 0.32673 | 0.31469 | 1 |
| Zxdc | 0.00000 | 0.00063 | 1.31823 | 4.93614 | 0.19538 | 0.58458 | 0.09412 | 0.11881 | 0.31947 | 1 |
| Agpat1 | 0.00002 | 0.01577 | 0.75775 | 2.16226 | 0.22516 | 0.63676 | 0.18824 | 0.11881 | 0.33415 | 1 |
| Lmbrl1 | 0.00014 | 0.04371 | 1.30028 | 3.57552 | 0.22548 | 0.68192 | 0.21176 | 0.11881 | 0.41759 | 1 |
| Gm15564 | 0.00009 | 0.03973 | 31.96359 | 57.16954 | 13.44261 | 19.28411 | 0.84706 | 0.69307 | 0.43412 | 1 |
| Lars2 | 0.00004 | 0.02873 | 50.80694 | 77.50809 | 24.26792 | 29.03921 | 0.96471 | 0.95050 | 0.45345 | 1 |
| Clk1 | 0.00013 | 0.04329 | 5.68946 | 6.85049 | 2.67219 | 3.30147 | 0.63529 | 0.56436 | 0.56112 | 1 |
| Slc25a37 | 0.00000 | 0.00974 | 6.20477 | 6.89637 | 2.89028 | 3.86915 | 0.62353 | 0.56436 | 0.59277 | 1 |
| mmu-mir-6236 | 0.00000 | 0.00063 | 9.41162 | 15.08656 | 1.96703 | 3.84897 | 0.63529 | 0.36634 | 0.67620 | 1 |

REFERENCES

Abrahamsen, B., Zhao, J., Asante, C. O., Cendan, C. M., Marsh, S., Martinez-Barbera, J. P., Nassar, M. A., Dickenson, A. H., and Wood, J. N. (2008). The cell and molecular basis of mechanical, cold, and inflammatory pain. Science 321, 702-705.

Adams, R. H., and Eichmann, A. (2010). Axon guidance molecules in vascular patterning. Cold Spring Harb Perspect Biol 2, a001875.

Andrae, J., Gallini, R., and Betsholtz, C. (2008). Role of platelet-derived growth factors in physiology and medicine. Genes Dev 22, 1276-1312.

Assas, B. M., Pennock, J. I., and Miyan, J. A. (2014). Calcitonin gene-related peptide is a key neurotransmitter in the neuro-immune axis. Front Neurosci 8, 23.

Baral, P., Udit, S., and Chiu, I. M. (2019). Pain and immunity: implications for host defence. Nat Rev Immunol.

Bellinger, D. L., Lorton, D., Felten, S. Y., and Felten, D. L. (1992). Innervation of lymphoid organs and implications in development, aging, and autoimmunity. Int J Immunopharmacol 14, 329-344.

Belvisi, M. G. (2002). Overview of the innervation of the lung. Curr Opin Pharmacol 2, 211-215.

Brierley, S. M., Jones, R. C., 3rd, Gebhart, G. F., and Blackshaw, L. A. (2004). Splanchnic and pelvic mechanosensory afferents signal different qualities of colonic stimuli in mice. Gastroenterology 127, 166-178.

Buettner, M., and Bode, U. (2012). Lymph node dissection—understanding the immunological function of lymph nodes. Clin Exp Immunol 169, 205-212.

Camp, J. G., Sekine, K., Gerber, T., Loeffler-Wirth, H., Binder, H., Gac, M., Kanton, S., Kageyama, J., Damm, G., Seehofer, D., et al. (2017). Multilineage communication regulates human liver bud development from pluripotency. Nature 546, 533-538.

Caterina, M. J. (2003). Vanilloid receptors take a TRP beyond the sensory afferent. Pain 105, 5-9.

Chang, R. B., Strochlic, D. E., Williams, E. K., Umans, B. D., and Liberles, S. D. (2015). Vagal Sensory Neuron Subtypes that Differentially Control Breathing. Cell 161, 622-633.

Chavan, S. S., Pavlov, V. A., and Tracey, K. J. (2017). Mechanisms and Therapeutic Relevance of Neuro-immune Communication. Immunity 46, 927-942.

Chiu, I. M., Heesters, B. A., Ghasemlou, N., Von Hehn, C. A., Zhao, F., Tran, J., Wainger, B., Strominger, A., Muralidharan, S., Horswill, A. R., et al. (2013). Bacteria activate sensory neurons that modulate pain and inflammation. Nature 501, 52-57.

Chiu, I. M., Hehn, C., and Woolf, C. J. (2012). Neurogenic inflammation and the peripheral nervous system in host defense and immunopathology. Nat Neurosci 15.

Cho, C., Wang, Y., Smallwood, P. M., Williams, J., and Nathans, J. (2019). Dlg1 activates beta-catenin signaling to regulate retinal angiogenesis and the blood-retina and blood-brain barriers. Elife 8.

Choi, I., Chung, H. K., Ramu, S., Lee, H. N., Kim, K. E., Lee, S., Yoo, J., Choi, D., Lee, Y. S., Aguilar, B., et al. (2011). Visualization of lymphatic vessels by Prox1-promoter directed GFP reporter in a bacterial artificial chromosome-based transgenic mouse. Blood 117, 362-365.

Cohen, J. N., Tewalt, E. F., Rouhani, S. J., Buonomo, E. L., Bruce, A. N., Xu, X., Bekiranov, S., Fu, Y. X., and Engelhard, V. H. (2014). Tolerogenic properties of lymphatic endothelial cells are controlled by the lymph node microenvironment. PLOS One 9, e87740.

Cohen, M., Giladi, A., Gorki, A. D., Solodkin, D. G., Zada, M., Hladik, A., Miklosi, A., Salame, T. M., Halpern, K. B., David, E., et al. (2018). Lung Single-Cell Signaling Interaction Map Reveals Basophil Role in Macrophage Imprinting. Cell 175, 1031-1044 e1018.

Eelen, G., Dubois, C., Cantelmo, A. R., Goveia, J., Bruning, U., DeRan, M., Jarugumilli, G., van Rijssel, J., Saladino, G., Comitani, F., et al. (2018). Role of glutamine synthetase in angiogenesis beyond glutamine synthesis. Nature 561, 63-69.

Ehling, M., Adams, S., Benedito, R., and Adams, R. H. (2013). Notch controls retinal blood vessel maturation and quiescence. Development 140, 3051-3061.

Felten, D. L., Felten, S. Y., Bellinger, D. L., and Lorton, D. (1992). Noradrenergic and peptidergic innervation of secondary lymphoid organs: role in experimental rheumatoid arthritis. Eur J Clin Invest 22 Suppl 1, 37-41.

Felten, D. L., Felten, S. Y., Carlson, S. L., Olschowka, J. A., and Livnat, S. (1985). Noradrenergic and peptidergic innervation of lymphoid tissue. J Immunol 135, 755s-765s.

Fink, T., and Weihe, E. (1988). Multiple neuropeptides in nerves supplying mammalian lymph nodes: messenger candidates for sensory and autonomic neuroimmunomodulation? Neurosci Lett 90, 39-44.

Fletcher, A. L., Malhotra, D., Acton, S. E., Lukacs-Kornek, V., Bellemare-Pelletier, A., Curry, M., Armant, M., and Turley, S. J. (2011). Reproducible isolation of lymph node stromal cells reveals site-dependent differences in fibroblastic reticular cells. Front Immunol 2, 35.

Foster, S. L., Seehus, C. R., Woolf, C. J., and Talbot, S. (2017). Sense and Immunity: Context-Dependent Neuro-Immune Interplay. Front Immunol 8, 1463.

Gautron, L., Sakata, I., Udit, S., Zigman, J. M., Wood, J. N., and Elmquist, J. K. (2011). Genetic tracing of Nav1.8-expressing vagal afferents in the mouse. J Comp Neurol 519, 3085-3101.

Gonzalez-Castillo, C., Ortuno-Sahagun, D., Guzman-Brambila, C., Pallas, M., and Rojas-Mayorquin, A. E. (2014). Pleiotrophin as a central nervous system neuromodulator, evidences from the hippocampus. Front Cell Neurosci 8, 443.

Hanes, W. M., Olofsson, P. S., Talbot, S., Tsaave, T., Ochani, M., Imperato, G. H., Levine, Y. A., Roth, J., Pascal, M. A., Foster, S. L., et al. (2016). Neuronal circuits modulate antigen flow through lymph nodes. Bioelectron Med 3, 18-28.

Hempel, C. M., Sugino, K., and Nelson, S. B. (2007). A manual method for the purification of fluorescently labeled neurons from the mammalian brain. Nat Protoc 2, 2924-2929.

Hilgenberg, L. G., Su, H., Gu, H., O'Dowd, D. K., and Smith, M. A. (2006). Alpha3Na+/K+-ATPase is a neuronal receptor for agrin. Cell 125, 359-369.

Karrer, U., Althage, A., Odermatt, B., Roberts, C. W., Korsmeyer, S. J., Miyawaki, S., Hengartner, H., and Zinkernagel, R. M. (1997). On the key role of secondary lymphoid organs in antiviral immune responses studied in alymphoplastic (aly/aly) and spleenless (Hox11(−)/−) mutant mice. J Exp Med 185, 2157-2170.

Kashem, S. W., Riedl, M. S., Yao, C., Honda, C. N., Vulchanova, L., and Kaplan, D. H. (2015). Nociceptive Sensory Fibers Drive Interleukin-23 Production from CD301b+ Dermal Dendritic Cells and Drive Protective Cutaneous Immunity. Immunity 43, 515-526.

Kuehn, E. D., Meltzer, S., Abraira, V. E., Ho, C. Y., and Ginty, D. D. (2019). Tiling and somatotopic alignment of mammalian low-threshold mechanoreceptors. Proc Natl Acad Sci USA 116, 9168-9177.

Kuka, M., and Iannacone, M. (2014). The role of lymph node sinus macrophages in host defense. Ann N Y Acad Sci 1319, 38-46.

Kulkarni, R. M., Greenberg, J. M., and Akeson, A. L. (2009). NFATc1 regulates lymphatic endothelial development. Mech Dev 126, 350-365.

Kumar, M. P., Du, J., Lagoudas, G., Jiao, Y., Sawyer, A., Drummond, D. C., Lauffenburger, D. A., and Raue, A. (2018). Analysis of Single-Cell RNA-Seq Identifies Cell-Cell Communication Associated with Tumor Characteristics. Cell Rep 25, 1458-1468 e1454.

Kupari, J., Haring, M., Agirre, E., Castelo-Branco, G., and Ernfors, P. (2019). An Atlas of Vagal Sensory Neurons and Their Molecular Specialization. Cell Rep 27, 2508-2523 e2504.

Lakkis, F. G., Arakelov, A., Konieczny, B. T., and Inoue, Y. (2000). Immunologic ‘ignorance’ of vascularized organ transplants in the absence of secondary lymphoid tissue. Nat Med 6, 686-688.

Larrivee, B., Freitas, C., Suchting, S., Brunet, I., and Eichmann, A. (2009). Guidance of vascular development: lessons from the nervous system. Circ Res 104, 428-441.

Lawson, S. N., Crepps, B., and Perl, E. R. (2002). Calcitonin gene-related peptide immunoreactivity and afferent receptive properties of dorsal root ganglion neurones in guinea-pigs. J Physiol 540, 989-1002.

Li, L., Rutlin, M., Abraira, V. E., Cassidy, C., Kus, L., Gong, S., Jankowski, M. P., Luo, W., Heintz, N., Koerber, H. R., et al. (2011). The functional organization of cutaneous low-threshold mechanosensory neurons. Cell 147, 1615-1627.

Lorton, D., Lubahn, C., Engan, C., Schaller, J., Felten, D. L., and Bellinger, D. L. (2000). Local application of capsaicin into the draining lymph nodes attenuates expression of adjuvant-induced arthritis. Neuroimmunomodulation 7, 115-125.

Lutter, S., Xie, S., Tatin, F., and Makinen, T. (2012). Smooth muscle-endothelial cell communication activates Reelin signaling and regulates lymphatic vessel formation. J Cell Biol 197, 837-849.

Mack, J. J., and Iruela-Arispe, M. L. (2018). NOTCH regulation of the endothelial cell phenotype. Curr Opin Hematol 25, 212-218.

Mackenzie, F., and Ruhrberg, C. (2012). Diverse roles for VEGF-A in the nervous system. Development 139, 1371-1380.

Malin, S., Molliver, D., Christianson, J. A., Schwartz, E. S., Cornuet, P., Albers, K. M., and Davis, B. M. (2011). TRPV1 and TRPA1 function and modulation are target tissue dependent. J Neurosci 31, 10516-10528.

Mao, C., and Obeid, L. M. (2008). Ceramidases: regulators of cellular responses mediated by ceramide, sphingosine, and sphingosine-1-phosphate. Biochim Biophys Acta 1781, 424-434.

Mason, M. R., Ehlert, E. M., Eggers, R., Pool, C. W., Hermening, S., Huseinovic, A., Timmermans, E., Blits, B., and Verhaagen, J. (2010). Comparison of AAV serotypes for gene delivery to dorsal root ganglion neurons. Mol Ther 18, 715-724.

McMahon, S. B., La Russa, F., and Bennett, D. L. (2015). Crosstalk between the nociceptive and immune systems in host defence and disease. Nat Rev Neurosci 16, 389-402.

Mempel, T. R., Henrickson, S. E., and Von Andrian, U. H. (2004). T-cell priming by dendritic cells in lymph nodes occurs in three distinct phases. Nature 427, 154-159.

Mickle, A. D., Won, S. M., Noh, K. N., Yoon, J., Meacham, K. W., Xue, Y., Mcllvried, L. A., Copits, B. A., Samineni, V. K., Crawford, K. E., et al. (2019). A wireless closed-loop system for optogenetic peripheral neuromodulation. Nature 565, 361-365.

Mithal, D. S., Banisadr, G., and Miller, R. J. (2012). CXCL12 signaling in the development of the nervous system. J Neuroimmune Pharmacol 7, 820-834.

Moore, T. C., Lami, J. L., and Spruck, C. H. (1989). Substance P increases lymphocyte traffic and lymph flow through peripheral lymph nodes of sheep. Immunology 67, 109-114.

Mooster, J. L., Le Bras, S., Massaad, M. J., Jabara, H., Yoon, J., Galand, C., Heesters, B. A., Burton, O. T., Mattoo, H., Manis, J., et al. (2015). Defective lymphoid organogenesis underlies the immune deficiency caused by a heterozygous S32I mutation in IkappaBalpha. J Exp Med 212, 185-202.

Nakai, A., Hayano, Y., Furuta, F., Noda, M., and Suzuki, K. (2014). Control of lymphocyte egress from lymph nodes through beta2-adrenergic receptors. J Exp Med 211, 2583-2598.

Nassar, M. A., Stirling, L. C., Forlani, G., Baker, M. D., Matthews, E. A., Dickenson, A. H., and Wood, J. N. (2004). Nociceptor-specific gene deletion reveals a major role for Nav1.7 (PN1) in acute and inflammatory pain. Proc Natl Acad Sci USA 101, 12706-12711.

Oaklander, A. L., and Siegel, S. M. (2005). Cutaneous innervation: form and function. J Am Acad Dermatol 53, 1027-1037.

Ordovas-Montanes, J., Rakoff-Nahoum, S., Huang, S., Riol-Blanco, L., Barreiro, O., and von Andrian, U. H. (2015). The Regulation of Immunological Processes by Peripheral Neurons in Homeostasis and Disease. Trends Immunol 36, 578-604.

Palazzo, E., Marconi, A., Truzzi, F., Dallaglio, K., Petrachi, T., Humbert, P., Schnebert, S., Perrier, E., Dumas, M., and Pincelli, C. (2012). Role of neurotrophins on dermal fibroblast survival and differentiation. J Cell Physiol 227, 1017-1025.

Pappu, R., Schwab, S. R., Cornelissen, I., Pereira, J. P., Regard, J. B., Xu, Y., Camerer, E., Zheng, Y. W., Huang, Y., Cyster, J. G., et al. (2007). Promotion of lymphocyte egress into blood and lymph by distinct sources of sphingosine-1-phosphate. Science 316, 295-298.

Pham, T. H., Baluk, P., Xu, Y., Grigorova, I., Bankovich, A. J., Pappu, R., Coughlin, S. R., McDonald, D. M., Schwab, S. R., and Cyster, J. G. (2010). Lymphatic endothelial cell sphingosine kinase activity is required for lymphocyte egress and lymphatic patterning. J Exp Med 207, 17-27.

Pinho-Ribeiro, F. A., Baddal, B., Haarsma, R., O'Seaghdha, M., Yang, N. J., Blake, K. J., Portley, M., Verri, W. A., Dale, J. B., Wessels, M. R., et al. (2018). Blocking Neuronal Signaling to Immune Cells Treats Streptococcal Invasive Infection. Cell 173, 1083-1097 e1022.

Rajendran, P. S., Challis, R. C., Fowlkes, C. C., Hanna, P., Tompkins, J. D., Jordan, M. C., Hiyari, S., Gabris-Weber, B. A., Greenbaum, A., Chan, K. Y., et al. (2019). Identification of peripheral neural circuits that regulate heart rate using optogenetic and viral vector strategies. Nat Commun 10, 1944.

Renier, N., Wu, Z., Simon, D. J., Yang, J., Ariel, P., and Tessier-Lavigne, M. (2014). iDISCO: a simple, rapid method to immunolabel large tissue samples for volume imaging. Cell 159, 896-910.
Rice, F. L., and Albrecht, P. J. (2008). Cutaneous mechanisms of tactile perception: morphological and chemical organization of the innervation to the skin. (San Diego: Academic Press).
Richardson, J. D., and Vasko, M. R. (2002). Cellular mechanisms of neurogenic inflammation. J Pharmacol Exp Ther 302, 839-845.
Riol-Blanco, L., Ordovas-Montanes, J., and Perro, M. (2014). Nociceptive sensory neurons drive interleukin-23-mediated psoriasiform skin inflammation. Nature 510.
Robertson, B. (1990). Wheat germ agglutinin binding in rat primary sensory neurons: a histochemical study. Histochemistry 94, 81-85.
Robinson, D. R., and Gebhart, G. F. (2008). Inside information: the unique features of visceral sensation. Mol Interv 8, 242-253.
Schnoor, M., Alcaide, P., Voisin, M. B., and van Buul, J. D. (2015). Crossing the Vascular Wall: Common and Unique Mechanisms Exploited by Different Leukocyte Subsets during Extravasation. Mediators Inflamm 2015, 946509.
Shepherd, A. J., Beresford, L. J., Bell, E. B., and Miyan, J. A. (2005a). Mobilisation of specific T cells from lymph nodes in contact sensitivity requires substance P. J Neuroimmunol 164, 115-123.
Shepherd, A. J., Downing, J. E., and Miyan, J. A. (2005b). Without nerves, immunology remains incomplete-in vivo veritas. Immunology 116, 145-163.
Shibuya, M. (2011). Vascular Endothelial Growth Factor (VEGF) and Its Receptor (VEGFR) Signaling in Angiogenesis: A Crucial Target for Anti- and Pro-Angiogenic Therapies. Genes Cancer 2, 1097-1105.
Sudhof, T. C. (2018). Towards an Understanding of Synapse Formation. Neuron 100, 276-293.
Suvas, S. (2017). Role of Substance P Neuropeptide in Inflammation, Wound Healing, and Tissue Homeostasis. J Immunol 199, 1543-1552.
Takahashi, Y., and Nakajima, Y. (1996). Dermatomes in the rat limbs as determined by antidromic stimulation of sensory C-fibers in spinal nerves. Pain 67, 197-202.
Thiriot, A., Perdomo, C., Cheng, G., Novitzky-Basso, I., McArdle, S., Kishimoto, J. K., Barreiro, O., Mazo, I., Triboulet, R., Ley, K., et al. (2017). Differential DARC/ACKR1 expression distinguishes venular from non-venular endothelial cells in murine tissues. BMC Biol 15, 45.
Usoskin, D., Furlan, A., Islam, S., Abdo, H., Lonnerberg, P., Lou, D., Hjerling-Leffler, J., Haeggstrom, J., Kharchenko, O., Kharchenko, P. V., et al. (2015). Unbiased classification of sensory neuron types by large-scale single-cell RNA sequencing. Nat Neurosci 18, 145-153.
Vaahtomeri, K., Karaman, S., Makinen, T., and Alitalo, K. (2017). Lymphangiogenesis guidance by paracrine and pericellular factors. Genes Dev 31, 1615-1634.
Vento-Tormo, R., Efremova, M., Botting, R. A., Turco, M. Y., Vento-Tormo, M., Meyer, K. B., Park, J. E., Stephenson, E., Polanski, K., Goncalves, A., et al. (2018). Single-cell reconstruction of the early maternal-fetal interface in humans. Nature 563, 347-353.
von Andrian, U. H. (1996). Intravital microscopy of the peripheral lymph node microcirculation in mice. Microcirculation 3, 287-300.
Williams, E. K., Chang, R. B., Strochlic, D. E., Umans, B. D., Lowell, B. B., and Liberles, S. D. (2016). Sensory Neurons that Detect Stretch and Nutrients in the Digestive System. Cell 166, 209-221.
Winkler, C., and Yao, S. (2014). The midkine family of growth factors: diverse roles in nervous system formation and maintenance. Br J Pharmacol 171, 905-912.
Wood, J. N., Emery, E. C., and Ernfors, P. (2018). Dorsal Root Ganglion Neuron Types and Their Functional Specialization (Oxford University Press).
Wu, H., Xiong, W. C., and Mei, L. (2010). To build a synapse: signaling pathways in neuromuscular junction assembly. Development 137, 1017-1033.
Wu, M., Du, Y., Liu, Y., He, Y., Yang, C., Wang, W., and Gao, F. (2014). Low molecular weight hyaluronan induces lymphangiogenesis through LYVE-1-mediated signaling pathways. PLOS One 9, e92857.
Yamano, T., Dobes, J., Voboril, M., Steinert, M., Brabec, T., Zietara, N., Dobesova, M., Ohnmacht, C., Laan, M., Peterson, P., et al. (2019). Aire-expressing ILC3-like cells in the lymph node display potent APC features. J Exp Med 216, 1027-1037.
Yang, F. C., Tan, T., Huang, T., Christianson, J., Samad, O. A., Liu, Y., Roberson, D., Davis, B. M., and Ma, Q. (2013). Genetic control of the segregation of pain-related sensory neurons innervating the cutaneous versus deep tissues. Cell Rep 5, 1353-1364.
Yang, X. M., Han, H. X., *Sui*, F., Dai, Y. M., Chen, M., and Geng, J. G. (2010). Slit-Robo signaling mediates lymphangiogenesis and promotes tumor lymphatic metastasis. Biochem Biophys Res Commun 396, 571-577.
Ye, X., Wang, Y., and Nathans, J. (2010). The Norrin/Frizzled4 signaling pathway in retinal vascular development and disease. Trends Mol Med 16, 417-425.
Zeng, W., Pirzgalska, R. M., Pereira, M. M., Kubasova, N., Barateiro, A., Seixas, E., Lu, Y. H., Kozlova, A., Voss, H., Martins, G. G., et al. (2015). Sympathetic neuro-adipose connections mediate leptin-driven lipolysis. Cell 163, 84-94.
Zhang, G., Brady, J., Liang, W. C., Wu, Y., Henkemeyer, M., and Yan, M. (2015). EphB4 forward signalling regulates lymphatic valve development. Nat Commun 6, 6625.
Zhou, P., Hwang, K. W., Palucki, D., Kim, O., Newell, K. A., Fu, Y. X., and Alegre, M. L. (2003). Secondary lymphoid organs are important but not absolutely required for allograft responses. Am J Transplant 3, 259-266.

Various modifications and variations of the described methods, pharmaceutical compositions, and kits of the invention will be apparent to those skilled in the art without departing from the scope and spirit of the invention. Although the invention has been described in connection with specific embodiments, it will be understood that it is capable of further modifications and that the invention as claimed should not be unduly limited to such specific embodiments. Indeed, various modifications of the described modes for carrying out the invention that are obvious to those skilled in the art are intended to be within the scope of the invention. This application is intended to cover any variations, uses, or adaptations of the invention following, in general, the principles of the invention and including such departures from the present disclosure come within known customary practice within the art to which the invention pertains and may be applied to the essential features herein before set forth.

What is claimed is:

1. A method of acquiring or maintaining lymph node (LN) homeostasis in skin-draining LNs, comprising administering a genetic modifying agent comprising a CRISPR-Cas protein and a guide RNA capable of forming a complex with the CRISPR-Cas protein and directing sequence-specific binding to the Calca gene encoding the protein of SEQ ID NO: 1 to a skin-draining LN of a subject with an autoimmune or inflammatory disease, wherein the genetic modifying agent modulates neural stimulation and/or efferent signaling of LN-innervating peptidergic nociceptor sensory neurons by regulating Calca expression or function.

2. The method of claim 1, wherein the LN-innervating nociceptor sensory neurons are characterized by the expression of one or more genes or gene products selected from:

a. one or more gene or gene products of Dhdh, Grin3a, Fam198b, Plekhg2, Rab8b, Cetn3, Slc30a7, Ankrd45, Prmt2, C530008M17Rik, Epb4.112, Klh124, Tead1, Aplpl, 2610035D17Rik, Sort1, Csf2ra, Slc1a5, Hn1, Plxdc2, Ccdc85a, Serpinb8, Fam174b, Plscr4, Axl, Rab3b, Caskin2, Prdx1, Efemp1, Gabrb1, Myt11, Lamb2, Ern2, Col6a5, Slc39a6, Fads3, Nrip3, Ncoa7, Tbc1d8, Plekho2, Rcn3, Sostdc1, Syt4, Bhlhb9, Ppp1r14c, Hmgn2, Mpzl1, Ifi2711, Lhfpl5, Lrrc58, Flrt1, Il13ra1, Mtmr11, Slc47a2, Calca, Rspo1, Rasip1, Cyp4v3, As3mt, Rcan3, Arxes1, Fam3a, Cnih2, Neat1, Ctnnd2, Jam2, Afap112, 9830001H06Rik, Tceal8, Sorbs2, Steap3, Bnip2, Sdc4, Pcsk5, Rarres2, Wnt9a, Hsd17b11, P4ha3, Tmem74, Itm2a, Terf1, Plxna3, Ctsc, Adamts2, Prkra, Rassf7, Npcd, Stard13, Tax1bp3, Dgkg, Malat1, Metrn, Slc9a3r1, Grn, Prss35, Psd, Ppfia2, Gm5424, Cd63, Adcy7, Kif13b, Syt16, Daam2, Prex2, Dusp16, Svil, Gpr35, Rgs16, Col1a2, Lsp1, Galnt10, Stac, Chd3, Nudt11, 2900008C10Rik, Shisa5, Pgrmc1, Pkn1, Rdh5, Shd, Fstl1, Lss, Nrxn1, Impact, Ap3b1, Sipx, H2afy, Pmepal, Cp, Hey2, Ptgerl, Nudt10, Snap47, Dgka, Tmtc4, Phip, Vldlr, Sepp1, Slc4a4, Lgr5, Bst2, Aldoc, Npy5r, Rasl11a, Tmem130, Zfp3611, Hap1, Syf2, Limd1, Cd79a, Jun, Zhx2, Gpr149, Hspg2, Agrp, Them4, Tada1, Smpdl3a, Gprasp1, Pnmal1, Tspan5, Nfkbia, Nxn, Cdkn1b, Tmbim1, Cyp2j9, Pip5klb, Kirrel3, Foxo1, F3, Arnt2, Mfsd2a, Entpd2, Col5a3, Tiam2, Cebpd, Pgm2l1, Cry1, Kenj10, Rnh1, Tmem229a, Pld5, Abcc4, Gprasp2, Fads2, Pnp, Ramp2, Col28a1, Arxes2, Fdps, Fam108c, Fkbp1b, Lima1, Slc7a14, Trp53i13, Dcaf12l1, A4galt, Rab31, Pla2g16, Sstr1, Junb, Irf6, Sod3, Pik3r1, Cyb561, Vwa1, Il4ra, Lcor1, Slc7a2, C1qtnf7, Asl, Abca8a, Qk, Slc25a27, Tle3, Rab34, Peli2, Notch1, 1700001L19Rik, Fbn1, Spint2, Tmem140, Man2a1, Fads1, Gja1, 5430417L22Rik, Psmb8, Fgf13, Fmo1, Fat1, Cyp2d22, Grb10, C4b, Itih5, Col8a1, Fam129b, Eif4ebp1, Pnck, Ezr, Fabp7, Camk2b, Ahi1, Whm, Samsn1, Hr, Bgn, Sox10, Dock6, Arhgef2, Lepre14, D4Wsu53e, Tspan6, Sema4d, Pik3ip1, Gria1, Wls, Rnase4, Megf10, Pdpn, Car11, St3gal1, Cyr61, Trip10, Acaa1a, Arhgap22, Slc41a3, Dpyd, Ngb, Vamp4, Sparc, Smarca1, Egfl8, Cartpt, Necab1, Gstp1, Ppap2b, Celf3, Igfbp5, Tceal5, Cald1, Hrh3, Psme1, Wnt3, Lrig1, Prss23, Phc1, Cdh19, Pdia5, Slc6a7, Ralgps2, Pls3, Kcnh6, Litaf, Shf, 2900056M20Rik, Celf2, Adamts5, 2810468N07Rik, Adcy5, Syt5, Bhlhe40, Chd5, Plekha4, Sema3b, Cnp, Vim, Nid1, Caly, Nudt17, Cst3, Ivns1abp, Slc16a2, Itgb8, Ptprz1, Aspa, Cmtm5, Fxyd1, Ssbp2, Ntrk2, Cdk18, Ucp2, Rgs9, Cdh13, Atpla2, Tagln2, St5, Ntsr2, Arhgap15, Tle2, Nynrin, Dusp1, Ttyh1, D430019H16Rik, Pde11a, Gadd45g, Chrna6, Tcp1112, Haus4, Fam89a, Lyn, Mmd2, Rit2, Hpcal4, Lama4, 6330403K07Rik, Kcnc2, Ndn, Emp2, Paqr6, Sft2d2, Atp2b4, Rnd3, Sh3kbp1, C530044C16Rik, Pcbd1, Ptn, Ncam1, Mboat2, Phactr2, Gpr3711, Scg2, Ndrg2, Btg2, Tle6, Ndrg1, Slc10a6, Klf6, Atp1b2, Gpr68, Dcn, Gpm6b, Ctxn1, Plp1, Marcksl1, Zbtb20, Pttg1ip, Hmgn3, Bex4, Hmgcs2, Phgdh, Mpz, Csrp2, Fbln5, Plekhb11, Usp11, Kl, Lpar1, Bex1, Fxyd6, Gal, Gfra3, Gpx3, Kcnmb2, Lig1, Npy1r, S100a11, Sstr2, Tac1, Tmem176a, Zcchc12, Tipv1, Nrsn1, Tmem176b, Ppfibp2, Adcyap1, Rxrg, Tcn2, Ly6e, Chrnb3, Serpine2, A730017C20Rik, Stmn1, Igfbp2, Acsbg1, Ednrb, Kcnk3, Gabrg3, Rsph9, Celf4, Sv2a, Bid, Entpd3, Capn9, Gpr137b, Tnr, Atg7, Acsl5, St3gal6, 6720468P15Rik, Seipina3g, Ctdsp1, Syt51, Mbnl2, Gm20139, Zfp954, Hs6st3, Selk, Tpk1, Ggta1, Hexb, Lrrn3, Plekhg1, Rasgef1b, Ube2e3, Cdh8, Actr3, Pdlim1, Nap111, Lpar5, Hmga2-ps1, 1830012O16Rik, Shcl, Lclatl, Aff2, 1700066M21Rik, Ttc39c, Xylt2, Sdcl, Mrgpra2b, Praf2, 2810032G03Rik, Trpv2, Gpr116, Adarb1, Hexa, Txndc11, Gm2115, Fam5b, 1700003M02Rik, Egfem1, Runx2, Mboat1, Camk2a, Ank, Luzp2, Ngfrap1, Arhgap1, Ptprt, Stt3b, Hagh, Tbrg1, Cited1, Igsf3, Rpl36a, Mapk4, Tm7sf3, Cntnap4, Anxa11, Tspan1, Lbh, Zdhhc13, Psd4, Tnfaip813, Ism1, Fam189a2, Arsb, Cyp2j12, Mrgpra2a, Ncf2, Gpr179, Oas1a, Tmem154, Gng12, Il17rc, Rnf125, Tubb2b, Otoa, Dcx, Far2, Samd12, Irak3, Tmem164, Spns2, Dgkz, Fbxo22, Kctd16, Lhfpl2, Hcn4, Acbd4, Rasgrp1, Ifit2, Samd14, Bhlhe41, Ddah1, Myt1, Cpe, Rnf7, Ahnak, Fam19a4, Ret, Bag2, Kdelc2, Slc35f5, Gnaq, Pvrl1, Rasgef1a, Kcnk18, Kenj11, Gnao1, Fam43a, Abcc8, Gpd11, Cpn1, Prokr1, Tpm4, 9530053A07Rik, Isl2, Lrrc59, Mvp, Actn1, Cab391, Bcar3, Lix1, Pitpnc1, Wnt2b, Cmtm7, Ttr, Zfp945, Ccdc43, Smyd3, Snx9, Zfp40, Gadl1, Atpla3, Abca5, Adam8, Paqr4, Ifi2712a, Prkar2b, Slc35f4, Grhl3, H2-D1, Snx7, Med10, 5830473C10Rik, Slc7a8, Hdac9, Mcfd2, Sh2d4a, Cds2, Fam83h, Slc7a7, Inadl, Lipa, Ugcg, Ssbp3, Tmem200a, Mrgprd, Cdk15, Agtrap, Ldb2, Pop5, Stom, Elk3, Eml1, Tpd52, Htr4, Etv1, Slc45a3, Dyrk4, Rpp25, Ap1ar, Rasa4, Kcnk13, Txn1, Serpina11, Aprt, Dtnbp1, Ptrh1, N28178, Ptma, Mustn1, Rarg, Ghr, Dok1, Arhgap6, Zadh2, Mlc1, Mal, Cd47, P2rx3, Rgs3, Osmr, Krt27, Hmox1, Mal2, Snx10, Klk5, Gnal, Ifit3, Fam107b, Gng2, Ets1, Pkig, Fam83d, Lap3, 3632451006Rik, Myola, Plcb3, Tspan14, Slc4a11, Zfp385b, Prkca, Cadm1, Dnajc5b, Cav2, Rab27b, Rcan2, Ston2, Dusp26, Tmem158, Kcng3, Kcnt1, Skp1a, Rab15, 9430021M05Rik, Fli1, Gna14, Scn11a, Neurog3, Golga7b, Lgals3, Dgkh, Fam178b, Cysltr2, Dpp10, Ptgdr, Stogal2, Arpc1b, Socs2, Rgs8, Ly86, Fez1, Cpne3, Bcl2114, Ccdc68, Slc22a18, Arap1, Arhgap36, Rgs10, Dapk2, Kcnip4, Tec, Tmem63a, Mrgpra3, Rhov, Uaca, Pstpip2, Serinc2, A3galt2, Acpp, Adk, Carhsp1, Cav1, Cd55, Cd82, Ctxn3, Fxyd2, Kcnip2, Klf5, Lxn, Moxd1, Nnat, Nt5e, Paqr5, Ppp1r1a, Scg3, Synpr, Tmem45b, Tmem79, Trpc3, Trpc6, Mmp25, Plxnc1, Cmtm8, Serping1, Mrgpra9, Gpm6a, Dgki, Grik1, Fam114a1, Plaur, Rgs4, Slc16a12, Slc9a3r2, Mical1, Rarres1, Hs6st2, Klhl5, Nbl1, Cyp4f39, Kcnn1, Ms4a3, Cd24a, Prkcd, Mrgprb5, Wipf3, Ryr2, Tecr, Dym, Diras2, Lrrc4c, Dclk2, Hrsp12, Egfl7, Dcunld4, Prrt2, Dbc1, Tsc22d3, Stx11, P2rx6, Greb1, Coro6, Wnt5a, Kif5c, Pld3, Fam69a, Nacc2, Tubb4a, Gnwd1, Krt28, Galm, Vamp1, Raly1, Pak3, Adcy8, Slitrk3, Luzp1, Ndp, Upp2, Klhl25, Rell2, Orai2, Opcml, Cntnap2, Lrrc8c, Sv2c, Foxj1, Camk1d, Scn4b, Adam23, Dpp6, Ankrd52, Ankrd29, Snap25, Tmem229b, Hs3st1, Ncam2, Abhd2, Camk2g, Tspyl4, Tm4sf1, Pcolce2, Cntn6, Eda, Adam22, Clu, Kank4, Nptn, Dkk3, Kndc1, Mmp15, Brmsl1, Hs3st3b1, P2ry2, Pid1, C1qtnf1, Irs2, Cyp46a1, Fgfr1, Depdc7, Grm8, Cnih3, Pqlc1, Esr1, Kcna2, Impdh1, Hgf, Sema5a, Pllp, Ppp3ca, Itgb6, Vstm2a, Sytl2, Mgll, Vwc21, Lingo3, Mctp1, Calm3, Lrrn1, Scn1a, Clec21, Cadm3, Mgst1, Lhfpl3, Pygb, Akr1b8, Chga, Lin7b, Parva, Rasgeflc, Begain, Fzd1, Bace2, Hapln3, Egflam, Chn2, Plcb1, Col11a1, Slc16a6, L3mbtl4, Fat3, Pde 2a, Cfh, Nrp2, Ptger3, Cplx1, Pvrl4, Syt2, Kit1, Tgfb2, Tnfrsf21, Pwwp2b, Golim4, Kcnab2, Lhfpl4, Prlr, Prrt3, Scn1b, Gm10754, Kcnip3, Sorcs3, Ngfr, Col16a1, Shank1, Scn8a, Ywhag, Nfasc, Hist1h2bc, 3110043O21Rik, Canikk1, Olfml3, Tuba4a, Nfia, Igsf21, Nr4a2, Ndrg3, Glrb, Pcdhac2, Atp1a1, Stbd1, Kcnt2, Prokr2, Lcp1, Fam81a, Rnf157, Tmem56, Paqr9, Nat81, Kcnv1, Kcnq2, Plxna2, Elfn1, Scn7a, Sorl1, Airn, Syt6, Tm9sf2, Spock3, Grm4, Cyp1b1, Cntn1, Epb4.113, Aox1, Kcnd1, Nap112, Plch2, P2ry1, Cntnap1, Adam11, 1110008P14Rik, Tmem47, Lgmn, Nefh, Vangl1, Sv2b, Pcp411, Fam126b, Chst2, Ckmt1, Phyhipl, Clrn1, Efhd2, Gpr158, Ust, Pcdhac1, Cdh4, Lpl, Hopx, Tagln3, Atp1b1, Pak1ip1, Lynx1, Serpinb1b, Spock1, Gng8, Smpd3, Bet3l, Prkcb, AI593442, Kcnip1, Fam19a1, Sh3gl2, Serpinb1a, Tmem25, Nefm, Rph3a, Thy1, Rasgrf1, Rasl10b, Nptx1, Cgnl1, Cplx2, Fgf12, Ly6h, S100b, Cpne6, Fxyd7, Rimkla, Nefl, Creg2, Susd2, Htr3b, Gm7271, D930028M14Rik, Htr3a, Abcg2, Fbxo2, S100a16, Lgi2, Gda, Fam196b, Acs16, Necab3, Adamtsl5, Lmo1, Cplx11, Clu1, Fgf9, Esrrg, Hs3st2, Fam65c, Lgi3, Fabp3, B3galt1, Gabra1, Epha6, Kcng4, Ptk7, Arhgef3, Htr7, Rnf128, Ppm1j, Prokrl1, Ntng1, Sema3d, Nefm1, Neto1, A330050F15Rik, Chchd10, Ehd3, Cish, Pcdh7, Nlgn1, Slc4a2, Endod1, Car2, Ano4, Kcnk1, Mest, Fam57b, Syt3, Cacng5, Lrrn11, Fam19a2, Vamp11, Kcna1, Lingo4, Nell2, Ankrd34c, Stac2, Cygb, Slitrk4, Hhatl, Arhgef4, Meis2, Elmo1, Tesc, P2rx61, Epn3, Bcat1, Atp2b2, Mab2112, Pcp4, Rcan21, Gm4980, Tmem163, Hapln1, Ptgfr, Mgst3, Hapln4, Baiap211, Htr1d, Tmem108;

b. Trpc4, Trpm8, Kchnh5, and Ache;

c. Thxa2r, Il33, Ptgir, and Cd1d; or d. Ptgir and Prokr2.

3. The method of claim 1, wherein, preferably, the nociceptor sensory neurons innervate an outer cortical region or medulla of LNs, more preferably, wherein the outer cortical region comprises a perivascular space and a capsular/subcapsular space.

4. The method of claim 1, wherein the CRISPR-Cas protein is part of a CRISPR system, and the CRISPR system comprises a guide RNA capable of forming a complex with the CRISPR-Cas protein and directing sequence-specific binding to the Calca gene, and wherein the CRISPR system comprises a CRISPR-Cas base editing system, a prime editor system, or a CAST system.

5. The method of claim 1, wherein modulating neural stimulation and/or efferent signaling of LN-innervating nociceptor sensory neurons comprises modulating an interaction with non-endothelial stroma by administering an agent that modulates the expression or function of one or more of:

a. Col3a1, Col5a2, Col5a1, Col6a1, Col6a2, Col6a3, Col1a2, Col1a2, Lama2, Thbs2, Fn1;

b. Vegfa, Ptn, Mdk, Cxcl12; and c. Pdgfra, Pdgfrb, Ntrk2.

6. The method of claim 1, wherein modulating neural stimulation and/or efferent signaling of LN-innervating nociceptor sensory neurons comprises modulating an interaction with non-venular blood endothelial cells (BEC 1) by administering an agent that modulates the expression or function of one or more of:

a. Lama5, Itga5, Hspg2;

b. Flt1, Notch4, Fzd5;

c. Sema3f, Sema7a, Nrp1, Plxnd1, Efnb1, Epha4; and d. Selp, Cxcl1.

7. The method of claim 1, wherein acquiring or maintaining lymph node (LN) homeostasis in skin-draining LNs is used to treat a subject suffering from a disease characterized by aberrant homeostasis or inflammation in the skin selected from the group consisting of an inflammatory disease and an autoimmune disease.

* * * * *